United States Patent
Chupak et al.

(10) Patent No.: US 9,850,225 B2
(45) Date of Patent: Dec. 26, 2017

(54) COMPOUNDS USEFUL AS IMMUNOMODULATORS

(71) Applicant: BRISTOL-MYERS SQUIBB COMPANY, Princeton, NJ (US)

(72) Inventors: Louis S. Chupak, Old Saybrook, CT (US); Min Ding, Glastonbury, CT (US); Scott W. Martin, Middletown, CT (US); Xiaofan Zheng, Cheshire, CT (US); Piyasena Hewawasam, Middletown, CT (US); Timothy P. Connolly, Portland, CT (US); Ningning Xu, Wallingford, CT (US); Kap-Sun Yeung, Madison, CT (US); Juliang Zhu, North Haven, CT (US); David R. Langley, Meriden, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/681,772

(22) Filed: Apr. 8, 2015

(65) Prior Publication Data
US 2015/0291549 A1   Oct. 15, 2015

Related U.S. Application Data

(60) Provisional application No. 61/979,337, filed on Apr. 14, 2014.

(51) Int. Cl.
| | |
|---|---|
| *C07D 319/18* | (2006.01) |
| *A61K 31/357* | (2006.01) |
| *C07D 405/12* | (2006.01) |
| *A61K 31/453* | (2006.01) |
| *C07D 405/14* | (2006.01) |
| *A61K 31/4545* | (2006.01) |
| *C07D 217/16* | (2006.01) |
| *A61K 31/472* | (2006.01) |
| *C07D 413/12* | (2006.01) |
| *A61K 31/5377* | (2006.01) |
| *C07D 417/12* | (2006.01) |
| *A61K 31/541* | (2006.01) |
| *A61K 31/496* | (2006.01) |
| *A61K 45/06* | (2006.01) |
| *C07C 255/54* | (2006.01) |
| *C07D 215/14* | (2006.01) |
| *C07D 215/18* | (2006.01) |
| *C07D 231/56* | (2006.01) |
| *C07D 405/04* | (2006.01) |
| *C07D 239/26* | (2006.01) |
| *C07D 261/08* | (2006.01) |
| *C07D 271/06* | (2006.01) |
| *C07D 207/26* | (2006.01) |
| *C07D 207/335* | (2006.01) |
| *C07D 213/30* | (2006.01) |
| *C07C 271/28* | (2006.01) |
| *C07C 317/22* | (2006.01) |
| *C07C 233/36* | (2006.01) |
| *C07C 235/42* | (2006.01) |

(Continued)

(52) U.S. Cl.
CPC .......... *C07D 319/18* (2013.01); *A61K 31/165* (2013.01); *A61K 31/277* (2013.01); *A61K 31/357* (2013.01); *A61K 31/40* (2013.01); *A61K 31/4015* (2013.01); *A61K 31/416* (2013.01); *A61K 31/4178* (2013.01); *A61K 31/427* (2013.01); *A61K 31/4245* (2013.01); *A61K 31/4433* (2013.01); *A61K 31/453* (2013.01); *A61K 31/4545* (2013.01); *A61K 31/47* (2013.01); *A61K 31/472* (2013.01); *A61K 31/496* (2013.01); *A61K 31/505* (2013.01); *A61K 31/5377* (2013.01); *A61K 31/541* (2013.01); *A61K 45/06* (2013.01); *C07C 233/36* (2013.01); *C07C 235/42* (2013.01); *C07C 255/13* (2013.01); *C07C 255/54* (2013.01); *C07C 271/28* (2013.01); *C07C 317/22* (2013.01); *C07D 207/26* (2013.01); *C07D 207/335* (2013.01); *C07D 213/30* (2013.01); *C07D 215/14* (2013.01); *C07D 215/18* (2013.01); *C07D 217/16* (2013.01); *C07D 231/56* (2013.01); *C07D 239/26* (2013.01); *C07D 261/08* (2013.01); *C07D 271/06* (2013.01); *C07D 405/04* (2013.01); *C07D 405/12* (2013.01); *C07D 405/14* (2013.01); *C07D 413/12* (2013.01); *C07D 417/12* (2013.01)

(58) Field of Classification Search
None
See application file for complete search history.

(56) References Cited

U.S. PATENT DOCUMENTS 5,977,117 A   11/1999   Chan et al.
7,968,552 B2   6/2011   Negoro et al.

FOREIGN PATENT DOCUMENTS

JP   2005-179281 A   7/2005
WO   WO 97/25321 A2   7/1997

(Continued)

*Primary Examiner* — Jeffrey S Lundgren
*Assistant Examiner* — Stephanie Springer
(74) *Attorney, Agent, or Firm* — Pamela A. Mingo

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

15 Claims, No Drawings

(51) Int. Cl.
*C07C 255/13* (2006.01)
*A61K 31/165* (2006.01)
*A61K 31/277* (2006.01)
*A61K 31/40* (2006.01)
*A61K 31/4015* (2006.01)
*A61K 31/416* (2006.01)
*A61K 31/4178* (2006.01)
*A61K 31/4245* (2006.01)
*A61K 31/427* (2006.01)
*A61K 31/4433* (2006.01)
*A61K 31/47* (2006.01)
*A61K 31/505* (2006.01)

(56) References Cited

FOREIGN PATENT DOCUMENTS

| WO | WO 2004/007439 A1 | 1/2004 |
|---|---|---|
| WO | WO 2004/080377 A2 | 9/2004 |
| WO | WO 2005/080367 A1 | 9/2005 |
| WO | WO 2007/017687 A2 | 2/2007 |
| WO | WO 2008/130514 A1 | 10/2008 |
| WO | WO 2015/034820 A1 | 3/2015 |

COMPOUNDS USEFUL AS IMMUNOMODULATORS

CROSS-REFERENCE TO RELATED APPLICATIONS

This application claims priority to Provisional Patent Application U.S. Ser. No. 61/979,337 filed Apr. 14, 2014 hereby incorporated by reference in its entirety.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir M e, Butte M J, Freeman G J, et al. PD-1 and its ligands in tolerance and immunity. Annu. Rev. Immunol. 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al, Immunity; 27:111-122 (2007)). The interaction of PD-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., New Engl J Med 2012). Preclinical animal models of tumors have shown that blockade of the PD-1/PD-L1 pathway by monoclonal antibodies can enhance the immune response and result in the immune response to a number of histologically distinct tumors (Dong H, Chen L. B7-H1 pathway and its role in the Evasion of tumor immunity. J Mol Med. 2003; 81(5):281-287; Dong H, Strome S E, Salamoa D R, et al. Tumor-associated B7-H1 promotes T-cell apoptosis: a potential mechanism of immune evasion. Nat Med. 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. Restoring function in exhausted CD8 T cells during chronic viral infection. Nature. 2006; 439 (7077):682-687). Humanized mice infected with HIV-1 show enhanced protection against viremia and reduced viral depletion of CD4+T cells (Palmer et al., J. Immunol 2013). Blockade of PD-1/PD-L1 through monoclonal antibodies to PD-L1 can restore in vitro antigen-specific functionality to T cells from HIV patients (Day, Nature 2006; Petrovas, J. Exp. Med. 2006; Trautman, Nature Med. 2006; D'Souza, J. Immunol. 2007; Zhang, Blood 2007; Kaufmann, Nature Imm. 2007; Kasu, J. Immunol. 2010; Porichis, Blood 2011), HCV patients [Golden-Mason, J. Virol. 2007; Jeung, J. Leuk. Biol. 2007; Urbani, J. Hepatol. 2008; Nakamoto, PLoS Path. 2009; Nakamoto, Gastroenterology 2008] or HBV patients (Boni, J. Virol. 2007; Fisicaro, Gastro. 2010; Fisicaro et al., Gastroenterology, 2012; Boni et al., Gastro., 2012; Penna et al., J Hep, 2012; Raziorrough, Hepatology 2009; Liang, World J Gastro. 2010; Zhang, Gastro. 2008).

Blockade of the PD-L1/CD80 interaction has also been shown to stimulate immunity (Yang J., et al., J Immunol. August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 and T cell apoptosis (Guignant, et al, Crit. Care (2011)). Antibodies directed to PD-L1 can reduce the level of Immune cell apoptosis (Zhang et al, Crit. Care (2011)). Furthermore, mice lacking PD-1 expression are more resistant to septic shock symptoms than wildtype mice (Yang J., et al. J Immunol. August 1; 187(3):1113-9 (2011)). Studies have revealed that blockade of the interactions of PD-Li using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., "Enhancing therapeutic vaccination by blocking PD-1-mediated inhibitory signals during chronic infection," The Journal of Experimental Medicine, vol. 205, no. 3, pp. 5-((3-555, 2008; A. C. Finnefrock, A. Tang, F. Li et al., "PD-1 blockade in rhesus macaques: impact on chronic infection and prophylactic vaccination," The Journal of Immunology, vol. 182, no. 2, pp. 980-987, 2009; M.-Y. Song, S.-H. Park, H. J. Nam, D.-H. Choi, and Y.-C. Sung, "Enhancement of vaccine-induced primary and memory CD8+t-cell responses by soluble PD-1," The Journal of Immunotherapy, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

The present disclosure also provides pharmaceutical compositions comprising a compound of formula (I) and/or a pharmaceutically acceptable salt thereof; and a pharmaceutically acceptable carrier.

The present disclosure also provides a method of treating a disease or disorder associated with the activity of PD-L1 including its interaction with other proteins such as PD-1 and B7-1(CD80), the method comprising administering to a patient in need thereof a compound of formula (I) and/or a pharmaceutically acceptable salt thereof. The present disclosure also provides processes and intermediates for making the compounds of formula (I) and/or salts thereof.

The present disclosure also provides a compound of formula (I) and/or a pharmaceutically acceptable salt thereof, for use in therapy.

The present disclosure also provides the use of the compounds of formula (I) and/or pharmaceutically acceptable salts thereof, for the manufacture of a medicament for the treatment or prophylaxis of PD-L1 related conditions, such as cancer and infectious diseases.

The compounds of formula (I) and compositions comprising the compounds of formula (I) may be used in treating, preventing, or curing various infectious diseases and cancer. Pharmaceutical compositions comprising these compounds are useful in treating, preventing, or slowing the progression of diseases or disorders in a variety of therapeutic areas, such as cancer and infectious diseases.

These and other features of the disclosure will be set forth in expanded form as the disclosure continues.

In a first aspect the present disclosure provides a compound of formula (I):

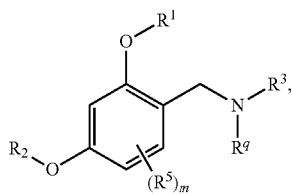

(I)

or a pharmaceutically acceptable salt thereof, wherein:
m is 0, 1, or 2;
$R^1$ is selected from hydrogen, —$(CH_2)_nX$ and —$(CH_2)_n$Ar; wherein
n is 1, 2, 3, or 4;
X is selected from —$CH_3$, —$CF_3$, CN, —$CO_2R^4$, —$C(O)NH_2$, $OR^4$, and pyrrolidonyl;
$R^4$ is H or $C_1$-$C_3$alkyl;
Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, ($C_1$-$C_4$alkyl)carbonyl, ($C_1$-$C_4$alkyl)sulfonyl, amido, aminocarbonyl, aminocarbonyl($C_1$-$C_3$alkyl), —$(CH_2)_qCO_2C_1$-$C_4$alkyl, —$(CH_2)_q$PH, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;

$R^2$ is selected from

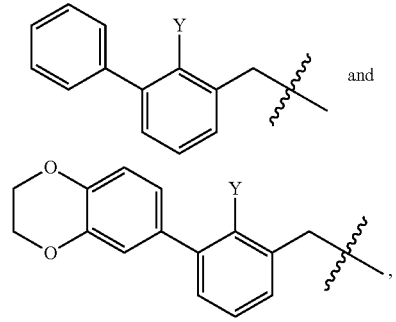

wherein Y is selected from cyano, chloro, and methyl;
$R^q$ is selected from hydrogen, $C_1$-$C_3$alkyl, and benzyl;
$R^3$ is selected from

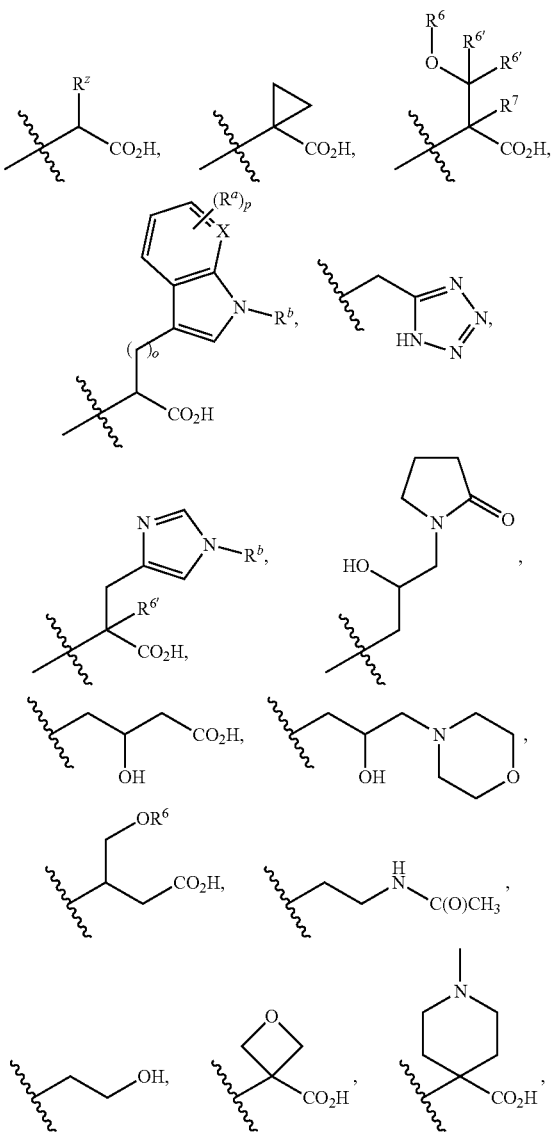

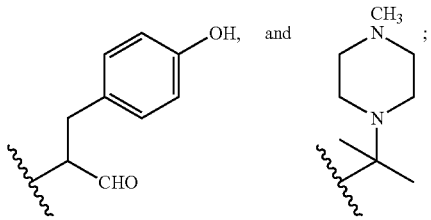

wherein $R^z$ is selected from $C_1$-$C_3$alkyl, $C_1$-$C_3$alkylsulfonyl$C_1$-$C_3$alkyl, $C_1$-$C_3$alkylsulfoxyl$C_1$-$C_3$alkyl, amido$C_1$-$C_3$alkyl, amino$C_1$-$C_4$alkyl, carboxy$C_1$-$C_3$alkyl, cyano$C_1$-$C_3$alkyl, dimethylamido$C_1$-$C_3$alkyl, dimethylamino$C_1$-$C_4$alkyl, halo$C_1$-$C_3$alkyl, hydroxy$C_1$-$C_3$alkyl, $C_1$-$C_3$alkylsulfanyl$C_1$-$C_3$alkyl, pyridinyl$C_1$-$C_3$alkyl, tetrazolyl$C_1$-$C_3$alkyl, imidazolyl$C_1$-$C_3$alkyl wherein the imidazole is optionally substituted with methyl or a benzyl group, phenyl$C_1$-$C_3$alkyl wherein the phenyl is optionally substituted with cyano, methyl, or hydroxy, thiazolyl$C_1$-$C_3$alkyl;

$R^6$ is selected from hydrogen, benzyl, and methyl;

each $R^{6'}$ is independently selected from hydrogen and methyl;

$R^7$ is selected from hydrogen, $C_1$-$C_3$alkyl, and benzyl;

o is 1 or 2;

X is CH or N;

p is 0 or 1;

$R^a$ is hydroxy; and $R^b$ is selected from hydrogen, benzyl, and methyl; or $R^3$ and $R^q$, together with the nitrogen atom to which they are attached, form a ring selected from

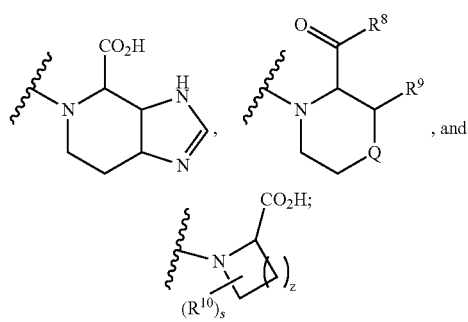

s is 0 or 1;

z is 1, 2, or 3; and $R^8$ is selected from hydroxy and —$NHSO_2R^{11}$;

$R^9$ is selected from hydrogen and —$CO_2H$;

$R^{10}$ is selected from halo and hydroxy;

$R^{11}$ is selected from trifluoromethyl, cyclopropyl, $C_1$-$C_3$alkyl, dimethylamino, and imidazolyl substituted with a methyl group;

Q is selected from $CH_2$, S, O, and $NCH_3$; and $R^5$ is selected from $C_2$-$C_4$alkenyl, $C_1$-$C_4$alkyl, cyano, methoxy, halo, and trifluoromethyl.

In a first embodiment of the first aspect $R^2$ is

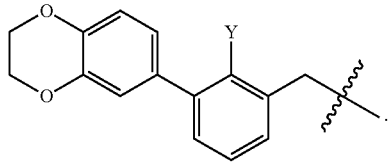

In a second embodiment of the first aspect $R^3$ is

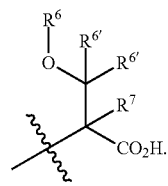

In a third embodiment of the first aspect $R^2$ is

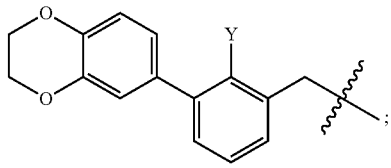

and $R^3$ is

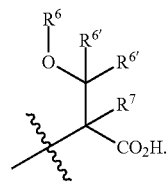

In another aspect the present disclosure provides a compound of formula (I):

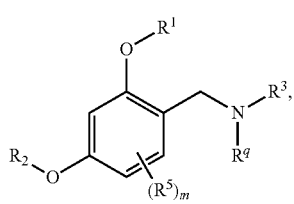

or a pharmaceutically acceptable salt thereof, wherein:

m is 0, 1, or 2;

$R^1$ is selected from hydrogen, —$(CH_2)_nX$ and —$(CH_2)_n$Ar; wherein n is 1, 2, 3, or 4;

X is selected from —$CH_3$, —$CF_3$, CN, —$CO_2R^4$, —$C(O)NH_2$, $OR^4$, and pyrrolidonyl;

$R^4$ is H or $C_1$-$C_3$alkyl;

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonylamino, $C_1$-$C_4$alkyl, ($C_1$-$C_4$alkyl)carbonyl, ($C_1$-$C_4$alkyl)sulfonyl, amido, aminocarbonyl, aminocarbonyl($C_1$-$C_3$alkyl), —$(CH_2)_qCO_2C_1$-$C_4$alkyl, —$(CH_2)_q$OH, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;

$R^2$ is selected from

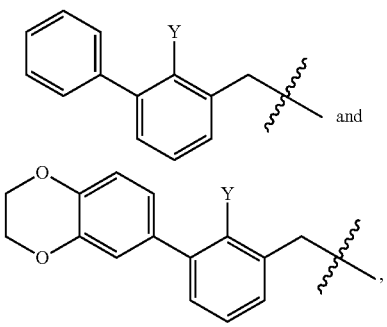

and

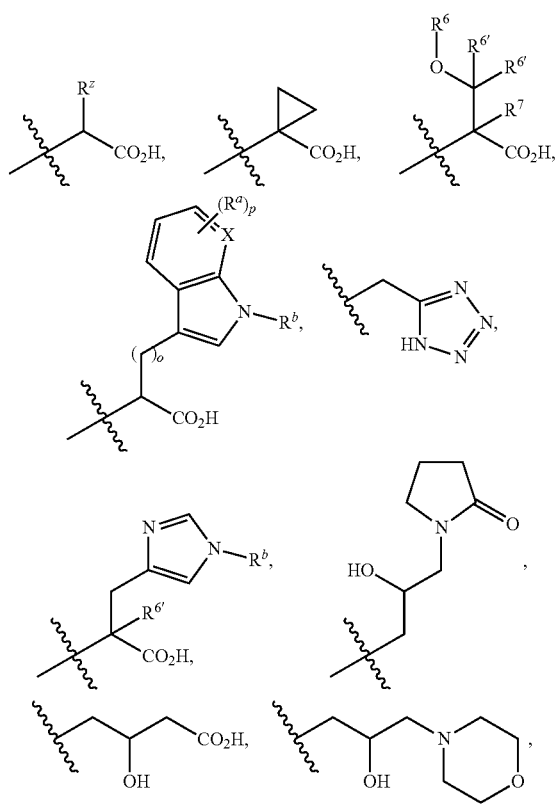

wherein Y is selected from cyano, chloro, and methyl;

$R^q$ is selected from hydrogen, $C_1$-$C_3$alkyl, and benzyl;

$R^3$ is selected from

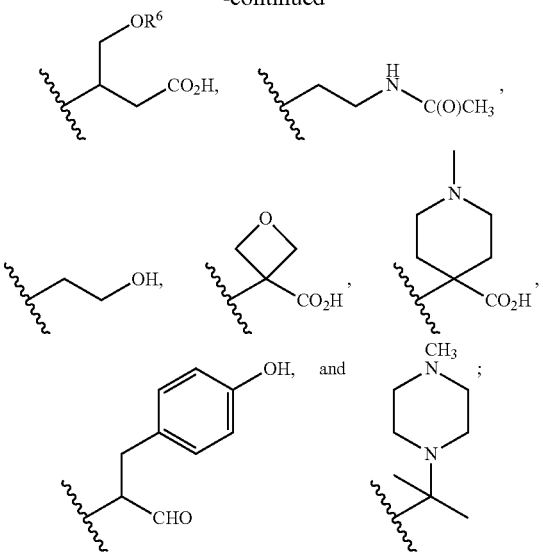

wherein $R^z$ is selected from $C_1$-$C_3$alkyl, $C_1$-$C_3$alkylsulfonyl$C_1$-$C_3$alkyl, $C_1$-$C_3$alkylsulfoxyl$C_1$-$C_3$alkyl, amido$C_1$-$C_3$alkyl, amino$C_1$-$C_3$alkyl, carboxy$C_1$-$C_3$alkyl, cyano$C_1$-$C_3$alkyl, dimethylamido$C_1$-$C_3$alkyl, dimethylamino$C_1$-$C_3$alkyl, halo$C_1$-$C_3$alkyl, hydroxy$C_1$-$C_3$alkyl, $C_1$-$C_3$alkylsulfanyl$C_1$-$C_3$alkyl, pyridinyl$C_1$-$C_3$alkyl, tetrazolyl$C_1$-$C_3$alkyl, imidazolyl$C_1$-$C_3$alkyl wherein the imidazole is optionally substituted with methyl or a benzyl group, phenyl$C_1$-$C_3$alkyl wherein the phenyl is optionally substituted with cyano, methyl, or hydroxy, thiazolyl$C_1$-$C_3$alkyl;

$R^6$ is selected from hydrogen, benzyl, and methyl;

each $R^{6'}$ is independently selected from hydrogen and methyl;

$R^7$ is selected from hydrogen, $C_1$-$C_3$alkyl, and benzyl;

o is 1 or 2;

X is CH or N;

p is 0 or 1;

$R^a$ is hydroxy; and $R^b$ is selected from hydrogen, benzyl, and methyl; or $R^3$ and $R^q$, together with the nitrogen atom to which they are attached, form a ring selected from

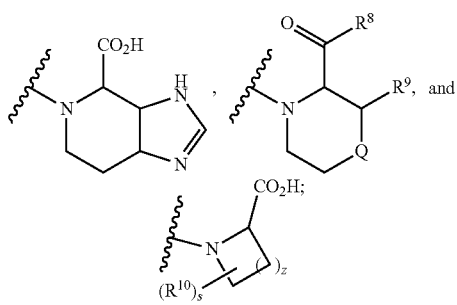

s is 0 or 1;

z is 1 or 2; and $R^8$ is selected from hydroxy and —$NHSO_2R^{11}$;

$R^9$ is selected from hydrogen and —$CO_2H$;

$R^{10}$ is selected from halo and hydroxy;

$R^{11}$ is selected from trifluoromethyl, cyclopropyl, $C_1$-$C_3$alkyl, dimethylamino, and imidazolyl substituted with a methyl group;

Q is selected from $CH_2$, S, O, and $NCH_3$; and $R^5$ is selected from $C_2$-$C_4$alkenyl, $C_1$-$C_4$alkyl, cyano, methoxy, halo, and In a second aspect the present disclosure provides a pharmaceutical composition comprising a compound of formula (I), or a pharmaceutically acceptable salt thereof, and a pharmaceutically acceptable carrier.

In a third aspect the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the third aspect the method further comprises administering an additional agent prior to, after, or simultaneously with the compound of formula (I), or the pharmaceutically acceptable salt thereof. In a second embodiment of the third aspect the additional agent is an antimicrobial agent, an antiviral agent, an agent that modifies gene expression, a cytotoxic agent, and/or an immune response modifier.

In a fourth aspect the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment of the fourth aspect the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a fifth aspect the present disclosure provides a method of treating an infectious disease in a subject in need thereof, the method comprising administering to the subject a therapeutically effective amount of a compound of formula (I), or a pharmaceutically acceptable salt thereof. In a first embodiment of the fifth aspect the infectious disease is caused by a virus. In a second embodiment of the fifth aspect the virus is selected from HIV, Hepatitis A, Hepatitis B, Hepatitis C, Hepatitis D, herpes viruses, papillomaviruses and influenza.

In a sixth aspect the present disclosure provides a method of treating septic shock in a subject in need thereof, the method comprising administering to the subject a therapeutically effective amount of a compound of formula (I), or a pharmaceutically acceptable salt thereof.

In a seventh aspect the present disclosure provides a method blocking the interaction of PD-L1 with PD-1 and/or CD80 in a subject, said method comprising administering to the subject a therapeutically effective amount of a compound of formula (I), or a pharmaceutically acceptable salt thereof. The features and advantages of the disclosure may be more readily understood by those of ordinary skill in the art upon reading the following detailed description. It is to be appreciated that certain features of the disclosure that are, for clarity reasons, described above and below in the context of separate embodiments, may also be combined to form a single embodiment. Conversely, various features of the disclosure that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_1$-$C_4$alkoxy," as used herein, refers to a $C_1$-$C_4$alkyl group attached to the parent molecular moiety through an oxygen atom.

The term "$C_1$-$C_4$alkoxycarbonyl," as used herein, refers to a $C_1$-$C_4$alkoxy group attached to the parent molecular moiety through a carbonyl group.

The term "$C_1$-$C_4$alkoxycarbonylamino," as used herein, refers to a $C_1$-$C_4$alkoxycarbonyl group attached to the parent molecular moiety through an —NH group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_4$alkylcarbonyl," as used herein, refers to a $C_1$-$C_4$alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl attached to the parent molecular moiety through a $C_1$-$C_3$alkyl group.

The term "$C_1$-$C_3$alkylsulfonyl," as used herein, refers to a $C_1$-$C_4$alkyl group attached to the parent molecular moiety through a sulfonyl group.

The term "$C_1$-$C_4$alkylsulfonyl," as used herein, refers to a $C_1$-$C_4$alkyl group attached to the parent molecular moiety through a sulfonyl group.

The term "$C_1$-$C_3$alkylsulfonyl$C_1$-$C_3$alkyl," as used herein, refers to a $C_1$-$C_3$alkylsulfonyl group attached to the parent molecular moiety through a $C_1$-$C_3$alkyl group.

The term "$C_1$-$C_3$alkylsulfoxyl," as used herein, refers to a $C_1$-$C_3$alkyl group attached to the parent molecular moiety through a sulfoxyl group.

The term "$C_1$-$C_3$alkylsulfoxyl$C_1$-$C_3$alkyl," as used herein, refers to a $C_1$-$C_3$alkylsulfoxyl group attached to the parent molecular moiety through a $C_1$-$C_3$alkyl group.

The term "amido," as used herein, refers to —C(O)NH$_2$.

The term "amidoC$_1$-C$_3$alkyl," as used herein, refers to an amido group attached to the parent molecular moiety through a C$_1$-C$_3$alkyl group.

The term "aminoC$_1$-C$_3$alkyl," as used herein, refers to an amino group attached to the parent molecular moiety through a C$_1$-C$_3$alkyl group.

The term "aminocarbonyl," as used herein, refers to an amino group attached to the parent molecular moiety through a carbonyl group.

The term "aminocarbonyl(C$_1$-C$_3$alkyl)," as used herein, refers to an aminocarbonyl group attached to the parent molecular moiety through a C$_1$-C$_3$alkyl group.

The term "carbonyl," as used herein, refers to —C(O)—.

The term "carboxy," as used herein, refers to —CO$_2$H.

The term "carboxyC$_1$-C$_3$alkyl," as used herein, refers to a carboxy group attached to the parent molecular moiety through a C$_1$-C$_3$alkyl group.

The term "cyano," as used herein, refers to —CN.

The term "cyanoC$_1$-C$_3$alkyl," as used herein, refers to a cyano group attached to the parent molecular moiety through a C$_1$-C$_3$alkyl group.

The term "dimethylamido," as used herein, refers to —C(O)N(CH$_3$)$_2$.

The term "dimethylamidoC$_1$-C$_3$alkyl," as used herein, refers to a dimethylamido group attached to the parent molecular moiety through a C$_1$-C$_3$alkyl group.

The term "dimethylamino," as used herein, refers to —N(CH$_3$)$_2$.

The term "dimethylaminoC$_1$-C$_3$alkyl," as used herein, refers to a dimethylamino group attached to the parent molecular moiety through a C$_1$-C$_3$alkyl group.

The term "formyl," as used herein, refers to —C(O)H.

The terms "halo" and "halogen," as used herein, refer to F, Cl, Br, or I.

The term "haloC$_1$-C$_3$alkyl," as used herein, refers to a C$_1$-C$_3$alkyl group substituted with one, two, or three halogen atoms.

The term "haloC$_1$-C$_4$alkyl," as used herein, refers to a C$_1$-C$_4$alkyl group substituted with one, two, or three halogen atoms.

The term "haloC$_1$-C$_4$alkoxy," as used herein, refers to a haloC$_1$-C$_4$alkyl group attached to the parent molecular moiety through an oxygen atom.

The term "hydroxy," as used herein, refers to —OH.

The term "hydroxyC$_1$-C$_3$alkyl," as used herein, refers to a hydroxy group attached to the parent molecular moiety through a C$_1$-C$_3$alkyl group.

The term "imidazolylC$_1$-C$_3$alkyl," as used herein, refers to an imidazolyl group attached to the parent molecular moiety through a C$_1$-C$_3$alkyl group.

The term "nitro," as used herein, refers to —NO$_2$.

The term "phenylC$_1$-C$_3$alkyl," as used herein, refers to a phenyl group attached to the parent molecular moiety through a C$_1$-C$_3$alkyl group.

The term "phenylcarbonyl," as used herein, refers to a phenyl group attached to the parent molecular moiety through a carbonyl group.

The tem "phenyloxy," as used herein, refers to a phenyl group attached to the parent molecular moiety through an oxygen atom.

The term "pyridinylC$_1$-C$_3$alkyl," as used herein, refers to a pyridinyl ring attached to the parent molecular moiety through a C$_1$-C$_3$alkyl group.

The term "sulfonyl," as used herein, refers to —SO$_2$—.

The term "sulfoxyl," as used herein, refers to —SO—.

The term "tetrazolylC$_1$-C$_3$alkyl," as used herein, refers to a tetrazolyl ring attached to the parent molecular moiety through a C$_1$-C$_3$alkyl group.

The term "thiazolylC$_1$-C$_3$alkyl," as used herein, refers to a thiazolyl group attached to the parent molecular moiety through a C$_1$-C$_3$alkyl group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as HIV or hepatitis B, hepatitis C, and hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and *acacia*; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) Int. Immunol. 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF. In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) Nature 393: 474-478) and can be used in conjunction with PD-L1 blockade (Ito, N. et al. (2000) Immunobiology 201 (5) 527-40). Activating compounds to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, Giardia, Malaria, Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*. In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) Proc. Natl. Acad. Sci. U.S.A. 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) J. Immunother Emphasis Tumor Immunol 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of formula (I) inhibit the PD-1/PD-L1 interaction with $IC_{50}$ values of 20 µM or less, for example, from 0.006 to 20 µM, as measured by the PD-1/PD-L1 Homogenous Time-Resolved Fluorescence (HTRF) binding assay. Preferably, the compounds of formula (I) inhibit the PD-1/PD-L1 interaction with $IC_{50}$ values from 0.006 to 100 nM.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

As used in the present specification, the following terms have the meanings indicated: TFA for trifluoroacetic acid, ACN for acetonitrile, min for minutes, RT for room temperature or retention time (context will dictate), DMAP for 4-N,N-dimethylaminopyridine; EDC for 1-ethyl-3-(3-dimethylaminopropyl)carbodiimide, DMF for N,N-dimethylformamide, h or hr for hrs; EtOAc for ethyl acetate; THF for tetrahydrofuran; EtOH for ethanol; Me for methyl; DMSO for dimethylsulfoxide; AcOH for acetic acid; and HATU for (1-[bis(dimethylamino)methylene]-1H-1,2,3-triazolo[4,5-b]pyridinium 3-oxid hexafluorophosphate).

Analytical LCMS injections were typically chosen from among the following methods to determine the final purity of intermediates and examples.

Conditions A: Acetonitrile conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Conditions M: Methanol conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Conditions T: TFA method: Column: Phenomenex LUNA C18, 2.0×50 mm 3 um, Start % B=0, Final % B=100, Gradient Time=4 min, Flow Rate=8 mL/min, Wavelength=220, Solvent Pair=Water-Methanol-0.1% TFA, Solvent A=90% Water-10% Methanol-0.1% TFA, Solvent B=10% Water-90% Methanol-0.1% TFA.

Conditions AA: Ammonium acetate method Column: Phenomenex LUNA C18, 2.0×50 mm, 3u, Start % B=0, Final % B=100, Gradient Time=4 min, Flow Rate=0.8 mL/min, Wavelength=220, Solvent Pair=ACN: Water Ammonium Actetate, Solvent A=5% ACN: 95% Water: 10 mM Ammonium Actetate Solvent B=95% ACN: 5% Water: 10 mM Ammonium Actetate.

Intermediate (3-bromo-2-methylphenyl)methanol

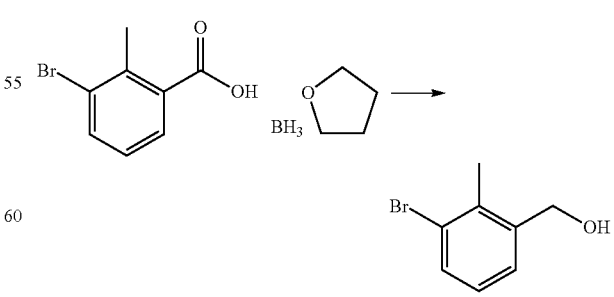

(See also Gao, Shuanhu; Wang, Qiaoling; Chen, Chuo *J. Am. Chem. Soc.* 2009, 131(4), 1410-1412 supplementary material page S15.)

Dissolved 3-bromo-2-methylbenzoic acid (8.4 g, 39.1 mmol) in tetrahydrofuran (100 mL) and cooled on ice/water. Added borane tetrahydrofuran complex (50.8 mL, 50.8 mmol) dropwise over 15-20 minutes. Stirred to room temperature over the weekend. Added 50 mL methanol dropwise to quench the excess borane. The solvent was removed by rotory evaporation. The solid was rotovaped from methanol to remove residual boron. 7.8 g of a pale yellow solid was isolated and used without further purification. $^1$H NMR (400 MHz, CHLOROFORM-d) δ 7.53 (dd, J=7.9, 0.9 Hz, 1H), 7.34 (d, J=7.3 Hz, 1H), 7.08 (t, J=7.8 Hz, 1H), 4.75 (s, 2H), 2.45 (s, 3H).

Intermediate (2-methylbiphenyl-3-yl)methanol

A mixture of (3-bromo-2-methylphenyl)methanol (2.071 g, 10.3 mmol), phenylboronic acid (2.51 g, 20.60 mmol) and [1,1'-bis(diphenylphosphino)ferrocene]dichloropalladium (II) dichloromethane complex (0.084 g, 0.103 mmol) in toluene (15.45 mL) and ethanol (5.15 mL) was placed under argon. To this solution was added sodium bicarbonate, 2M (15.45 mL, 30.9 mmol) and the mixture was heated at 80° C. for 30 minutes. The reaction mixture was diluted with 20 mL ethyl acetate and 5 mL water. The organic portion was concentrated by rotatory evaporation. The crude product was chromatographed on silica gel eluting with 0-40% ethyl acetate in hexane to afford 2 g of an off-white solid. $^1$H NMR (400 MHz, CHLOROFORM-d) δ 7.47-7.29 (m, 7H), 7.23 (s, 1H), 4.80 (d, J=5.6 Hz, 2H), 2.27 (s, 3H), 1.63-1.59 (m, 1H).

Intermediate (3-(2,3-dihydrobenzo[b][1,4]dioxin-6-yl)-2-methylphenyl)methanol

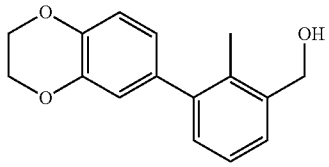 [SMILES: Cc1c(CO)cccc1-c1ccc2c(c1)OCCO2]

Tetrahydrofuran solvent and aqueous 0.5M potassium tribasic phosphate solutions were sparged with nitrogen for 15 minutes prior to dispensing for use. In a 1 L rb flask charge (2,3-dihydrobenzo[b][1,4]dioxin-6-yl)boronic acid (5.201 g, 28.9 mmol), (3-bromo-2-methylphenyl)methanol (5.00 g, 24.87 mmol) and chloro(2-dicyclohexylphosphino-2',4',6'-tri-i-propyl-1,1'-biphenyl)(2'-amino-1,1'-biphenyl-2-yl) palladium(II) (also known as second generation XPhos precatalyst, CAS number 1310584-14-5, See Kinzel, Tom; Zhang, Yong; Buchwald, Stephen L. *J. Am. Chem. Soc.* 2010, 132(40), 14073-14075.) (0.588 g, 0.747 mmol), add previously deoxygenated tetrahydrofuran (124 mL) and 0.5 M aq Pottasium phosphate, tribasic solution (124 mL, 62.2 mmol), place under nitrogen and sparge with additional nitrogen for 10 minutes. The reaction was stirred under nitrogen at room temperature for 2 days. Ethyl acetate (300 mL) was added to the reaction followed by 200 mL of brine then the reaction was partitioned in a sepratory funnel. The organic extract was washed again (1×) with brine and dried over magnesium sulfate, filtered and solvent removed in vacuo using a rotary evaporator. The crude reaction product (7.84 g dark oil) was purified by silica gel chromatography eluting with a step gradient of 25% ethyl acetate in hexanes and 30% ethyl acetate in hexanes. The purified product (6.19 g, 95% yield) was obtained as a brown oil. $^1$H NMR (CHLOROFORM-d) δ: 7.37 (dd, J=7.4, 1.1 Hz, 1H), 7.21-7.26 (m, 1H), 7.17-7.21 (m, 1H), 6.91 (d, J=8.2 Hz, 1H), 6.82 (d, J=2.0 Hz, 1H), 6.77 (dd, J=8.3, 2.1 Hz, 1H), 4.77 (s, 2H), 4.31 (s, 4H), 2.27 (s, 3H).

Intermediate (2-chloro-3-(2,3-dihydrobenzo[b][1,4]dioxin-6-yl)phenyl)methanol

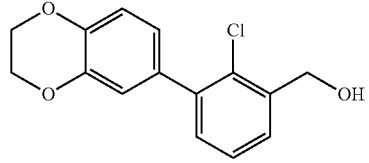 [SMILES: OCc1cccc(-c2ccc3c(c2)OCCO3)c1Cl]

The title compound was prepared in 70% yield from (3-bromo-2-chlorophenyl)methanol in a manner similar to (3-(2,3-dihydrobenzo[b][1,4]dioxin-6-yl)-2-methylphenyl)methanol. $^1$H NMR (400 MHz, CHLOROFORM-d) δ 7.49 (dd, J=7.3, 1.2 Hz, 1H), 7.36-7.22 (m, 2H), 7.00-6.86 (m, 3H), 4.84 (br. s., 2H), 4.31 (s, 4H), 2.74 (t, J=6.0 Hz, 1H).

Intermediate ethyl 2-amino-3-chlorobenzoate

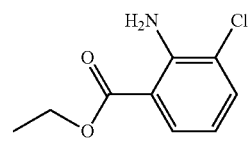

Ethanol (180 mL) and 2-amino-3-chlorobenzoic acid (12.0 g, 69.9 mmol) were stirred in a 500 mL round bottom flask until a clear solution was obtained. Sulfuric acid (17.5 mL, 328 mmol) was added drop wise over 15 min. After addition, the reaction was heated at reflux for 48 hours. The reaction was quenched in ice and neutralized with saturated aqueous sodium bicarbonate solution and extracted with ethyl acetate (3×500 mL). The combined organic portions were washed with brine (1×200 mL), dried over sodium sulfate and the solvent removed under vacuum. A brown residue was obtained. The residue was dissolved in ethyl acetate (200 mL) and washed with saturated sodium bicarbonate solution (2×100 mL), water (1×100 mL), brine (1×50 mL), dried over sodium sulfate and the solvent removed under vacuum. 12.5 g of a brown solid was obtained and used in the next step without further purification. ¹H NMR (400 MHz, CHLOROFORM-d) δ 7.83 (dd, J=8.0, 1.2 Hz, 1H), 7.40 (dd, J=8.0, 1.2 Hz, 1H), 6.6 (t, J=8.0 Hz, 1H), 4.34 (q, J=7.2 Hz, 2H), 1.39 (t, J=7.2 Hz, 3H).

Intermediate ethyl 3-chloro-2-cyanobenzoate

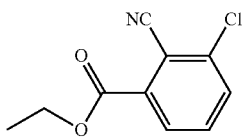

Ethyl 2-amino-3-chlorobenzoate (1.0 g, 5.01 mmol) and water (12 mL) were combined in a 100 mL round bottom flaske and cooled to 0° C. Hydrochloric acid (3.0 mL, 99 mmol) was added. A solution of sodium nitrite (0.86 g, 12.46 mmol) in water (12 mL) was added drop wise over 15 minutes. After addition was complete, the reaction was stirred at 0° C. for 1 hour. After 1 hour, the reaction containing the diazonium species was neutralized with saturated aqueous sodium carbonate solution and kept at 0° C. for cyanation. Separately, water (12 mL) and copper(II) sulfate pentahydrate (1.5 g, 6.01 mmol) were stirred together in a 250 mL round bottom flaske to give a blue solution. Toluene (12 mL) was added and the mixture was cooled to 0° C. Potassium cyanide (1.46 g, 22.42 mmol) was added and the color changed to brown. This brown mixture was heated to 60° C. Added, the above prepared diazonium salt through an addition funnel slowly over 15 minutes. The diazonium salt temperature maintained at 0° C. After addition the reaction temperature was maintained at 70° C. for 1 hour. The reaction was diluted with ethyl acetate (100 mL) and filtered through a celite bed and the bed was washed with ethyl acetate (2×50 mL). The aqueous layer was extracted with ethyl acetate (1×100 mL). The combined organic portions were washed with water (1×25 mL), brine solution (1×25 mL) and dried over sodium sulfate. The solvent was removed under vacuum to give a brown solid. The crude material was purified on a 24 g silica gel column using petroleum ether:ethyl acetate as eluent. The product eluted at 10% ethyl acetate. The collected fractions were evaporated to give the title compound (0.7 g, 66%) as pale orange solid. ¹H NMR (400 MHz, CHLOROFORM-d) δ 8.03 (dd, J=8.0, 1.2 Hz, 1H), 7.71 (dd, J=8.0, 1.2 Hz, 1H), 7.71 (t, J=8.0 Hz, 1H), 4.80 (q, J=7.2 Hz, 2H), 1.47 (t, J=7.2 Hz, 3H).

Intermediate ethyl 3-chloro-2-cyanobenzoic acid

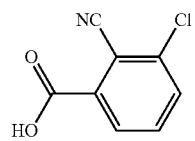 [SMILES: N#Cc1c(Cl)cccc1C(=O)O]

Lithium hydroxide hydrate (0.925 g, 22.04 mmol) was added to a suspension of ethyl 3-chloro-2-cyanobenzoate (3.85 g, 18.37 mmol) in 1,4-Dioxane (40 mL) and water (40 mL). A clear solution was obtained. Stirred for 5 hours. TLC with 6:4 petroleum ether:ethyl acetate showed no remaining starting material. The solvent was evaporated under vacuum and the residue was dissolved in 50 mL of water. The pH of the aqueous layer was adjusted to 1 using 1.5N hydrochloric acid. A white solid precipitated. Stirred for 15 minutes, collected the white solid by filtration and washed with 25 mL water. Dried overnight under vacuum. The off-white solid was azeotroped with 20 mL toluene two times to remove moisture and give the product as an off-white solid (3.3 g, 98%). ¹H NMR (400 MHz, CHLOROFORM-d) δ 8.11 (dd, J=8.0, 1.2 Hz, 1H), 7.78 (dd, J=8.0, 1.2 Hz, 1H), 7.65 (t, J=8.0 Hz, 1H).

Intermediate 2-chloro-6-(hydroxymethyl)benzonitrile

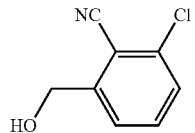 [SMILES: N#Cc1c(Cl)cccc1CO]

To a solution of 3-chloro-2-cyanobenzoic acid (500 mg, 2.75 mmol) in tetrahydrofuran (15 mL) at 0° C. was added borane tetrahydrofuran complex (2.75 mL, 5.51 mmol). Stirred for 5 hours. The reaction was monitored by HPLC and showed 39% product and 58% starting material. Borane tetrahydrofuran complex (2.75 mL, 5.51 mmol) was added and the reaction stirred for 3 hours. HPLC monitoring showed 71% product and 6% starting material. Stirred overnight. The reaction was cooled to −5° C. and slowly quenched with 5 mL methanol, stirred for 10 minutes at −5° C. and 10 minutes at room temperature. The solvent was evaporated. The crude residue showed partial nitrile reduction by LCMS. Chromatographed on a silica gel column using petroleum ether and acetone as eluent. The product was eluted at 8% acetone in petroleum ether. The collected fractions were evaporated to produce an off-white solid (0.2 g, 42%). ¹H NMR (400 MHz, CHLOROFORM-d) δ: 7.61 (t, J=9.8 Hz, 1H), 7.50 (dd, J=9.8, 1.0 Hz, 1H), 7.40 (dd, J=9.8, 1.0 Hz, 1H), 4.89 (s, 2H), 3.0 (bs, 1H).

Intermediate 2-(2,3-dihydrobenzo[b][1,4]dioxin-6-yl)-6-(hydroxymethyl)benzonitrile

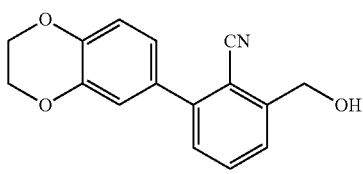 [SMILES: N#Cc1c(CO)cccc1-c1ccc2c(c1)OCCO2]

The title compound was prepared in 60% yield from 2-chloro-6-(hydroxymethyl)benzonitrile in a manner similar to (3-(2,3-dihydrobenzo[b][1,4]dioxin-6-yl)-2-methylphenyl)methanol. $^1$H NMR (400 MHz, CHLOROFORM-d) δ 7.49 (dd, J=7.3, 1.2 Hz, 1H), 7.36-7.22 (m, 2H), 7.00-6.86 (m, 3H), 4.84 (br. s., 2H), 4.31 (s, 4H), 2.74 (t, J=6.0 Hz, 1H).

Intermediate 4-(3-(2,3-dihydrobenzo[b][1,4]dioxin-6-yl)-2-methylbenzyloxy)-2-hydroxy-6-methylbenzaldehyde

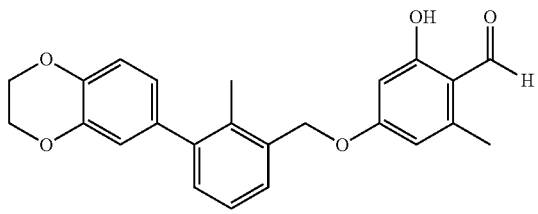 [SMILES: Cc1cc(OCc2cccc(-c3ccc4c(c3)OCCO4)c2C)cc(O)c1C=O]

Combined 2,4-dihydroxy-6-methylbenzaldehyde (131 mg, 0.858 mmol), triphenylphosphine (225 mg, 0.858 mmol) and (3-(2,3-dihydrobenzo[b][1,4]dioxin-6-yl)-2-methylphenyl)methanol (200 mg, 0.780 mmol) in dry tetrahydrofuran (6 mL) and cooled to 0° C. Diisopropyl azodicarboxylate (0.167 mL, 0.858 mmol) in tetrahydrofuran (6 mL) was added dropwise. The resulting yellow solution was allowed to slowly warm to room temperature overnight. Solvent was removed by rotary evaporator. The crude was purified with 5:1 hexanes:ethyl acetate on a 24 g silica gel column Collected fractions to afford the desired product (300 mg, 98% yield) as white solid.

Intermediate 3-((5-(3-(2,3-dihydrobenzo[b][1,4]dioxin-6-yl)-2-methylbenzyloxy)-2-formyl-3-methylphenoxy)methyl)benzonitrile

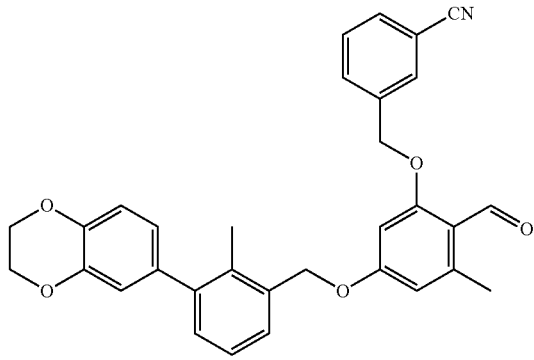 [SMILES: Cc1cc(OCc2cccc(-c3ccc4c(c3)OCCO4)c2C)cc(OCc2cccc(C#N)c2)c1C=O]

Cesium carbonate (167 mg, 0.512 mmol), 4-((3-(2,3-dihydrobenzo[b][1,4]dioxin-6-yl)-2-methylbenzyl)oxy)-2-hydroxy-6-methylbenzaldehyde (100 mg, 0.256 mmol) and 3-(bromomethyl)benzonitrile (100 mg, 0.512 mmol) were stirred in dimethyl formamide at room temperature for 3 hours. The mixture was diluted with ethyl acetate, neutralized with dilute hydrochloric acid (0.1 N) and washed with water and brine. Dried over sodium sulfate. Filtered and removed the solvent by rotary evaporation. The residue was purified with 1:1 to 1:2 hexanes:ethyl acetate on a 24 g silica gel column. Collected fractions to afford a white solid (90 mg, 69.5% yield). $^1$H NMR (CHLOROFORM-D) δ: 10.60 (s, 1H), 7.63-7.77 (m, 3H), 7.49-7.58 (m, 1H), 7.33-7.42 (m, 1H), 7.23-7.32 (m, 2H), 6.93 (d, 1H), 6.85 (d, 1H), 6.79 (m, 1H), 6.53 (s, 1H), 6.48 (d, 1H), 5.15 (d, 4H), 4.33 (s, 4H), 2.61-2.67 (m, 3H), 2.28 (s, 3H).

Example 1000

N-(2-(2-(3-cyanobenzyloxy)-4-(3-(2,3-dihydrobenzo[b][1,4]dioxin-6-yl)-2-methylbenzyloxy)-6-methylbenzylamino)ethyl)acetamide

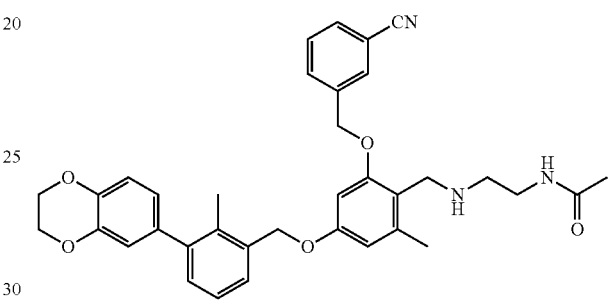

To a dimethyl formamide (1 mL) solution of 3-((5-((3-(2,3-dihydrobenzo[b][1,4]dioxin-6-yl)-2-methylbenzyl)oxy)-2-formyl-3-methylphenoxy)methyl)benzonitrile (19 mg, 0.038 mmol) was added N-(2-aminoethyl)acetamide (11.52 mg, 0.113 mmol) and the reaction was stirred for 2 hours at room temperature. Sodium cyanoborohydride (7.09 mg, 0.113 mmol) and Acetic acid (2.151 μl, 0.038 mmol) were added and the reaction was stirred at room temperature overnight. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min Fractions containing the desired product were combined and dried via centrifugal evaporation. The yield of the product was 13.6 mg, and its estimated purity by LCMS analysis was 100%. LCMS Condition A: 2.07 minutes, M+1=592.3. $^1$H NMR (DMSO-$d_6$) δ 7.90-7.98 (m, 1H), 7.76-7.84 (m, 3H), 7.60-7.65 (m, 1H), 7.40 (d, 1H), 7.23 (m, 1H), 7.16 (d, 1H), 6.93 (d, 1H), 6.71-6.81 (m, 2H), 6.61 (s, 1H), 6.56 (s, 1H), 5.18 (s, 2H), 5.08 (s, 2H), 4.29 (s, 4H), 3.69 (m, 2H), 3.12 (m, 2H), 2.57 (m, 2H), 2.32 (s, 3H), 2.20 (s, 3H), 1.76 (s, 3H).

The following examples were prepared by reductive amination in the same manner as N-(2-(2-(3-cyanobenzyloxy)-4-(3-(2,3-dihydrobenzo[b][1,4]dioxin-6-yl)-2-methylbenzyloxy)-6-methylbenzylamino)ethyl)acetamide from 3-((5-(3-(2,3-dihydrobenzo[b][1,4]dioxin-6-yl)-2-methylbenzyloxy)-2-formyl-3-methylphenoxy)methyl)benzonitrile and an appropriate amine.

Example 1001

(R)-2-(2-(3-cyanobenzyloxy)-4-(3-(2,3-dihydrobenzo[b][1,4]dioxin-6-yl)-2-methylbenzyloxy)-6-methylbenzylamino)-3-hydroxy-2-methylpropanoic acid

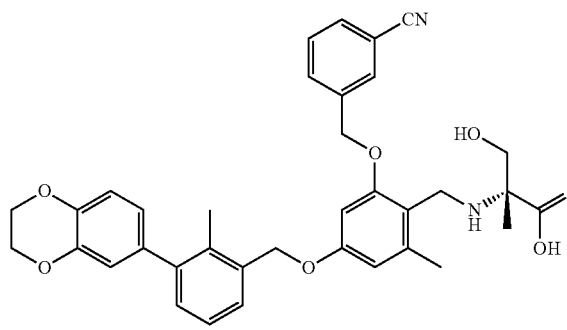

LCMS Condition A: 1.99 minutes, M+1=596.2, M−1=594.3. $^1$H NMR (DMSO-d$_6$) δ 8.02 (s, 1H), 7.93-7.97 (m, 2H), 7.81 (d, 1H), 7.60 (m, 1H), 7.40 (d, 1H), 7.24 (m, 1H), 7.17 (d, 1H), 6.93 (d, 1H), 6.73-6.79 (m, 2H), 6.69 (s, 1H), 6.62 (s, 1H), 5.23 (s, 2H), 5.12 (s, 2H), 4.29 (s, 4H), 4.02 (br. s., 2H), 3.63 (d, 1H), 3.56 (d, 1H), 2.37 (s, 3H), 2.19 (s, 3H), 1.26 (s, 3H).

Example 1002

(R)-2-(2-(3-cyanobenzyloxy)-4-(3-(2,3-dihydrobenzo[b][1,4]dioxin-6-yl)-2-methylbenzyloxy)-6-methylbenzylamino)-3-hydroxypropanoic acid

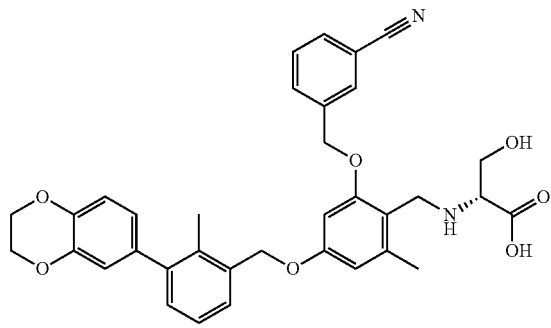 [SMILES: Cc1cc(OCc2cccc(-c3ccc4c(c3)OCCO4)c2C)cc(OCc2cccc(C#N)c2)c1CN[C@H](CO)C(=O)O]

LCMS Condition A: 1.90 minutes, M+1=595.3, M−1=593.2. $^1$H NMR (DMSO-d$_6$) δ 8.01 (s, 1H), 7.92 (d, 1H), 7.80 (d, 1H), 7.60 (m, 1H), 7.39 (d, 1H), 7.23 (m, 1H), 7.16 (d, 1H), 6.92 (d, 1H), 6.72-6.79 (m, 2H), 6.68 (s, 1H), 6.63 (s, 1H), 5.24 (d, 2H), 5.10 (s, 2H), 4.28 (s, 4H), 4.15 (br. s., 2H), 3.83 (d, 1H), 3.58-3.66 (m, 1H), 3.21 (d, 1H), 2.35 (s, 3H), 2.18 (s, 3H).

Example 1003

(S)-4-(2-(3-cyanobenzyloxy)-4-(3-(2,3-dihydrobenzo[b][1,4]dioxin-6-yl)-2-methylbenzyloxy)-6-methylbenzylamino)-3-hydroxybutanoic acid

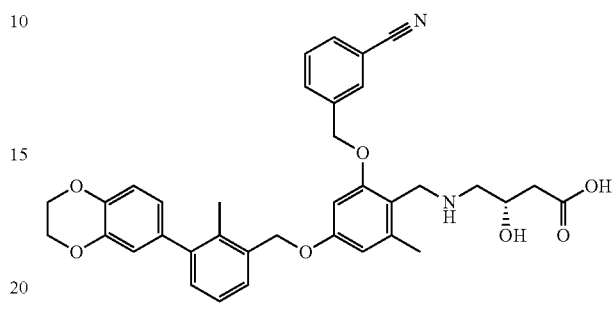

LCMS Condition A: 1.87 minutes, M+1=609.3, M−1=607.2. $^1$H NMR (DMSO-d$_6$) δ 7.96 (s, 1H), 7.80-7.87 (m, 2H), 7.62 (m, 1H), 7.53-7.54 (m, 1H), 7.41 (d, 1H), 7.24 (m, 1H), 7.17 (d, 1H), 6.93 (d, 1H), 6.74-6.79 (m, 2H), 6.64 (s, 1H), 6.59 (s, 1H), 5.19 (s, 2H), 5.10 (s, 2H), 4.29 (s, 4H), 3.89-3.93 (m, 1H), 2.90 (s, 2H), 2.74 (s, 2H), 2.68 (br. s., 2H), 2.37 (br. s., 1H), 2.34 (s, 3H), 2.22-2.31 (m, 1H), 2.20 (s, 3H).

Example 1004

(S)-1-(2-(3-cyanobenzyloxy)-4-(3-(2,3-dihydrobenzo[b][1,4]dioxin-6-yl)-2-methylbenzyloxy)-6-methylbenzyl)piperidine-2-carboxylic acid

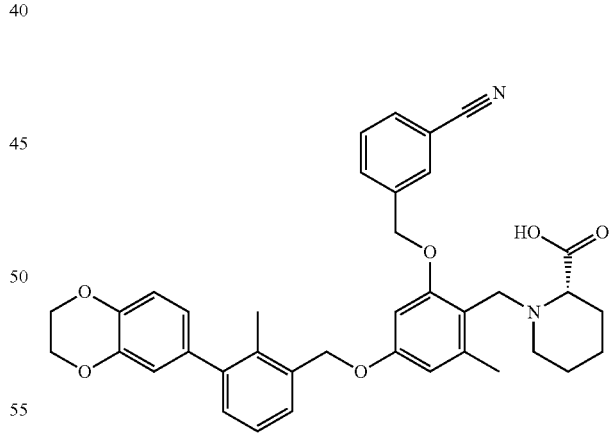

LCMS Condition A: 1.97 minutes, M+1=619.3, M−1=617.3. $^1$H NMR (DMSO-d$_6$) δ 7.96 (s, 3H), 7.86 (d, 1H), 7.81 (d, 1H), 7.62 (m, 1H), 7.40 (d, 1H), 7.24 (m, 1H), 7.17 (d, 1H), 6.93 (d, 1H), 6.74-6.80 (m, 2H), 6.62 (s, 1H), 6.58 (s, 1H), 5.19 (s, 2H), 5.09 (s, 2H), 4.29 (s, 4H), 3.89-3.94 (m, 1H), 3.71 (d, 1H), 3.13 (br. s., 1H), 2.93 (br. s., 1H), 2.90 (s, 2H), 2.74 (s, 2H), 2.37 (s, 3H), 2.20 (s, 3H), 1.76 (br. s., 2H), 1.45 (br. s., 2H).

Intermediate 5-((5-(3-(2,3-dihydrobenzo[b][1,4]dioxin-6-yl)-2-methylbenzyloxy)-2-formyl-3-methylphenoxy)methyl)nicotinonitrile

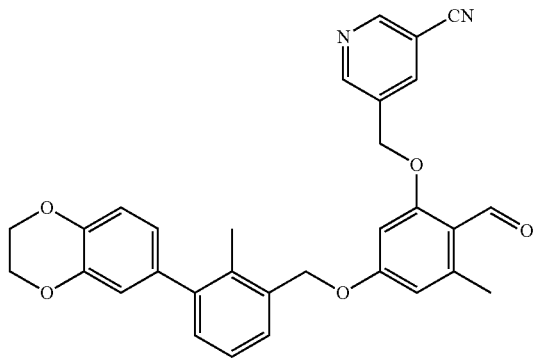 [SMILES: Cc1cc(OCc2cccc(-c3ccc4c(c3)OCCO4)c2C)cc(OCc2cncc(C#N)c2)c1C=O]

Cesium carbonate (125 mg, 0.384 mmol), 4-((3-(2,3-dihydrobenzo[b][1,4]dioxin-6-yl)-2-methylbenzyl)oxy)-2-hydroxy-6-methylbenzaldehyde (100 mg, 0.256 mmol) and 5-(chloromethyl)nicotinonitrile (78 mg, 0.512 mmol) were stirred at 75° C. for 3 hours in dimethyl formamide (1 mL). The reaction was filtered and concentrated. The residue was purified with 1:2 to 2:1 hexane:ethyl acetate on a 24 g silica gel column. Collected fractions to afford a white solid, 113 mg (87% yield). $^1$H NMR (DMSO-d$_6$) δ 10.45 (s, 1H), 9.00 (d, 1H), 9.03 (d, 1H), 8.51 (s, 1H), 7.44 (d, 1H), 7.26 (m, 1H), 7.19 (d, 1H), 6.93 (d, 1H), 6.85 (s, 1H), 6.75-6.80 (m, 2H), 6.68 (s, 1H), 5.37 (s, 2H), 5.25 (s, 2H), 4.29 (s, 4H), 2.51 (s, 3H), 2.22 (s, 3H).

The following examples were prepared by reductive amination in the same manner as N-(2-(2-(3-cyanobenzyloxy)-4-(3-(2,3-dihydrobenzo[b][1,4]dioxin-6-yl)-2-methylbenzyloxy)-6-methylbenzylamino)ethyl)acetamide from 5-((5-(3-(2,3-dihydrobenzo[b][1,4]dioxin-6-yl)-2-methylbenzyloxy)-2-formyl-3-methylphenoxy)methyl)nicotinonitrile and an appropriate amine.

Example 1005

N-(2-(2-((5-cyanopyridin-3-yl)methoxy)-4-(3-(2,3-dihydrobenzo[b][1,4]dioxin-6-yl)-2-methylbenzyloxy)-6-methylbenzylamino)ethyl)acetamide

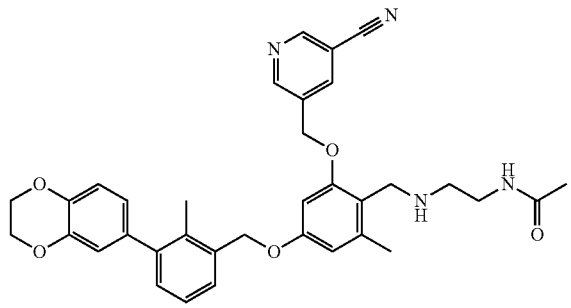 [SMILES: CC(=O)NCCNCc1c(C)cc(OCc2cccc(-c3ccc4c(c3)OCCO4)c2C)cc1OCc1cncc(C#N)c1]

LCMS Condition A: 1.77 minutes, M+1=593.4, M−1=591.3. $^1$H NMR (DMSO-d$_6$) δ 8.98 (s, 1H), 9.00 (s, 1H), 8.42 (s, 1H), 7.41 (d, 1H), 7.24 (s, 1H), 7.17 (s, 1H), 6.93 (d, 1H), 6.74-6.80 (m, 2H), 6.65 (s, 1H), 6.58 (s, 1H), 5.23 (s, 2H), 5.09 (s, 2H), 4.29 (s, 4H), 3.12 (d, 2H), 2.90 (s, 1H), 2.74 (s, 1H), 2.56 (m, 2H), 2.33 (s, 3H), 2.20 (s, 3H), 1.76 (s, 3H).

Example 1006

(S)-4-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxybutanoic acid

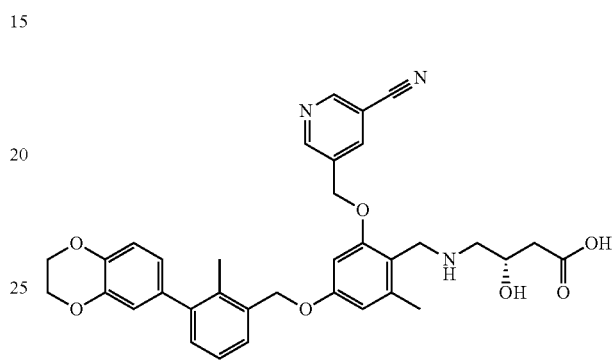

LCMS Condition A: 1.68 minutes, M+1=610.3, M−1=608.3. $^1$H NMR (DMSO-d$_6$) δ 9.00 (br. s., 2H), 8.45 (s, 1H), 7.41 (d, 1H), 7.24 (m, 1H), 7.17 (d, 1H), 6.93 (d, 1H), 6.74-6.79 (m, 2H), 6.68 (s, 1H), 6.61 (s, 1H), 5.24 (s, 2H), 5.11 (s, 2H), 4.29 (s, 4H), 3.86-3.94 (m, 2H), 3.79-3.86 (m, 2H), 2.69 (br. s., 2H), 2.38 (d, 1H), 2.35 (s, 3H), 2.27 (m, 1H), 2.20 (s, 3H).

Example 1007

(R)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxypropanoic acid

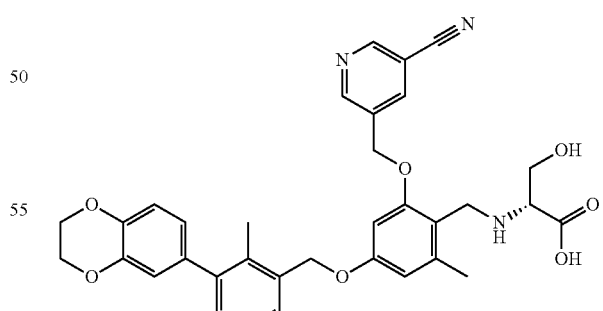

LCMS Condition A: 1.67 minutes, M+1=596.3, M−1=594.3. $^1$H NMR (DMSO-d$_6$) δ 9.04 (s, 1H), 9.01 (d, 1H), 8.53 (s, 1H), 7.41 (d, 1H), 7.24 (m, 1H), 7.17 (d, 1H), 6.93 (d, 1H), 6.72-6.80 (m, 3H), 6.65 (s, 1H), 5.20-5.35 (m, 2H), 5.13 (s, 2H), 4.29 (s, 4H), 4.06-4.16 (m, 2H), 3.78 (m, 1H), 3.59 (m, 1H), 3.16 (m, 1H), 2.36 (s, 3H), 2.20 (s, 3H).

Example 1008

(R)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxy-2-methyl-propanoic acid

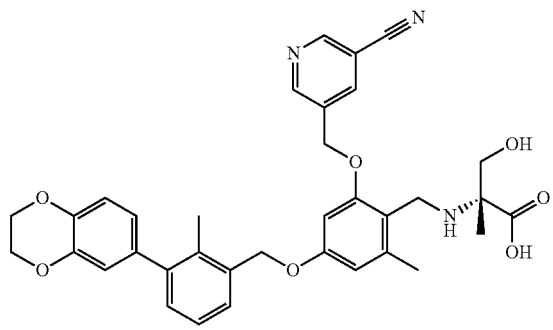 [SMILES: Cc1cc(OCc2cccc(-c3ccc4c(c3)OCCO4)c2C)cc(OCc2cncc(C#N)c2)c1CN[C@](C)(CO)C(=O)O]

LCMS Condition A: 1.73 minutes, M+1=610.3, M−1=608.3. $^1$H NMR (DMSO-d$_6$) δ 9.02 (s, 1H), 8.98 (s, 1H), 8.50 (s, 1H), 7.39 (d, 1H), 7.23 (m, 1H), 7.16 (d, 1H), 6.93 (d, 1H), 6.70-6.78 (m, 3H), 6.65 (s, 1H), 5.24-5.30 (m, 2H), 5.13 (s, 2H), 4.27 (s, 4H), 4.03-4.18 (m, 2H), 3.69 (d, 1H), 3.62 (br. s., 1H), 2.38 (s, 3H), 2.19 (s, 3H), 1.29 (s, 3H).

Example 1009

(S)-1-(2-((5-cyanopyridin-3-yl)methoxy)-4-(3-(2,3-dihydrobenzo[b][1,4]dioxin-6-yl)-2-methylbenzyloxy)-6-methylbenzyl)piperidine-2-carboxylic acid

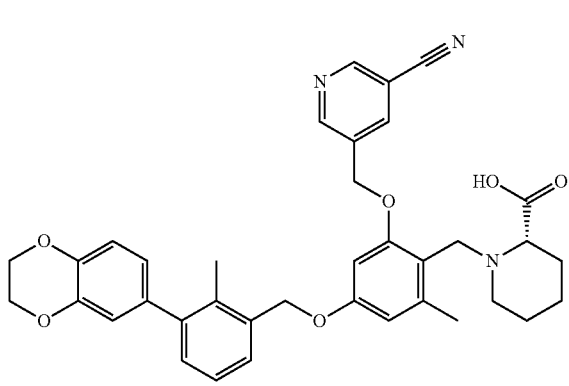 [SMILES: Cc1cc(OCc2cccc(-c3ccc4c(c3)OCCO4)c2C)cc(OCc2cncc(C#N)c2)c1CN1CCCC[C@H]1C(=O)O]

LCMS Condition A: 1.79 minutes, M+1=620.2, M−1=618.2. $^1$H NMR (DMSO-d$_6$) δ 9.01 (br. s., 2H), 8.45 (s, 1H), 7.96 (s, 1H), 7.41 (d, 1H), 7.24 (m, 1H), 7.17 (d, 1H), 6.93 (d, 1H), 6.74-6.80 (m, 2H), 6.67 (s, 1H), 6.60 (s, 1H), 5.21-5.26 (m, 2H), 5.10 (s, 2H), 4.29 (s, 4H), 3.93 (d, 1H), 3.74 (d, 1H), 3.13-3.17 (m, 1H), 2.90 (s, 2H), 2.74 (s, 2H), 2.37 (s, 3H), 2.20 (s, 3H), 1.76 (br. s., 2H), 1.46 (br. s., 2H).

Example 1010

(S)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxy-2-methyl-propanoic acid

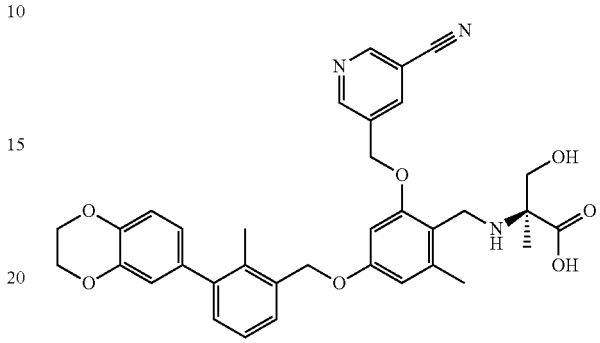

LCMS Condition A: 1.71 minutes, M+1=610.3, M−1=608.3. $^1$H NMR (DMSO-d$_6$) δ 9.04 (s, 1H), 8.99 (s, 1H), 8.52 (s, 1H), 7.40 (d, 1H), 7.21-7.26 (m, 1H), 7.17 (d, 1H), 6.93 (d, 1H), 6.72-6.79 (m, 3H), 6.65 (s, 1H), 5.27 (s, 2H), 5.14 (s, 2H), 4.28 (s, 4H), 4.10 (d, 2H), 3.67 (d, 1H), 3.59 (d, 1H), 2.38 (s, 3H), 2.19 (s, 3H), 1.28 (s, 3H).

Intermediate 2-hydroxy-4-((2-methyl-[1,1'-biphenyl]-3-yl)methoxy)benzaldehyde

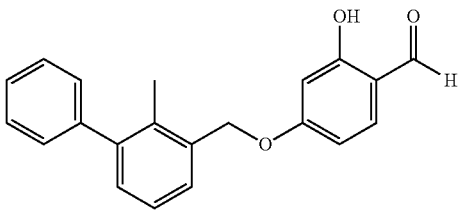 [SMILES: Cc1c(COc2ccc(C=O)c(O)c2)cccc1-c1ccccc1]

Combined 2,4-dihydroxybenzaldehyde (3.14 g, 22.75 mmol), triphenylphosphine (5.97 g, 22.75 mmol) and (2-methyl-[1,1'-biphenyl]-3-yl)methanol (4.1 g, 20.68 mmol) in dry tetrahydrofuran (50 mL) and cooled on an ice/water bath. Added diisopropyl azodicarboxylate (4.33 mL, 22.25 mmol) in tetrahydrofuran (50 mL) dropwise. The resulting yellow solution was allowed to slowly warm to room temperature with stirring overnight. Excess solvent was removed by rotary evaporator. The reaction mixture was chromatoghraphed with 0-20% ethyl acetate in hexanes on silica gel to give the desired product (4.2 g, 64%). $^1$H NMR (400 MHz, CHLOROFORM-d) δ 11.53 (s, 1H), 9.76 (s, 1H), 7.51-7.29 (m, 11H), 6.67 (dd, J=8.6, 2.2 Hz, 1H), 6.60 (d, J=2.0 Hz, 1H), 5.17 (s, 2H), 2.26 (s, 3H).

Example 1011

(S)-4-((2-((3-cyanobenzyl)oxy)-4-((2-methyl-[1,1'-biphenyl]-3-yl)methoxy)benzyl)amino)-3-hydroxybutanoic acid

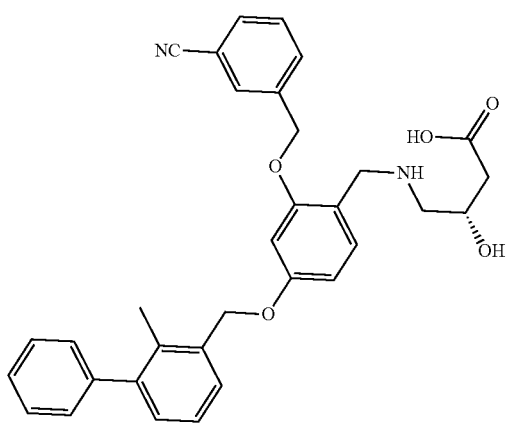 [SMILES: Cc1c(COc2ccc(CNC[C@@H](O)CC(=O)O)c(OCc3cccc(C#N)c3)c2)cccc1-c1ccccc1]

Added a solution of 3-(bromomethyl)benzonitrile (21.68 mg, 0.111 mmol) and triethyl amine (15.41 μl, 0.111 mmol) in 0.5 mL dimethylformamide to 2-hydroxy-4-((2-methyl-[1,1'-biphenyl]-3-yl)methoxy)benzaldehyde (32 mg, 0.101 mmol) and stirred overnight at room temperature. Added sodium triacetoxyhydroborate (63.9 mg, 0.302 mmol) and (S)-4-amino-3-hydroxybutanoic acid (23.95 mg, 0.201 mmol) and stirred overnight at room temperature. The crude material was purified via preparative LCMS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 30 minutes, then a 5-minute hold at 100% B; Flow: 20 mL/minutes Fractions containing the desired product were combined and dried via centrifugal evaporation.

The yield of the product was 5.0 mg, and its estimated purity by LCMS analysis was 99%. Two analytical LCMS injections were used to determine the final purity. Injection 1 Conditions A: LCMS: 2.0 minutes, M+1=537.4, M−1=535.4, EM=536.2. Injection 2 Conditions M: LCMS: 3.0 minutes, M+1=537.3, M−1=535.4, EM=536.2. $^1$H NMR (600 MHz, DMSO-$d_6$) δ 7.95 (s, 1H), 7.85 (d, J=7.7 Hz, 1H), 7.80 (d, J=7.3 Hz, 1H), 7.62 (t, J=7.7 Hz, 1H), 7.48-7.42 (m, 3H), 7.40-7.36 (m, 1H), 7.34-7.24 (m, 4H), 7.20 (d, J=7.7 Hz, 1H), 6.79 (s, 1H), 6.69 (dd, J=8.4, 1.8 Hz, 1H), 5.22 (s, 2H), 5.13 (s, 2H), 3.94 (quin, J=5.8 Hz, 1H), 3.84 (br. s., 1H), 2.67 (d, J=3.3 Hz, 2H), 2.38 (d, J=13.9 Hz, 1H), 2.33-2.25 (m, 1H), 2.19 (s, 3H), 1.19-1.02 (m, 1H).

Intermediate 3-((2-formyl-5-((2-methylbiphenyl-3-yl)methoxy)phenoxy)methyl)benzonitrile

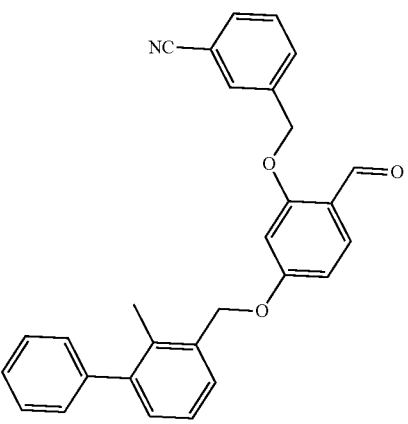 [SMILES: Cc1c(COc2ccc(C=O)c(OCc3cccc(C#N)c3)c2)cccc1-c1ccccc1]

Cesium carbonate (307 mg, 0.942 mmol), 2-hydroxy-4-((2-methyl-[1,1'-biphenyl]-3-yl)methoxy)benzaldehyde (200 mg, 0.628 mmol) and 3-(bromomethyl)benzonitrile (185 mg, 0.942 mmol) were heated at 75° C. for 3 hrs in dimethyl formamide (4 mL). Neutralized with dilute hydrochloric acid (0.1 N), washed with water and brine and dried oversodium sulfate. The residue was purified with 3:1 hexanes:ethyl acetate on a 12 g silica gel column) Collected fractions to afford 170 mg of the title compound as white film. LCMS Condition A: 1.5 minutes, M+1=434.3, EM=433.2.

The following examples were prepared by reductive amination in the same manner as N-(2-(2-(3-cyanobenzyloxy)-4-(3-(2,3-dihydrobenzo[b][1,4]dioxin-6-yl)-2-methylbenzyloxy)-6-methylbenzylamino)ethyl)acetamide from 3-((2-formyl-5-((2-methylbiphenyl-3-yl)methoxy)phenoxy)methyl)benzonitrile and an appropriate amine. LCMS characterization data is provided in tablular form.

Example 1012

(2S,3S)-2-((2-((3-cyanobenzyl)oxy)-4-((2-methyl-[1,1'-biphenyl]-3-yl)methoxy)benzyl)amino)-3-hydroxybutanoic acid

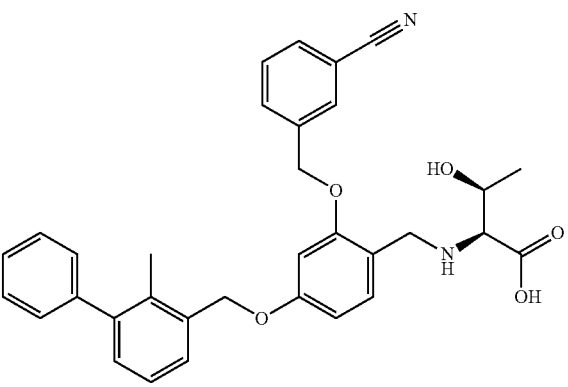 [SMILES: Cc1c(COc2ccc(CN[C@H](C(=O)O)[C@H](C)O)c(OCc3cccc(C#N)c3)c2)cccc1-c1ccccc1]

¹H NMR (DMSO-d₆) δ 8.02 (s, 1H), 7.91 (d, 1H), 7.82 (d, 1H), 7.62 (m, 1H), 7.43-7.49 (m, 3H), 7.37-7.41 (m, 1H), 7.26-7.35 (m, 4H), 7.21 (d, 1H), 6.83 (s, 1H), 6.72 (d, 1H), 5.21-5.28 (m, 2H), 5.15 (s, 2H), 3.95-4.07 (m, 3H), 3.10 (d, 1H), 2.19 (s, 3H), 1.06 (d, 3H).

Example 1013

(2R,3R)-2-((2-((3-cyanobenzyl)oxy)-4-((2-methyl-[1,1'-biphenyl]-3-yl)methoxy)benzyl)amino)-3-hydroxybutanoic acid

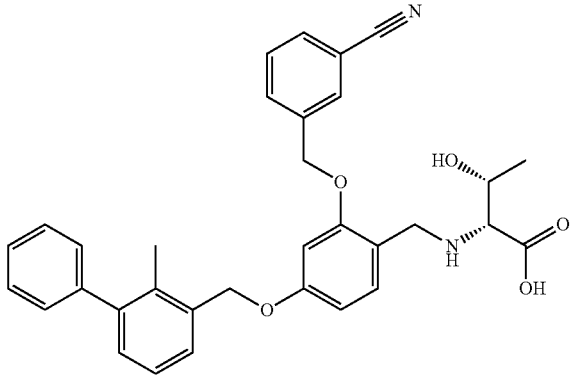 [SMILES: Cc1c(COc2ccc(CN[C@@H](C(=O)O)[C@@H](C)O)c(OCc3cccc(C#N)c3)c2)cccc1-c1ccccc1]

¹H NMR (DMSO-d₆) δ 8.02 (s, 1H), 7.91 (d, 1H), 7.82 (d, 1H), 7.62 (m, 1H), 7.43-7.49 (m, 3H), 7.37-7.41 (m, 1H), 7.26-7.35 (m, 4H), 7.21 (d, 1H), 6.83 (s, 1H), 6.69-6.75 (m, 1H), 5.20-5.28 (m, 2H), 5.15 (s, 2H), 3.96-4.08 (m, 3H), 3.11 (d, 1H), 2.19 (s, 3H), 1.06 (d, 3H).

Example 1014

2-((2-((3-cyanobenzyl)oxy)-4-((2-methyl-[1,1'-biphenyl]-3-yl)methoxy)benzyl)amino)-3-hydroxy-2-methylpropanoic acid

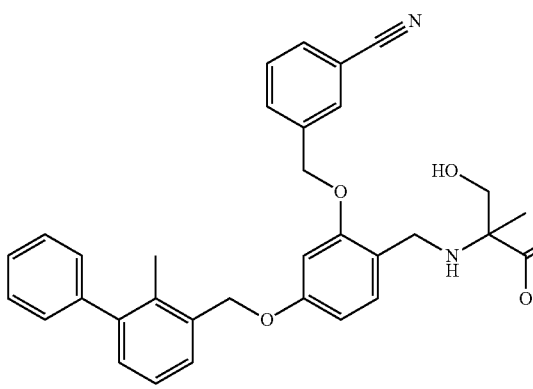

¹H NMR (DMSO-d₆) δ 8.01 (s, 1H), 7.93 (d, 1H), 7.81 (d, 1H), 7.58-7.64 (m, 1H), 7.46 (m, 3H), 7.36-7.42 (m, 2H), 7.25-7.35 (m, 3H), 7.20 (d, 1H), 6.83 (s, 1H), 6.73 (d, 1H), 5.25 (s, 2H), 5.16 (s, 2H), 4.01 (s, 2H), 3.64 (d, 1H), 3.55 (d, 1H), 2.19 (s, 3H), 1.26 (s, 3H).

Example 1015

(2R,3S)-2-((2-((3-cyanobenzyl)oxy)-4-((2-methyl-[1,1'-biphenyl]-3-yl)methoxy)benzyl)amino)-3-hydroxybutanoic acid

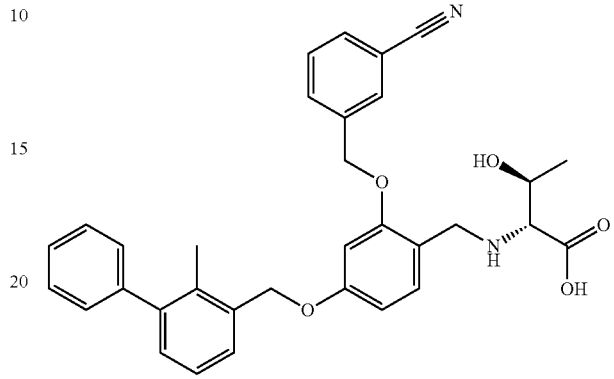

¹H NMR (DMSO-d₆) δ 8.01 (s, 1H), 7.90 (d, 1H), 7.82 (d, 1H), 7.62 (m, 1H), 7.42-7.51 (m, 3H), 7.36-7.42 (m, 1H), 7.24-7.36 (m, 4H), 7.21 (d, 1H), 6.82 (s, 1H), 6.72 (d, 1H), 5.19-5.28 (m, 2H), 5.15 (s, 2H), 3.94-4.04 (m, 2H), 3.87-3.94 (m, 1H), 3.87 (br. s., 1H), 3.64 (br. s., 2H), 2.96 (d, 1H), 2.19 (s, 3H), 1.14 (d, 3H).

Example 1016

(R)-2-((2-((3-cyanobenzyl)oxy)-4-((2-methyl-[1,1'-biphenyl]-3-yl)methoxy)benzyl)amino)-3-hydroxypropanoic acid

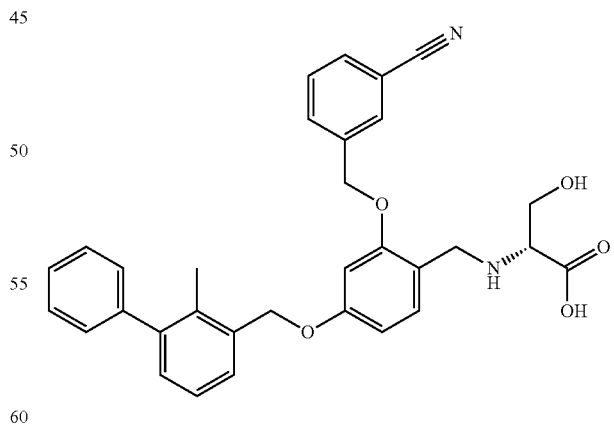

¹H NMR (DMSO-d₆) δ 8.02 (s, 1H), 7.92 (d, J=7.7 Hz, 1H), 7.81 (d, J=7.7 Hz, 1H), 7.61 (t, J=7.7 Hz, 1H), 7.46 (q, J=7.3 Hz, 3H), 7.26-7.41 (m, 5H), 7.20 (d, J=7.7 Hz, 1H), 6.83 (s, 1H), 6.72 (d, J=8.8 Hz, 1H), 5.21-5.29 (m, 2H), 5.15 (s, 2H), 3.99-4.16 (m, 2H), 3.91 (s, 1H), 3.75 (dd, J=11.2, 4.2 Hz, 2H), 2.74 (s, 1H), 2.19 (s, 3H).

Example 1017

2-((2-((3-cyanobenzyl)oxy)-4-((2-methyl-[1,1'-biphenyl]-3-yl)methoxy)benzyl)amino)-3-hydroxypropanoic acid

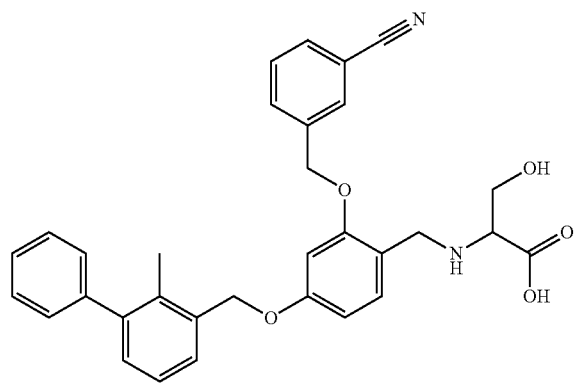 [SMILES: Cc1c(COc2ccc(CNC(CO)C(=O)O)c(OCc3cccc(C#N)c3)c2)cccc1-c1ccccc1]

$^1$H NMR (DMSO-d$_6$) δ 8.02 (br. s., 1H), 7.87-7.98 (m, 2H), 7.81 (d, J=7.3 Hz, 1H), 7.62 (t, J=7.3 Hz, 1H), 7.25-7.49 (m, 8H), 7.20 (d, J=7.3 Hz, 1H), 6.83 (br. s., 1H), 6.73 (d, J=8.1 Hz, 1H), 5.20-5.32 (m, 2H), 5.15 (br. s., 2H), 3.99-4.22 (m, 2H), 3.91 (s, 1H), 3.76 (br. s., 1H), 3.66 (br. s., 1H), 2.74 (s, 1H), 2.19 (s, 3H).

Example 1018

(S)-2-((2-((3-cyanobenzyl)oxy)-4-((2-methyl-[1,1'-biphenyl]-3-yl)methoxy)benzyl)amino)-3-hydroxypropanoic acid

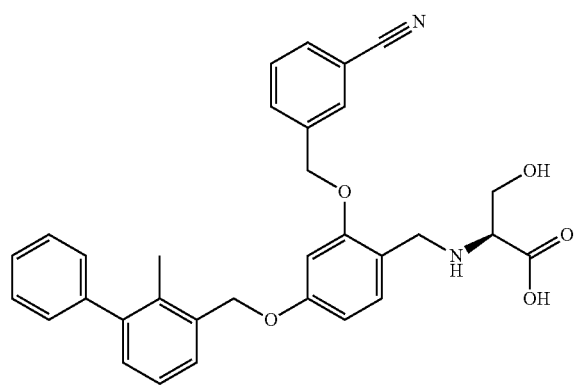 [SMILES: Cc1c(COc2ccc(CN[C@@H](CO)C(=O)O)c(OCc3cccc(C#N)c3)c2)cccc1-c1ccccc1]

$^1$H NMR (DMSO-d$_6$) δ 8.02 (s, 1H), 7.92 (d, 1H), 7.81 (d, 1H), 7.61 (m, 1H), 7.46 (m, 3H), 7.25-7.42 (m, 5H), 7.20 (d, 1H), 6.83 (s, 1H), 6.73 (d, 1H), 5.20-5.30 (m, 2H), 5.15 (s, 2H), 4.11 (d, 1H), 4.05 (d, 1H), 3.76 (m, 1H), 3.65 (m, 1H), 3.18 (m, 1H), 2.19 (s, 3H), 1.91 (s, 1H).

Example 1019

(S)-2-((2-((3-cyanobenzyl)oxy)-4-((2-methyl-[1,1'-biphenyl]-3-yl)methoxy)benzyl)amino)-3-hydroxy-2-methylpropanoic acid

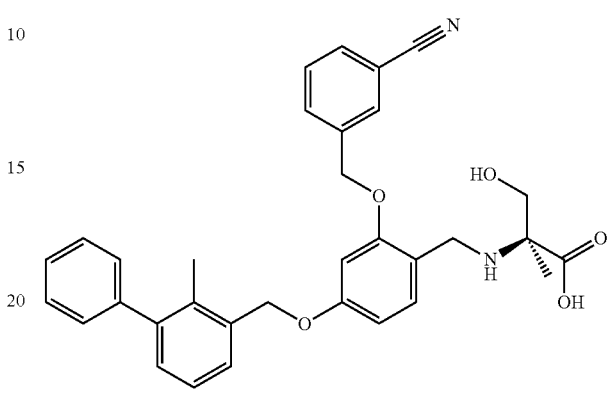

$^1$H NMR (DMSO-d$_6$) δ 8.01 (s, 1H), 7.93 (d, 1H), 7.81 (d, 1H), 7.61 (m, 1H), 7.42-7.50 (m, 3H), 7.35-7.42 (m, 2H), 7.24-7.35 (m, 3H), 7.20 (d, 1H), 6.82 (s, 1H), 6.73 (d, 1H), 5.25 (s, 2H), 5.16 (s, 2H), 4.02 (s, 2H), 3.65 (d, 1H), 3.56 (d, 1H), 2.19 (s, 3H), 1.91 (s, 1H), 1.26 (s, 3H).

Example 1020

2-((2-((3-cyanobenzyl)oxy)-4-((2-methyl-[1,1'-biphenyl]-3-yl)methoxy)benzyl)amino)-2-(hydroxymethyl)-3-methylbutanoic acid

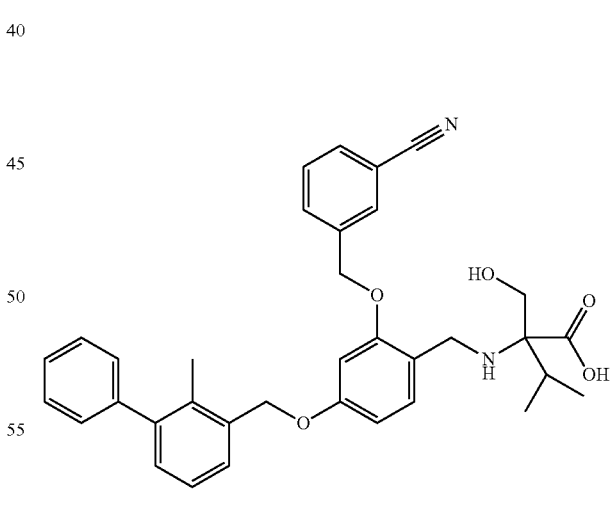

$^1$H NMR (DMSO-d$_6$) δ 8.02 (s, 1H), 7.93 (d, 1H), 7.80 (d, 1H), 7.60 (m, 1H), 7.42-7.50 (m, 3H), 7.36-7.42 (m, 1H), 7.24-7.36 (m, 4H), 7.20 (d, 1H), 6.84 (s, 1H), 6.72 (d, 1H), 5.27 (s, 2H), 5.16 (s, 2H), 4.07 (d, 1H), 3.98 (d, 1H), 3.79 (s, 2H), 2.19 (s, 3H), 2.10-2.17 (m, 1H), 0.96 (d, 3H), 0.83 (d, 3H).

Example 1021

(S)-3-((2-((3-cyanobenzyl)oxy)-4-((2-methyl-[1,1'-biphenyl]-3-yl)methoxy)benzyl)amino)-4-hydroxybutanoic acid

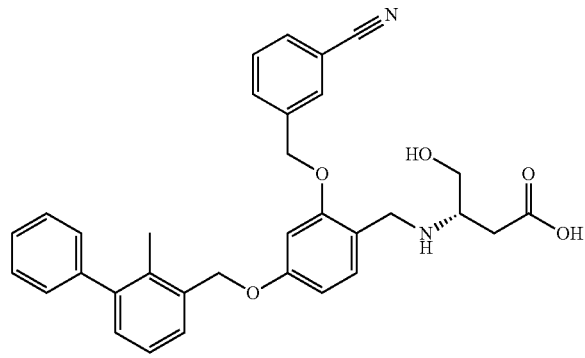 [SMILES: Cc1c(COc2ccc(CN[C@H](CO)CC(=O)O)c(OCc3cccc(C#N)c3)c2)cccc1-c1ccccc1]

$^1$H NMR (DMSO-$d_6$) δ 7.99 (s, 1H), 7.89 (d, 1H), 7.81 (d, 1H), 7.61 (m, 1H), 7.46 (m, 3H), 7.36-7.42 (m, 1H), 7.25-7.34 (m, 4H), 7.20 (d, 1H), 6.80 (s, 1H), 6.70 (d, 1H), 5.23 (s, 2H), 5.14 (s, 2H), 3.98 (d, 1H), 3.86 (d, 1H), 3.53 (m, 2H), 2.98 (d, 1H), 2.10-2.27 (m, 5H), 1.90 (s, 1H).

Example 1022

(R)-3-((2-((3-cyanobenzyl)oxy)-4-((2-methyl-[1,1'-biphenyl]-3-yl)methoxy)benzyl)amino)-4-hydroxybutanoic acid

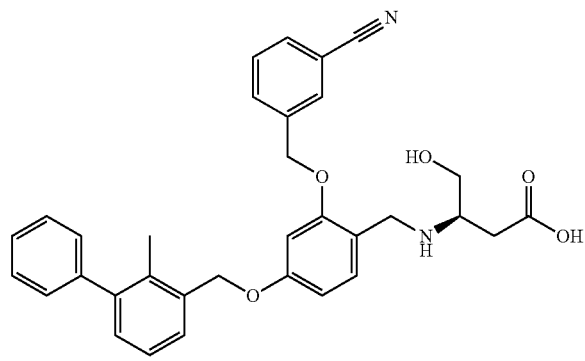 [SMILES: Cc1c(COc2ccc(CN[C@@H](CO)CC(=O)O)c(OCc3cccc(C#N)c3)c2)cccc1-c1ccccc1]

$^1$H NMR (DMSO-$d_6$) δ 7.99 (s, 1H), 7.89 (d, 1H), 7.81 (d, 1H), 7.61 (m, 1H), 7.46 (m, 3H), 7.36-7.42 (m, 1H), 7.25-7.35 (m, 4H), 7.20 (d, 1H), 6.81 (s, 1H), 6.70 (d, 1H), 5.23 (s, 2H), 5.15 (s, 2H), 3.98 (d, 1H), 3.85 (d, 1H), 3.53 (m, 1H), 3.43 (d, 1H), 2.98 (br. s., 1H), 2.11-2.27 (m, 5H).

Example 1023

(R)-2-((2-((3-cyanobenzyl)oxy)-4-((2-methyl-[1,1'-biphenyl]-3-yl)methoxy)benzyl)amino)-3-hydroxy-2-methylpropanoic acid

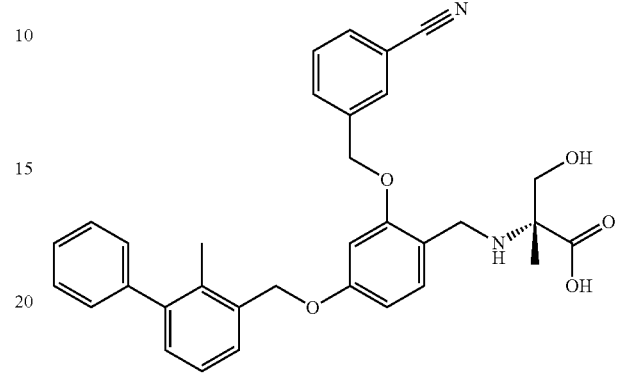

$^1$H NMR (DMSO-$d_6$) δ 8.01 (s, 1H), 7.91-7.96 (m, 1H), 7.81 (d, 1H), 7.61 (m, 1H), 7.42-7.50 (m, 3H), 7.39 (m, 2H), 7.24-7.35 (m, 3H), 7.20 (d, 1H), 6.82 (s, 1H), 6.73 (d, 1H), 5.25 (s, 2H), 5.16 (s, 2H), 4.01 (s, 2H), 3.64 (d, 1H), 3.55 (d, 1H), 2.19 (s, 3H), 1.26 (s, 3H).

| Example | LCMS Method | RT (min) | M$^{+1}$ | M$^{-1}$ |
|---|---|---|---|---|
| Example 1012: (2S,3S)-2-((2-((3-cyanobenzyl)oxy)-4-((2-methyl-[1,1'-biphenyl]-3-yl)methoxy)benzyl)amino)-3-hydroxybutanoic acid | A | 1.89 | 537.4 | 535.4 |
| Example 1013: (2R,3R)-2-((2-((3-cyanobenzyl)oxy)-4-((2-methyl-[1,1'-biphenyl]-3-yl)methoxy)benzyl)amino)-3-hydroxybutanoic acid | A | 1.9 | 537.4 | 535.5 |
| Example 1014: 2-((2-((3-cyanobenzyl)oxy)-4-((2-methyl-[1,1'-biphenyl]-3-yl)methoxy)benzyl)amino)-3-hydroxy-2-methylpropanoic acid | A | 2.13 | 537.4 | 535.4 |
| Example 1015: (2R,3S)-2-((2-((3-cyanobenzyl)oxy)-4-((2-methyl-[1,1'-biphenyl]-3-yl)methoxy)benzyl)amino)-3-hydroxybutanoic acid | A | 1.92 | 537.4 | 535.4 |
| Example 1016: (R)-2-((2-((3-cyanobenzyl)oxy)-4-((2-methyl-[1,1'-biphenyl]-3-yl)methoxy)benzyl)amino)-3-hydroxypropanoic acid | A | 1.98 | 523.3 | 521.4 |
| Example 1017: 2-((2-((3-cyanobenzyl)oxy)-4-((2-methyl-[1,1'-biphenyl]-3-yl)methoxy)benzyl)amino)-3-hydroxypropanoic acid | A | 2.01 | 523.3 | 521.3 |
| Example 1018: (S)-2-((2-((3-cyanobenzyl)oxy)-4-((2-methyl-[1,1'-biphenyl]-3-yl)methoxy)benzyl)amino)-3-hydroxypropanoic acid | A | 1.87 | 523.3 | 521.3 |
| Example 1019: (S)-2-((2-((3-cyanobenzyl)oxy)-4-((2-methyl-[1,1'-biphenyl]-3-yl)methoxy)benzyl)amino)-3-hydroxy-2-methylpropanoic acid | A | 1.93 | 537.4 | 535.3 |
| Example 1020: 2-((2-((3-cyanobenzyl)oxy)-4-((2-methyl-[1,1'-biphenyl]-3-yl)methoxy)benzyl)amino)-2-(hydroxymethyl)-3-methylbutanoic acid | A | 2.06 | 565.4 | 563.4 |
| Example 1021: (S)-3-((2-((3-cyanobenzyl)oxy)-4-((2-methyl-[1,1'-biphenyl]-3-yl)methoxy)benzyl)amino)-4-hydroxybutanoic acid | A | 1.85 | 537.3 | 535.3 |

-continued

| Example | LCMS Method | RT (min) | M$^{+1}$ | M$^{-1}$ |
|---|---|---|---|---|
| Example 1022: (R)-3-((2-((3-cyanobenzyl)oxy)-4-((2-methyl-[1,1'-biphenyl]-3-yl)methoxy)benzyl)amino)-4-hydroxybutanoic acid | A | 1.85 | 537.3 | 535.4 |
| Example 1023: (R)-2-((2-((3-cyanobenzyl)oxy)-4-((2-methyl-[1,1'-biphenyl]-3-yl)methoxy)benzyl)amino)-3-hydroxy-2-methylpropanoic acid | A | 1.89 | 537.4 | 535.3 |

Example 1335

N-(2-((2-methoxy-4-((2-methyl-[1,1'-biphenyl]-3-yl)methoxy)benzyl)amino)ethyl)acetamide

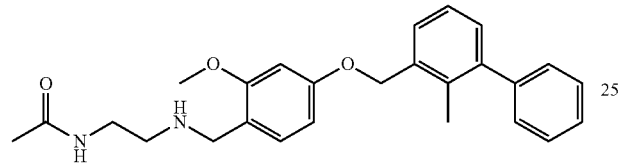

Methyl iodide (65 mg) was dissolved in 3 mL of DMF. 2-hydroxy-4-((2-methyl-[1,1'-biphenyl]-3-yl)methoxy)benzaldehyde (0.016 g, 0.05 mmol) and potassium carbonate (0.021 g, 0.150 mmol) were combined in 0.5 mL of the methyl iodide (6.25 µl, 0.100 mmol) solution. The reaction was heated at 80° C. for 3 hours. The cooled reaction was filtered through a 500 mg StratoSpheres™ PL-Thiol MP SPE column containing 1.5 mmol of free thiol to scavange any remaining methyl iodide. The column was preconditioned with methanol. The reaction was allowed to pass through the column under gravity and the column further eluted with 1 mL methanol.

The eluent was combined with N-(2-aminoethyl)acetamide (0.015 g, 0.150 mmol) and SODIUM triacetoxyborohydride (0.032 g, 0.150 mmol) and stirred overnight. LCMS analysis was consistent with a mixture of starting material and unreduced imine (M+1=417). Added sodium triacetoxyborohydride (0.032 g, 0.150 mmol) and N-(2-aminoethyl)acetamide (0.015 g, 0.150 mmol) and stirred overnight.

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 25 minutes, then a 5-minute hold at 100% B; Flow: 20 mL/min. Fractions containing the desired product were combined and dried via centrifugal evaporation. The yield of the product was 5.4 mg, and its estimated purity by LCMS analysis was 100%. LCMS Condition A: 1.68 minutes, M+1=419.4; $^1$H NMR (500 MHz, DMSO-d$_6$) δ 7.86-7.80 (m, 1H), 7.46 (t, J=7.3 Hz, 3H), 7.39 (s, 1H), 7.32 (d, J=7.9 Hz, 2H), 7.31-7.26 (m, 1H), 7.20 (d, J=9.2 Hz, 2H), 6.66 (s, 1H), 6.64-6.59 (m, 1H), 5.13 (s, 2H), 3.78 (s, 3H), 3.60 (s, 2H), 3.13 (d, J=6.1 Hz, 2H), 2.55-2.52 (m, 2H), 2.21 (s, 3H).

Examples 1024 through 1120 were prepared utilizing the two-step procedure described for Example 1335: N-(2-((2-methoxy-4-((2-methyl-[1,1'-biphenyl]-3-yl)methoxy)benzyl)amino)ethyl)acetamide. The appropriate alkyl bromide was utilized in place of methyl iodide to alkylate the phenolic oxygen and N-(2-aminoethyl)acetamide was utilized for reductive amination to provide the desired example. Characterization data is provided in the table following the examples.

Example 1024

N-(2-((2-(benzyloxy)-4-((2-methyl-[1,1'-biphenyl]-3-yl)methoxy)benzyl)amino)ethyl)acetamide

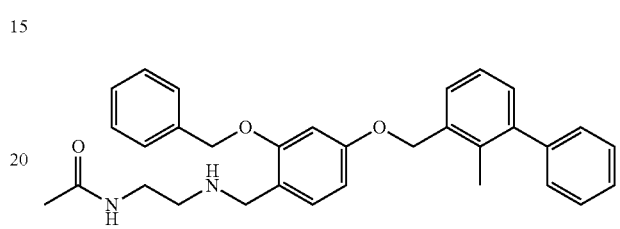

Example 1025

N-(2-((4-((2-methyl-[1,1'-biphenyl]-3-yl)methoxy)-2-((3-methylbenzyl)oxy)benzyl)amino)ethyl)acetamide

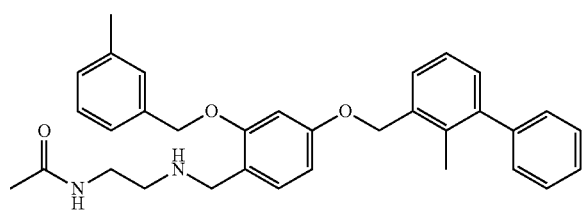 [SMILES: CC(=O)NCCNCc1ccc(OCc2cccc(-c3ccccc3)c2C)cc1OCc1cccc(C)c1]

Example 1026

N-(2-((4-((2-methyl-[1,1'-biphenyl]-3-yl)methoxy)-2-(2,2,2-trifluoroethoxy)benzyl)amino)ethyl)acetamide

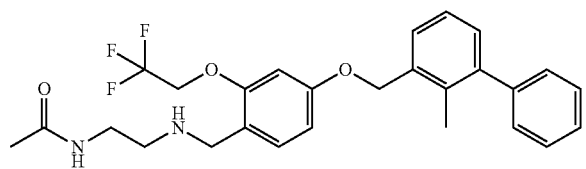 [SMILES: CC(=O)NCCNCc1ccc(OCc2cccc(-c3ccccc3)c2C)cc1OCC(F)(F)F]

Example 1027

N-(2-((4-((2-methyl-[1,1'-biphenyl]-3-yl)methoxy)-2-propoxybenzyl)amino)ethyl)acetamide

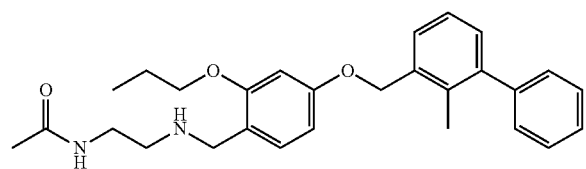 [SMILES: CCCOc1cc(OCc2cccc(-c3ccccc3)c2C)ccc1CNCCNC(C)=O]

Example 1028

N-(2-((2-((3-cyanobenzyl)oxy)-4-((2-methyl-[1,1'-biphenyl]-3-yl)methoxy)benzyl)amino)ethyl)acetamide

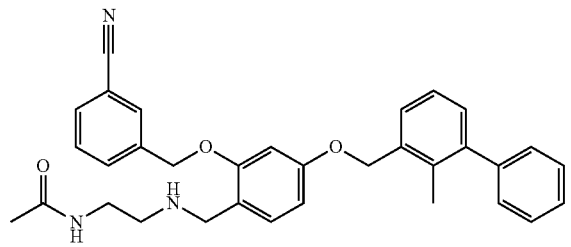 [SMILES: CC(=O)NCCNCc1ccc(OCc2cccc(-c3ccccc3)c2C)cc1OCc1cccc(C#N)c1]

Example 1029

N-(2-((2-((4-cyanobenzyl)oxy)-4-((2-methyl-[1,1'-biphenyl]-3-yl)methoxy)benzyl)amino)ethyl)acetamide

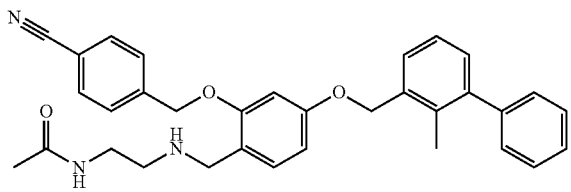 [SMILES: CC(=O)NCCNCc1ccc(OCc2cccc(-c3ccccc3)c2C)cc1OCc1ccc(C#N)cc1]

Example 1030

N-(2-((2-(2-hydroxyethoxy)-4-((2-methyl-[1,1'-biphenyl]-3-yl)methoxy)benzyl)amino)ethyl)acetamide

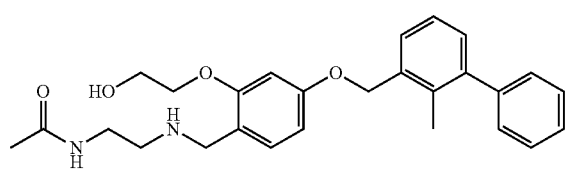 [SMILES: CC(=O)NCCNCc1ccc(OCc2cccc(-c3ccccc3)c2C)cc1OCCO]

Example 1031

2-(2-(((2-acetamidoethyl)amino)methyl)-5-((2-methyl-[1,1'-biphenyl]-3-yl)methoxy)phenoxy)acetamide

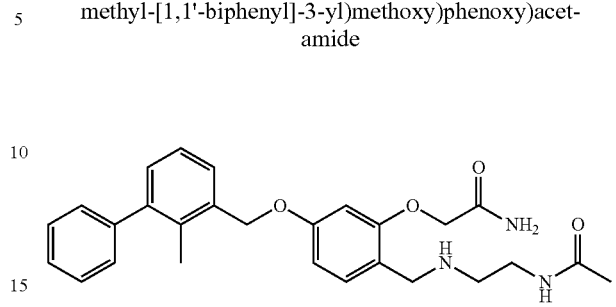

Example 1032 methyl 5-(2-(((2-acetamidoethyl)amino)methyl)-5-((2-methyl-[1,1'-biphenyl]-3-yl)methoxy)phenoxy)pentanoate

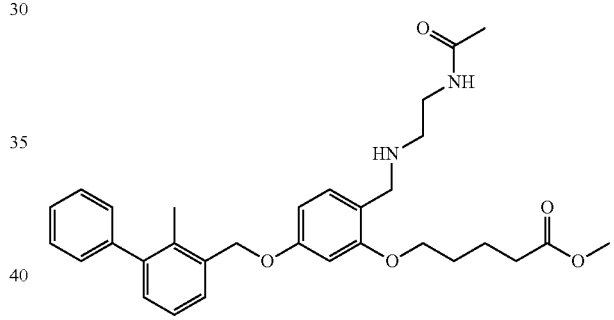

Example 1033

N-(2-((4-((2-methyl-[1,1'-biphenyl]-3-yl)methoxy)-2-phenethoxybenzyl)amino)ethyl)acetamide

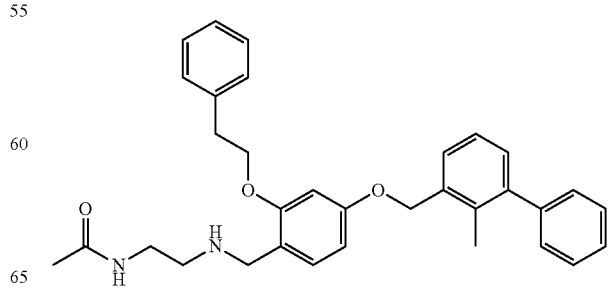

Example 1034 methyl 3-((2-(((2-acetamidoethyl)amino)methyl)-5-((2-methyl-[1,1'-biphenyl]-3-yl)methoxy)phenoxy)methyl)benzoate

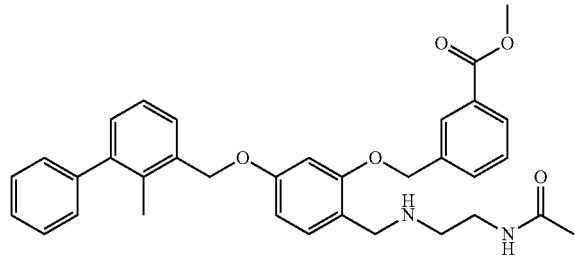 [SMILES: COC(=O)c1cccc(COc2cc(OCc3cccc(-c4ccccc4)c3C)ccc2CNCCNC(C)=O)c1]

Example 1035

N-(2-((2-(3-hydroxypropoxy)-4-((2-methyl-[1,1'-biphenyl]-3-yl)methoxy)benzyl)amino)ethyl)acetamide

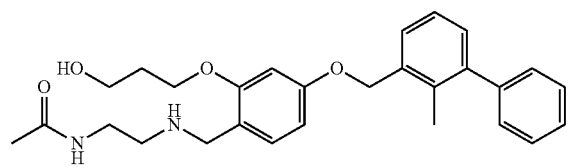 [SMILES: CC(=O)NCCNCc1ccc(OCc2cccc(-c3ccccc3)c2C)cc1OCCCO]

Example 1036 methyl 4-(2-(((2-acetamidoethyl)amino)methyl)-5-((2-methyl-[1,1'-biphenyl]-3-yl)methoxy)phenoxy)butanoate

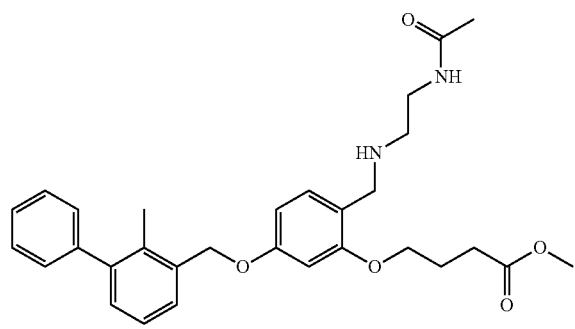 [SMILES: COC(=O)CCCOc1cc(OCc2cccc(-c3ccccc3)c2C)ccc1CNCCNC(C)=O]

Example 1037

N-(2-((2-((3-(hydroxymethyl)benzyl)oxy)-4-((2-methyl-[1,1'-biphenyl]-3-yl)methoxy)benzyl)amino)ethyl)acetamide

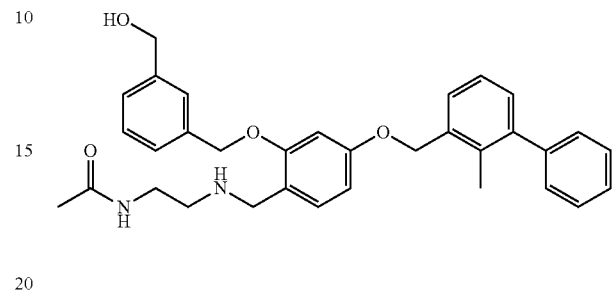

Example 1038

N-(2-((2-((2-(hydroxymethyl)benzyl)oxy)-4-((2-methyl-[1,1'-biphenyl]-3-yl)methoxy)benzyl)amino)ethyl)acetamide

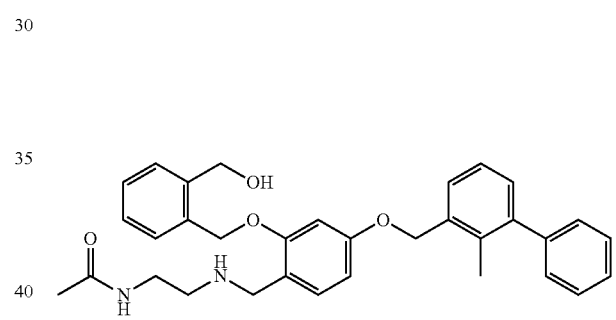

Example 1039

4-((2-(((2-acetamidoethyl)amino)methyl)-5-((2-methyl-[1,1'-biphenyl]-3-yl)methoxy)phenoxy)methyl)benzamide

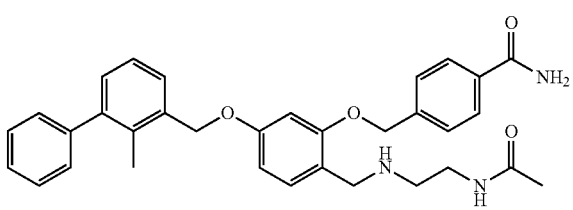 [SMILES: CC(=O)NCCNCc1ccc(OCc2cccc(-c3ccccc3)c2C)cc1OCc1ccc(C(N)=O)cc1]

Example 1040

N-(2-((2-((4-acetylbenzyl)oxy)-4-((2-methyl-[1,1'-biphenyl]-3-yl)methoxy)benzyl)amino)ethyl)acetamide

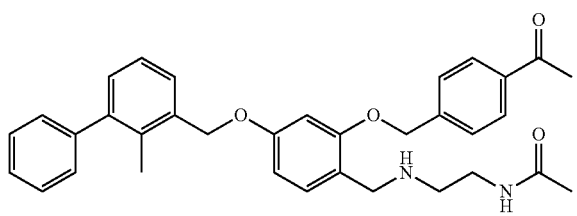 [SMILES: CC(=O)NCCNCc1ccc(OCc2cccc(-c3ccccc3)c2C)cc1OCc1ccc(C(C)=O)cc1]

Example 1041

N-(2-((4-((2-methyl-[1,1'-biphenyl]-3-yl)methoxy)-2-((2-(methylsulfonyl)benzyl)oxy)benzyl)amino)ethyl)acetamide

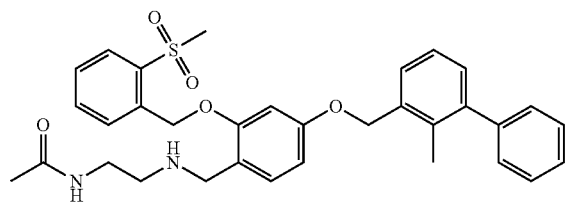 [SMILES: CC(=O)NCCNCc1ccc(OCc2cccc(-c3ccccc3)c2C)cc1OCc1ccccc1S(C)(=O)=O]

Example 1042

N-(2-((2-(3-methoxypropoxy)-4-((2-methyl-[1,1'-biphenyl]-3-yl)methoxy)benzyl)amino)ethyl)acetamide

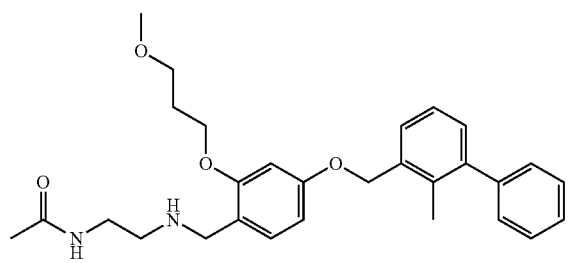 [SMILES: COCCCOc1cc(OCc2cccc(-c3ccccc3)c2C)ccc1CNCCNC(C)=O]

Example 1043

4-((2-(((2-acetamidoethyl)amino)methyl)-5-((2-methyl-[1,1'-biphenyl]-3-yl)methoxy)phenoxy)methyl)benzoic acid

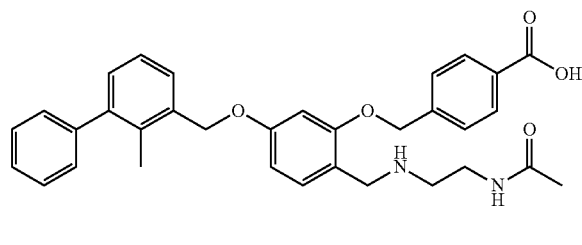 [SMILES: CC(=O)NCCNCc1ccc(OCc2cccc(-c3ccccc3)c2C)cc1OCc1ccc(C(=O)O)cc1]

Example 1044

N-(2-((2-ethoxy-4-((2-methyl-[1,1'-biphenyl]-3-yl)methoxy)benzyl)amino)ethyl)acetamide

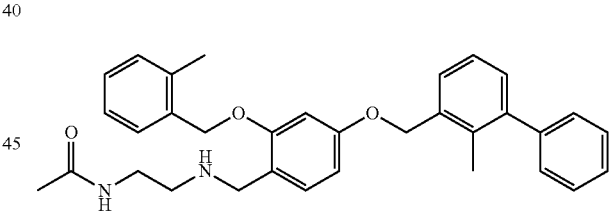

Example 1045

N-(2-((4-((2-methyl-[1,1'-biphenyl]-3-yl)methoxy)-2-((2-methylbenzyl)oxy)benzyl)amino)ethyl)acetamide Example 1046

N-(2-((2-((4-(tert-butyl)benzyl)oxy)-4-((2-methyl-[1,1'-biphenyl]-3-yl)methoxy)benzyl)amino)ethyl)acetamide

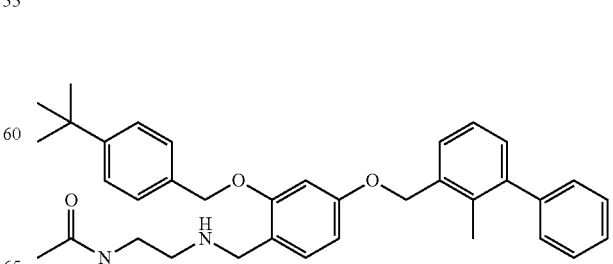

Example 1047

N-(2-((4-((2-methyl-[1,1'-biphenyl]-3-yl)methoxy)-2-((4-methylbenzyl)oxy)benzyl)amino)ethyl)acetamide

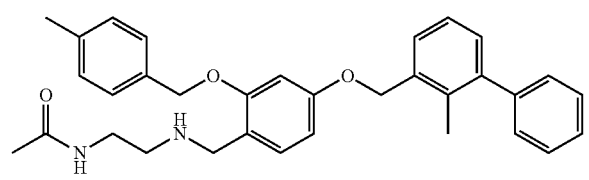

Example 1048

N-(2-((2-((2-fluorobenzyl)oxy)-4-((2-methyl-[1,1'-biphenyl]-3-yl)methoxy)benzyl)amino)ethyl)acetamide

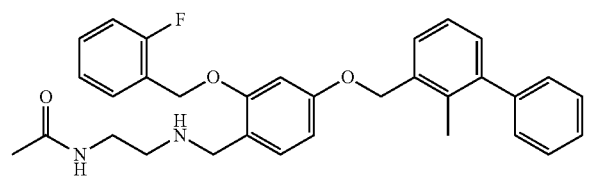 [SMILES: CC(=O)NCCNCc1ccc(OCc2cccc(-c3ccccc3)c2C)cc1OCc1ccccc1F]

Example 1049

N-(2-((2-((2,6-difluorobenzyl)oxy)-4-((2-methyl-[1,1'-biphenyl]-3-yl)methoxy)benzyl)amino)ethyl)acetamide

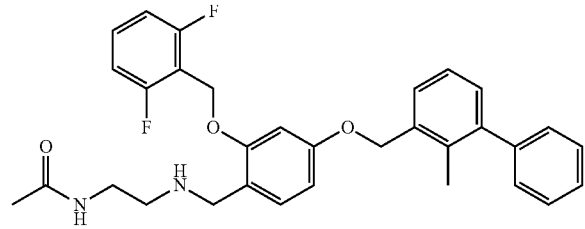 [SMILES: CC(=O)NCCNCc1ccc(OCc2cccc(-c3ccccc3)c2C)cc1OCc1c(F)cccc1F]

Example 1050

N-(2-((2-((3-fluorobenzyl)oxy)-4-((2-methyl-[1,1'-biphenyl]-3-yl)methoxy)benzyl)amino)ethyl)acetamide

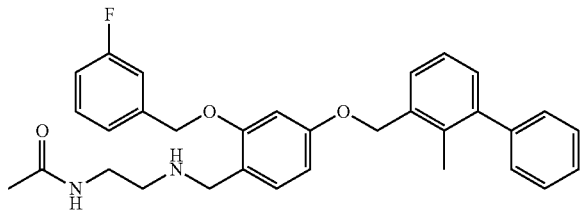 [SMILES: CC(=O)NCCNCc1ccc(OCc2cccc(-c3ccccc3)c2C)cc1OCc1cccc(F)c1]

Example 1051

N-(2-((4-((2-methyl-[1,1'-biphenyl]-3-yl)methoxy)-2-((3-(trifluoromethyl)benzyl)oxy)benzyl)amino)ethyl)acetamide

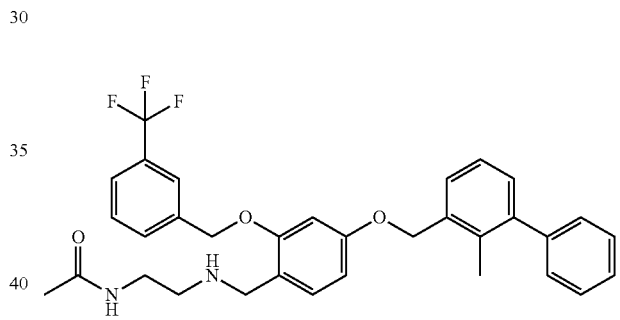

Example 1052

N-(2-((4-((2-methyl-[1,1'-biphenyl]-3-yl)methoxy)-2-((4-(trifluoromethyl)benzyl)oxy)benzyl)amino)ethyl)acetamide

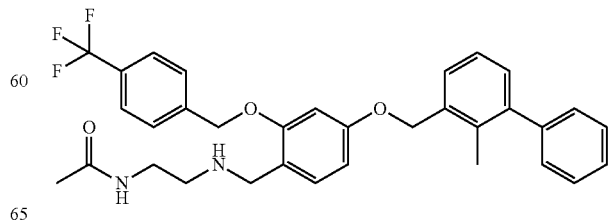

Example 1053

N-(2-((2-((2-chlorobenzyl)oxy)-4-((2-methyl-[1,1'-biphenyl]-3-yl)methoxy)benzyl)amino)ethyl)acetamide

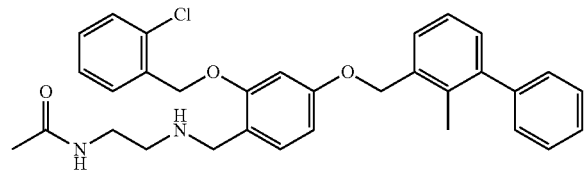 [SMILES: CC(=O)NCCNCc1ccc(OCc2cccc(-c3ccccc3)c2C)cc1OCc1ccccc1Cl]

Example 1054

N-(2-((2-((3-chlorobenzyl)oxy)-4-((2-methyl-[1,1'-biphenyl]-3-yl)methoxy)benzyl)amino)ethyl)acetamide

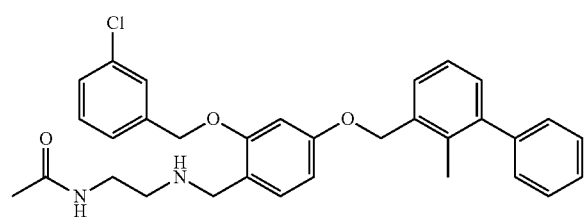

Example 1055

N-(2-((2-((2-cyanobenzyl)oxy)-4-((2-methyl-[1,1'-biphenyl]-3-yl)methoxy)benzyl)amino)ethyl)acetamide

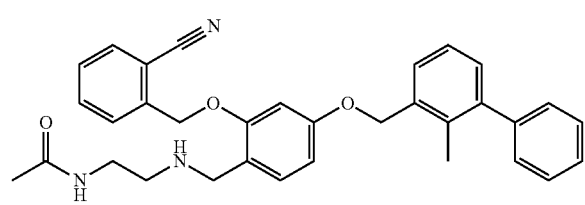 [SMILES: CC(=O)NCCNCc1ccc(OCc2cccc(-c3ccccc3)c2C)cc1OCc1ccccc1C#N]

Example 1056

N-(2-((4-((2-methyl-[1,1'-biphenyl]-3-yl)methoxy)-2-(naphthalen-2-ylmethoxy)benzyl)amino)ethyl)acetamide

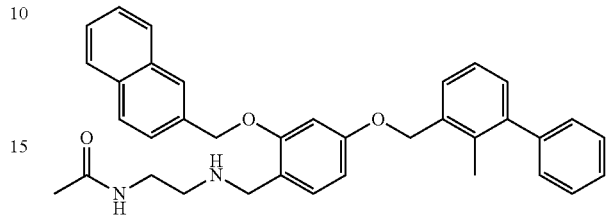

Example 1057

N-(2-((4-((2-methyl-[1,1'-biphenyl]-3-yl)methoxy)-2-((2-nitrobenzyl)oxy)benzyl)amino)ethyl)acetamide

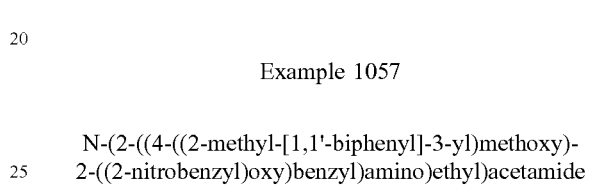

Example 1058

N-(2-((4-((2-methyl-[1,1'-biphenyl]-3-yl)methoxy)-2-((4-nitrobenzyl)oxy)benzyl)amino)ethyl)acetamide

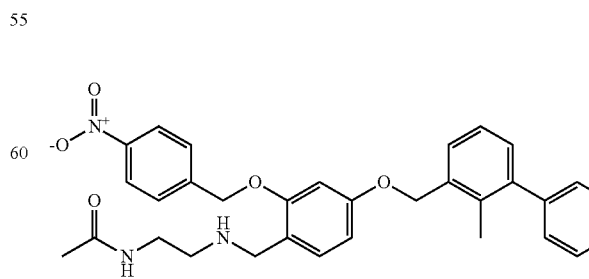

Example 1059

N-(2-((2-((3,4-difluorobenzyl)oxy)-4-((2-methyl-[1,1'-biphenyl]-3-yl)methoxy)benzyl)amino)ethyl)acetamide

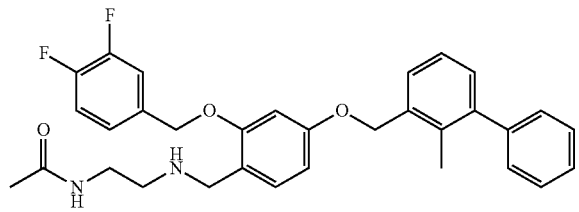

Example 1060

N-(2-((2-((2,5-difluorobenzyl)oxy)-4-((2-methyl-[1,1'-biphenyl]-3-yl)methoxy)benzyl)amino)ethyl)acetamide

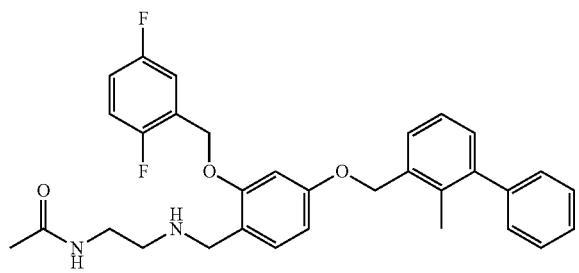 [SMILES: CC(=O)NCCNCc1ccc(OCc2cccc(-c3ccccc3)c2C)cc1OCc1cc(F)ccc1F]

Example 1061

N-(2-((2-((3,5-bis(trifluoromethyl)benzyl)oxy)-4-((2-methyl-[1,1'-biphenyl]-3-yl)methoxy)benzyl)amino)ethyl)acetamide

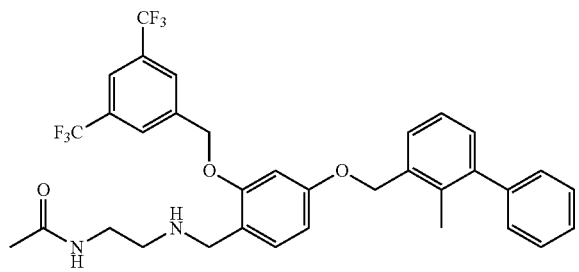 [SMILES: CC(=O)NCCNCc1ccc(OCc2cccc(-c3ccccc3)c2C)cc1OCc1cc(C(F)(F)F)cc(C(F)(F)F)c1]

Example 1062

N-(2-((2-((3,5-difluorobenzyl)oxy)-4-((2-methyl-[1,1'-biphenyl]-3-yl)methoxy)benzyl)amino)ethyl)acetamide

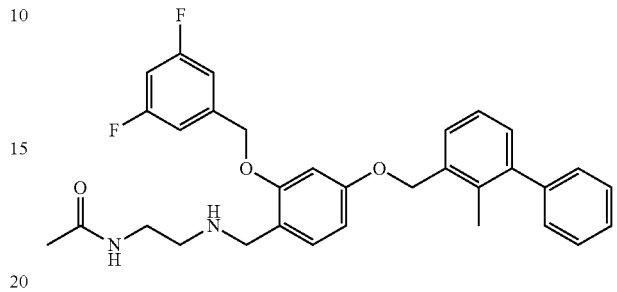

Example 1063

N-(2-((4-((2-methyl-[1,1'-biphenyl]-3-yl)methoxy)-2-(naphthalen-1-ylmethoxy)benzyl)amino)ethyl)acetamide

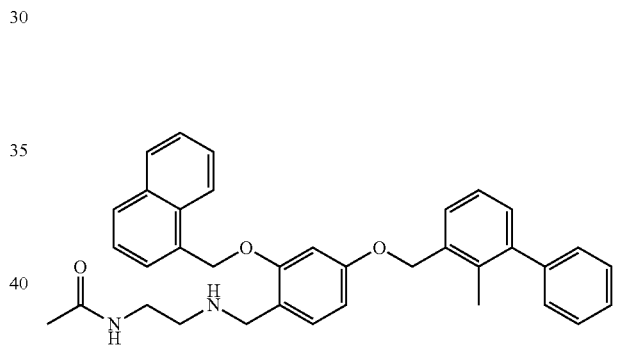

Example 1064

N-(2-((2-((2,4-difluorobenzyl)oxy)-4-((2-methyl-[1,1'-biphenyl]-3-yl)methoxy)benzyl)amino)ethyl)acetamide

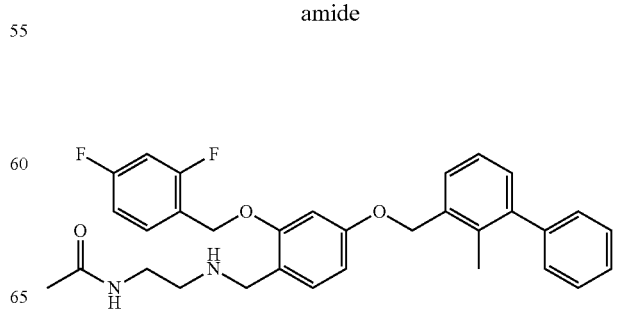

Example 1065

N-(2-((2-((3,5-dimethylbenzyl)oxy)-4-((2-methyl-[1,1'-biphenyl]-3-yl)methoxy)benzyl)amino)ethyl)acetamide

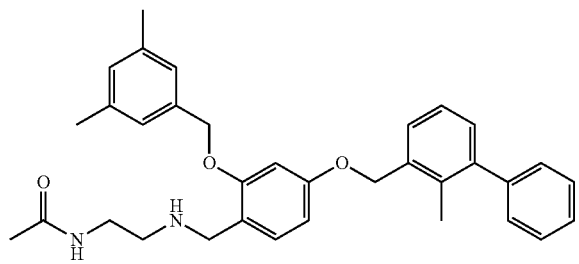 [SMILES: CC(=O)NCCNCc1ccc(OCc2cccc(-c3ccccc3)c2C)cc1OCc1cc(C)cc(C)c1]

Example 1066

N-(2-((4-((2-methyl-[1,1'-biphenyl]-3-yl)methoxy)-2-((2-(trifluoromethyl)benzyl)oxy)benzyl)amino)ethyl)acetamide

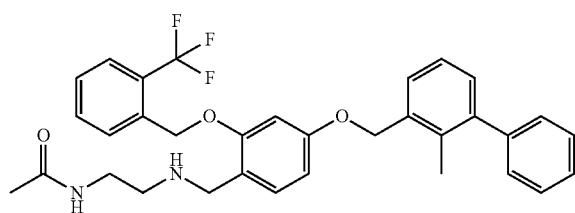 [SMILES: CC(=O)NCCNCc1ccc(OCc2cccc(-c3ccccc3)c2C)cc1OCc1ccccc1C(F)(F)F]

Example 1067 methyl 4-((2-(((2-acetamidoethyl)amino)methyl)-5-((2-methyl-[1,1'-biphenyl]-3-yl)methoxy)phenoxy)methyl)benzoate

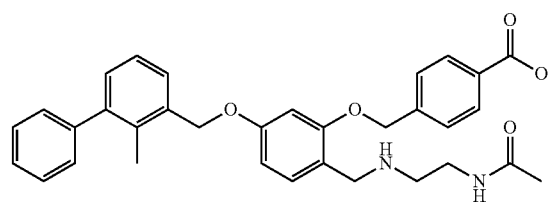

Example 1068

N-(2-((2-((4-chlorobenzyl)oxy)-4-((2-methyl-[1,1'-biphenyl]-3-yl)methoxy)benzyl)amino)ethyl)acetamide

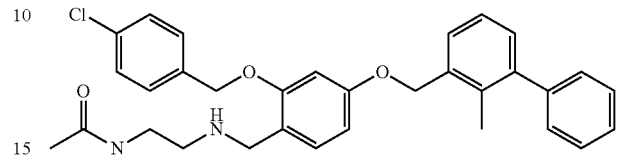

Example 1069

N-(2-((2-((3,4-dichlorobenzyl)oxy)-4-((2-methyl-[1,1'-biphenyl]-3-yl)methoxy)benzyl)amino)ethyl)acetamide

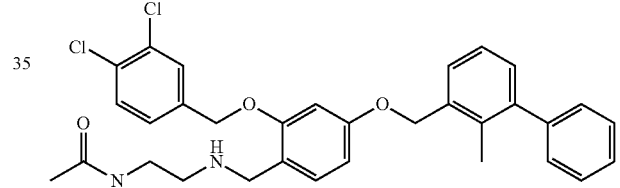

Example 1070

N-(2-((2-((2-fluoro-3-methylbenzyl)oxy)-4-((2-methyl-[1,1'-biphenyl]-3-yl)methoxy)benzyl)amino)ethyl)acetamide

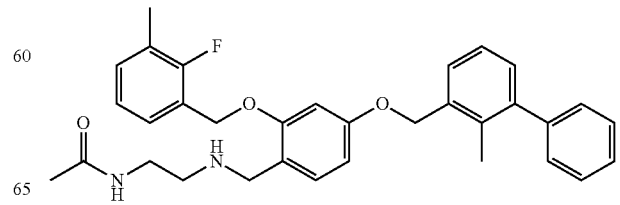

61

Example 1071

N-(2-((2-((2,3-difluorobenzyl)oxy)-4-((2-methyl-[1,1'-biphenyl]-3-yl)methoxy)benzyl)amino)ethyl)acetamide

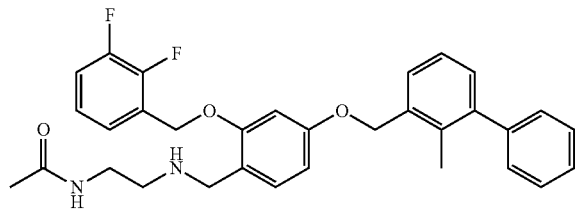 [SMILES: CC(=O)NCCNCc1ccc(OCc2cccc(-c3ccccc3)c2C)cc1OCc1cccc(F)c1F]

Example 1072

N-(2-((2-((3-chloro-2-fluorobenzyl)oxy)-4-((2-methyl-[1,1'-biphenyl]-3-yl)methoxy)benzyl)amino)ethyl)acetamide

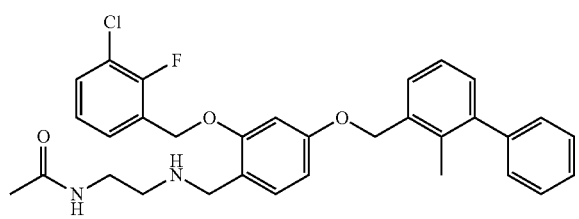 [SMILES: CC(=O)NCCNCc1ccc(OCc2cccc(-c3ccccc3)c2C)cc1OCc1cccc(Cl)c1F]

Example 1073

N-(2-((2-((3-benzoylbenzyl)oxy)-4-((2-methyl-[1,1'-biphenyl]-3-yl)methoxy)benzyl)amino)ethyl)acetamide

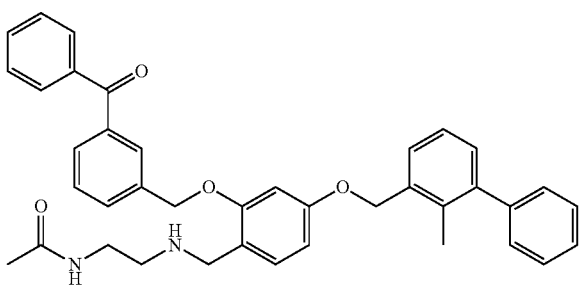 [SMILES: CC(=O)NCCNCc1ccc(OCc2cccc(-c3ccccc3)c2C)cc1OCc1cccc(C(=O)c2ccccc2)c1]

62

Example 1074

N-(2-((4-((2-methyl-[1,1'-biphenyl]-3-yl)methoxy)-2-(quinolin-8-ylmethoxy)benzyl)amino)ethyl)acetamide

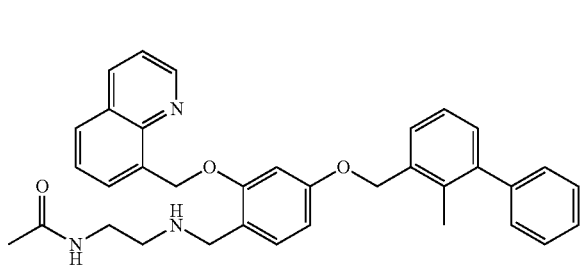 [SMILES: CC(=O)NCCNCc1ccc(OCc2cccc(-c3ccccc3)c2C)cc1OCc1cccc2cccnc12]

Example 1075

N-(2-((2-((4-fluorobenzyl)oxy)-4-((2-methyl-[1,1'-biphenyl]-3-yl)methoxy)benzyl)amino)ethyl)acetamide

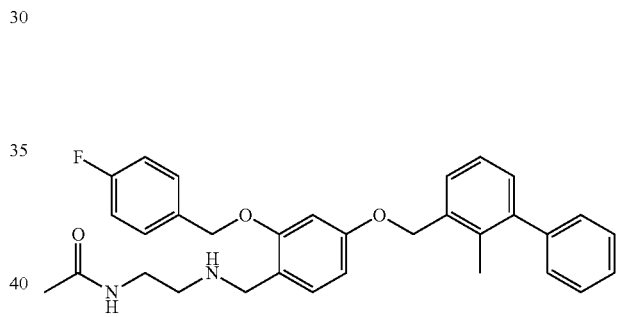

Example 1076

N-(2-((4-((2-methyl-[1,1'-biphenyl]-3-yl)methoxy)-2-(3-nitrobenzyl)oxy)benzyl)amino)ethyl)acetamide

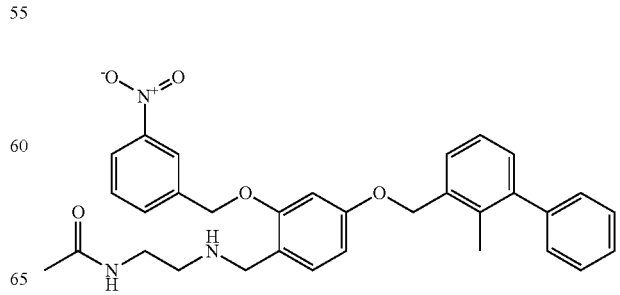

Example 1077

N-(2-((2-((3-(2-fluorophenoxyl)benzyl)oxy)-4-((2-methyl-[1,1'-biphenyl]-3-yl)methoxy)benzyl)amino)ethyl)acetamide

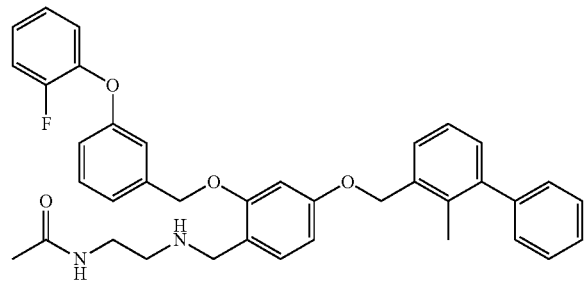 [SMILES: CC(=O)NCCNCc1ccc(OCc2cccc(-c3ccccc3)c2C)cc1OCc1cccc(Oc2ccccc2F)c1]

Example 1078

N-(2-((2-((3-(4-fluorophenoxyl)benzyl)oxy)-4-((2-methyl-[1,1'-biphenyl]-3-yl)methoxy)benzyl)amino)ethyl)acetamide

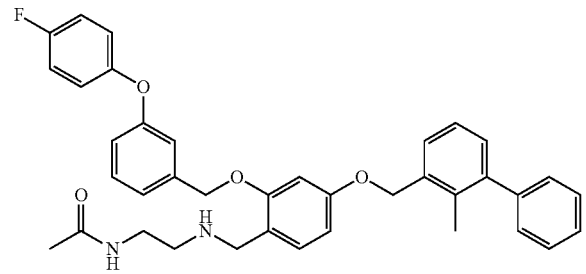 [SMILES: CC(=O)NCCNCc1ccc(OCc2cccc(-c3ccccc3)c2C)cc1OCc1cccc(Oc2ccc(F)cc2)c1]

Example 1079

N-(2-((2-((2-fluoro-3-(trifluoromethyl)benzyl)oxy)-4-((2-methyl-[1,1'-biphenyl]-3-yl) methoxy)benzyl) amino)ethyl)acetamide

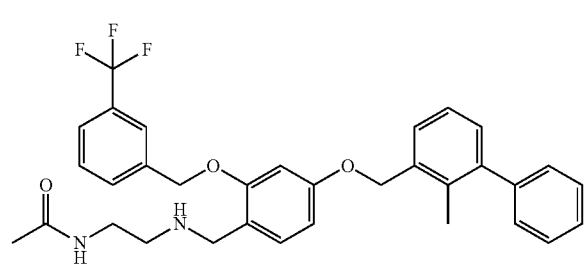 [SMILES: CC(=O)NCCNCc1ccc(OCc2cccc(-c3ccccc3)c2C)cc1OCc1cccc(C(F)(F)F)c1]

Example 1080

N-(2-((2-((2-fluoro-5-(trifluoromethyl)benzyl)oxy)-4-((2-methyl-[1,1'-biphenyl]-3-yl) methoxy)benzyl) amino)ethyl)acetamide

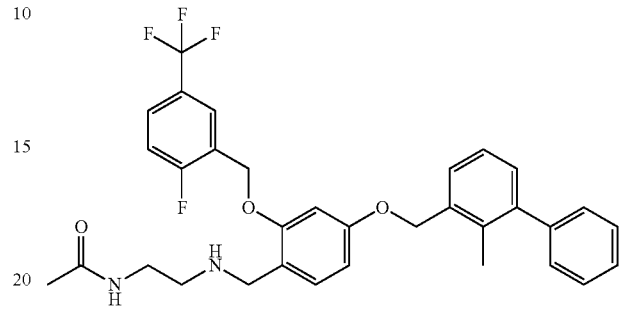

Example 1081

N-(2-((2-((3-fluoro-5-(trifluoromethyl)benzyl)oxy)-4-((2-methyl-[1,1'-biphenyl]-3-yl) methoxy)benzyl) amino)ethyl)acetamide

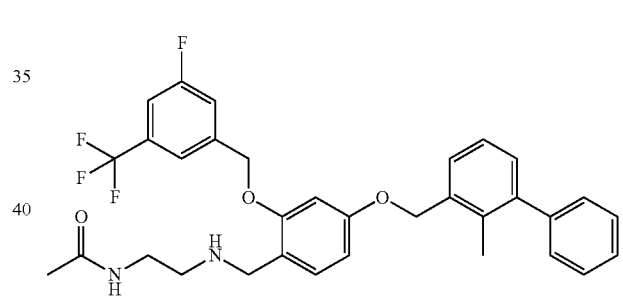

Example 1082

N-(2-((4-((2-methyl-[1,1'-biphenyl]-3-yl)methoxy)-2-((3-(trifluoromethoxy)benzyl)oxy)benzyl)amino)ethyl)acetamide

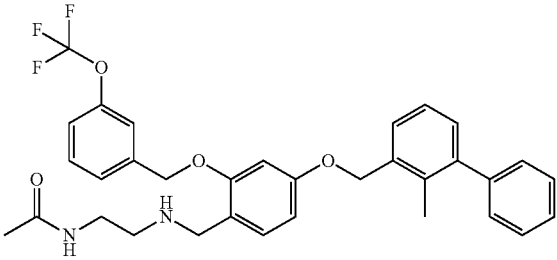 [SMILES: CC(=O)NCCNCc1ccc(OCc2cccc(-c3ccccc3)c2C)cc1OCc1cccc(OC(F)(F)F)c1]

Example 1083

N-(2-((2-((4-chloro-2-(trifluoromethyl)quinolin-6-yl)methoxy)-4-((2-methyl-[1,1'-biphenyl]-3-yl)methoxy)benzyl)amino)ethyl)acetamide

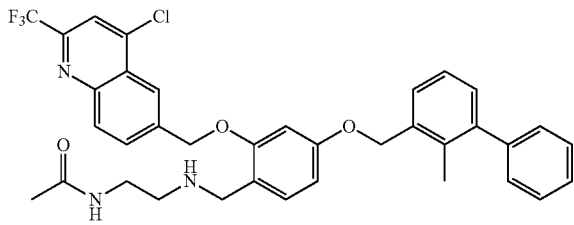 [SMILES: CC(=O)NCCNCc1ccc(OCc2cccc(-c3ccccc3)c2C)cc1OCc1ccc2nc(C(F)(F)F)cc(Cl)c2c1]

Example 1084

N-(2-((4-((2-methyl-[1,1'-biphenyl]-3-yl)methoxy)-2-((4-(methylsulfonyl)benzyl)oxy)benzyl)amino)ethyl)acetamide

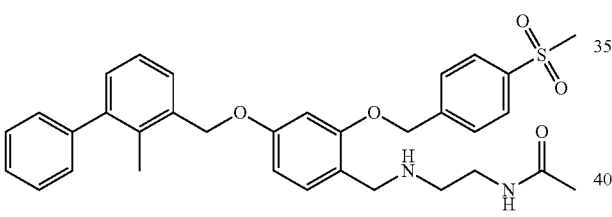

Example 1085

N-(2-((2-((2-(difluoromethoxy)benzyl)oxy)-4-((2-methyl-[1,1'-biphenyl]-3-yl)methoxy)benzyl)amino)ethyl)acetamide

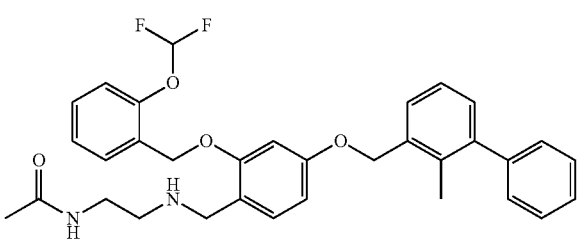 [SMILES: CC(=O)NCCNCc1ccc(OCc2cccc(-c3ccccc3)c2C)cc1OCc1ccccc1OC(F)F]

Example 1086

N-(2-((2-((3-methoxybenzyl)oxy)-4-((2-methyl-[1,1'-biphenyl]-3-yl)methoxy)benzyl)amino)ethyl)acetamide

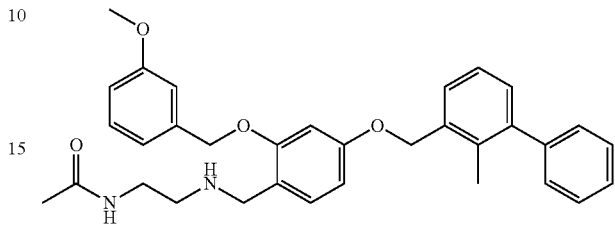

Example 1087

N-(2-((4-((2-methyl-[1,1'-biphenyl]-3-yl)methoxy)-2-((2-(trifluoromethoxy)benzyl)oxy)benzyl)amino)ethyl)acetamide

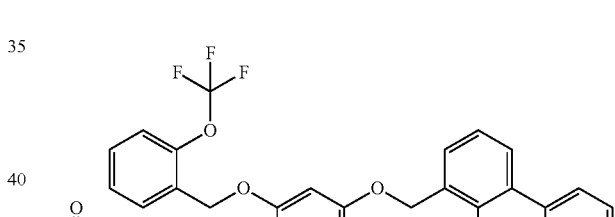

Example 1088

N-(2-((2-((4-(difluoromethoxy)benzyl)oxy)-4-((2-methyl-[1,1'-biphenyl]-3-yl)methoxy)benzyl)amino)ethyl)acetamide

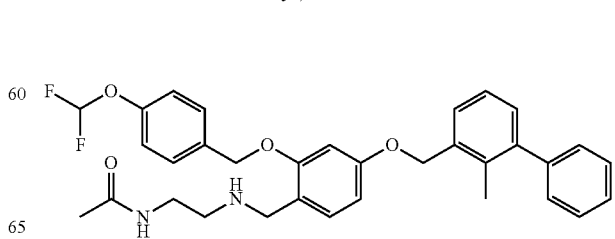

Example 1089

N-(2-((2-((2'-cyano-[1,1'-biphenyl]-4-yl)methoxy)-4-((2-methyl-[1,1'-biphenyl]-3-yl) methoxy)benzyl) amino)ethyl)acetamide

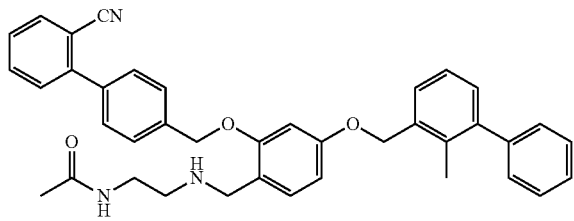 [SMILES: CC(=O)NCCNCc1ccc(OCc2cccc(-c3ccccc3)c2C)cc1OCc1ccc(-c2ccccc2C#N)cc1]

Example 1090

N-(2-((2-((4-methoxybenzyl)oxy)-4-((2-methyl-[1,1'-biphenyl]-3-yl)methoxy)benzyl)amino)ethyl)acetamide

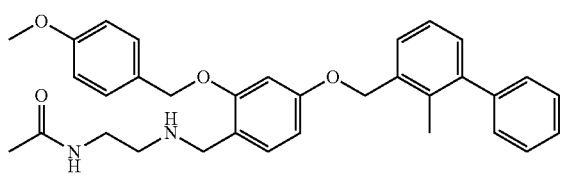 [SMILES: COc1ccc(COc2cc(OCc3cccc(-c4ccccc4)c3C)ccc2CNCCNC(C)=O)cc1]

Example 1091

N-(2-((2-((3-chloro-5-fluorobenzyl)oxy)-4-((2-methyl-[1,1'-biphenyl]-3-yl)methoxy)benzyl)amino) ethyl)acetamide

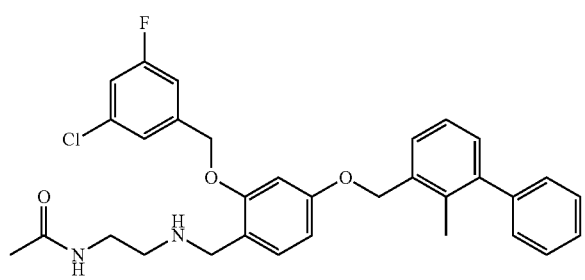

Example 1092

N-(2-((2-((2,6-difluoro-3-methoxybenzyl)oxy)-4-((2-methyl-[1,1'-biphenyl]-3-yl)methoxy)benzyl) amino)ethyl)acetamide

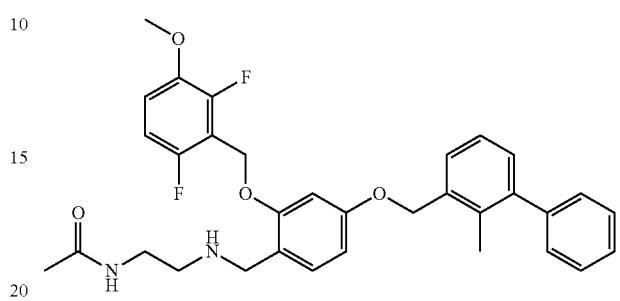

Example 1093

N-(2-((2-((4-fluoro-3-methoxybenzyl)oxy)-4-((2-methyl-[1,1'-biphenyl]-3-yl)methoxy)benzyl)amino) ethyl)acetamide

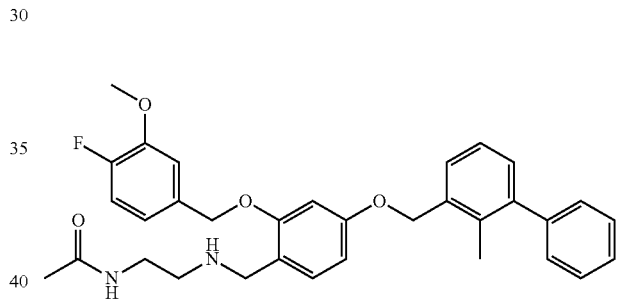

Example 1094

N-(2-((2-((2-fluoro-5-methylbenzyl)oxy)-4-((2-methyl-[1,1'-biphenyl]-3-yl)methoxy)benzyl)amino) ethyl)acetamide

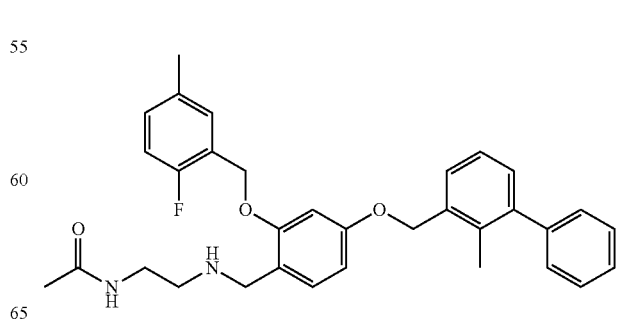

69

Example 1095

N-(2-((2-((5-cyano-2-fluorobenzyl)oxy)-4-((2-methyl-[1,1'-biphenyl]-3-yl)methoxy)benzyl)amino)ethyl)acetamide

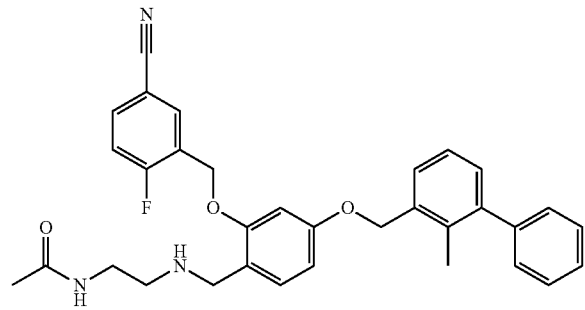 [SMILES: CC(=O)NCCNCc1ccc(OCc2cccc(-c3ccccc3)c2C)cc1OCc1cc(C#N)ccc1F]

Example 1096

N-(2-((2-((3-fluoro-5-methoxybenzyl)oxy)-4-((2-methyl-[1,1'-biphenyl]-3-yl)methoxy)benzyl)amino)ethyl)acetamide

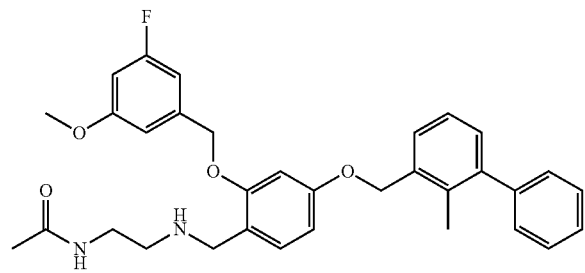 [SMILES: COc1cc(F)cc(COc2cc(OCc3cccc(-c4ccccc4)c3C)ccc2CNCCNC(C)=O)c1]

Example 1097

N-(2-((2-((4-bromo-2-cyanobenzyl)oxy)-4-((2-methyl-[1,1'-biphenyl]-3-yl)methoxy)benzyl)amino)ethyl)acetamide

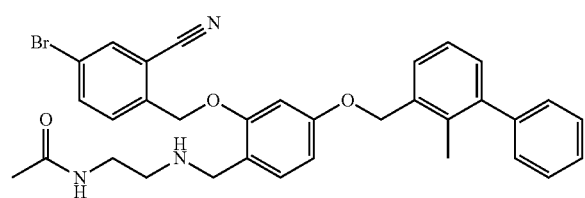 [SMILES: CC(=O)NCCNCc1ccc(OCc2cccc(-c3ccccc3)c2C)cc1OCc1ccc(Br)cc1C#N]

70

Example 1098

N-(2-((2-((1H-indazol-5-yl)methoxy)-4-((2-methyl-[1,1'-biphenyl]-3-yl)methoxy)benzyl)amino)ethyl)acetamide

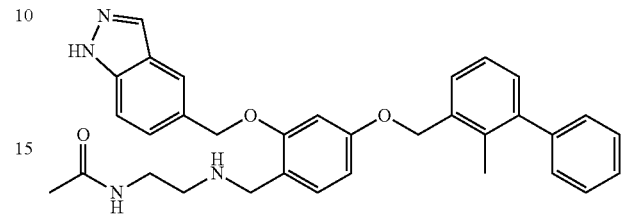

Example 1099

N-(2-((4-((2-methyl-[1,1'-biphenyl]-3-yl)methoxy)-2-((1-(tetrahydro-2H-pyran-2-yl)-1H-indazol-5-yl)methoxy)benzyl)amino)ethyl)acetamide

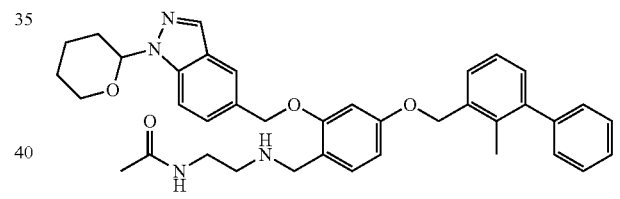

Example 1100

N-(2-((4-((2-methyl-[1,1'-biphenyl]-3-yl)methoxy)-2-(pyrimidin-4-ylmethoxy)benzyl)amino)ethyl)acetamide

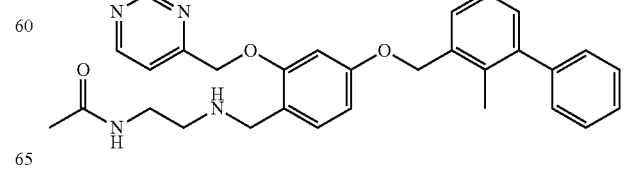

| 71 | 72 |
|---|---|
| Example 1101 | Example 1104 | methyl 2-(3-((2-(((2-acetamidoethyl)amino)methyl)-5-((2-methyl-[1,1'-biphenyl]-3-yl) methoxy)phenoxy)methyl)phenyl)acetate N-(2-((2-((5-methyl-1,2,4-oxadiazol-3-yl)methoxy)-4-((2-methyl-[1,1'-biphenyl]-3-yl) methoxy)benzyl)amino)ethyl)acetamide

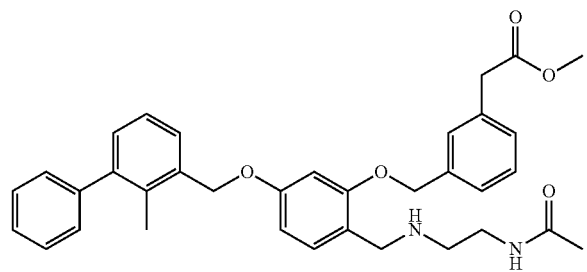 [SMILES: COC(=O)Cc1cccc(COc2cc(OCc3cccc(-c4ccccc4)c3C)ccc2CNCCNC(C)=O)c1]

Example 1102

N-(2-((2-((1H-indazol-6-yl)methoxy)-4-((2-methyl-[1,1'-biphenyl]-3-yl)methoxy)benzyl)amino)ethyl)acetamide Example 1105 tert-butyl 3-((2-(((2-acetamidoethyl)amino)methyl)-5-((2-methyl-[1,1'-biphenyl]-3-yl) methoxy)phenoxy)methyl)benzoate

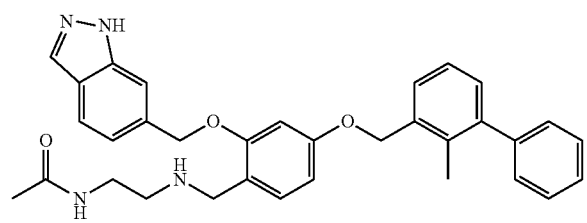 [SMILES: CC(=O)NCCNCc1ccc(OCc2cccc(-c3ccccc3)c2C)cc1OCc1ccc2cn[nH]c2c1]

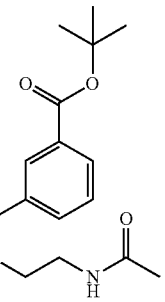

Example 1103 methyl 3-((2-(((2-acetamidoethyl)amino)methyl)-5-((2-methyl-[1,1'-biphenyl]-3-yl) methoxy)phenoxy)methyl)-4-fluorobenzoate Example 1106

N-(2-((2-((3-fluoro-5-(trifluoromethoxy)benzyl)oxy)-4-((2-methyl-[1,1'-biphenyl]-3-yl) methoxy)benzyl)amino)ethyl)acetamide

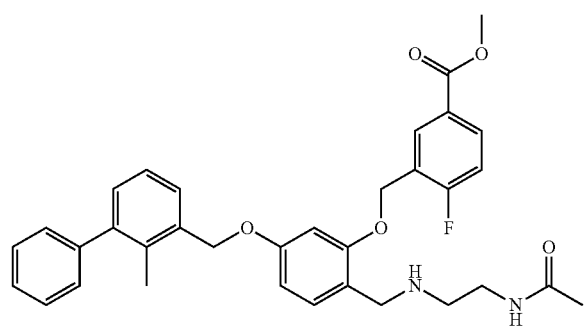 [SMILES: COC(=O)c1ccc(F)c(COc2cc(OCc3cccc(-c4ccccc4)c3C)ccc2CNCCNC(C)=O)c1]

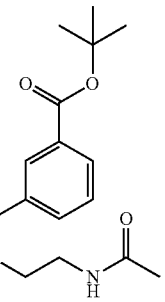

Example 1107

N-(2-((2-((3,5-dimethoxybenzyl)oxy)-4-((2-methyl-[1,1'-biphenyl]-3-yl)methoxy benzyl)amino)ethyl)acetamide

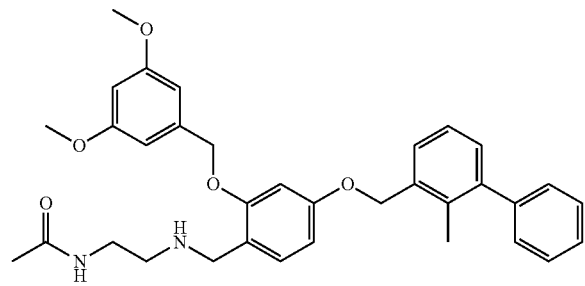 [SMILES: COc1cc(COc2cc(OCc3cccc(-c4ccccc4)c3C)ccc2CNCCNC(C)=O)cc(OC)c1]

Example 1108

N-(2-((2-((4-fluoro-3-methylbenzyl)oxy)-4-((2-methyl-[1,1'-biphenyl]-3-yl)methoxy)benzyl)amino)ethyl)acetamide

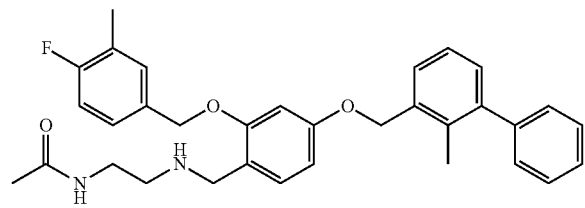 [SMILES: CC(=O)NCCNCc1ccc(OCc2cccc(-c3ccccc3)c2C)cc1OCc1ccc(F)c(C)c1]

Example 1109

N-(2-((2-((5-chloro-2-fluorobenzyl)oxy)-4-((2-methyl-[1,1'-biphenyl]-3-yl)methoxy benzyl)amino)ethyl)acetamide

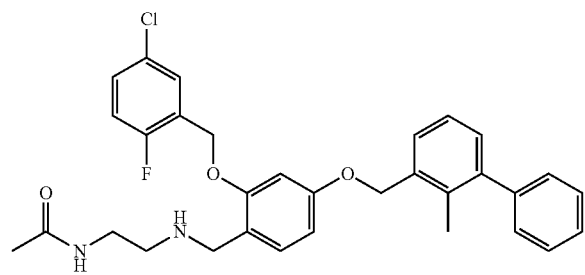 [SMILES: CC(=O)NCCNCc1ccc(OCc2cccc(-c3ccccc3)c2C)cc1OCc1cc(Cl)ccc1F]

Example 1110

N-(2-((2-((3-chloro-4-fluorobenzyl)oxy)-4-((2-methyl-[1,1'-biphenyl]-3-yl)methoxy)benzyl)amino)ethyl)acetamide

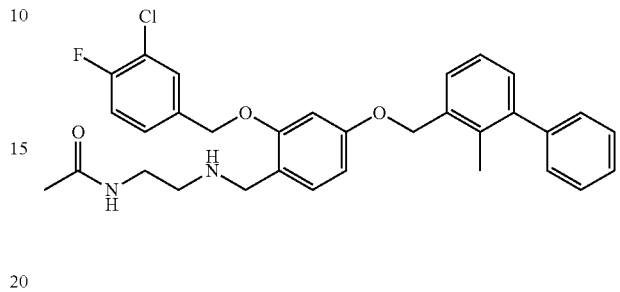

Example 1111

N-(2-((4-((2-methyl-[1,1'-biphenyl]-3-yl)methoxy)-2-(pyridin-4-ylmethoxy)benzyl)amino)ethyl)acetamide

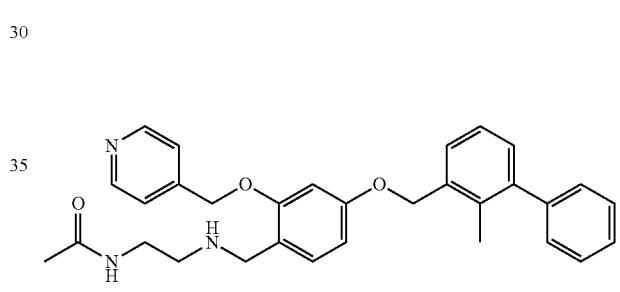

Example 1112

N-(2-((2-((3-(1H-pyrrol-1-yl)benzyl)oxy)-4-((2-methyl-[1,1'-biphenyl]-3-yl)methoxy)benzyl)amino)ethyl)acetamide

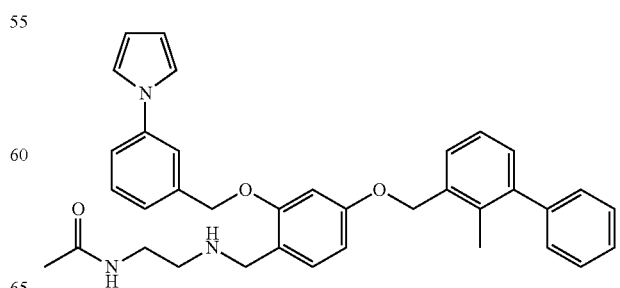

Example 1113

N-(2-((2-((3-fluoro-5-methylbenzyl)oxy)-4-((2-methyl-[1,1'-biphenyl]-3-yl)methoxy)benzyl)amino)ethyl)acetamide

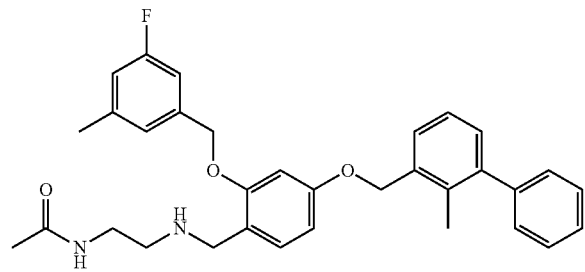 [SMILES: CC(=O)NCCNCc1ccc(OCc2cccc(-c3ccccc3)c2C)cc1OCc1cc(C)cc(F)c1]

Example 1114

N-(2-((2-((3-cyano-4-fluorobenzyl)oxy)-4-((2-methyl-[1,1'-biphenyl]-3-yl)methoxy)benzyl)amino)ethyl)acetamide

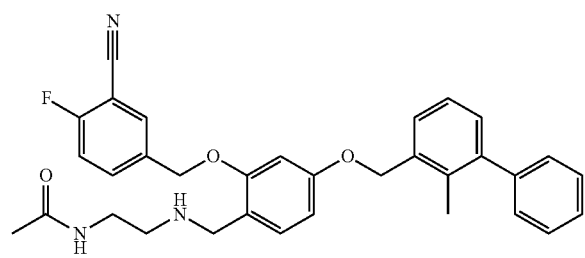 [SMILES: CC(=O)NCCNCc1ccc(OCc2cccc(-c3ccccc3)c2C)cc1OCc1ccc(F)c(C#N)c1]

Example 1115

N-(2-((4-((2-methyl-[1,1'-biphenyl]-3-yl)methoxy)-2-((5-methylisoxazol-3-yl)methoxy)benzyl)amino)ethyl)acetamide

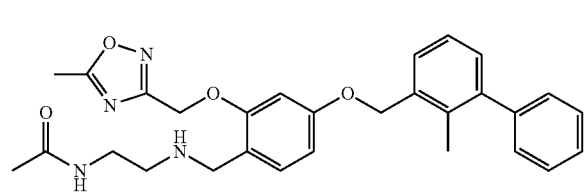 [SMILES: CC(=O)NCCNCc1ccc(OCc2cccc(-c3ccccc3)c2C)cc1OCc1noc(C)n1]

Example 1116

N-(2-((2-((3-(difluoromethoxy)benzyl)oxy)-4-((2-methyl-[1,1'-biphenyl]-3-yl)methoxy)benzyl)amino)ethyl)acetamide

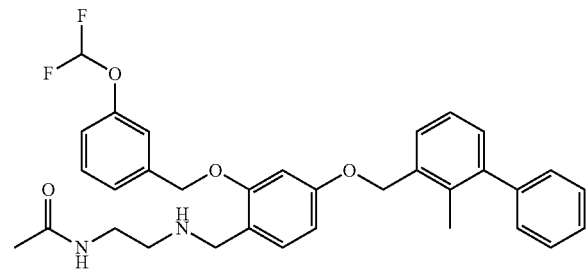 [SMILES: CC(=O)NCCNCc1ccc(OCc2cccc(-c3ccccc3)c2C)cc1OCc1cccc(OC(F)F)c1]

Example 1117

N-(2-((4-((2-methyl-[1,1'-biphenyl]-3-yl)methoxy)-2-(pyridin-3-ylmethoxy)benzyl)amino)ethyl)acetamide

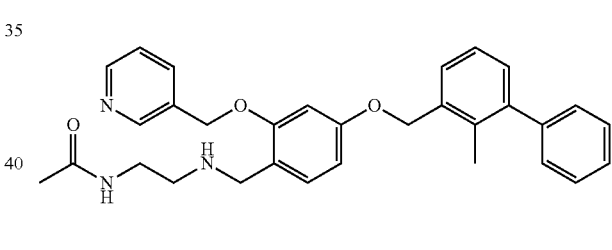

Example 1118

N-(2-((2-(isoquinolin-1-ylmethoxy)-4-((2-methyl-[1,1'-biphenyl]-3-yl)methoxy)benzyl)amino)ethyl)acetamide

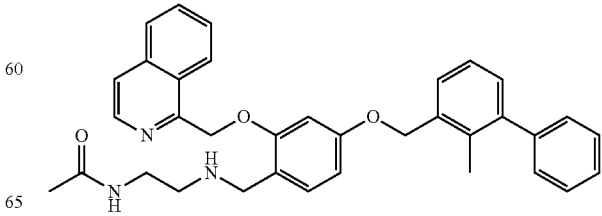

Example 1119 tert-butyl (3-((2-(((2-acetamidoethyl)amino)methyl)-5-((2-methyl-[1,1'-biphenyl]-3-yl) methoxy)phenoxy)methyl)phenyl)carbamate

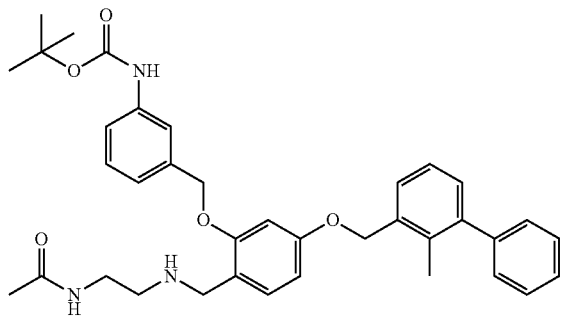 [SMILES: CC(=O)NCCNCc1ccc(OCc2cccc(-c3ccccc3)c2C)cc1OCc1cccc(NC(=O)OC(C)(C)C)c1]

Example 1120

(S)—N-(2-((4-((2-methyl-[1,1'-biphenyl]-3-yl)methoxy)-2-((5-oxopyrrolidin-2-yl)methoxy)benzyl)amino)ethyl)acetamide

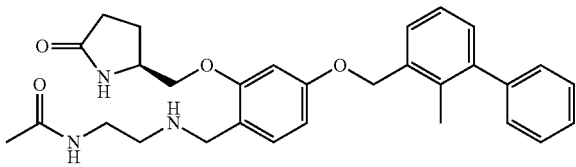 [SMILES: CC(=O)NCCNCc1ccc(OCc2cccc(-c3ccccc3)c2C)cc1OC[C@@H]1CCC(=O)N1]

TABLE

| Example | LCMS Method | Retention Time (min) | M+1 |
|---|---|---|---|
| Example 1024: N-(2-((2-(benzyloxy)-4-((2-methyl-[1,1'-biphenyl]-3-yl)methoxy)benzyl)amino)ethyl)acetamide | M | 3.13 | 495.4 |
| Example 1025: N-(2-((4-((2-methyl-[1,1'-biphenyl]-3-yl)methoxy)-2-((3-methylbenzyl)oxy)benzyl)amino)ethyl)acetamide | M | 3.17 | 509.4 |
| Example 1026: N-(2-((4-((2-methyl-[1,1'-biphenyl]-3-yl)methoxy)-2-(2,2,2-trifluoroethoxy)benzyl)amino)ethyl)acetamide | A | 1.91 | 487.4 |
| Example 1027: N-(2-((4-((2-methyl-[1,1'-biphenyl]-3-yl)methoxy)-2-propoxybenzyl)amino)ethyl)acetamide | A | 1.96 | 447.4 |
| Example 1028: N-(2-((2-((3-cyanobenzyl)oxy)-4-((2-methyl-[1,1'-biphenyl]-3-yl)methoxy)benzyl)amino)ethyl)acetamide | A | 1.98 | 520.3 |
| Example 1029: N-(2-((2-((4-cyanobenzyl)oxy)-4-((2-methyl-[1,1'-biphenyl]-3-yl)methoxy)benzyl)amino)ethyl)acetamide | M | 3.13 | 520.2 |
| Example 1030: N-(2-((2-(2-hydroxyethoxy)-4-((2-methyl-[1,1'-biphenyl]-3-yl)methoxy)benzyl)amino)ethyl)acetamide | A | 1.64 | 449.4 |
| Example 1031: 2-(2-(((2-acetamidoethyl)amino)methyl)-5-((2-methyl-[1,1'-biphenyl]-3-yl)methoxy)phenoxy)acetamide | M | 2.55 | 462.4 |
| Example 1032: methyl 5-(2-(((2-acetamidoethyl)amino)methyl)-5-((2-methyl-[1,1'-biphenyl]-3-yl)methoxy)phenoxy)pentanoate | A | 2.14 | 519.4 |
| Example 1033: N-(2-((4-((2-methyl-[1,1'-biphenyl]-3-yl)methoxy)-2-phenethoxybenzyl)amino)ethyl)acetamide | M | 3.12 | 509.4 |
| Example 1034: methyl 3-((2-(((2-acetamidoethyl)amino)methyl)-5-((2-methyl-[1,1'-biphenyl]-3-yl)methoxy)phenoxy)methyl)benzoate | M | 3.06 | 553.6 |
| Example 1035: N-(2-((2-(3-hydroxypropoxy)-4-((2-methyl-[1,1'-biphenyl]-3-yl)methoxy)benzyl)amino)ethyl)acetamide | M | 2.82 | 463.4 |
| Example 1036: methyl 4-(2-(((2-acetamidoethyl)amino)methyl)-5-((2-methyl-[1,1'-biphenyl]-3-yl)methoxy)phenoxy)butanoate | M | 2.97 | 505.4 |
| Example 1037: N-(2-((2-((3-(hydroxymethyl)benzyl)oxy)-4-((2-methyl-[1,1'-biphenyl]-3-yl)methoxy)benzyl)amino)ethyl)acetamide | A | 1.83 | 525.4 |
| Example 1038: N-(2-((2-((2-(hydroxymethyl)benzyl)oxy)-4-((2-methyl-[1,1'-biphenyl]-3-yl)methoxy)benzyl)amino)ethyl)acetamide | M | 2.89 | 525.5 |
| Example 1039: 4-(2-(((2-acetamidoethyl)amino)methyl)-5-((2-methyl-[1,1'-biphenyl]-3-yl)methoxy)phenoxy)methyl)benzamide | M | 2.83 | 538.4 |
| Example 1040: N-(2-((2-((4-acetylbenzyl)oxy)-4-((2-methyl-[1,1'-biphenyl]-3-yl)methoxy)benzyl)amino)ethyl)acetamide | A | 2.09 | 537.4 |
| Example 1041: N-(2-((4-((2-methyl-[1,1'-biphenyl]-3-yl)methoxy)-2-((2-(methylsulfonyl)benzyl)oxy)benzyl)amino)ethyl)acetamide | M | 2.9 | 573.4 |
| Example 1042: N-(2-((2-(3-methoxypropoxy)-4-((2-methyl-[1,1'-biphenyl]-3-yl)methoxy)benzyl)amino)ethyl)acetamide | A | 2.04 | 477.4 |
| Example 1043: 4-(2-(((2-acetamidoethyl)amino)methyl)-5-((2-methyl-[1,1'-biphenyl]-3-yl)methoxy)phenoxy)methyl)benzoic acid | A | 1.71 | 539.4 |
| Example 1044: N-(2-((2-ethoxy-4-((2-methyl-[1,1'-biphenyl]-3-yl)methoxy)benzyl)amino)ethyl)acetamide | A | 1.76 | 433.5 |
| Example 1045: N-(2-((4-((2-methyl-[1,1'-biphenyl]-3-yl)methoxy)-2-((2-methylbenzyl)oxy)benzyl)amino)ethyl)acetamide | M | 3.16 | 509.3 |
| Example 1046: N-(2-((2-((4-(tert-butyl)benzyl)oxy)-4-((2-methyl-[1,1'-biphenyl]-3-yl)methoxy)benzyl)amino)ethyl)acetamide | M | 3.35 | 551.1 |
| Example 1047: N-(2-((4-((2-methyl-[1,1'-biphenyl]-3-yl)methoxy)-2-((4-methylbenzyl)oxy)benzyl)amino)ethyl)acetamide | M | 3.17 | 509.4 |
| Example 1048: N-(2-((2-((2-fluorobenzyl)oxy)-4-((2-methyl-[1,1'-biphenyl]-3-yl)methoxy)benzyl)amino)ethyl)acetamide | M | 3.09 | 513.4 |
| Example 1049: N-(2-((2-((2,6-difluorobenzyl)oxy)-4-((2-methyl-[1,1'-biphenyl]-3-yl)methoxy)benzyl)amino)ethyl)acetamide | M | 3.08 | 531.2 |

TABLE-continued

LCMS Characterization for Examples

| Example | LCMS Method | Retention Time (min) | M+1 |
|---|---|---|---|
| Example 1050: N-(2-((2-((3-fluorobenzyl)oxy)-4-((2-methyl-[1,1'-biphenyl]-3-yl)methoxy)benzyl)amino)ethyl)acetamide | M | 3.08 | 513.4 |
| Example 1051: N-(2-((4-((2-methyl-[1,1'-biphenyl]-3-yl)methoxy)-2-((3-(trifluoromethyl)benzyl)oxy)benzyl)amino)ethyl)acetamide | M | 3.16 | 563.4 |
| Example 1052: N-(2-((4-((2-methyl-[1,1'-biphenyl]-3-yl)methoxy)-2-((4-(trifluoromethyl)benzyl)oxy)benzyl)amino)ethyl)acetamide | A | 2.22 | 563.2 |
| Example 1053: N-(2-((2-((2-chlorobenzyl)oxy)-4-((2-methyl-[1,1'-biphenyl]-3-yl)methoxy)benzyl)amino)ethyl)acetamide | M | 3.4 | 529.2 |
| Example 1054: N-(2-((2-((3-chlorobenzyl)oxy)-4-((2-methyl-[1,1'-biphenyl]-3-yl)methoxy)benzyl)amino)ethyl)acetamide | A | 2.16 | 529.2 |
| Example 1055: N-(2-((2-((2-cyanobenzyl)oxy)-4-((2-methyl-[1,1'-biphenyl]-3-yl)methoxy)benzyl)amino)ethyl)acetamide | A | 1.98 | 520.3 |
| Example 1056: N-(2-((4-((2-methyl-[1,1'-biphenyl]-3-yl)methoxy)-2-(naphthalen-2-ylmethoxy)benzyl)amino)ethyl)acetamide | A | 2.24 | 545.3 |
| Example 1057: N-(2-((4-((2-methyl-[1,1'-biphenyl]-3-yl)methoxy)-2-((2-nitrobenzyl)oxy)benzyl)amino)ethyl)acetamide | A | 2.06 | 540.2 |
| Example 1058: N-(2-((4-((2-methyl-[1,1'-biphenyl]-3-yl)methoxy)-2-((4-nitrobenzyl)oxy)benzyl)amino)ethyl)acetamide | A | 2.05 | 540.3 |
| Example 1059: N-(2-((2-((3,4-difluorobenzyl)oxy)-4-((2-methyl-[1,1'-biphenyl]-3-yl)methoxy)benzyl)amino)ethyl)acetamide | M | 3.28 | 531.2 |
| Example 1060: N-(2-((2-((2,5-difluorobenzyl)oxy)-4-((2-methyl-[1,1'-biphenyl]-3-yl)methoxy)benzyl)amino)ethyl)acetamide | A | 2.09 | 531.2 |
| Example 1061: N-(2-((2-((3,5-bis(trifluoromethyl)benzyl)oxy)-4-((2-methyl-[1,1'-biphenyl]-3-yl)methoxy)benzyl)amino)ethyl)acetamide | A | 2.37 | 631.2 |
| Example 1062: N-(2-((2-((3,5-difluorobenzyl)oxy)-4-((2-methyl-[1,1'-biphenyl]-3-yl)methoxy)benzyl)amino)ethyl)acetamide | A | 2.26 | 531.4 |
| Example 1063: N-(2-((4-((2-methyl-[1,1'-biphenyl]-3-yl)methoxy)-2-(naphthalen-1-ylmethoxy)benzyl)amino)ethyl)acetamide | M | 3.24 | 545.4 |
| Example 1064: N-(2-((2-((2,4-difluorobenzyl)oxy)-4-((2-methyl-[1,1'-biphenyl]-3-yl)methoxy)benzyl)amino)ethyl)acetamide | M | 3.12 | 531.4 |
| Example 1065: N-(2-((2-((3,5-dimethylbenzyl)oxy)-4-((2-methyl-[1,1'-biphenyl]-3-yl)methoxy)benzyl)amino)ethyl)acetamide | M | 3.27 | 523.4 |
| Example 1066: N-(2-((4-((2-methyl-[1,1'-biphenyl]-3-yl)methoxy)-2-((2-(trifluoromethyl)benzyl)oxy)benzyl)amino)ethyl)acetamide | M | 3.23 | 563.4 |
| Example 1067: methyl 4-(((2-acetamidoethyl)amino)methyl)-5-((2-methyl-[1,1'-biphenyl]-3-yl)methoxy)phenoxy)methyl)benzoate | M | 3.04 | 553.4 |
| Example 1068: N-(2-((2-((4-chlorobenzyl)oxy)-4-((2-methyl-[1,1'-biphenyl]-3-yl)methoxy)benzyl)amino)ethyl)acetamide | A | 2.23 | 529.4 |
| Example 1069: N-(2-((2-((3,4-dichlorobenzyl)oxy)-4-((2-methyl-[1,1'-biphenyl]-3-yl)methoxy)benzyl)amino)ethyl)acetamide | M | 3.24 | 563.6 |
| Example 1070: N-(2-((2-((2-fluoro-3-methylbenzyl)oxy)-4-((2-methyl-[1,1'-biphenyl]-3-yl)methoxy)benzyl)amino)ethyl)acetamide | M | 3.2 | 549.6 |
| Example 1071: N-(2-((2-((2,3-difluorobenzyl)oxy)-4-((2-methyl-[1,1'-biphenyl]-3-yl)methoxy)benzyl)amino)ethyl)acetamide | A | 2.25 | 531.4 |
| Example 1072: N-(2-((2-((3-chloro-2-fluorobenzyl)oxy)-4-((2-methyl-[1,1'-biphenyl]-3-yl)methoxy)benzyl)amino)ethyl)acetamide | M | 3.2 | 547.4 |
| Example 1073: N-(2-((2-((3-benzoylbenzyl)oxy)-4-((2-methyl-[1,1'-biphenyl]-3-yl)methoxy)benzyl)amino)ethyl)acetamide | M | 3.15 | 599.4 |
| Example 1074: N-(2-((4-((2-methyl-[1,1'-biphenyl]-3-yl)methoxy)-2-(quinolin-8-ylmethoxy)benzyl)amino)ethyl)acetamide | M | 3.07 | 546.4 |
| Example 1075: N-(2-((2-((4-fluorobenzyl)oxy)-4-((2-methyl-[1,1'-biphenyl]-3-yl)methoxy)benzyl)amino)ethyl)acetamide | M | 3.07 | 513.4 |
| Example 1076: N-(2-((4-((2-methyl-[1,1'-biphenyl]-3-yl)methoxy)-2-((3-nitrobenzyl)oxy)benzyl)amino)ethyl)acetamide | M | 3.23 | 540.2 |
| Example 1077: N-(2-((2-((3-(2-fluorophenoxy)benzyl)oxy)-4-((2-methyl-[1,1'-biphenyl]-3-yl)methoxy)benzyl)amino)ethyl)acetamide | M | 3.24 | 605.6 |
| Example 1078: N-(2-((2-((3-(4-fluorophenoxy)benzyl)oxy)-4-((2-methyl-[1,1'-biphenyl]-3-yl)methoxy)benzyl)amino)ethyl)acetamide | M | 3.27 | 605.6 |
| Example 1079: N-(2-((2-((2-fluoro-3-(trifluoromethyl)benzyl)oxy)-4-((2-methyl-[1,1'-biphenyl]-3-yl)methoxy)benzyl)amino)ethyl)acetamide | M | 3.19 | 581.6 |
| Example 1080: N-(2-((2-((2-fluoro-5-(trifluoromethyl)benzyl)oxy)-4-((2-methyl-[1,1'-biphenyl]-3-yl)methoxy)benzyl)amino)ethyl)acetamide | M | 3.18 | 581.6 |
| Example 1081: N-(2-((2-((3-fluoro-5-(trifluoromethyl)benzyl)oxy)-4-((2-methyl-[1,1'-biphenyl]-3-yl)methoxy)benzyl)amino)ethyl)acetamide | M | 3.2 | 581.6 |
| Example 1082: N-(2-((4-((2-methyl-[1,1'-biphenyl]-3-yl)methoxy)-2-((3-(trifluoromethoxy)benzyl)oxy)benzyl)amino)ethyl)acetamide | M | 3.21 | 579.4 |
| Example 1083: N-(2-((2-((4-chloro-2-(trifluoromethyl)quinolin-6-yl)methoxy)-4-((2-methyl-[1,1'-biphenyl]-3-yl)methoxy)benzyl)amino)ethyl)acetamide | A | 2.42 | 648.4 |
| Example 1084: N-(2-((4-((2-methyl-[1,1'-biphenyl]-3-yl)methoxy)-2-((4-(methylsulfonyl)benzyl)oxy)benzyl)amino)ethyl)acetamide | M | 2.74 | 573.3 |
| Example 1085: N-(2-((2-((2-(difluoromethoxy)benzyl)oxy)-4-((2-methyl-[1,1'-biphenyl]-3-yl)methoxy)benzyl)amino)ethyl)acetamide | A | 2.09 | 561.8 |

TABLE-continued

LCMS Characterization for Examples

| Example | LCMS Method | Retention Time (min) | M+1 |
|---|---|---|---|
| Example 1086: N-(2-((2-((3-methoxybenzyl)oxy)-4-((2-methyl-[1,1'-biphenyl]-3-yl)methoxy)benzyl)amino)ethyl)acetamide | A | 2.07 | 525.3 |
| Example 1087: N-(2-((4-((2-methyl-[1,1'-biphenyl]-3-yl)methoxy)-2-((2-(trifluoromethoxy)benzyl)oxy)benzyl)amino)ethyl)acetamide | M | 3.24 | 579.3 |
| Example 1088: N-(2-((2-((4-(difluoromethoxy)benzyl)oxy)-4-((2-methyl-[1,1'-biphenyl]-3-yl)methoxy)benzyl)amino)ethyl)acetamide | A | 2.2 | 561.4 |
| Example 1089: N-(2-((2-((2'-cyano-[1,1'-biphenyl]-4-yl)methoxy)-4-((2-methyl-[1,1'-biphenyl]-3-yl)methoxy)benzyl)amino)ethyl)acetamide | M | 3.11 | 596.4 |
| Example 1090: N-(2-((2-((4-methoxybenzyl)oxy)-4-((2-methyl-[1,1'-biphenyl]-3-yl)methoxy)benzyl)amino)ethyl)acetamide | A | 2.16 | 525.3 |
| Example 1091: N-(2-((2-((3-chloro-5-fluorobenzyl)oxy)-4-((2-methyl-[1,1'-biphenyl]-3-yl)methoxy)benzyl)amino)ethyl)acetamide | M | 3.21 | 547.3 |
| Example 1092: N-(2-((2-((2,6-difluoro-3-methoxybenzyl)oxy)-4-((2-methyl-[1,1'-biphenyl]-3-yl)methoxy)benzyl)amino)ethyl)acetamide | A | 2.16 | 561.3 |
| Example 1093: N-(2-((2-((4-fluoro-3-methoxybenzyl)oxy)-4-((2-methyl-[1,1'-biphenyl]-3-yl)methoxy)benzyl)amino)ethyl)acetamide | A | 2.17 | 543.3 |
| Example 1094: N-(2-((2-((2-fluoro-5-methylbenzyl)oxy)-4-((2-methyl-[1,1'-biphenyl]-3-yl)methoxy)benzyl)amino)ethyl)acetamide | M | 3.15 | 527.3 |
| Example 1095: N-(2-((2-((5-cyano-2-fluorobenzyl)oxy)-4-((2-methyl-[1,1'-biphenyl]-3-yl)methoxy)benzyl)amino)ethyl)acetamide | M | 2.96 | 538.3 |
| Example 1096: N-(2-((2-((3-fluoro-5-methoxybenzyl)oxy)-4-((2-methyl-[1,1'-biphenyl]-3-yl)methoxy)benzyl)amino)ethyl)acetamide | M | 3.11 | 543.4 |
| Example 1097: N-(2-((2-((4-bromo-2-cyanobenzyl)oxy)-4-((2-methyl-[1,1'-biphenyl]-3-yl)methoxy)benzyl)amino)ethyl)acetamide | A | 2.15 | 600.3 |
| Example 1098: N-(2-((2-((1H-indazol-5-yl)methoxy)-4-((2-methyl-[1,1'-biphenyl]-3-yl)methoxy)benzyl)amino)ethyl)acetamide | M | 2.91 | 535.6 |
| Example 1099: N-(2-((4-((2-methyl-[1,1'-biphenyl]-3-yl)methoxy)-2-((1-(tetrahydro-2H-pyran-2-yl)-1H-indazol-5-yl)methoxy)benzyl)amino)ethyl)acetamide | M | 3.09 | 619.4 |
| Example 1100: N-(2-((4-((2-methyl-[1,1'-biphenyl]-3-yl)methoxy)-2-(pyrimidin-4-ylmethoxy)benzyl)amino)ethyl)acetamide | A | 1.81 | 497.3 |
| Example 1101: methyl 2-(3-((2-(((2-acetamidoethyl)amino)methyl)-5-((2-methyl-[1,1'-biphenyl]-3-yl)methoxy)phenoxy)methyl)phenyl)acetate | M | 2.98 | 567.3 |
| Example 1102: N-(2-((2-((1H-indazol-6-yl)methoxy)-4-((2-methyl-[1,1'-biphenyl]-3-yl)methoxy)benzyl)amino)ethyl)acetamide | M | 2.93 | 535.3 |
| Example 1103: methyl 3-((2-(((2-acetamidoethyl)amino)methyl)-5-((2-methyl-[1,1'-biphenyl]-3-yl)methoxy)phenoxy)methyl)-4-fluorobenzoate | M | 3.1 | 571.4 |
| Example 1104: N-(2-((2-((5-methyl-1,2,4-oxadiazol-3-yl)methoxy)-4-((2-methyl-[1,1'-biphenyl]-3-yl)methoxy)benzyl)amino)ethyl)acetamide | M | 2.81 | 501.5 |
| Example 1105: tert-butyl 3-((2-(((2-acetamidoethyl)amino)methyl)-5-((2-methyl-[1,1'-biphenyl]-3-yl)methoxy)phenoxy)methyl)benzoate | M | 3.27 | 595.4 |
| Example 1106: N-(2-((2-((3-fluoro-5-(trifluoromethoxy)benzyl)oxy)-4-((2-methyl-[1,1'-biphenyl]-3-yl)methoxy)benzyl)amino)ethyl)acetamide | M | 3.24 | 597.3 |
| Example 1107: N-(2-((2-((3,5-dimethoxybenzyl)oxy)-4-((2-methyl-[1,1'-biphenyl]-3-yl)methoxy)benzyl)amino)ethyl)acetamide | M | 3.09 | 555.6 |
| Example 1108: N-(2-((2-((4-fluoro-3-methylbenzyl)oxy)-4-((2-methyl-[1,1'-biphenyl]-3-yl)methoxy)benzyl)amino)ethyl)acetamide | A | 2.15 | 527.6 |
| Example 1109: N-(2-((2-((5-chloro-2-fluorobenzyl)oxy)-4-((2-methyl-[1,1'-biphenyl]-3-yl)methoxy)benzyl)amino)ethyl)acetamide | A | 2.14 | 547.6 |
| Example 1110: N-(2-((2-((3-chloro-4-fluorobenzyl)oxy)-4-((2-methyl-[1,1'-biphenyl]-3-yl)methoxy)benzyl)amino)ethyl)acetamide | A | 2.15 | 547.6 |
| Example 1111: N-(2-((4-((2-methyl-[1,1'-biphenyl]-3-yl)methoxy)-2-(pyridin-4-ylmethoxy)benzyl)amino)ethyl)acetamide | A | 1.68 | 496.5 |
| Example 1112: N-(2-((2-((3-(1H-pyrrol-1-yl)benzyl)oxy)-4-((2-methyl-[1,1'-biphenyl]-3-yl)methoxy)benzyl)amino)ethyl)acetamide | M | 3.18 | 560.6 |
| Example 1113: N-(2-((2-((3-fluoro-5-methylbenzyl)oxy)-4-((2-methyl-[1,1'-biphenyl]-3-yl)methoxy)benzyl)amino)ethyl)acetamide | A | 2.14 | 527.6 |
| Example 1114: N-(2-((2-((3-cyano-4-fluorobenzyl)oxy)-4-((2-methyl-[1,1'-biphenyl]-3-yl)methoxy)benzyl)amino)ethyl)acetamide | A | 1.99 | 538.5 |
| Example 1115: N-(2-((4-((2-methyl-[1,1'-biphenyl]-3-yl)methoxy)-2-((5-methylisoxazol-3-yl)methoxy)benzyl)amino)ethyl)acetamide | A | 1.82 | 500.5 |
| Example 1116: N-(2-((2-((3-(difluoromethoxy)benzyl)oxy)-4-((2-methyl-[1,1'-biphenyl]-3-yl)methoxy)benzyl)amino)ethyl)acetamide | A | 2.08 | 561.5 |
| Example 1117: N-(2-((4-((2-methyl-[1,1'-biphenyl]-3-yl)methoxy)-2-(pyridin-3-ylmethoxy)benzyl)amino)ethyl)acetamide | M | 2.8 | 496.3 |
| Example 1118: N-(2-((2-((isoquinolin-1-ylmethoxy)-4-((2-methyl-[1,1'-biphenyl]-3-yl)methoxy)benzyl)amino)ethyl)acetamide | M | 3 | 546.6 |
| Example 1119: tert-butyl (3-((2-(((2-acetamidoethyl)amino)methyl)-5-((2-methyl-[1,1'-biphenyl]-3-yl)methoxy)phenoxy)methyl)phenyl)carbamate | A | 2.28 | 610.5 |
| Example 1120: (S)-N-(2-((4-((2-methyl-[1,1'-biphenyl]-3-yl)methoxy)-2-((5-oxopyrrolidin-2-yl)methoxy)benzyl)amino)ethyl)acetamide | A | 1.61 | 502.5 |

Intermediate 4-((3-(2,3-dihydrobenzo[b][1,4]dioxin-6-yl)-2-methylbenzyl)oxy)-2-hydroxy benzaldehyde

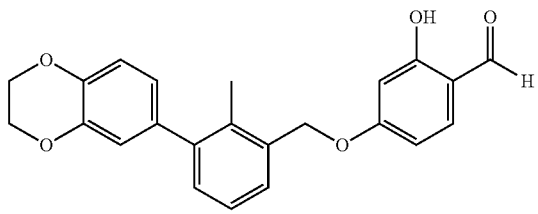 [SMILES: Cc1c(COc2ccc(C=O)c(O)c2)cccc1-c1ccc2c(c1)OCCO2]

Combined 2,4-dihydroxybenzaldehyde (0.356 g, 2.58 mmol), triphenylphosphine (0.675 g, 2.58 mmol) and (3-(2,3-dihydrobenzo[b][1,4]dioxin-6-yl)-2-methylphenyl)methanol (0.6 g, 2.341 mmol) in dry tetrahydrofuran (10 mL) and cooled on an ice/water bath. Added diisopropyl azodicarboxylate (0.501 mL, 2.58 mmol) in tetrahydrofuran (10 mL) dropwise. The resulting yellow solution was allowed to slowly warm to room temperature with stirring overnight. Excess solvent was removed by rotary evaporation. The reaction mixture containing the product was purified on silica gel using ethyl acetate in hexanes as eluent to provide the title compound (0.5 g, 56%). $^1$H NMR (400 MHz, CHLOROFORM-d) δ 11.52 (s, 1H), 9.76 (s, 1H), 7.49 (d, J=8.6 Hz, 1H), 7.43-7.36 (m, 1H), 7.31-7.25 (m, 2H, coincident with residual chloroform), 6.94 (d, J=8.3 Hz, 1H), 6.85 (d, J=2.0 Hz, 1H), 6.81 (s, 1H), 6.69-6.63 (m, 1H), 6.59 (d, J=2.0 Hz, 1H), 5.16 (s, 2H), 4.33 (s, 4H), 2.28 (s, 3H).

Example: 1121

(S)-4-(2-(3-cyanobenzyloxy)-4-(3-(2,3-dihydrobenzo[b][1,4]dioxin-6-yl)-2-methylbenzyloxy)benzylamino)-3-hydroxybutanoic acid

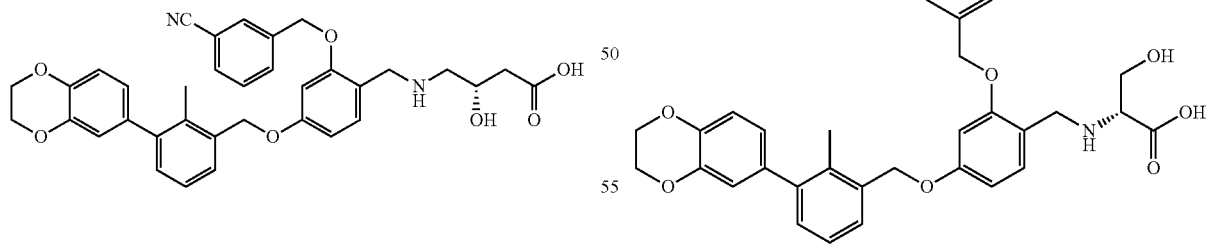

Added a solution of triethyl amine (15.33 µl, 0.110 mmol) in dimethylformamide (1000 µl) to 3-(bromomethyl)benzonitrile (21.56 mg, 0.110 mmol) and 4-((3-(2,3-dihydrobenzo[b][1,4]dioxin-6-yl)-2-methylbenzyl)oxy)-2-hydroxybenzaldehyde (37.6 mg, 0.1 mmol) and stirred overnight at room temperature. Added sodium triacetoxyhydroborate (63.6 mg, 0.300 mmol) and (S)-4-amino-3-hydroxybutanoic acid (23.82 mg, 0.200 mmol) and stirred at room temperature for 72 hours. The crude material was purified via preparative LCMS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/minutes Fractions containing the desired product were combined and dried via centrifugal evaporation. The yield of the product was 3.1 mg, and its estimated purity by LCMS analysis was 100%. Two analytical LCMS injections were used to determine the final purity. LCMS Condition A: 1.7 minutes, M+1=595.3, M−1=593.2, EM=594.2. LCMS Condition M: 3.0 minutes, M+1=595.3, M−1=593.3, EM=594.2. $^1$H NMR (500 MHz, DMSO-d$_6$) δ 7.95 (s, 1H), 7.85 (d, J=8.1 Hz, 1H), 7.81 (d, J=7.7 Hz, 1H), 7.65-7.60 (m, 1H), 7.41 (d, J=7.3 Hz, 1H), 7.29-7.21 (m, 2H), 7.16 (d, J=7.3 Hz, 1H), 6.93 (d, J=8.1 Hz, 1H), 6.80-6.73 (m, 3H), 6.68 (d, J=8.4 Hz, 1H), 5.22 (s, 2H), 5.11 (s, 2H), 4.29 (s, 4H), 3.91 (t, J=5.9 Hz, 1H), 3.84-3.69 (m, 2H), 2.62 (d, J=5.9 Hz, 2H), 2.41-2.22 (m, 2H), 2.20 (s, 3H).

The following examples were prepared in a similar manner as (S)-4-(2-(3-cyanobenzyloxy)-4-(3-(2,3-dihydrobenzo[b][1,4]dioxin-6-yl)-2-methylbenzyloxy) benzylamino)-3-hydroxybutanoic acid from 3-((5-(3-(2,3-dihydrobenzo[b][1,4]dioxin-6-yl)-2-methylbenzyloxy)-2-formylphenoxy)methyl)benzonitrile and the appropriate amine. LCMS for these examples is given in tabular form.

Example 1122

(R)-2-(2-(3-cyanobenzyloxy)-4-(3-(2,3-dihydrobenzo[b][1,4]dioxin-6-yl)-2-methylbenzyloxy)benzylamino)-3-hydroxypropanoic acid

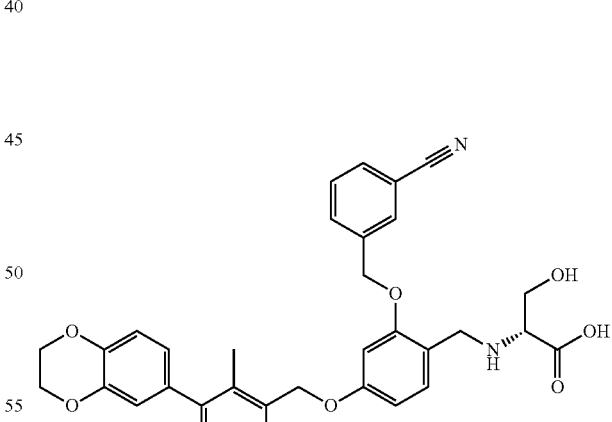

$^1$H NMR (DMSO-d$_6$) δ 8.01 (s, 1H), 7.91 (d, 1H), 7.81 (d, 1H), 7.61 (m, 1H), 7.40 (d, 1H), 7.34 (d, 1H), 7.23 (m, 1H), 7.17 (d, 1H), 6.93 (d, 1H), 6.82 (br. s., 1H), 6.69-6.80 (m, 3H), 5.20-5.29 (m, 2H), 5.13 (s, 2H), 4.29 (s, 4H), 4.12 (d, 1H), 4.05 (d, 1H), 3.90 (s, 1H), 3.71-3.80 (m, 1H), 3.65 (m, 1H), 3.18 (br. s., 1H), 2.19 (s, 3H).

Example 1123

(2R,3S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

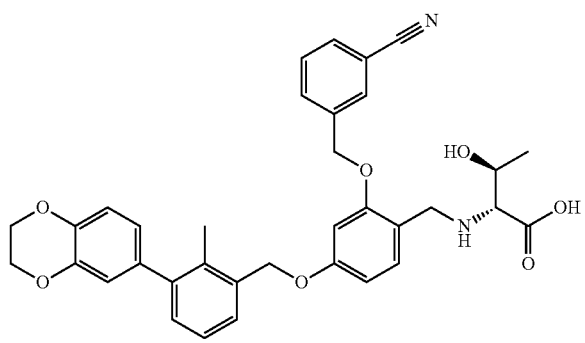 [SMILES: Cc1c(COc2ccc(CN[C@@H](C(=O)O)[C@H](C)O)c(OCc3cccc(C#N)c3)c2)cccc1-c1ccc2c(c1)OCCO2]

Example 1124

2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

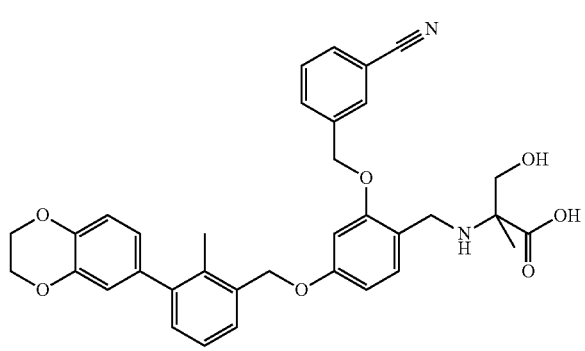 [SMILES: Cc1c(COc2ccc(CNC(C)(CO)C(=O)O)c(OCc3cccc(C#N)c3)c2)cccc1-c1ccc2c(c1)OCCO2]

Example 1125

(2R,3R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

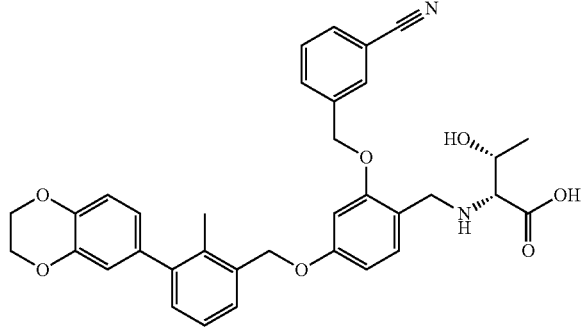 [SMILES: Cc1c(COc2ccc(CN[C@@H](C(=O)O)[C@@H](C)O)c(OCc3cccc(C#N)c3)c2)cccc1-c1ccc2c(c1)OCCO2]

$^1$H NMR (DMSO-$d_6$) δ 8.02 (s, 1H), 7.90 (d, 1H), 7.82 (d, 1H), 7.62 (m, 1H), 7.41 (d, 1H), 7.33 (d, 1H), 7.24 (m, 1H), 7.17 (d, 1H), 6.93 (d, 1H), 6.68-6.84 (m, 4H), 5.20-5.28 (m, 2H), 5.13 (s, 2H), 4.29 (s, 4H), 3.94-4.08 (m, 3H), 3.10 (d, 1H), 2.20 (s, 3H), 1.06 (d, 3H).

Example 1126

(S)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid

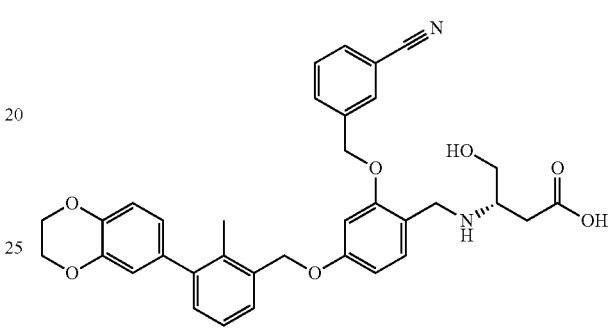

$^1$H NMR (METHANOL-$d_4$) δ 7.93 (s, 1H), 7.88 (d, 1H), 7.68-7.73 (m, 1H), 7.56-7.62 (m, 1H), 7.32-7.41 (m, 2H), 7.14-7.24 (m, 2H), 6.89 (d, 1H), 6.77 (d, 1H), 6.67-6.76 (m, 3H), 5.30 (s, 2H), 5.14 (s, 2H), 4.34 (d, 1H), 4.29 (s, 4H), 4.21 (d, 1H), 3.90 (m, 1H), 3.64 (m, 1H), 3.35-3.44 (m, 2H), 2.39-2.57 (m, 2H), 2.22 (s, 3H).

Example 1127

(R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

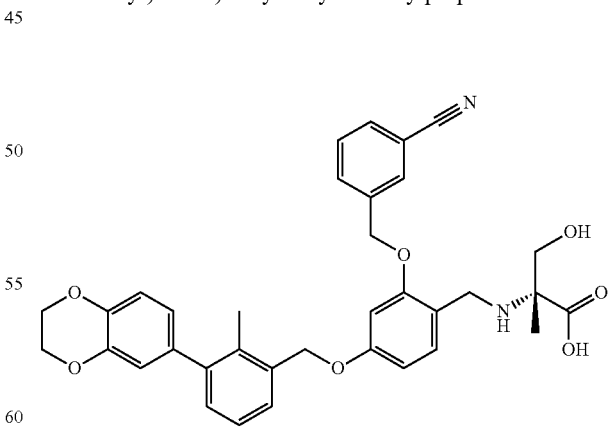

$^1$H NMR (METHANOL-$d_4$) δ 8.00 (s, 2H), 7.87-7.96 (m, 2H), 7.71 (d, 1H), 7.60 (m, 1H), 7.33-7.44 (m, 2H), 7.14-7.23 (m, 2H), 6.89 (d, 1H), 6.80 (d, 1H), 6.70-6.77 (m, 3H), 5.29 (s, 2H), 5.15 (s, 2H), 4.29 (s, 4H), 4.25 (s, 2H), 3.95 (d, 1H), 3.74 (d, 1H), 2.22 (s, 3H), 1.45 (s, 3H).

Example 1128

(S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

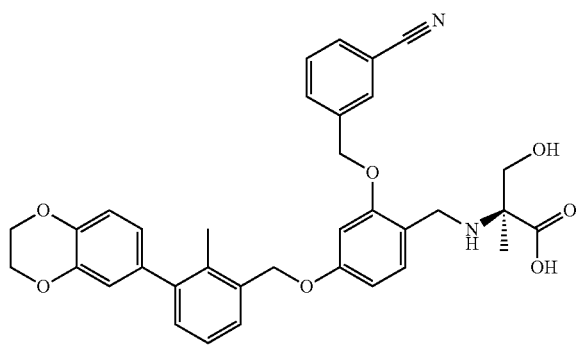 [SMILES: Cc1c(COc2ccc(CN[C@@](C)(CO)C(=O)O)c(OCc3cccc(C#N)c3)c2)cccc1-c1ccc2c(c1)OCCO2]

$^1$H NMR (DMSO-d$_6$) δ 8.01 (s, 1H), 7.93 (d, 1H), 7.81 (d, 1H), 7.61 (m, 1H), 7.37 (d, 1H), 7.40 (d, 1H), 7.23 (m, 1H), 7.17 (d, 1H), 6.93 (d, 1H), 6.81 (s, 1H), 6.78 (d, 1H), 6.68-6.77 (m, 2H), 5.24 (s, 2H), 5.14 (s, 2H), 4.29 (s, 4H), 3.63 (d, 1H), 3.55 (d, 1H), 3.18 (s, 1H), 2.20 (s, 3H), 1.91 (s, 1H), 1.26 (s, 3H).

Example 1129

(R)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid

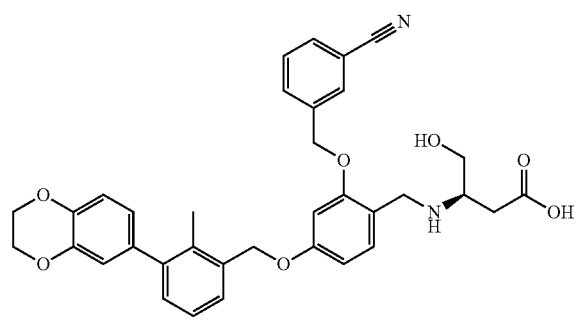 [SMILES: Cc1c(COc2ccc(CN[C@@H](CO)CC(=O)O)c(OCc3cccc(C#N)c3)c2)cccc1-c1ccc2c(c1)OCCO2]

$^1$H NMR (METHANOL-d$_4$) δ 7.94 (s, 1H), 7.89 (d, 1H), 7.71 (d, 1H), 7.59 (m, 1H), 7.32-7.40 (m, 2H), 7.14-7.24 (m, 2H), 6.89 (d, 1H), 6.78 (d, 1H), 6.69-6.77 (m, 3H), 5.31 (s, 2H), 5.14 (s, 2H), 4.32-4.38 (m, 1H), 4.29 (s, 4H), 4.17-4.25 (m, 1H), 3.90 (m, 1H), 3.64 (m, 1H), 3.36-3.43 (m, 2H), 2.40-2.58 (m, 2H), 2.22 (s, 3H).

| Example | LCMS Method | RT (min) | M$^{+1}$ | M$^{-1}$ |
|---|---|---|---|---|
| Example 1122: (R)-2-(2-(3-cyanobenzyloxy)-4-(3-(2,3-dihydrobenzo[b][1,4]dioxin-6-yl)-2-methylbenzyloxy)benzylamino)-3-hydroxypropanoic acid | A | 1.8 | 581.3 | 579.4 |
| Example 1123: (2R,3S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | M | 2.76 | 595.4 | 593.5 |
| Example 1124: 2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid | A | 1.75 | 595.3 | 593.4 |
| Example 1125: (2R,3R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | A | 1.8 | 595.4 | 593.4 |
| Example 1126: (S)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid | A | 1.76 | 595.3 | 593.3 |
| Example 1127: (R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid | A | 1.87 | 595.3 | 593.4 |
| Example 1128: (S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid | A | 1.79 | 595.3 | 593.4 |
| Example 1129: (R)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid | A | 1.67 | 595.6 | 593.7 |

Intermediate 2-((5-(3-(2,3-dihydrobenzo[b][1,4]dioxin-6-yl)-2-methylbenzyloxy)-2-formylphenoxy)methyl)isonicotinonitrile

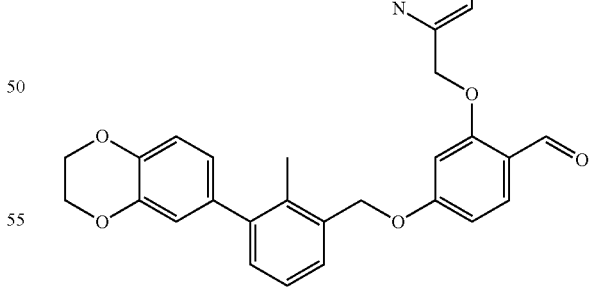

Cesium carbonate (173 mg, 0.531 mmol), 4-((3-(2,3-dihydrobenzo[b][1,4]dioxin-6-yl)-2-methylbenzyl)oxy)-2-hydroxy-6-methylbenzaldehyde (100 mg, 0.256 mmol) and 3-(bromomethyl)benzonitrile (81 mg, 0.531 mmol) were stirred in dimethyl formamide at 75° C. overnight. The mixture was diluted with ethyl acetate, neutralized with dilute hydrochloric acid (0.1 N) and washed with water and brine. Dried over sodium sulfate. Filtered and removed the solvent by rotary evaporation. The residue was purified with 2:3 hexanes:ethyl acetate on a 24 g silica gel column. Collected fractions to afford a white solid (18 mg, 13.8% yield).

The following examples were prepared by reductive amination from 2-((5-(3-(2,3-dihydrobenzo[b][1,4]dioxin-6-yl)-2-methylbenzyloxy)-2-formylphenoxy)methyl)isonicotinonitrile and an appropriate amine using a method similar to that used to prepare (S)-4-(2-(3-cyanobenzyloxy)-4-(3-(2,3-dihydrobenzo[b][1,4]dioxin-6-yl)-2-methylbenzyloxy)benzylamino)-3-hydroxybutanoic acid.

Example 1130

N-(2-(2-((4-cyanopyridin-2-yl)methoxy)-4-(3-(2,3-dihydrobenzo[b][1,4]dioxin-6-yl)-2-methylbenzyloxy)benzylamino)ethyl)acetamide

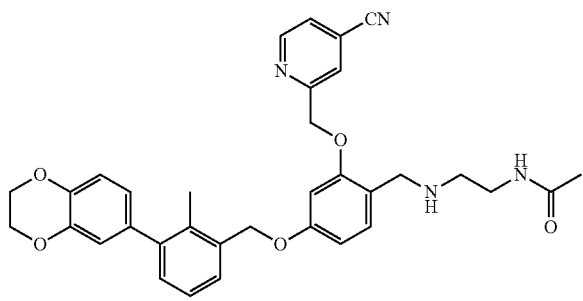 [SMILES: CC(=O)NCCNCc1ccc(OCc2cccc(-c3ccc4c(c3)OCCO4)c2C)cc1OCc1cc(C#N)ccn1]

LCMS Condition A: 1.87 minutes, M+1=579.3. $^1$H NMR (DMSO-d$_6$) δ 8.85 (d, 1H), 7.91-8.04 (m, 1H), 7.72-7.91 (m, 2H), 7.40 (d, 1H), 7.20-7.27 (m, 2H), 7.16 (d, 1H), 6.93 (d, 1H), 6.71-6.82 (m, 3H), 6.66 (d, 1H), 5.30 (s, 2H), 5.10 (s, 2H), 4.29 (s, 4H), 3.71 (m, 2H), 3.11-3.19 (m, 2H), 2.56 (m, 2H), 2.19 (s, 3H), 1.77 (s, 3H).

Example 1131

(R)-2-(2-((4-cyanopyridin-2-yl)methoxy)-4-(3-(2,3-dihydrobenzo[b][1,4]dioxin-6-yl)-2-methylbenzyloxy)benzylamino)-3-hydroxy-2-methylpropanoic acid

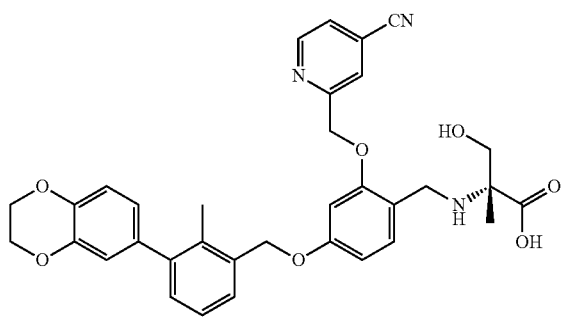 [SMILES: Cc1c(COc2ccc(CN[C@](C)(CO)C(=O)O)c(OCc3cc(C#N)ccn3)c2)cccc1-c1ccc2c(c1)OCCO2]

LCMS Condition A: 1.81 minutes, M+1=596.2, M−1=594.3. $^1$H NMR (DMSO-d$_6$) δ 8.84 (d, 1H), 8.10 (s, 1H), 7.83 (d, 1H), 7.36 (d, 1H), 7.39 (d, 1H), 7.20-7.24 (m, 1H), 7.14-7.18 (m, 1H), 6.93 (d, 1H), 6.83 (s, 1H), 6.70-6.79 (m, 3H), 5.38 (s, 2H), 5.13 (s, 2H), 4.29 (s, 4H), 4.06 (s, 2H), 3.60 (s, 2H), 2.18 (s, 3H), 1.30 (s, 3H).

Example 1132

(S)-1-(2-((4-cyanopyridin-2-yl)methoxy)-4-(3-(2,3-dihydrobenzo[b][1,4]dioxin-6-yl)-2-methylbenzyloxy)benzyl)piperidine-2-carboxylic acid

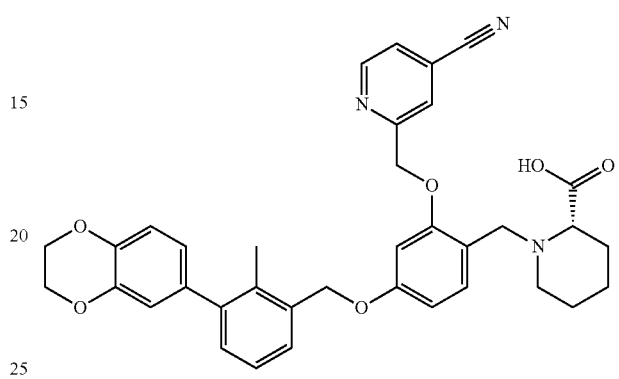

LCMS Condition A: 1.81 minutes, M+1=606.3, M−1=604.3. $^1$H NMR (DMSO-d$_6$) δ 8.84 (d, 1H), 8.09 (s, 1H), 7.96 (s, 1H), 7.83 (d, 1H), 7.40 (d, 1H), 7.33 (d, 1H), 7.23 (m, 1H), 7.16 (d, 1H), 6.93 (d, 1H), 6.68-6.82 (m, 4H), 5.28-5.33 (m, 2H), 5.11 (s, 2H), 4.29 (s, 4H), 4.02 (d, 1H), 3.81 (d, 1H), 3.17 (d, 1H), 3.00 (br. s., 1H), 2.44 (br. s., 1H), 2.20 (s, 3H), 1.83 (br. s., 1H), 1.76 (br. s., 1H), 1.53 (br. s., 3H), 1.37 (br. s., 1H).

Intermediate 3-((2-formyl-3-methoxy-5-((2-methylbiphenyl-3-yl)methoxy)phenoxy)methyl)benzonitrile

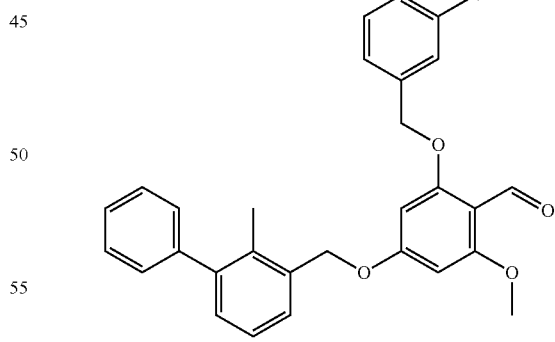

Cesium carbonate (112 mg, 0.344 mmol), 2-hydroxy-6-methoxy-4-((2-methyl-[1,1'-biphenyl]-3-yl)methoxy)benzaldehyde (40 mg, 0.115 mmol), and 3-(bromomethyl)benzonitrile (67.5 mg, 0.344 mmol) were heated at 75° C. overnight in dimethyl formamide (1 mL). Neutralized with dilute hydrochloric acid (0.1 N) and washed with water and brine and dried over sodium sulfate. The residue was purified with 2:1 hexane:ethyl acetate on a 12 g silica gel column) Collected fractions to afford 28 mg of the title compound as a colorless film. ¹H NMR (500 MHz, DMSO-d₆) δ 10.31 (s, 1H), 8.03 (s, 1H), 7.84 (dd, J=19.6, 7.9 Hz, 2H), 7.69-7.58 (m, 1H), 7.54-7.44 (m, 3H), 7.40 (d, J=7.3 Hz, 1H), 7.36-7.28 (m, 3H), 7.24 (d, J=7.3 Hz, 1H), 6.55 (s, 1H), 6.49 (s, 1H), 3.88 (s, 3H), 2.23 (s, 3H).

Example 1133

(S)-4-((2-((3-cyanobenzyl)oxy)-6-methoxy-4-((2-methyl-[1,1'-biphenyl]-3-yl)methoxy)benzyl)amino)-3-hydroxybutanoic acid

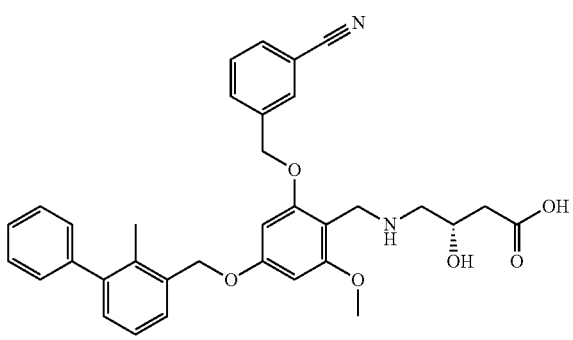 [SMILES: COc1cc(OCc2cccc(-c3ccccc3)c2C)cc(OCc2cccc(C#N)c2)c1CNC[C@@H](O)CC(=O)O]

A dimethy formamide (2 mL) solution of 3-((2-formyl-3-methoxy-5-((2-methyl-[1,1'-biphenyl]-3-yl)methoxy)phenoxy)methyl)benzonitrile (26 mg, 0.056 mmol) was combined with (S)-4-amino-3-hydroxybutanoic acid (20.04 mg, 0.168 mmol) and stirred at room temperature for 1 hour. Sodium cyanoborohydride 10.6 mg, 0.168 mmol) and 3 drops of acetic acid (3.21 μl, 0.056 mmol) were added. Stirred at room temperature overnight. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 7-minute hold at 100% B; Flow: 20 mL/min Fractions containing the desired product were combined and dried via centrifugal evaporation. The yield of the product was 12.3 mg, and its estimated purity by LCMS analysis was 100%. ¹H NMR (DMSO-d₆) δ 7.95 (s, 1H), 7.85 (d, 1H), 7.81 (d, 1H), 7.62 (m, 1H), 7.47 (m, 3H), 7.39 (m, 1H), 7.27-7.34 (m, 3H), 7.21 (d, 1H), 6.49 (s, 1H), 6.44 (s, 1H), 5.22 (s, 2H), 5.17 (s, 2H), 3.76-3.99 (m, 4H), 2.63 (d, 2H), 2.55 (s, 2H), 2.34 (m, 1H), 2.26 (m, 1H), 2.21 (s, 3H), 1.91 (s, 1H). LCMS Condition A: 2.03 minutes, M+1=567.4, M−1=565.4, EM=566.2.

The following examples were prepared in a similar manner as (S)-4-((2-((3-cyanobenzyl)oxy)-6-methoxy-4-((2-methyl-[1,1'-biphenyl]-3-yl)methoxy)benzyl)amino)-3-hydroxybutanoic acid from 3-((2-formyl-3-methoxy-5-((2-methylbiphenyl-3-yl)methoxy)phenoxy)methyl)benzonitrile and the appropriate amine by reductive amination. LCMS for these examples is given in tabular form.

Example 1134

(R)-2-((2-((3-cyanobenzyl)oxy)-6-methoxy-4-((2-methyl-[1,1'-biphenyl]-3-yl)methoxy)benzyl)amino)-3-hydroxypropanoic acid

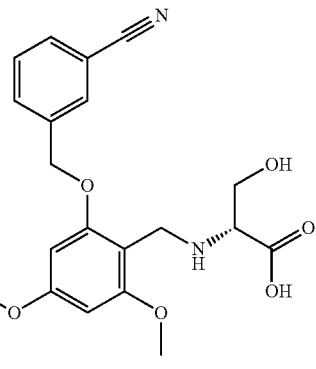

¹H NMR (DMSO-d₆) δ 7.99 (s, 1H), 7.96 (s, 1H), 7.78-7.93 (m, 3H), 7.57-7.65 (m, 1H), 7.47 (m, 3H), 7.39 (m, 1H), 7.26-7.35 (m, 3H), 7.21 (d, 1H), 6.48 (s, 1H), 6.52 (s, 1H), 5.22-5.27 (m, 2H), 5.18 (s, 2H), 4.04-4.16 (m, 2H), 3.91 (s, 1H), 3.83 (s, 3H), 3.72 (br. s., 1H), 3.57-3.65 (m, 1H), 3.09 (br. s., 1H), 2.21 (s, 3H).

Example 1135

(2R,3S)-2-((2-((3-cyanobenzyl)oxy)-6-methoxy-4-((2-methyl-[1,1'-biphenyl]-3-yl)methoxy)benzyl)amino)-3-hydroxybutanoic acid

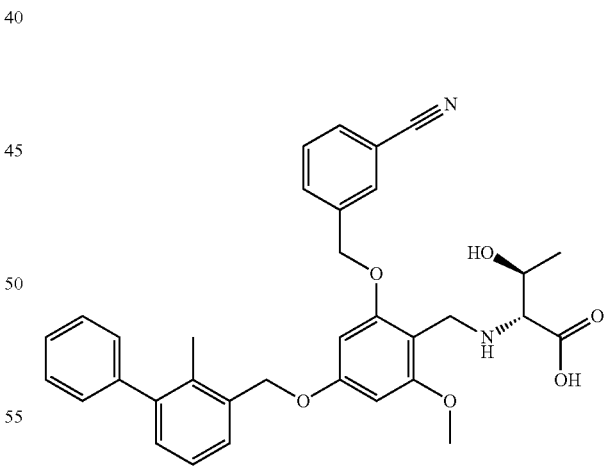

¹H NMR (DMSO-d₆) δ 8.01 (br. s., 1H), 7.90 (d, 1H), 7.82 (d, 1H), 7.62 (d, 1H), 7.47 (br. s., 3H), 7.40 (d, 1H), 7.25-7.35 (m, 3H), 7.21 (d, 1H), 6.52 (br. s., 1H), 6.48 (br. s., 1H), 5.23 (d, 2H), 5.18 (br. s., 2H), 4.07 (br. s., 2H), 3.89-3.99 (m, 1H), 3.83 (s, 3H), 3.75-3.96 (m, 5H), 2.85-2.95 (m, 2H), 2.74 (s, 1H), 2.21 (br. s., 3H), 1.16 (d, 3H).

Example 1136

(2S,3S)-2-((2-((3-cyanobenzyl)oxy)-6-methoxy-4-((2-methyl-[1,1'-biphenyl]-3-yl)methoxy)benzyl)amino)-3-hydroxybutanoic acid

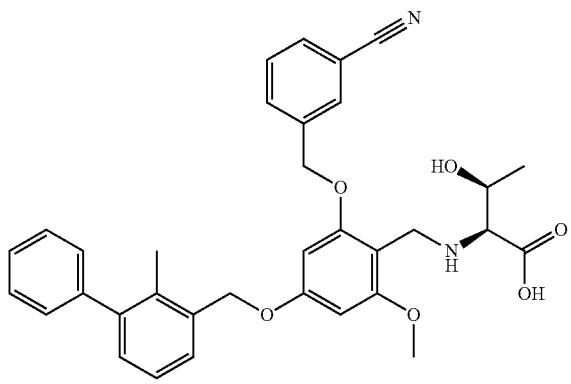 [SMILES: COc1cc(OCc2cccc(-c3ccccc3)c2C)cc(OCc2cccc(C#N)c2)c1CN[C@H](C(=O)O)[C@H](C)O]

$^1$H NMR (DMSO-d$_6$) δ 7.99 (s, 1H), 7.89 (d, 1H), 7.81 (d, 1H), 7.61 (m, 1H), 7.43-7.51 (m, 3H), 7.36-7.43 (m, 1H), 7.26-7.33 (m, 3H), 7.21 (d, 1H), 6.48 (s, 1H), 6.52 (s, 1H), 5.24 (d, 2H), 5.18 (s, 2H), 4.07-4.18 (m, 2H), 3.99-4.07 (m, 1H), 3.84 (s, 3H), 3.10 (d, 1H), 2.90 (s, 1H), 2.74 (s, 1H), 2.20 (s, 3H), 1.04 (d, 3H).

Example 1137

2-((2-((3-cyanobenzyl)oxy)-6-methoxy-4-((2-methyl-[1,1'-biphenyl]-3-yl)methoxy)benzyl)amino)-3-hydroxy-2-methylpropanoic acid

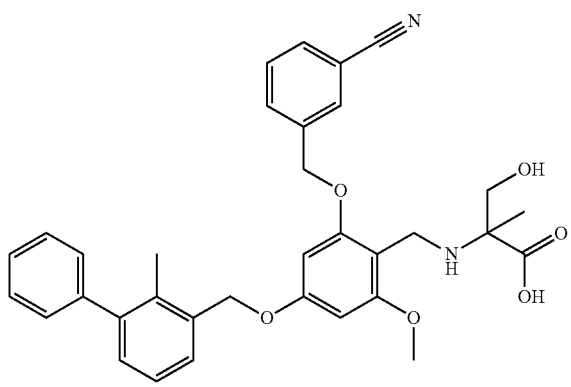 [SMILES: COc1cc(OCc2cccc(-c3ccccc3)c2C)cc(OCc2cccc(C#N)c2)c1CNC(C)(CO)C(=O)O]

$^1$H NMR (DMSO-d$_6$) δ 8.00 (s, 1H), 7.96 (s, 1H), 7.91 (d, 1H), 7.80 (d, 1H), 7.60 (m, 1H), 7.44-7.49 (m, 2H), 7.37-7.41 (m, 1H), 7.26-7.34 (m, 2H), 7.20-7.23 (m, 1H), 6.51 (s, 1H), 6.48 (s, 1H), 5.15-5.28 (m, 3H), 4.05 (s, 1H), 3.83 (s, 2H), 3.64 (d, 1H), 3.53 (d, 1H), 2.20 (s, 2H), 1.24 (s, 2H).

Example 1138

(2R,3R)-2-((2-((3-cyanobenzyl)oxy)-6-methoxy-4-((2-methyl-[1,1'-biphenyl]-3-yl)methoxy)benzyl)amino)-3-hydroxybutanoic acid $^1$H NMR (DMSO-d$_6$) δ 8.00 (s, 1H), 7.90 (d, 1H), 7.81 (d, 1H), 7.61 (m, 1H), 7.43-7.51 (m, 3H), 7.36-7.42 (m, 1H), 7.26-7.35 (m, 3H), 7.21 (d, 1H), 6.50 (s, 1H), 6.46 (s, 1H), 5.16-5.25 (m, 4H), 4.02 (br. s., 2H), 3.91 (br. s., 1H), 3.82 (s, 3H), 2.88-2.98 (m, 1H), 2.21 (s, 3H), 1.05 (d, 3H).

| Example | LCMS Method | RT (min) | M$^{+1}$ | M$^{-1}$ |
|---|---|---|---|---|
| Example 1134: (R)-2-((2-((3-cyanobenzyl)oxy)-6-methoxy-4-((2-methyl-[1,1'-biphenyl]-3-yl)methoxy)benzyl)amino)-3-hydroxypropanoic acid | A | 1.92 | 553.5 | 551.5 |
| Example 1135: (2R,3S)-2-((2-((3-cyanobenzyl)oxy)-6-methoxy-4-((2-methyl-[1,1'-biphenyl]-3-yl)methoxy)benzyl)amino)-3-hydroxybutanoic acid | A | 1.96 | 567.5 | 565.5 |
| Example 1136: (2S,3S)-2-((2-((3-cyanobenzyl)oxy)-6-methoxy-4-((2-methyl-[1,1'-biphenyl]-3-yl)methoxy)benzyl)amino)-3-hydroxybutanoic acid | A | 2.08 | 567.4 | 565.5 |
| Example 1137: 2-((2-((3-cyanobenzyl)oxy)-6-methoxy-4-((2-methyl-[1,1'-biphenyl]-3-yl)methoxy)benzyl)amino)-3-hydroxy-2-methylpropanoic acid | A | 1.96 | 567.3 | 565.3 |
| Example 1138: (2R,3R)-2-((2-((3-cyanobenzyl)oxy)-6-methoxy-4-((2-methyl-[1,1'-biphenyl]-3-yl)methoxy)benzyl)amino)-3-hydroxybutanoic acid | A | 1.93 | 567.4 | 565.4 |

Intermediate 3-((5-(3-(2,3-dihydrobenzo[b][1,4]dioxin-6-yl)-2-methylbenzyloxy)-2-formyl-3-methoxyphenoxy)methyl)benzonitrile

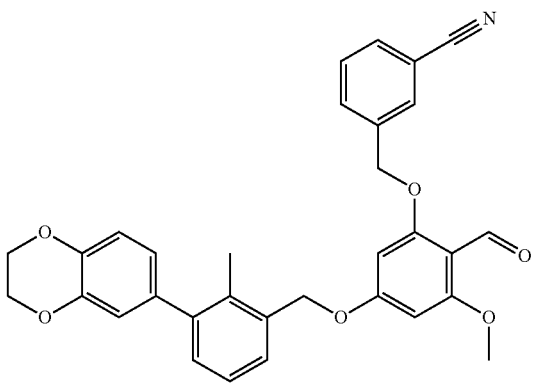 [SMILES: COc1cc(OCc2cccc(-c3ccc4c(c3)OCCO4)c2C)cc(OCc2cccc(C#N)c2)c1C=O]

A dimethyl formamide (3 mL) mixture of cesium carbonate (120 mg, 0.369 mmol), 4-((3-(2,3-dihydrobenzo[b][1,4]dioxin-6-yl)-2-methylbenzyl)oxy)-2-hydroxy-6-methoxybenzaldehyde (100 mg, 0.246 mmol) and 3-(bromomethyl)benzonitrile (72.4 mg, 0.369 mmol) was heated at 75° C. overnight. The reaction was neutralized with dilute hydrochloric acid (0.1 N) and washed with water and brine and dried over sodium sulfate. The residue was purified with 2:1 hexane:ethyl acetate on a 12 g silica gel column to give the title compound (80 mg) as a white film. $^1$H NMR (400 MHz, CHLOROFORM-d) δ 10.47 (s, 1H), 7.85-7.80 (m, 1H), 7.79-7.75 (m, 1H), 7.67-7.63 (m, 1H), 7.58-7.51 (m, 1H), 7.41-7.34 (m, 1H), 7.31-7.29 (m, 2H partially obscured by chloroform), 6.96-6.92 (m, 1H), 6.86-6.83 (m, 1H), 6.82-6.77 (m, 1H), 6.31-6.25 (m, 1H), 6.24-6.18 (m, 1H), 5.19 (s, 2H), 5.15 (s, 2H), 4.34 (s, 4H), 3.94 (s, 3H), 2.30 (s, 3H).

Example 1139

(R)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid

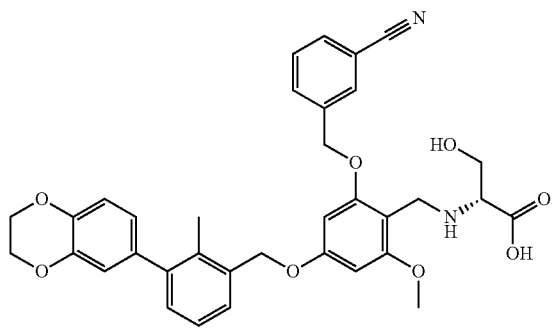 [SMILES: COc1cc(OCc2cccc(-c3ccc4c(c3)OCCO4)c2C)cc(OCc2cccc(C#N)c2)c1CN[C@H](CO)C(=O)O]

To a dimethyl formamide (1 mL) solution of 3-((5-((3-(2,3-dihydrobenzo[b][1,4]dioxin-6-yl)-2-methylbenzyl)oxy)-2-formyl-3-methoxyphenoxy)methyl)benzonitrile (20 mg, 0.038 mmol) was added (R)-2-amino-3-hydroxypropanoic acid (12.09 mg, 0.115 mmol). Stirred at room temperature for 1 hr. Sodium cyanoborohydride (7.23 mg, 0.115 mmol) and 3 drops of acetic acid (2.195 μl, 0.038 mmol) were added and the reaction was stirred at room temperature overnight. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min. Fractions containing the desired product were combined and dried via centrifugal evaporation. The yield of the product was 6.5 mg, and its estimated purity by LCMS analysis was 100%. $^1$H NMR (DMSO-$d_6$) δ 8.00 (br. s., 1H), 7.90 (d, 1H), 7.82 (d, 1H), 7.61 (m, 1H), 7.43 (d, 1H), 7.25 (m, 1H), 7.18 (d, 1H), 6.93 (d, 1H), 6.70-6.84 (m, 2H), 6.48 (s, 1H), 6.52 (s, 1H), 5.20-5.30 (m, 2H), 5.16 (br. s, 2H), 4.29 (br. s., 4H), 4.06-4.21 (m, 2H), 3.74-3.82 (m, 1H), 3.60-3.64 (m, 1H), 3.13 (br. s., 2H), 2.90 (s, 1H), 2.74 (s, 1H), 2.22 (br. s., 3H). LCMS Condition A: 1.85 minutes, M+1=611.4, M−1=609.4, EM=610.2.

The following examples were prepared in a similar manner as (R)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid from 3-((5-((3-(2,3-dihydrobenzo[b][1,4]dioxin-6-yl)-2-methylbenzyl)oxy)-2-formyl-3-methoxyphenoxy)methyl)benzonitrile and the appropriate amine. LCMS for these examples is given in tabular form.

Example 1140

(S)-4-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxybutanoic acid

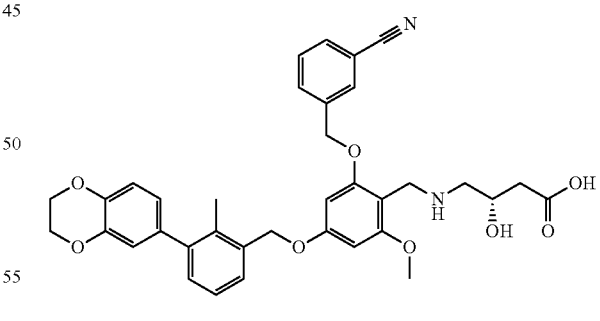

$^1$H NMR (DMSO-$d_6$) δ 7.95 (s, 1H), 7.85 (d, 1H), 7.81 (d, 1H), 7.61 (m, 1H), 7.42 (d, 1H), 7.24 (m, 1H), 7.18 (d, 1H), 6.93 (d, 1H), 6.71-6.82 (m, 2H), 6.48 (s, 1H), 6.43 (s, 1H), 5.21 (s, 2H), 5.14 (s, 2H), 4.28-4.28 (m, 1H), 4.29 (s, 4H), 3.84-3.93 (m, 1H), 3.82 (br. s., 2H), 3.80 (s, 3H), 2.62 (d, 2H), 2.33 (m, 1H), 2.25 (m, 1H), 2.22 (s, 3H).

Example 1141

(S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid

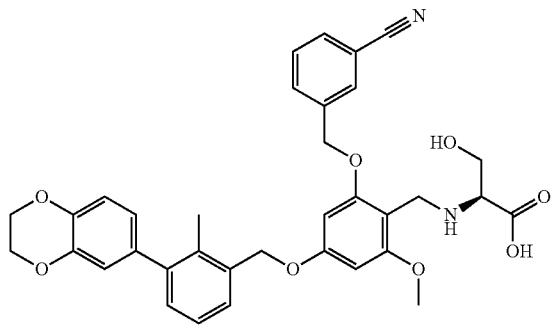 [SMILES: COc1cc(OCc2cccc(-c3ccc4c(c3)OCCO4)c2C)cc(OCc2cccc(C#N)c2)c1CN[C@@H](CO)C(=O)O]

$^1$H NMR (DMSO-d$_6$) δ 8.00 (br. s., 1H), 7.90 (d, 1H), 7.82 (d, 1H), 7.61 (m, 1H), 7.43 (d, 1H), 7.25 (m, 1H), 7.18 (d, 1H), 6.93 (d, 1H), 6.72-6.82 (m, 2H), 6.52 (br. s., 1H), 6.48 (br. s., 1H), 5.20-5.30 (m, 2H), 5.16 (br. s., 2H), 4.29 (s, 4H), 4.06-4.22 (m, 2H), 3.84 (s, 3H), 3.78 (d, 1H), 3.58-3.67 (m, 1H), 3.13 (br. s., 1H), 2.22 (s, 3H).

Example 1142

(S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxy-2-methylpropanoic acid

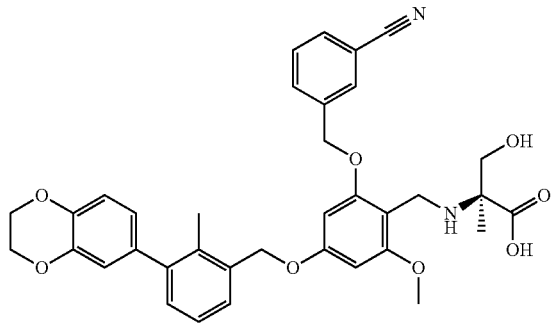 [SMILES: COc1cc(OCc2cccc(-c3ccc4c(c3)OCCO4)c2C)cc(OCc2cccc(C#N)c2)c1CN[C@@](C)(CO)C(=O)O]

$^1$H NMR (DMSO-d$_6$) δ 8.00 (s, 1H), 7.91 (d, 1H), 7.81 (d, 1H), 7.61 (m, 1H), 7.42 (d, 1H), 7.24 (m, 1H), 7.18 (d, 1H), 6.93 (d, 1H), 6.71-6.81 (m, 2H), 6.51 (s, 1H), 6.48 (s, 1H), 5.20-5.29 (m, 2H), 5.17 (s, 2H), 4.29 (s, 4H), 4.08 (s, 2H), 3.84 (s, 3H), 3.66 (d, 1H), 3.55 (d, 1H), 2.21 (s, 3H), 1.25 (s, 3H)

| Example | LCMS Method | RT (min) | M$^{+1}$ | M$^{-1}$ |
|---|---|---|---|---|
| Example 1140: (S)-4-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxybutanoic acid | A | 1.8 | 625.5 | 623.3 |
| Example 1141: (S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid | A | 1.82 | 611.3 | 609.4 |
| Example 1142: (S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxy-2-methylpropanoic acid | A | 1.86 | 625.4 | 623.4 |

Intermediate 5-(2-formyl-5-((2-methylbiphenyl-3-yl)methoxy)phenoxy)pentanenitrile

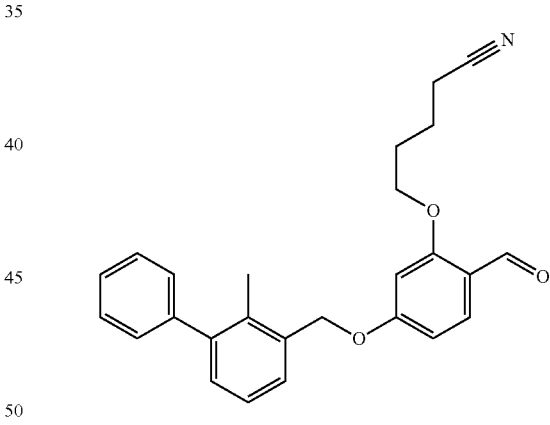

Dimethyl formamide (4 mL) containing cesium carbonate (115 mg, 0.353 mmol), 2-hydroxy-4-((2-methyl-[1,1'-biphenyl]-3-yl)methoxy)benzaldehyde (75 mg, 0.236 mmol), and 5-chlorovaleronitrile (41.5 mg, 0.353 mmol) was heated at 75° C. overnight. The mixture was filtered and neutralized with dilute hydrochloric acid (0.1 N). Washed with water and brine and dried over sodium sulfate. The residue was purified with 3:1 hexane:ethyl acetate on a 12 g silica gel column Collected fractions containing the title compound to afford the colorless film. $^1$H NMR (500 MHz, DMSO-d$_6$) δ 10.24 (s, 1H), 7.70 (d, J=8.4 Hz, 1H), 7.53-7.44 (m, 3H), 7.42-7.36 (m, 1H), 7.35-7.28 (m, 3H), 7.23 (d, J=7.7 Hz, 1H), 6.86 (s, 1H), 6.80 (d, J=8.8 Hz, 1H), 5.28 (s, 2H), 4.19 (t, J=6.1 Hz, 2H), 2.61 (t, J=7.0 Hz, 2H), 2.51 (br. s., 3H), 1.95-1.85 (m, 2H), 1.83-1.72 (m, 2H).

Example 1143

(R)-2-((2-(4-cyanobutoxy)-4-((2-methyl-[1,1'-biphenyl]-3-yl)methoxy)benzyl)amino)-3-hydroxypropanoic acid

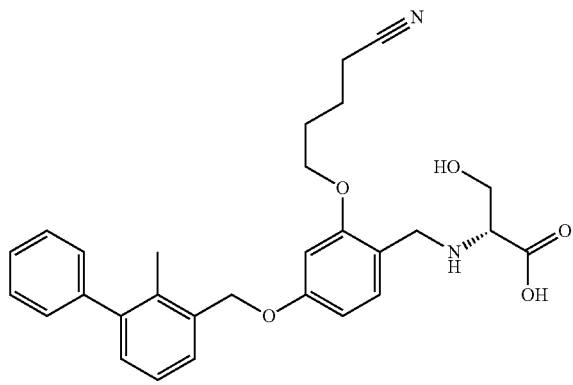 [SMILES: Cc1c(COc2ccc(CN[C@H](CO)C(=O)O)c(OCCCCC#N)c2)cccc1-c1ccccc1]

A dimethyl formamide (1 mL) solution of 5-(2-formyl-5-((2-methyl-[1,1'-biphenyl]-3-yl)methoxy)phenoxy)pentanenitrile (20 mg, 0.050 mmol) and (R)-2-amino-3-hydroxypropanoic acid (15.78 mg, 0.150 mmol) was stirred at room temperature for 1 hr. Sodium cyanoborohydride (9.44 mg, 0.150 mmol) and 3 drops of acetic acid (2.87 µl, 0.050 mmol) were added and the reaction was stirred at room temperature overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 98%.

$^1$H NMR (DMSO-$d_6$) δ 7.46 (m, 3H), 7.36-7.42 (m, 1H), 7.26-7.35 (m, 4H), 7.21 (d, 1H), 6.76 (s, 1H), 6.68 (d, 1H), 5.16 (s, 2H), 3.98-4.12 (m, 4H), 3.77 (m, 1H), 3.65 (m, 2H), 3.17 (d, 1H), 2.58 (m, 2H), 2.20 (s, 3H), 1.84-1.93 (m, 2H), 1.74-1.81 (m, 2H). LCMS Condition M: 2.81 minutes, M+1=489.5, M−1=487.6, EM=488.2.

Example 1144

(S)-4-((2-(4-cyanobutoxy)-4-((2-methyl-[1,1'-biphenyl]-3-yl)methoxy)benzyl)amino)-3-hydroxybutanoic acid

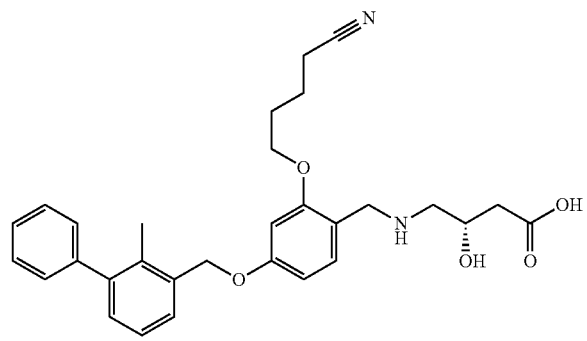 [SMILES: Cc1c(COc2ccc(CNC[C@@H](O)CC(=O)O)c(OCCCCC#N)c2)cccc1-c1ccccc1]

A dimethyl formamide (1 mL) solution of 5-(2-formyl-5-((2-methyl-[1,1'-biphenyl]-3-yl)methoxy)phenoxy)pentanenitrile (20 mg, 0.050 mmol) and (S)-4-amino-3-hydroxybutanoic acid (17.89 mg, 0.150 mmol) was stirred at room temperature for 1 hr. Sodium cyanoborohydride (9.44 mg, 0.150 mmol) and 3 drops of acetic acid (2.87 µl, 0.050 mmol) were added and the reaction was stirred at room temperature overnight. The crude material was purified via preparative LC/MS with the following conditions: Column: XBridge C18, 19×mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-100% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 99%. $^1$H NMR (DMSO-$d_6$) δ 7.47 (m, 3H), 7.36-7.42 (m, 1H), 7.26-7.36 (m, 3H), 7.20 (d, 1H), 7.23 (d, 1H), 6.70 (s, 1H), 6.65 (d, 1H), 5.14 (s, 2H), 4.03 (m, 2H), 3.88-3.94 (m, 2H), 2.56-2.65 (m, 4H), 2.40 (m, 1H), 2.28 (m, 1H), 2.21 (s, 3H), 1.91 (s, 1H), 1.81-1.88 (m, 2H), 1.71-1.79 (m, 2H). LCMS Condition A: 2.0 minutes, M+1=503.3, M−1=501.3, EM=502.3.

Intermediate 4-((2-chloro-3-(2,3-dihydrobenzo[b][1,4]dioxin-6-yl)benzyl)oxy)-2-hydroxybenzaldehyde

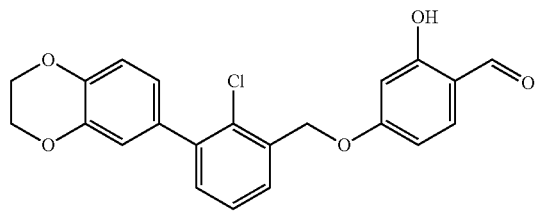 [SMILES: O=Cc1ccc(OCc2cccc(-c3ccc4c(c3)OCCO4)c2Cl)cc1O]

Combined 2,4-dihydroxybenzaldehyde (212 mg, 1.538 mmol), triphenylphosphine (404 mg, 1.538 mmol) and (2-chloro-3-(2,3-dihydrobenzo[b][1,4]dioxin-6-yl)phenyl)methanol (387 mg, 1.399 mmol) in dry tetrahydrofuran (4 mL) and cooled on an ice/water bath. Added diisopropyl azodicarboxylate (0.299 mL, 1.538 mmol) in tetrahydrofuran (4 mL) dropwise. The resulting yellow solution was allowed to slowly warm to room temperature with stirring over night. Partioned between ethyl acetate and water. The organic portion was concentrated by rotory evaporation. Chromatographed with 0-50% ethyl acetate in hexanes on silica gel. The fractions containing the desired mass by LCMS analysis were combined. NMR suggested a mixture of products (two aldehyde peaks). This material (368 mg) was used without further purification in the preparation of 3-((5-((2-chloro-3-(2,3-dihydrobenzo[b][1,4]dioxin-6-yl)benzyl)oxy)-2-formylphenoxy)methyl)benzonitrile.

Intermediate 3-((5-((2-chloro-3-(2,3-dihydrobenzo[b][1,4]dioxin-6-yl)benzyl)oxy)-2-formylphenoxy)methyl)benzonitrile

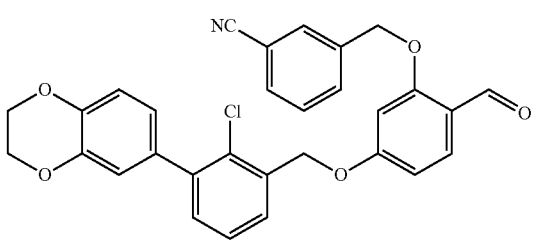 [SMILES: N#Cc1cccc(COc2cc(OCc3cccc(-c4ccc5c(c4)OCCO5)c3Cl)ccc2C=O)c1]

Dissolved 4-((2-chloro-3-(2,3-dihydrobenzo[b][1,4]dioxin-6-yl)benzyl)oxy)-2-hydroxybenzaldehyde (368 mg, 0.927 mmol) and cesium carbonate (604 mg, 1.855 mmol) in dimethylformamide (5 mL). Added 3-(bromomethyl)benzonitrile (273 mg, 1.391 mmol) in dimethylformamide (5 mL). Stirred at room temperature over the weekend. Diluted with 100 mL diethyl ether and a ppt formed. The solvent was removed by rotory evaporation. Resuspended in ethylacetate and adsorbed on to silica gel. Chromatographed the residue on 40 g silica gel with 0-100% ethylacetate in hexanes. The product presented as a flattened peak consistent with poor solubility. The title compound (180 mg, 38%) was isolated as white solid after removal of solvent. $^1$H NMR (400 MHz, DMSO-$d_6$) δ 10.28 (s, 1H), 8.02 (s, 1H), 7.90-7.80 (m, 3H), 7.74 (d, J=8.8 Hz, 1H), 7.64 (s, 2H), 7.42 (d, J=16.1 Hz, 2H), 6.99-6.77 (m, 5H), 5.35 (d, J=14.2 Hz, 4H), 4.30 (s, 4H).

Example 1145

(S)-1-(4-(2-chloro-3-(2,3-dihydrobenzo[b][1,4]dioxin-6-yl)benzyloxy)-2-(3-cyanobenzyloxyl)benzyl)piperidine-2-carboxylic acid

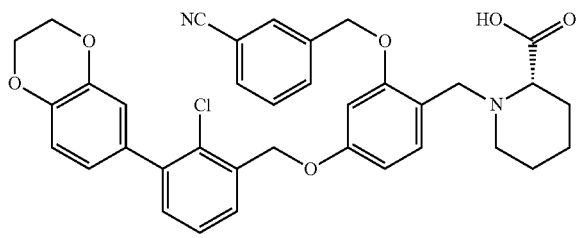 [SMILES: N#Cc1cccc(COc2cc(OCc3cccc(-c4ccc5c(c4)OCCO5)c3Cl)ccc2CN2CCCC[C@H]2C(=O)O)c1]

Combined sodium cyanoborohydride (6.87 mg, 0.109 mmol), (S)-piperidine-2-carboxylic acid (10.60 mg, 0.082 mmol) and 3-((5-((2-chloro-3-(2,3-dihydrobenzo[b][1,4]dioxin-6-yl)benzyl)oxy)-2-formylphenoxy)methyl)benzonitrile (28 mg, 0.055 mmol) in dimethylformamide (1 mL) and acetic acid (0.050 mL). Stirred at room temperature overnight. The crude material was purified via preparative LCMS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 20 minutes, then a 5-minute hold at 100% B; Flow: 20 mL/minutes Fractions containing the desired product were combined and dried via centrifugal evaporation. The yield of the product was 9.5 mg, and its estimated purity by LCMS analysis was 100%. Two analytical LCMS injections were used to determine the final purity. LCMS Condition A: 1.8 minutes, M+1=625.3, M−1=623.3, EM=624.2. Condition M: LCMS: 2.8 minutes, M+1=625.3, M−1=623.3, EM=624.2. $^1$H NMR (500 MHz, DMSO-$d_6$) δ 7.96 (s, 2H), 7.83 (dd, J=19.1, 7.7 Hz, 2H), 7.62 (t, J=7.9 Hz, 1H), 7.58 (d, J=7.3 Hz, 1H), 7.45-7.40 (m, 1H), 7.35 (dd, J=13.9, 8.1 Hz, 2H), 6.98-6.93 (m, 1H), 6.92 (s, 1H), 6.88 (d, J=8.1 Hz, 1H), 6.79 (s, 1H), 6.69 (d, J=8.1 Hz, 1H), 5.23 (s, 2H), 5.20 (s, 2H), 4.30 (s, 4H), 3.98-3.71 (m, 3H), 2.96 (br. s., 1H), 2.41 (br. s., 1H), 1.87-1.67 (m, 2H), 1.58-1.31 (m, 4H).

The following examples were prepared in the same manner as (S)-1-(4-(2-chloro-3-(2,3-dihydrobenzo[b][1,4]dioxin-6-yl)benzyloxy)-2-(3-cyanobenzyloxyl)benzyl)piperidine-2-carboxylic acid from 3-((5-((2-chloro-3-(2,3-dihydrobenzo[b][1,4]dioxin-6-yl)benzyl)oxy)-2-formylphenoxy)methyl)benzonitrile and an appropriate amine. LCMS characterization data is given in tabular form.

Example 1146

(R)-2-(4-(2-chloro-3-(2,3-dihydrobenzo[b][1,4]dioxin-6-yl)benzyloxy)-2-(3-cyanobenzyloxy)benzylamino)-3-hydroxypropanoic acid

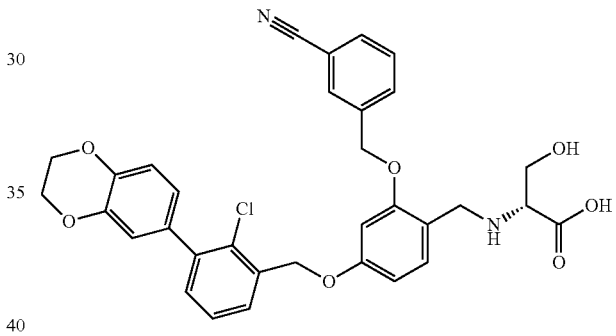

The title compound was prepared from (R)-2-amino-3-hydroxypropanoic acid. $^1$H NMR (500 MHz, DMSO-$d_6$) δ 8.02 (s, 1H), 7.92 (d, J=7.9 Hz, 1H), 7.82 (d, J=7.6 Hz, 1H), 7.61 (t, J=7.8 Hz, 1H), 7.57 (d, J=7.3 Hz, 1H), 7.45-7.39 (m, 1H), 7.36 (d, J=8.2 Hz, 2H), 6.97-6.93 (m, 1H), 6.92 (d, J=1.8 Hz, 1H), 6.88 (d, J=8.2 Hz, 1H), 6.83 (s, 1H), 6.70 (d, J=6.4 Hz, 1H), 5.30-5.22 (m, 2H), 5.21 (s, 2H), 4.30 (s, 4H), 4.13-4.01 (m, 2H), 3.80-3.72 (m, 1H), 3.65 (dd, J=11.3, 6.7 Hz, 1H), 3.18 (t, J=5.5 Hz, 1H).

Example 1147

(S)-4-(4-(2-chloro-3-(2,3-dihydrobenzo[b][1,4]dioxin-6-yl)benzyloxy)-2-(3-cyanobenzyloxy)benzylamino)-3-hydroxybutanoic acid

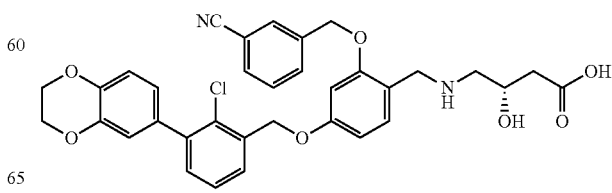

The title compound was prepared from (S)-4-amino-3-hydroxybutanoic acid. ¹H NMR (500 MHz, DMSO-d₆) δ 7.95 (s, 1H), 7.90-7.78 (m, 2H), 7.67-7.60 (m, 1H), 7.57 (d, J=7.3 Hz, 1H), 7.46-7.39 (m, 1H), 7.39-7.34 (m, 1H), 7.30 (d, J=8.1 Hz, 1H), 6.98-6.93 (m, 1H), 6.91 (s, 1H), 6.90-6.85 (m, 1H), 6.79 (s, 1H), 6.67 (d, J=7.3 Hz, 1H), 5.23 (s, 2H), 5.20 (s, 2H), 4.30 (s, 4H), 3.97-3.92 (m, 1H), 3.88-3.78 (m, 2H), 2.66 (d, J=5.1 Hz, 2H), 2.44-2.36 (m, 1H), 2.33-2.23 (m, 1H).

Example 1148

(R)-2-(4-(2-chloro-3-(2,3-dihydrobenzo[b][1,4]dioxin-6-yl)benzyloxy)-2-(3-cyanobenzyloxy)benzylamino)-3-hydroxy-2-methylpropanoic acid

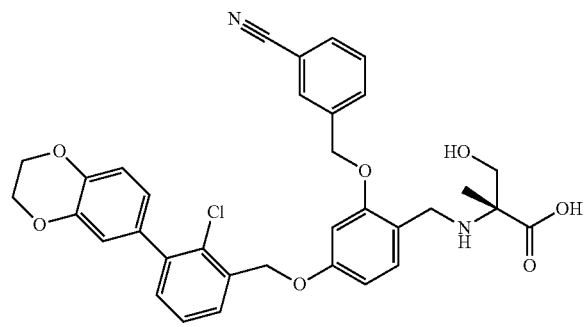 [SMILES: C[C@](CO)(NCc1ccc(OCc2cccc(-c3ccc4c(c3)OCCO4)c2Cl)cc1OCc1cccc(C#N)c1)C(=O)O]

The title compound was prepared from (R)-2-amino-3-hydroxy-2-methylpropanoic acid. ¹H NMR (500 MHz, DMSO-d₆) δ 8.01 (s, 1H), 7.93 (d, J=7.7 Hz, 1H), 7.81 (d, J=7.7 Hz, 1H), 7.60 (t, J=7.9 Hz, 1H), 7.56 (d, J=6.6 Hz, 1H), 7.45-7.34 (m, 3H), 6.95 (d, J=8.4 Hz, 1H), 6.91 (d, J=1.8 Hz, 1H), 6.89-6.85 (m, 1H), 6.82 (s, 1H), 6.73-6.66 (m, 1H), 5.25 (s, 2H), 5.22 (s, 2H), 4.30 (s, 4H), 4.01 (s, 2H), 3.68-3.61 (m, 1H), 3.56 (d, J=11.4 Hz, 1H), 1.26 (s, 3H).

Example 1149

(S)-2-(4-(2-chloro-3-(2,3-dihydrobenzo[b][1,4]dioxin-6-yl)benzyloxy)-2-(3-cyanobenzyloxy)benzylamino)-3-hydroxy-2-methylpropanoic acid

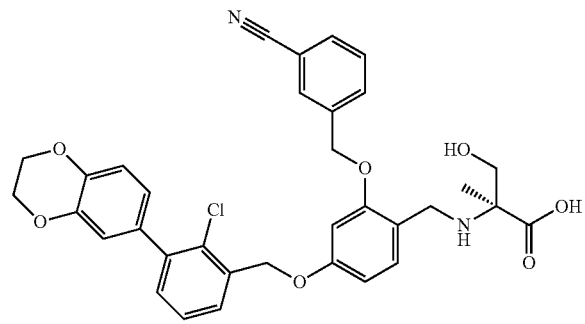 [SMILES: C[C@@](CO)(NCc1ccc(OCc2cccc(-c3ccc4c(c3)OCCO4)c2Cl)cc1OCc1cccc(C#N)c1)C(=O)O]

The title compound was prepared from (S)-2-amino-3-hydroxy-2-methylpropanoic acid. ¹H NMR (500 MHz, DMSO-d₆) δ 8.01 (s, 1H), 7.93 (d, J=7.7 Hz, 1H), 7.81 (d, J=7.7 Hz, 1H), 7.61 (t, J=7.7 Hz, 1H), 7.56 (d, J=7.3 Hz, 1H), 7.44-7.34 (m, 3H), 6.95 (d, J=8.1 Hz, 1H), 6.91 (s, 1H), 6.89-6.85 (m, 1H), 6.82 (s, 1H), 6.70 (d, J=8.4 Hz, 1H), 5.25 (s, 2H), 5.22 (s, 2H), 4.30 (s, 4H), 4.01 (s, 2H), 3.66-3.61 (m, 1H), 3.56 (d, J=11.4 Hz, 1H), 1.26 (s, 3H).

Example 1150

N-(2-(4-(2-chloro-3-(2,3-dihydrobenzo[b][1,4]dioxin-6-yl)benzyloxy)-2-(3-cyanobenzyloxy)benzylamino)ethyl)acetamide

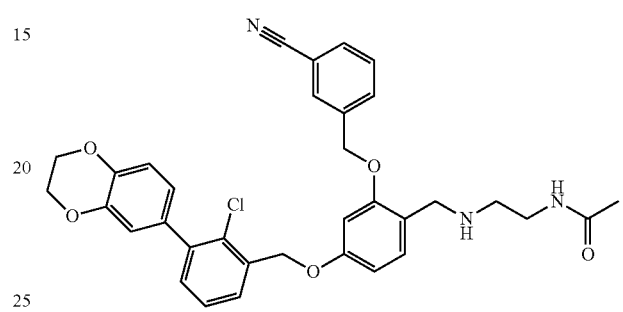

The title compound was prepared from N-(2-aminoethyl)acetamide. ¹H NMR (500 MHz, DMSO-d₆) δ 7.93 (s, 1H), 7.83 (d, J=4.4 Hz, 2H), 7.66-7.60 (m, 1H), 7.57 (d, J=6.2 Hz, 1H), 7.45-7.39 (m, 1H), 7.38-7.33 (m, 1H), 7.25 (d, J=8.4 Hz, 1H), 6.98-6.93 (m, 1H), 6.92 (d, J=1.8 Hz, 1H), 6.90-6.86 (m, 1H), 6.76 (d, J=1.8 Hz, 1H), 6.63 (dd, J=8.3, 2.0 Hz, 1H), 5.21 (s, 2H), 5.19 (s, 2H), 4.30 (s, 4H), 3.13 (q, J=6.2 Hz, 2H), 2.55 (t, J=6.4 Hz, 2H), 1.77 (s, 3H).

| Example | LCMS Method | RT (min) | M⁺¹ | M⁻¹ |
|---|---|---|---|---|
| Example 1146: (R)-2-(4-(2-chloro-3-(2,3-dihydrobenzo[b][1,4]dioxin-6-yl)benzyloxy)-2-(3-cyanobenzyloxy)benzylamino)-3-hydroxypropanoic acid | M | 2.8 | 601.2 | 599.3 |
| Example 1147: (S)-4-(4-(2-chloro-3-(2,3-dihydrobenzo[b][1,4]dioxin-6-yl)benzyloxy)-2-(3-cyanobenzyloxy)benzylamino)-3-hydroxybutanoic acid | A | 1.8 | 615.3 | 613.3 |
| Example 1148: (R)-2-(4-(2-chloro-3-(2,3-dihydrobenzo[b][1,4]dioxin-6-yl)benzyloxy)-2-(3-cyanobenzyloxy)benzylamino)-3-hydroxy-2-methylpropanoic acid | M | 2.8 | 615.3 | 613.3 |
| Example 1150: N-(2-(4-(2-chloro-3-(2,3-dihydrobenzo[b][1,4]dioxin-6-yl)benzyloxy)-2-(3-cyanobenzyloxy)benzylamino)ethyl)acetamide | A | 1.9 | 598.3 | 656.3 (+AcOH) |
| Example: 1149 (S)-2-(4-(2-chloro-3-(2,3-dihydrobenzo[b][1,4]dioxin-6-yl)benzyloxy)-2-(3-cyanobenzyloxy)benzylamino)-3-hydroxy-2-methylpropanoic acid | M | 2.8 | 615.3 | 613.3 |

Intermediate 5-((5-(2-chloro-3-(2,3-dihydrobenzo[b][1,4]dioxin-6-yl)benzyloxy)-2-formyl-4-methylphenoxy)methyl)nicotinonitrile

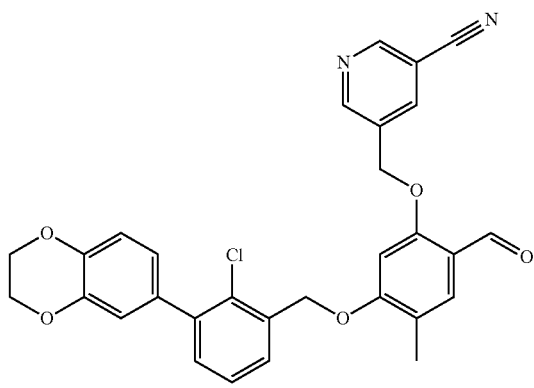 [SMILES: Cc1cc(C=O)c(OCc2cncc(C#N)c2)cc1OCc1cccc(-c2ccc3c(c2)OCCO3)c1Cl]

Cesium carbonate (178 mg, 0.548 mmol), 4-((2-chloro-3-(2,3-dihydrobenzo[b][1,4]dioxin-6-yl)benzyl)oxy)-2-hydroxy-5-methylbenzaldehyde (150 mg, 0.365 mmol) and 5-(chloromethyl)nicotinonitrile (111 mg, 0.730 mmol) were stirred at 75° C. for 3 hours in dimethyl formamide (2 mL). The reaction was filtered and concentrated. The residue was purified with 1:2 to 2:1 hexane:ethyl acetate on a 24 g silica gel column) Collected fractions to afford a white solid as the desired product (110 mg, 57%). $^1$H NMR (400 MHz, CHLOROFORM-d) δ 10.34 (s, 1H), 8.92-8.88 (m, 2H), 8.08 (s, 1H), 7.73 (s, 1H), 7.57-7.49 (m, 1H), 7.40-7.34 (m, 2H), 7.02-6.88 (m, 3H), 6.51 (s, 1H), 5.34 (s, 2H), 5.22 (s, 2H), 4.35 (s, 4H), 2.32 (s, 3H).

The following examples were prepared by reductive amination in the same manner as (S)-1-(4-(2-chloro-3-(2,3-dihydrobenzo[b][1,4]dioxin-6-yl)benzyloxy)-2-(3-cyanobenzyloxyl)benzyl)piperidine-2-carboxylic acid from 5-((5-(2-chloro-3-(2,3-dihydrobenzo[b][1,4]dioxin-6-yl)benzyloxy)-2-formyl-4-methylphenoxy)methyl)nicotinonitrile and an appropriate amine.

Example 1151

5-((5-(2-chloro-3-(2,3-dihydrobenzo[b][1,4]dioxin-6-yl)benzyloxy)-2-((2-hydroxyethylamino)methyl)-4-methylphenoxy)methyl)nicotinonitrile

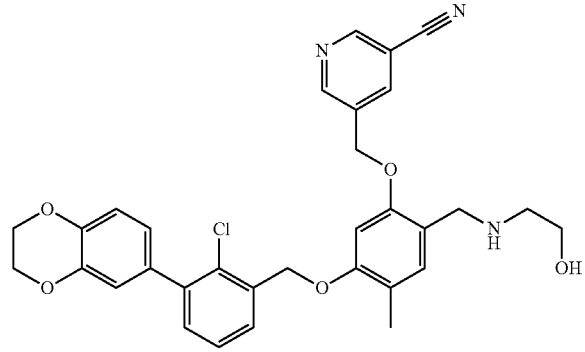 [SMILES: Cc1cc(CNCCO)c(OCc2cncc(C#N)c2)cc1OCc1cccc(-c2ccc3c(c2)OCCO3)c1Cl]

LCMS Condition A: 1.83 minutes, M+1=572.2. $^1$H NMR (DMSO-d$_6$) δ 8.97 (s, 1H), 9.00 (s, 1H), 8.42 (s, 1H), 7.59 (d, 1H), 7.42 (m, 1H), 7.36 (d, 1H), 7.11 (s, 1H), 6.85-6.97 (m, 4H), 5.28 (s, 2H), 5.22 (s, 2H), 4.30 (s, 4H), 3.47 (m, 2H), 2.90 (s, 1H), 2.74 (s, 1H), 2.58 (m, 2H), 2.14 (s, 3H).

Example 1152

(S)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid

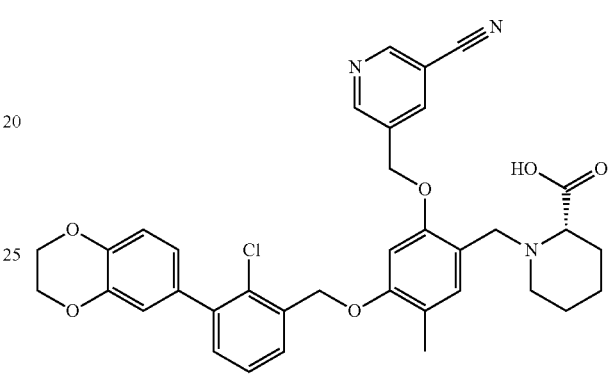

LCMS Condition A: 1.80 minutes, M+1=640.2, M−1=638.2. $^1$H NMR (DMSO-d$_6$) δ 9.00 (s, 2H), 8.48 (s, 1H), 7.60 (d, 1H), 7.41-7.45 (m, 1H), 7.36-7.38 (m, 1H), 7.19 (s, 1H), 6.92-6.97 (m, 2H), 6.88-6.91 (m, 2H), 5.30 (d, 2H), 5.24 (s, 2H), 4.30 (s, 4H), 3.94 (s, 1H), 3.71-3.77 (m, 1H), 3.14 (m, 1H), 2.94 (br. s., 1H), 2.39 (d, 1H), 2.14 (s, 3H), 1.83 (br. s., 1H), 1.75 (d, 1H), 1.51 (br. s., 3H), 1.37 (br. s., 1H).

Example 1153

(R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid

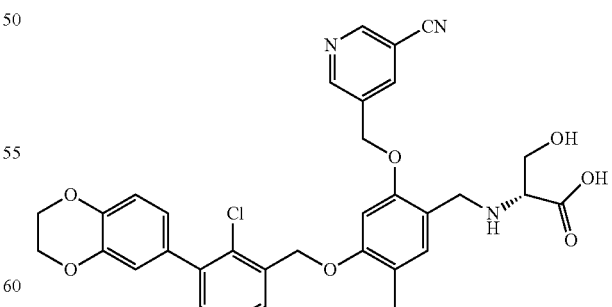

LCMS Condition A: 1.70 minutes, M+1=616.2, M−1=614.2. $^1$H NMR (DMSO-d$_6$) δ 9.04 (s, 1H), 9.01 (s, 1H), 8.53 (s, 1H), 7.60 (d, 1H), 7.43 (m, 1H), 7.37 (d, 1H), 7.22 (s, 1H), 6.92-6.97 (m, 3H), 6.88-6.91 (m, 1H), 5.28-

5.35 (m, 2H), 5.25 (s, 2H), 4.30 (s, 4H), 4.08 (d, 1H), 4.00 (d, 1H), 3.74 (m, 1H), 3.63 (m, 1H), 3.11-3.19 (m, 1H), 2.14 (s, 3H).

Example 1154

(S)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid

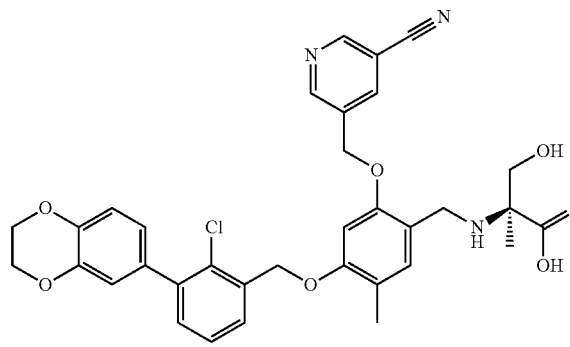

LCMS Condition A: 1.74 minutes, M+1=630.3, M−1=628.2 $^1$H NMR (DMSO-d$_6$) δ 9.03 (s, 1H), 8.99 (s, 1H), 8.52 (s, 1H), 7.58 (d, 1H), 7.40-7.44 (m, 1H), 7.35-7.38 (m, 1H), 7.25 (s, 1H), 6.87-6.97 (m, 4H), 5.32 (s, 2H), 5.26 (s, 2H), 4.30 (s, 4H), 3.99 (s, 2H), 3.64 (d, 1H), 3.55 (d, 1H), 2.15 (s, 3H), 1.26 (s, 3H).

Example 1155

(R)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid

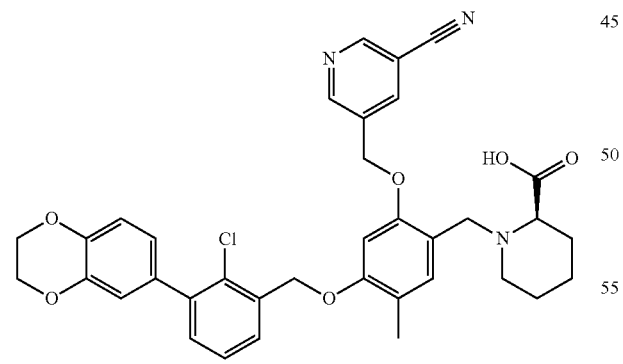

LCMS Condition A: 1.80 minutes, M+1=640.2, M−1=638.3. $^1$H NMR (DMSO-d$_6$) δ 8.94-9.05 (m, 2H), 8.48 (s, 1H), 7.60 (d, 1H), 7.43 (m, 1H), 7.37 (d, 1H), 7.19 (s, 1H), 6.92-6.97 (m, 2H), 6.88-6.91 (m, 2H), 5.26-5.32 (m, 2H), 5.24 (s, 2H), 4.30 (s, 4H), 3.89-3.97 (m, 1H), 3.72-3.78 (m, 1H), 3.14 (m, 1H), 2.94 (br. s., 1H), 2.39 (d, 1H), 2.14 (s, 3H), 1.83 (br. s., 1H), 1.75 (d, 1H), 1.52 (br. s., 3H), 1.37 (br. s., 1H).

Example 1156

(R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid

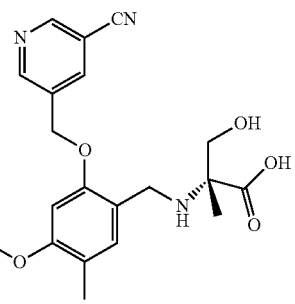

LCMS Condition A: 1.76 minutes, M+1=630.3, M−1=628.3. $^1$H NMR (DMSO-d$_6$) δ 9.03 (s, 1H), 8.99 (s, 1H), 8.52 (s, 1H), 7.58 (d, 1H), 7.42 (m, 1H), 7.37 (d, 1H), 7.25 (s, 1H), 6.87-6.97 (m, 4H), 5.32 (s, 2H), 5.26 (s, 2H), 4.30 (s, 4H), 3.99 (s, 2H), 3.64 (d, 1H), 3.55 (d, 1H), 2.15 (s, 3H), 1.26 (s, 3H).

Intermediate 5-chloro-2,4-dihydroxybenzaldehyde

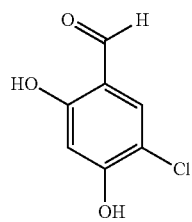 [SMILES: O=Cc1cc(Cl)c(O)cc1O]

5-Chloro-2,4-dihydroxybenzaldehyde was prepared using the literature procedure: Vogel, H; Goeldner, M. et. al. *Angew. Chem. Int. Ed.* 2007, 46, 3505-3508, Supplemental information, page 6. The compound was further purified by silica gel chromatography employing ethyl acetate:hexanes (1:5) as eluent. $^1$H NMR (CHLOROFORM-d): 11.26 (s, 1H), 9.70 (d, J=0.5 Hz, 1H), 7.53 (s, 1H), 6.62 (s, 1H), 6.21 (br. s., 1H).

Intermediate

5-chloro-4-((3-(2,3-dihydrobenzo[b][1,4]dioxin-6-yl)-2-methylbenzyl)oxy)-2-hydroxybenzaldehyde

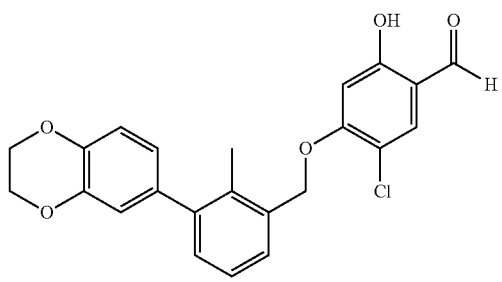 [SMILES: Cc1c(COc2cc(O)c(C=O)cc2Cl)cccc1-c1ccc2c(c1)OCCO2]

Diisopropyl azodicarboxylate (0.532 mL, 2.68 mmol) in tetrahydrofuran (3 mL) was added dropwise to a cooled (0° C.) solution of 5-chloro-2,4-dihydroxybenzaldehyde (421 mg, 2.440 mmol), triphenylphosphine (711 mg, 2.71 mmol) and (3-(2,3-dihydrobenzo[b][1,4]dioxin-6-yl)-2-methylphenyl)methanol (686 mg, 2.68 mmol) in dry tetrahydrofuran (7 mL). The resulting reaction mixture was allowed to slowly warm to room temperature with stirring overnight. The product was filtered from the reaction using a buchner filter funnel and rinsed with tetrahydrofuran (approx. 5 mL) then dried in vacuo at room temperature to yield 393 mg of a near colorless solid. $^1$H NMR (CHLOROFORM-d) δ: 11.44 (s, 1H), 9.71 (s, 1H), 7.56 (s, 1H), 7.45 (dd, J=6.5, 2.4 Hz, 1H), 7.23-7.27 (m, 2H), 6.92 (d, J=8.2 Hz, 1H), 6.84 (d, J=2.0 Hz, 1H), 6.79 (dd, J=8.2, 2.0 Hz, 1H), 6.64 (s, 1H), 5.21 (s, 2H), 4.32 (s, 4H), 2.28 (s, 3H).

Intermediate

3-((4-chloro-5-((3-(2,3-dihydrobenzo[b][1,4]dioxin-6-yl)-2-methylbenzyl)oxy)-2-formylphenoxy)methyl)benzonitrile

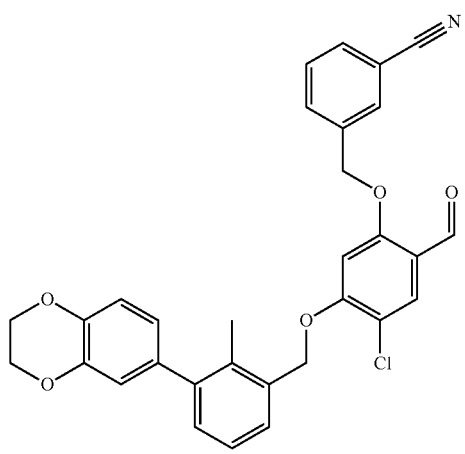

5-Chloro-4-((3-(2,3-dihydrobenzo[b][1,4]dioxin-6-yl)-2-methylbenzyl)oxy)-2-hydroxybenzaldehyde (180 mg, 0.438 mmol) was partially suspended in dimethylformamide (4.3 mL), cesium carbonate (180 mg, 0.552 mmol) was added and the reaction stirred for approximately 5 minutes in which it appeared to exhibit improved solubility. 3-cyanobenzyl bromide (94 mg, 0.479 mmol) was added to the reaction. The reaction was capped and stirred at room temperature overnight. Volatiles were removed from the reaction and the solid residue was partitioned between dichloromethane and water. The aqueous phase was extracted once with dichloromethane. The organic extracts were combined and washed with brine then dried over sodium sulfate. The drying agent was removed by filtration and solvent removed in vacuo to yield the title compound (241 mg) as a colorless solid. A solvate of *0.45 dichloromethane was observed in the proton NMR. $^1$H NMR (CHLOROFORM-d) δ: 10.33 (s, 1H), 7.92 (s, 1H), 7.73 (s, 1H), 7.69 (d, J=1.3 Hz, 1H), 7.68 (s, 1H), 7.53-7.58 (m, 1H), 7.37-7.41 (m, 1H), 7.25-7.27 (m, 2H), 6.93 (d, J=8.2 Hz, 1H), 6.82 (d, J=2.0 Hz, 1H), 6.78 (dd, J=8.2, 2.0 Hz, 1H), 6.61 (s, 1H), 5.21 (s, 2H), 5.19 (s, 2H), 4.32 (s, 4H), 2.29 (s, 3H).

Example 1157

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

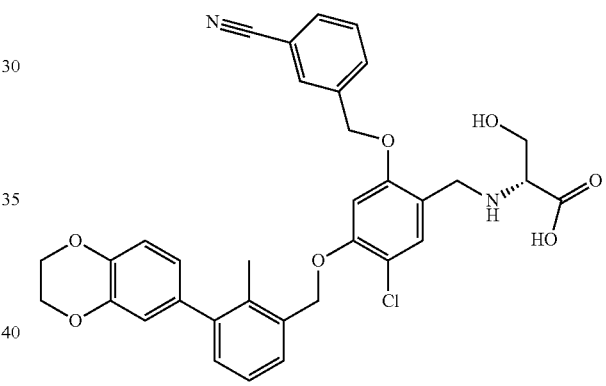

Dissolved 3-((4-chloro-5-((3-(2,3-dihydrobenzo[b][1,4]dioxin-6-yl)-2-methylbenzyl)oxy)-2-formylphenoxy)methyl)benzonitrile, *0.45 methylene chloride (32 mg, 0.057 mmol) in dimethylformamide (568 uL), add D-serine (9.9 mg, 0.094 mmol), methanol (142 μl) and acetic acid (14.2 μl). Sodium cyanoborohydride (8.8 mg, 0.140 mmol) was added to the opaque reaction solution. The reaction was capped and stirred at room temperature for 2 days. The reaction was diluted to approximately 2 mL using tetrahydrofuran and 2 drops of water added to help solubilize salts. The reaction was filtered through a 0.45 um syringe filter and product was purified by reverse phase HPLC using the following conditions:

Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-100% B over 15 minutes, then a 5-minute hold at 100% B; Flow: 20 mL/minutes Fractions containing the desired product were combined and dried via centrifugal evaporation.

The yield of the product was 17.1 mg, and its estimated purity by LCMS analysis was 94%. Two analytical LCMS injections were used to determine the final purity. $^1$H NMR (DMSO-d$_6$) δ: 8.01 (s, 1H), 7.90 (d, J=8.1 Hz, 1H), 7.82 (d, J=7.7 Hz, 1H), 7.61 (t, J=7.9 Hz, 1H), 7.50 (s, 1H), 7.43 (d, J=7.7 Hz, 1H), 7.20-7.27 (m, 1H), 7.15-7.19 (m, 1H), 7.11 (s, 1H), 6.92 (d, J=8.1 Hz, 1H), 6.68-6.83 (m, 2H), 5.27-5.37 (m, 2H), 5.24 (s, 2H), 4.28 (s, 4H), 3.93-4.04 (m, 2H), 3.60-3.75 (m, 3H), 3.47 (br. s., 4H), 3.18 (t, J=5.3 Hz, 1H), 2.23 (s, 3H). LCMS Condition A: 1.79 minutes, M−1: 613, Exact Mass: 614.

The following examples were prepared in the same manner as (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid from 3-((4-chloro-5-((3-(2,3-dihydrobenzo[b][1,4]dioxin-6-yl)-2-methylbenzyl)oxy)-2-formylphenoxy)methyl)benzonitrile and the appropriate amine to provide the title examples in a reductive amination reaction. LCMS characterization data for these examples is given in tabular form following the examples.

Example 1158

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid

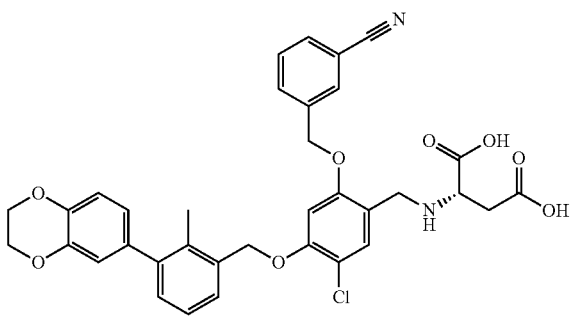 [SMILES: Cc1c(COc2cc(OCc3cccc(C#N)c3)c(CN[C@@H](CC(=O)O)C(=O)O)cc2Cl)cccc1-c1ccc2c(c1)OCCO2]

Example 1159

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-hydroxyphenyl)propanoic acid Example 1160

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(methylthio)propanoic acid

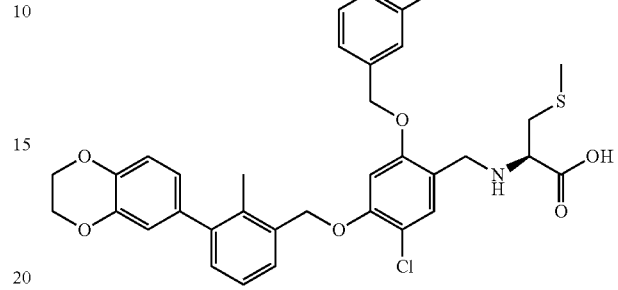

Example 1161

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(4-hydroxyphenyl)acetic acid

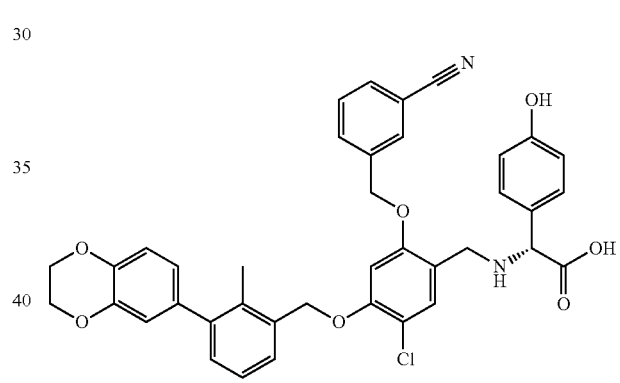

Example 1162

2-((5-chloro-2-((3-cyanobenzyl)oxy)-4-((3-(2,3-dihydrobenzo[b][1,4]dioxin-6-yl)-2-methylbenzyl)oxy)benzyl)amino)-3,3,3-trifluoropropanoic acid

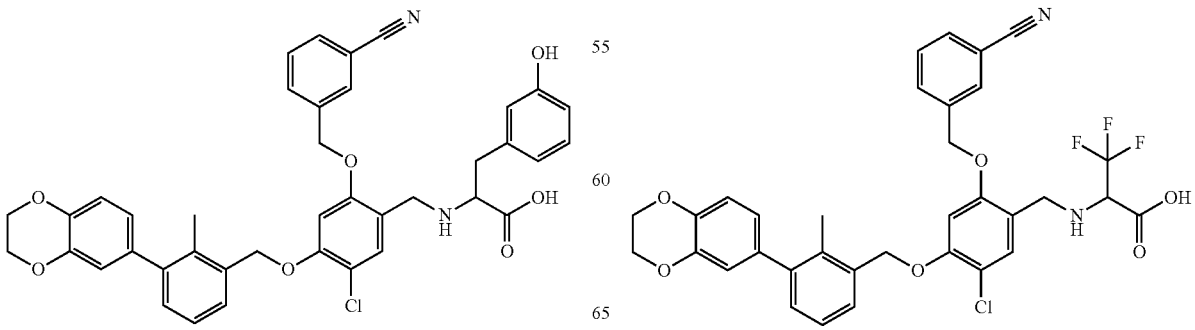

Example 1163

(2R,3R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

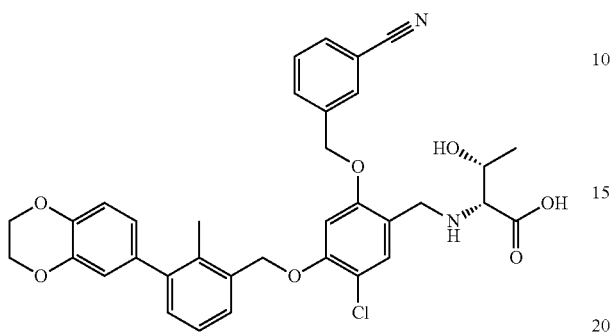

Example 1164

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)propanoic acid

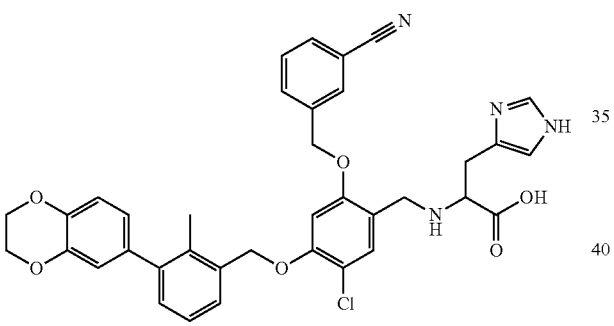

Example 1165

1-(5-chloro-2-((3-cyanobenzyl)oxy)-4-((3-(2,3-dihydrobenzo[b][1,4]dioxin-6-yl)-2-methylbenzyl)oxy)benzyl)pyrrolidine-2-carboxylic acid

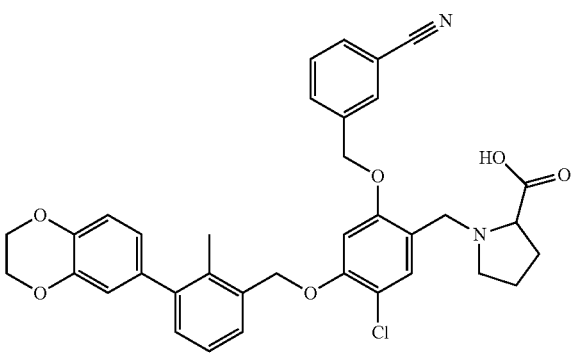 [SMILES: Cc1c(COc2cc(OCc3cccc(C#N)c3)c(CN3CCCC3C(=O)O)cc2Cl)cccc1-c1ccc2c(c1)OCCO2]

Example 1166

(2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid

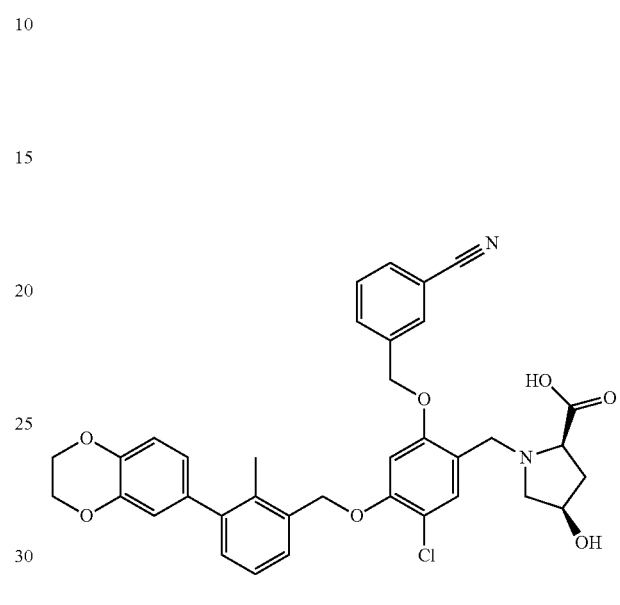

Example 1167

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(5-hydroxy-1H-indol-3-yl)propanoic acid

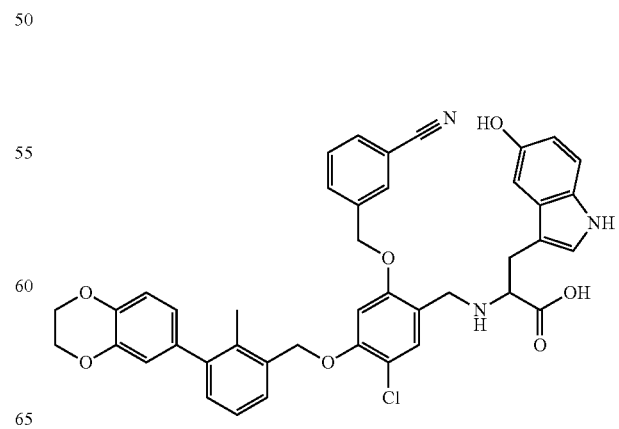

Example 1168

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-indol-3-yl)propanoic acid Example 1171

(S)-2-(benzyl(5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

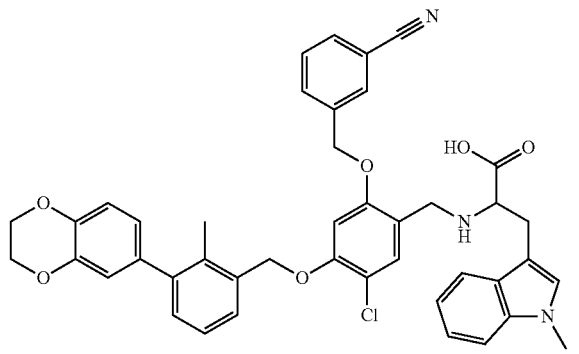 [SMILES: Cc1c(COc2cc(OCc3cccc(C#N)c3)c(CNC(Cc3cn(C)c4ccccc34)C(=O)O)cc2Cl)cccc1-c1ccc2c(c1)OCCO2]

Example 1169

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid

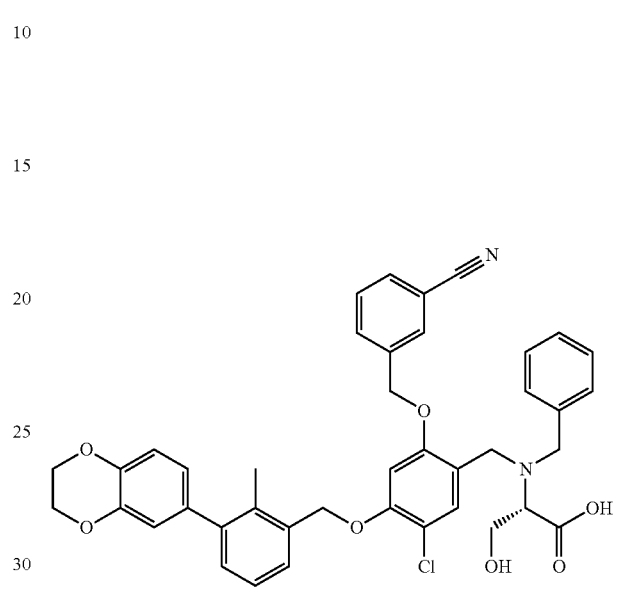

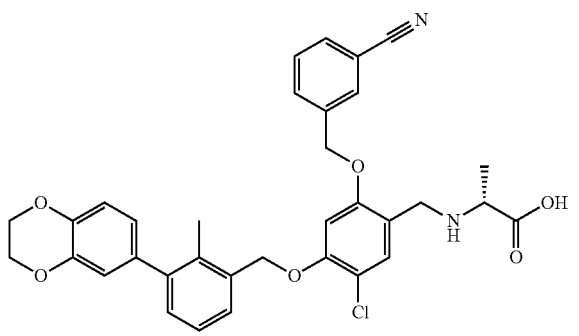 [SMILES: Cc1c(COc2cc(OCc3cccc(C#N)c3)c(CN[C@H](C)C(=O)O)cc2Cl)cccc1-c1ccc2c(c1)OCCO2]

Example 1170

3-((4-chloro-5-((3-(2,3-dihydrobenzo[b][1,4]dioxin-6-yl)-2-methylbenzyl)oxy)-2-(((2-hydroxyethyl)amino)methyl)phenoxy)methyl)benzonitrile Example 1172

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(dimethylamino)propanoic acid

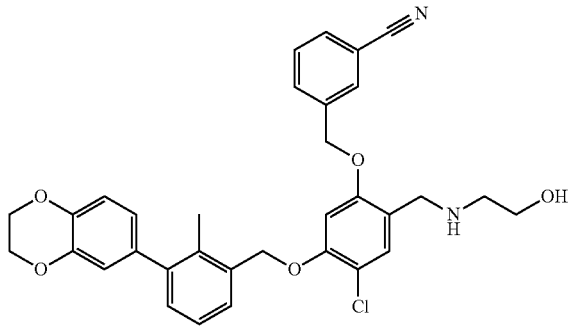 [SMILES: Cc1c(COc2cc(OCc3cccc(C#N)c3)c(CNCCO)cc2Cl)cccc1-c1ccc2c(c1)OCCO2]

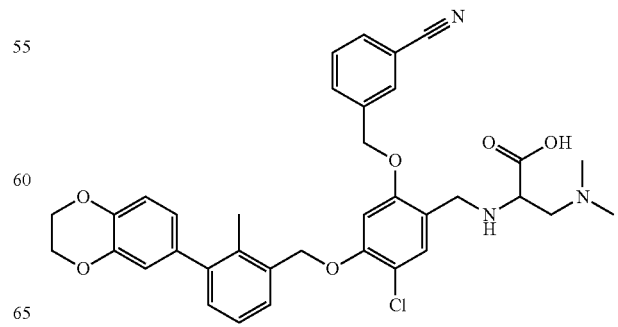

Example 1173

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-6-(dimethylamino)hexanoic acid

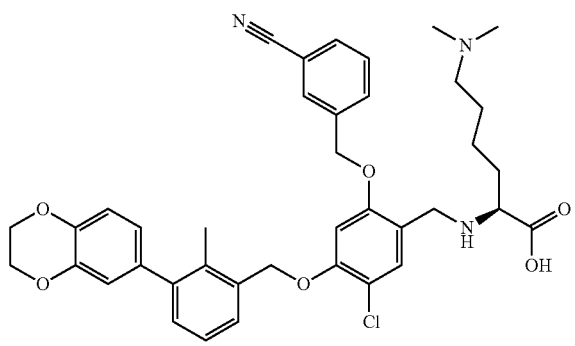 [SMILES: Cc1c(COc2cc(OCc3cccc(C#N)c3)c(CN[C@@H](CCCCN(C)C)C(=O)O)cc2Cl)cccc1-c1ccc2c(c1)OCCO2]

Example 1174

(2S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfinyl)butanoic acid

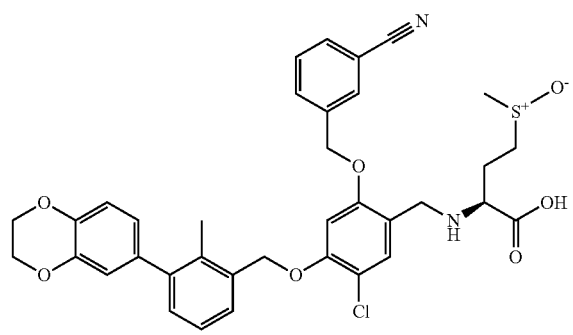 [SMILES: Cc1c(COc2cc(OCc3cccc(C#N)c3)c(CN[C@@H](CC[S+](C)[O-])C(=O)O)cc2Cl)cccc1-c1ccc2c(c1)OCCO2]

Example 1175

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid

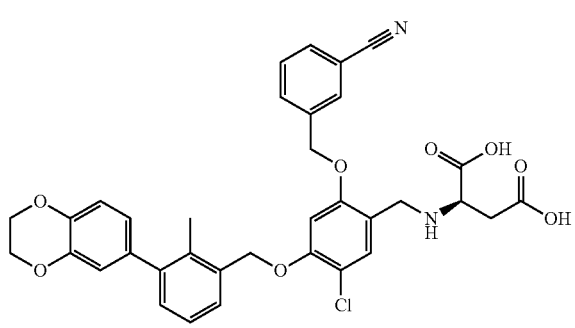 [SMILES: Cc1c(COc2cc(OCc3cccc(C#N)c3)c(CN[C@H](CC(=O)O)C(=O)O)cc2Cl)cccc1-c1ccc2c(c1)OCCO2]

Example 1176

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-4-yl)propanoic acid

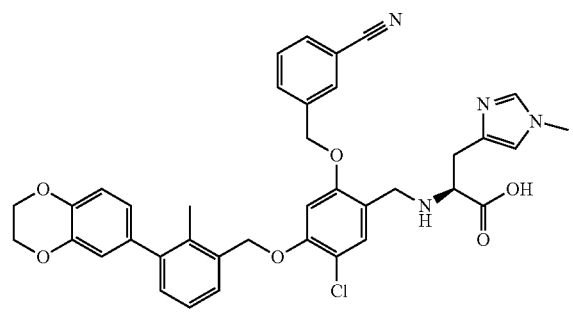 [SMILES: Cc1c(COc2cc(OCc3cccc(C#N)c3)c(CN[C@@H](Cc3cn(C)cn3)C(=O)O)cc2Cl)cccc1-c1ccc2c(c1)OCCO2]

Example 1177

1-((5-chloro-2-((3-cyanobenzyl)oxy)-4-((3-(2,3-dihydrobenzo[b][1,4]dioxin-6-yl)-2-methylbenzyl)oxy)benzyl)amino)cyclopropanecarboxylic acid

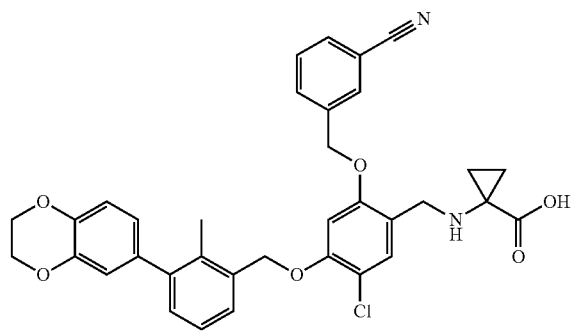 [SMILES: Cc1c(COc2cc(OCc3cccc(C#N)c3)c(CNC3(C(=O)O)CC3)cc2Cl)cccc1-c1ccc2c(c1)OCCO2]

Example 1178

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-2-yl)propanoic acid

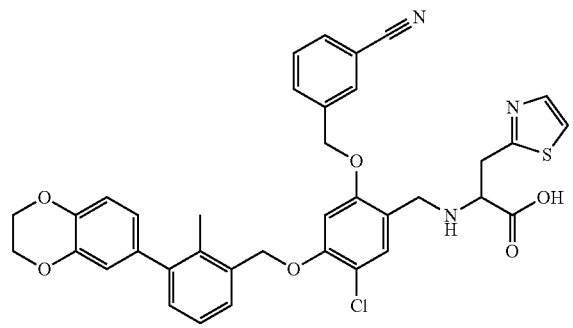 [SMILES: Cc1c(COc2cc(OCc3cccc(C#N)c3)c(CNC(Cc3nccs3)C(=O)O)cc2Cl)cccc1-c1ccc2c(c1)OCCO2]

119

Example 1179

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxy-3-methylbutanoic acid

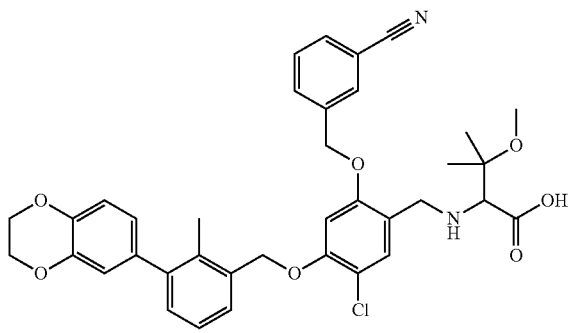 [SMILES: COC(C)(C)C(NCc1cc(Cl)c(OCc2cccc(-c3ccc4c(c3)OCCO4)c2C)cc1OCc1cccc(C#N)c1)C(=O)O]

Example 1180

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-cyanopropanoic acid

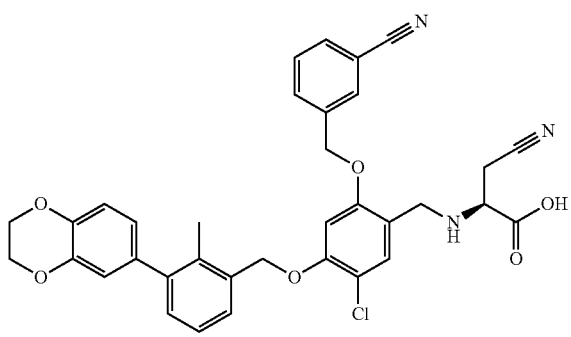 [SMILES: Cc1c(COc2cc(OCc3cccc(C#N)c3)c(CN[C@@H](CC#N)C(=O)O)cc2Cl)cccc1-c1ccc2c(c1)OCCO2]

Example 1181

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2-hydroxyphenyl)propanoic acid

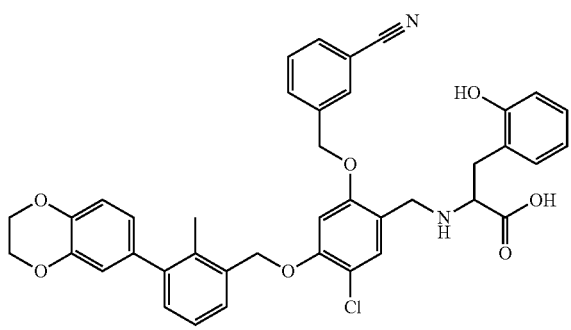 [SMILES: Cc1c(COc2cc(OCc3cccc(C#N)c3)c(CNC(Cc3ccccc3O)C(=O)O)cc2Cl)cccc1-c1ccc2c(c1)OCCO2]

120

Example 1182

2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid

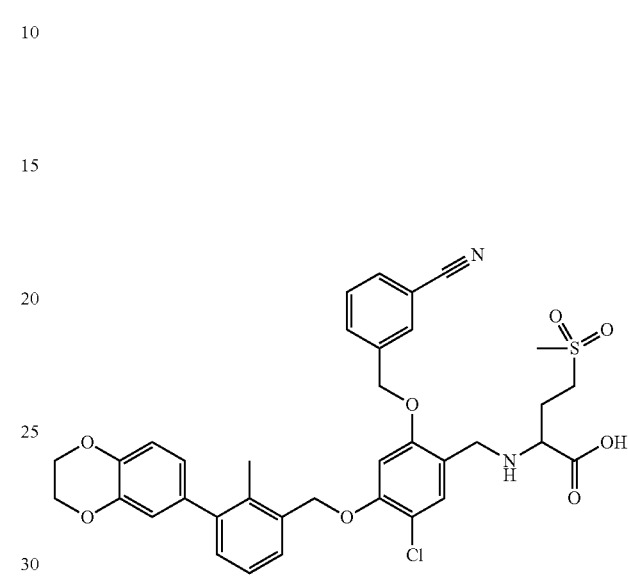

Example 1183

(S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)-3-hydroxypropanoic acid

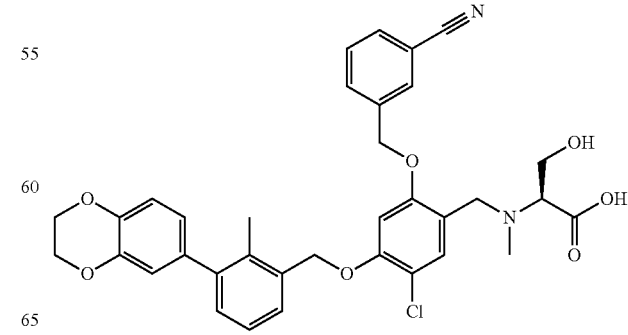

Example 1184

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxypropanoic acid Example 1186

(S)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino) propanoic acid

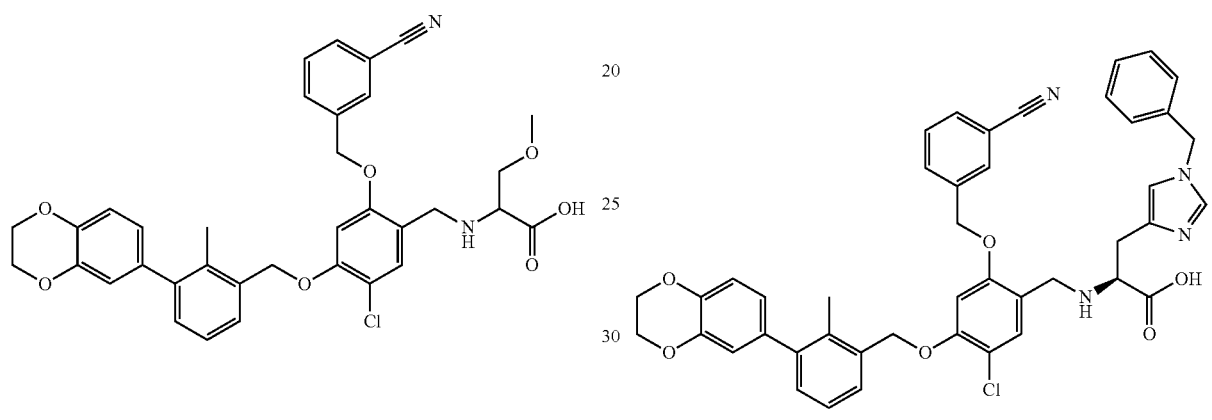

Example 1185

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-pyrrolo[2,3-b]pyridin-3-yl)propanoic acid Example 1187

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(4-hydroxyphenyl)propanoic acid

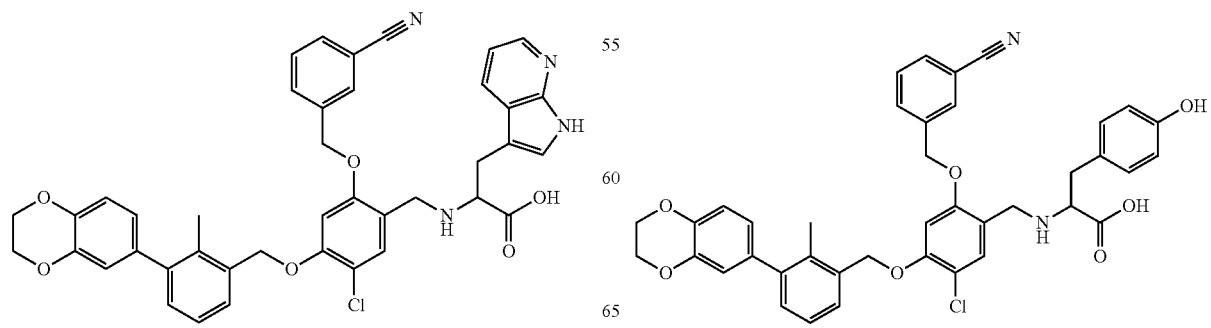

Example 1188

2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)propanoic acid

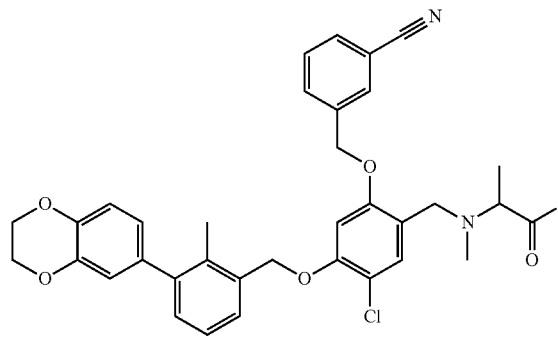

Example 1189

(2S,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

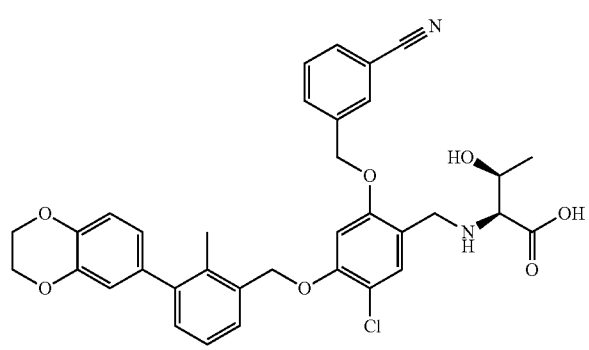 [SMILES: Cc1c(COc2cc(OCc3cccc(C#N)c3)c(CN[C@H](C(=O)O)[C@H](C)O)cc2Cl)cccc1-c1ccc2c(c1)OCCO2]

Example 1190

(2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2,3-dicarboxylic acid

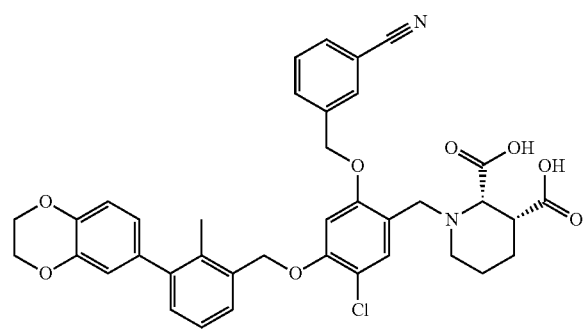 [SMILES: Cc1c(COc2cc(OCc3cccc(C#N)c3)c(CN3CCC[C@@H](C(=O)O)[C@H]3C(=O)O)cc2Cl)cccc1-c1ccc2c(c1)OCCO2]

Example 1191

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)-2-methyl-propanoic acid

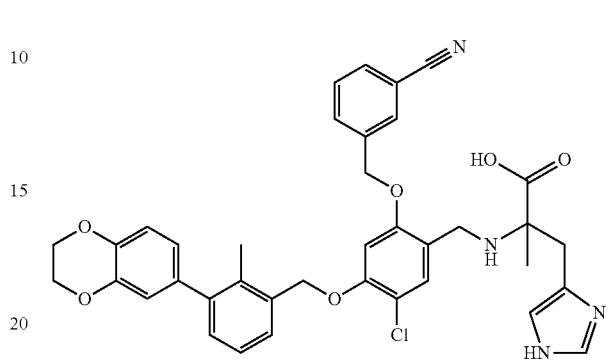

Example 1192

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-indol-3-yl)propanoic acid

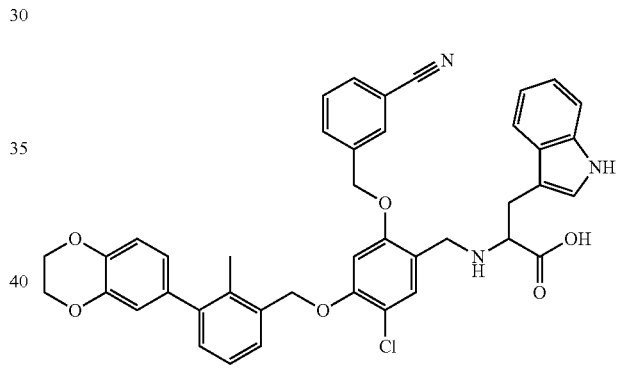

Example 1193

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)butanoic acid

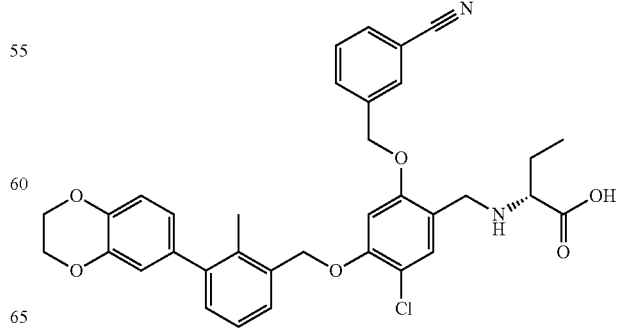

125

Example 1194

(R)-3-(benzyloxy)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid

126

Example 1196

(2S,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid

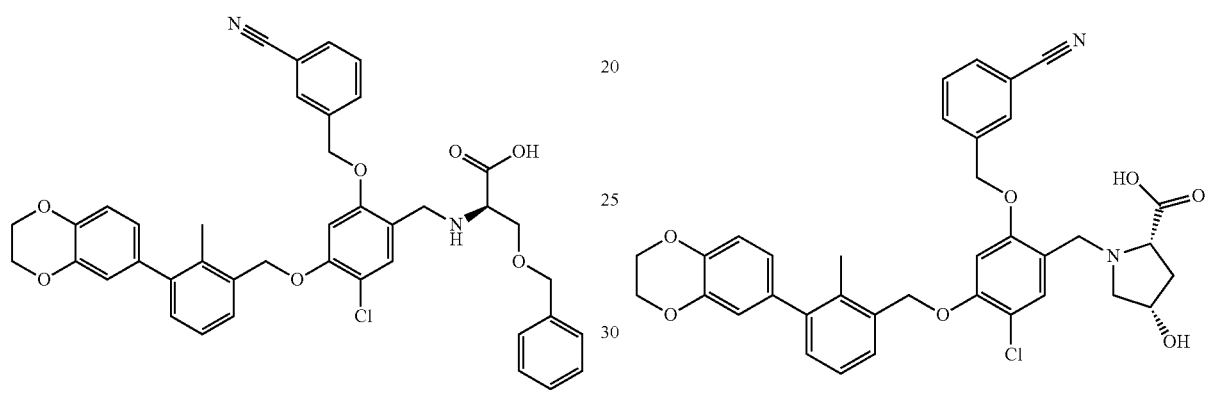

Example 1195

(2R,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

Example 1197

(2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid

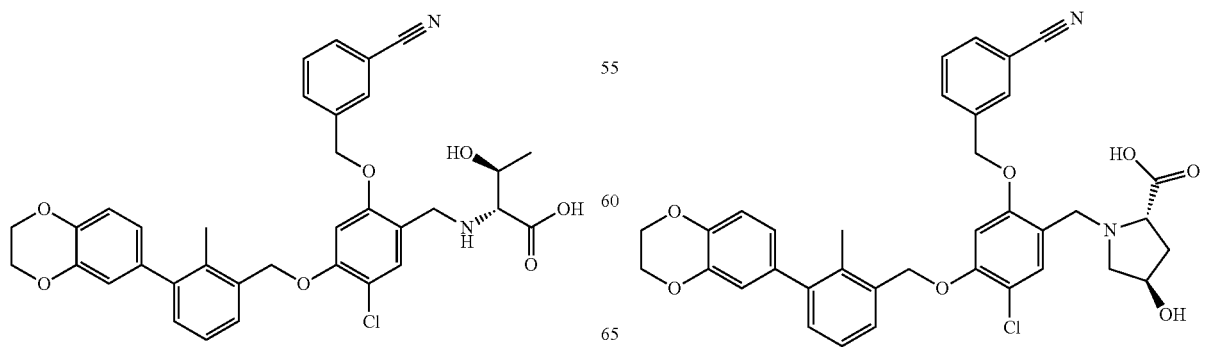

Example 1198

(R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid

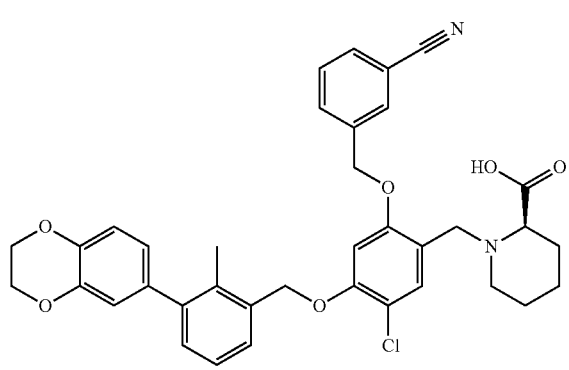 [SMILES: Cc1c(COc2cc(OCc3cccc(C#N)c3)c(CN3CCCC[C@@H]3C(=O)O)cc2Cl)cccc1-c1ccc2c(c1)OCCO2]

Example 1199

(2R,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid

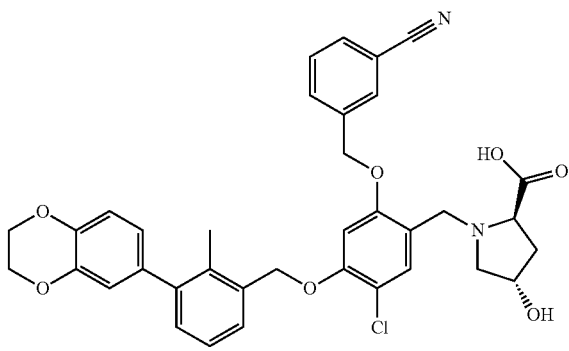 [SMILES: Cc1c(COc2cc(OCc3cccc(C#N)c3)c(CN3C[C@@H](O)C[C@@H]3C(=O)O)cc2Cl)cccc1-c1ccc2c(c1)OCCO2]

Example 1200

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid

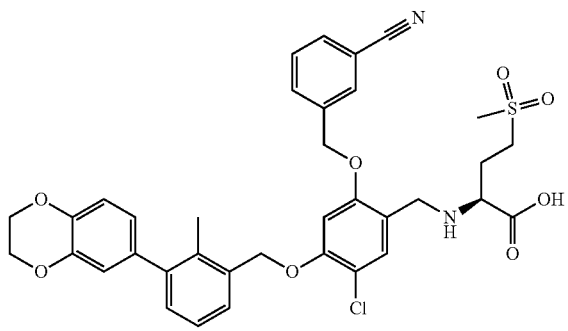 [SMILES: Cc1c(COc2cc(OCc3cccc(C#N)c3)c(CN[C@@H](CCS(C)(=O)=O)C(=O)O)cc2Cl)cccc1-c1ccc2c(c1)OCCO2]

Example 1201

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)butanoic acid

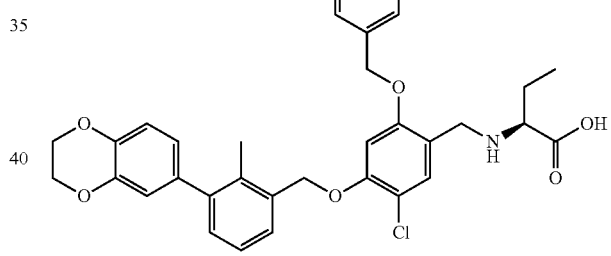

Example 1202

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylthio)butanoic acid

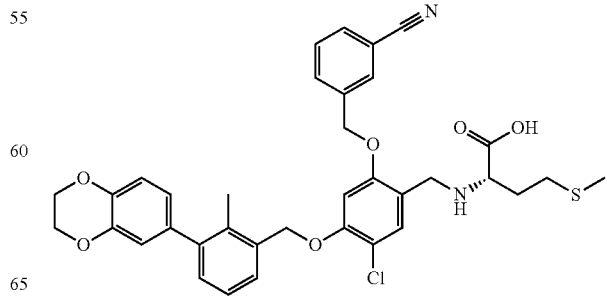

Example 1203

(S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)succinic acid

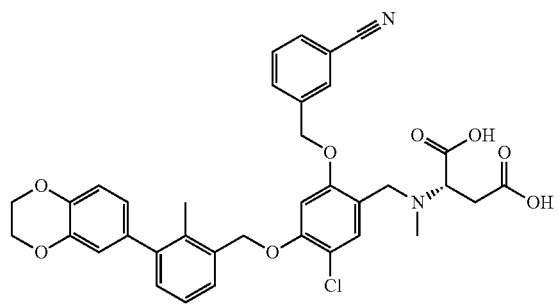 [SMILES: Cc1c(COc2cc(OCc3cccc(C#N)c3)c(CN(C)[C@@H](CC(=O)O)C(=O)O)cc2Cl)cccc1-c1ccc2c(c1)OCCO2]

Example 1204

(2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid

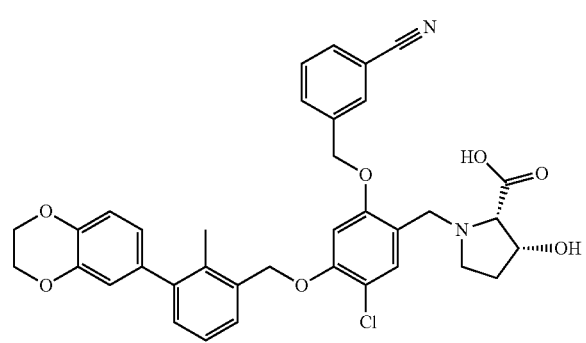 [SMILES: Cc1c(COc2cc(OCc3cccc(C#N)c3)c(CN3CC[C@@H](O)[C@H]3C(=O)O)cc2Cl)cccc1-c1ccc2c(c1)OCCO2]

Example 1205

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid

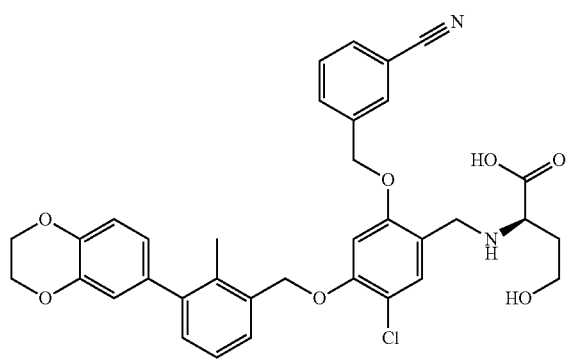 [SMILES: Cc1c(COc2cc(OCc3cccc(C#N)c3)c(CN[C@H](CCO)C(=O)O)cc2Cl)cccc1-c1ccc2c(c1)OCCO2]

Example 1206

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid

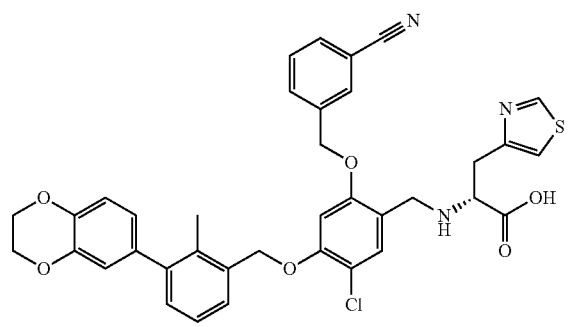 [SMILES: Cc1c(COc2cc(OCc3cccc(C#N)c3)c(CN[C@H](Cc3cscn3)C(=O)O)cc2Cl)cccc1-c1ccc2c(c1)OCCO2]

Example 1207

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-5-yl)propanoic acid

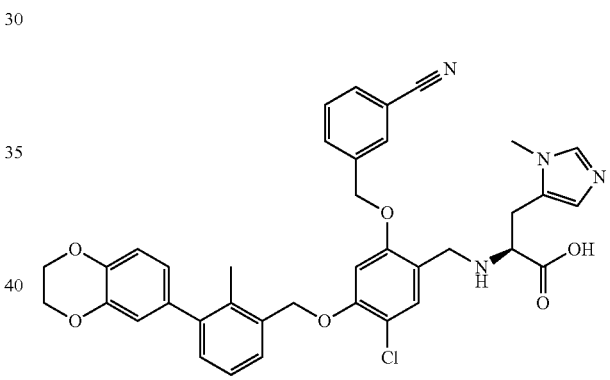

Example 1208

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid

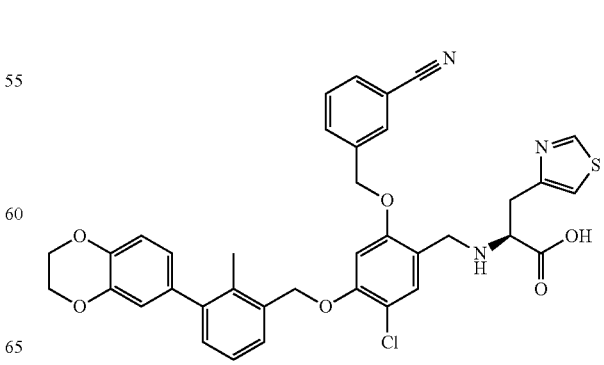

131

Example 1209

1-(5-chloro-2-((3-cyanobenzyl)oxy)-4-((3-(2,3-dihydrobenzo[b][1,4]dioxin-6-yl)-2-methylbenzyl)oxy)benzyl)azetidine-2-carboxylic acid

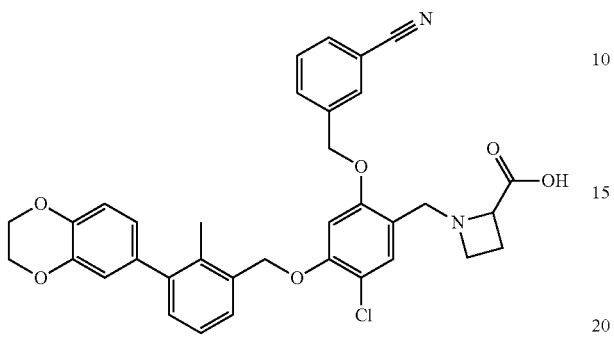

Example 1210

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-3-methylbutanoic acid

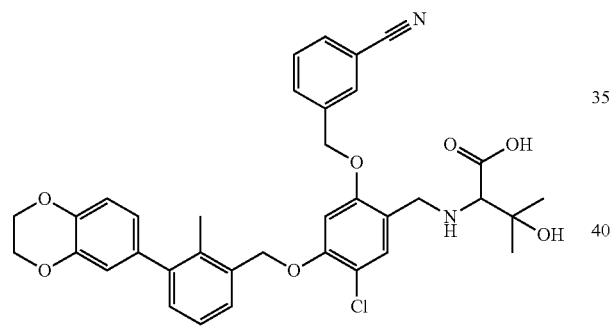

Example 1211

2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(1H-indol-3-yl)acetic acid

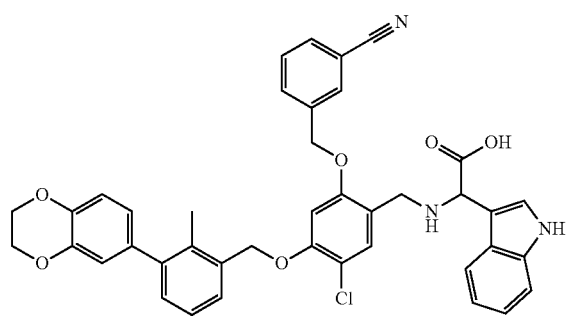 [SMILES: Cc1c(COc2cc(OCc3cccc(C#N)c3)c(CNC(C(=O)O)c3c[nH]c4ccccc34)cc2Cl)cccc1-c1ccc2c(c1)OCCO2]

132

Example 1212

3-((4-chloro-5-((3-(2,3-dihydrobenzo[b][1,4]dioxin-6-yl)-2-methylbenzyl)oxy)-2-(((2-hydroxy-3-morpholinopropyl)amino)methyl)phenoxy)methyl)benzonitrile

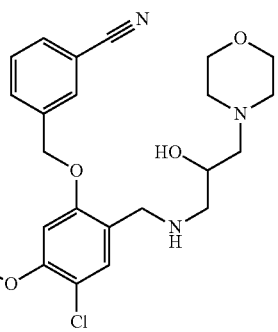

Example 1213

4-(5-chloro-2-((3-cyanobenzyl)oxy)-4-((3-(2,3-dihydrobenzo[b][1,4]dioxin-6-yl)-2-methylbenzyl)oxy)benzyl)morpholine-3-carboxylic acid

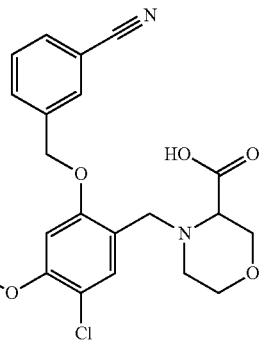

Example 1214

2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(hydroxymethyl)-3-methylbutanoic acid

Example 1216

2-((5-chloro-2-((3-cyanobenzyl)oxy)-4-((3-(2,3-dihydrobenzo[b][1,4]dioxin-6-yl)-2-methylbenzyl)oxy)benzyl)amino)-4,4,4-trifluorobutanoic acid

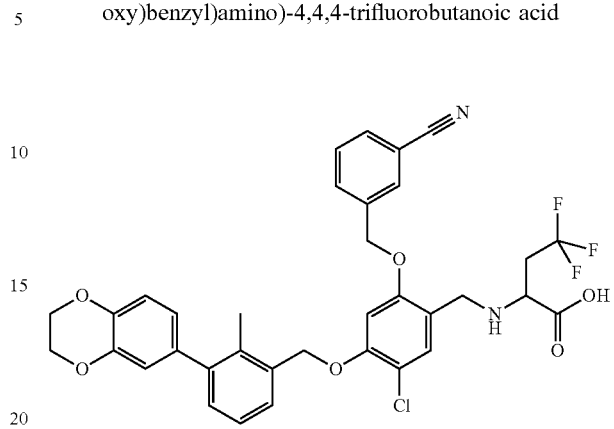

Example 1217

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-cyanophenyl)propanoic acid

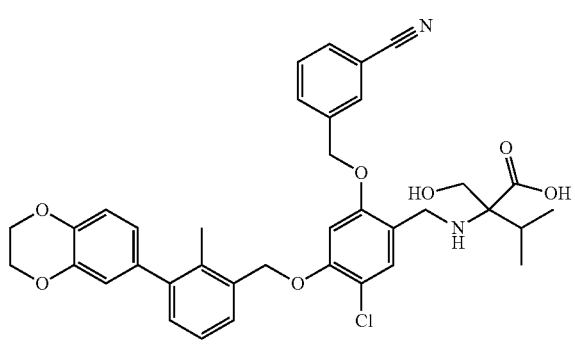 [SMILES: Cc1c(COc2cc(OCc3cccc(C#N)c3)c(CNC(CO)(C(=O)O)C(C)C)cc2Cl)cccc1-c1ccc2c(c1)OCCO2]

Example 1215

(2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-fluoropyrrolidine-2-carboxylic acid

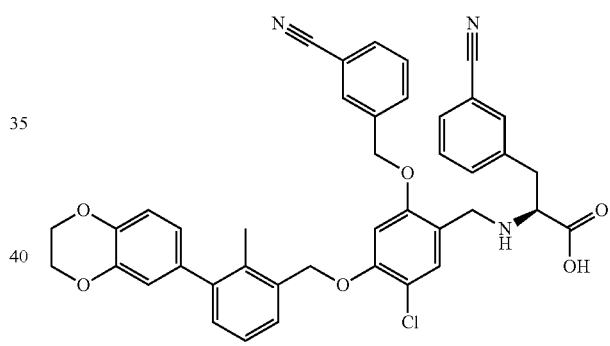

Example 1218

2-benzyl-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

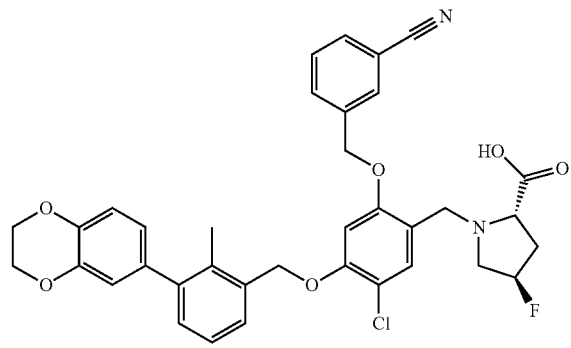 [SMILES: Cc1c(COc2cc(OCc3cccc(C#N)c3)c(CN3C[C@H](F)C[C@H]3C(=O)O)cc2Cl)cccc1-c1ccc2c(c1)OCCO2]

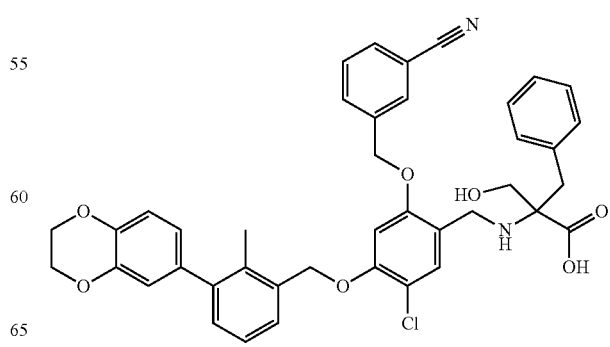

135

Example 1219

(2S,3S)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid

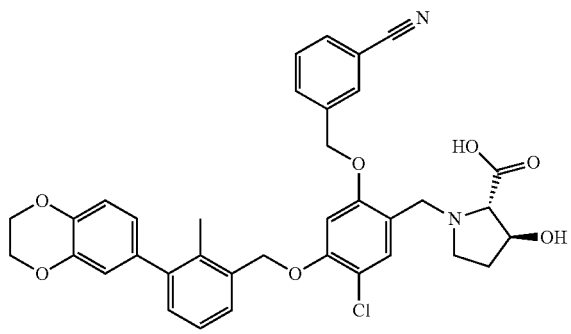 [SMILES: Cc1c(COc2cc(OCc3cccc(C#N)c3)c(CN3CC[C@H](O)[C@H]3C(=O)O)cc2Cl)cccc1-c1ccc2c(c1)OCCO2]

Example 1220

4-((5-chloro-2-((3-cyanobenzyl)oxy)-4-((3-(2,3-dihydrobenzo[b][1,4]dioxin-6-yl)-2-methylbenzyl)oxy)benzyl)amino)-1-methylpiperidine-4-carboxylic acid

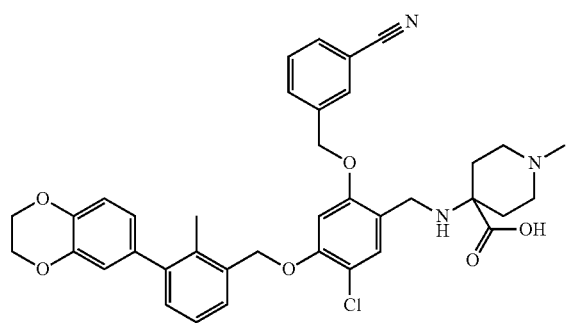 [SMILES: Cc1c(COc2cc(OCc3cccc(C#N)c3)c(CNC3(C(=O)O)CCN(C)CC3)cc2Cl)cccc1-c1ccc2c(c1)OCCO2]

Example 1221

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(pyridin-2-yl)propanoic acid

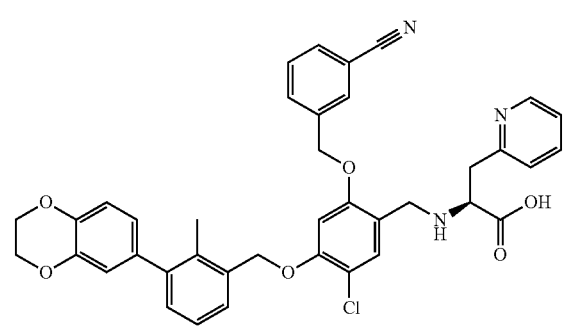 [SMILES: Cc1c(COc2cc(OCc3cccc(C#N)c3)c(CN[C@@H](Cc3ccccn3)C(=O)O)cc2Cl)cccc1-c1ccc2c(c1)OCCO2]

136

Example 1222

(S)-4-(5-chloro-2-((3-cyanobenzyl)oxy)-4-((3-(2,3-dihydrobenzo[b][1,4]dioxin-6-yl)-2-methylbenzyl)oxy)benzyl)thiomorpholine-3-carboxylic acid

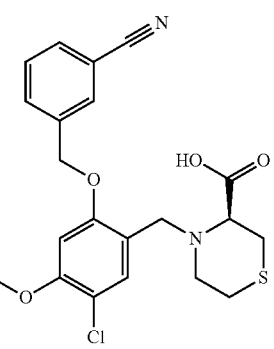

Example 1223

3-((4-chloro-5-((3-(2,3-dihydrobenzo[b][1,4]dioxin-6-yl)-2-methylbenzyl)oxy)-2-(((2-methyl-1-(4-methylpiperazin-1-yl)propan-2-yl)amino)methyl)phenoxy)methyl)benzonitrile

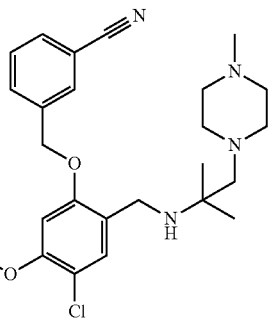

137

Example 1224

1-(5-chloro-2-((3-cyanobenzyl)oxy)-4-((3-(2,3-dihydrobenzo[b][1,4]dioxin-6-yl)-2-methylbenzyl)oxy)benzyl)-4-methylpiperazine-2-carboxylic acid

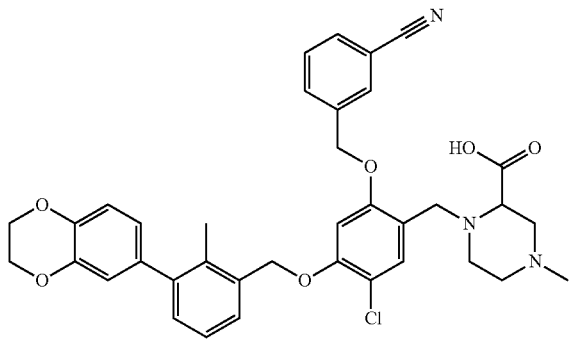 [SMILES: Cc1c(COc2cc(OCc3cccc(C#N)c3)c(CN3CCN(C)CC3C(=O)O)cc2Cl)cccc1-c1ccc2c(c1)OCCO2]

Example 1225

3-((4-chloro-5-((3-(2,3-dihydrobenzo[b][1,4]dioxin-6-yl)-2-methylbenzyl)oxy)-2-((2-hydroxy-3-(2-oxopyrrolidin-1-yl)propyl)amino)methyl)phenoxy)methyl)benzonitrile

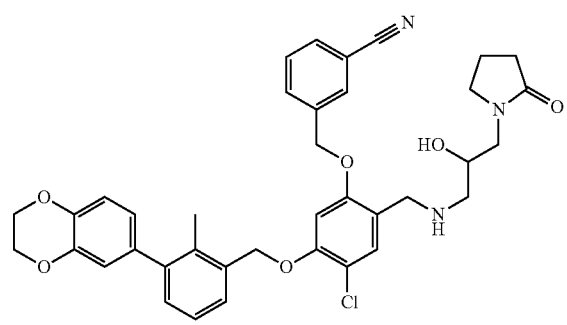 [SMILES: Cc1c(COc2cc(OCc3cccc(C#N)c3)c(CNCC(O)CN3CCCC3=O)cc2Cl)cccc1-c1ccc2c(c1)OCCO2]

Example 1226

5-(5-chloro-2-((3-cyanobenzyl)oxy)-4-((3-(2,3-dihydrobenzo[b][1,4]dioxin-6-yl)-2-methylbenzyl)oxy)benzyl)-4,5,6,7-tetrahydro-3H-imidazo[4,5-c]pyridine-4-carboxylic acid

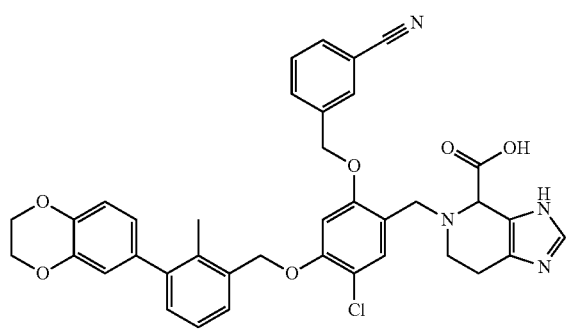 [SMILES: Cc1c(COc2cc(OCc3cccc(C#N)c3)c(CN3CCc4nc[nH]c4C3C(=O)O)cc2Cl)cccc1-c1ccc2c(c1)OCCO2]

138

Example 1227

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2H-tetrazol-2-yl)propanoic acid

Example 1228

(R)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid

Example 1229

3-((2-((((1H-tetrazol-5-yl)methyl)amino)methyl)-4-chloro-5-((3-(2,3-dihydrobenzo[b][1,4]dioxin-6-yl)-2-methylbenzyl)oxy)phenoxy)methyl)benzonitrile

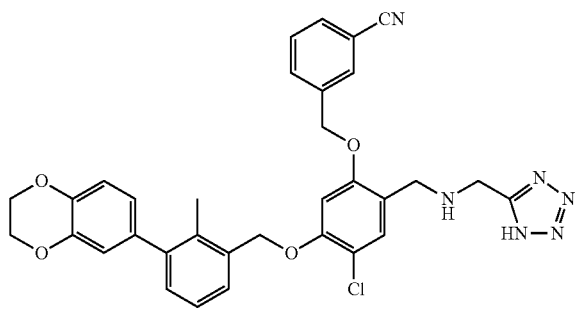 [SMILES: Cc1c(COc2cc(OCc3cccc(C#N)c3)c(CNCc3nnn[nH]3)cc2Cl)cccc1-c1ccc2c(c1)OCCO2]

Example 1230

(S)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid

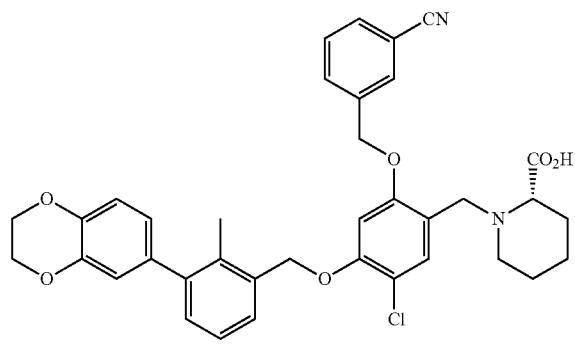 [SMILES: Cc1c(COc2cc(OCc3cccc(C#N)c3)c(CN3CCCC[C@H]3C(=O)O)cc2Cl)cccc1-c1ccc2c(c1)OCCO2]

$^1$H NMR (DMSO-$d_6$) δ: 7.96 (s, 1H), 7.82 (t, J=8.1 Hz, 2H), 7.57-7.66 (m, 1H), 7.40-7.47 (m, 2H), 7.21-7.28 (m, 1H), 7.14-7.20 (m, 1H), 7.07 (s, 1H), 6.92 (d, J=8.4 Hz, 1H), 6.71-6.80 (m, 2H), 5.28 (s, 2H), 5.22 (s, 2H), 4.28 (s, 4H), 3.63-3.84 (m, 2H), 3.16 (dd, J=7.5, 4.2 Hz, 1H), 2.90 (d, J=10.3 Hz, 1H), 2.27-2.38 (m, 1H), 2.23 (s, 3H), 1.65-1.86 (m, 2H), 1.49 (br. s., 3H), 1.37 (br. s., 1H).

| Example | LCMS Method | RT (min) | M$^{+1}$ | M$^{-1}$ |
|---|---|---|---|---|
| Example 1158: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid | M | 2.78 | | 644 |
| Example 1159: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-hydroxyphenyl)propanoic acid | A | 1.96 | 691.1 | |
| Example 1160: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(methylthio)propanoic acid | M | 2.92 | 645.4 | |
| Example 1161: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(4-hydroxyphenyl)acetic acid | A | 1.92 | 677.2 | |
| Example 1162: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3,3,3-trifluoropropanoic acid | A | 1.99 | 653.3 | |
| Example 1163: (2R,3R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | M | 2.85 | 629.2 | |
| Example 1164: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)propanoic acid | M | 2.84 | 665 | |
| Example 1164: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)propanoic acid | A | 1.83 | 665.1 | |
| Example 1165: 1-(5-chloro-2-((3-cyanobenzyl)oxy)-4-((3-(2,3-dihydrobenzo[b][1,4]dioxin-6-yl)-2-methylbenzyl)oxy)benzyl)pyrrolidine-2-carboxylic acid | M | 2.86 | 625.1 | |
| Example 1166: (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid | M | 2.84 | 641.2 | |
| Example 1167: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(5-hydroxy-1H-indol-3-yl)propanoic acid | M | 2.78 | 730.1 | |
| Example 1168: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-indol-3-yl)propanoic acid | M | 3.06 | 728.1 | |
| Example 1169: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid | A | 1.86 | 599.2 | |
| Example 1170: 3-((4-chloro-5-((3-(2,3-dihydrobenzo[b][1,4]dioxin-6-yl)-2-methylbenzyl)oxy)-2-(((2-hydroxyethyl)amino)methyl)phenoxy)methyl)benzonitrile | A | 2.01 | 571 | |
| Example 1171: (S)-2-(benzyl(5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid | M | 2.98 | 705.2 | |
| Example 1172: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(dimethylamino)propanoic acid | M | 2.91 | 642.1 | |
| Example 1173: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-6-(dimethylamino)hexanoic acid | A | 1.7 | 684.2 | |

| Example | LCMS Method | RT (min) | M+1 | M−1 |
|---|---|---|---|---|
| Example 1174: (2S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfinyl)butanoic acid | A | 1.74 | 675.1 | |
| Example 1175: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid | A | 1.57 | 643.1 | |
| Example 1176: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-4-yl)propanoic acid | A | 1.74 | 679.2 | |
| Example 1177: 1-((5-chloro-2-((3-cyanobenzyl)oxy)-4-((3-(2,3-dihydrobenzo[b][1,4]dioxin-6-yl)-2-methylbenzyl)oxy)benzyl)amino)cyclopropanecarboxylic acid | A | 1.9 | 611.2 | |
| Example 1178: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-2-yl)propanoic acid | A | 1.97 | 682.4 | |
| Example 1179: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxy-3-methylbutanoic acid | A | 1.96 | 657.1 | |
| Example 1180: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-cyanopropanoic acid | A | 1.8 | 1247.2 | |
| Example 1181: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2-hydroxyphenyl)propanoic acid | A | 1.92 | 691.1 | |
| Example 1182: 2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid | A | 1.85 | 691.1 | |
| Example 1183: (S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)-3-hydroxypropanoic acid | A | 1.88 | 629.1 | |
| Example 1184: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxypropanoic acid | M | 2.9 | 629.1 | |
| Example 1185: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-pyrrolo[2,3-b]pyridin-3-yl)propanoic acid | M | 2.84 | 715.1 | |
| Example 1185: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-pyrrolo[2,3-b]pyridin-3-yl)propanoic acid | A | 1.85 | 715.2 | |
| Example 1186: (S)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid | M | 2.99 | 755.8 | |
| Example 1187: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(4-hydroxyphenyl)propanoic acid | M | 2.84 | 691.1 | |
| Example 1188: 2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)propanoic acid | M | 2.85 | 613.1 | |
| Example 1189: (2S,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | A | 1.83 | 629.2 | |
| Example 1190: (2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2,3-dicarboxylic acid | M | 2.76 | 683.4 | |
| Example 1191: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)-2-methylpropanoic acid | M | 2.86 | 680 | |
| Example 1192: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-indol-3-yl)propanoic acid | A | 2.01 | 714 | |
| Example 1193: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)butanoic acid | A | 1.89 | 613.1 | |
| Example 1194: (R)-3-(benzyloxy)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid | M | 3.07 | 705.1 | |
| Example 1195: (2R,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | A | 1.85 | 628.9 | |
| Example 1196: (2S,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid | M | 2.84 | 641.1 | |
| Example 1197: (2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid | A | 1.85 | 641 | |
| Example 1198: (R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid | A | 1.93 | 639 | |
| Example 1199: (2R,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid | A | 1.85 | 641.1 | |
| Example 1200: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid | A | 1.84 | 691.2 | |
| Example 1201: (S)-2-((5-chloro-2-((3-cyanobenzyl)oxy)-4-((3-(2,3-dihydrobenzo[b][1,4]dioxin-6-yl)-2- | A | 1.89 | 613.4 | |

| Example | LCMS Method | RT (min) | M+1 | M−1 |
|---|---|---|---|---|
| methylbenzyl)oxy)benzyl)amino)butanoic acid | | | | |
| Example 1202: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylthio)butanoic acid | A | 1.96 | 659.1 | |
| Example 1203: (S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)succinic acid | A | 1.63 | 657.4 | |
| Example 1204: (2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid | M | 2.85 | 641.2 | |
| Example 1205: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid | M | 2.85 | 629.1 | |
| Example 1206: (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid | A | 1.95 | 682.2 | |
| Example 1207: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-5-yl)propanoic acid | M | 2.77 | 1680 | |
| Example 1208: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid | M | 2.89 | 682.8 | |
| Example 1209: 1-(5-chloro-2-((3-cyanobenzyl)oxy)-4-((3-(2,3-dihydrobenzo[b][1,4]dioxin-6-yl)-2-methylbenzyl)oxy)benzyl)azetidine-2-carboxylic acid | M | 2.83 | 611.1 | |
| Example 1210: 2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-3-methylbutanoic acid | A | 1.87 | 643 | |
| Example 1211: 2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(1H-indol-3-yl)acetic acid | A | 2 | 700.1 | |
| Example 1212: 3-((4-chloro-5-((3-(2,3-dihydrobenzo[b][1,4]dioxin-6-yl)-2-methylbenzyl)oxy)-2-(((2-hydroxy-3-morpholinopropyl)amino)methyl)phenoxy)methyl)benzonitrile | M | 3.02 | 670.1 | |
| Example 1213: 4-(5-chloro-2-((3-cyanobenzyl)oxy)-4-((3-(2,3-dihydrobenzo[b][1,4]dioxin-6-yl)-2-methylbenzyl)oxy)benzyl)morpholine-3-carboxylic acid | A | 1.81 | 641.2 | |
| Example 1214: 2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(hydroxymethyl)-3-methylbutanoic acid | M | 2.93 | 657.4 | |
| Example 1215: (2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-fluoropyrrolidine-2-carboxylic acid | M | 2.88 | 643 | |
| Example 1216: 2-((5-chloro-2-((3-cyanobenzyl)oxy)-4-((3-(2,3-dihydrobenzo[b][1,4]dioxin-6-yl)-2-methylbenzyl)oxy)benzyl)amino)-4,4,4-trifluorobutanoic acid | A | 1.94 | 665.2 | |
| Example 1217: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-cyanophenyl)propanoic acid | M | 2.92 | 698.3 | |
| Example 1218: 2-benzyl-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid | A | 2.04 | 705.2 | |
| Example 1219: (2S,3S)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid | M | 2.86 | 641.2 | |
| Example 1220: 4-((5-chloro-2-((3-cyanobenzyl)oxy)-4-((3-(2,3-dihydrobenzo[b][1,4]dioxin-6-yl)-2-methylbenzyl)oxy)benzyl)amino)-1-methylpiperidine-4-carboxylic acid | A | 1.8 | 668.2 | |
| Example 1221: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(pyridin-2-yl)propanoic acid | A | 1.99 | 676.1 | |
| Example 1222: (S)-4-(5-chloro-2-((3-cyanobenzyl)oxy)-4-((3-(2,3-dihydrobenzo[b][1,4]dioxin-6-yl)-2-methylbenzyl)oxy)benzyl)thiomorpholine-3-carboxylic acid | M | 2.92 | 657.2 | |
| Example 1223: 3-((4-chloro-5-((3-(2,3-dihydrobenzo[b][1,4]dioxin-6-yl)-2-methylbenzyl)oxy)-2-(((2-methyl-1-(4-methylpiperazin-1-yl)propan-2-yl)amino)methyl)phenoxy)methyl)benzonitrile | M | 3.04 | 681.2 | |
| Example 1224: 1-(5-chloro-2-((3-cyanobenzyl)oxy)-4-((3-(2,3-dihydrobenzo[b][1,4]dioxin-6-yl)-2-methylbenzyl)oxy)benzyl)-4-methylpiperazine-2-carboxylic acid | A | 1.89 | 654 | |
| Example 1225: 3-((4-chloro-5-((3-(2,3-dihydrobenzo[b][1,4]dioxin-6-yl)-2-methylbenzyl)oxy)-2-(((2-hydroxy-3-(2-oxopyrrolidin-1-yl)propyl)amino)methyl)phenoxy)methyl)benzonitrile | M | 2.98 | 668.2 | |
| Example 1226: 5-(5-chloro-2-((3-cyanobenzyl)oxy)-4-((3-(2,3-dihydrobenzo[b][1,4]dioxin-6-yl)-2-methylbenzyl)oxy)benzyl)-4,5,6,7-tetrahydro-3H-imidazo[4,5-c]pyridine-4-carboxylic acid | A | 1.83 | 677.2 | |
| Example 1227: (S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2H-tetrazol-2-yl)propanoic acid | A | 1.85 | 667.3 | |
| Example 1228: (R)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid | M | 3.01 | 754.9 | |
| Example 1229: 3-((2-((((1H-tetrazol-5-yl)methyl)amino)methyl)-4-chloro-5-((3-(2,3-dihydrobenzo[b][1,4]dioxin-6-yl)-2-methylbenzyl)oxy)phenoxy)methyl)benzonitrile | A | 1.87 | 609.3 | |

| Example | LCMS Method | RT (min) | M+1 | M-1 |
|---|---|---|---|---|
| Example 1230: (S)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid | M | 2.88 | 639.2 | |

Intermediate 5-chloro-2,4-dihydroxybenzaldehyde

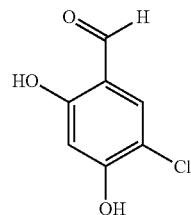

5-Chloro-2,4-dihydroxybenzaldehyde was prepared using the literature procedure: Vogel, H; Goeldner, M. et. al. *Angew. Chem. Int. Ed.* 2007, 46, 3505-3508, Supplemental information, page 6. The compound was further purified by silica gel chromatography employing ethyl acetate:hexanes (1:5) as eluent. $^1$H NMR (CHLOROFORM-d) δ 11.26 (s, 1H), 9.70 (d, J=0.5 Hz, 1H), 7.53 (s, 1H), 6.62 (s, 1H), 6.21 (br. s., 1H).

Intermediate 5-chloro-4-((3-(2,3-dihydrobenzo[b][1,4]dioxin-6-yl)-2-methylbenzyl)oxy)-2-hydroxybenzaldehyde

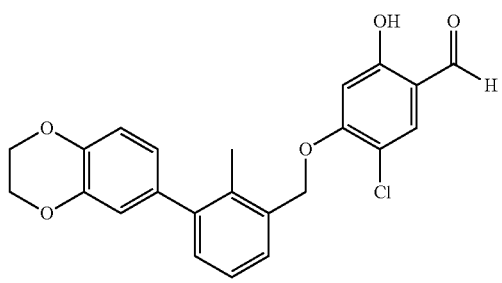 [SMILES: Cc1c(COc2cc(O)c(C=O)cc2Cl)cccc1-c1ccc2c(c1)OCCO2]

Diisopropyl azodicarboxylate (0.532 mL, 2.68 mmol) in tetrahydrofuran (3 mL) was added dropwise to a cooled (0° C.) solution of 5-chloro-2,4-dihydroxybenzaldehyde (421 mg, 2.440 mmol), triphenylphosphine (711 mg, 2.71 mmol) and (3-(2,3-dihydrobenzo[b][1,4]dioxin-6-yl)-2-methylphenyl)methanol (686 mg, 2.68 mmol) in dry tetrahydrofuran (7 mL). The resulting reaction mixture was allowed to slowly warm to room temperature with stirring overnight. The product was filtered from the reaction using a buchner filter funnel and rinsed with tetrahydrofuran (approx. 5 mL) then dried in vacuo at room temperature to yield 393 mg of a near colorless solid. $^1$H NMR (CHLOROFORM-d) δ: 11.44 (s, 1H), 9.71 (s, 1H), 7.56 (s, 1H), 7.45 (dd, J=6.5, 2.4 Hz, 1H), 7.23-7.27 (m, 2H), 6.92 (d, J=8.2 Hz, 1H), 6.84 (d, J=2.0 Hz, 1H), 6.79 (dd, J=8.2, 2.0 Hz, 1H), 6.64 (s, 1H), 5.21 (s, 2H), 4.32 (s, 4H), 2.28 (s, 3H).

Intermediate 3-((4-chloro-5-((3-(2,3-dihydrobenzo[b][1,4]dioxin-6-yl)-2-methylbenzyl)oxy)-2-formylphenoxy)methyl)benzonitrile

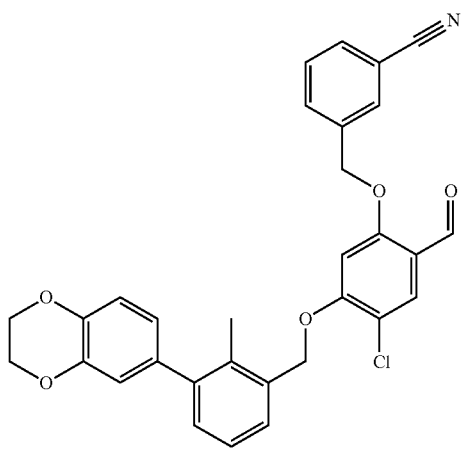 [SMILES: Cc1c(COc2cc(OCc3cccc(C#N)c3)c(C=O)cc2Cl)cccc1-c1ccc2c(c1)OCCO2]

5-Chloro-4-((3-(2,3-dihydrobenzo[b][1,4]dioxin-6-yl)-2-methylbenzyl)oxy)-2-hydroxybenzaldehyde (180 mg, 0.438 mmol) was partially suspended in dimethylformamide (4.3 mL), cesium carbonate (180 mg, 0.552 mmol) was added and the reaction stirred for approximately 5 minutes in which it appeared to exhibit improved solubility. 3-cyanobenzyl bromide (94 mg, 0.479 mmol) was added to the reaction. The reaction was capped and stirred at room temperature overnight. Volatiles were removed from the reaction and the solid residue was partitioned between dichloromethane and water. The aqueous phase was extracted once with dichloromethane. The organic extracts were combined and washed with brine then dried over sodium sulfate. The drying agent was removed by filtration and solvent removed in vacuo to yield the title compound (241 mg) as a colorless solid. A solvate of *0.45 dichloromethane was observed in the proton NMR. $^1$H NMR (CHLOROFORM-d) δ: 10.33 (s, 1H), 7.92 (s, 1H), 7.73 (s, 1H), 7.69 (d, J=1.3 Hz, 1H), 7.68 (s, 1H), 7.53-7.58 (m, 1H), 7.37-7.41 (m, 1H), 7.25-7.27 (m, 2H), 6.93 (d, J=8.2 Hz, 1H), 6.82 (d, J=2.0 Hz, 1H), 6.78 (dd, J=8.2, 2.0 Hz, 1H), 6.61 (s, 1H), 5.21 (s, 2H), 5.19 (s, 2H), 4.32 (s, 4H), 2.29 (s, 3H).

Example 1157

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

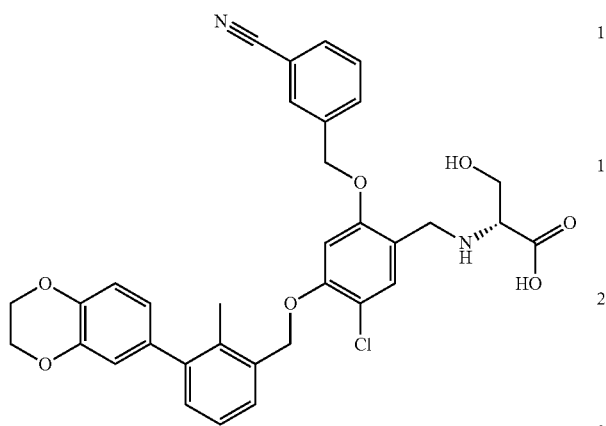

Dissolved 3-((4-chloro-5-((3-(2,3-dihydrobenzo[b][1,4]dioxin-6-yl)-2-methylbenzyl)oxy)-2-formylphenoxy)methyl)benzonitrile, *0.45 methylene chloride (32 mg, 0.057 mmol) in dimethylformamide (568 uL), add D-serine (9.9 mg, 0.094 mmol), methanol (142 μl) and acetic acid (14.2 μl). Sodium cyanoborohydride (8.8 mg, 0.140 mmol) was added to the opaque reaction solution. The reaction was capped and stirred at room temperature for 2 days. The reaction was diluted to approximately 2 mL using tetrahydrofuran and 2 drops of water added to help solubilize salts. The reaction was filtered through a 0.45 um syringe filter and product was purified by reverse phase HPLC using the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-100% B over 15 minutes, then a 5-minute hold at 100% B; Flow: 20 mL/minutes Fractions containing the desired product were combined and dried via centrifugal evaporation.

The yield of the product was 17.1 mg, and its estimated purity by LCMS analysis was 94%. Two analytical LCMS injections were used to determine the final purity. $^1$H NMR (DMSO-$d_6$) δ: 8.01 (s, 1H), 7.90 (d, J=8.1 Hz, 1H), 7.82 (d, J=7.7 Hz, 1H), 7.61 (t, J=7.9 Hz, 1H), 7.50 (s, 1H), 7.43 (d, J=7.7 Hz, 1H), 7.20-7.27 (m, 1H), 7.15-7.19 (m, 1H), 7.11 (s, 1H), 6.92 (d, J=8.1 Hz, 1H), 6.68-6.83 (m, 2H), 5.27-5.37 (m, 2H), 5.24 (s, 2H), 4.28 (s, 4H), 3.93-4.04 (m, 2H), 3.60-3.75 (m, 3H), 3.47 (br. s., 4H), 3.18 (t, J=5.3 Hz, 1H), 2.23 (s, 3H). LCMS Condition A: 1.79 minutes, M–1: 613, Exact Mass: 614.

The following examples were prepared in the same manner as (R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid from 3-((4-chloro-5-((3-(2,3-dihydrobenzo[b][1,4]dioxin-6-yl)-2-methylbenzyl)oxy)-2-formylphenoxy)methyl)benzonitrile and the appropriate amines in a reductive amination reaction.

Example 1243

3-((5-chloro-2-((3-cyanobenzyl)oxy)-4-((3-(2,3-dihydrobenzo[b][1,4]dioxin-6-yl)-2-methylbenzyl)oxy)benzyl)amino)oxetane-3-carboxylic acid

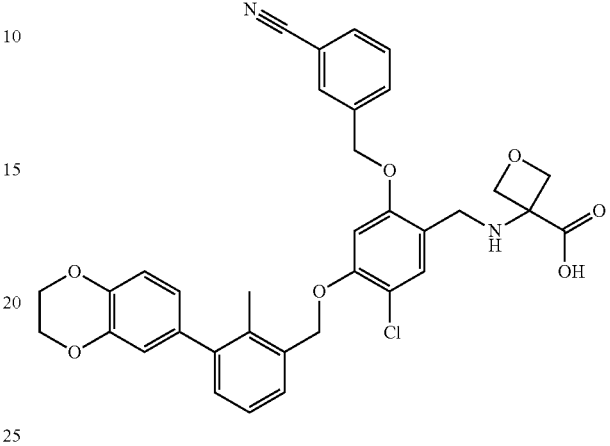

LCMS Condition M: 2.85 minutes, M–1=625.5. $^1$H NMR (DMSO-$d_6$) δ 7.97 (br. s., 1H), 7.85 (d, J=7.7 Hz, 1H), 7.81 (d, J=7.3 Hz, 1H), 7.61 (t, J=7.7 Hz, 1H), 7.37-7.47 (m, 2H), 7.19-7.26 (m, 1H), 7.17 (d, J=7.3 Hz, 1H), 7.07 (br. s., 1H), 6.88-6.95 (m, 1H), 6.68-6.80 (m, 2H), 5.29 (s, 2H), 5.23 (s, 2H), 4.68 (d, J=6.2 Hz, 2H), 4.40-4.48 (m, 2H), 4.28 (s, 4H), 3.65-3.72 (m, 1H), 2.23 (s, 3H).

Example 1244

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

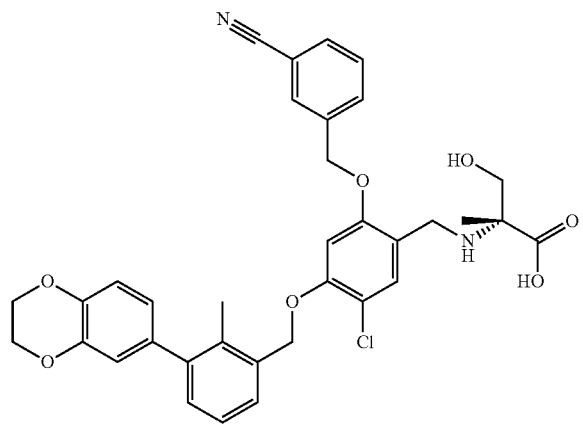 [SMILES: Cc1c(COc2cc(OCc3cccc(C#N)c3)c(CN[C@](C)(CO)C(=O)O)cc2Cl)cccc1-c1ccc2c(c1)OCCO2]

LCMS Condition A: 1.79 minutes, M–1=627.5. $^1$H NMR (DMSO-$d_6$) δ 8.01 (s, 1H), 7.92 (d, J=8.1 Hz, 1H), 7.81 (d, J=7.7 Hz, 1H), 7.61 (t, J=7.7 Hz, 1H), 7.55 (s, 1H), 7.42 (d, J=7.0 Hz, 1H), 7.19-7.26 (m, 1H), 7.14-7.19 (m, 1H), 7.10 (s, 1H), 6.92 (d, J=8.4 Hz, 1H), 6.69-6.79 (m, 2H), 5.27-5.35 (m, 2H), 5.25 (s, 2H), 4.28 (s, 4H), 3.97 (s, 2H), 3.50-3.68 (m, 3H), 2.23 (s, 3H), 1.25 (s, 3H).

Example 1245

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

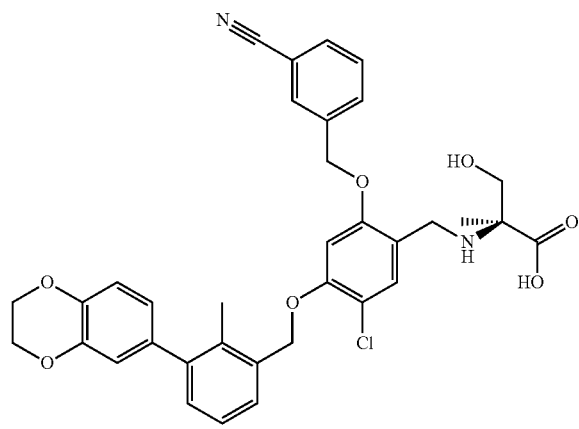 [SMILES: Cc1c(COc2cc(OCc3cccc(C#N)c3)c(CN[C@@](C)(CO)C(=O)O)cc2Cl)cccc1-c1ccc2c(c1)OCCO2]

LCMS Condition M: 2.85 minutes, M+1=629.4, M−1=627.3. $^1$H NMR (DMSO-d$_6$) δ: 8.01 (s, 1H), 7.92 (d, J=8.1 Hz, 1H), 7.81 (d, J=7.7 Hz, 1H), 7.61 (t, J=7.7 Hz, 1H), 7.55 (s, 1H), 7.42 (d, J=7.0 Hz, 1H), 7.19-7.26 (m, 1H), 7.14-7.19 (m, 1H), 7.10 (s, 1H), 6.92 (d, J=8.4 Hz, 1H), 6.69-6.79 (m, 2H), 5.27-5.35 (m, 2H), 5.25 (s, 2H), 4.28 (s, 4H), 3.97 (s, 2H), 3.50-3.68 (m, 3H), 2.23 (s, 3H), 1.25 (s, 3H).

Example 1246

(S)-4-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

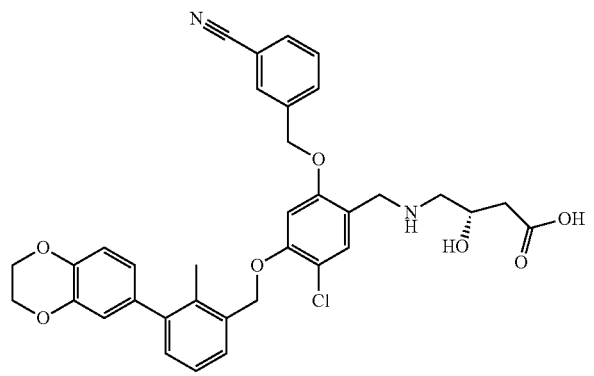 [SMILES: Cc1c(COc2cc(OCc3cccc(C#N)c3)c(CNC[C@@H](O)CC(=O)O)cc2Cl)cccc1-c1ccc2c(c1)OCCO2]

LCMS Condition M: 2.85 minutes, M+1=629.5, M−1=627.5. $^1$H NMR (DMSO-d$_6$) δ 7.96 (s, 1H), 7.85 (d, J=7.7 Hz, 1H), 7.81 (d, J=8.1 Hz, 1H), 7.58-7.66 (m, 1H), 7.39-7.48 (m, 2H), 7.23 (t, J=7.5 Hz, 1H), 7.13-7.19 (m, 1H), 7.09 (s, 1H), 6.92 (d, J=8.1 Hz, 1H), 6.70-6.80 (m, 2H), 5.29 (s, 2H), 5.23 (s, 2H), 4.27 (s, 4H), 3.91-4.00 (m, 1H), 3.81 (br. s., 2H), 2.65 (br. s., 2H), 2.40 (dd, J=15.4, 4.8 Hz, 1H), 2.27 (dd, J=15.4, 6.6 Hz, 1H), 2.23 (s, 3H).

Example 1247

N-(2-((5-chloro-2-((3-cyanobenzyl)oxy)-4-((3-(2,3-dihydrobenzo[b][1,4]dioxin-6-yl)-2-methylbenzyl)oxy)benzyl)amino)ethyl)acetamide

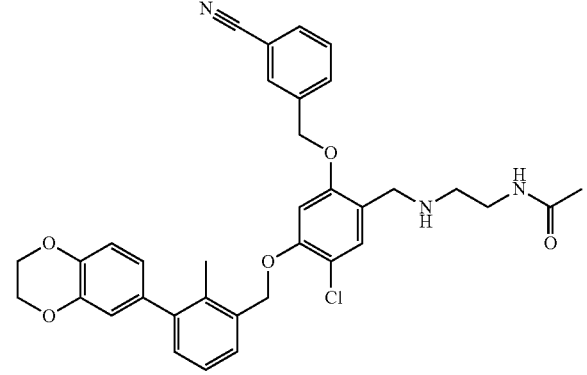 [SMILES: CC(=O)NCCNCc1cc(Cl)c(OCc2cccc(-c3ccc4c(c3)OCCO4)c2C)cc1OCc1cccc(C#N)c1]

LCMS Condition M: 2.96 minutes, M+1=612.2. $^1$H NMR (DMSO-d$_6$) δ 7.96 (s, 1H), 7.91 (t, J=5.1 Hz, 1H), 7.83 (t, J=7.3 Hz, 2H), 7.63 (t, J=7.9 Hz, 1H), 7.40-7.46 (m, 2H), 7.21-7.27 (m, 1H), 7.15-7.19 (m, 1H), 7.08 (s, 1H), 6.92 (d, J=8.1 Hz, 1H), 6.77 (d, J=1.8 Hz, 1H), 6.74 (dd, J=8.3, 2.0 Hz, 1H), 5.29 (s, 2H), 5.23 (s, 2H), 4.28 (s, 4H), 3.75 (s, 2H), 3.13-3.20 (m, 2H), 2.61 (t, J=6.4 Hz, 2H), 2.23 (s, 3H), 1.78 (s, 3H).

Intermediate 3-chloro-2,4-dihydroxybenzaldehyde

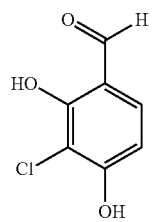 [SMILES: O=Cc1ccc(O)c(Cl)c1O]

3-Chloro-2,4-dihydroxybenzaldehyde was prepared using the literature procedure Ciufolini, M. A.; Tan, J. S. *Org. Lett.* 2006, 8(21), 4771-4774, supplemental material page 4. The compound was further purified by silica gel column chromatography employing 30% ethyl acetate in hexanes (v/v) as eluent. $^1$H NMR (CHLOROFORM-d) δ: 12.01 (s, 1H), 9.74 (s, 1H), 7.43 (d, J=8.5 Hz, 1H), 6.73 (d, J=8.7 Hz, 1H), 6.33 (br. s., 1H).

Intermediate 3-chloro-2-hydroxy-4-((2-methyl-[1,1'-biphenyl]-3-yl)methoxy)benzaldehyde

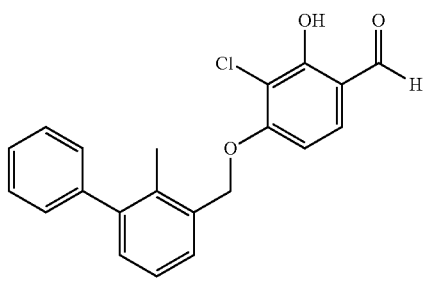 [SMILES: Cc1c(COc2ccc(C=O)c(O)c2Cl)cccc1-c1ccccc1]

Diisopropyl azodicarboxylate (0.758 mL, 3.82 mmol) in tetrahydrofuran (8.5 mL) was added dropwise to a cooled (0° C.) solution of 3-chloro-2,4-dihydroxybenzaldehyde (600 mg, 3.48 mmol), triphenylphosphine (1016 mg, 3.87 mmol) and 2-methyl-3-biphenylmethanol (758 mg, 3.82 mmol) in dry tetrahydrofuran (8.5 mL). The resulting reaction mixture was allowed to slowly warm to room temperature with stirring overnight. The crude product was purified by silica gel column chromatography employing 60% hexanes in dichloromethane (v/v) as eluent to yield 491 mg of the title compound as a colorless solid. $^1$H NMR (CHLOROFORM-d) δ: 11.80 (s, 1H), 9.77 (s, 1H), 7.47-7.50 (m, 2H), 7.42-7.46 (m, 2H), 7.35-7.40 (m, 1H), 7.31-7.34 (m, 2H), 7.28-7.31 (m, 2H), 6.78 (d, J=8.7 Hz, 1H), 5.30 (s, 2H), 2.28 (s, 3H).

Intermediate 3-((2-chloro-6-formyl-3-((2-methyl-[1,1'-biphenyl]-3-yl)methoxy)phenoxy)methyl)benzonitrile

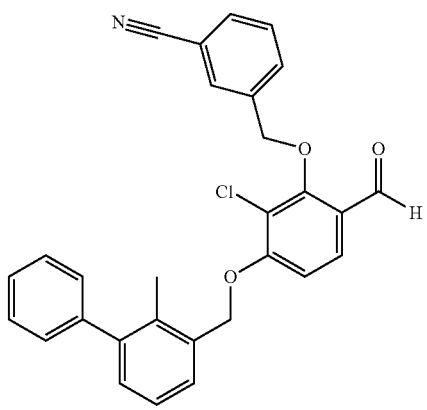 [SMILES: Cc1c(COc2ccc(C=O)c(OCc3cccc(C#N)c3)c2Cl)cccc1-c1ccccc1]

Dissolve 3-chloro-2-hydroxy-4-((2-methyl-[1,1'-biphenyl]-3-yl)methoxy)benzaldehyde (80 mg, 0.227 mmol) in dimethylformamide (2.2 mL) then add cesium carbonate (88 mg, 0.270 mmol) and 3-cyanobenzyl bromide (50 mg, 0.255 mmol). Cap the reaction and stir at room temperature overnight. Remove volatiles in vacuo using a rotary evaporator and partition the colorless reaction residue between dichloromethane and water. Wash the organic extract with brine and dry over sodium sulfate. Filter off the drying agent and remove solvent in vacuo to yield 105 mg of the title compound as a colorless solid. The product was used without further purification. $^1$H NMR (CHLOROFORM-d) δ: 10.11 (s, 1H), 7.82 (d, J=8.8 Hz, 2H), 7.77 (d, J=8.2 Hz, 1H), 7.67-7.71 (m, 1H), 7.53-7.58 (m, 1H), 7.50 (dd, J=7.0, 2.0 Hz, 1H), 7.42-7.47 (m, 2H), 7.35-7.40 (m, 1H), 7.28-7.35 (m, 4H), 7.04 (d, J=8.7 Hz, 1H), 5.30 (s, 2H), 5.18 (s, 2H), 2.29 (s, 3H).

Example 1231

(R)-2-((3-chloro-2-((3-cyanobenzyl)oxy)-4-((2-methyl-[1,1'-biphenyl]-3-yl)methoxy)benzyl)amino)-3-hydroxypropanoic acid

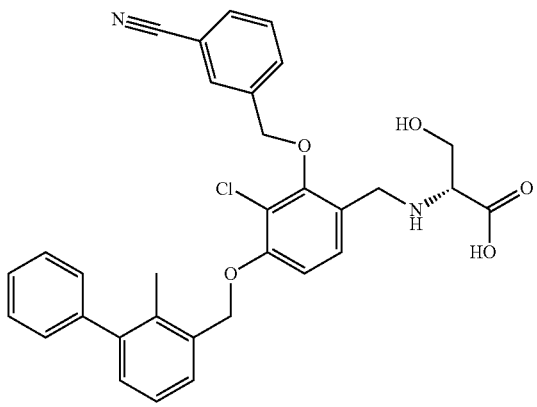 [SMILES: Cc1c(COc2ccc(CN[C@H](CO)C(=O)O)c(OCc3cccc(C#N)c3)c2Cl)cccc1-c1ccccc1]

Dimethylformamide (336 μL) and methanol (319 μL) was added to 3-((2-chloro-6-formyl-3-((2-methyl-[1,1'-biphenyl]-3-yl)methoxy)phenoxy)methyl)benzonitrile (30 mg, 0.064 mmol) and D-serine (10.8 mg, 0.103 mmol). Dimethylformamide (336 μL) was added to the reaction suspension followed by acetic acid (16.8 μL). The reaction was gently heated, vortexed then cooled to room temperature. The reaction was an semiopaque mixture. Sodium cyanoborohydride (10.6 mg, 0.169 mmol) was added to the reaction and the reaction was capped and stirred at room temperature for 2 days. Volatiles were remove from the reaction in vacuo using a rotary evaporator. dimethylformamide (1 mL) was added to the reaction residue with some acetonitrile and tetrahydrofuran in attempt to solubilize. The reaction mixture was heated then filtered through a 0.45 um syringe filter. Upon cooling precipitation occurs. Remove solvents in vacuo and re-dissolve reaction residue in tetrahydrofuran (1 mL) and dimethylformamide (1 mL). The crude material was purified via preparative LCMS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-90% B over 15 minutes, then a 8-minute hold at 100% B; Flow: 20 mL/minutes. Fractions containing the desired product were combined and dried via centrifugal evaporation. The yield of the product was 13.7 mg, and its estimated purity by LCMS analysis was 98%. Two analytical LCMS injections were used to determine the final purity. $^1$H NMR (DMSO-$d_6$) δ: 7.99 (s, 1H), 7.91 (d, J=7.7 Hz, 1H), 7.85 (d, J=7.7 Hz, 1H), 7.64 (t, J=7.7 Hz, 1H), 7.51 (d, J=7.3 Hz, 1H), 7.41-7.49 (m, 3H), 7.35-7.41 (m, 1H), 7.27-7.34 (m, 3H), 7.21 (d, J=7.3 Hz, 2H), 5.27 (s, 2H), 5.04-5.12 (m, 2H), 3.94-4.01 (m, 1H), 3.85-3.93 (m, 1H), 3.58-3.69 (m, 3H), 3.18 (t, J=4.6 Hz, 1H), 2.22 (s, 3H), 1.23 (br. s., 1H). LCMS Condition A: 1.89 minutes, M−1: 555, M+H: 557; Exact Mass: 556.

Example 1232

(S)-4-((3-chloro-2-((3-cyanobenzyl)oxy)-4-((2-methyl-[1,1'-biphenyl]-3-yl)methoxy)benzyl)amino)-3-hydroxybutanoic acid

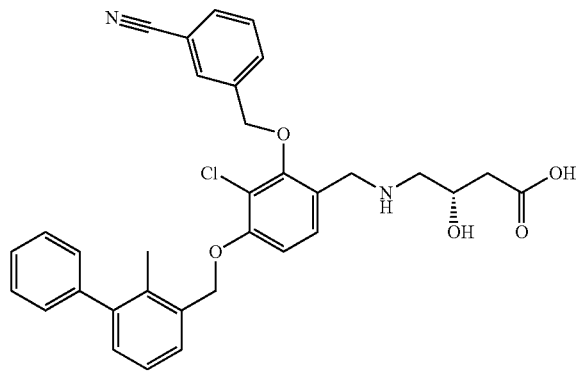 [SMILES: Cc1c(COc2ccc(CNC[C@@H](O)CC(=O)O)c(OCc3cccc(C#N)c3)c2Cl)cccc1-c1ccccc1]

Dimethylformamide (336 μL) and methanol (319 μL) was added to 3-((2-chloro-6-formyl-3-((2-methyl-[1,1'-biphenyl]-3-yl)methoxy)phenoxy)methyl)benzonitrile (30 mg, 0.064 mmol) and (S)-4-amino-3-hydroxybutanoic acid (8.1 mg, 0.068 mmol). dimethylformamide (336 μL) was added to the reaction suspension then acetic acid (16.8 μL). The reaction was gently heated, vortexed then cooled to room temperature. The reaction was a semiopaque mixture. Sodium cyanoborohydride (10.3 mg, 0.164 mmol) was added to the reaction and the reaction was capped and stirred at room temperature for 5 days. Tetrahydrofuran (0.9 mL) was added to the reaction and the reaction filtered through a 0.45 um syringe filter. The crude material was purified via preparative LCMS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 15 minutes, then a 5-minute hold at 100% B; Flow: 20 mL/minutes Fractions containing the desired product were combined and dried via centrifugal evaporation.

The yield of the product was 1.7 mg, and its estimated purity by LCMS analysis was 100%. Two analytical LCMS injections were used to determine the final purity. $^1$H NMR (DMSO-d$_6$) δ: 7.95 (s, 1H), 7.86 (dd, J=16.5, 8.1 Hz, 2H), 7.65 (t, J=7.9 Hz, 1H), 7.52 (d, J=8.1 Hz, 1H), 7.43-7.48 (m, 2H), 7.35-7.41 (m, 2H), 7.27-7.34 (m, 3H), 7.14-7.25 (m, 2H), 5.25 (s, 2H), 5.07 (s, 2H), 3.86-3.92 (m, 1H), 3.33-3.76 (m, 3H), 2.51 (br. s., 1H), 2.33-2.40 (m, 1H), 2.17-2.25 (m, 4H), 1.90 (s, 1H), 1.03 (d, J=5.9 Hz, 1H). LCMS Condition A: 1.96 minutes, M−1: 569.3, M+H: 571.3; Exact Mass: 570.

The following examples were prepared by reductive amination in the same manner as (S)-4-((3-chloro-2-((3-cyanobenzyl)oxy)-4-((2-methyl-[1,1'-biphenyl]-3-yl)methoxy) benzyl)amino)-3-hydroxybutanoic acid from 3-((2-chloro-6-formyl-3-((2-methyl-[1,1'-biphenyl]-3-yl)methoxy) phenoxy)methyl)benzonitrile and an appropriate amine.

Example 1233

(S)-1-(3-chloro-2-(3-cyanobenzyloxy)-4-((2-methyl-biphenyl-3-yl)methoxy)benzyl)piperidine-2-carboxylic acid

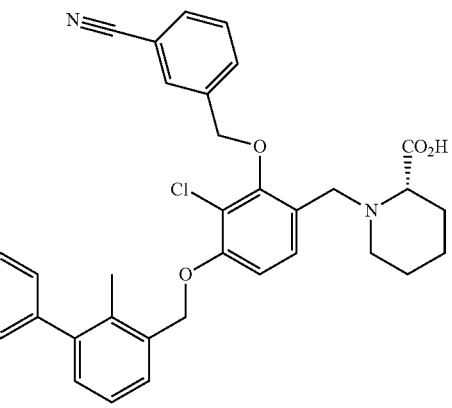

LCMS Condition A: 2.12 minutes, M+1=581.3, M−1=579.3. $^1$H NMR (DMSO-d$_6$) δ 7.96 (s, 1H), 7.88 (d, J=7.7 Hz, 1H), 7.84 (d, J=7.7 Hz, 1H), 7.60-7.68 (m, 1H), 7.52 (d, J=7.3 Hz, 1H), 7.43-7.49 (m, 2H), 7.27-7.41 (m, 5H), 7.21 (d, J=7.7 Hz, 1H), 7.18 (d, J=8.8 Hz, 1H), 5.25 (s, 2H), 4.99-5.15 (m, 2H), 3.80 (d, J=13.2 Hz, 1H), 3.56 (d, J=13.2 Hz, 1H), 3.11 (t, J=5.3 Hz, 1H), 2.86 (d, J=7.3 Hz, 1H), 2.23 (s, 4H), 1.64-1.74 (m, 2H), 1.33-1.48 (m, J=11.7 Hz, 4H).

Example 1234

N-(2-(3-chloro-2-(3-cyanobenzyloxy)-4-((2-methyl-biphenyl-3-yl)methoxy)benzylamino)ethyl)acetamide

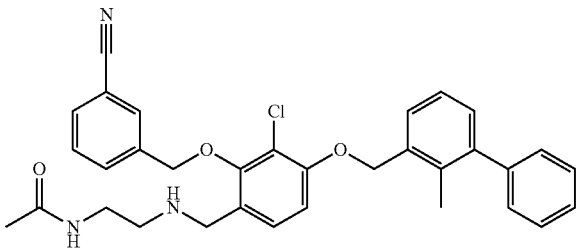 [SMILES: CC(=O)NCCNCc1ccc(OCc2cccc(-c3ccccc3)c2C)c(Cl)c1OCc1cccc(C#N)c1]

LCMS Condition A: 2.27 minutes, M+1=554.3. $^1$H NMR (DMSO-d$_6$) δ: 7.95 (s, 1H), 7.86 (t, J=8.9 Hz, 2H), 7.77 (t, J=5.3 Hz, 1H), 7.60-7.69 (m, 1H), 7.52 (d, J=7.3 Hz, 1H), 7.42-7.49 (m, 2H), 7.27-7.41 (m, 5H), 7.21 (d, J=7.6 Hz, 1H), 7.16 (d, J=8.8 Hz, 1H), 5.25 (s, 2H), 5.07 (s, 2H), 3.66 (s, 2H), 3.10 (q, J=6.4 Hz, 2H), 2.51-2.54 (m, 2H), 2.23 (s, 3H), 1.76 (s, 3H).

Intermediate 3-chloro-4-((3-(2,3-dihydrobenzo[b][1,4]dioxin-6-yl)-2-methylbenzyl)oxy)-2-hydroxybenzaldehyde

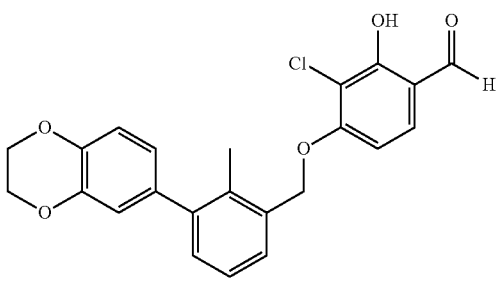 [SMILES: Cc1c(COc2ccc(C=O)c(O)c2Cl)cccc1-c1ccc2c(c1)OCCO2]

Diisopropyl azodicarboxylate (0.253 mL, 1.275 mmol) in tetrahydrofuran (2.5 mL) was added dropwise to a cooled (0° C.) solution of 3-chloro-2,4-dihydroxybenzaldehyde (200 mg, 1.159 mmol), triphenylphosphine (342 mg, 1.304 mmol) and (3-(2,3-dihydrobenzo[b][1,4]dioxin-6-yl)-2-methylphenyl)methanol (340 mg, 1.327 mmol) in dry tetrahydrofuran (2.9 mL). The resulting reaction mixture was allowed to slowly warm to room temperature with stirring overnight. The crude reaction product was purified by silica gel column (55 g) chromatography using 30% hexanes in dichloromethane as eluent to yield 174 mg of the title compound as a colorless solid. $^1$H NMR (CHLOROFORM-d) δ 11.80 (s, 1H), 9.77 (s, 1H), 7.42-7.51 (m, 2H), 7.23-7.27 (m, 2H), 6.92 (d, J=8.2 Hz, 1H), 6.84 (d, J=2.0 Hz, 1H), 6.75-6.81 (m, 2H), 5.28 (s, 2H), 4.32 (s, 4H), 2.29 (s, 3H).

Intermediate 3-((2-chloro-3-((3-(2,3-dihydrobenzo[b][1,4]dioxin-6-yl)-2-methylbenzyl)oxy)-6-formylphenoxy)methyl)benzonitrile

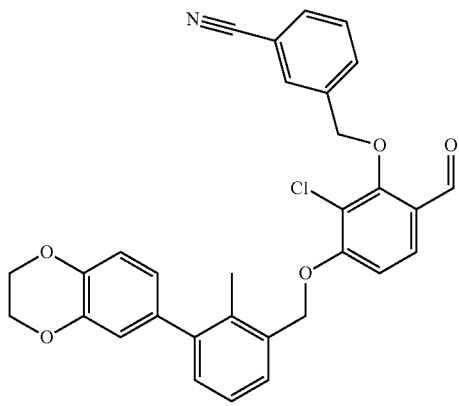 [SMILES: Cc1c(COc2ccc(C=O)c(OCc3cccc(C#N)c3)c2Cl)cccc1-c1ccc2c(c1)OCCO2]

Dissolve 3-chloro-4-((3-(2,3-dihydrobenzo[b][1,4]dioxin-6-yl)-2-methylbenzyl)oxy)-2-hydroxybenzaldehyde (151 mg, 0.368 mmol) in dimethylformamide (3.5 mL). It was necessary to gently heat reaction to dissolve substrate in dimethylformamide. The reagents cesium carbonate (150 mg, 0.460 mmol) and 3-cyanobenzyl bromide (79 mg, 0.404 mmol) were added and the reaction capped and stirred overnight at room temperature. Remove volatiles in vacuo using a rotary evaporator and the colorless reaction residue was partitioned between dichloromethane and water. The aqueous portion was extracted with dichloromethane. The organic extracts were combined and washed with brine then dried over sodium sulfate. The drying agent was filtered off and solvent removed in vacuo to yield 105 mg of the title compound as a colorless solid. The product was used without further purification. $^1$H NMR (CHLOROFORM-d) δ: 10.11 (d, J=0.5 Hz, 1H), 7.79-7.85 (m, 2H), 7.77 (d, J=7.7 Hz, 1H), 7.69 (dt, J=7.8, 1.3 Hz, 1H), 7.52-7.58 (m, 1H), 7.46 (dd, J=6.5, 2.5 Hz, 1H), 7.27-7.30 (m, J=3.9 Hz, 2H), 7.03 (d, J=8.5 Hz, 1H), 6.93 (d, J=8.2 Hz, 1H), 6.85 (d, J=2.0 Hz, 1H), 6.80 (dd, J=8.3, 2.1 Hz, 1H), 5.28 (s, 2H), 5.17 (s, 2H), 4.32 (s, 4H), 2.31 (s, 3H).

Example 1235

(R)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

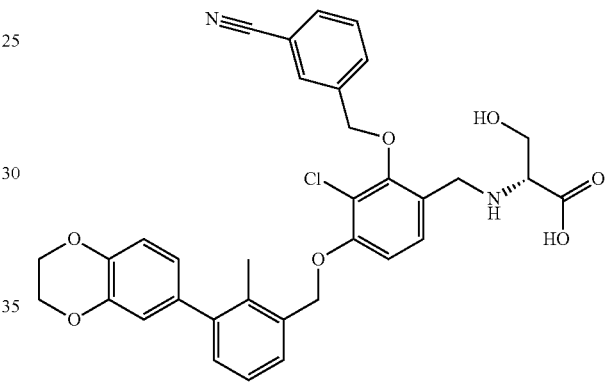

Dimethylformamide (284 µL) and methanol (270 µl) were added to 3-((2-chloro-3-((3-(2,3-dihydrobenzo[b][1,4]dioxin-6-yl)-2-methylbenzyl)oxy)-6-formylphenoxy)methyl)benzonitrile (30 mg, 0.057 mmol) and D-serine (10.7 mg, 0.102 mmol). Dimethylformamide (284 µL) was added to the reaction suspension then acetic acid (14.2 µL). Sodium cyanoborohydride (7.2 mg, 0.115 mmol) was added to the reaction and the reaction was vortexed then capped and stirred at room temperature for 2 days. Water (2 drops) and tetrahydrofuran (0.9 mL) was added to the reaction. The reaction was subject to vortex mixing then filtered through a 0.45 um syringe filter. The crude material was purified via preparative LCMS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/minutes Fractions containing the desired product were combined and dried via centrifugal evaporation.

The yield of the product was 10.9 mg, and its estimated purity by LCMS analysis was 96%. Two analytical LCMS injections were used to determine the final purity. $^1$H NMR (DMSO-d$_6$) δ 7.99 (s, 1H), 7.91 (d, J=7.7 Hz, 1H), 7.85 (d, J=7.3 Hz, 1H), 7.64 (t, J=7.9 Hz, 1H), 7.47 (d, J=7.7 Hz, 1H), 7.43 (d, J=8.4 Hz, 1H), 7.26 (t, J=7.5 Hz, 1H), 7.14-7.22 (m, 2H), 6.92 (d, J=8.1 Hz, 1H), 6.72-6.80 (m, 2H), 5.24 (s, 2H), 5.02-5.15 (m, 2H), 4.28 (s, 4H), 3.92-3.99

(m, 1H), 3.87 (t, J=13.6 Hz, 1H), 3.55-3.69 (m, 3H), 3.39 (br. s., 2H), 2.23 (s, 3H). LCMS Condition A: 1.77 minutes, M−1: 613.5, M+H: 615.5; Exact Mass: 614.

The following examples were prepared by reductive amination in the same manner as (R)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid from 3-((2-chloro-3-((3-(2,3-dihydrobenzo[b][1,4]dioxin-6-yl)-2-methylbenzyl)oxy)-6-formylphenoxy)methyl)benzonitrile and an appropriate amine.

Example 1236

(S)-1-(3-chloro-2-(3-cyanobenzyloxy)-4-(3-(2,3-dihydrobenzo[b][1,4]dioxin-6-yl)-2-methylbenzyloxy)benzyl)piperidine-2-carboxylic acid

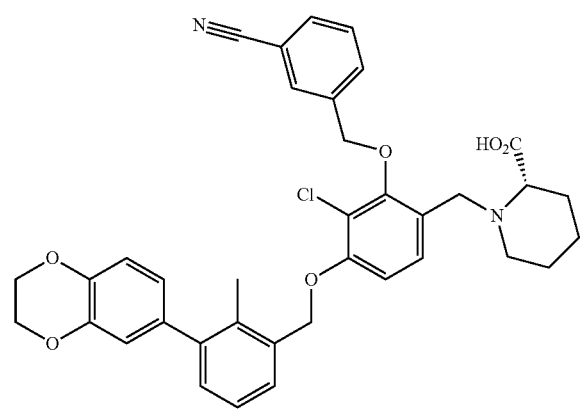 [SMILES: Cc1c(COc2ccc(CN3CCCC[C@H]3C(=O)O)c(OCc3cccc(C#N)c3)c2Cl)cccc1-c1ccc2c(c1)OCCO2]

LCMS Condition A: 2.07 minutes, M+1=639.4, M−1=637.4. $^1$H NMR (DMSO-d$_6$) δ 7.95 (s, 1H), 7.88 (d, J=7.7 Hz, 1H), 7.84 (d, J=7.7 Hz, 1H), 7.64 (t, J=7.9 Hz, 1H), 7.47 (d, J=7.7 Hz, 1H), 7.34 (d, J=8.4 Hz, 1H), 7.26 (t, J=7.5 Hz, 1H), 7.13-7.21 (m, 2H), 6.92 (d, J=8.1 Hz, 1H), 6.71-6.81 (m, 2H), 5.23 (s, 2H), 4.98-5.15 (m, 2H), 4.28 (s, 4H), 3.76-3.83 (m, 1H), 3.33-3.63 (m, 7H), 3.12 (t, J=5.0 Hz, 1H), 2.80-2.88 (m, J=8.8 Hz, 1H), 2.23 (s, 4H), 1.70 (br. s., 2H), 1.42 (br. s., 4H).

Example 1237

N-(2-((3-chloro-2-((3-cyanobenzyl)oxy)-4-((3-(2,3-dihydrobenzo[b][1,4]dioxin-6-yl)-2-methylbenzyl)oxy)benzyl)amino)ethyl)acetamide

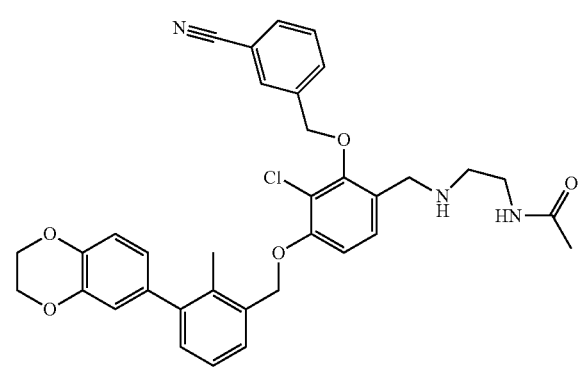 [SMILES: CC(=O)NCCNCc1ccc(OCc2cccc(-c3ccc4c(c3)OCCO4)c2C)c(Cl)c1OCc1cccc(C#N)c1]

LCMS Condition A: 2.15 minutes, M+1=612.3. $^1$H NMR (DMSO-d$_6$) δ 7.97 (s, 1H), 7.88 (dd, J=13.6, 7.7 Hz, 3H), 7.61-7.71 (m, 1H), 7.48 (d, J=7.3 Hz, 1H), 7.39 (d, J=8.4 Hz, 1H), 7.27 (t, J=7.7 Hz, 1H), 7.11-7.22 (m, 2H), 6.93 (d, J=8.1 Hz, 1H), 6.71-6.82 (m, 2H), 5.24 (s, 2H), 5.08 (s, 2H), 4.29 (s, 4H), 3.14 (d, J=5.9 Hz, 2H), 2.57 (br. s., 2H), 2.24 (s, 3H), 1.77 (s, 3H).

Example 1238

(S)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

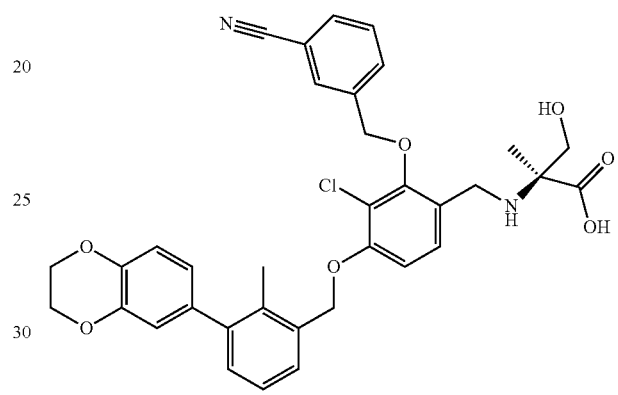

LCMS Condition A: 2.03 minutes, M+1=629.4, M−1=627.3. $^1$H NMR (DMSO-d$_6$) δ 8.00 (s, 1H), 7.93 (d, J=7.7 Hz, 1H), 7.85 (d, J=8.1 Hz, 1H), 7.64 (t, J=7.7 Hz, 1H), 7.48 (d, J=8.1 Hz, 2H), 7.23-7.29 (m, 1H), 7.19 (dd, J=17.2, 8.1 Hz, 2H), 6.92 (d, J=8.1 Hz, 1H), 6.71-6.81 (m, 2H), 5.26 (s, 2H), 5.04-5.16 (m, 2H), 4.28 (s, 4H), 3.83-3.95 (m, 2H), 3.48-3.61 (m, 3H), 2.23 (s, 3H), 1.21 (s, 3H).

Example 1239

(R)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

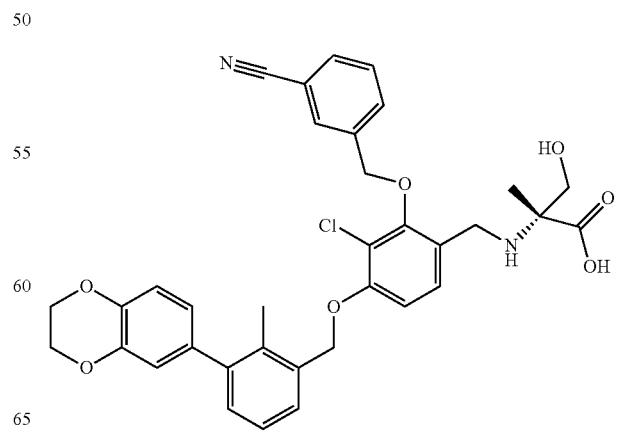

LCMS Condition A: 2.03 minutes, M+1=629.4, M−1=627.3. $^1$H NMR (DMSO-d$_6$) δ 8.00 (s, 1H), 7.93 (d, J=7.7 Hz, 1H), 7.85 (d, J=8.1 Hz, 1H), 7.64 (t, J=7.7 Hz, 1H), 7.48 (d, J=8.1 Hz, 2H), 7.23-7.29 (m, 1H), 7.19 (dd, J=17.2, 8.1 Hz, 2H), 6.92 (d, J=8.1 Hz, 1H), 6.71-6.81 (m, 2H), 5.26 (s, 2H), 5.04-5.16 (m, 2H), 4.28 (s, 4H), 3.83-3.95 (m, 2H), 3.48-3.61 (m, 3H), 2.23 (s, 3H), 1.21 (s, 3H).

Example 1240

(S)-4-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

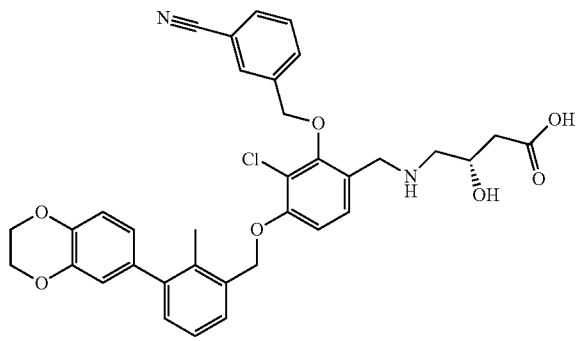 [SMILES: Cc1c(COc2ccc(CNC[C@@H](O)CC(=O)O)c(OCc3cccc(C#N)c3)c2Cl)cccc1-c1ccc2c(c1)OCCO2]

LCMS Condition A: 1.83 minutes, M+1=629.3, M−1=627.3. $^1$H NMR (DMSO-d$_6$) δ 7.95 (s, 1H), 7.86 (dd, J=15.4, 8.4 Hz, 2H), 7.65 (t, J=7.7 Hz, 1H), 7.47 (d, J=7.3 Hz, 1H), 7.37 (d, J=8.4 Hz, 1H), 7.26 (t, J=7.5 Hz, 1H), 7.12-7.21 (m, 2H), 6.92 (d, J=8.1 Hz, 1H), 6.72-6.80 (m, 2H), 5.23 (s, 2H), 4.98-5.09 (m, 2H), 4.29-4.51 (m, 1H), 4.28 (s, 4H), 3.86-3.94 (m, 1H), 3.23-3.74 (m, 2H), 2.52 (br. s., 1H), 2.33-2.42 (m, 1H), 2.17-2.25 (m, 4H).

Intermediate 2-((2-chloro-4-formyl-5-hydroxyphenoxy)methyl)-6-(2,3-dihydrobenzo[b][1,4]dioxin-6-yl)benzonitrile

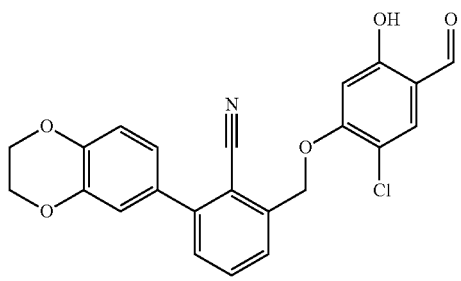 [SMILES: N#Cc1c(COc2cc(O)c(C=O)cc2Cl)cccc1-c1ccc2c(c1)OCCO2]

Diisopropyl azodicarboxylate (0.160 mL, 0.810 mmol) in tetrahydrofuran (2 mL) was added dropwise to a cooled (0° C.) solution of 5-chloro-2,4-dihydroxybenzaldehyde (127 mg, 0.736 mmol), triphenylphosphine (212 mg, 0.810 mmol) and 2-(2,3-dihydrobenzo[b][1,4]dioxin-6-yl)-6-(hydroxymethyl)benzonitrile (211.6 mg, 0.792 mmol) in dry tetrahydrofuran (5 mL). The resulting reaction mixture was allowed to slowly warm to room temperature with stirring overnight. Solvent was removed from the reaction mixture and the mixture dissolved in dichloromethane and hexanes added. The crude product was applied to a 24 g Isco redi-sep silica gel cartridge and chromatography performed on a Biotage Isolera One system employing the following conditions:

CV=column volume=33.6 mL; % A=Hexanes; % B=Dichloromethane; Collection wavelength=254 nm, flow rate=35 mL/minutes; Gradient: 70% B to 100% B with the following gradient:

1 A/B 70% 2.0 CV
2 A/B 70%-90% 4.0 CV
3 A/B 90% 3.0 CV
4 A/B 90%-100% 2.0 CV
5 A/B 100% 5.4 CV

Fractions were further analyzed using TLC and pure product fractions were combined and solvent removed in vacuo using a rotary evaporator to yield 83.8 mg of the title compound as a colorless solid. $^1$H NMR (CHLOROFORM-d) δ 11.41 (s, 1H), 9.73 (d, J=0.5 Hz, 1H), 7.70-7.74 (m, 1H), 7.65-7.70 (m, 1H), 7.59 (s, 1H), 7.48 (dd, J=7.6, 1.3 Hz, 1H), 7.09 (d, J=2.0 Hz, 1H), 7.05-7.08 (m, 1H), 6.98-7.01 (m, 1H), 6.65 (s, 1H), 5.43 (s, 2H), 4.30-4.35 (m, 4H).

Intermediate 2-((2-chloro-5-((3-cyanobenzyl)oxy)-4-formylphenoxy)methyl)-6-(2,3-dihydrobenzo[b][1,4]dioxin-6-yl)benzonitrile

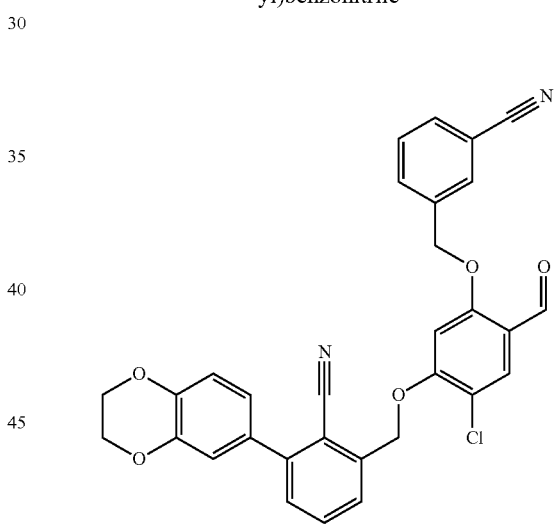

Dissolve 2-((2-chloro-4-formyl-5-hydroxyphenoxy)methyl)-6-(2,3-dihydrobenzo[b][1,4]dioxin-6-yl)benzonitrile (78.7 mg, 0.187 mmol) in dimethylformamide (2 mL). The reagents cesium carbonate (74.4 mg, 0.228 mmol) and 3-cyanobenzyl bromide (40.7 mg, 0.208 mmol) were added and the reaction capped and stirred overnight at room temperature. Remove volatiles in vacuo using a rotary evaporator and the pale yellow reaction residue was partitioned between dichloromethane and water. The aqueous portion was extracted with dichloromethane. The organic extracts were combined and washed with brine then dried over sodium sulfate. The drying agent was filtered off and solvent removed in vacuo to yield 106 mg of the title compound as a pale yellow solid. The product was used without further purification. $^1$H NMR (CHLOROFORM-d) δ 10.35 (s, 1H), 7.94 (s, 1H), 7.64-7.79 (m, 5H), 7.52-7.58 (m, 1H), 7.49 (d, J=8.5 Hz, 1H), 7.09 (d, J=2.0 Hz, 1H), 7.03-7.07 (m, 1H), 6.98-7.03 (m, 1H), 6.71 (s, 1H), 5.46 (s, 2H), 5.24 (s, 2H), 4.34 (s, 4H).

Example 1241

(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxy-2-methylpropanoic acid

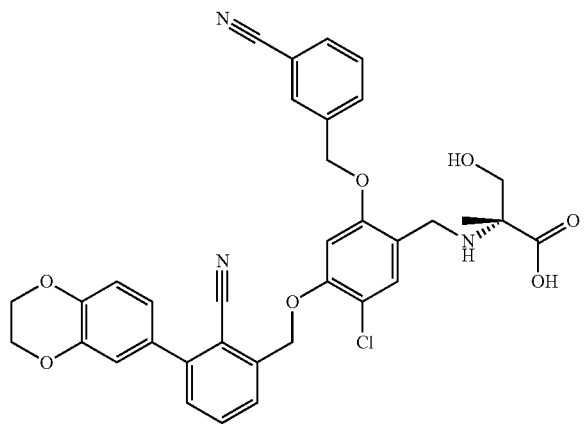 [SMILES: C[C@](CO)(NCc1cc(Cl)c(OCc2cccc(-c3ccc4c(c3)OCCO4)c2C#N)cc1OCc1cccc(C#N)c1)C(=O)O]

2-((2-Chloro-5-((3-cyanobenzyl)oxy)-4-formylphenoxy)methyl)-6-(2,3-dihydrobenzo[b][1,4]dioxin-6-yl)benzonitrile, 0.2 acetonitrile (20 mg, 0.037 mmol) was dissolve in dimethylformamide (436 µl). It was necessary to gently heat to dissolve. Methyl D-serine (13.8 mg, 0.116 mmol) was added to the reaction followed by acetic acid (21.8 µl). Sodium cyanoborohydride (6.9 mg, 0.110 mmol) was added to the yellow heterogeneous reaction and the reaction was vortexed then capped and stirred at room temperature for 2.5 days. The reaction was diluted using tetrahydrofuran, heated using a heat gun and filtered through a 0.45 um syringe filter for purification by HPLC. The crude material was purified via preparative LCMS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 15 minutes, then a 5-minute hold at 100% B; Flow: 20 mL/minutes Fractions containing the desired product were combined and dried via centrifugal evaporation. The yield of the product was 11.7 mg, and its estimated purity by LCMS analysis was 96%. Two analytical LCMS injections were used to determine the final purity. $^1$H NMR (DMSO-d$_6$) δ 7.99 (br. s., 1H), 7.91 (d, J=7.7 Hz, 1H), 7.80 (d, J=7.3 Hz, 1H), 7.71-7.78 (m, 1H), 7.68 (d, J=7.3 Hz, 1H), 7.52-7.63 (m, 3H), 7.10 (d, J=12.8 Hz, 2H), 6.95-7.07 (m, 2H), 5.42 (br. s., 2H), 5.26-5.35 (m, 2H), 4.31 (br. s., 4H), 3.92-4.03 (m, 2H), 3.49-3.70 (m, 1H), 1.26 (s, 3H). Condition M: LCMS: 2.70 minutes, M−1: 638.5; Exact Mass: 639.

The title compound was prepared by reductive amination in the same manner as (R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxy-2-methylpropanoic acid from 2-((2-chloro-5-((3-cyanobenzyl)oxy)-4-formylphenoxy)methyl)-6-(2,3-dihydrobenzo[b][1,4]dioxin-6-yl)benzonitrile and an appropriate amine.

Example 1242

(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid

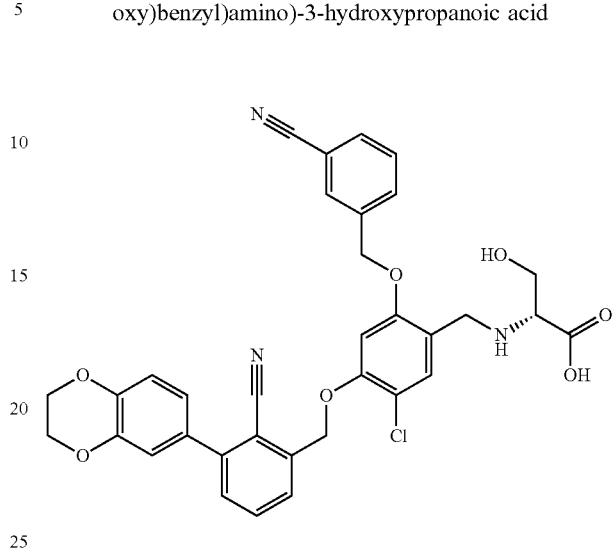

The title compound was prepared by reductive amination in the same manner as (R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxy-2-methylpropanoic acid from 2-((2-chloro-5-((3-cyanobenzyl)oxy)-4-formylphenoxy)methyl)-6-(2,3-dihydrobenzo[b][1,4]dioxin-6-yl)benzonitrile and (R)-2-amino-3-hydroxypropanoic acid. LCMS Condition M: 2.6 minutes, M−1=624.3. $^1$H NMR (DMSO-d$_6$) δ 7.99 (s, 1H), 7.89 (d, J=7.9 Hz, 1H), 7.82 (d, J=7.7 Hz, 1H), 7.74-7.79 (m, 1H), 7.68 (d, J=6.8 Hz, 1H), 7.56-7.63 (m, 2H), 7.52 (s, 1H), 7.12 (s, 1H), 7.10 (d, J=2.0 Hz, 1H), 7.04-7.08 (m, 1H), 7.00-7.04 (m, 1H), 5.41 (s, 2H), 5.26-5.35 (m, 2H), 5.06 (br. s., 1H), 4.28-4.35 (m, 4H), 3.97 (s, 2H), 3.67-3.74 (m, 1H), 3.59-3.66 (m, 1H), 3.20 (br. s., 1H).

Intermediate 5-((4-chloro-5-((3-(2,3-dihydrobenzo[b][1,4]dioxin-6-yl)-2-methylbenzyl)oxy)-2-formylphenoxy)methyl)nicotinonitrile

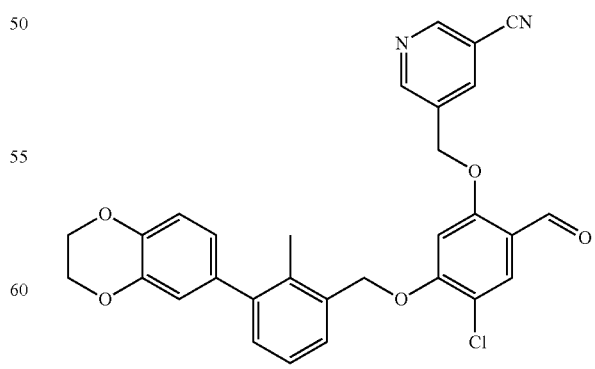

Cesium carbonate (159 mg, 0.487 mmol), 5-chloro-4-((3-(2,3-dihydrobenzo[b][1,4]dioxin-6-yl)-2-methylbenzyl)oxy)-2-hydroxybenzaldehyde (100 mg, 0.243 mmol) were combined in dimethylformamide (1 mL). Added 5-(chloromethyl)nicotinonitrile (74.3 mg, 0.487 mmol) and stirred at 75° C. for 3 hours. The reaction was neutralized with dilute hydrochloric acid (0.1 N) and washed with water and brine. The organic portion was dried over Sodium sulfate. The residue was purified on a 12 g silica gel column eluting with 1:1 to 1:2 hexane:ethyl acetate to give the title compound 92 mg, 72%). LCMS: 1.5 minutes, M+1=527.3, EM=526.1 (Start % B=0, Final % B=98, Gradient Time=1.5 min, Flow Rate=0.8 mL/min, Wavelength=220, Solvent Pair=ACN: Water: 0.05% TFA, Solvent A=100% Water: 0.05% TFA, Solvent B=100% ACN: 0.05% TFA, Column=Waters Aquity UPLC BEH C18 2.1×50 mm 1.7 U, Oven Temp.=40° C.).

Example 1244

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid

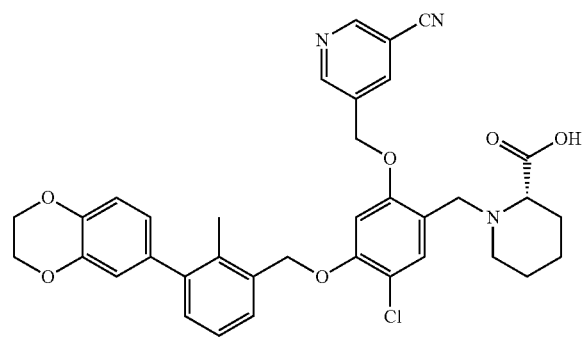 [SMILES: Cc1c(COc2cc(OCc3cncc(C#N)c3)c(CN3CCCC[C@H]3C(=O)O)cc2Cl)cccc1-c1ccc2c(c1)OCCO2]

A dimethylformamide (1 mL) solution of 5-((4-chloro-5-((3-(2,3-dihydrobenzo[b][1,4]dioxin-6-yl)-2-methylbenzyl)oxy)-2-formylphenoxy)methyl)nicotinonitrile (19 mg, 0.036 mmol) was added to (S)-piperidine-2-carboxylic acid (4.66 mg, 0.036 mmol) and stirred at room temperature for 2 hours. Sodium cyanoborohydride (6.80 mg, 0.108 mmol) and acetic acid (2.064 µl, 0.036 mmol) were added and the reaction stirred at room temperature overnight. The crude material was purified via preparative LCMS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/minutes Fractions containing the desired product were combined and dried via centrifugal evaporation. The yield of the product was 5.1 mg (22%), and its estimated purity by LCMS analysis was 99%. Two analytical LCMS injections were used to determine the final purity. LCMS Condition A: 1.9 minutes, M+1=640.4, M−1=638.3, EM=639.2. Condition M: LCMS: 2.8 minutes, M+1=640.4, M−1=638.4, EM=639.2. $^1$H NMR (600 MHz, DMSO-d$_6$) δ 9.01 (d, J=5.1 Hz, 2H), 8.46 (s, 1H), 7.51-7.39 (m, 2H), 7.25 (t, J=7.5 Hz, 1H), 7.18 (d, J=7.7 Hz, 1H), 7.11 (s, 1H), 6.93 (d, J=8.1 Hz, 1H), 6.79 (s, 1H), 6.76 (d, J=8.4 Hz, 1H), 5.38-5.30 (m, 2H), 5.25 (s, 2H), 4.29 (s, 4H), 3.80 (d, J=9.9 Hz, 1H), 3.72-3.59 (m, 1H), 3.14 (br. s., 1H), 2.31 (br. s., 1H), 2.25 (s, 3H), 1.80 (br. s., 1H), 1.72 (d, J=8.4 Hz, 1H), 1.49 (br. s., 3H), 1.37 (br. s., 1H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-((4-chloro-5-((3-(2,3-dihydrobenzo[b][1,4]dioxin-6-yl)-2-methylbenzyl)oxy)-2-formylphenoxy)methyl)nicotinonitrile and the appropriate amine. LCMS for these examples is given in tabular form.

Example 1248

(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxy-2-methylpropanoic acid

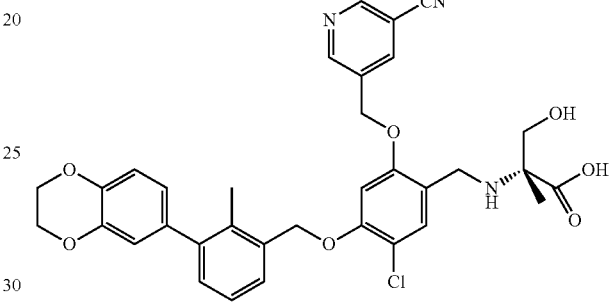

$^1$H NMR (600 MHz, DMSO-d$_6$) δ 9.03 (s, 1H), 9.01 (s, 1H), 8.51 (s, 1H), 7.55 (s, 1H), 7.44 (d, J=7.3 Hz, 1H), 7.27-7.21 (m, 1H), 7.18 (d, J=7.3 Hz, 1H), 7.12 (s, 1H), 6.93 (d, J=8.4 Hz, 1H), 6.78 (s, 1H), 6.75 (d, J=8.4 Hz, 1H), 5.40-5.32 (m, 2H), 5.28 (s, 2H), 4.29 (s, 4H), 3.96 (br. s., 2H), 3.66-3.58 (m, 1H), 3.57-3.49 (m, 1H), 2.24 (s, 3H), 1.24 (s, 3H).

Example 1249

(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxypropanoic acid

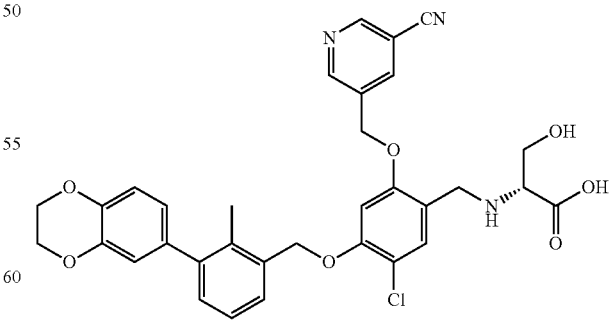

$^1$H NMR (600 MHz, DMSO-d$_6$) δ 9.02 (d, J=9.9 Hz, 2H), 8.52 (br. s., 1H), 7.52 (s, 1H), 7.45 (d, J=7.0 Hz, 1H), 7.25 (t, J=7.5 Hz, 1H), 7.18 (d, J=7.3 Hz, 1H), 7.14 (s, 1H), 6.93 (d, J=8.1 Hz, 1H), 6.82-6.72 (m, 2H), 5.41-5.31 (m, 2H), 5.27 (s, 2H), 4.29 (s, 4H), 4.08-3.93 (m, 2H), 3.71 (d, J=6.2 Hz, 1H), 3.63 (d, J=6.2 Hz, 1H), 3.17 (d, J=5.5 Hz, 1H), 2.24 (s, 3H).

Example 1250

(S)-4-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxybutanoic acid

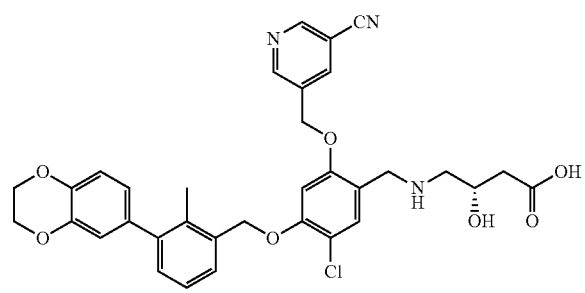 [SMILES: Cc1c(COc2cc(OCc3cncc(C#N)c3)c(CNC[C@@H](O)CC(=O)O)cc2Cl)cccc1-c1ccc2c(c1)OCCO2]

¹H NMR (600 MHz, DMSO-d₆) δ 9.05-8.96 (m, 2H), 8.44 (br. s., 1H), 7.45 (d, J=7.7 Hz, 1H), 7.42-7.37 (m, 1H), 7.27-7.22 (m, 1H), 7.19-7.15 (m, 1H), 7.13-7.05 (m, 1H), 6.96-6.87 (m, 1H), 6.81-6.69 (m, 2H), 5.39-5.29 (m, 2H), 5.27-5.19 (m, 2H), 4.33-4.21 (m, 4H), 3.78-3.67 (m, 1H), 3.66-3.43 (m, 2H), 2.59-2.53 (m, 2H), 2.42-2.33 (m, 1H), 2.28-2.18 (m, 5H).

Example 1251

N-(2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)ethyl)acetamide

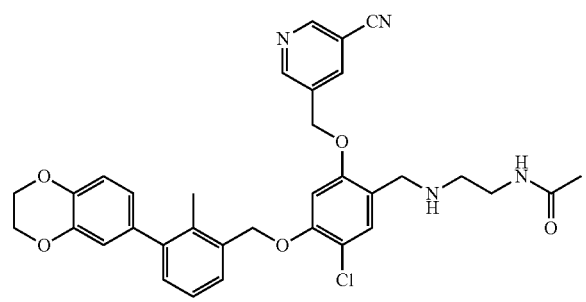

¹H NMR (600 MHz, DMSO-d₆) δ 9.00 (d, J=18.0 Hz, 2H), 8.43 (br. s., 1H), 7.79 (d, J=5.1 Hz, 1H), 7.45 (d, J=7.3 Hz, 1H), 7.38 (s, 1H), 7.28-7.21 (m, 1H), 7.18 (d, J=7.7 Hz, 1H), 7.09 (s, 1H), 6.93 (d, J=8.1 Hz, 1H), 6.81-6.72 (m, 2H), 5.32 (s, 2H), 5.24 (s, 2H), 4.29 (s, 4H), 3.12 (q, J=6.0 Hz, 2H), 2.55-2.51 (m, 2H), 2.25 (s, 3H), 1.93-1.85 (m, 5H).

Example 1252

(S)-2-(5-chloro-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid

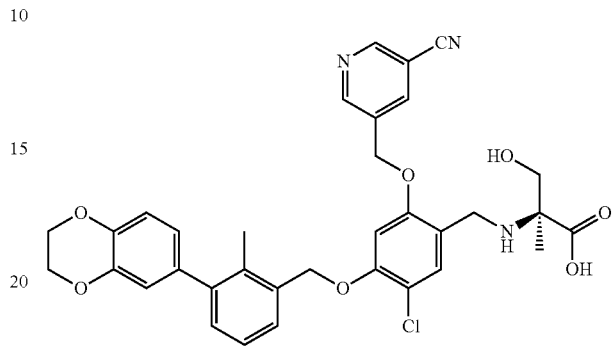

¹H NMR (DMSO-d₆) δ 9.01 (s, 1H), 9.04 (s, 1H), 8.52 (s, 1H), 7.54 (s, 1H), 7.44 (s, 1H), 7.24 (s, 1H), 7.19 (s, 1H), 7.13 (s, 1H), 6.93 (d, 1H), 6.74-6.80 (m, 2H), 5.36 (s, 2H), 5.27 (s, 2H), 4.29 (s, 4H), 3.60 (d, 1H), 3.52 (d, 1H), 2.90 (s, 1H), 2.74 (s, 1H), 2.24 (s, 3H), 1.23 (s, 3H).

| Example | LCMS Method | RT (min) | M + 1 | M – 1 |
| --- | --- | --- | --- | --- |
| Example 1248: (R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxy-2-methylpropanoic acid | A | 1.8 | 630.3 | 628.3 |
| Example 1249: (R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxypropanoic acid | A | 1.8 | 616.3 | 614.3 |
| Example 1250: (S)-4-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxybutanoic acid | A | 1.7 | 630.3 | 628.2 |
| Example 1251: N-(2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)ethyl)acetamide | M | 2.9 | 613.3 | 611.4 |
| Example 1252: ((S)-2-(5-chloro-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid | A | 1.74 | 630.2 | 628.2 |

Intermediate 2-((5-bromopyridin-3-yl)methoxy)-5-chloro-4-(3-(2,3-dihydrobenzo[b][1,4]dioxin-6-yl)-2-methylbenzyloxy)benzaldehyde

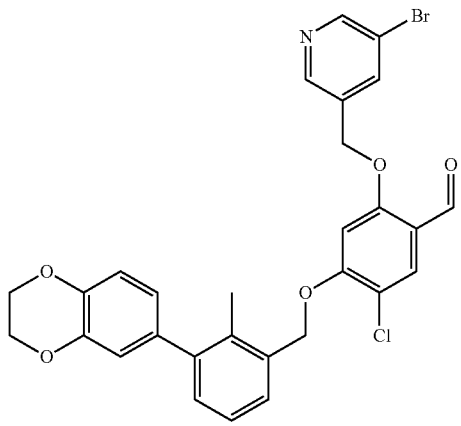 [SMILES: Cc1c(COc2cc(OCc3cncc(Br)c3)c(C=O)cc2Cl)cccc1-c1ccc2c(c1)OCCO2]

Cesium carbonate (159 mg, 0.487 mmol), 5-chloro-4-((3-(2,3-dihydrobenzo[b][1,4]dioxin-6-yl)-2-methylbenzyl)oxy)-2-hydroxybenzaldehyde (100 mg, 0.243 mmol) and 5-(chloromethyl)nicotinonitrile (74.3 mg, 0.487 mmol) were stirred at 75° C. for 3 hours in dimethyl formamide (1 mL).

The reaction was neutralized with dilute hydrochloric acid (0.1 N) and washed with water and brine. Dried over sodium sulfate. The residue was purified with 1:1 to 1:2 hexane:ethyl acetate on a 12 g silica gel column Collected fractions to afford a yellow solid as desired product. LCMS Condition T: 1.46 minutes, M+1=527.3.

The following examples were prepared by reductive amination in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 2-((5-bromopyridin-3-yl)methoxy)-5-chloro-4-(3-(2,3-dihydrobenzo[b][1,4]dioxin-6-yl)-2-methylbenzyloxy)benzaldehyde and the appropriate amine.

Example 1254

(R)-2-(2-((5-bromopyridin-3-yl)methoxy)-5-chloro-4-(3-(2,3-dihydrobenzo[b][1,4]dioxin-6-yl)-2-methylbenzyloxy)benzylamino)-3-hydroxy-2-methylpropanoic acid

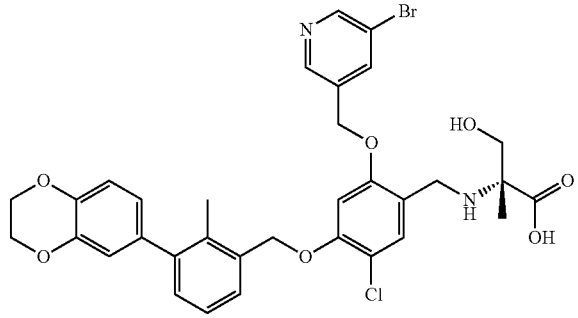 [SMILES: Cc1c(COc2cc(OCc3cncc(Br)c3)c(CN[C@](C)(CO)C(=O)O)cc2Cl)cccc1-c1ccc2c(c1)OCCO2]

LCMS Condition A: 1.85 minutes, M+1=685.1, M−1=683.2. $^1$H NMR (DMSO-d$_6$) δ 8.74 (s, 1H), 8.70 (s, 1H), 8.28 (s, 1H), 7.52 (s, 1H), 7.45 (d, 1H), 7.25 (s, 1H), 7.17-7.20 (m, 1H), 7.13 (s, 1H), 6.93 (d, 1H), 6.74-6.80 (m, 2H), 5.28 (d, 4H), 4.29 (s, 4H), 3.57 (d, 1H), 3.51 (d, 1H), 2.90 (s, 1H), 2.74 (s, 1H), 2.25 (s, 3H), 1.22 (s, 3H).

Example 1255

N-(2-(2-((5-bromopyridin-3-yl)methoxy)-5-chloro-4-(3-(2,3-dihydrobenzo[b][1,4]dioxin-6-yl)-2-methylbenzyloxy)benzylamino)ethyl)acetamide

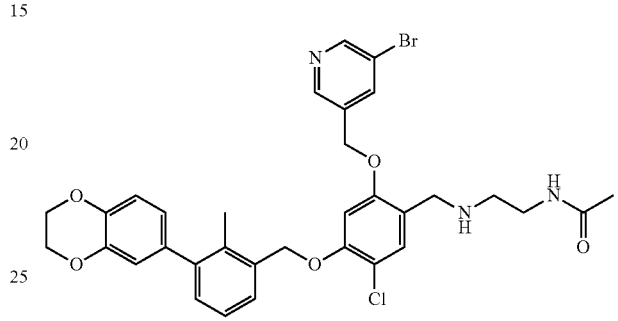

LCMS Condition A: 1.93 minutes, M+1=668.3, M−1=664.5. $^1$H NMR (DMSO-d$_6$) δ 8.69-8.72 (m, 2H), 8.20 (s, 1H), 7.80 (br. s., 1H), 7.46 (d, 1H), 7.38 (s, 1H), 7.25 (m, 1H), 7.18 (d, 1H), 7.10 (s, 1H), 6.93 (d, 1H), 6.75-6.80 (m, 2H), 5.28 (s, 2H), 5.24 (s, 2H), 4.29 (s, 4H), 3.12 (m, 2H), 2.90 (s, 1H), 2.74 (s, 1H), 2.53-2.55 (m, 2H), 2.25 (s, 3H), 1.78 (s, 3H).

Intermediate 5-((4-chloro-5-((3-(2,3-dihydrobenzo[b][1,4]dioxin-6-yl)-2-methylbenzyl)oxy)-2-formylphenoxy)methyl)nicotinonitrile

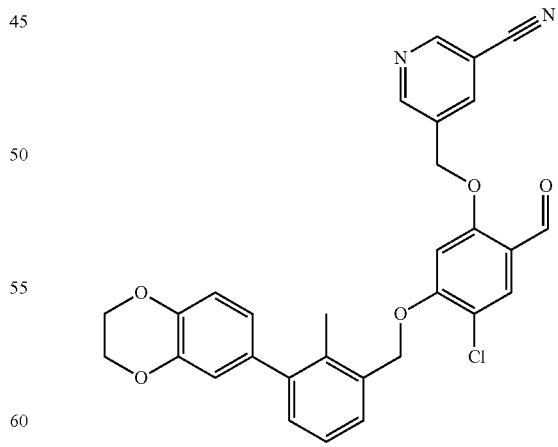

5-Chloro-4-((3-(2,3-dihydrobenzo[b][1,4]dioxin-6-yl)-2-methylbenzyl)oxy)-2-hydroxybenzaldehyde (1.06 g, 2.58 mmol) was partially suspended in DMF (25 mL) and cesium carbonate (1.186 g, 3.64 mmol) was added and the reaction stirred for approximately 8 minutes in which it appeared to exhibit improved solubility. 5-(chloromethyl)nicotinonitrile (433 mg, 2.84 mmol) was added to the reaction. The reaction was placed under an nitrogen atmosphere and heated at 75 C for three hours. The reaction solvent was removed in vacuuo using a rotary evaporator and the solid residue was partitioned between dichloromethane and saturated aqueous sodium bicarbonate. The organic extract was washed with water and dried over sodium sulfate. The drying agent was removed by filtration and solvent removed in vacuuo to yield the crude product as a brown/beige solid. The crude product was triturated with ethyl acetate and the product was filtered using a buchner funnel to yield 851 mg of product as a beige solid after drying in vacuuo. The product was used without further purification. $^1$H NMR (CHLOROFORM-d) δ 10.29 (s, 1H), 8.92 (d, J=1.9 Hz, 1H), 8.91 (d, J=2.0 Hz, 1H), 8.09 (t, J=2.0 Hz, 1H), 7.93 (s, 1H), 7.38-7.42 (m, 1H), 7.28 (s, 2H), 7.26 (br. s., 1H), 6.93 (d, J=8.2 Hz, 1H), 6.83 (d, J=2.0 Hz, 1H), 6.78 (dd, J=8.2, 2.0 Hz, 1H), 6.64 (s, 1H), 5.25 (s, 2H), 5.22 (s, 2H), 4.32 (s, 4H), 2.30 (s, 3H).

Example 1253

(S)-1-(5-chloro-2-((5-cyanopyridin-3-yl)methoxy)-4-((3-(2,3-dihydrobenzo[b][1,4]dioxin-6-yl)-2-methyl-benzyl)oxy)benzyl)piperidine-2-carboxylic acid, TFA salt

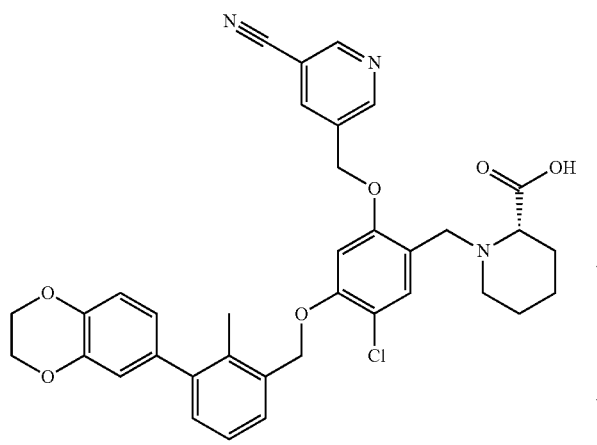

5-((4-Chloro-5-((3-(2,3-dihydrobenzo[b][1,4]dioxin-6-yl)-2-methylbenzyl)oxy)-2-formylphenoxy)methyl)nicotinonitrile (300 mg, 0.569 mmol) was dissolved in DMF (6.3 mL) with heating then allowed to cool briefly before adding L-pipecolic acid (226 mg, 1.748 mmol) and sodium triacetoxyborohydride (374 mg, 1.765 mmol). The reaction was capped and stirred at room temperature for 3 days. To the reaction was added 5 drops of water and approximately 3-5 mL of acetonitrile. The reaction was stirred with vortexing then filtered through Whatman \#1 paper using a Buchner funnel. The precipitate was rinsed with a small amount of acetonitrile. The filtrate crude product mixture was purified by reverse phase HPLC in 5×2 mL injections under the following conditions using a Shimadzu Prep HPLC system using discovery software:
Column: Waters Sunfire C18, 19 mm×150 mm
Flow Rate: 25 mL/min
% A: 10% acetonitrile-90% water-0.1% TFA
% B: 90% acetonitrile-10% water-0.1% TFA
Detection: UV at 220 nm
Gradient 0% B to 100% B over 20 minutes, Hold at 100% B for 10 minutes.
Retention time of product=11.9 minutes.
Product fraction were combined and solvent removed in vacuuo using a rotary evaporator. Transfer using DCM to a vial followed by solvent removal and drying yielded 204 mg of product as a colorless amorphous solid.
LCMS-Shimadzu HPLC system: running Discover software,
Gradient:
Start % B=0
Final % B=100
Gradient Time=4 min then hold 100% B for 1 min.
Flow Rate=0.8 mL/min
Wavelength=220 nm
Solvent Pair=ACN: Water Ammonium Actetate
Solvent A=5% ACN: 95% Water: 10 mM Ammonium Actetate
Solvent B=95% ACN: 5% Water: 10 mM Ammonium Actetate
Column 2=Phenomenex LUNA C18, 50×2, 3u
Retention Time=2.8 min., M−1: 638.4, M+1: 640.2
$^1$H NMR (CHLOROFORM-d) δ 8.91 (br. s., 1H), 8.84 (s, 1H), 8.02-8.39 (m, 1H), 7.41-7.54 (m, 1H), 7.37 (dd, J=6.4, 2.4 Hz, 1H), 7.20-7.26 (m, 2H), 6.92 (d, J=8.2 Hz, 1H), 6.82 (d, J=2.0 Hz, 1H), 6.77 (dd, J=8.3, 2.1 Hz, 1H), 6.65 (s, 1H), 5.17-5.25 (m, 2H), 5.15 (s, 2H), 4.43 (br. s., 2H), 4.31 (s, 4H), 2.72-2.86 (m, 1H), 2.28 (s, 3H), 2.15-2.25 (m, 1H), 2.02 (s, 1H), 1.84 (br. s., 3H), 1.36-1.71 (m, 2H). NMR revealed a *0.3 DCM solvate.

Example 1256

(S)-1-(5-chloro-2-((5-cyanopyridin-3-yl)methoxy)-4-((3-(2,3-dihydrobenzo[b][1,4]dioxin-6-yl)-2-methyl-benzyl)oxy)benzyl)-N-(methylsulfonyl)piperidine-2-carboxamide

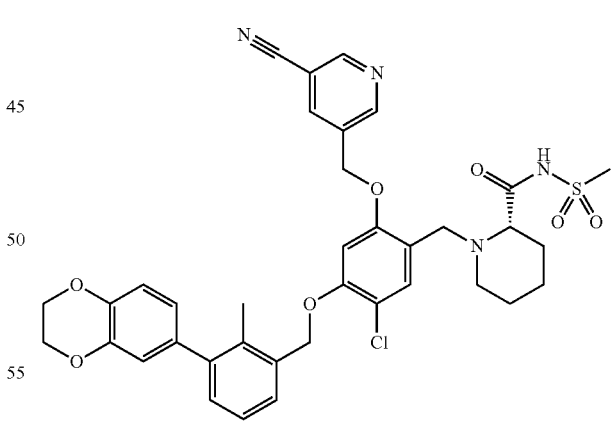

In a vial containing (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid, TFA (8.0 mg, 10.61 μmol), add dichloromethane (150 μl), DMAP (8.4 mg, 0.069 mmol), methanesulfonamide (3.9 mg, 0.041 mmol) and finally EDC (7.1 mg, 0.037 mmol). The reaction was capped and stirred at room temperature for 22 hours. The reaction solvent was removed in vacuuo using a rotary evaporator and the reaction residue was dissolved in 0.5 mL of DMF and further diluted with 0.4 mL of acetonitrile. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/min. Fractions containing the desired product were combined and dried via centrifugal evaporation.

The yield of the product was 6.9 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-$d_6$) δ: 9.01 (s, 2H), 8.51 (s, 1H), 7.58 (s, 1H), 7.46 (d, J=7.3 Hz, 1H), 7.22-7.28 (m, 1H), 7.18 (d, J=7.3 Hz, 1H), 7.13 (s, 1H), 6.92 (d, J=8.1 Hz, 1H), 6.79 (d, J=1.8 Hz, 1H), 6.76 (d, J=8.1 Hz, 1H), 5.36 (s, 2H), 5.26 (s, 2H), 4.28 (s, 4H), 4.01 (d, J=13.9 Hz, 1H), 3.80 (br. s., 1H), 2.99 (d, J=12.1 Hz, 1H), 2.84 (s, 3H), 2.42 (br. s., 1H), 2.24 (s, 3H), 1.83-1.88 (m, 1H), 1.63 (t, J=10.3 Hz, 1H), 1.53 (br. s., 2H), 1.33 (br. s., 1H) LC/MS (acetonitrile:water:ammonium acetate) 1.85 min., M−1: 715.2, M+H: 717.3; Exact Mass: 716.

A series of acylsulfonamides and acylsulfamides were synthesized as outline in the procedure below for (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Example 1257

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide

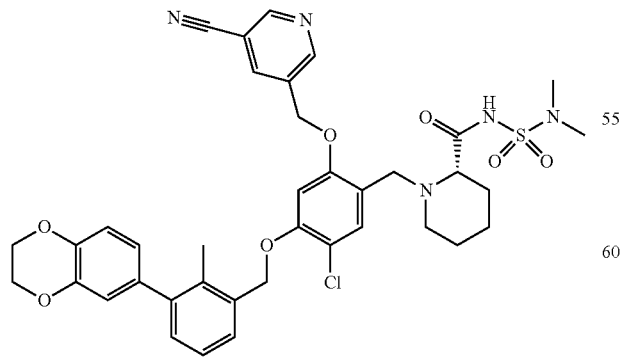

(S)-1-(5-Chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid, TFA*0.3 methylene chloride (15 mg, 0.019 mmol), was dissolved in dichloromethane (200 μl) and DMAP (15.2 mg, 0.124 mmol), dimethylsulfamide (9.8 mg, 0.079 mmol added to the reaction followed by EDC (13.3 mg, 0.069 mmol). The reaction was capped and stirred at room temperature for 17.5 hours. The reaction solvent was removed in vacuuo using a rotary evaporator and the reaction residue was dissolved in 0.5 mL of DMF and further diluted with 0.5 mL of acetonitrile.

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min Fractions containing the desired product were combined and dried via centrifugal evaporation. The yield of the product was 9.9 mg, and its estimated purity by LCMS analysis was 94%. Two analytical LC/MS injections were used to determine the final purity. Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-$d_6$) δ 9.01 (d, J=4.8 Hz, 2H), 8.47 (s, 1H), 7.53 (s, 1H), 7.46 (d, J=7.3 Hz, 1H), 7.22-7.28 (m, 1H), 7.18 (d, J=7.7 Hz, 1H), 7.14 (s, 1H), 6.92 (d, J=8.1 Hz, 1H), 6.78 (s, 1H), 6.76 (d, J=8.1 Hz, 1H), 5.32-5.40 (m, 2H), 5.26 (s, 2H), 4.28 (s, 5H), 3.86 (d, J=13.9 Hz, 1H), 3.72-3.79 (m, 1H), 3.34 (br. s., 1H), 3.27 (br. s., 1H), 2.98 (d, J=11.7 Hz, 1H), 2.68 (s, 6H), 2.41 (br. s., 1H), 1.88 (br. s., 1H), 1.57-1.72 (m, 2H), 1.54 (br. s., 2H), 1.36 (br. s., 1H) LC/MS (acetonitrile:wate:ammonium acetate) 2.02 min., M−1: 744.3, M+H: 746.3; Exact Mass: 745.

Example 1258

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-((trifluoromethyl)sulfonyl)piperidine-2-carboxamide

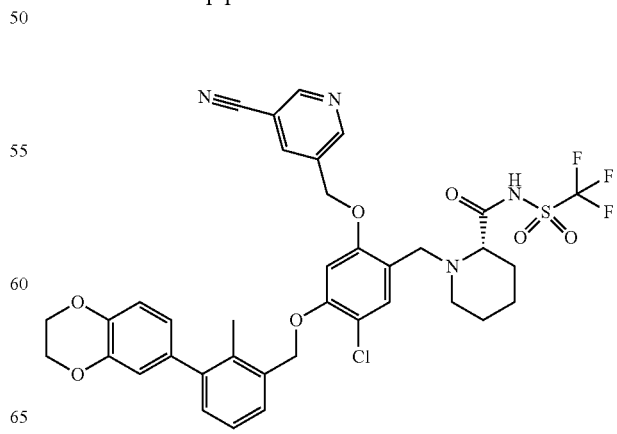

Prepared in similar fashion as above (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Purification and analysis: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-90% B over 15 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-d$_6$) δ 9.32 (br. s., 1H), 9.03 (d, J=3.3 Hz, 2H), 8.43-8.55 (m, 1H), 7.55 (s, 1H), 7.46 (d, J=7.3 Hz, 1H), 7.22-7.30 (m, 1H), 7.17-7.22 (m, 2H), 6.93 (d, J=8.4 Hz, 1H), 6.79 (d, J=1.8 Hz, 1H), 6.76 (dd, J=8.4, 1.8 Hz, 1H), 5.39 (s, 2H), 5.30 (s, 2H), 4.23-4.31 (m, 5H), 4.13 (d, J=12.5 Hz, 1H), 3.72-3.81 (m, 1H), 3.18 (d, J=11.7 Hz, 1H), 2.82 (br. s., 1H), 2.25 (s, 3H), 2.09 (d, J=16.1 Hz, 1H), 1.56-1.72 (m, 4H), 1.42 (br. s., 1H). LC/MS (acetonitrile:water:ammonium acetate) 2.12 min., M−1: 769.3, M+H: 771.3; Exact Mass: 770.

Example 1259

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-(cyclopropylsulfonyl)piperidine-2-carboxamide

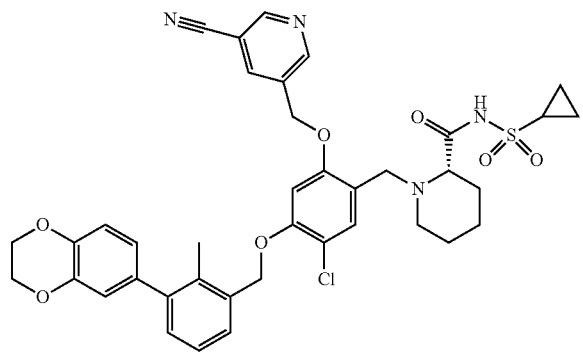 [SMILES: Cc1c(COc2cc(OCc3cncc(C#N)c3)c(CN3CCCC[C@H]3C(=O)NS(=O)(=O)C3CC3)cc2Cl)cccc1-c1ccc2c(c1)OCCO2]

Prepared in similar fashion as above (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Purification and analysis: The crude material was purified via preparative LC/MS with the following conditions: Column: waters xbridge c-18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/min Fractions containing the desired product were combined and dried via centrifugal evaporation. The yield of the product was 10.3 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-d$_6$) δ 9.03 (s, 2H), 8.50 (s, 1H), 7.63 (s, 1H), 7.47 (d, J=7.7 Hz, 1H), 7.23-7.30 (m, 1H), 7.14-7.21 (m, 2H), 6.93 (d, J=8.4 Hz, 1H), 6.79 (d, J=1.8 Hz, 1H), 6.76 (dd, J=8.1, 1.8 Hz, 1H), 5.38 (s, 2H), 5.29 (s, 2H), 4.28 (s, 4H), 4.10-4.17 (m, 1H), 4.02-4.09 (m, 1H), 3.08 (d, J=11.7 Hz, 1H), 2.82-2.88 (m, 1H), 2.60-2.70 (m, 1H), 2.25 (s, 3H), 1.99 (d, J=12.8 Hz, 1H), 1.53-1.72 (m, 4H), 1.31-1.46 (m, J=11.0 Hz, 1H), 0.83-0.92 (m, 2H), 0.78 (d, J=7.7 Hz, 2H). LC/MS (acetonitrile:water:ammonium acetate) 1.77 min., M−1: 741.5, M+H: 743.3; Exact Mass: 742.

Example 1260

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-(isopropylsulfonyl)piperidine-2-carboxamide

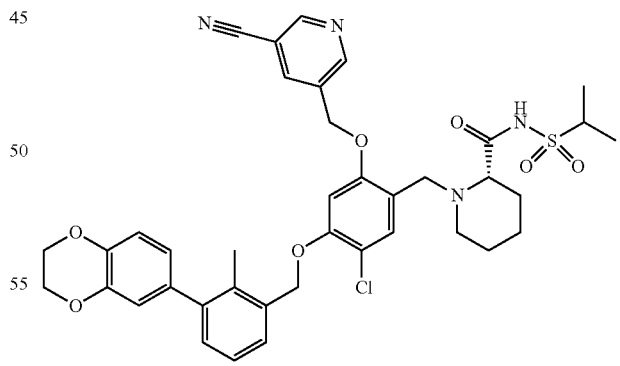

Prepared in similar fashion as above (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Purification and analysis: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-d$_6$) δ 9.02 (s, 2H), 8.49 (s, 1H), 7.61 (s, 1H), 7.46 (d, J=7.3 Hz, 1H), 7.23-7.29 (m, 1H), 7.14-7.21 (m, 2H), 6.93 (d, J=8.1 Hz, 1H), 6.79 (d, J=1.8 Hz, 1H), 6.76 (dd, J=8.3, 2.0 Hz, 1H), 5.38 (s, 2H), 5.28 (s, 2H), 4.28 (s, 4H), 4.04-4.13 (m, 1H), 3.97-4.04 (m, 1H), 3.51-3.60 (m, J=13.6, 6.8, 6.8 Hz, 1H), 3.06 (d, J=11.7 Hz, 1H), 2.57-2.67 (m, 1H), 2.24 (s, 3H), 1.99 (d, J=12.5 Hz, 1H), 1.51-1.74 (m, 4H), 1.33-1.45 (m, J=15.4 Hz, 1H), 1.17 (dd, J=6.8, 1.7 Hz, 6H). LC/MS (acetonitrile:water:ammonium acetate) 1.81 min., M−1: 743.4, M+H: 745.3; Exact Mass: 744.

Example 1261

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-((1-methyl-1H-imidazol-4-yl)sulfonyl)piperidine-2-carboxamide

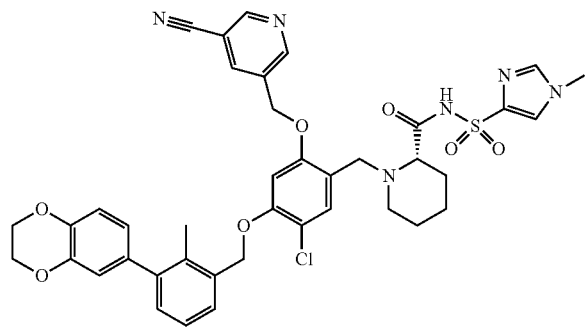 [SMILES: Cc1c(COc2cc(OCc3cncc(C#N)c3)c(CN3CCCC[C@H]3C(=O)NS(=O)(=O)c3cn(C)cn3)cc2Cl)cccc1-c1ccc2c(c1)OCCO2]

Prepared in similar fashion as above (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Purification and analysis: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10 mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 12.7 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm).

LC/MS (acetonitrile:water:ammonium acetate) 1.86 min., M−1: 781.3; M+H: 783.3; Exact Mass: 782.

Example 1262

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-((4-methylpiperazin-1-yl)sulfonyl)piperidine-2-carboxamide

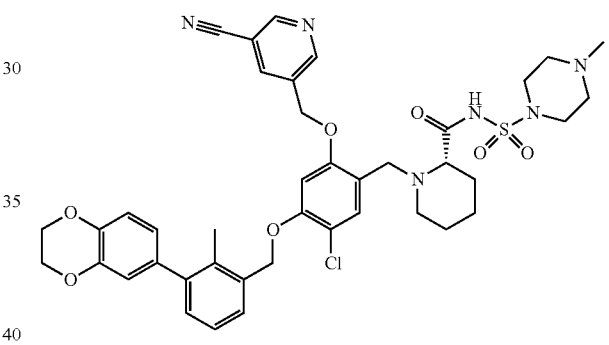

Prepared in similar fashion as above (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N—(N,N-dimethylsulfamoyl)piperidine-2-carboxamide.

Purification and analysis: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10 mM ammonium acetate; Gradient: 25-70% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate;

Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. $^1$H NMR (DMSO-$d_6$) δ 8.99 (d, J=5.1 Hz, 2H), 8.46 (s, 1H), 7.52 (s, 1H), 7.46 (d, J=7.3 Hz, 1H), 7.22-7.28 (m, 1H), 7.17 (d, J=7.3 Hz, 1H), 7.09 (s, 1H), 6.92 (d, J=8.1 Hz, 1H), 6.78 (s, 1H), 6.76 (dd, J=8.4, 1.8 Hz, 1H), 5.33 (s, 2H), 5.23 (s, 2H), 4.28 (s, 5H), 3.79 (d, J=13.9 Hz, 2H), 3.48 (d, J=13.2 Hz, 2H), 2.98 (br. s., 3H), 2.85 (br. s., 1H), 2.26 (br. s., 2H), 2.21-2.25 (m, 3H), 2.12 (s, 3H), 1.75 (s, 2H), 1.55-1.68 (m, 2H), 1.45 (br. s., 2H), 1.20-1.30 (m, 1H). LC/MS (acetonitrile:water:ammonium acetate) 1.98 min., M−1: 799.3; M+H: 801.5; Exact Mass: 800.

Example 1263

(R)-2-((5-chloro-4-((3-(2,3-dihydrobenzo[b][1,4]dioxin-6-yl)-2-methylbenzyl)oxy)-2-hydroxybenzyl)amino)-3-hydroxy-2-methylpropanoic acid, TFA

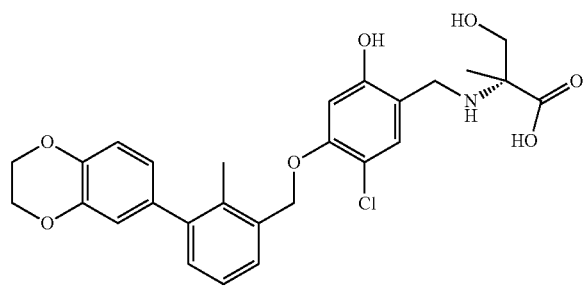 [SMILES: Cc1c(COc2cc(O)c(CN[C@](C)(CO)C(=O)O)cc2Cl)cccc1-c1ccc2c(c1)OCCO2]

Dissolve 5-((4-chloro-5-((3-(2,3-dihydrobenzo[b][1,4]dioxin-6-yl)-2-methylbenzyl)oxy)-2-formylphenoxy)methyl)nicotinonitrile (150 mg, 0.285 mmol) in DMF (2.7 mL) with heating, add acetic acid (0.135 mL) and allow to cool briefly before adding 2-methyl-D-serine (86 mg, 0.722 mmol). Sodium cyanoborohydride (39 mg, 0.621 mmol) was added to the reaction. The reaction was capped and stirred at room temperature for 24 hours. Analysis of the reaction by LCMS indicated a significant by-product (title compound). The reaction was then placed in a freezer overnight. The reaction was diluted with tetrahydrofuran and filtered through a Buchner funnel rinsing the filter pad with tetrahydrofuran. The filtrate was diluted to a final volume of 6 mL using tetrahydrofuran and the mixture was purified by reverse phase HPLC in three 2 mL injections on a Shimadzu Prep HPLC running discovery software:
Column: Waters Sunfire C18, 19 mm×150 mm
Flow Rate: 25 mL/min
% A: 10% acetonitrile-90% water-0.1% TFA
% B: 90% acetonitrile-10% water-0.1% TFA
Detection: UV at 220 nm
Gradient 0% B to 100% B over 20 minutes, Hold at 100% B for 10 minutes.
Retention time of the title compound=10.9-11.0 minutes.
Fractions containing the desired product were dried via centrifugal evaporation then dissolve in dichloromethane, combined into a sample vial and concentrated with a nitrogen sweep then the final remaining solvent was removed in vacuuo using a rotary evaporator. The product was dried in vacuuo at room temperature to yield 36.0 mg of the title compound as a colorless film. $^1$H NMR (CHLOROFORM-d) δ 7.39 (t, J=4.3 Hz, 1H), 7.17 (d, J=4.4 Hz, 3H), 6.88 (d, J=8.4 Hz, 1H), 6.78 (d, J=1.9 Hz, 1H), 6.72 (dd, J=8.3, 2.0 Hz, 1H), 6.65 (br. s., 1H), 4.97 (br. s., 2H), 4.28 (s, 4H), 3.88 (d, J=19.2 Hz, 3H), 3.65 (br. s., 3H), 2.15-2.22 (m, 3H), 1.35 (br. s., 3H).

LCMS-Shimadzu HPLC system: running Discover software,

Gradient:

Start % B=0

Final % B=100

Gradient Time=4 min then hold 100% B for 1 min.

Flow Rate=0.8 mL/min

Wavelength=220 nm

Solvent Pair=ACN: Water Ammonium Actetate

Solvent A=5% ACN: 95% Water: 10 mM Ammonium Actetate

Solvent B=95% ACN: 5% Water: 10 mM Ammonium Actetate

Column 2=Phenomenex LUNA C18, 50×2, 3u

Retention Time=2.55 min., M−1: 512.1

Intermediate 4-((3-(2,3-dihydrobenzo[b][1,4]dioxin-6-yl)-2-methylbenzyl)oxy)-2-hydroxy-5-methylbenzaldehyde

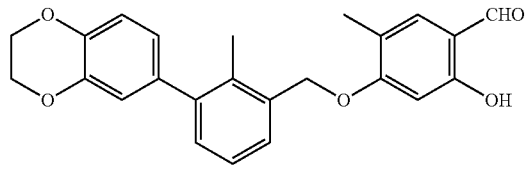 [SMILES: Cc1cc(C=O)c(O)cc1OCc1cccc(-c2ccc3c(c2)OCCO3)c1C]

Triphenylphosphine (207 mg, 0.789 mmol) was added to a solution of (3-(2,3-dihydrobenzo[b][1,4]dioxin-6-yl)-2-methylphenyl)methanol (168 mg, 0.657 mmol) and 2,4-dihydroxy-5-methylbenzaldehyde (100 mg, 0.657 mmol) in tetrahydrofuran (5 mL). The reaction mixture was stirred at 0° C. for 15 minutes. Diisopropyl azodicarboxylate (0.153 mL, 0.789 mmol) was added dropwise. The reaction mixture was then warmed to room temperature and stirred overnight. It was then concentrated and the residue was purified on a silica gel column using hexanes to 20% ethyl acetate in hexanes as eluent to give a white solid as the final product 4-((3-(2,3-dihydrobenzo[b][1,4]dioxin-6-yl)-2-methylbenzyl)oxy)-2-hydroxy-5-methylbenzaldehyde (85 mg, 0.218 mmol, 33.1% yield). LCMS Condition T: 4.46 min, 391.0 (MH$^+$). $^1$H NMR (400 MHz, CDCl$_3$) δ 11.46 (s, 1H), 9.71 (s, 1H), 7.42 (dd, J=6.2, 2.6 Hz, 1H), 7.23-7.31 (m, 3H), 6.93 (d, J=8.1 Hz, 1H), 6.84 (d, J=2.0 Hz, 1H), 6.75-6.82 (m, 1H), 6.55 (s, 1H), 5.14 (s, 2H), 4.32 (s, 4H), 2.26 (s, 3H), 2.22 (s, 3H).

Intermediate 3-((5-((3-(2,3-dihydrobenzo[b][1,4]dioxin-6-yl)-2-methylbenzyl)oxy)-2-formyl-4-methylphenoxy)methyl)benzonitrile

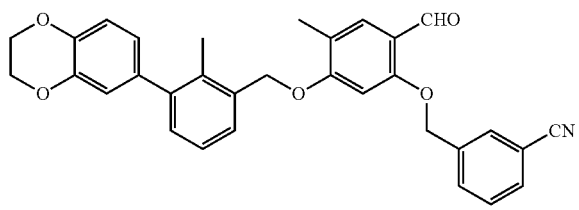 [SMILES: Cc1cc(C=O)c(OCc2cccc(C#N)c2)cc1OCc1cccc(-c2ccc3c(c2)OCCO3)c1C]

To a solution of 4-((3-(2,3-dihydrobenzo[b][1,4]dioxin-6-yl)-2-methylbenzyl)oxy)-2-hydroxy-5-methylbenzaldehyde (85 mg, 0.218 mmol) in dimethylformamide (2 mL), 3-(bromomethyl)benzonitrile (46.9 mg, 0.239 mmol) and cesium carbonate (106 mg, 0.327 mmol) were added. The reaction mixture was stirred at room temperature for 3 days. Water was added and a white solid was collected as the final product 3-((5-((3-(2,3-dihydrobenzo[b][1,4]dioxin-6-yl)-2-methylbenzyl)oxy)-2-formyl-4-methylphenoxy)methyl)benzonitrile (100 mg, 0.198 mmol, 91% yield). LCMS Condition T: 4.535 min, 506 (MH+). $^1$H NMR (400 MHz, CDCl$_3$) δ 10.36 (s, 1H), 7.74 (s, 1H), 7.63-7.73 (m, 3H), 7.50-7.58 (m, 1H), 7.34-7.41 (m, 1H), 7.23-7.28 (m, 1H), 6.93 (d, J=8.1 Hz, 1H), 6.83 (d, J=2.2 Hz, 1H), 6.78 (dd, J=8.2, 2.1 Hz, 1H), 6.52 (s, 1H), 5.20 (s, 2H), 5.13 (s, 2H), 4.32 (s, 4H), 2.27 (s, 3H), 2.22 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 3-((5-((3-(2,3-dihydrobenzo[b][1,4]dioxin-6-yl)-2-methylbenzyl)oxy)-2-formyl-4-methylphenoxy)methyl)benzonitrile and the appropriate amine. LCMS for these examples is given in tabular form.

Example 1264

N-(2-((2-((3-cyanobenzyl)oxy)-4-((3-(2,3-dihydrobenzo[b][1,4]dioxin-6-yl)-2-methylbenzyl)oxy)-5-methylbenzyl)amino)ethyl)acetamide

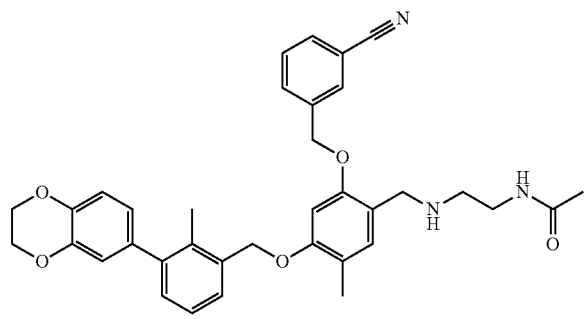 [SMILES: CC(=O)NCCNCc1cc(C)c(OCc2cccc(-c3ccc4c(c3)OCCO4)c2C)cc1OCc1cccc(C#N)c1]

$^1$H NMR (500 MHz, DMSO-d$_6$) δ 7.93 (s, 1H), 7.74-7.85 (m, 3H), 7.61 (t, J=7.7 Hz, 1H), 7.41 (d, J=7.3 Hz, 1H), 7.23 (t, J=7.5 Hz, 1H), 7.15 (d, J=7.3 Hz, 1H), 7.08 (s, 1H), 6.92 (d, J=8.4 Hz, 1H), 6.85 (s, 1H), 6.68-6.81 (m, 2H), 5.22 (s, 2H), 5.10 (s, 2H), 4.28 (s, 4H), 3.44-3.79 (br, s, 2H), 3.11 (q, J=6.4 Hz, 2H), 2.52 (t, J=6.2 Hz, 2H), 2.22 (s, 3H), 2.10 (s, 3H), 1.76 (s, 3H).

Example 1265

(S)-4-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxybutanoic acid

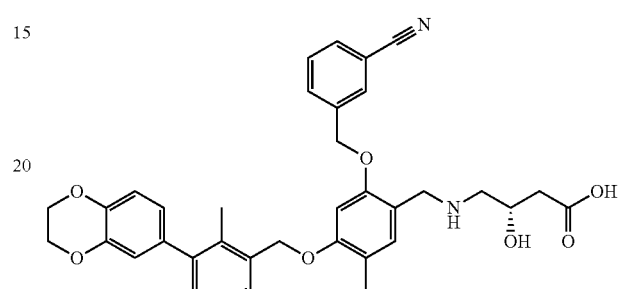

Example 1266

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxypropanoic acid

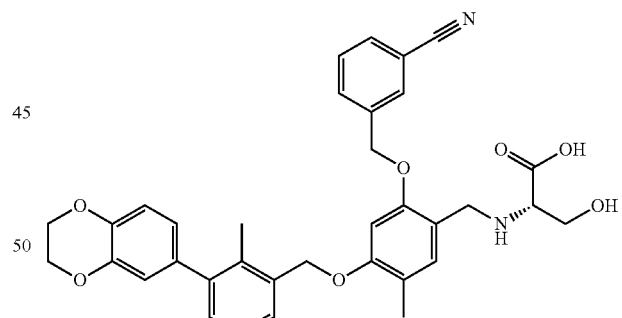

$^1$H NMR (500 MHz, DMSO-d$_6$) δ 8.03 (s, 1H), 7.92 (d, J=8.1 Hz, 1H), 7.81 (d, J=7.3 Hz, 1H), 7.60 (t, J=7.9 Hz, 1H), 7.41 (d, J=7.3 Hz, 1H), 7.20-7.27 (m, 1H), 7.12-7.20 (m, 2H), 6.88-6.95 (m, 2H), 6.78 (s, 1H), 6.75 (d, J=8.1 Hz, 1H), 5.23-5.32 (m, 2H), 5.14 (s, 2H), 4.28 (s, 4H), 3.98-4.12 (m, 2H), 3.76 (dd, J=11.6, 4.6 Hz, 1H), 3.64 (dd, J=11.2, 7.2 Hz, 1H), 3.17 (s, 1H), 2.21 (s, 3H), 2.10 (s, 3H).

Example 1267

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid

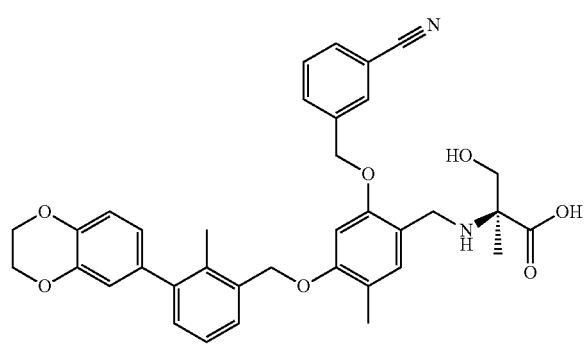 [SMILES: Cc1cc(CN[C@@](C)(CO)C(=O)O)c(OCc2cccc(C#N)c2)cc1OCc1cccc(-c2ccc3c(c2)OCCO3)c1C]

$^1$H NMR (500 MHz, DMSO-d$_6$) δ 8.02 (s, 1H), 7.93 (d, J=8.1 Hz, 1H), 7.80 (d, J=7.7 Hz, 1H), 7.59 (t, J=7.9 Hz, 1H), 7.41 (d, J=7.3 Hz, 1H), 7.19-7.26 (m, 2H), 7.16 (d, J=7.3 Hz, 1H), 6.88-6.96 (m, 2H), 6.78 (s, 1H), 6.75 (d, J=8.4 Hz, 1H), 5.27 (s, 2H), 5.15 (s, 2H), 4.28 (s, 4H), 3.98 (s, 2H), 3.50-3.70 (m, 2H), 2.22 (s, 3H), 2.11 (s, 3H), 1.26 (s, 3H).

Example 1268

(S)-1-(2-((3-cyanobenzyl)oxy)-4-((3-(2,3-dihydrobenzo[b][1,4]dioxin-6-yl)-2-methylbenzyl)oxy)-5-methylbenzyl)piperidine-2-carboxylic acid

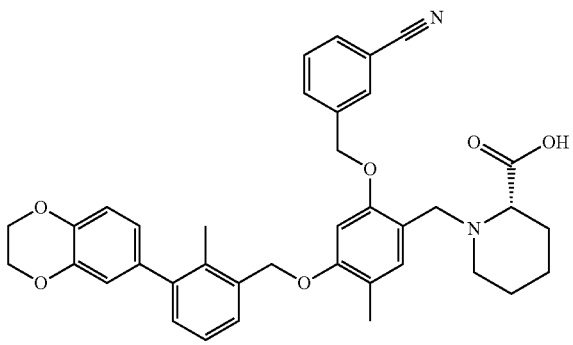 [SMILES: Cc1cc(CN2CCCC[C@H]2C(=O)O)c(OCc2cccc(C#N)c2)cc1OCc1cccc(-c2ccc3c(c2)OCCO3)c1C]

$^1$H NMR (500 MHz, DMSO-d$_6$) δ 7.97 (s, 1H), 7.85 (d, J=7.7 Hz, 1H), 7.80 (d, J=7.7 Hz, 1H), 7.56-7.65 (m, 1H), 7.42 (d, J=7.3 Hz, 1H), 7.24 (t, J=7.7 Hz, 1H), 7.12-7.20 (m, 2H), 6.85-6.94 (m, 2H), 6.79 (s, 1H), 6.76 (d, J=8.4 Hz, 1H), 5.18-5.33 (m, 2H), 5.13 (s, 2H), 4.28 (s, 4H), 3.94 (d, J=13.2 Hz, 1H), 3.78 (d, J=12.8 Hz, 1H), 3.08-3.21 (m, 1H), 2.93-3.00 (m, 1H), 2.38-2.47 (m, 1H), 2.22 (s, 3H), 2.10 (s, 3H), 1.80-1.88 (m, 1H), 1.64-1.76 (m, 1H), 1.45-1.55 (br. m, 3H), 1.31-1.41 (m, 1H).

Example 1269

(R)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid

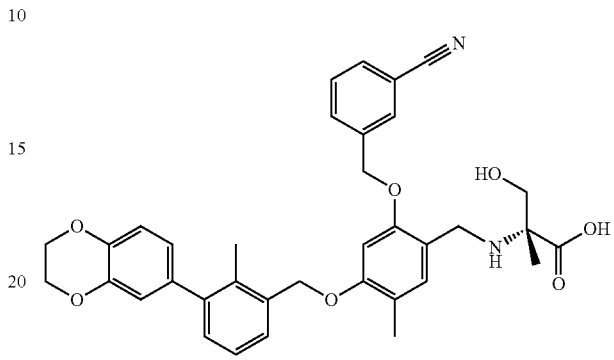

$^1$H NMR (500 MMz, DMSO-d$_6$) δ 8.01 (s, 1H), 7.93 (d, J=7.7 Hz, 1H), 7.80 (d, J=7.3 Hz, 1H), 7.59 (t, J=7.7 Hz, 1H), 7.41 (d, J=7.3 Hz, 1H), 7.19-7.26 (m, 2H), 7.16 (d, J=7.3 Hz, 1H), 6.89-6.94 (m, 2H), 6.78 (s, 1H), 6.75 (d, J=8.1 Hz, 1H), 5.27 (s, 2H), 5.15 (s, 2H), 4.28 (s, 4H), 3.11-3.70 (m, 4H), 2.22 (s, 3H), 2.10 (s, 3H), 1.26 (s, 3H)

| Example | LCMS Method | RT (min) | M + 1 | M − 1 |
|---|---|---|---|---|
| Example 1264: N-(2-((2-((3-cyanobenzyl)oxy)-4-((3-(2,3-dihydrobenzo[b][1,4]dioxin-6-yl)-2-methylbenzyl)oxy)-5-methylbenzyl)amino)ethyl)acetamide | M | 2.96 | 592.6 | 590.6 |
| Example 1265: (S)-4-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxybutanoic acid | M | 2.9 | 609.6 | 607.6 |
| Example 1266: (S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxypropanoic acid | M | 2.89 | 595.3 | 593.3 |
| Example 1267: (S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid | M | 2.91 | 609.4 | 607.4 |
| Example 1268: (S)-1-(2-((3-cyanobenzyl)oxy)-4-((3-(2,3-dihydrobenzo[b][1,4]dioxin-6-yl)-2-methylbenzyl)oxy)-5-methylbenzyl)piperidine-2-carboxylic acid | M | 2.94 | 619.6 | 617.7 |
| Example 1269: (R)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid | M | 2.88 | 609.3 | 607.4 |

Intermediate 5-((5-((3-(2,3-dihydrobenzo[b][1,4]dioxin-6-yl)-2-methylbenzyl)oxy)-2-formyl-4-methylphenoxy)methyl)-2-fluorobenzonitrile

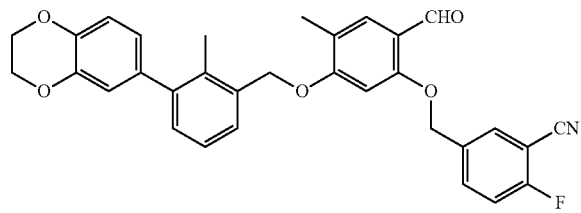 [SMILES: Cc1cc(C=O)c(OCc2ccc(F)c(C#N)c2)cc1OCc1cccc(-c2ccc3c(c2)OCCO3)c1C]

To a solution of 4-((3-(2,3-dihydrobenzo[b][1,4]dioxin-6-yl)-2-methylbenzyl)oxy)-2-hydroxy-5-methylbenzaldehyde (85 mg, 0.218 mmol) in dimethylformamide (2 mL), 5-(bromomethyl)-2-fluorobenzonitrile (51.3 mg, 0.239 mmol) and cesium carbonate (106 mg, 0.327 mmol) were added. The reaction mixture was stirred at room temperature overnight. Water was added and a yellowish solid was collected as crude product. Triturated with ethyl acetate to give a white solid as final product 5-((5-((3-(2,3-dihydrobenzo[b][1,4]dioxin-6-yl)-2-methylbenzyl)oxy)-2-formyl-4-methylphenoxy)methyl)-2-fluorobenzonitrile (86 mg, 0.164 mmol, 75% yield). LCMS Condition T: 4.511 min, 524 (MH$^+$). $^1$H NMR (400 MHz, CDCl$_3$) δ: 10.33 (s, 1H), 7.65-7.74 (m, 3H), 7.35-7.41 (m, 1H), 7.24-7.31 (m, 3H), 6.93 (d, J=8.1 Hz, 1H), 6.83 (d, J=2.0 Hz, 1H), 6.74-6.81 (m, 1H), 6.52 (s, 1H), 5.15 (d, J=1.7 Hz, 4H), 4.32 (s, 4H), 2.28 (s, 3H), 2.23 (s, 3H).

The following examples were prepared in the same manner as 5-((5-((3-(2,3-dihydrobenzo[b][1,4]dioxin-6-yl)-2-methylbenzyl)oxy)-2-formyl-4-methylphenoxy)methyl)-2-fluorobenzonitrile from 4-((3-(2,3-dihydrobenzo[b][1,4]dioxin-6-yl)-2-methylbenzyl)oxy)-2-hydroxy-5-methylbenzaldehyde and the appropriate amine. LCMS for these examples is given in tabular form.

Example 1270

(S)-4-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxybutanoic acid

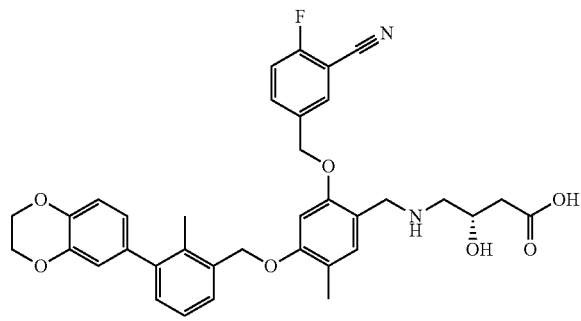 [SMILES: Cc1cc(CNC[C@@H](O)CC(=O)O)c(OCc2ccc(F)c(C#N)c2)cc1OCc1cccc(-c2ccc3c(c2)OCCO3)c1C]

$^1$H NMR (500 MHz, DMSO-d$_6$) δ 8.08 (d, J=5.1 Hz, 1H), 7.92-7.97 (m, 1H), 7.55 (t, J=9.0 Hz, 1H), 7.41 (d, J=7.0 Hz, 1H), 7.23 (t, J=7.3 Hz, 1H), 7.19 (s, 1H), 7.16 (d, J=7.7 Hz, 1H), 6.88-6.94 (m, 2H), 6.78 (s, 1H), 6.75 (d, J=8.4 Hz, 1H), 5.23 (s, 2H), 5.15 (s, 2H), 4.28 (s, 4H), 3.98-4.07 (m, 1H), 3.87-3.94 (m, 2H), 2.67-2.83 (m, 2H), 2.38-2.45 (m, 1H), 2.27-2.36 (m, 1H), 2.22 (s, 3H), 2.10 (s, 3H).

Example 1271

N-(2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)ethyl)acetamide

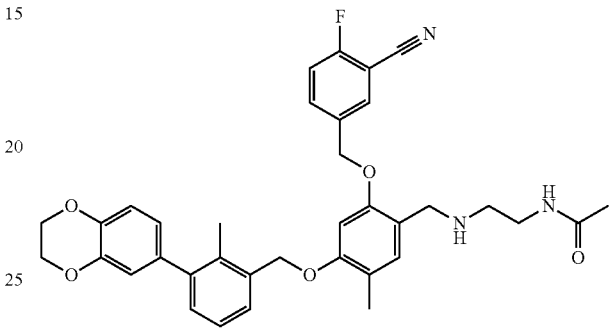

$^1$H NMR (500 MHz, DMSO-d$_6$) δ 8.03 (d, J=6.2 Hz, 1H), 7.80-7.92 (m, 2H), 7.55 (t, J=9.2 Hz, 1H), 7.41 (d, J=7.3 Hz, 1H), 7.23 (t, J=7.5 Hz, 1H), 7.15 (d, J=7.0 Hz, 1H), 7.08 (s, 1H), 6.92 (d, J=8.1 Hz, 1H), 6.85 (s, 1H), 6.77 (d, J=1.8 Hz, 1H), 6.75 (dd, J=8.3, 2.0 Hz, 1H), 5.19 (s, 2H), 5.11 (s, 2H), 4.27 (s, 4H), 3.40 (d, J=6.2 Hz, 2H), 3.12 (q, J=6.4 Hz, 2H), 2.54 (t, J=6.4 Hz, 2H), 2.21 (s, 3H), 2.09 (s, 3H), 1.77 (s, 3H).

Example 1272

(S)-1-(2-((3-cyano-4-fluorobenzyl)oxy)-4-((3-(2,3-dihydrobenzo[b][1,4]dioxin-6-yl)-2-methylbenzyl)oxy)-5-methylbenzyl)piperidine-2-carboxylic acid

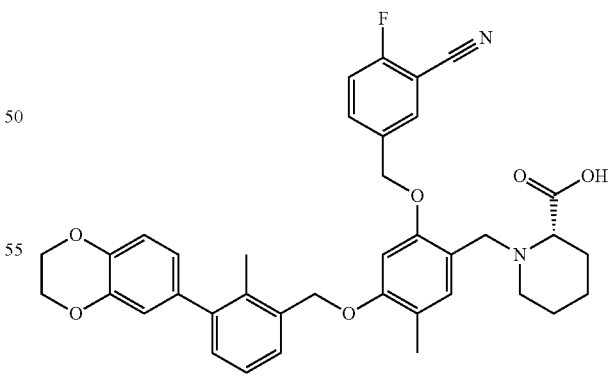

$^1$H NMR (500 MHz, DMSO-d$_6$) δ 8.08 (d, J=5.1 Hz, 1H), 7.85-8.01 (m, 1H), 7.55 (t, J=9.0 Hz, 1H), 7.42 (d, J=7.3 Hz, 1H), 7.24 (t, J=7.5 Hz, 1H), 7.13-7.21 (m, 2H), 6.88-6.95 (m, 2H), 6.78 (s, 1H), 6.76 (d, J=8.4 Hz, 1H), 5.18-5.27 (m, 2H), 5.14 (s, 2H), 4.28 (s, 4H), 3.93-4.03 (m, 1H), 3.75-3.87 (m, 1H), 3.12-3.18 (m, 1H), 2.94-3.01 (m, 1H), 2.41-2.48

(m, 1H), 2.22 (s, 3H), 2.10 (s, 3H), 1.82-1.89 (m, 1H), 1.66-1.76 (m, 1H), 1.47-1.56 (m, 3H), 1.30-1.40 (m, 1H).

Example 1273

(R)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methyl-propanoic acid

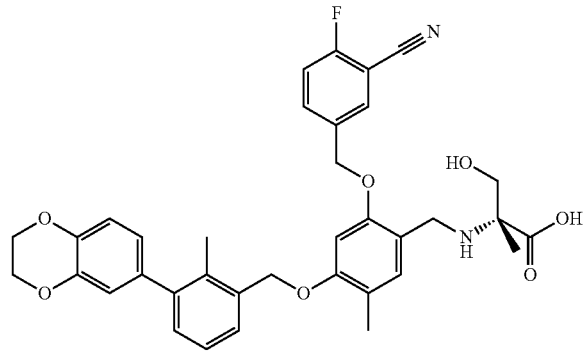 [SMILES: Cc1cc(CN[C@](C)(CO)C(=O)O)c(OCc2ccc(F)c(C#N)c2)cc1OCc1cccc(-c2ccc3c(c2)OCCO3)c1C]

$^1$H NMR (500 MHz, DMSO-d$_6$) δ 8.09 (d, J=5.5 Hz, 1H), 7.96-8.04 (m, 1H), 7.52 (t, J=9.0 Hz, 1H), 7.41 (d, J=7.7 Hz, 1H), 7.23 (t, J=7.7 Hz, 1H), 7.10-7.20 (m, 2H), 6.92 (d, J=8.4 Hz, 1H), 6.88 (s, 1H), 6.78 (s, 1H), 6.75 (dd, J=8.4, 1.5 Hz, 1H), 5.22 (s, 2H), 5.14 (s, 2H), 4.28 (s, 4H), 3.85 (br. s., 2H), 3.32-3.57 (m, 2H), 2.21 (s, 3H), 2.09 (s, 3H), 1.19 (s, 3H).

Example 1274

(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxypropanoic acid

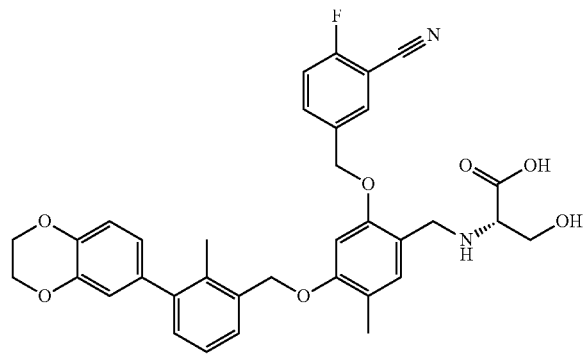 [SMILES: Cc1cc(CN[C@@H](CO)C(=O)O)c(OCc2ccc(F)c(C#N)c2)cc1OCc1cccc(-c2ccc3c(c2)OCCO3)c1C]

$^1$H NMR (500 MHz, DMSO-d$_6$) δ 8.13 (br. s., 1H), 7.92-8.04 (m, 1H), 7.54 (t, J=9.0 Hz, 1H), 7.41 (d, J=7.3 Hz, 1H), 7.23 (t, J=7.5 Hz, 1H), 7.19 (s, 1H), 7.16 (d, J=7.3 Hz, 1H), 6.90-6.94 (m, 1H), 6.78 (s, 1H), 6.75 (dd, J=8.1, 1.5 Hz, 1H), 5.21-5.29 (m, 2H), 5.15 (s, 2H), 4.28 (s, 4H), 3.99-4.13 (m, 2H), 3.75-3.80 (m, 1H), 3.64 (dd, J=11.2, 7.2 Hz, 1H), 3.16-3.21 (m, 1H), 2.22 (s, 3H), 2.10 (s, 3H).

Example 1275

(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methyl-propanoic acid

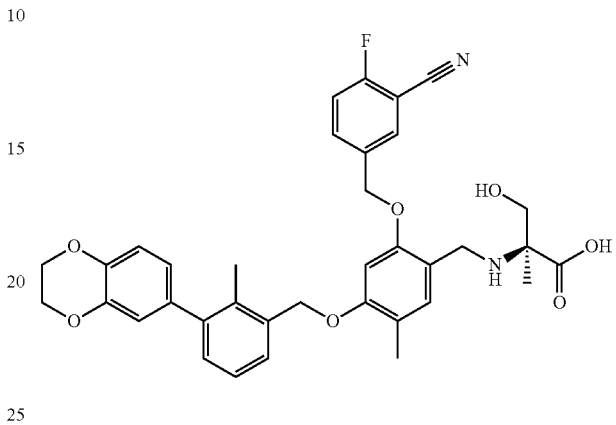

$^1$H NMR (500 MHz, DMSO-d$_6$) δ 8.09 (d, J=5.5 Hz, 1H), 7.99 (d, J=5.5 Hz, 1H), 7.52 (t, J=9.0 Hz, 1H), 7.41 (d, J=7.3 Hz, 1H), 7.18-7.25 (m, 1H), 7.10-7.17 (m, 2H), 6.92 (d, J=8.1 Hz, 1H), 6.88 (s, 1H), 6.78 (s, 1H), 6.75 (d, J=8.4 Hz, 1H), 5.22 (s, 2H), 5.13 (s, 2H), 4.28 (s, 4H), 3.81 (br. s., 2H), 3.11-3.55 (m, 2H), 2.21 (s, 3H), 2.09 (s, 3H), 1.18 (s, 3H).

| Example | LCMS Method | RT (min) | M + 1 | M − 1 |
|---|---|---|---|---|
| Example 1270: (S)-4-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxybutanoic acid | M | 2.93 | 627.4 | 625.3 |
| Example 1271: N-(2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)ethyl)acetamide | M | 2.92 | 610.4 | |
| Example 1272: (S)-1-(2-((3-cyano-4-fluorobenzyl)oxy)-4-((3-(2,3-dihydrobenzo[b][1,4]dioxin-6-yl)-2-methylbenzyl)oxy)-5-methylbenzyl)piperidine-2-carboxylic acid | M | 2.95 | 637.6 | 635.6 |
| Example 1273: (R)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid | A | 1.8 | | 625.2 |
| Example 1274: (S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxypropanoic acid | M | 2.92 | | 611.6 |
| Example 1275: (S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid | A | 1.82 | | 625.2 |

Intermediate 4-((3-(2,3-dihydrobenzo[b][1,4]dioxin-6-yl)-2-methylbenzyl)oxy)-5-methyl-2-(pyridin-3-ylmethoxy)benzaldehyde

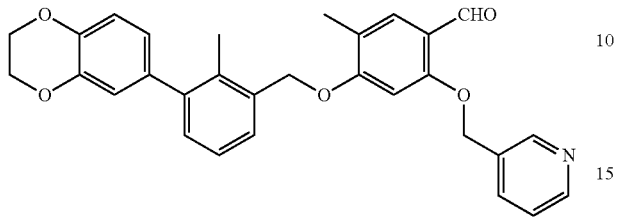

To a solution of 4-((3-(2,3-dihydrobenzo[b][1,4]dioxin-6-yl)-2-methylbenzyl)oxy)-2-hydroxy-5-methylbenzaldehyde (85 mg, 0.218 mmol) in dimethylformamide (2 mL), 3-(bromomethyl)pyridine, hydrobromide (60.6 mg, 0.239 mmol) and cesium carbonate (177 mg, 0.544 mmol) were added. The reaction mixture was stirred at room temperature overnight. Water was added and a brownish solid was collected as final product 4-((3-(2,3-dihydrobenzo[b][1,4]dioxin-6-yl)-2-methylbenzyl)oxy)-5-methyl-2-(pyridin-3-ylmethoxy)benzaldehyde (90 mg, 0.187 mmol, 86% yield). LCMS Condition T: 3.916 min, 482 (MH$^+$). $^1$H NMR (400 MHz, CDCl$_3$) δ: 10.35 (s, 1H), 8.70 (d, J=1.7 Hz, 1H), 8.63 (dd, J=4.8, 1.6 Hz, 1H), 7.80 (d, J=7.8 Hz, 1H), 7.69 (s, 1H), 7.32-7.44 (m, 3H), 7.23-7.30 (m, 1H), 6.93 (d, J=8.1 Hz, 1H), 6.84 (d, J=2.2 Hz, 1H), 6.79 (dd, J=8.3, 2.2 Hz, 1H), 6.58 (s, 1H), 5.20 (s, 2H), 5.14 (s, 2H), 4.32 (s, 4H), 2.28 (s, 3H), 2.22 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 4-((3-(2,3-dihydrobenzo[b][1,4]dioxin-6-yl)-2-methylbenzyl)oxy)-5-methyl-2-(pyridin-3-ylmethoxy)benzaldehyde and the appropriate amine. LCMS for these examples is given in tabular form.

Example 1276

N-(2-((4-((3-(2,3-dihydrobenzo[b][1,4]dioxin-6-yl)-2-methylbenzyl)oxy)-5-methyl-2-(pyridin-3-ylmethoxy)benzyl)amino)ethyl)acetamide

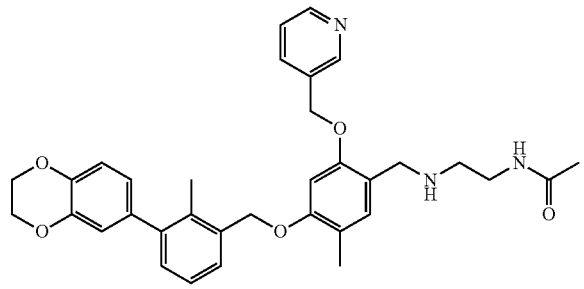 [SMILES: CC(=O)NCCNCc1cc(C)c(OCc2cccc(-c3ccc4c(c3)OCCO4)c2C)cc1OCc1cccnc1]

$^1$H NMR (500 MHz, DMSO-d$_6$) δ 8.67 (s, 1H), 8.53 (d, J=4.0 Hz, 1H), 7.87 (d, J=7.7 Hz, 1H), 7.80-7.84 (m, 1H), 7.37-7.48 (m, 2H), 7.23 (t, J=7.5 Hz, 1H), 7.15 (d, J=7.7 Hz, 1H), 7.06 (s, 1H), 6.92 (d, J=8.4 Hz, 1H), 6.89 (s, 1H), 6.73-6.79 (m, 2H), 5.20 (s, 2H), 5.11 (s, 2H), 4.27 (s, 4H), 3.59 (s, 2H), 3.09 (q, J=6.2 Hz, 2H), 2.50 (m, 2H), 2.22 (s, 3H), 2.09 (s, 3H), 1.76 (s, 3H).

Example 1277

(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxypropanoic acid

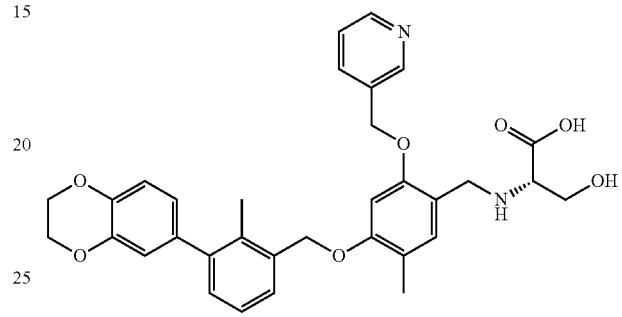

$^1$H NMR (500 MHz, DMSO-d$_6$) δ 8.75 (s, 1H), 8.55 (d, J=4.0 Hz, 1H), 8.01 (d, J=7.7 Hz, 1H), 7.34-7.55 (m, 2H), 7.24 (t, J=7.5 Hz, 1H), 7.19 (s, 1H), 7.16 (d, J=7.7 Hz, 1H), 6.99 (s, 1H), 6.92 (d, J=8.1 Hz, 1H), 6.79 (s, 1H), 6.76 (dd, J=8.3, 1.7 Hz, 1H), 5.21-5.32 (m, 2H), 5.16 (s, 2H), 4.28 (s, 4H), 3.95-4.11 (m, 2H), 3.73-3.80 (m, 1H), 3.65 (dd, J=11.4, 7.0 Hz, 1H), 3.15-3.20 (m, 1H), 2.22 (s, 3H), 2.10 (s, 3H).

Example 1278

(S)-4-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxybutanoic acid

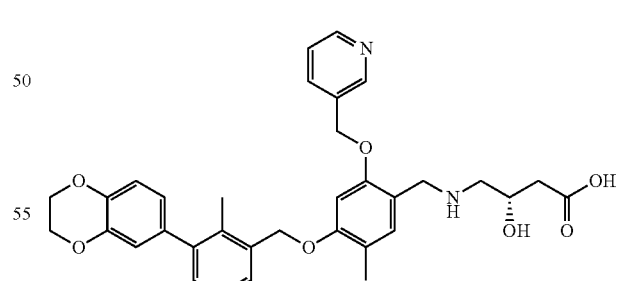

$^1$H NMR (500 MHz, DMSO-d$_6$) δ 8.69 (br. s., 1H), 8.53 (d, J=3.3 Hz, 1H), 7.91 (d, J=7.7 Hz, 1H), 7.35-7.50 (m, 2H), 7.24 (t, J=7.5 Hz, 1H), 7.16 (d, J=7.3 Hz, 1H), 7.08 (s, 1H), 6.88-6.94 (m, 2H), 6.79 (s, 1H), 6.76 (d, J=8.4 Hz, 1H), 5.21 (s, 2H), 5.13 (s, 2H), 4.28 (s, 4H), 3.76-3.84 (m, 1H), 3.61-3.73 (m, 2H), 2.51-2.57 (m, 2H), 2.22 (s, br, 4H), 2.09 (s, br, 4H).

Example 1279

(S)-1-(4-((3-(2,3-dihydrobenzo[b][1,4]dioxin-6-yl)-2-methylbenzyl)oxy)-5-methyl-2-(pyridin-3-ylmethoxy)benzyl)piperidine-2-carboxylic acid

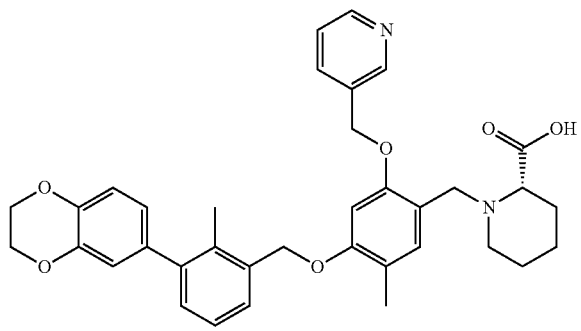 [SMILES: Cc1cc(CN2CCCC[C@H]2C(=O)O)c(OCc2cccnc2)cc1OCc1cccc(-c2ccc3c(c2)OCCO3)c1C]

¹H NMR (500 MHz, DMSO-d₆) δ 8.71 (br. s., 1H), 8.54 (d, J=4.0 Hz, 1H), 7.91 (d, J=7.7 Hz, 1H), 7.40-7.47 (m, 2H), 7.25 (t, J=7.3 Hz, 1H), 7.12-7.22 (m, 2H), 6.96 (s, 1H), 6.92 (d, J=8.1 Hz, 1H), 6.79 (s, 1H), 6.76 (d, J=8.1 Hz, 1H), 5.19-5.27 (m, 2H), 5.15 (s, 2H), 4.28 (s, 4H), 3.86-3.96 (m, 1H), 3.75 (d, J=12.5 Hz, 1H), 2.86-2.99 (m, 2H), 2.35-2.44 (m, 1H), 2.23 (s, 3H), 2.10 (s, 3H), 1.79-1.87 (m, 1H), 1.65-1.75 (m, 1H), 1.50 (br. s., 3H), 1.30-1.40 (m, 1H).

Example 1280

(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid

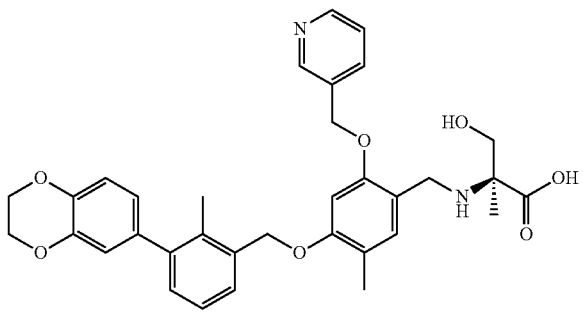 [SMILES: Cc1cc(CN[C@@](C)(CO)C(=O)O)c(OCc2cccnc2)cc1OCc1cccc(-c2ccc3c(c2)OCCO3)c1C]

¹H NMR (500 MHz, DMSO-d₆) δ 8.73 (s, 1H), 8.53 (d, J=4.4 Hz, 1H), 8.01 (d, J=7.7 Hz, 1H), 7.35-7.46 (m, 2H), 7.24 (t, J=7.5 Hz, 1H), 7.21 (s, 1H), 7.16 (d, J=7.7 Hz, 1H), 6.97 (s, 1H), 6.92 (d, J=8.1 Hz, 1H), 6.79 (s, 1H), 6.76 (d, J=8.1 Hz, 1H), 5.26 (s, 2H), 5.17 (s, 2H), 4.28 (s, 4H), 3.95 (br. s., 2H), 3.41-3.74 (m, 2H), 2.22 (s, 3H), 2.10 (s, 3H), 1.23 (s, 3H).

Example 1281

(R)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid

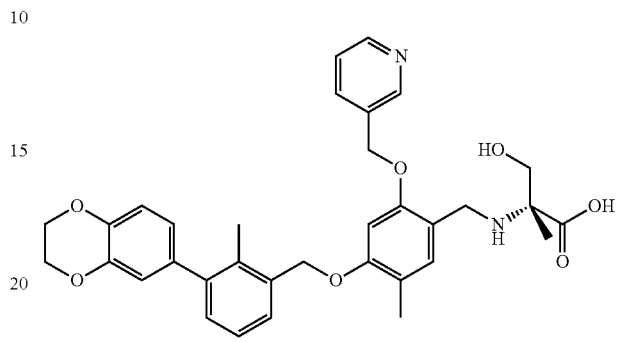

¹H NMR (500 MHz, DMSO-d₆) δ 8.73 (s, 1H), 8.53 (d, J=4.8 Hz, 1H), 8.01 (d, J=7.7 Hz, 1H), 7.36-7.46 (m, 2H), 7.24 (t, J=7.5 Hz, 1H), 7.21 (s, 1H), 7.16 (d, J=7.7 Hz, 1H), 6.97 (s, 1H), 6.92 (d, J=8.4 Hz, 1H), 6.79 (s, 1H), 6.76 (d, J=8.4 Hz, 1H), 5.26 (s, 2H), 5.17 (s, 2H), 4.28 (s, 4H), 3.95 (br. s., 2H), 3.47-3.70 (m, 2H), 2.22 (s, 3H), 2.11 (s, 3H), 1.23 (s, 3H).

| Example | LCMS Method | RT (min) | M + 1 | M − 1 |
|---|---|---|---|---|
| Example 1276: N-(2-((4-((3-(2,3-dihydrobenzo[b][1,4]dioxin-6-yl)-2-methylbenzyl)oxy)-5-methyl-2-(pyridin-3-ylmethoxy)benzyl)amino)ethyl)acetamide | M | 2.79 | 568.4 | |
| Example 1277: (S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxypropanoic acid | A | 1.73 | | 569.5 |
| Example 1278: (S)-4-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxybutanoic acid | M | 2.72 | 585.3 | 583.3 |
| Example 1279: (S)-1-(4-((3-(2,3-dihydrobenzo[b][1,4]dioxin-6-yl)-2-methylbenzyl)oxy)-5-methyl-2-(pyridin-3-ylmethoxy)benzyl)piperidine-2-carboxylic acid | A | 1.86 | 595.3 | 593.4 |
| Example 1280: (S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid | A | 1.76 | 585.3 | 583.4 |
| Example 1281: (R)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid | A | 1.77 | 585.4 | 583.3 |

Intermediate 5-((5-(3-(2,3-dihydrobenzo[b][1,4]dioxin-6-yl)-2-methylbenzyloxy)-2-formyl-4-methylphenoxy)methyl)nicotinonitrile

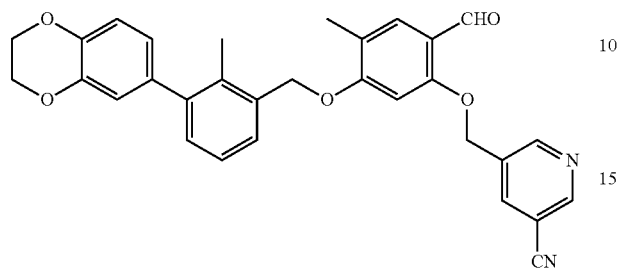

To a solution of 4-((3-(2,3-dihydrobenzo[b][1,4]dioxin-6-yl)-2-methylbenzyl)oxy)-2-hydroxy-5-methylbenzaldehyde (102 mg, 0.261 mmol) in DMF (3 mL), 5-(chloromethyl)nicotinonitrile (43.8 mg, 0.287 mmol) and cesium carbonate (170 mg, 0.523 mmol) were added. The reaction mixture was stirred at 75° C. for 3 hr. LC/MS shown completion of reaction. It was then added water and a beige solid was collected as final product 5-((5-((3-(2,3-dihydrobenzo[b][1,4]dioxin-6-yl)-2-methylbenzyl)oxy)-2-formyl-4-methylphenoxy)methyl)nicotinonitrile (129 mg, 0.255 mmol, 97% yield). LCMS Condition T: 4.38 min, 507 (MH$^+$). $^1$H NMR (400 MHz, CDCl$_3$) δ 10.33 (s, 1H), 8.89-8.94 (m, 2H), 8.12 (s, 1H), 7.72 (s, 1H), 7.35-7.44 (m, 1H), 7.24-7.32 (m, 2H), 6.94 (d, J=8.1 Hz, 1H), 6.85 (d, J=2.0 Hz, 1H), 6.80 (dd, J=8.3, 2.0 Hz, 1H), 6.56 (s, 1H), 5.25 (s, 2H), 5.18 (s, 2H), 4.34 (s, 4H), 2.30 (s, 3H), 2.25 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-((5-(3-(2,3-dihydrobenzo[b][1,4]dioxin-6-yl)-2-methylbenzyloxy)-2-formyl-4-methylphenoxy)methyl)nicotinonitrile and the appropriate amine. LCMS for these examples is given in tabular form.

Example 1282

N-(2-(2-((5-cyanopyridin-3-yl)methoxy)-4-(3-(2,3-dihydrobenzo[b][1,4]dioxin-6-yl)-2-methylbenzyloxy)-5-methylbenzylamino)ethyl)acetamide

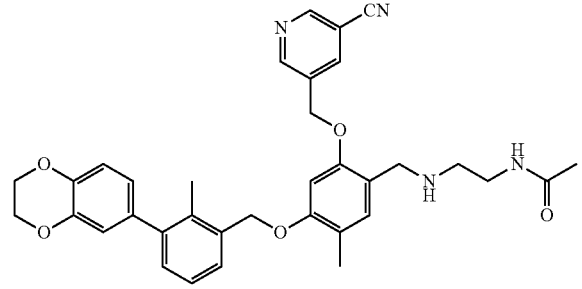 [SMILES: CC(=O)NCCNCc1cc(C)c(OCc2cccc(-c3ccc4c(c3)OCCO4)c2C)cc1OCc1cncc(C#N)c1]

$^1$H NMR (DMSO-d$_6$) δ 9.01 (d, J=1.5 Hz, 1H), 8.98 (s, 1H), 8.42 (s, 1H), 7.76-7.82 (m, 1H), 7.43 (d, J=7.3 Hz, 1H), 7.24 (t, J=7.5 Hz, 1H), 7.17 (d, J=7.3 Hz, 1H), 7.09 (s, 1H), 6.93 (d, J=8.1 Hz, 1H), 6.89 (s, 1H), 6.80 (d, J=1.8 Hz, 1H), 6.75-6.78 (m, 1H), 5.28 (s, 2H), 5.13 (s, 2H), 4.29 (s, 4H), 3.50-3.75 (m, 2H), 3.09-3.15 (m, 2H), 2.53 (t, J=6.6 Hz, 2H), 2.23 (s, 3H), 2.11 (s, 3H), 1.77 (s, 3H).

Example 1283

(S)-4-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxybutanoic acid

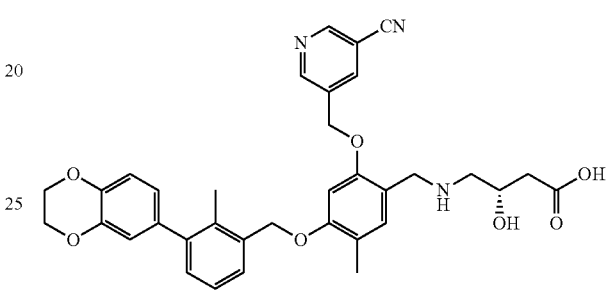

$^1$H NMR (DMSO-d$_6$) δ 9.00 (s, 2H), 8.45 (s, 1H), 7.43 (d, J=7.3 Hz, 1H), 7.24 (t, J=7.5 Hz, 1H), 7.17 (d, J=7.7 Hz, 1H), 7.13 (s, 1H), 6.91-6.95 (m, 2H), 6.80 (s, 1H), 6.77 (d, J=8.4 Hz, 1H), 5.30 (s, 2H), 5.15 (s, 2H), 4.29 (s, 4H), 3.70-3.93 (m, 3H), 2.63 (d, J=5.9 Hz, 2H), 2.34-2.41 (m, 1H), 2.20-2.30 (m, 4H), 2.12 (s, 3H).

Example 1284

(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxypropanoic acid

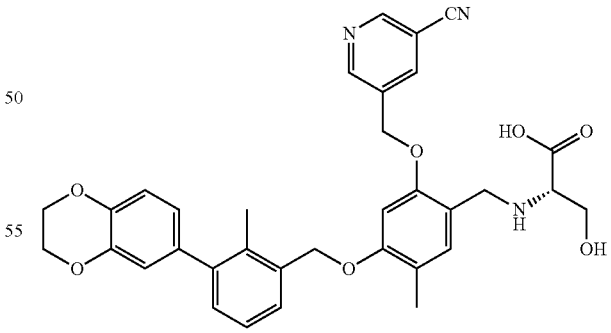

$^1$H NMR (DMSO-d$_6$) δ 9.05 (s, 1H), 9.01 (s, 1H), 8.55 (s, 1H), 7.44 (d, J=7.3 Hz, 1H), 7.25 (t, J=7.5 Hz, 1H), 7.20 (s, 1H), 7.17 (d, J=7.3 Hz, 1H), 6.97 (s, 1H), 6.93 (d, J=8.4 Hz, 1H), 6.80 (s, 1H), 6.74-6.79 (m, 1H), 5.28-5.40 (m, 2H), 5.17 (s, 2H), 4.29 (s, 4H), 4.06-4.13 (m, 1H), 3.98-4.05 (m, 1H), 3.75 (dd, J=11.4, 4.4 Hz, 1H), 3.64 (dd, J=11.0, 7.0 Hz, 1H), 3.13-3.20 (m, 2H), 2.23 (s, 3H), 2.12 (s, 3H).

Example 1285

(S)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid

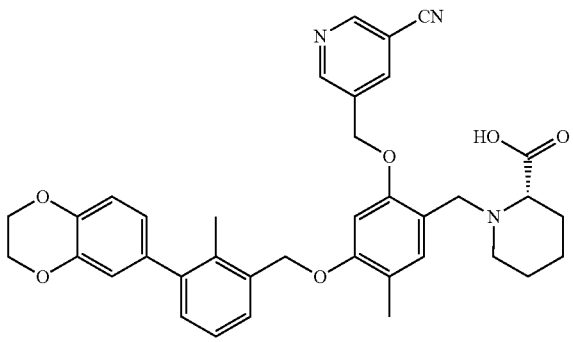 [SMILES: Cc1cc(CN2CCCC[C@H]2C(=O)O)c(OCc2cncc(C#N)c2)cc1OCc1cccc(-c2ccc3c(c2)OCCO3)c1C]

$^1$H NMR (DMSO-d$_6$) δ 8.99-9.03 (m, 2H), 8.50 (s, 1H), 7.45 (d, J=7.7 Hz, 1H), 7.25 (t, J=7.5 Hz, 1H), 7.16-7.20 (m, 2H), 6.91-6.96 (m, 2H), 6.80 (s, 1H), 6.77 (d, J=8.1 Hz, 1H), 5.27-5.36 (m, 2H), 5.16 (s, 2H), 4.29 (s, 4H), 3.96 (d, J=13.2 Hz, 1H), 3.77 (d, J=12.8 Hz, 1H), 3.12-3.17 (m, 1H), 2.92-3.00 (m, 1H), 2.38-2.46 (m, 1H), 2.24 (s, 3H), 2.11 (s, 3H), 1.81-1.89 (m, 1H), 1.68-1.77 (m, 1H), 1.47-1.56 (br. s., 3H), 1.32-1.41 (m, 1H).

Example 1286

(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid

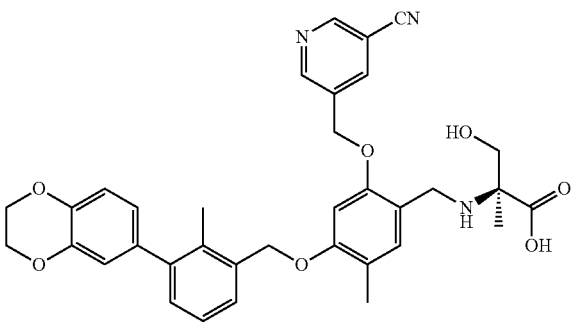 [SMILES: Cc1cc(CN[C@@](C)(CO)C(=O)O)c(OCc2cncc(C#N)c2)cc1OCc1cccc(-c2ccc3c(c2)OCCO3)c1C]

$^1$H NMR (DMSO-d$_6$) δ 9.04 (s, 1H), 9.00 (s, 1H), 8.53 (s, 1H), 7.43 (d, J=7.7 Hz, 1H), 7.21-7.28 (m, 2H), 7.13-7.20 (m, 1H), 6.95 (s, 1H), 6.93 (d, J=8.1 Hz, 1H), 6.80 (s, 1H), 6.74-6.78 (m, 1H), 5.33 (s, 2H), 5.18 (s, 2H), 4.29 (s, 4H), 3.22-3.65 (m, 4H), 2.23 (s, 3H), 2.12 (s, 3H), 1.25 (s, 3H).

Example 1287

(R)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid

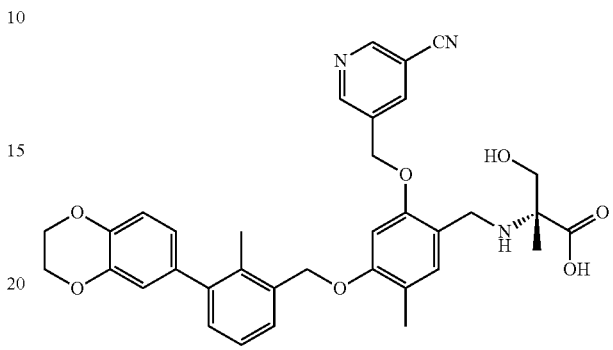

$^1$H NMR (DMSO-d$_6$) δ 9.04 (s, 1H), 9.00 (d, J=1.5 Hz, 1H), 8.53 (s, 1H), 7.43 (d, J=7.0 Hz, 1H), 7.21-7.28 (m, 2H), 7.17 (d, J=7.3 Hz, 1H), 6.95 (s, 1H), 6.93 (d, J=8.4 Hz, 1H), 6.80 (d, J=1.8 Hz, 1H), 6.74-6.78 (m, 1H), 5.33 (s, 2H), 5.18 (s, 2H), 4.29 (s, 4H), 3.24-3.67 (m, 4H), 2.23 (s, 3H), 2.12 (s, 3H), 1.25 (s, 3H).

Example 1288

(R)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid

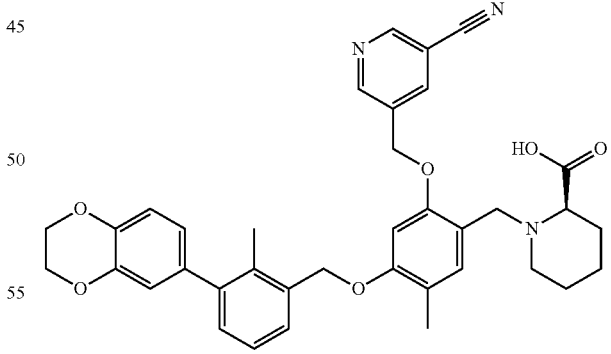

$^1$H NMR (DMSO-d$_6$) δ 8.99-9.03 (m, 2H), 8.49 (s, 1H), 7.45 (d, J=7.3 Hz, 1H), 7.22-7.29 (m, 1H), 7.14-7.21 (m, 2H), 6.89-6.97 (m, 2H), 6.81 (d, J=1.8 Hz, 1H), 6.75-6.79 (m, 1H), 5.27-5.35 (m, 2H), 5.16 (s, 2H), 4.29 (s, 4H), 3.95 (d, J=13.2 Hz, 1H), 3.76 (d, J=12.8 Hz, 1H), 3.14 (dd, J=8.3, 3.9 Hz, 1H), 2.92-3.00 (m, 1H), 2.36-2.44 (m, 1H), 2.24 (s, 3H), 2.11 (s, 3H), 1.81-1.88 (m, 1H), 1.65-1.78 (m, 1H), 1.52 (br. s., 3H), 1.32-1.41 (m, 1H).

| Example | LCMS Method | RT (min) | M + 1 | M − 1 |
|---|---|---|---|---|
| Example 1282: N-(2-(2-((5-cyanopyridin-3-yl)methoxy)-4-(3-(2,3-dihydrobenzo[b][1,4]dioxin-6-yl)-2-methylbenzyloxy)-5-methylbenzylamino)ethyl)acetamide | A | 1.84 | 593.3 | |
| Example 1283: (S)-4-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxybutanoic acid | A | 1.75 | 610.15 | |
| Example 1284: (S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxypropanoic acid | A | 1.76 | | 594.1 |
| Example 1285: (S)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid | A | 1.82 | 620.3 | |
| Example 1286: (S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid | A | 1.7 | 610.3 | |
| Example 1287: (R)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid | M | 2.79 | 610.3 | |
| Example 1288: (R)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid | A | 1.8 | 620.3 | |

Intermediate 4-((3-(2,3-dihydrobenzo[b][1,4]dioxin-6-yl)-2-methylbenzyl)oxy)-5-ethyl-2-hydroxybenzaldehyde

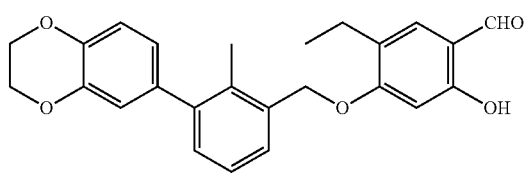 [SMILES: CCc1cc(C=O)c(O)cc1OCc1cccc(-c2ccc3c(c2)OCCO3)c1C]

To a solution of 3-((5-((3-(2,3-dihydrobenzo[b][1,4]dioxin-6-yl)-2-methylbenzyl)oxy)-2-formyl-4-vinylphenoxy)methyl)benzonitrile (60 mg, 0.116 mmol) in tetrahydrofuran (5 mL), 10% Pd/C (5 mg) was added. The reaction mixture was stirred under a H2 balloon for 4 hrs. It was then filtered through celite and washed with methanol. The filtrate was then concentrated to give an off-white solid as crude product. The crude product was then purified by biotage column using hexanes to 25% ethyl acetate in hexanes as eluent. The product came out at ~20% ethyl acetate in hexanes. Fractions were collected and concentrated to give a white solid as final product 4-((3-(2,3-dihydrobenzo[b][1,4]dioxin-6-yl)-2-methylbenzyl)oxy)-5-ethyl-2-hydroxybenzaldehyde (27 mg, 0.067 mmol, 57.6% yield). LC/MS method T: 4.610 min, 405 (MH+). $^1$H NMR (400 MHz, CDCl$_3$) δ 11.48 (s, 1H), 9.75 (s, 1H), 7.43 (dd, J=6.5, 2.6 Hz, 1H), 7.31 (s, 1H), 7.26-7.29 (m, 2H), 6.94 (d, J=8.3 Hz, 1H), 6.86 (d, J=2.0 Hz, 1H), 6.79-6.83 (m, 1H), 6.57 (s, 1H), 5.16 (s, 2H), 4.33 (s, 4H), 2.66 (q, J=7.3 Hz, 2H), 2.28 (s, 3H), 1.23 (t, J=7.3 Hz, 3H).

Intermediate 3-((5-((3-(2,3-dihydrobenzo[b][1,4]dioxin-6-yl)-2-methylbenzyl)oxy)-4-ethyl-2-formylphenoxy)methyl)benzonitrile

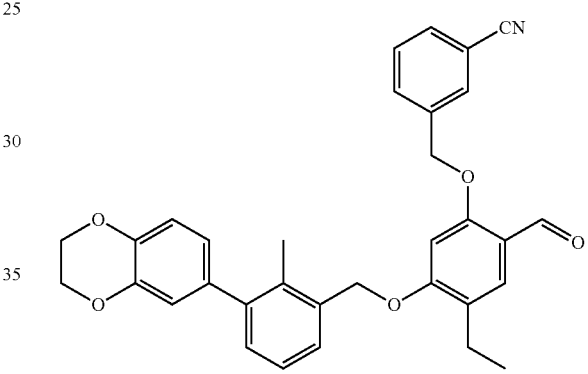

To a solution of 4-((3-(2,3-dihydrobenzo[b][1,4]dioxin-6-yl)-2-methylbenzyl)oxy)-5-ethyl-2-hydroxybenzaldehyde (26 mg, 0.064 mmol) in DMF (1 mL), 3-(bromomethyl)benzonitrile (13.86 mg, 0.071 mmol) and cesium carbonate (41.9 mg, 0.129 mmol) were added. The reaction mixture was stirred at RT for 3 hr. LC/MS shown completion of reaction. It was then added water and a beige solid was collected as final product 3-((5-((3-(2,3-dihydrobenzo[b][1,4]dioxin-6-yl)-2-methylbenzyl)oxy)-4-ethyl-2-formylphenoxy)methyl)benzonitrile (29 mg, 0.056 mmol, 87% yield). LC/MS method T: 4.59 min, 520 (MH+). $^1$H NMR (400 MHz, CDCl$_3$) δ 10.39 (s, 1H), 7.64-7.78 (m, 4H), 7.52-7.59 (m, 1H), 7.35-7.41 (m, 1H), 7.25-7.30 (m, 2H), 6.95 (d, J=8.3 Hz, 1H), 6.85 (d, J=2.0 Hz, 1H), 6.80 (dd, J=8.3, 2.2 Hz, 1H), 6.55 (s, 1H), 5.21 (s, 2H), 5.14 (s, 2H), 4.34 (s, 4H), 2.66 (q, J=7.4 Hz, 2H), 2.28 (s, 3H), 1.22 (t, J=7.6 Hz, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 3-((5-((3-(2,3-dihydrobenzo[b][1,4]dioxin-6-yl)-2-methylbenzyl)oxy)-4-ethyl-2-formylphenoxy)methyl)benzonitrile and the appropriate amine.

Example 1289

N-(2-(2-(3-cyanobenzyloxy)-4-(3-(2,3-dihydrobenzo[b][1,4]dioxin-6-yl)-2-methylbenzyloxy)-5-ethylbenzylamino)ethyl)acetamide

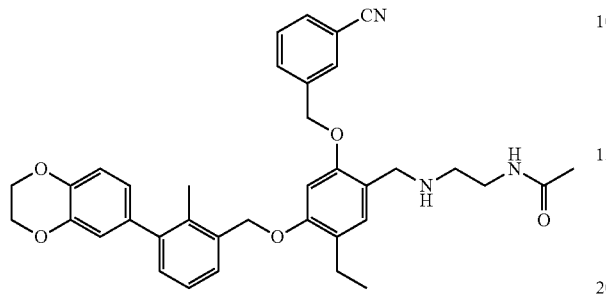

LCMS Condition M: 3.0 min, 606.4 (M+H). $^1$H NMR (DMSO-d$_6$) δ 7.95 (s, 1H), 7.78-7.86 (m, 3H), 7.59-7.67 (m, 1H), 7.42 (d, J=7.3 Hz, 1H), 7.25 (t, J=7.5 Hz, 1H), 7.17 (d, J=7.7 Hz, 1H), 7.10 (s, 1H), 6.93 (d, J=8.1 Hz, 1H), 6.87 (s, 1H), 6.79 (s, 1H), 6.76 (d, J=8.1 Hz, 1H), 5.24 (s, 2H), 5.11 (s, 2H), 4.29 (s, 4H), 3.48-3.77 (m, 2H), 3.09-3.16 (m, 2H), 2.50-2.57 (m, 4H), 2.23 (s, 3H), 1.77 (s, 3H), 1.10 (t, J=7.5 Hz, 3H).

Example 1290

(S)-2-(2-(3-cyanobenzyloxy)-4-(3-(2,3-dihydrobenzo[b][1,4]dioxin-6-yl)-2-methylbenzyloxy)-5-ethylbenzylamino)-3-hydroxy-2-methylpropanoic acid

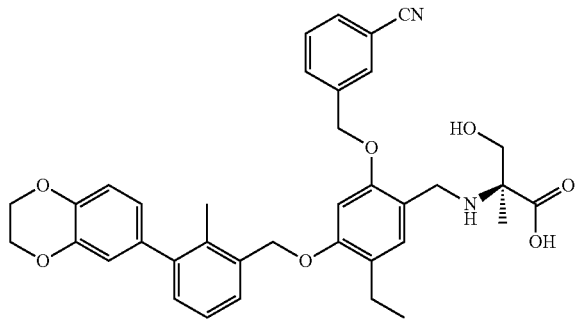 [SMILES: CCc1cc(CN[C@@](C)(CO)C(=O)O)c(OCc2cccc(C#N)c2)cc1OCc1cccc(-c2ccc3c(c2)OCCO3)c1C]

LCMS Condition A: 1.95 min, 623.3 (M+H). $^1$H NMR (DMSO-d$_6$) δ 8.03 (s, 1H), 7.94 (d, J=8.1 Hz, 1H), 7.81 (d, J=7.3 Hz, 1H), 7.60 (t, J=7.7 Hz, 1H), 7.41 (d, J=7.3 Hz, 1H), 7.20-7.29 (m, 2H), 7.17 (d, J=7.0 Hz, 1H), 6.90-6.98 (m, 2H), 6.78 (s, 1H), 6.76 (d, J=8.1 Hz, 1H), 5.28 (s, 2H), 5.16 (s, 2H), 4.29 (s, 4H), 4.02 (s, 2H), 3.66 (d, J=11.4 Hz, 1H), 3.57 (d, J=11.4 Hz, 1H), 2.50-2.57 (m, 2H), 2.22 (s, 3H), 1.27 (s, 3H), 1.11 (t, J=7.5 Hz, 3H).

Example 1291

(R)-2-(2-(3-cyanobenzyloxy)-4-(3-(2,3-dihydrobenzo[b][1,4]dioxin-6-yl)-2-methylbenzyloxy)-5-ethylbenzylamino)-3-hydroxy-2-methylpropanoic acid

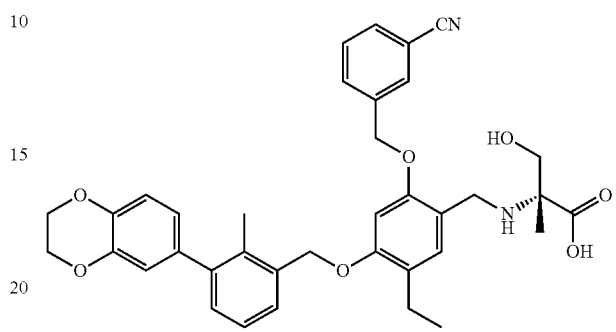

LCMS Condition A: 1.94 min, 623.3 (M+H). $^1$H NMR (DMSO-d$_6$) δ 8.03 (s, 1H), 7.94 (d, J=8.1 Hz, 1H), 7.81 (d, J=7.7 Hz, 1H), 7.60 (t, J=7.7 Hz, 1H), 7.41 (d, J=7.3 Hz, 1H), 7.20-7.28 (m, 2H), 7.17 (d, J=7.7 Hz, 1H), 6.90-6.98 (m, 2H), 6.79 (s, 1H), 6.76 (d, J=8.4 Hz, 1H), 5.28 (s, 2H), 5.16 (s, 2H), 4.29 (s, 4H), 4.01 (s, 2H), 3.66 (d, J=11.0 Hz, 1H), 3.56 (d, J=11.4 Hz, 1H), 2.50-2.57 (m, 2H), 2.23 (s, 3H), 1.27 (s, 3H), 1.11 (t, J=7.5 Hz, 3H).

Intermediate: 3-((5-(3-(2,3-dihydrobenzo[b][1,4]dioxin-6-yl)-2-methylbenzyloxy)-2-formyl-4-vinylphenoxy)methyl)benzonitrile

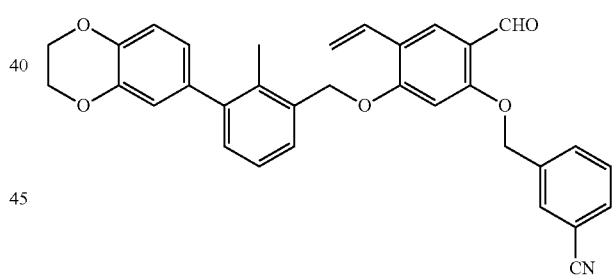

In a microwave vial, 3-((4-bromo-5-((3-(2,3-dihydrobenzo[b][1,4]dioxin-6-yl)-2-methylbenzyl)oxy)-2-formylphenoxy)methyl)benzonitrile (200 mg, 0.351 mmol), Bis(triphenylphosphine)palladium(II) chloride (24.61 mg, 0.035 mmol) and lithium chloride (74.3 mg, 1.753 mmol) were added. Then it was sealed, vacuumed and purged with nitrogen. DMF (12 mL) and tributyl(vinyl)stannane (0.123 mL, 0.421 mmol) were added. The reaction mixture was heated at 80° C. for overnight. LC/MS shown completion of reaction. It was added a solution of KF and was stirred at rt for 2 days. A greyish solid was filtered off and the reaction mixture was extracted with ethyl acetate (25 mL). The organic layer was separated, dried (MgSO4) and concentrated to give a greyish solid as crude product. The crude product was then purified by biotage column using hexanes to 20% ethyl acetate in hexanes as eluent. The product came out at ~15% ethyl acetate in hexanes. Fractions were collected and concentrated to give a yellowish solid as final product 3-((5-((3-(2,3-dihydrobenzo[b][1,4]dioxin-6-yl)-2-methylbenzyl)oxy)-2-formyl-4-vinylphenoxy)methyl)benzonitrile (115 mg, 0.222 mmol, 63.4% yield). LC/MS: method T: 4.55 min, 518 (MH+). ¹H NMR (400 MHz, CDCl₃) δ: 10.40 (s, 1H), 8.07 (s, 1H), 7.76 (s, 1H), 7.66-7.74 (m, 2H), 7.52-7.60 (m, 1H), 7.34-7.39 (m, 1H), 7.25-7.31 (m, 2H), 6.91-7.03 (m, 2H), 6.84 (d, J=2.0 Hz, 1H), 6.79 (dd, J=8.2, 2.1 Hz, 1H), 6.56 (s, 1H), 5.79 (dd, J=17.6, 1.2 Hz, 1H), 5.24-5.30 (m, 1H), 5.23 (s, 2H), 5.17 (s, 2H), 4.34 (s, 4H), 2.28 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 3-((5-(3-(2,3-dihydrobenzo[b][1,4]dioxin-6-yl)-2-methylbenzyloxy)-2-formyl-4-vinylphenoxy)methyl)benzonitrile and the appropriate amine.

Example 1292

N-(2-(2-(3-cyanobenzyloxy)-4-(3-(2,3-dihydrobenzo[b][1,4]dioxin-6-yl)-2-methylbenzyloxy)-5-vinylbenzylamino)ethyl)acetamide

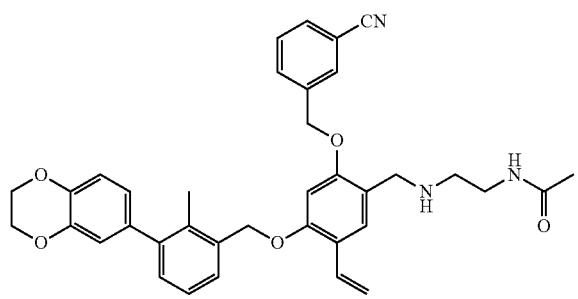 [SMILES: C=Cc1cc(CNCCNC(C)=O)c(OCc2cccc(C#N)c2)cc1OCc1cccc(-c2ccc3c(c2)OCCO3)c1C]

LCMS Condition A: 2.08 min, 604.3 (M+H). ¹H NMR (DMSO-d₆) δ 7.96 (s, 1H), 7.76-7.91 (m, 3H), 7.56-7.70 (m, 1H), 7.50 (s, 1H), 7.41 (d, J=7.3 Hz, 1H), 7.25 (t, J=7.5 Hz, 1H), 7.14-7.21 (m, 1H), 6.85-6.96 (m, 3H), 6.73-6.82 (m, 2H), 5.66 (d, J=16.9 Hz, 1H), 5.29 (s, 2H), 5.16 (s, 2H), 5.12 (d, J=12.1 Hz, 1H), 4.29 (s, 4H), 3.69 (s, 2H), 3.09-3.19 (m, 2H), 2.56 (t, J=6.6 Hz, 2H), 2.22 (s, 3H), 1.77 (s, 3H).

Example 1293

(S)-1-(2-(3-cyanobenzyloxy)-4-(3-(2,3-dihydrobenzo[b][1,4]dioxin-6-yl) -2-methylbenzyloxy)-5-vinylbenzyl)piperidine-2-carboxylic acid

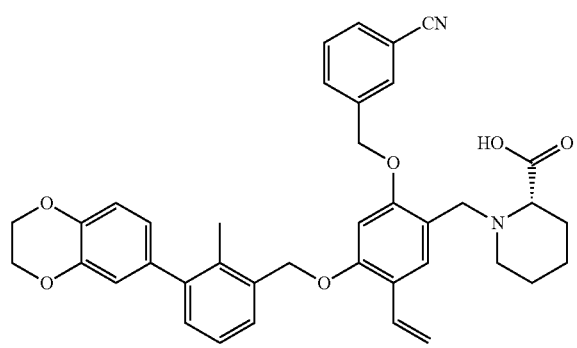 [SMILES: C=Cc1cc(CN2CCCC[C@H]2C(=O)O)c(OCc2cccc(C#N)c2)cc1OCc1cccc(-c2ccc3c(c2)OCCO3)c1C]

LCMS Condition M: 2.93 min, 631.3 (M+H), 629.3 (M−H). ¹H NMR (DMSO-d₆) δ 8.00 (s, 1H), 7.87 (d, J=7.7 Hz, 1H), 7.82 (d, J=7.7 Hz, 1H), 7.63 (t, J=7.7 Hz, 1H), 7.57 (s, 1H), 7.42 (d, J=7.7 Hz, 1H), 7.25 (t, J=7.5 Hz, 1H), 7.18 (d, J=7.3 Hz, 1H), 6.84-6.98 (m, 3H), 6.80 (d, J=1.8 Hz, 1H), 6.77 (d, J=8.4 Hz, 1H), 5.63 (d, J=17.6 Hz, 1H), 5.31 (s, 2H), 5.18 (s, 2H), 5.15 (d, J=11.7 Hz, 1H), 4.29 (s, 4H), 3.97 (d, J=13.6 Hz, 1H), 3.81 (d, J=13.6 Hz, 1H), 3.13-3.22 (m, 1H), 2.95-3.03 (m, 1H), 2.40-2.48 (m, 1H), 2.22 (s, 3H), 1.81-1.89 (m, 1H), 1.70-1.79 (m, 1H), 1.46-1.57 (m, 3H), 1.33-1.43 (m, 1H).

Intermediate 5-(5-(3-(2,3-dihydrobenzo[b][1,4]dioxin-6-yl)-2-methylbenzyloxy)-2-formyl-4-methylphenoxy)pentanenitrile

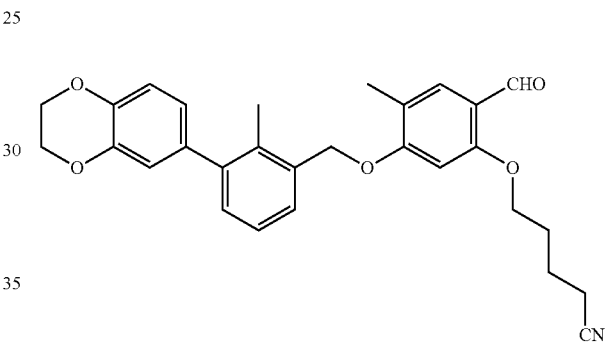

To a solution of 4-((3-(2,3-dihydrobenzo[b][1,4]dioxin-6-yl)-2-methylbenzyl)oxy)-2-hydroxy-5-methylbenzaldehyde (100 mg, 0.256 mmol) in DMF (5 mL), 5-chloropentanenitrile (33.1 mg, 0.282 mmol) and cesium carbonate (125 mg, 0.384 mmol) were added. The reaction mixture was stirred at RT for 4 hr. LC/MS shown completion of reaction. It was added water and a black solid was collected as final product 5-(5-((3-(2,3-dihydrobenzo[b][1,4]dioxin-6-yl)-2-methylbenzyl)oxy)-2-formyl-4-methylphenoxy)pentanenitrile (92 mg, 0.195 mmol, 76% yield). LC/MS method T: 4.33 min, 472 (MH+). ¹H NMR (400 MHz, CDCl₃) δ 10.32 (s, 1H), 7.67 (s, 1H), 7.40-7.46 (m, 1H), 7.25-7.31 (m, 2H), 6.94 (d, J=8.3 Hz, 1H), 6.85 (d, J=2.0 Hz, 1H), 6.80 (dd, J=8.3, 2.0 Hz, 1H), 6.52 (s, 1H), 5.18 (s, 2H), 4.34 (s, 4H), 4.15 (t, J=6.0 Hz, 2H), 2.50 (t, J=6.8 Hz, 2H), 2.30 (s, 3H), 2.22 (s, 3H), 2.02-2.10 (m, 2H), 1.91-1.99 (m, 2H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-(5-(3-(2,3-dihydrobenzo[b][1,4]dioxin-6-yl)-2-methylbenzyloxy)-2-formyl-4-methylphenoxy)pentanenitrile and the appropriate amine by reductive amination.

Example 1294

N-(2-(2-(4-cyanobutoxy)-4-(3-(2,3-dihydrobenzo[b][1,4]dioxin-6-yl)-2-methylbenzyloxy)-5-methylbenzylamino)ethyl)acetamide

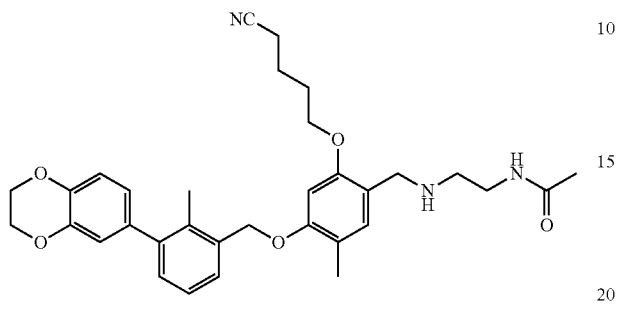

LCMS Condition A: 1.9 min, 558.3 (M+H). ¹H NMR (DMSO-d$_6$) δ 7.79-7.85 (m, 1H), 7.47 (d, J=7.3 Hz, 1H), 7.26 (t, J=7.7 Hz, 1H), 7.17 (d, J=7.3 Hz, 1H), 7.05 (s, 1H), 6.93 (d, J=8.1 Hz, 1H), 6.73-6.81 (m, 3H), 5.14 (s, 2H), 4.29 (s, 4H), 4.05 (t, J=5.9 Hz, 2H), 3.35-3.65 (m, 2H), 3.09-3.16 (m, 2H), 2.60 (t, J=7.0 Hz, 2H), 2.54 (t, J=6.2 Hz, 2H), 2.24 (s, 3H), 2.10 (s, 3H), 1.69-1.88 (m, 7H).

Example 1295

(S)-4-(2-(4-cyanobutoxy)-4-(3-(2,3-dihydrobenzo[b][1,4]dioxin-6-yl)-2-methylbenzyloxy)-5-methylbenzylamino)-3-hydroxybutanoic acid

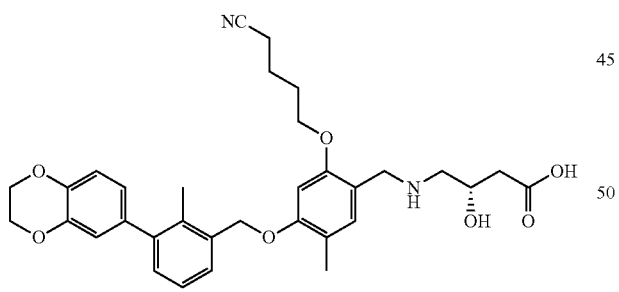

LCMS Condition A: 1.74 min, 575.3 (M+H). ¹H NMR (DMSO-d$_6$) δ 7.47 (d, J=7.3 Hz, 1H), 7.26 (t, J=7.7 Hz, 1H), 7.17 (d, J=7.3 Hz, 1H), 7.09 (s, 1H), 6.93 (d, J=8.1 Hz, 1H), 6.78-6.83 (m, 2H), 6.76 (dd, J=8.3, 2.0 Hz, 1H), 5.16 (s, 2H), 4.29 (s, 4H), 4.07 (t, J=6.1 Hz, 2H), 3.87-3.94 (m, 1H), 3.54-3.84 (m, 2H), 2.56-2.66 (m, 4H), 2.34-2.44 (m, 1H), 2.28 (dd, J=15.4, 5.9 Hz, 1H), 2.24 (s, 3H), 2.10 (s, 3H), 1.80-1.89 (m, 2H), 1.72-1.80 (m, 2H).

Example 1296

(S)-1-(2-(4-cyanobutoxy)-4-(3-(2,3-dihydrobenzo[b][1,4]dioxin-6-yl)-2-methylbenzyloxy)-5-methylbenzyl)piperidine-2-carboxylic acid

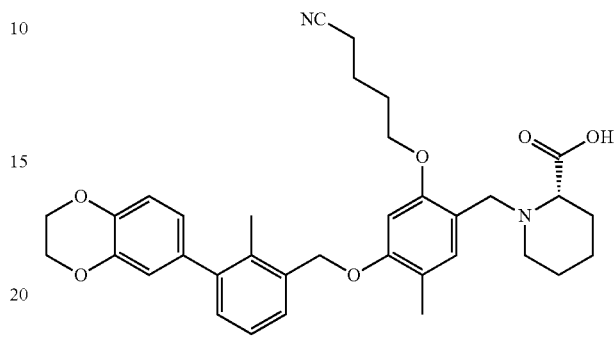

LCMS Condition A: 1.85 min, 585.3 (M+H). ¹H NMR (DMSO-d$_6$) δ 7.48 (d, J=7.3 Hz, 1H), 7.23-7.30 (m, 1H), 7.14-7.21 (m, 2H), 6.93 (d, J=8.4 Hz, 1H), 6.79-6.84 (m, 2H), 6.77 (dd, J=8.3, 2.0 Hz, 1H), 5.17 (s, 2H), 4.29 (s, 4H), 4.07 (t, J=5.9 Hz, 2H), 3.97 (d, J=13.2 Hz, 1H), 3.82 (d, J=12.8 Hz, 1H), 3.15 (dd, J=8.4, 4.0 Hz, 1H), 2.97-3.04 (m, 1H), 2.60 (t, J=7.0 Hz, 2H), 2.46-2.52 (m, 1H), 2.24 (s, 3H), 2.08-2.14 (m, 3H), 1.80-1.90 (m, 3H), 1.68-1.80 (m, 3H), 1.48-1.59 (m, 3H), 1.33-1.43 (m, 1H).

Example 1297

(S)-2-(2-(4-cyanobutoxy)-4-(3-(2,3-dihydrobenzo[b][1,4]dioxin-6-yl)-2-methylbenzyloxy)-5-methylbenzylamino)-3-hydroxy-2-methylpropanoic acid

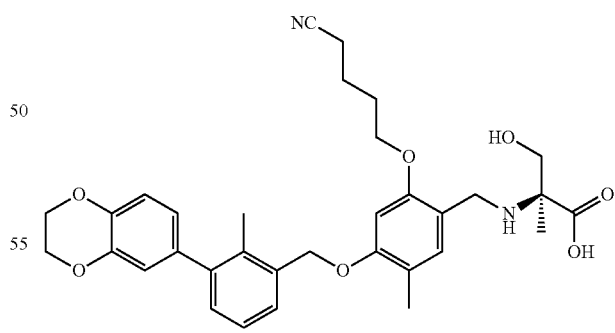

LCMS Condition A: 1.78 min, 575.3 (M+H). ¹H NMR (DMSO-d$_6$) δ 7.43 (d, J=7.3 Hz, 1H), 7.25 (t, J=7.7 Hz, 1H), 7.11-7.18 (m, 2H), 6.92 (d, J=8.8 Hz, 1H), 6.82 (s, 1H), 6.70-6.77 (m, 2H), 5.16 (s, 2H), 4.25 (s, 4H), 3.95-4.13 (m, 4H), 3.73 (d, J=11.7 Hz, 1H), 3.58 (d, J=11.4 Hz, 1H), 2.50-2.55 (m, 2H), 2.20 (s, 3H), 2.07 (s, 3H), 1.81-1.89 (m, 2H), 1.70-1.81 (m, 2H), 1.31 (s, 3H).

Intermediate 5-bromo-2,4-dihydroxybenzaldehyde

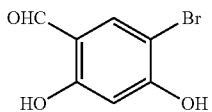

To a solution of 5-bromo-2,4-dimethoxybenzaldehyde (1 g, 4.08 mmol) in dichloromethane (100 mL), boron tribromide (1.929 mL, 20.40 mmol) was added dropwise at −78° C. The reaction mixture was then warmed to room temperature and stirred for 3 days. The reaction mixture was then quenched with ice and 1N aqueous sodium hydroxide solution was added to adjust the pH to approximately 10. The aqueous portion was separated and acidified to pH 3 with 1N hydrochloric acid solution. Extracted with ethyl acetate (2×50 mL) and the organic layers were combined, dried over magnesium sulfate and concentrated to give a brownish solid as crude product. The crude product was then purified by silica gel column using hexanes to 30% ethyl acetate in hexanes as eluent to give an off-white solid as final product 5-bromo-2,4-dihydroxybenzaldehyde (585 mg, 2.70 mmol, 66.1% yield). LCMS Condition AA: 1.69 min, 215, 217 (M−H). $^1$H NMR (400 MHz, CDCl$_3$) δ 11.25 (s, 1H), 9.70 (s, 1H), 7.66 (s, 1H), 6.63 (s, 1H), 6.13 (br. s, 1H).

Intermediate 5-bromo-2-hydroxy-4-((2-methylbiphenyl-3-yl)methoxy)benzaldehyde

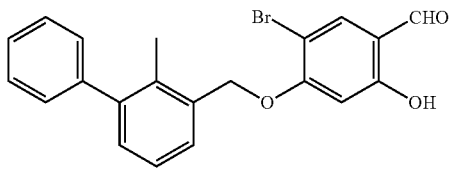 [SMILES: Cc1c(COc2cc(O)c(C=O)cc2Br)cccc1-c1ccccc1]

To a solution of (2-methyl-[1,1'-biphenyl]-3-yl)methanol (100 mg, 0.507 mmol) and 5-bromo-2,4-dihydroxybenzaldehyde (100 mg, 0.461 mmol) in tetrahydrofuran (5 mL), triphenylphosphine (145 mg, 0.553 mmol) was added. The reaction mixture was stirred at 0° C. for 15 minutes. Diisopropylazodicarboxylate (0.108 mL, 0.553 mmol) was added dropwise in tetrahydrofuran (5 mL). The reaction mixture was then warmed to room temperature and stirred overnight. The reaction mixture was concentrated and to the residue was added acetonitrile. A light yellow solid precipitated and was collected as the final product 5-bromo-2-hydroxy-4-((2-methyl-[1,1'-biphenyl]-3-yl)methoxy)benzaldehyde (62 mg, 0.156 mmol, 33.9% yield).

Intermediate 5-((4-bromo-2-formyl-5-((2-methylbiphenyl-3-yl)methoxy)phenoxy)methyl)nicotinonitrile

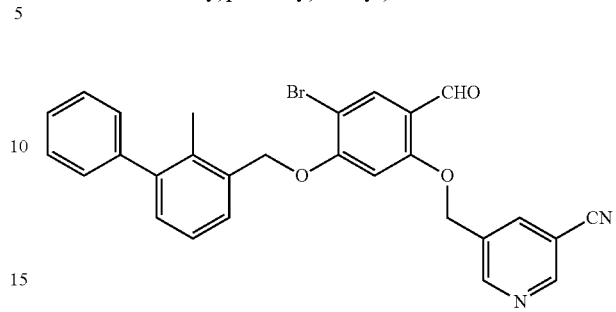

To a solution of 5-bromo-2-hydroxy-4-((2-methyl-[1,1'-biphenyl]-3-yl)methoxy)benzaldehyde (62 mg, 0.156 mmol) in dimethyl formamide (3 mL), 5-(chloromethyl)nicotinonitrile (26.2 mg, 0.172 mmol) and cesium carbonate (102 mg, 0.312 mmol) were added. The reaction mixture was stirred at 75° C. for 3 hours. LC/MS shown completion of reaction. Water was added and a brownish solid was collected as the title compound (60 mg, 0.117 mmol, 74.9% yield). $^1$H NMR (400 MHz, CHLOROFORM-d) δ 10.28 (s, 1H), 8.93 (s, 2H), 8.16-8.07 (m, 2H), 7.50-7.43 (m, 3H), 7.42-7.36 (m, 1H), 7.36-7.30 (m, 4H), 6.65 (s, 1H), 5.28 (s, 2H), 5.25 (s, 2H), 2.31 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-((4-bromo-2-formyl-5-((2-methylbiphenyl-3-yl)methoxy)phenoxy)methyl)nicotinonitrile and the appropriate amine by reductive amination.

Example 1298

(S)-1-(5-bromo-2-((5-cyanopyridin-3-yl)methoxy)-4-((2-methylbiphenyl-3-yl)methoxy)benzyl)piperidine-2-carboxylic acid

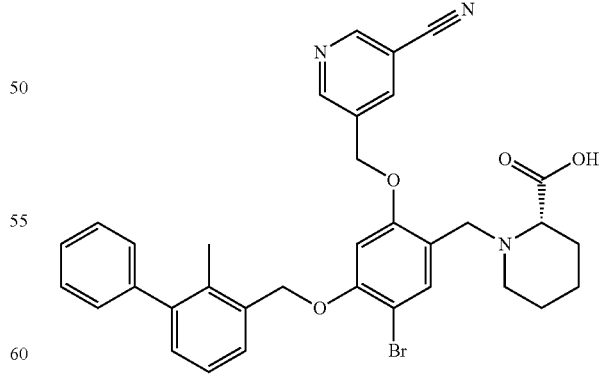

LCMS Condition A: 1.91 min, 626.2 (MH+). $^1$H NMR (DMSO-d$_6$) δ 8.99-9.04 (m, 2H), 8.47 (s, 1H), 7.57 (s, 1H), 7.53 (d, J=7.3 Hz, 1H), 7.44-7.50 (m, 2H), 7.37-7.42 (m, 1H), 7.31-7.36 (m, 2H), 7.28-7.31 (m, 1H), 7.22 (d, J=7.3 Hz, 1H), 7.11 (s, 1H), 5.31-5.40 (m, 2H), 5.27 (s, 2H), 3.30-3.83 (m, 3H), 2.86-2.94 (m, 1H), 2.27-2.35 (m, 1H), 2.25 (s, 3H), 1.67-1.86 (m, 2H), 1.50 (br. s., 3H), 1.33-1.42 (m, 1H).

Intermediate 5-bromo-4-((3-(2,3-dihydrobenzo[b][1,4]dioxin-6-yl)-2-methylbenzyl)oxy)-2-hydroxybenzaldehyde

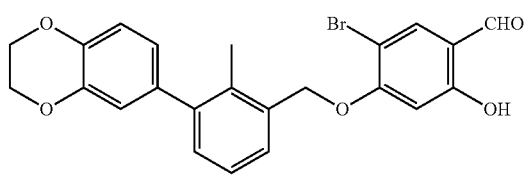 [SMILES: Cc1c(COc2cc(O)c(C=O)cc2Br)cccc1-c1ccc2c(c1)OCCO2]

Triphenylphosphine (363 mg, 1.382 mmol) was added to a solution of (3-(2,3-dihydrobenzo[b][1,4]dioxin-6-yl)-2-methylphenyl)methanol (325 mg, 1.267 mmol) and 5-bromo-2,4-dihydroxybenzaldehyde (250 mg, 1.152 mmol) in tetrahydrofuran (5 mL). The reaction mixture was stirred at 0° C. for 15 minutes. Diisopropyl azodicarboxylate (0.269 mL, 1.382 mmol) was added dropwise. The reaction mixture was then warmed to room temperature and stirred for 3 days. The reaction mixture was then concentrated and to the residue was added ethyl acetate. A white precipitate was collected as the final product 5-bromo-4-((3-(2,3-dihydrobenzo[b][1,4]dioxin-6-yl)-2-methylbenzyl)oxy)-2-hydroxybenzaldehyde (298 mg, 0.655 mmol, 56.8% yield). LCMS Condition AA: 3.865 min, 453, 455 (M–H⁻). ¹H NMR (400 MHz, CDCl₃) δ: 11.45 (s, 1H), 9.71 (s, 1H), 7.72 (s, 1H), 7.48 (dd, J=6.7, 2.3 Hz, 1H), 7.22-7.31 (m, 2H), 6.92 (d, J=8.3 Hz, 1H), 6.84 (d, J=2.2 Hz, 1H), 6.79 (dd, J=8.3, 2.0 Hz, 1H), 6.62 (s, 1H), 5.21 (s, 2H), 4.32 (s, 4H), 2.28 (s, 3H).

Intermediate 3-((4-bromo-5-((3-(2,3-dihydrobenzo[b][1,4]dioxin-6-yl)-2-methylbenzyl)oxy)-2-formylphenoxy)methyl)benzonitrile

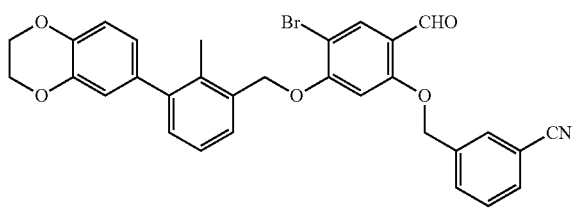 [SMILES: Cc1c(COc2cc(OCc3cccc(C#N)c3)c(C=O)cc2Br)cccc1-c1ccc2c(c1)OCCO2]

To a solution of 5-bromo-4-((3-(2,3-dihydrobenzo[b][1,4]dioxin-6-yl)-2-methylbenzyl)oxy)-2-hydroxybenzaldehyde (295 mg, 0.648 mmol) in dimethylformamide (3 mL), 3-(bromomethyl)benzonitrile (140 mg, 0.713 mmol) and cesium carbonate (317 mg, 0.972 mmol) were added. The reaction mixture was stirred at room temperature for 2 hours. Water was added and a white solid was collected as final product 3-((4-bromo-5-((3-(2,3-dihydrobenzo[b][1,4]dioxin-6-yl)-2-methylbenzyl)oxy) -2-formylphenoxy)methyl)benzonitrile (370 mg, 0.649 mmol, 100% yield). LCMS Condition T: 4.56 min, 570, 572 (MH⁺). ¹H NMR (400 MHz, CDCl₃) δ 10.31 (s, 1H), 8.09 (s, 1H), 7.73 (s, 1H), 7.65-7.72 (m, 2H), 7.52-7.59 (m, 1H), 7.38-7.43 (m, 1H), 7.24-7.28 (m, 2H), 6.93 (d, J=8.3 Hz, 1H), 6.82 (d, J=2.0 Hz, 1H), 6.78 (dd, J=8.2, 2.1 Hz, 1H), 6.58 (s, 1H), 5.21 (s, 2H), 5.19 (s, 2H), 4.32 (s, 4H), 2.29 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 3-((4-bromo-5-((3-(2,3-dihydrobenzo[b][1,4]dioxin-6-yl)-2-methylbenzyl)oxy)-2-formylphenoxy)methyl)benzonitrile and the appropriate amine. LCMS for these examples is given in tabular form.

Example 1299

N-(2-((5-bromo-2-((3-cyanobenzyl)oxy)-4-((3-(2,3-dihydrobenzo[b][1,4]dioxin-6-yl)-2-methylbenzyl)oxy)benzyl)amino)ethyl)acetamide

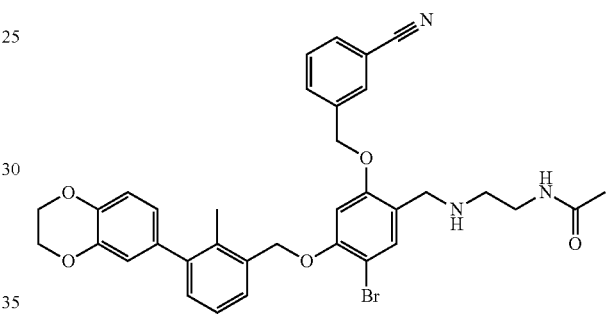

¹H NMR (500 MHz, DMSO-d₆) δ 7.94 (s, 1H), 7.73-7.85 (m, 3H), 7.59-7.66 (m, 1H), 7.50 (s, 1H), 7.46 (d, J=7.3 Hz, 1H), 7.24 (t, J=7.3 Hz, 1H), 7.17 (d, J=7.3 Hz, 1H), 7.03 (s, 1H), 6.92 (d, J=8.1 Hz, 1H), 6.77 (s, 1H), 6.75 (d, J=8.4 Hz, 1H), 5.27 (s, 2H), 5.20 (s, 2H), 4.28 (s, 4H), 3.43 (br. s., 2H), 3.11 (q, J=5.7 Hz, 2H), 2.51 (t, J=6.6 Hz, 2H), 2.24 (s, 3H), 1.77 (s, 3H).

Example 1300

(S)-4-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid

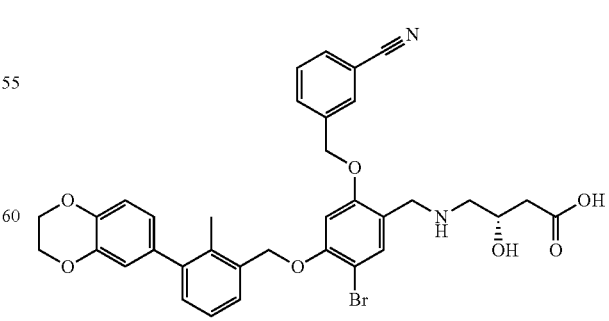

¹H NMR (500 MHz, DMSO-d₆) δ 7.96 (s, 1H), 7.80-7.87 (m, 2H), 7.58-7.67 (m, 1H), 7.52 (s, 1H), 7.46 (d, J=7.3 Hz,

1H), 7.20-7.28 (m, 1H), 7.17 (d, J=7.7 Hz, 1H), 7.05 (s, 1H), 6.92 (d, J=8.1 Hz, 1H), 6.77 (s, 1H), 6.75 (d, J=8.1 Hz, 1H), 5.28 (s, 2H), 5.21 (s, 2H), 4.28 (s, 4H), 3.85-3.91 (m, 1H), 3.65-3.75 (m, 2H), 2.51-2.57 (m, 2H), 2.33-2.40 (m, 1H), 2.14-2.29 (m, 4H).

Example 1301

(S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid

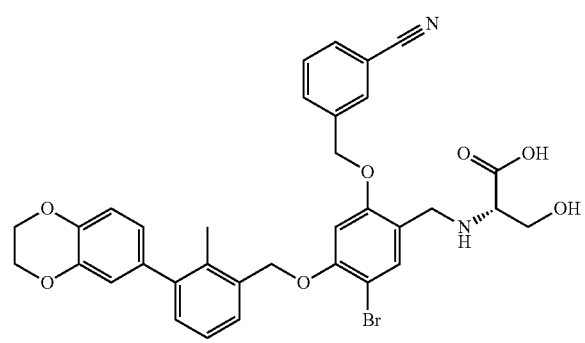 [SMILES: Cc1c(COc2cc(OCc3cccc(C#N)c3)c(CN[C@@H](CO)C(=O)O)cc2Br)cccc1-c1ccc2c(c1)OCCO2]

¹H NMR (500 MHz, DMSO-d₆) δ 8.02 (br. s., 1H), 7.90 (d, J=7.0 Hz, 1H), 7.82 (d, J=7.7 Hz, 1H), 7.57-7.69 (m, 2H), 7.45 (d, J=7.0 Hz, 1H), 7.24 (t, J=7.3 Hz, 1H), 7.13-7.21 (m, 1H), 7.08 (s, 1H), 6.92 (d, J=8.4 Hz, 1H), 6.68-6.83 (m, 2H), 5.27-5.38 (m, 2H), 5.23 (s, 2H), 4.28 (s, 4H), 3.13-3.78 (m, 5H), 2.24 (s, 3H).

Example 1302

(S)-1-(5-bromo-2-((3-cyanobenzyl)oxy)-4-((3-(2,3-dihydrobenzo[b][1,4]dioxin-6-yl)-2-methylbenzyl)oxy)benzyl)piperidine-2-carboxylic acid

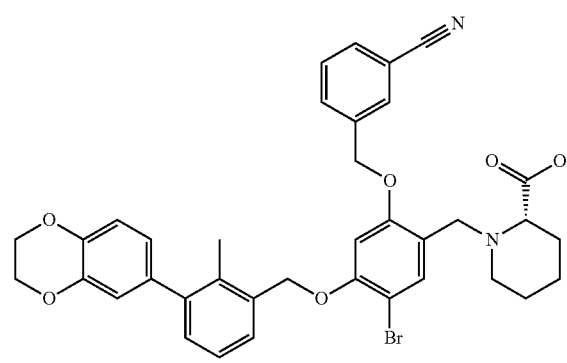

¹H NMR (500 MHz, DMSO-d₆) δ 7.96 (s, 1H), 7.82 (t, J=8.3 Hz, 2H), 7.62 (t, J=7.7 Hz, 1H), 7.56 (s, 1H), 7.46 (d, J=7.7 Hz, 1H), 7.20-7.28 (m, 1H), 7.17 (d, J=7.7 Hz, 1H), 7.05 (s, 1H), 6.92 (d, J=8.1 Hz, 1H), 6.78 (s, 1H), 6.75 (d, J=8.4 Hz, 1H), 5.29 (s, 2H), 5.22 (s, 2H), 4.28 (s, 4H), 3.77 (d, J=13.6 Hz, 1H), 3.63 (d, J=13.2 Hz, 1H), 2.89 (br. s., 1H), 2.29 (br. s., 1H), 2.24 (s, 3H), 1.65-1.85 (m, 2H), 1.48 (br. s., 3H), 1.37 (br. s., 1H)

Example 1303

(R)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

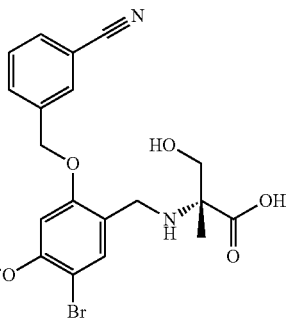

¹H NMR (500 MHz, DMSO-d₆) δ 8.01 (s, 1H), 7.92 (d, J=8.1 Hz, 1H), 7.82 (d, J=7.7 Hz, 1H), 7.67 (s, 1H), 7.61 (t, J=7.7 Hz, 1H), 7.45 (d, J=7.7 Hz, 1H), 7.20-7.27 (m, 1H), 7.12-7.20 (m, 1H), 7.07 (s, 1H), 6.92 (d, J=8.4 Hz, 1H), 6.77 (s, 1H), 6.74 (d, J=8.1 Hz, 1H), 5.31 (s, 2H), 5.25 (s, 2H), 4.28 (s, 4H), 3.12-3.65 (m, 4H), 2.24 (s, 3H), 1.24 (s, 3H).

Example 1304

(S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid

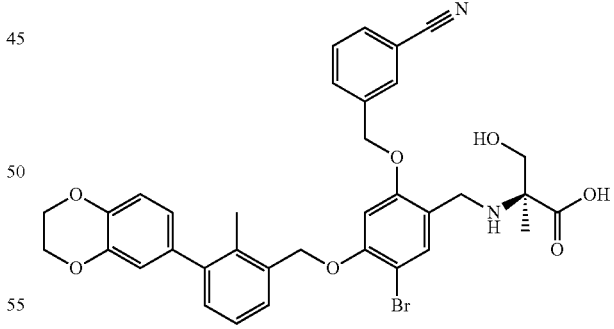

¹H NMR (500 MHz, DMSO-d₆) δ 8.01 (s, 1H), 7.91 (d, J=7.7 Hz, 1H), 7.82 (d, J=7.7 Hz, 1H), 7.67 (s, 1H), 7.61 (t, J=7.5 Hz, 1H), 7.45 (d, J=7.7 Hz, 1H), 7.20-7.27 (m, 1H), 7.17 (d, J=7.3 Hz, 1H), 7.07 (s, 1H), 6.92 (d, J=8.4 Hz, 1H), 6.77 (s, 1H), 6.74 (d, J=8.8 Hz, 1H), 5.31 (s, 2H), 5.25 (s, 2H), 4.28 (s, 4H), 3.10-3.65 (m, 4H), 2.24 (s, 3H), 1.24 (s, 3H).

| Example | LCMS Method | RT (min) | M + 1 | M − 1 |
|---|---|---|---|---|
| Example 1299: N-(2-((5-bromo-2-((3-cyanobenzyl)oxy)-4-((3-(2,3-dihydrobenzo[b][1,4]dioxin-6-yl)-2-methylbenzyl)oxy)benzyl)amino)ethyl)acetamide | A | 2.06 | 656.3 | |
| Example 1300: (S)-4-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid | A | 1.83 | 673.3 | 671.3 |
| Example 1301: (S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid | A | 1.85 | 659.2 | 657.3 |
| Example 1302: (S)-1-(5-bromo-2-((3-cyanobenzyl)oxy)-4-((3-(2,3-dihydrobenzo[b][1,4]dioxin-6-yl)-2-methylbenzyl)oxy)benzyl)piperidine-2-carboxylic acid | M | 2.87 | | 681.3 |
| Example 1303: (R)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid | M | 2.86 | 673.3 | 671.3 |
| Example 1304: (S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid | M | 2.87 | 673.3 | 671.3 |

Intermediate 2-(2,3-dihydrobenzo[b][1,4]dioxin-6-yl)-6-((4-formyl-5-hydroxy-2-methylphenoxy)methyl)benzonitrile

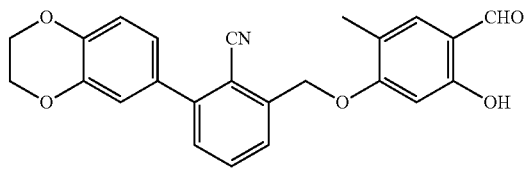 [SMILES: Cc1cc(C=O)c(O)cc1OCc1cccc(-c2ccc3c(c2)OCCO3)c1C#N]

Diisopropyl azodicarboxylate (0.160 mL, 0.823 mmol) in tetrahydrofuran (3 mL) was added dropwise to a cooled (0° C.) solution of 2,4-dihydroxy-5-methylbenzaldehyde (125 mg, 0.823 mmol), triphenylphosphine (216 mg, 0.823 mmol) and 2-(2,3-dihydrobenzo[b][1,4]dioxin-6-yl)-6-(hydroxymethyl)benzonitrile (200 mg, 0.748 mmol) in dry tetrahydrofuran (3 mL). The resulting reaction mixture was allowed to slowly warm to room temperature with stirring overnight. The product was filtered from the reaction using a buchner filter funnel and rinsed with tetrahydrofuran (approx. 5 mL) then dried in vacuo at room temperature to yield 75 mg of a white solid. LCMS Condition T: 1.38 minutes, M+1=402.0.

Intermediate 5-((5-(2-cyano-3-(2,3-dihydrobenzo[b][1,4]dioxin-6-yl)benzyloxy)-2-formyl-4-methylphenoxy)methyl)nicotinonitrile

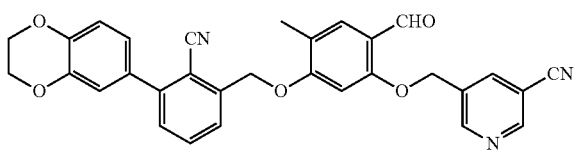 [SMILES: Cc1cc(C=O)c(OCc2cncc(C#N)c2)cc1OCc1cccc(-c2ccc3c(c2)OCCO3)c1C#N]

Cesium carbonate (146 mg, 0.448 mmol), 2-(2,3-dihydrobenzo[b][1,4]dioxin-6-yl)-6-((4-formyl-5-hydroxy-2-methylphenoxy)methyl)benzonitrile (120 mg, 0.299 mmol) and 5-(chloromethyl)nicotinonitrile (91 mg, 0.598 mmol) were stirred at 75° C. for 2 hours in dimethyl formamide (2 mL). The reaction was filtered and concentrated. The residue was purified with 1:2 to 2:1 hexane:ethyl acetate on a 24 g silica gel column) Collected fractions to afford a white solid as the desired product (110 mg, 71%).

$^1$H NMR (500 MHz, DMSO-d$_6$) δ 10.27 (s, 1H), 9.02 (s, 2H), 8.52 (s, 1H), 7.82-7.68 (m, 2H), 7.64-7.53 (m, 2H), 7.17-6.96 (m, 4H), 5.46 (d, J=5.9 Hz, 4H), 4.32 (s, 4H), 3.42 (s, 7H), 2.14 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-((5-(2-cyano-3-(2,3-dihydrobenzo[b][1,4]dioxin-6-yl)benzyloxy)-2-formyl-4-methylphenoxy)methyl)nicotinonitrile and the appropriate amine by reductive amination.

Example 1305

N-(2-(4-(2-cyano-3-(2,3-dihydrobenzo[b][1,4]dioxin-6-yl)benzyloxy)-2-((5-cyanopyridin-3-yl)methoxy)-5-methylbenzylamino)ethyl)acetamide

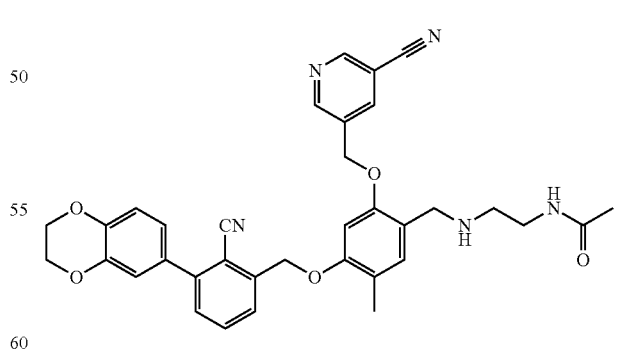

LCMS Condition A: 1.70 minutes, M+1=604.3. $^1$H NMR (DMSO-d$_6$) δ 9.00 (s, 1H), 8.97 (s, 1H), 8.41 (s, 1H), 7.75 (d, 1H), 7.66-7.70 (m, 1H), 7.56 (d, 1H), 7.10-7.13 (m, 2H), 7.01-7.08 (m, 2H), 6.90 (s, 1H), 5.30 (d, 4H), 4.32 (s, 4H), 3.65 (s, 2H), 3.13 (d, 2H), 2.90 (s, 1H), 2.74 (s, 1H), 2.54 (m, 2H), 2.12 (s, 3H), 1.77 (s, 3H).

Example 1306

5-((5-(2-cyano-3-(2,3-dihydrobenzo[b][1,4]dioxin-6-yl)benzyloxy)-2-((2-hydroxyethylamino)methyl)-4-methylphenoxy)methyl)nicotinonitrile

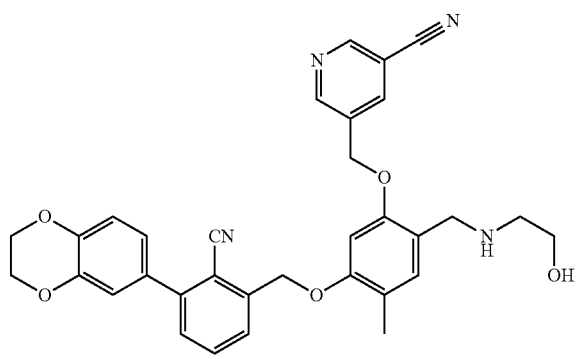 [SMILES: Cc1cc(CNCCO)c(OCc2cncc(C#N)c2)cc1OCc1cccc(-c2ccc3c(c2)OCCO3)c1C#N]

LCMS Condition M: 2.55 minutes, M+1=563.2, M−1=561.3. $^1$H NMR (DMSO-d$_6$) δ 8.98 (s, 1H), 9.01 (s, 1H), 8.42 (s, 1H), 7.76 (m, 1H), 7.69 (d, 1H), 7.57 (d, 1H), 7.12 (d, 2H), 7.01-7.08 (m, 2H), 6.92 (s, 1H), 5.31 (d, 4H), 4.32 (s, 4H), 3.91 (s, 1H), 3.72 (s, 1H), 2.62 (m, 2H), 2.08-2.14 (m, 3H), 1.91 (s, 2H).

Example 1307

(S)-4-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxybutanoic acid

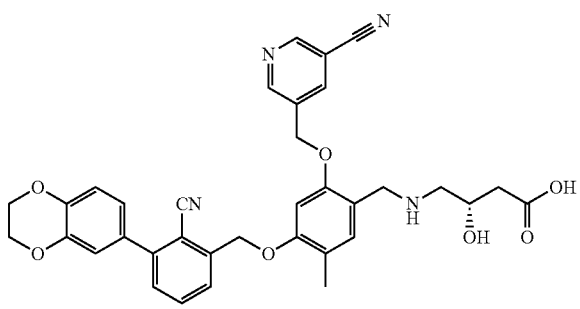 [SMILES: Cc1cc(CNC[C@@H](O)CC(=O)O)c(OCc2cncc(C#N)c2)cc1OCc1cccc(-c2ccc3c(c2)OCCO3)c1C#N]

LCMS Condition A: 1.53 minutes, M+1=621.2, M−1=619.2. $^1$H NMR (DMSO-d$_6$) δ 9.00 (d, 2H), 8.44 (s, 1H), 7.76 (m, 1H), 7.68 (d, 1H), 7.57 (d, 1H), 7.15 (s, 1H), 7.11 (s, 1H), 7.01-7.08 (m, 2H), 6.93 (s, 1H), 5.31 (d, 4H), 4.32 (s, 4H), 3.88-3.93 (m, 2H), 3.74-3.81 (m, 2H), 2.63 (d, 2H), 2.39 (m, 1H), 2.27 (m, 1H), 2.13 (s, 3H).

Example 1308

(S)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid

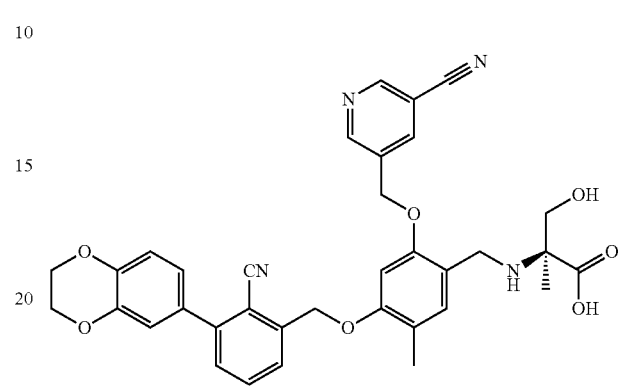

LCMS Condition A: 1.61 minutes, M+1=621.2, M−1=619.2. $^1$H NMR (DMSO-d$_6$) δ 9.03 (s, 1H), 8.99-9.01 (m, 1H), 8.51 (s, 1H), 7.74 (d, 1H), 7.69 (s, 1H), 7.57 (d, 1H), 7.26 (s, 1H), 7.10 (d, 1H), 7.01-7.07 (m, 2H), 6.96 (s, 1H), 5.34 (d, 4H), 4.32 (s, 4H), 4.00 (s, 2H), 3.63 (s, 1H), 3.57 (s, 1H), 2.13 (s, 3H), 1.26 (s, 3H).

Example 1309

(S)-1-(4-(2-cyano-3-(2,3-dihydrobenzo[b][1,4]dioxin-6-yl)benzyloxy)-2-((5-cyanopyridin-3-yl)methoxy)-5-methylbenzyl)piperidine-2-carboxylic acid

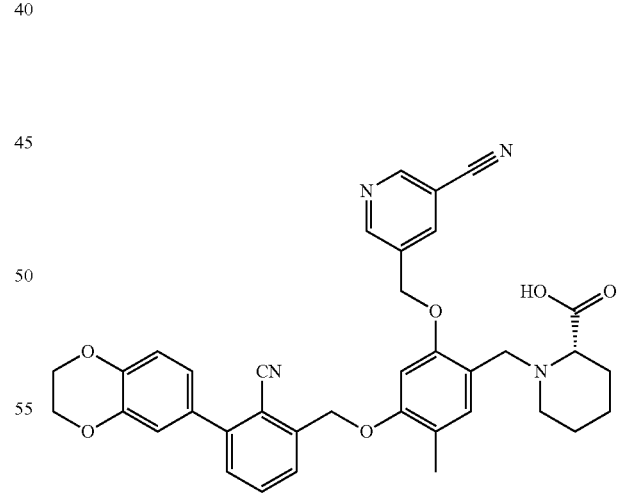

LCMS Condition A: 1.69 minutes, M+1=631.3, M−1=629.4. $^1$H NMR (DMSO-d$_6$) δ 9.00 (s, 2H), 8.48 (s, 1H), 7.76 (m, 1H), 7.70 (d, 1H), 7.57 (d, 1H), 7.20 (s, 1H), 7.11 (d, 1H), 7.01-7.08 (m, 2H), 6.94 (s, 1H), 5.28-5.35 (m, 4H), 4.32 (s, 4H), 3.96 (d, 1H), 3.77 (d, 1H), 3.15 (m, 1H), 2.95 (br. s., 1H), 2.12 (s, 3H), 1.84 (br. s., 1H), 1.68-1.77 (m, 1H), 1.52 (br. s., 3H), 1.36 (br. s., 1H).

Example 1310

(R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid

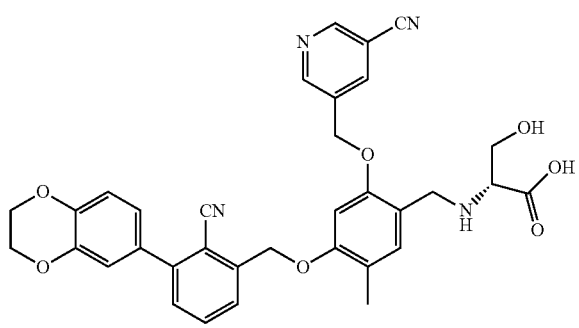 [SMILES: Cc1cc(CN[C@H](CO)C(=O)O)c(OCc2cncc(C#N)c2)cc1OCc1cccc(-c2ccc3c(c2)OCCO3)c1C#N]

LCMS Condition A: 1.57 minutes, M+1=607.2, M−1=605.3. $^1$H NMR (DMSO -d$_6$) δ 9.02 (m, 1H), 8.53 (s, 1H), 7.76 (m, 1H), 7.69 (d, 1H), 7.57 (d, 1H), 7.22 (s, 1H), 7.11 (d, 1H), 7.01-7.08 (m, 1H), 6.98 (s, 1H), 5.29-5.38 (m, 3H), 4.32 (s, 3H), 4.10 (d, 1H), 4.03 (d, 1H), 3.76 (m, 1H), 3.64 (m, 1H), 2.13 (s, 2H).

Example 1311

(R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid

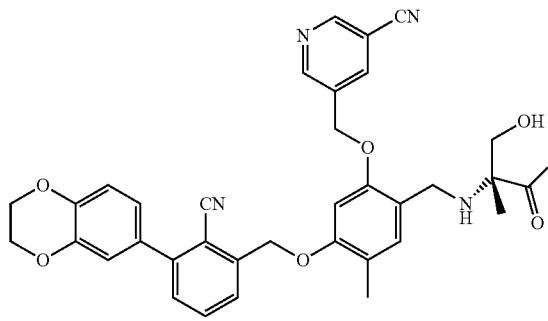

LCMS Condition A: 1.61 minutes, M+1=621.3, M−1=619.4. $^1$H NMR (DMSO -d$_6$) δ 9.00 (d, 1H), 9.03 (d, 1H), 8.52 (s, 1H), 7.75 (m, 1H), 7.68 (d, 1H), 7.57 (d, 1H), 7.25 (s, 1H), 7.11 (d, 1H), 7.01-7.08 (m, 2H), 6.96 (s, 1H), 5.34 (d, 4H), 4.32 (s, 4H), 3.99 (s, 2H), 3.64 (d, 1H), 3.55 (d, 1H), 2.14 (s, 3H), 1.25 (s, 3H).

Intermediate 2-(2-bromo-4-formyl-5-hydroxyphenoxy)methyl)-6-(2,3-dihydrobenzo[b][1,4]dioxin-6-yl)benzonitrile

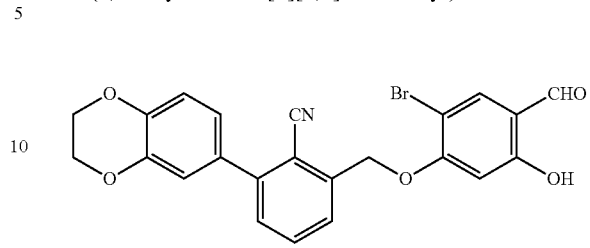

Triphenylphosphine (145 mg, 0.553 mmol) was added to a solution of 2-(2,3-dihydrobenzo[b][1,4]dioxin-6-yl)-6-(hydroxymethyl)benzonitrile (135 mg, 0.507 mmol) and 5-bromo-2,4-dihydroxybenzaldehyde (100 mg, 0.461 mmol) in tetrahydrofuran (5 mL). The reaction mixture was stirred at 0° C. for 15 minutes. Diisopropyl azodicarboxylate (0.108 mL, 0.553 mmol) was added dropwise. The reaction mixture was then warmed to room temperature and stirred for 3 days. The reaction mixture was concentrated and the residue was triturated with acetonitrile. An off-white solid was collected as crude product. The crude product was then purified by silica gel column using hexanes to 25% ethyl acetate in hexanes as eluent to give a white solid as final product 2-((2-bromo-4-formyl-5-hydroxyphenoxy)methyl)-6-(2,3-dihydrobenzo[b][1,4]dioxin-6-yl)benzonitrile (60 mg, 0.129 mmol, 27.9% yield).

LCMS Condition T: 4.131 min, 466, 468 (MH$^+$). $^1$H NMR (400 MHz, CDCl$_3$) δ 11.41 (s, 1H), 9.73 (s, 1H), 7.73-7.78 (m, 2H), 7.65-7.72 (m, 1H), 7.48 (d, J=7.6 Hz, 1H), 7.07-7.11 (m, 1H), 7.06 (d, J=2.2 Hz, 1H), 6.98-7.02 (m, 1H), 6.63 (s, 1H), 5.44 (s, 2H), 4.33 (s, 4H).

Intermediate 2-((2-bromo-5-((3-cyanobenzyl)oxy)-4-formylphenoxy)methyl)-6-(2,3-dihydrobenzo[b][1,4]dioxin-6-yl)benzonitrile

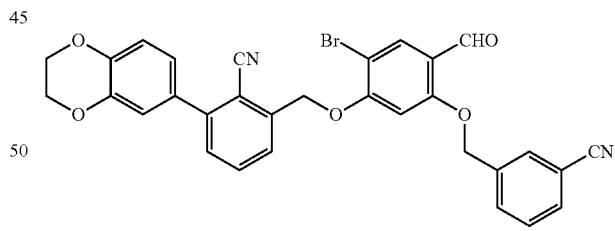

To a solution of 2-((2-bromo-4-formyl-5-hydroxyphenoxy)methyl)-6-(2,3-dihydrobenzo[b][1,4]dioxin-6-yl)benzonitrile (60 mg, 0.129 mmol) in dimethylformamide (1.5 mL), 3-(bromomethyl)benzonitrile (27.7 mg, 0.142 mmol) and cesium carbonate (62.9 mg, 0.193 mmol) were added. The reaction mixture was stirred at room temperature for 2 hr. Water was added and a white solid was collected as the final product 2-((2-bromo-5-((3-cyanobenzyl)oxy)-4-formylphenoxy)methyl)-6-(2,3-dihydrobenzo[b][1,4]dioxin-6-yl)benzonitrile (71 mg, 0.122 mmol, 95% yield).

LCMS Condition AA: 3.751 min, 581, 583 (MH$^+$). $^1$H NMR (400 MHz, CDCl$_3$) δ 10.33 (s, 1H), 8.11 (s, 1H), 7.81 (d, J=7.3 Hz, 1H), 7.63-7.77 (m, 4H), 7.52-7.59 (m, 1H), 7.48 (d, J=7.1 Hz, 1H), 7.09 (d, J=2.2 Hz, 1H), 7.03-7.07 (m, 1H), 6.98-7.02 (m, 1H), 6.69 (s, 1H), 5.46 (s, 2H), 5.25 (s, 2H), 4.34 (s, 4H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 2-((2-bromo-5-((3-cyanobenzyl)oxy)-4-formylphenoxy)methyl)-6-(2,3-dihydrobenzo[b][1,4]dioxin-6-yl)benzonitrile and the appropriate amine.

Example 1312

(S)-2-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid

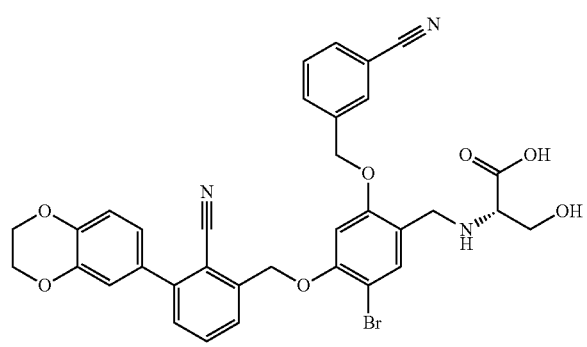 [SMILES: N#Cc1cccc(COc2cc(OCc3cccc(-c4ccc5c(c4)OCCO5)c3C#N)c(Br)cc2CN[C@@H](CO)C(=O)O)c1]

LCMS Condition A: 1.67 minutes, M−1=668.1. $^1$H NMR (500 MHz, DMSO-d$_6$) δ 7.99 (s, 1H), 7.90 (d, J=7.7 Hz, 1H), 7.73-7.83 (m, 2H), 7.64-7.72 (m, 2H), 7.60 (t, J=7.9 Hz, 1H), 7.57 (d, J=8.1 Hz, 1H), 6.97-7.12 (m, 4H), 5.40 (s, 2H), 5.26-5.35 (m, 2H), 4.31 (s, 4H), 4.01 (s, 2H), 3.71-3.77 (m, 1H), 3.59-3.67 (m, 1H), 3.17-3.22 (m, 1H).

Example 1313

(S)-1-(5-bromo-4-((2-cyano-3-(2,3-dihydrobenzo[b][1,4]dioxin-6-yl)benzyl)oxy)-2-((3-cyanobenzyl)oxy)benzyl)piperidine-2-carboxylic acid

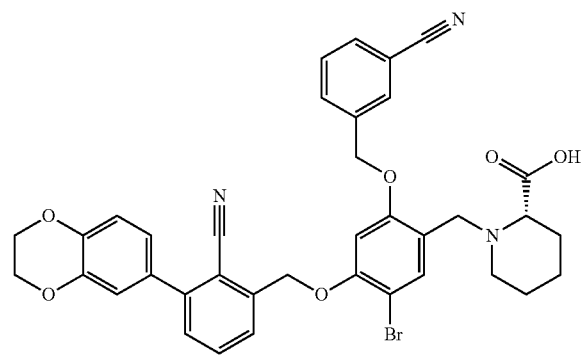 [SMILES: N#Cc1cccc(COc2cc(OCc3cccc(-c4ccc5c(c4)OCCO5)c3C#N)c(Br)cc2CN2CCCC[C@H]2C(=O)O)c1]

LCMS Condition A: 1.75 minutes, M+1=694.3, M−1=692.3. $^1$H NMR (500 MHz, DMSO-d$_6$) δ 7.90 (s, 1H), 7.73-7.84 (m, 3H), 7.69 (d, J=7.7 Hz, 1H), 7.58-7.64 (m, 2H), 7.56 (d, J=7.7 Hz, 1H), 7.10 (s, 1H), 6.98-7.07 (m, 3H), 5.37 (s, 2H), 5.26 (s, 2H), 4.31 (s, 4H), 3.72-3.79 (m, 1H), 2.82-2.90 (m, 2H), 2.03-2.13 (br. s., 1H), 1.82 (s, 3H), 1.61-1.76 (m, 2H), 1.48-1.55 (m, 1H), 1.37-1.47 (m, 2H), 1.19-1.33 (m, 1H).

Example 1314

(S)-4-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxybutanoic acid

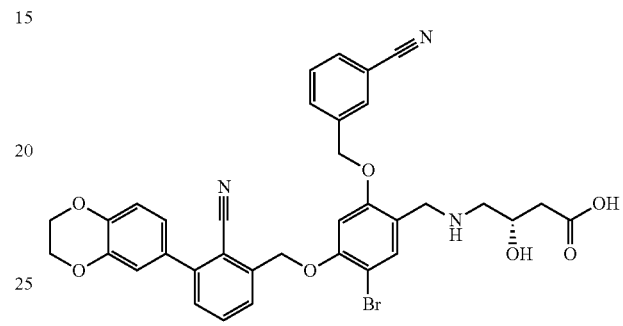

LCMS Condition A: 1.65 minutes, M−1=682.2. $^1$H NMR (500 MHz, DMSO-d$_6$) δ 7.93 (s, 1H), 7.72-7.86 (m, 3H), 7.69 (d, J=7.3 Hz, 1H), 7.61 (t, J=7.7 Hz, 1H), 7.51-7.58 (m, 2H), 7.08-7.12 (m, 1H), 6.97-7.07 (m, 3H), 5.38 (s, 2H), 5.28 (s, 2H), 4.31 (s, 4H), 3.81-3.93 (m, 1H), 3.64-3.77 (m, 2H), 2.50-2.57 (m, 2H), 2.29-2.38 (m, 1H), 2.16-2.24 (m, 1H).

Example 1315

N-(2-((5-bromo-4-((2-cyano-3-(2,3-dihydrobenzo[b][1,4]dioxin-6-yl)benzyl)oxy)-2-((3-cyanobenzyl)oxy)benzyl)amino)ethyl)acetamide

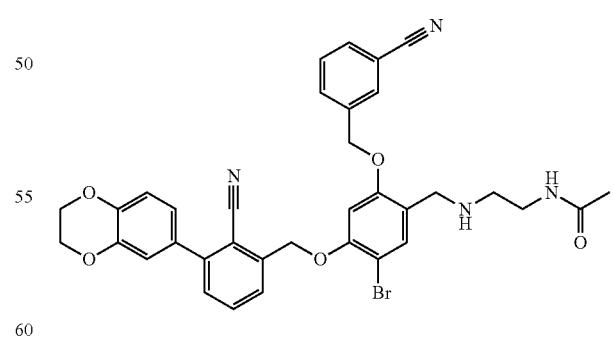

$^1$H NMR (500 MHz, DMSO-d$_6$) δ 7.91 (s, 1H), 7.78-7.84 (m, 3H), 7.73-7.78 (m, 1H), 7.69 (d, J=7.3 Hz, 1H), 7.61 (t, J=7.7 Hz, 1H), 7.57 (d, J=7.3 Hz, 1H), 7.52 (s, 1H), 7.08-7.11 (m, 1H), 6.99-7.08 (m, 3H), 5.37 (s, 2H), 5.27 (s, 2H), 4.31 (s, 4H), 3.65 (s, 2H), 3.07-3.13 (m, 2H), 2.52 (t, J=6.2 Hz, 2H), 1.77 (s, 3H).

Intermediate 5-((4-bromo-5-(3-(2,3-dihydrobenzo[b][1,4]dioxin-6-yl)-2-methylbenzyloxy)-2-formylphenoxy)methyl)nicotinonitrile

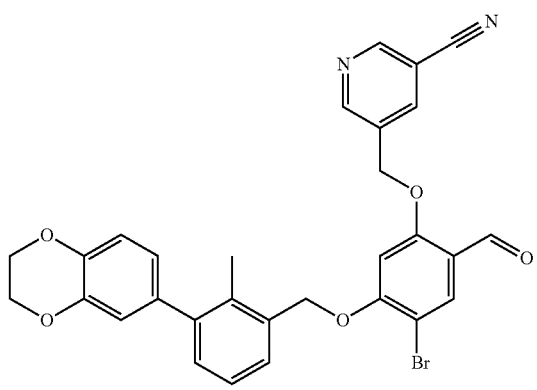 [SMILES: Cc1c(COc2cc(OCc3cncc(C#N)c3)c(C=O)cc2Br)cccc1-c1ccc2c(c1)OCCO2]

To a solution of 5-bromo-4-((3-(2,3-dihydrobenzo[b][1,4]dioxin-6-yl)-2-methylbenzyl)oxy)-2-hydroxybenzaldehyde (106 mg, 0.233 mmol) in DMF (3 mL), 5-(chloromethyl)nicotinonitrile (39.1 mg, 0.256 mmol) and cesium carbonate (152 mg, 0.466 mmol) were added. The reaction mixture was stirred at 75° C. for 3 hr. LC/MS shown completion of reaction. Water was added and a beige solid was collected as final product 5-((4-bromo-5-((3-(2,3-dihydrobenzo[b][1,4]dioxin-6-yl)-2-methylbenzyl)oxy)-2-formylphenoxy)methyl)nicotinonitrile (110 mg, 0.193 mmol, 83% yield). LC/MS method T: 4.36 min, 571, 573 (MH+). $^1$H NMR (400 Mhz, CDCl$_3$) δ: 10.27 (s, 1H), 8.92 (s, 2H), 8.10 (s, 2H), 7.44 (t, J=4.5 Hz, 1H), 7.22-7.34 (m, 2H), 6.94 (d, J=8.1 Hz, 1H), 6.84 (d, J=2.0 Hz, 1H), 6.79 (dd, J=8.2, 2.1 Hz, 1H), 6.63 (s, 1H), 5.26 (s, 2H), 5.24 (s, 2H), 4.33 (s, 4H), 2.32 (s, 3H).

The following examples were prepared in the same manner as (S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid from 5-((4-bromo-5-(3-(2,3-dihydrobenzo[b][1,4]dioxin-6-yl)-2-methylbenzyloxy)-2-formylphenoxy)methyl)nicotinonitrile and the appropriate amine.

Example 1316

(S)-4-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxybutanoic acid

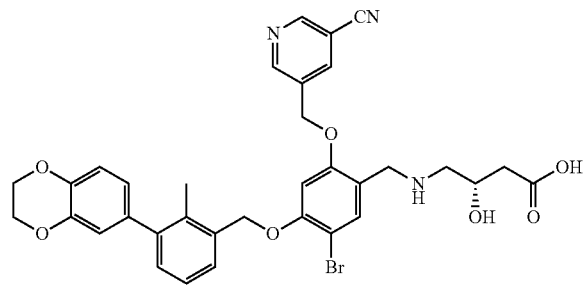 [SMILES: Cc1c(COc2cc(OCc3cncc(C#N)c3)c(CNC[C@@H](O)CC(=O)O)cc2Br)cccc1-c1ccc2c(c1)OCCO2]

$^1$H NMR (DMSO-d$_6$) δ 8.98-9.05 (m, 2H), 8.45 (s, 1H), 7.55 (s, 1H), 7.48 (d, J=7.7 Hz, 1H), 7.25 (t, J=7.5 Hz, 1H), 7.18 (d, J=7.0 Hz, 1H), 7.09 (s, 1H), 6.94 (d, J=8.1 Hz, 1H), 6.79 (s, 1H), 6.75-6.78 (m, 1H), 5.34 (s, 2H), 5.25 (s, 2H), 4.29 (s, 4H), 3.82-3.94 (m, 1H), 3.66-3.76 (m, 2H), 2.55 (d, J=5.5 Hz, 2H), 2.33-2.41 (m, 1H), 2.18-2.28 (m, 4H).

Example 1317

N-(2-(5-bromo-2-((5-cyanopyridin-3-yl)methoxy)-4-(3-(2,3-dihydrobenzo[b][1,4]dioxin-6-yl)-2-methylbenzyloxy)benzylamino)ethyl)acetamide

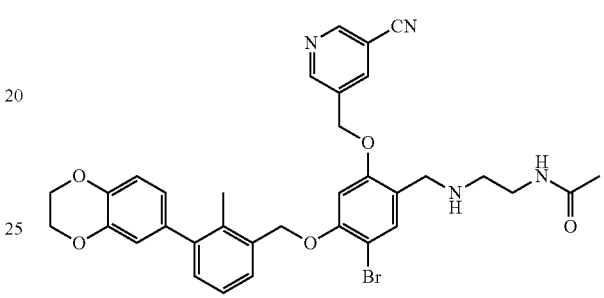

$^1$H NMR (DMSO-d$_6$) δ 9.02 (s, 1H), 8.99 (s, 1H), 8.44 (s, 1H), 7.76-7.83 (m, 1H), 7.52 (s, 1H), 7.48 (d, J=7.3 Hz, 1H), 7.25 (t, J=7.5 Hz, 1H), 7.18 (d, J=7.3 Hz, 1H), 7.07 (s, 1H), 6.94 (d, J=8.1 Hz, 1H), 6.79 (s, 1H), 6.76 (d, J=8.1 Hz, 1H), 5.33 (s, 2H), 5.24 (s, 2H), 4.29 (s, 4H), 3.50-3.75 (m, 2H), 3.08-3.15 (m, 2H), 2.50-2.55 (m, 2H), 2.26 (s, 3H), 1.78 (s, 3H).

Example 1318

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxypropanoic acid

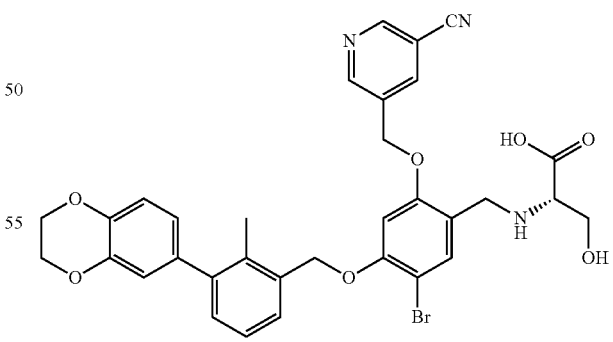

$^1$H NMR (DMSO-d$_6$) δ 9.04 (s, 1H), 9.02 (s, 1H), 8.53 (s, 1H), 7.61 (s, 1H), 7.48 (d, J=7.7 Hz, 1H), 7.25 (t, J=7.5 Hz, 1H), 7.18 (d, J=7.7 Hz, 1H), 7.10 (s, 1H), 6.93 (d, J=8.4 Hz, 1H), 6.79 (s, 1H), 6.76 (d, J=8.1 Hz, 1H), 5.30-5.41 (m, 2H), 5.25 (s, 2H), 4.29 (s, 4H), 3.30-3.65 (m, 4H), 3.01 (t, J=6.1 Hz, 1H), 2.25 (s, 3H).

Example 1319

(S)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid

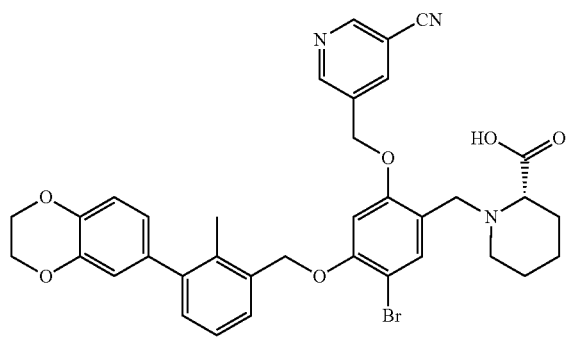 [SMILES: Cc1c(COc2cc(OCc3cncc(C#N)c3)c(CN3CCCC[C@H]3C(=O)O)cc2Br)cccc1-c1ccc2c(c1)OCCO2]

$^1$H NMR (DMSO-d$_6$) δ 8.99-9.03 (m, 2H), 8.47 (s, 1H), 7.58 (s, 1H), 7.49 (d, J=7.3 Hz, 1H), 7.22-7.29 (m, 1H), 7.16-7.21 (m, 1H), 7.08 (s, 1H), 6.93 (d, J=8.1 Hz, 1H), 6.79 (s, 1H), 6.77 (d, J=8.1 Hz, 1H), 5.34 (s, 2H), 5.24 (s, 2H), 4.29 (s, 5H), 3.50-3.85 (m, 3H), 2.86-2.91 (m, 1H), 2.18-2.28 (m, 4H), 1.65-1.83 (m, 2H), 1.43-1.55 (m, 3H), 1.30-1.39 (m, 1H).

Example 1320

(R)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid

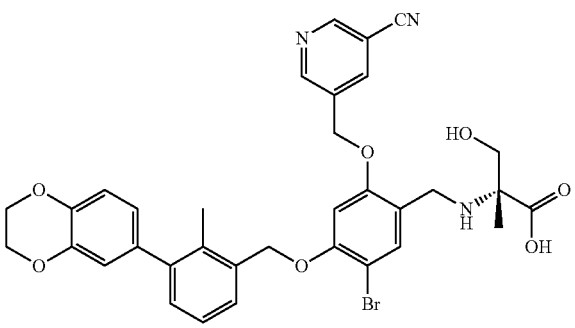 [SMILES: Cc1c(COc2cc(OCc3cncc(C#N)c3)c(CN[C@](C)(CO)C(=O)O)cc2Br)cccc1-c1ccc2c(c1)OCCO2]

$^1$H NMR (DMSO-d$_6$) δ 9.03 (s, 1H), 9.01 (s, 1H), 8.52 (s, 1H), 7.67 (s, 1H), 7.47 (d, J=7.3 Hz, 1H), 7.21-7.28 (m, 1H), 7.15-7.20 (m, 1H), 7.09 (s, 1H), 6.93 (d, J=8.1 Hz, 1H), 6.78 (s, 1H), 6.72-6.78 (m, 1H), 5.36 (s, 2H), 5.27 (s, 2H), 4.29 (s, 4H), 3.30-3.64 (m, 4H), 2.25 (s, 3H), 1.21 (s, 3H).

Example 1321

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid

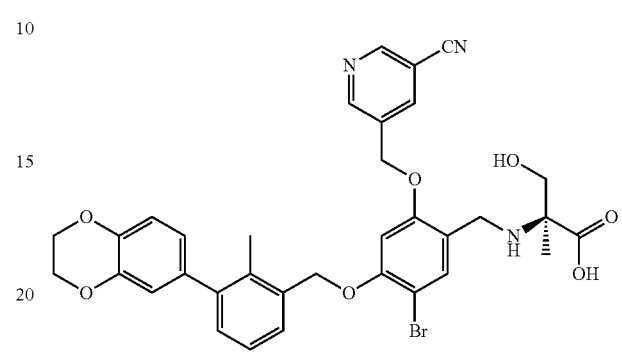

$^1$H NMR (DMSO-d$_6$) δ 9.03 (s, 1H), 9.01 (d, J=1.5 Hz, 1H), 8.52 (s, 1H), 7.67 (s, 1H), 7.47 (d, J=7.3 Hz, 1H), 7.22-7.27 (m, 1H), 7.16-7.20 (m, 1H), 7.10 (s, 1H), 6.93 (d, J=8.1 Hz, 1H), 6.79 (d, J=1.8 Hz, 1H), 6.76 (dd, J=8.1, 1.8 Hz, 1H), 5.36 (s, 2H), 5.27 (s, 2H), 4.29 (s, 5H), 3.24-3.61 (m, 4H), 2.25 (s, 3H), 1.21 (s, 3H).

Example 1322

5-((4-bromo-5-(3-(2,3-dihydrobenzo[b][1,4]dioxin-6-yl)-2-methylbenzyloxy)-2-((2-hydroxyethylamino)methyl)phenoxy)methyl)nicotinonitrile

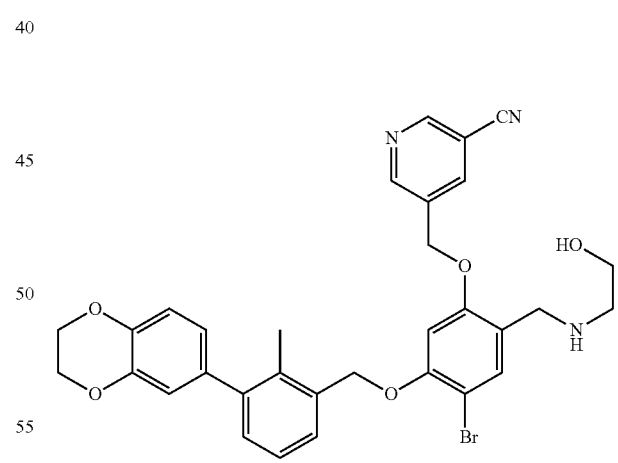

$^1$H NMR (DMSO-d$_6$) δ 9.03 (d, J=1.8 Hz, 1H), 9.00 (s, 1H), 8.44 (s, 1H), 7.54 (s, 1H), 7.48 (d, J=7.0 Hz, 1H), 7.22-7.28 (m, 1H), 7.18 (d, J=7.3 Hz, 1H), 7.09 (s, 1H), 6.94 (d, J=8.1 Hz, 1H), 6.79 (d, J=1.8 Hz, 1H), 6.76 (dd, J=8.3, 2.0 Hz, 1H), 5.34 (s, 2H), 5.24 (s, 2H), 4.29 (s, 4H), 3.72 (s, 2H), 3.48 (t, J=5.5 Hz, 2H), 2.59 (t, J=5.5 Hz, 2H), 2.26 (s, 3H).

Example 1323

(R)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid

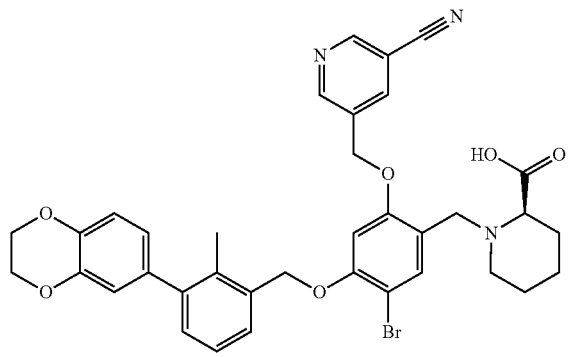

¹H NMR (DMSO-d₆) δ 8.99-9.03 (m, 2H), 8.47 (s, 1H), 7.58 (s, 1H), 7.48 (d, J=7.3 Hz, 1H), 7.22-7.29 (m, 1H), 7.19 (d, J=7.3 Hz, 1H), 7.10 (s, 1H), 6.93 (d, J=8.1 Hz, 1H), 6.79 (d, J=1.8 Hz, 1H), 6.76 (dd, J=8.1, 1.8 Hz, 1H), 5.31-5.40 (m, 2H), 5.25 (s, 2H), 4.29 (s, 4H), 3.83 (d, J=13.9 Hz, 1H), 3.66 (d, J=13.9 Hz, 1H), 3.13-3.17 (m, 1H), 2.90-2.95 (m, 1H), 2.29-2.36 (m, 1H), 2.26 (s, 3H), 1.67-1.87 (m, 2H), 1.50 (br. s., 3H), 1.32-1.42 (m, 1H).

| Example | LCMS Method | RT (min) | M + 1 | M − 1 |
|---|---|---|---|---|
| Example 1322: 5-((4-bromo-5-(3-(2,3-dihydrobenzo[b][1,4]dioxin-6-yl)-2-methylbenzyloxy)-2-((2-hydroxyethylamino)methyl)phenoxy)methyl)nicotinonitrile | A | 1.92 | 616.2 | |
| Example 1323: (R)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid | A | 1.81 | 684.2 | |
| Example 1321: (S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid | A | 1.76 | 674.1 | |
| Example 1318: (S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxypropanoic acid | A | 1.73 | 660.2 | |
| Example 1319: (S)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid | A | 1.82 | 684.3 | |
| Example 1320: (R)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid | A | 1.76 | 674.3 | |
| Example 1316: (S)-4-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxybutanoic acid | M | 2.74 | | 672.2 |
| Example 1317: N-(2-(5-bromo-2-((5-cyanopyridin-3-yl)methoxy)-4-(3-(2,3-dihydrobenzo[b][1,4]dioxin-6-yl)-2-methylbenzyloxy)benzylamino)ethyl)acetamide | A | 1.93 | 657.2 | |

Intermediate 5-((2-formyl-5-((2-methylbiphenyl-3-yl)methoxy)phenoxy)methyl)-4-methylnicotinonitrile

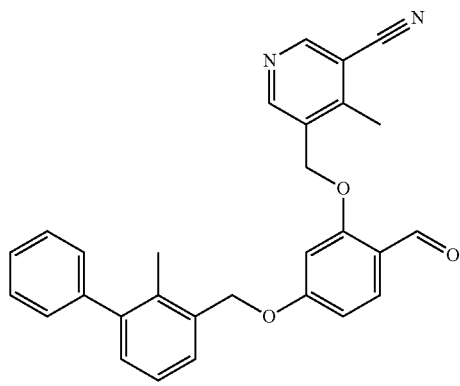 [SMILES: Cc1c(C#N)cncc1COc1cc(OCc2cccc(-c3ccccc3)c2C)ccc1C=O]

To a dimethyl formamide (4 mL) mixture of cesium carbonate (101 mg, 0.311 mmol) was added 2-hydroxy-4-((2-methyl-[1,1'-biphenyl]-3-yl)methoxy)benzaldehyde (66 mg, 0.207 mmol), followed by 5-(chloromethyl)-4-methylnicotinonitrile (51.8 mg, 0.311 mmol). Heated at room temperature for 3 hours. The mixture was neutralized with dilute hydrochloric acid (0.1 N) and washed with water and brine and dried over sodium sulfate. The residue was purified with 3:1 hexane:ethyl acetate on a 12 g silica gel column Collected fractions to afford the title compound as a white film, 73 mg (80% yield). ¹H NMR (CHLOROFORM-d) δ: 10.29 (s, 1H), 8.83 (s, 1H), 8.86 (s, 1H), 7.93 (d, 1H), 7.42-7.50 (m, 3H), 7.37-7.42 (m, 1H), 7.30-7.36 (m, 4H), 7.29 (s, 5H), 6.80 (m, 1H), 6.69 (d, 1H), 5.21 (d, 4H), 2.65 (s, 3H), 2.29 (s, 3H), 1.61 (br. s., 9H). LCMS: 1.49 minutes, M+1=149.2, EM=148.1 (Start % B=0, Final % B=98, Gradient Time=1.5 min, Flow Rate=0.8 mL/min, Wavelength=220).

Intermediate

5-(chloromethyl)-4-methylnicotinonitrile

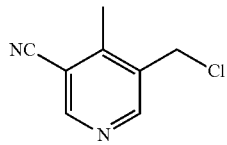

A mixture of (5-bromo-4-methylpyridin-3-yl)methanol (100 mg, 0.495 mmol) and Copper(I)cyanide (111 mg, 1.237 mmol) in Pyridine (2 mL) was heated for 20 hrs in a sealed tube at 160° C. After cooling to room temperature, the reaction was taken up in 1 mL of concentrated aqueous ammonia and 3 mL of saturated ammonium chloride solution Stirred for 2 hours. The mixture was then extracted with a dichloromethane:isopropyl alcohol (85:15) solution, dried over sodium sulfate and then concentrated under reduced pressure and used in next step.

To a dichloromethane (3 mL) solution of 5-(hydroxymethyl)-4-methylnicotinonitrile (100 mg, 0.675 mmol) was added thionyl chloride (0.099 mL, 1.350 mmol) and the reaction was stirred at room temperature overnight. TLC showed the reaction was complete. The solvent was removed and the crude was diluted with ethyl acetate and washed with sodium bicarbonate and brine. Concentrated and obtained light brown oil (80 mg, 70% yield).

Example 1324

(R)-2-(2-((5-cyano-4-methylpyridin-3-yl)methoxy)-4-((2-methylbiphenyl-3-yl)methoxy)benzylamino)-3-hydroxypropanoic acid

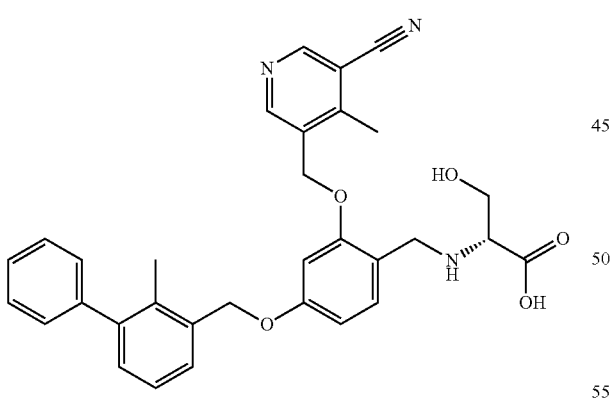

A dimethyl formamide (2 mL) solution of 5-((2-formyl-5-((2-methyl-[1,1'-biphenyl]-3-yl)methoxy)phenoxy) methyl)-4-methylnicotinonitrile (20 mg, 0.045 mmol) and (R)-2-amino-3-hydroxypropanoic acid (14.06 mg, 0.134 mmol) was stirred at room temperature for 1 hour. Sodium cyanoborohydride (8.41 mg, 0.134 mmol) and 3 drops of acetic acid (2.55 µl, 0.045 mmol) were added and the reaction was stirred at room temperature overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 96%. $^1$H NMR (DMSO-$d_6$) δ 8.92 (d, 2H), 7.47 (m, 3H), 7.27-7.41 (m, 5H), 7.21 (d, 1H), 6.98 (s, 1H), 6.75 (d, 1H), 5.26-5.34 (m, 2H), 5.18 (s, 2H), 3.96-4.07 (m, 2H), 3.68 (d, 1H), 3.60 (m, 1H), 3.15 (m, 1H), 2.58 (s, 3H), 2.17-2.22 (m, 3H). LCMS Condition A: 1.91 minutes, M+1=538.3, M−1=536.3, EM=537.2.

Intermediate

3-((5-(3-(2,3-dihydrobenzo[b][1,4]dioxin-6-yl)-2-methylbenzyloxy)-2-formylphenoxy)methyl)benzamide

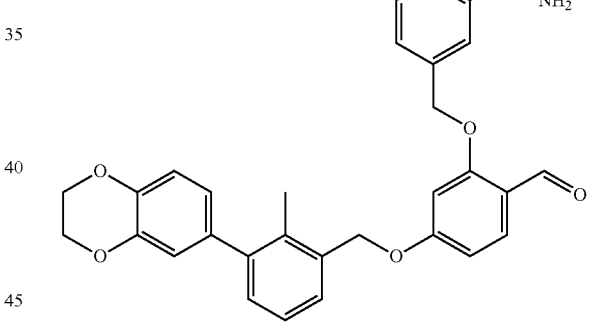

A dimethyl formamide (6 mL) mixture of cesium carbonate (260 mg, 0.797 mmol), 4-((3-(2,3-dihydrobenzo[b][1,4] dioxin-6-yl)-2-methylbenzyl)oxy)-2-hydroxybenzaldehyde (200 mg, 0.531 mmol), and 3-(chloromethyl)benzamide (111 mg, 0.638 mmol) was heated at 75° C. for 4 hours. LC/MS indicated ~60% conversion. The reaction mixture was neutralized with dilute hydrochloric acid (0.1 N) and washed with water and brine and dried over sodium sulfate. The residue was purified with 3:1 hexane:ethyl acetate on a 12 g silica gel column Collected fractions to afford the light yellow solid, 120 mg (42% yield, 95% pure). LCMS Condition A: 1.33 minutes, M+1=510.3, EM=509.2.

Example 1325

(R)-2-((2-((3-carbamoylbenzyl)oxy)-4-((3-(2,3-dihydrobenzo[b][1,4]dioxin-6-yl)-2-methylbenzyl)oxy)benzyl)amino)-3-hydroxypropanoic acid

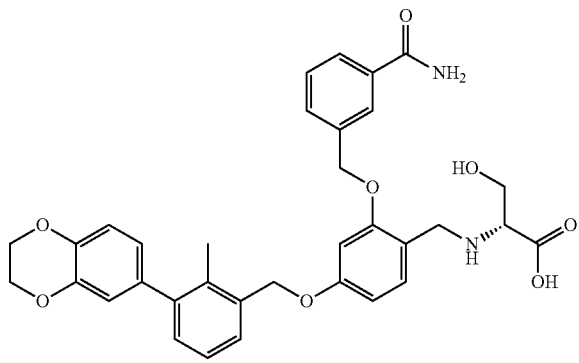 [SMILES: Cc1c(COc2ccc(CN[C@H](CO)C(=O)O)c(OCc3cccc(C(N)=O)c3)c2)cccc1-c1ccc2c(c1)OCCO2]

A dimethyl formamide (2 mL) solution of 3-((5-((3-(2,3-dihydrobenzo[b][1,4]dioxin-6-yl)-2-methylbenzyl)oxy)-2-formylphenoxy)methyl)benzamide (20 mg, 0.039 mmol) and D-serine (12.37 mg, 0.118 mmol) was stirred at room temperature for 1 hr. Sodium cyanoborohydride (7.40 mg, 0.118 mmol) and 3 drops of acetic acid (2.247 μl, 0.039 mmol) were added and the reaction was stirred at room temperature for 48 hours. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min Fractions containing the desired product were combined and dried via centrifugal evaporation. The yield of the product was 7.2 mg, and its estimated purity by LCMS analysis was 99%. $^1$H NMR (DMSO-$d_6$) δ 8.90 (br. s., 1H), 8.24 (s, 1H), 7.86 (d, 1H), 7.64 (d, 1H), 7.47 (m, 1H), 7.39 (d, 1H), 7.42 (d, 1H), 7.22-7.28 (m, 2H), 7.17 (d, 1H), 6.93 (d, 1H), 6.87 (s, 1H), 6.79 (s, 1H), 6.76 (d, 1H), 6.72 (d, 1H), 5.21 (s, 2H), 5.14 (s, 2H), 4.29 (s, 4H), 4.22 (d, 1H), 4.03 (d, 1H), 3.76 (m, 1H), 3.65 (m, 1H), 2.21 (s, 3H), 1.91 (s, 1H). LCMS Condition A: 1.65 minutes, M+1=599.3, M−1=597.4, EM=598.2.

Example 1326

(R)-2-((2-((3-carbamoylbenzyl)oxy)-4-((3-(2,3-dihydrobenzo[b][1,4]dioxin-6-yl)-2-methylbenzyl)oxy)benzyl)amino)-3-hydroxy-2-methylpropanoic acid

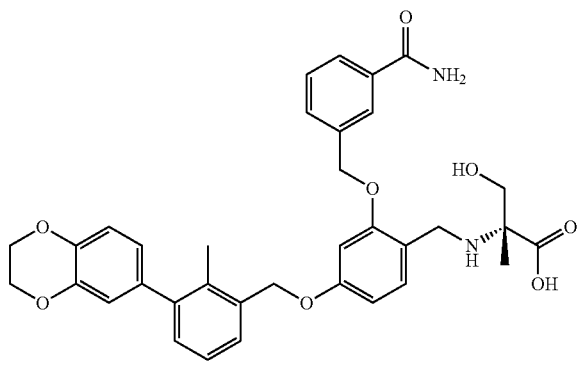 [SMILES: Cc1c(COc2ccc(CN[C@](C)(CO)C(=O)O)c(OCc3cccc(C(N)=O)c3)c2)cccc1-c1ccc2c(c1)OCCO2]

A dimethyl formamide (2 mL) solution of 3-((5-((3-(2,3-dihydrobenzo[b][1,4]dioxin-6-yl)-2-methylbenzyl)oxy)-2-formylphenoxy)methyl)benzamide (20 mg, 0.039 mmol) and (R)-2-amino-3-hydroxy-2-methylpropanoic acid (14.03 mg, 0.118 mmol) was stirred at room temperature for 1 hr. Sodium cyanoborohydride (7.40 mg, 0.118 mmol) and 3 drops of acetic acid (2.247 μl, 0.039 mmol) were added and the reaction was stirred at room temperature for a week. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 98%. $^1$H NMR (DMSO-$d_6$) δ 8.84 (br. s., 1H), 8.23 (s, 1H), 7.96 (s, 1H), 7.85 (d, 1H), 7.65 (d, 1H), 7.46 (m, 1H), 7.41 (d, 1H), 7.37 (d, 1H), 7.19-7.27 (m, 2H), 7.17 (d, 1H), 6.93 (d, 1H), 6.88 (s, 1H), 6.73-6.81 (m, 2H), 6.71 (d, 1H), 5.23 (s, 2H), 5.15 (s, 2H), 4.29 (s, 4H), 3.99-4.11 (m, 2H), 3.64-3.69 (m, 1H), 3.56 (d, 1H), 3.18 (s, 1H), 2.20 (s, 3H), 1.26 (s, 3H). LCMS Condition A: 1.67 minutes, M+1=613.3, M−1=611.2, EM=612.2.

Intermediate 5-((2-formyl-5-((2-methylbiphenyl-3-yl)methoxy)phenoxy)methyl)nicotinonitrile

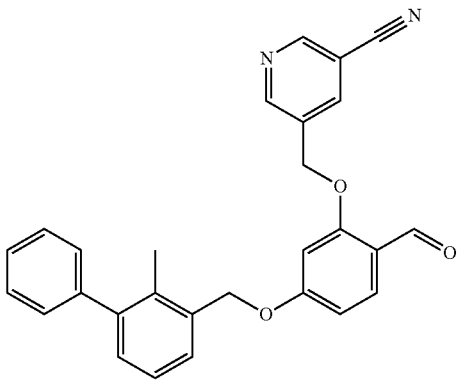 [SMILES: Cc1c(COc2ccc(C=O)c(OCc3cncc(C#N)c3)c2)cccc1-c1ccccc1]

To a dimethyl formamide (6 mL) mixture of cesium carbonate (230 mg, 0.707 mmol) were added 2-hydroxy-4-((2-methyl-[1,1'-biphenyl]-3-yl)methoxy)benzaldehyde (150 mg, 0.471 mmol) and 5-(chloromethyl)nicotinonitrile (86 mg, 0.565 mmol). The reaction was heated at 75° C. overnight. The mixture was neutralized with dilute hydrochloric acid (0.1 N) and washed with water and brine and dried over sodium sulfate. The residue was purified with 1:1 hexane:ethyl acetate on a 24 g silica gel column) Collected fractions to afford the light yellow solid, 100 mg (49% yield).

$^1$H NMR (DMSO-$d_6$) δ 10.28 (s, 1H), 8.97-9.07 (m, 2H), 8.54 (s, 1H), 7.75 (d, 1H), 7.47 (m, 3H), 7.37-7.42 (m, 1H), 7.28-7.35 (m, 3H), 7.23 (d, 1H), 7.00 (s, 1H), 6.87 (d, 1H), 5.42 (s, 2H), 5.30 (s, 2H), 2.21 (s, 3H). LCMS Condition A: 2.24 minutes, M+1=435.5, EM=434.4.

Example 1327

(R)-2-((2-((5-cyanopyridin-3-yl)methoxy)-4-((2-methyl-[1,1'-biphenyl]-3-yl)methoxy)benzyl)amino)-3-hydroxypropanoic acid

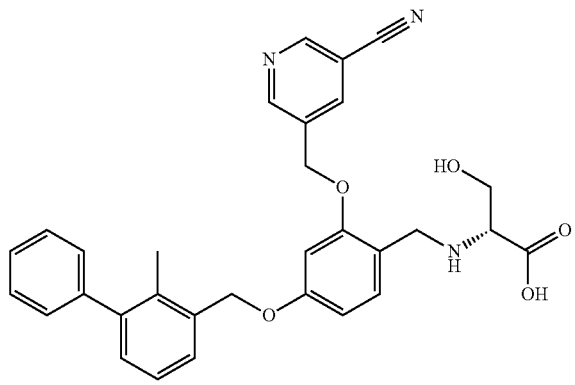 [SMILES: Cc1c(COc2ccc(CN[C@H](CO)C(=O)O)c(OCc3cncc(C#N)c3)c2)cccc1-c1ccccc1]

A dimethyl formamide (2 mL) solution of 5-((2-formyl-5-((2-methylbiphenyl-3-yl)methoxy)phenoxy)methyl) nicotinonitrile (15 mg, 0.035 mmol) and (R)-2-amino-3-hydroxypropanoic acid (10.88 mg, 0.104 mmol) was stirred at room temperature for 1 hr. Sodium cyanoborohydride (6.51 mg, 0.104 mmol) and 3 drops of acetic acid (1.976 µl, 0.035 mmol) were added and the reaction was stirred at room temperature for 48 hours. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 5.1 mg, and its estimated purity by LCMS analysis was 99%. $^1$H NMR (DMSO-d$_6$) δ: 9.01 (s, 1H), 9.04 (s, 1H), 8.53 (s, 1H), 7.96 (s, 1H), 7.43-7.49 (m, 3H), 7.26-7.41 (m, 5H), 7.21 (d, 1H), 6.87 (s, 1H), 6.74 (d, 1H), 5.23-5.35 (m, 2H), 5.16 (s, 2H), 4.09 (d, 1H), 4.01 (d, 1H), 3.70 (d, 1H), 3.62 (m, 1H), 3.13 (m, 1H), 2.20 (s, 3H), 1.91 (s, 1H). LCMS Condition A: 1.79 minutes, M+1=524.3, M−1=522.3, EM=523.2.

The following examples were prepared in the same manner as (R)-2-((2-((5-cyanopyridin-3-yl)methoxy)-4-((2-methyl-[1,1'-biphenyl]-3-yl)methoxy)benzyl)amino) -3-hydroxypropanoic acid from 5-((2-formyl-5-((2-methylbiphenyl-3-yl)methoxy)phenoxy)methyl) nicotinonitrile and the appropriate amine.

Example 1328

(S)-4-((2-((5-cyanopyridin-3-yl)methoxy)-4-((2-methyl-[1,1'-biphenyl]-3-yl)methoxy)benzyl)amino)-3-hydroxybutanoic acid

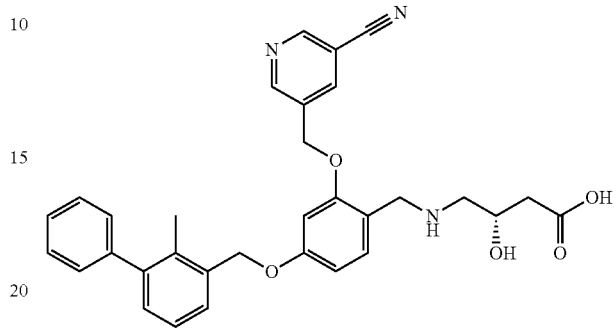

$^1$H NMR (DMSO-d$_6$) δ 8.98-9.02 (m, 2H), 8.45 (s, 1H), 7.44-7.50 (m, 3H), 7.37-7.41 (m, 1H), 7.26-7.35 (m, 4H), 7.21 (d, 1H), 6.81-6.84 (m, 1H), 6.71 (d, 1H), 5.27 (s, 2H), 5.15 (s, 2H), 3.85-3.94 (m, 2H), 3.71-3.85 (m, 1H), 2.60 (d, 2H), 2.36 (m, 1H), 2.17-2.27 (m, 4H), 1.90 (s, 2H). LCMS Condition A: 1.73 minutes, M+1=538.3, M−1=536.3, EM=537.2.

Example 1329

(S)-1-(2-((5-cyanopyridin-3-yl)methoxy)-4-((2-methyl-[1,1'-biphenyl]-3-yl)methoxy)benzyl)piperidine-2-carboxylic acid

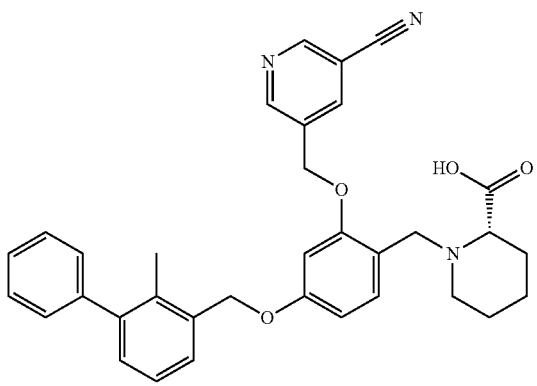 [SMILES: Cc1c(COc2ccc(CN3CCCC[C@H]3C(=O)O)c(OCc3cncc(C#N)c3)c2)cccc1-c1ccccc1]

$^1$H NMR (DMSO-d$_6$) δ 9.01 (br. s., 2H), 8.48 (s, 1H), 7.44-7.49 (m, 3H), 7.37-7.41 (m, 1H), 7.26-7.35 (m, 4H), 7.21 (d, 1H), 6.84 (s, 1H), 6.73 (d, 1H), 5.25-5.32 (m, 2H), 5.15 (s, 2H), 3.93 (d, 1H), 3.74 (d, 1H), 2.95 (br. s., 1H), 2.38 (br. s., 1H), 2.20 (s, 3H), 1.81 (br. s., 1H), 1.76 (d, 1H), 1.51 (br. s., 3H), 1.36 (br. s., 1H). LCMS Condition A: 1.74 minutes, M+1=548.5, M−1=546.5, EM=547.3.

Intermediate 5-((5-(3-(2,3-dihydrobenzo[b][1,4]dioxin-6-yl)-2-methylbenzyloxy)-2-formylphenoxy)methyl)-2-fluorobenzonitrile

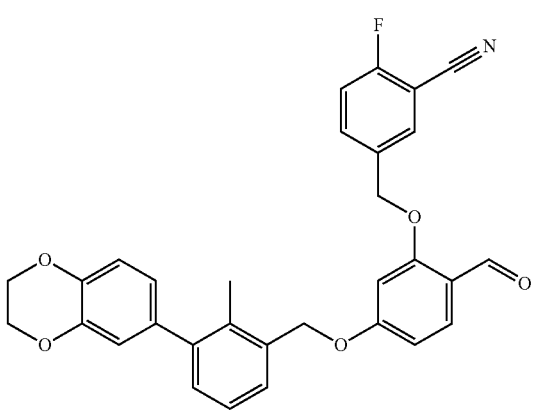 [SMILES: Cc1c(COc2ccc(C=O)c(OCc3ccc(F)c(C#N)c3)c2)cccc1-c1ccc2c(c1)OCCO2]

To a dimethyl formamide (1 mL) mixture of potassium carbonate (26.4 mg, 0.191 mmol) and added 4-((3-(2,3-dihydrobenzo[b][1,4]dioxin-6-yl)-2-methylbenzyl)oxy)-2-hydroxybenzaldehyde (24 mg, 0.064 mmol) was added 5-(bromomethyl)-2-fluorobenzonitrile (20.47 mg, 0.096 mmol). The reaction was stirred at room temperature overnight. The reaction was neutralized with dilute hydrochloric acid (0.1 N) and washed with water and brine and dried over sodium sulfate. The residue was purified with 2:1 hexane:ethyl acetate; 12 g silica gel column) Collected fractions to afford the title compound as a white film, 15 mg (46% yield). LCMS Condition A: 1.52 minutes, M+1=510.3, EM=509.2.

Example 1330

(S)-4-((2-((3-cyano-4-fluorobenzyl)oxy)-4-((3-(2,3-dihydrobenzo[b][1,4]dioxin-6-yl)-2-methylbenzyl)oxy)benzyl)amino)-3-hydroxybutanoic acid

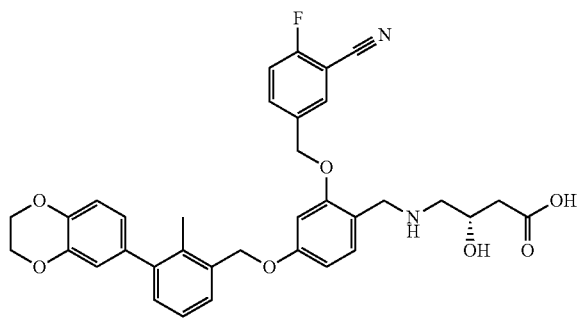 [SMILES: Cc1c(COc2ccc(CNC[C@@H](O)CC(=O)O)c(OCc3ccc(F)c(C#N)c3)c2)cccc1-c1ccc2c(c1)OCCO2]

A dimethyl formamide (2 mL) solution of 5-((5-((3-(2,3-dihydrobenzo[b][1,4]dioxin-6-yl)-2-methylbenzyl)oxy)-2-formylphenoxy)methyl)-2-fluorobenzonitrile (15 mg, 0.029 mmol) and (S)-4-amino-3-hydroxybutanoic acid (10.52 mg, 0.088 mmol) was stirred at room temperature for 1 hr. Sodium cyanoborohydride (5.55 mg, 0.088 mmol) and 3 drops of acetic acid (1.685 µl, 0.029 mmol) were added and the reaction was stirred at room temperature overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 30 minutes, then a 5-minute hold at 100% B; Flow: 20 mL/min Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 45-85% B over 20 minutes, then a 5-minute hold at 100% B; Flow: 20 mL/min. Fractions containing the desired product were combined and dried via centrifugal evaporation.

The yield of the product was 1.7 mg, and its estimated purity by LCMS analysis was 100%. $^1$H NMR (DMSO-$d_6$) δ 8.05 (d, 1H), 7.92 (d, 1H), 7.57 (m, 1H), 7.41 (d, 1H), 7.21-7.29 (m, 2H), 7.17 (d, 1H), 6.93 (d, 1H), 6.73-6.80 (m, 3H), 6.68 (d, 1H), 5.18 (s, 2H), 5.12 (s, 2H), 4.29 (s, 4H), 3.86-3.93 (m, 1H), 3.70-3.82 (m, 3H), 2.59 (d, 2H), 2.35 (m, 1H), 2.22-2.28 (m, 1H), 2.20 (s, 3H), 1.90 (s, 1H). LCMS Condition M: 2.8 minutes, M+1=613.3, M−1=611.3, EM=612.2.

Intermediate 2-fluoro-5-((2-formyl-5-((2-methylbiphenyl-3-yl)methoxy)phenoxy)methyl)benzonitrile

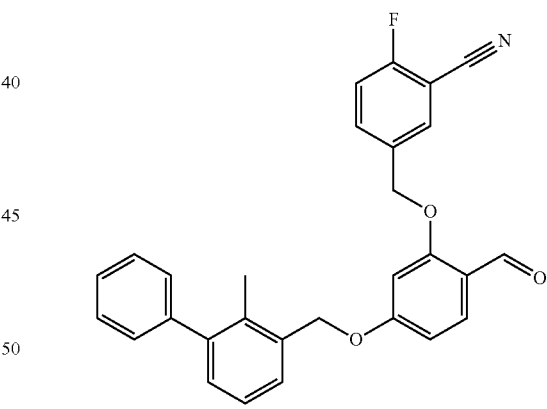

To a dimethyl formamide (4 mL) mixture of potassium carbonate (130 mg, 0.942 mmol) and 2-hydroxy-4-((2-methyl-[1,1'-biphenyl]-3-yl)methoxy)benzaldehyde (100 mg, 0.314 mmol) was added 5-(bromomethyl)-2-fluorobenzonitrile (101 mg, 0.471 mmol). The reaction was stirred at room temperature overnight. The reaction was neutralized with dilute hydrochloric acid (0.1 N) and washed with water and brine and dried over sodium sulfate. The residue was purified with 2:1 hexane:ethyl acetate on a 24 g silica gel column) Collected fractions to afford the title compound as a white film, 150 mg (100% yield). LCMS Condition A: 1.57 minutes, M+1=452.3, EM=451.2.

Example 1331

(S)-4-((2-((3-cyano-4-fluorobenzyl)oxy)-4-((2-methyl-[1,1'-biphenyl]-3-yl)methoxy)benzyl)amino)-3-hydroxybutanoic acid

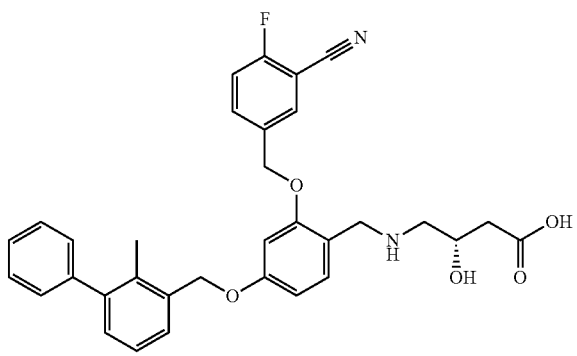 [SMILES: Cc1c(COc2ccc(CNC[C@@H](O)CC(=O)O)c(OCc3ccc(F)c(C#N)c3)c2)cccc1-c1ccccc1]

A dimethyl formamide (2 mL) solution of 2-fluoro-5-((2-formyl-5-((2-methyl-[1,1'-biphenyl]-3-yl)methoxy)phenoxy)methyl)benzonitrile (15 mg, 0.033 mmol) and (S)-4-amino-3-hydroxybutanoic acid (11.87 mg, 0.100 mmol) was stirred at room temperature for 1 hr. Sodium cyanoborohydride (6.26 mg, 0.100 mmol) and 3 drops of acetic acid (1.902 µl, 0.033 mmol) were added and the reaction was stirred at room temperature overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 45-95% B over 25 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 99%. $^1$H NMR (DMSO-$d_6$) δ 8.06 (d, 1H), 7.91-7.96 (m, 1H), 7.57 (m, 1H), 7.43-7.49 (m, 3H), 7.37-7.41 (m, 1H), 7.26-7.34 (m, 4H), 7.20 (d, 1H), 6.79 (s, 1H), 6.70 (d, 1H), 5.19 (s, 2H), 5.15 (s, 2H), 3.94 (m, 1H), 3.91 (s, 1H), 3.78-3.86 (m, 2H), 2.66 (d, 2H), 2.39 (m, 1H), 2.28 (m, 1H), 2.19 (s, 3H), 1.91 (s, 1H). LCMS Condition A: 1.85 minutes, M+1=555.3, M−1=553.3, EM=554.2.

The following examples were prepared in the same manner as (S)-4-((2-((3-cyano-4-fluorobenzyl)oxy)-4-((2-methyl-[1,1'-biphenyl]-3-yl)methoxy)benzyl)amino)-3-hydroxybutanoic acid from 2-fluoro-5-((2-formyl-5-((2-methylbiphenyl-3-yl)methoxy)phenoxy)methyl) benzonitrile and the appropriate amine. LCMS for these examples is given in tabular form.

Example 1114

N-(2-((2-((3-cyano-4-fluorobenzyl)oxy)-4-((2-methyl-[1,1'-biphenyl]-3-yl)methoxy)benzyl)amino)ethyl)acetamide

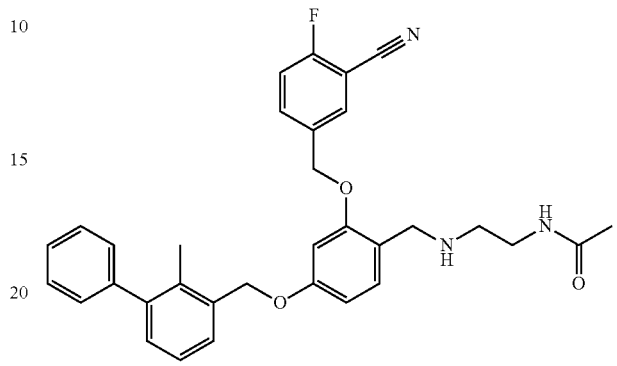

$^1$H NMR (DMSO-$d_6$) δ 8.03 (d, 1H), 7.90 (m, 1H), 7.79 (br. s., 1H), 7.58 (m, 1H), 7.43-7.49 (m, 3H), 7.37-7.41 (m, 1H), 7.32 (d, 2H), 7.18-7.30 (m, 3H), 6.76 (s, 1H), 6.67 (d, 1H), 5.17 (s, 2H), 5.13 (s, 2H), 3.66 (s, 2H), 3.13 (m, 2H), 2.53-2.57 (m, 2H), 2.20 (s, 3H), 1.77 (s, 3H).

Example 1332

(R)-2-((2-((3-cyano-4-fluorobenzyl)oxy)-4-((2-methyl-[1,1'-biphenyl]-3-yl)methoxy)benzyl)amino)-3-hydroxypropanoic acid

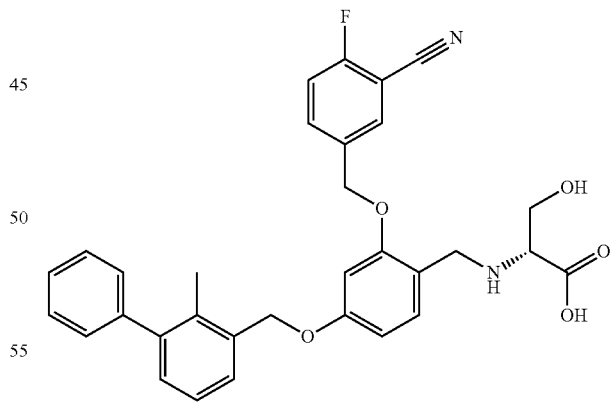

$^1$H NMR (DMSO-$d_6$) δ 8.14 (d, 1H), 8.01 (m, 1H), 7.56 (m, 1H), 7.43-7.49 (m, 3H), 7.34-7.41 (m, 2H), 7.26-7.34 (m, 3H), 7.20 (d, 1H), 6.84 (s, 1H), 6.71-6.75 (m, 1H), 5.18-5.26 (m, 2H), 5.16 (s, 2H), 4.12 (d, 1H), 4.05 (d, 1H), 3.77 (m, 1H), 3.65 (m, 1H), 3.18 (d, 1H), 2.19 (s, 3H).

Example 1333

(R)-2-((2-((3-cyano-4-fluorobenzyl)oxy)-4-((2-methyl-[1,1'-biphenyl]-3-yl)methoxy)benzyl)amino)-3-hydroxy-2-methylpropanoic acid

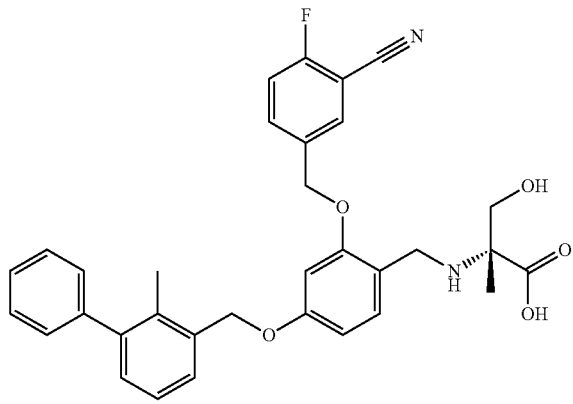 [SMILES: Cc1c(COc2ccc(CN[C@](C)(CO)C(=O)O)c(OCc3ccc(F)c(C#N)c3)c2)cccc1-c1ccccc1]

$^1$H NMR (DMSO-d$_6$) δ 8.12 (d, 1H), 8.02 (m, 1H), 7.55 (m, 1H), 7.43-7.49 (m, 3H), 7.37-7.41 (m, 2H), 7.26-7.33 (m, 3H), 7.20 (d, 1H), 6.82-6.85 (m, 1H), 6.73 (m, 1H), 5.21 (s, 2H), 5.17 (s, 2H), 4.02 (s, 2H), 3.65 (d, 1H), 3.56 (d, 1H), 2.19 (s, 3H), 1.23-1.28 (m, 3H).

Example 1334

(S)-1-(2-((3-cyano-4-fluorobenzyl)oxy)-4-((2-methyl-[1,1'-biphenyl]-3-yl)methoxy)benzyl)piperidine-2-carboxylic acid

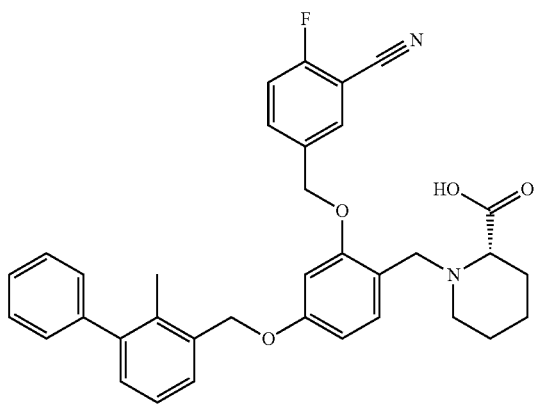 [SMILES: Cc1c(COc2ccc(CN3CCCC[C@H]3C(=O)O)c(OCc3ccc(F)c(C#N)c3)c2)cccc1-c1ccccc1]

$^1$H NMR (DMSO-d$_6$) δ 8.03-8.13 (m, 1H), 7.91-7.95 (m, 1H), 7.57 (m, 1H), 7.47 (m, 3H), 7.39 (m, 1H), 7.26-7.36 (m, 4H), 7.21 (d, 1H), 6.81 (d, 1H), 6.72 (m, 1H), 5.17-5.23 (m, 2H), 5.15 (s, 2H), 3.95 (d, 1H), 3.79 (d, 1H), 3.16 (m, 1H), 2.98 (d, 1H), 2.39-2.46 (m, 1H), 2.20 (s, 3H), 1.83 (br. s., 1H), 1.69-1.79 (m, 1H), 1.52 (br. s., 3H), 1.38 (br. s., 1H).

Intermediate ethyl 5-((4-chloro-5-((3-(2,3-dihydrobenzo[b][1,4]dioxin-6-yl)-2-methylbenzyl)oxy)-2-formylphenoxy)methyl)nicotinate

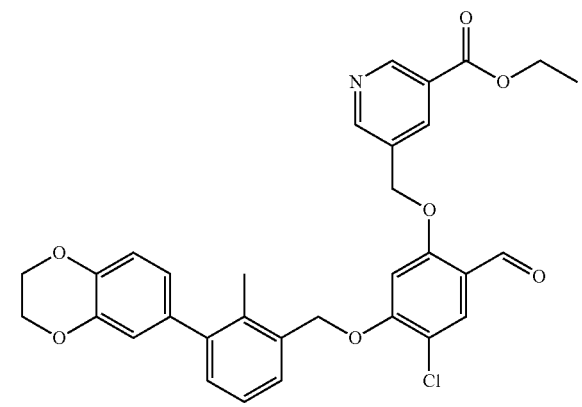 [SMILES: CCOC(=O)c1cncc(COc2cc(OCc3cccc(-c4ccc5c(c4)OCCO5)c3C)c(Cl)cc2C=O)c1]

A mixture of 5-chloro-4-((3-(2,3-dihydrobenzo[b][1,4]dioxin-6-yl)-2-methylbenzyl)oxy)-2-hydroxybenzaldehyde (200 mg, 0.487 mmol), ethyl 5-(bromomethyl)nicotinate (154 mg, 0.633 mmol), cesium carbonate (238 mg, 0.730 mmol) in DMF (4 mL) was stirred at room temperature for 18 hrs.

The reaction mixture was neutralized with diluted HCl (0.1 N) and washed with water and brine, dried over Na$_2$SO$_4$. The residue was purified via Biotage (2:1 Hexane/EtOAc; 24 g silicon column) The desired fractions were collected to afford 223 mg (80%) of the target compound as a light yellow solid. $^1$H NMR (400 MHz, CHLOROFORM-d) δ 10.33 (s, 1H), 9.27 (d, J=2.0 Hz, 1H), 8.88 (d, J=2.3 Hz, 1H), 8.42 (t, J=2.1 Hz, 1H), 7.94 (s, 1H), 7.47-7.40 (m, 1H), 7.33-7.26 (m, 2H), 6.94 (d, J=8.3 Hz, 1H), 6.85 (d, J=2.0 Hz, 1H), 6.80 (dd, J=8.2, 2.1 Hz, 1H), 6.70 (s, 1H), 5.26 (s, 2H), 5.25 (s, 2H), 4.47 (q, J=7.0 Hz, 2H), 4.33 (s, 4H), 2.32 (s, 3H), 1.45 (t, J=7.2 Hz, 3H).

Example 2000

(S)-2-((5-chloro-4-((3-(2,3-dihydrobenzo[b][1,4]dioxin-6-yl)-2-methylbenzyl)oxy)-2-((5-(ethoxycarbonyl)pyridin-3-yl)methoxy)benzyl)amino)-3-hydroxy-2-methylpropanoic acid

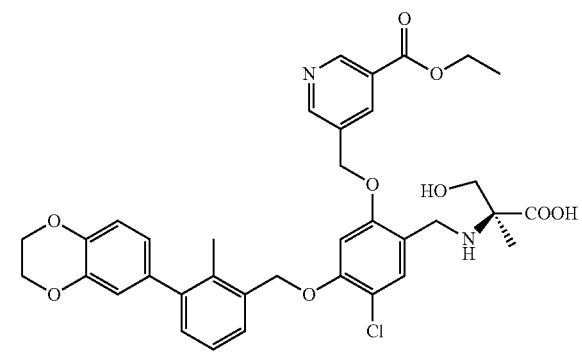 [SMILES: CCOC(=O)c1cncc(COc2cc(OCc3cccc(-c4ccc5c(c4)OCCO5)c3C)c(Cl)cc2CN[C@@](C)(CO)C(=O)O)c1]

A mixture of ethyl 5-((4-chloro-5-((3-(2,3-dihydrobenzo[b][1,4]dioxin-6-yl)-2-methylbenzyl)oxy)-2-formylphenoxy)methyl)nicotinate (30 mg, 0.052 mmol), (S)-2-amino-3-hydroxy-2-methylpropanoic acid (18.68 mg, 0.157 mmol) and sodium triacetoxyhydroborate (34.3 mg, 0.162 mmol) in DMF (1 mL) was stirred at room temperature for 20 hrs. The reaction mixture was filtered, and the solvent was removed. 60% of the resulting residue was used directly for the next reaction without further purification. 40% of the crude compound was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min Fractions containing the desired product were combined and dried via centrifugal evaporation. The yield of the product was 8.4 mg (59%). $^1$H NMR (500 MHz, DMSO-$d_6$) δ 9.06 (s, 1H), 9.00 (s, 1H), 8.46 (s, 1H), 7.55 (s, 1H), 7.45 (d, J=7.3 Hz, 1H), 7.28-7.21 (m, 1H), 7.20-7.13 (m, 2H), 6.93 (d, J=8.4 Hz, 1H), 6.80-6.72 (m, 2H), 5.39 (s, 2H), 5.27 (s, 2H), 4.36 (q, J=7.2 Hz, 2H), 4.28 (s, 4H), 3.95 (s, 2H), 3.61 (d, J=11.4 Hz, 1H), 3.4-3.52 (m, 1H), 2.23 (s, 3H), 1.33 (t, J=7.2 Hz, 3H), 1.23 (s, 3H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.78 min, ESI m/z 677 (M+1), 675 (M-1). LCMS (Injection 2 conditions) Rt=2.89 min, ESI m/z 677 (M+1), 675 (M-1).

Example 2001

(S)-5-((2-(((2-carboxy-1-hydroxypropan-2-yl)amino)methyl)-4-chloro-5-((3-(2,3-dihydrobenzo[b][1,4]dioxin-6-yl)-2-methylbenzyl)oxy)phenoxy)methyl)nicotinic acid

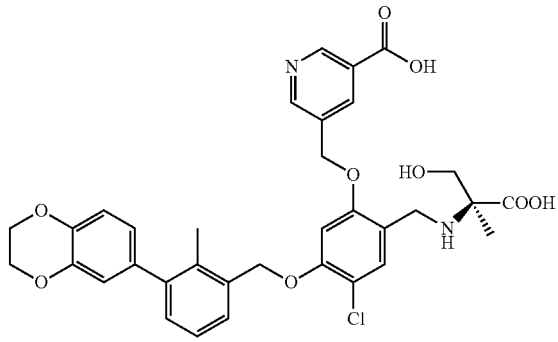 [SMILES: Cc1c(COc2cc(OCc3cncc(C(=O)O)c3)c(CN[C@@](C)(CO)C(=O)O)cc2Cl)cccc1-c1ccc2c(c1)OCCO2]

Lithium hydroxide (10.46 mg, 0.437 mmol) was added to a solution of (S)-2-((5-chloro-4-((3-(2,3-dihydrobenzo[b][1,4]dioxin-6-yl)-2-methylbenzyl)oxy)-2-((5-(ethoxycarbonyl)pyridin-3-yl)methoxy)benzyl)amino)-3-hydroxy-2-methylpropanoic acid (Example 2000) (21.13 mg, 0.0312 mmol) in THF (1 mL) and EtOH (1 mL), and the mixture was heated at 100° C. for 15 min. The solvent was removed, and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 minutes, then a 5-minute hold at 100% B; Flow: 20 mL/min. Fractions containing the desired product were combined and dried via centrifugal evaporation. The target compound was yield 4.5 mg (22%). $^1$H NMR (500 MHz, DMSO-$d_6$) δ 8.95 (s, 1H), 8.72 (s, 1H), 8.49 (s, 1H), 7.54 (s, 1H), 7.49 (d, J=7.3 Hz, 1H), 7.30-7.23 (m, 1H), 7.22-7.16 (m, 2H), 6.93 (d, J=8.1 Hz, 1H), 6.81-6.72 (m, 2H), 5.31 (d, J=12.5 Hz, 4H), 4.28 (s, 4H), 3.99 (s, 2H), 3.65 (d, J=11.0 Hz, 1H), 3.56 (d, J=11.0, 1H) 2.26 (s, 3H), 1.27 (s, 3H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.390 min, ESI m/z 649 (M+1), 647 (M-1).

LCMS (Injection 2 conditions) Rt=2.520 min, ESI m/z 649 (M+1), 647 (M-1).

Intermediate (S)-methyl 5-(((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoate

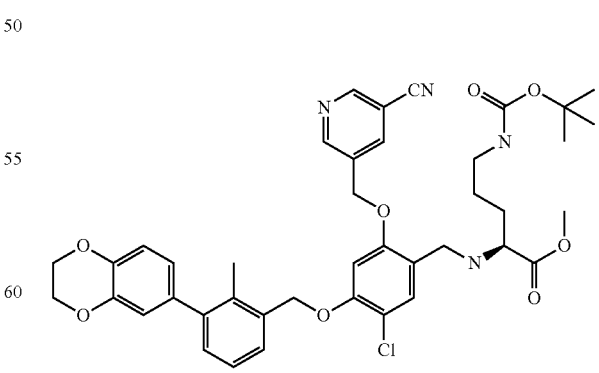

A mixture of 5-((4-chloro-5-((3-(2,3-dihydrobenzo[b][1,4]dioxin-6-yl)-2-methylbenzyl)oxy)-2-formylphenoxy)methyl)nicotinonitrile (37.9 mg, 0.072 mmol) (crude), H-Orn(boc)-OMe HCl (20.36 mg, 0.072 mmol) and sodium triacetoxyboraohydride (47.3 mg, 0.223 mmol) in DMF (1 mL) was stirred at room temperature for 7 hrs. Additional H-Orn(Boc)-OMe HCl (20.36 mg, 0.072 mmol) and sodium triacetoxyboraohydride (47.3 mg, 0.223 mmol) were added. The mixture was stirred at rt (room temperature) for two days. The solvent was removed, and the resulting residue was partitioned between dichloromethane and water. The aqueous phase was extracted once with dichloromethane. The organic extracts were combined and washed with brine and then dried over sodium sulfate. The drying agent was removed by filtration and solvent removed in vacuuo. The residue was used directly for the next step reaction without further purification.

Example 2002

(S)-5-((2-(((4-amino-1-carboxybutyl)amino)methyl)-4-chloro-5-((3-(2,3-dihydrobenzo[b][1,4]dioxin-6-yl)-2-methylbenzyl)oxy)phenoxy)methyl)nicotinic acid

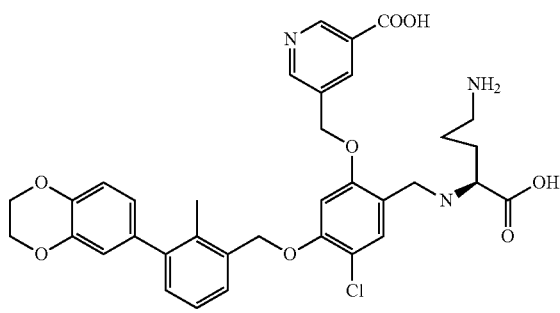 [SMILES: Cc1c(COc2cc(OCc3cncc(C(=O)O)c3)c(CN[C@@H](CCCN)C(=O)O)cc2Cl)cccc1-c1ccc2c(c1)OCCO2]

Lithium hydroxide (24.14 mg, 1.008 mmol) was added to a solution of (S)-methyl 5-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoate (54.5 mg, 0.072 mmol) (crude) in THF (2 mL), and EtOH (2 mL). The mixture was heated in a microwave tube at 100° C. for 30 min. Additional lithium hydroxide (24.14 mg, 1.008 mmol) was added, and the reaction mixture heated in microwave at 100° C. for 2 hr. The solvent was removed. The residue was dissolved in CH$_2$Cl$_2$ (5 mL), and treated with trifluoroacetic acid (1 mL) at 0° C. The mixture was stirred at rt for 20 hr. The solvent was removed. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 25 minutes, then a 5-minute hold at 100% B; Flow: 20 mL/min Fractions containing the desired product were combined and dried via centrifugal evaporation. The yield of the product was 1.3 mg (2.6%). $^1$H NMR (500 MHz, DMSO-d$_6$) δ 8.92 (s, 1H), 8.64 (s, 1H), 8.42 (s, 1H), 7.49 (d, J=6.2 Hz, 1H), 7.40 (s, 1H), 7.27 (t, J=7.3 Hz, 1H), 7.22-7.15 (m, 2H), 6.93 (d, J=8.1 Hz, 1H), 6.82-6.74 (m, 2H), 5.35-5.23 (m, 4H), 4.29 (s, 4H), 3.91 (s, 1H), 3.81 (d, J=11.7 Hz, 1H), 3.75-3.69 (m, 1H), 2.75 (br. s., 2H), 2.26 (s, 3H), 1.68 (br. s., 4H). Two analytical LC/MS injections were used to determine the final purity.

Injection 1 conditions: Column: Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm.

Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.464 min, ESI m/z 662 (M+1), 660 (M−1).

LCMS (Injection 2 conditions) Rt=2.976 min, ESI m/z 662 (M+1), 660 (M−1).

Example 2003

(S)-5-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoic acid

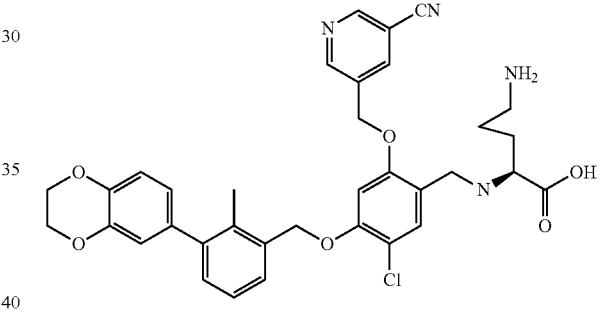

Lithium hydroxide (24.14 mg, 1.008 mmol) was added to a solution of(S)-methyl 5-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoate (54.5 mg, 0.072 mmol) (crude) in THF (1 mL), and EtOH (1 mL). The mixture was heated in microwave tube at 100° C. for 30 min. The solvent was removed. The resulting residue was dissolved in CH$_2$Cl$_2$ (5 mL), and mixture was treated with trifluoroacetic acid (1 mL), and stirred at rt for 4 hr. The solvent was removed. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 40 minutes, then a 5-minute hold at 100% B; Flow: 20 mL/min Fractions containing the desired product were combined and dried via centrifugal evaporation. The material was further purified via preparative LC/MS with the following conditions: Column: XBridge C18, 19×200 mm, 5-µm particles;

Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min Fractions containing the desired product were combined and dried via centrifugal evaporation. The yield of the product was 3.6 mg (7.5%)$^1$H NMR (500 MHz, DMSO-$d_6$) δ 9.00 (d, J=5.9 Hz, 2H), 8.47 (s, 1H), 7.44 (d, J=7.3 Hz, 1H), 7.38 (s, 1H), 7.27-7.22 (m, 1H), 7.19-7.15 (m, 1H), 7.08 (s, 1H), 6.93 (d, J=8.1 Hz, 1H), 6.80-6.73 (m, 2H), 5.32 (s, 2H), 5.23 (s, 2H), 4.28 (s, 4H), 3.66 (d, J=13.6 Hz, 1H), 3.61 (br. s., 1H), 2.83 (br. s., 1H), 2.71 (br. s., 1H), 2.69-2.62 (m, 1H), 2.24 (s, 3H), 1.69 (br. s., 1H), 1.57 (br. s., 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.61 min, ESI m/z 641 (M−1).

LCMS (Injection 2 conditions) Rt=2.67 min, ESI m/z 643 (M+1).

Intermediate (S)-tert-butyl 6-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoate

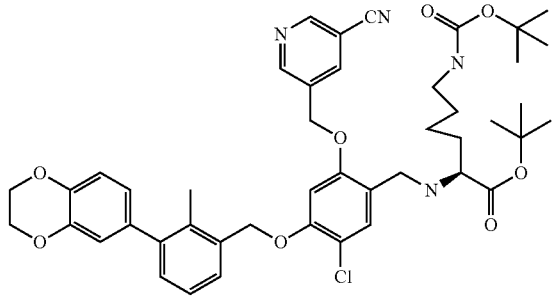 [SMILES: Cc1c(COc2cc(OCc3cncc(C#N)c3)c(CN[C@@H](CCCCNC(=O)OC(C)(C)C)C(=O)OC(C)(C)C)cc2Cl)cccc1-c1ccc2c(c1)OCCO2]

(S)-tert-butyl 6-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoate (58 mg, 0.072 mmol, crude) was obtained from 5-((4-chloro-5-((3-(2,3-dihydrobenzo[b][1,4]dioxin-6-yl)-2-methylbenzyl)oxy)-2-formylphenoxy)methyl)nicotinonitrile (7) and H-Lys(Boc)-OTBu HCl using the procedure described above for (S)-methyl 5-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoate.

Example 2004

(S)-6-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoic acid

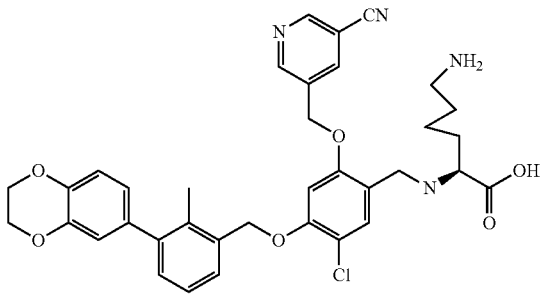 [SMILES: Cc1c(COc2cc(OCc3cncc(C#N)c3)c(CN[C@@H](CCCCN)C(=O)O)cc2Cl)cccc1-c1ccc2c(c1)OCCO2]

(S)-6-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoic acid (1.5 mg, 3%) was obtained from (S)-tert-butyl 6-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoate using the procedure described above for (S)-5-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoic acid (Example 2003). The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 40 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.00 (d, J=6.6 Hz, 2H), 8.48 (br. s., 1H), 7.47-7.37 (m, 2H), 7.27-7.20 (m, 1H), 7.17 (d, J=7.3 Hz, 1H), 7.08 (s, 1H), 6.93 (d, J=8.4 Hz, 1H), 6.81-6.72 (m, 2H), 5.32 (br. s., 2H), 5.23 (br. s., 2H), 4.28 (s, 4H), 3.72 (d, J=13.6 Hz, 1H), 3.63 (d, J=13.6 Hz, 1H), 2.90-2.83 (m, 1H), 2.70 (br. s., 2H), 2.24 (s, 3H), 1.51 (d, J=5.1 Hz, 4H), 1.43-1.25 (m, 2H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.57 min, ESI m/z 657 (M+1), 655 (M−1).

LCMS (Injection 2 conditions) Rt=2.65 min, ESI m/z 657 (M+1).

Intermediates (S)-methyl 4-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoate

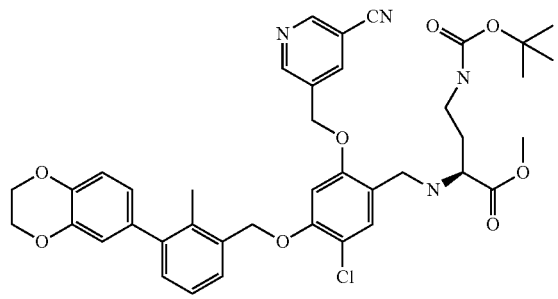 [SMILES: COC(=O)[C@H](CCNC(=O)OC(C)(C)C)NCc1cc(Cl)c(OCc2cccc(-c3ccc4c(c3)OCCO4)c2C)cc1OCc1cncc(C#N)c1]

(S)-methyl 4-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoate (53.5 mg, 0.072 mmol, cude) was obtained from 5-((4-chloro-5-((3-(2,3-dihydrobenzo[b][1,4]dioxin-6-yl)-2-methylbenzyl)oxy)-2-formylphenoxy)methyl)nicotinonitrile and H-Dab(Boc)-OMe HCl using the procedure described for (S)-methyl 5-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoate.

Example 2005

(S)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoic acid

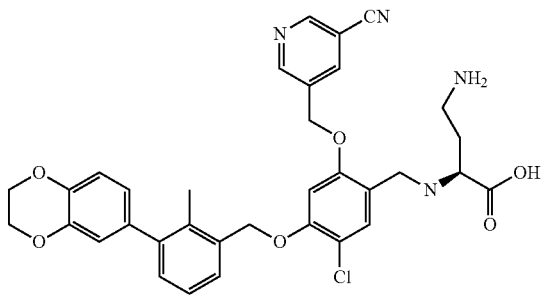 [SMILES: Cc1c(COc2cc(OCc3cncc(C#N)c3)c(CN[C@@H](CCN)C(=O)O)cc2Cl)cccc1-c1ccc2c(c1)OCCO2]

(S)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoic acid (1.5 mg, 3.2%) was obtained from (S)-methyl 4-((tert-butoxycarbonyl)amino)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoate using the procedure described above for (S)-5-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoic acid (Example 2003). The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. $^1$H NMR (400 MHz, METHANOL-$d_4$) δ 9.04 (d, J=2.2 Hz, 1H), 8.85 (d, J=2.2 Hz, 1H), 8.51 (t, J=2.1 Hz, 1H), 7.43 (dd, J=7.2, 1.3 Hz, 1H), 7.39 (s, 1H), 7.25-7.16 (m, 2H), 7.01 (s, 1H), 6.89 (d, J=8.1 Hz, 1H), 6.78-6.72 (m, 2H), 5.33 (s, 2H), 5.25 (s, 2H), 4.29 (s, 4H), 3.98-3.91 (m, 1H), 3.89-3.82 (m, 1H), 3.45 (dd, J=9.5, 8.3 Hz, 1H), 3.39-3.35 (m, 1H), 3.31-3.25 (m, 1H), 2.47-2.37 (m, 1H), 2.29 (s, 3H), 1.95-1.85 (m, 1H).

Two analytical LC/MS injections were used to determine the final purity.

Injection 1 conditions: Column: Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm.

Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.925 min, ESI m/z 629 (M+1), 627 (M−1).

LCMS (Injection 2 conditions) Rt=3.110 min, ESI m/z 628 (M+1).

Example 2006

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-6-(dimethylamino)hexanoic acid

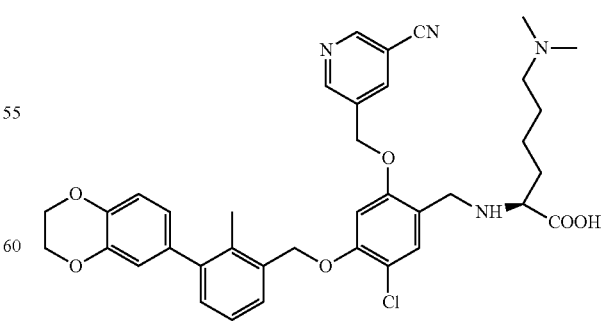

The mixture of 5-((4-chloro-5-((3-(2,3-dihydrobenzo[b][1,4]dioxin-6-yl)-2-methylbenzyl)oxy)-2-formylphenoxy)methyl)nicotinonitrile (37.9 mg, 0.072 mmol) (crude), (S)-

2-amino-6-(dimethylamino)hexanoic acid, TFA (87 mg, 0.216 mmol) and sodium triacetoxyborohydride (47.3 mg, 0.223 mmol) in DMF (1 mL) was stirred at room temperature overnight. Another amount of sodium triacetoxyborohydride (47.3 mg, 0.223 mmol) was added and mixture was stirred at rt for two days. The mixture was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 minutes, then a 5-minute hold at 100% B; Flow: 20 mL/min Fractions containing the desired product were combined and dried via centrifugal evaporation. The yield of the product was 18.1 mg (35%). $^1$H NMR (500 MHz, DMSO-d$_6$) δ 9.02 (s, 2H), 8.51 (s, 1H), 7.50-7.40 (m, 2H), 7.28-7.21 (m, 1H), 7.18 (d, J=7.3 Hz, 1H), 7.12 (s, 1H), 6.93 (d, J=8.1 Hz, 1H), 6.81-6.72 (m, 2H), 5.41-5.30 (m, 2H), 5.26 (s, 2H), 4.28 (s, 4H), 3.92-3.77 (m, 2H), 3.05 (t, J=6.1 Hz, 1H), 2.24 (s, 3H), 2.17 (d, J=5.9 Hz, 2H), 2.12 (s, 6H), 1.58 (br. s., 2H), 1.32 (br. s., 4H).

Two analytical LC/MS injections were used to determine the final purity.

Injection 1 conditions: Column: Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.68 min, ESI m/z 685 (M+1), 683 (M−1).

LCMS (Injection 2 conditions) Rt=2.95 min, ESI m/z 685 (M+1), 683 (M−1).

Example 2007

(2S,5S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-5-hydroxypiperidine-2-carboxylic acid

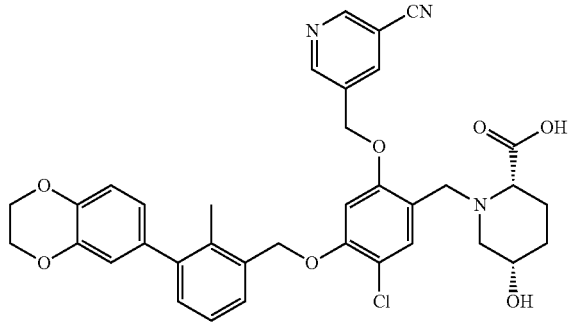 [SMILES: Cc1c(COc2cc(OCc3cncc(C#N)c3)c(CN3C[C@@H](O)CC[C@H]3C(=O)O)cc2Cl)cccc1-c1ccc2c(c1)OCCO2]

A mixture of 5-((4-chloro-5-((3-(2,3-dihydrobenzo[b][1,4]dioxin-6-yl)-2-methylbenzyl)oxy)-2-formylphenoxy)methyl)nicotinonitrile (37.9 mg, 0.072 mmol) and (2S,5S)-5-hydroxypiperidine-2-carboxylic acid, TFA (18.66 mg, 0.072 mmol) in DMF (1 mL) was stirred at room temperature for 1 hr. Sodium cyanoborohydride (13.57 mg, 0.216 mmol) and acetic acid (4.12 µl, 0.072 mmol) were then added, and the reaction mixture was stirred at room temperature for 2.5 days. The mixture was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 minutes, then a 5-minute hold at 100% B; Flow: 20 mL/min Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 0.8 mg (2%). $^1$H NMR (400 MHz, METHANOL-d$_4$) δ 8.98 (d, J=2.2 Hz, 1H), 8.91 (d, J=2.0 Hz, 1H), 8.48 (t, J=2.0 Hz, 1H), 7.51 (s, 1H), 7.42 (dd, J=7.2, 1.8 Hz, 1H), 7.26-7.17 (m, 2H), 7.06 (s, 1H), 6.90 (d, J=8.1 Hz, 1H), 6.78-6.73 (m, 2H), 5.40 (s, 2H), 5.30 (s, 2H), 4.67 (d, J=13.2 Hz, 1H), 4.30 (s, 4H), 4.18 (d, J=13.0 Hz, 1H), 4.04 (br. s., 1H), 3.52 (dd, J=10.8, 3.9 Hz, 1H), 3.19-3.10 (m, 1H), 3.07-3.00 (m, 1H), 2.29 (s, 3H), 2.27-2.17 (m, 1H), 2.13-2.04 (m, 1H), 1.85-1.72 (m, 2H).

Two analytical LC/MS injections were used to determine the final purity.

Injection 1 conditions: Column: Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.62 min, ESI m/z 656 (M+1), 654 (M−1).

LCMS (Injection 2 conditions) Rt=2.77 min, ESI m/z 656 (M+1), 654 (M−1).

Example 2008

(2S,4R)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-4-hydroxypiperidine-2-carboxylic acid

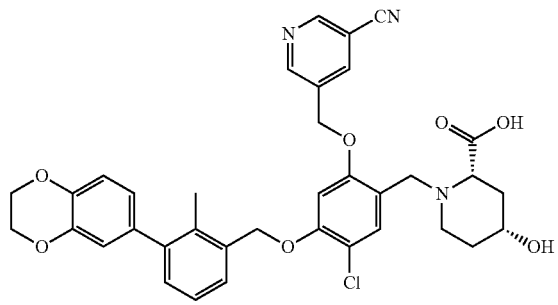 [SMILES: Cc1c(COc2cc(OCc3cncc(C#N)c3)c(CN3CC[C@@H](O)C[C@H]3C(=O)O)cc2Cl)cccc1-c1ccc2c(c1)OCCO2]

(2S,4R)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-4-hydroxypiperidine-2-carboxylic acid 6.5 g, (14%) was obtained from 5-((4-chloro-5-((3-(2,3-dihydrobenzo[b][1,4]dioxin-6-yl)-2-methylbenzyl)oxy)-2-formylphenoxy)methyl)nicotinonitrile and (2S,4R)-4-hydroxypiperidine-2-carboxylic acid, TFA using the procedure described above for (2S,5S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-5-hydroxypiperidine-2-carboxylic acid (Example 2007). The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03-8.98 (m, 2H), 8.47 (s, 1H), 7.49-7.44 (m, 2H), 7.29-7.23 (m, 1H), 7.21-7.17 (m, 1H), 7.11 (s, 1H), 6.93 (d, J=8.1 Hz, 1H), 6.81-6.74 (m, 2H), 5.33 (s, 2H), 5.25 (s, 2H), 4.29 (s, 4H), 3.73 (d, J=13.6 Hz, 1H), 3.54-3.50 (m, 1H), 3.48 (br. s., 1H), 3.03 (dd, J=11.0, 2.9 Hz, 1H), 2.81 (d, J=11.7 Hz, 1H), 2.25 (s, 3H), 2.15 (t, J=12.3 Hz, 1H), 2.00 (d, J=13.6 Hz, 1H), 1.68 (d, J=12.1 Hz, 1H), 1.51 (q, J=11.2 Hz, 1H), 1.40-1.31 (m, 1H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.56 min, ESI m/z 656 (M+1).

LCMS (Injection 2 conditions) Rt=2.72 min, ESI m/z 656 (M+1), 654 (M−1).

The following Examples 2009 to 2013 were prepared from the reaction between 5-((4-chloro-5-((3-(2,3-dihydrobenzo[b][1,4]dioxin-6-yl)-2-methylbenzyl)oxy)-2-formylphenoxy)methyl)nicotinonitrile (25, or 30, or 60 mg) and the corresponding amino acids (3 equiv.) using sodium triacetoxyborohydride (3.1 equiv.) in DMF (1 mL, or 2 mL) at room temperature.

Example 2009

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-2-yl)propanoic acid

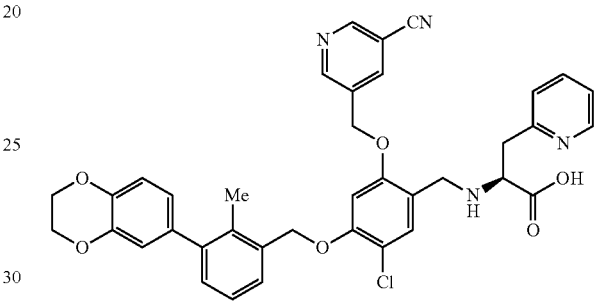

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 35 minutes, then a 5-minute hold at 100% B; Flow: 20 mL/min Fractions containing the desired product were combined and dried via centrifugal evaporation. The yield of the product was 9.4 mg, and its estimated purity by LCMS analysis was 98%. $^1$H NMR (500 MHz, DMSO-$d_6$) 8.96 (s, 1H), 8.93 (s, 1H), 8.40 (s, 1H), 8.23 (d, J=4.4 Hz, 1H), 7.67 (t, J=7.5 Hz, 1H), 7.43 (s, 1H), 7.40 (d, J=7.7 Hz, 1H), 7.24 (m, 2H), 7.17 (m, 2H), 7.09 (s, 1H), 6.92 (d, J=8.1 Hz, 1H), 6.75 (s, 1H), 6.73 (d, overlapped with s, 1H), 5.36 (d, J=4.0 Hz, 2H), 5.25 (s, 2H), 4.26 (s, 4H), 4.09 (d, J=6.6 Hz, 2H), 3.63 (dd, J=8.4, 3.7 Hz, 1H), 3.24 (m, 1H), 3.07 (m, 1H), 2.22 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt=1.80 min, ESI m/z 677.3 (M+H), 675.2 (M−H). Rt=Retention time.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt=2.80 min, ESI m/z 677.3 (M+H), 675.2 (M−H).

Example 2010

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-3-yl)propanoic acid

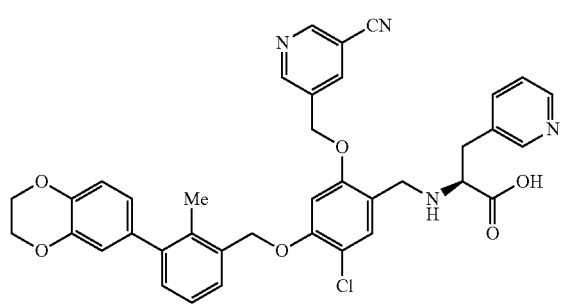 [SMILES: Cc1c(COc2cc(OCc3cncc(C#N)c3)c(CN[C@@H](Cc3cccnc3)C(=O)O)cc2Cl)cccc1-c1ccc2c(c1)OCCO2]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 minutes, then a 5-minute hold at 100% B; Flow: 20 mL/min Fractions containing the desired product were combined and dried via centrifugal evaporation. The yield of the product was 17.8 mg, and its estimated purity by LCMS analysis was 100%. $^1$H NMR (500 MHz, DMSO-$d_6$) δ 9.00 (s, 1H), 8.96 (s, 1H), 8.41 (br s, 2H), 8.38 (d, J=4.8 Hz, 1H), 7.62 (d, J=8.1 Hz, 1H), 7.44 (d, J=7.7 Hz, 1H), 7.25 (m, 3H), 7.18 (d, J=7.3 Hz, 1H), 7.07 (s, 1H), 6.93 (d, J=8.1 Hz, 1H), 6.78 (s, 1H), 6.76 (d, J=9.5 Hz, 1H), 5.29 (s, 2H), 5.23 (s, 2H), 4.29 (s, 4H), 3.73 (m, 2H), 3.35 (t, J=6.6 Hz, 1H), 2.96 (m, 1H), 2.86 (m, 1H), 2.24 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Rt=1.77 min, ESI m/z 677.0 (M+H), 675.0 (M−H).

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. Rt=3.39 min, ESI m/z 677.0 (M+H), 675.1 (M−H).

Example 2011

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-4-yl)propanoic acid

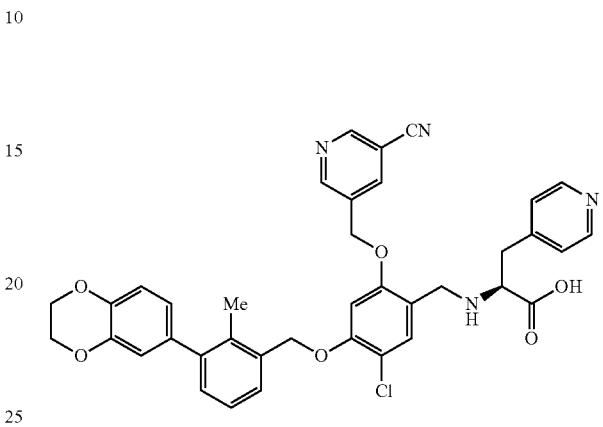

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 minutes, then a 5-minute hold at 100% B; Flow: 20 mL/min Fractions containing the desired product were combined and dried via centrifugal evaporation. The yield of the product was 12.5 mg, and its estimated purity by LCMS analysis was 96%. $^1$H NMR (500 MHz, DMSO-$d_6$) δ 9.00 (s, 1H), 8.96 (s, 1H), 8.39 (m, 3H), 7.43 (d, J=7.3 Hz, 1H), 7.28 (s, 1H), 7.25-7.21 (m, 3H), 7.17 (m, 1H), 7.06 (s, 1H), 6.93 (d, J=8.4 Hz, 1H), 6.78 (s, 1H), 6.76 (d, J=8.1 Hz, 1H), 5.29 (s, 2H), 5.23 (s, 2H), 4.28 (s, 4H), 3.76 (m, 2H), 3.42 (t, J=6.4 Hz, 1H), 2.98 (m, 1H), 2.87 (m, 1H), 2.23 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Rt=1.74 min, ESI m/z 677.0 (M+H), 675.3 (M−H).

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. Rt=2.56 min, ESI m/z 677.1 (M+H), 675.1 (M−H).

Example 2012

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanedioic acid

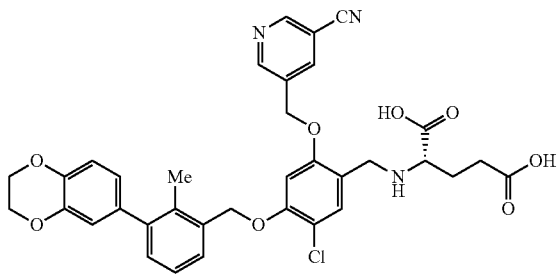 [SMILES: Cc1c(COc2cc(OCc3cncc(C#N)c3)c(CN[C@@H](CCC(=O)O)C(=O)O)cc2Cl)cccc1-c1ccc2c(c1)OCCO2]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min Fractions containing the desired product were combined and dried via centrifugal evaporation. The yield of the product was 4.1 mg, and its estimated purity by LCMS analysis was 100%.

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt=1.47 min, ESI m/z 658.6 (M+H), 656.6 (M−H).

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt=2.58 min, ESI m/z 658.7 (M+H), 656.6 (M−H).

Example 2013

2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)acetic acid

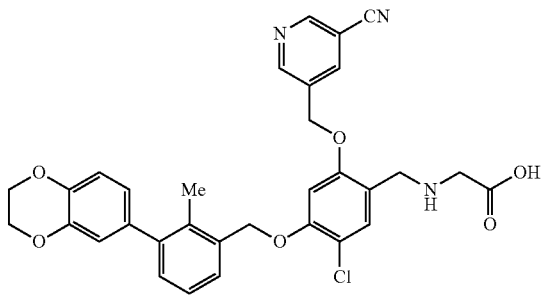 [SMILES: Cc1c(COc2cc(OCc3cncc(C#N)c3)c(CNCC(=O)O)cc2Cl)cccc1-c1ccc2c(c1)OCCO2]

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 15 minutes, then a 5-minute hold at 100% B; Flow: 20 mL/min Fractions containing the desired product were combined and dried via centrifugal evaporation. The yield of the product was 5.7 mg, and its estimated purity by LCMS analysis was 100%. $^1$H NMR (500 MHz, DMSO-d$_6$) δ 9.03 (d, J=4.8 Hz, 2H), 8.51 (s, 1H), 7.52 (s, 1H), 7.45 (d, J=7.3 Hz, 1H), 7.25 (m, 1H), 7.19 (d, J=7.7 Hz, 1H), 7.14 (s, 1H), 6.93 (d, J=8.1 Hz, 1H), 6.79 (s, 1H), 6.76 (d, J=8.8 Hz, 1H), 5.37 (s, 2H), 5.28 (s, 2H), 4.29 (s, 4H), 3.98 (s, 2H), 3.12 (s, 2H), 2.24 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt=1.72 min, ESI m/z 586.2 (M+H), 584.1 (M−H).

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt=2.86 min, ESI m/z 586.2 (M+H), 584.1 (M−H).

LC-MS Methods

Condition N-1:
Column=Phenomenex, 2.0×50 mm, 3 μm
Start % B=0; Final % B=100
Gradient time=4 min; Stop time=5 min
Flow Rate=0.8 mL/min; Wavelength=220 nm
Solvent A=0.1% TFA in 10% methanol/90% water
Solvent B=0.1% TFA in 90% methanol/10% water
Oven temp.=40° C.

SCP-1
Waters BEH C18, 2.0×50 mm, 1.7-μm particles;
Mobile Phase A: 5:95 acetonitrile:water with 10 mM ammonium acetate;
Mobile Phase B: 95:5 acetonitrile:water with 10 mM ammonium acetate;
Temperature: 50° C.; Gradient: 0% B, 0-100% B over 3 minutes, then a 0.5-minute hold at 100% B;
Flow: 1 mL/min; Detection: UV at 220 nm.

Example 3000

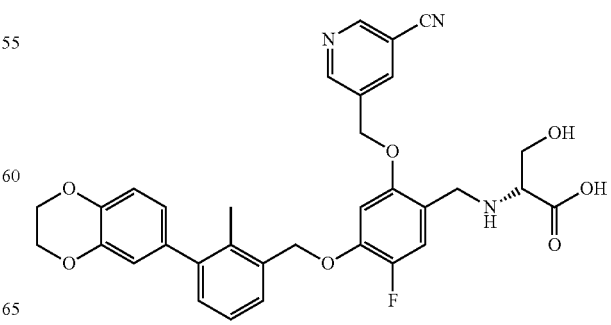

Example 3000

Step a

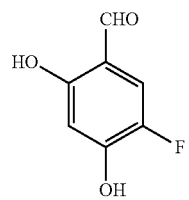 [SMILES: O=Cc1cc(F)c(O)cc1O]

To a solution of Selectfluor® fluorinating reagent (10.46 g, 29.5 mmol) in acetonitrile (40 mL), was added 2,4-dihydroxybenzaldehyde (3.0 g, 21.72 mmol). The reaction mixture was stirred at rt for 4 days. The reaction was diluted with water and EtOAc, then the organic phase was separated and washed with sat. NaCl, dried over anhydrous $Na_2SO_4$, filtered and concentrated to yield the crude product, which was purified on silica gel (0-35% EtOAc/hex) to yield 5-fluoro-2,4-dihydroxybenzaldehyde (0.9 g). $^1$H NMR (400 MHz, CHLOROFORM-d) δ ppm 11.26 (s, 1H), 9.69 (s, 1H), 7.26 (d, J=9.8 Hz, 1H), 6.59 (d, J=7.3 Hz, 1H).

Example 3000

Step b

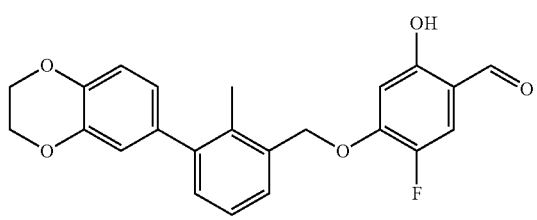 [SMILES: Cc1c(COc2cc(O)c(C=O)cc2F)cccc1-c1ccc2c(c1)OCCO2]

To a solution of (3-(2,3-dihydrobenzo[b][1,4]dioxin-6-yl)-2-methylphenyl)methanol (1.642 g, 6.41 mmol), 5-fluoro-2,4-dihydroxybenzaldehyde (1 g, 6.41 mmol) and triphenylphosphine (2.016 g, 7.69 mmol) in THF (40 mL) was added a solution of diisopropyl azodicarboxylate (1.513 ml, 7.69 mmol) in THF (5 mL) dropwise at 0° C. The resulting mixture was stirred at rt for 3 days. The solvent was removed then the residue was purified by silica chromatography (0-35% EtOAc/hexane) to yield 4-((3-(2,3-dihydrobenzo[b][1,4]dioxin-6-yl)-2-methylbenzyl)oxy)-5-fluoro-2-hydroxybenzaldehyde (1.0 g, 2.54 mmol, 39.6% yield). $^1$H NMR (400 MHz, CHLOROFORM-d) δ ppm 11.40 (s, 1H), 9.69 (s, 1H), 7.43-7.35 (m, 1H), 7.28-7.23 (m, 3H), 6.92 (d, J=8.3 Hz, 1H), 6.86-6.76 (m, 2H), 6.65 (d, J=6.8 Hz, 1H), 5.20 (s, 2H), 4.32 (s, 4H), 2.32-2.23 (m, 3H). LC/MS (Cond. N-1): [M+Na]$^+$417.20, RT=4.469 min.

Example 3000

Step c

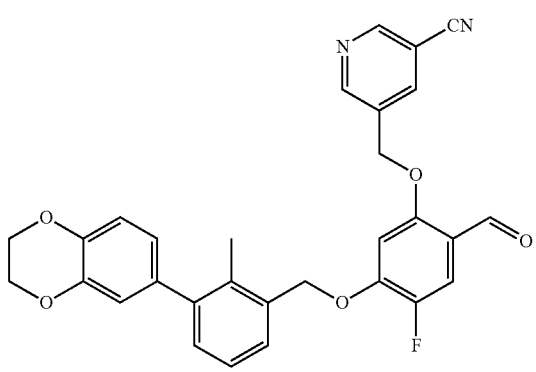 [SMILES: Cc1c(COc2cc(OCc3cncc(C#N)c3)c(C=O)cc2F)cccc1-c1ccc2c(c1)OCCO2]

A stirred mixture of 4-((3-(2,3-dihydrobenzo[b][1,4]dioxin-6-yl)-2-methylbenzyl)oxy)-5-fluoro-2-hydroxybenzaldehyde (0.23 g, 0.583 mmol), 5-(chloromethyl)nicotinonitrile (0.089 g, 0.583 mmol) and $Cs_2CO_3$ (0.228 g, 0.700 mmol), NaI (8.7 mg, 0.058 mmol) in DMF (4 mL) was heated at 75° C. for 3 h. The reaction mixture was allowed to cool to rt, diluted with water and EtOAc, the organic phase was washed with sat. NaCl, dried ($Na_2SO_4$) and concentrated. The residue was purified by silica gel (0-100% EtOAC in hexane) to yield 5-((5-((3-(2,3-dihydrobenzo[b][1,4]dioxin-6-yl)-2-methylbenzyl)oxy)-4-fluoro-2-formylphenoxy)methyl)nicotinonitrile (0.22 g, 0.431 mmol, 73.9% yield) as a white solid. $^1$H NMR (400 MHz, CHLOROFORM-d) δ ppm 10.31 (d, J=3.0 Hz, 1H), 8.91 (dd, J=4.4, 2.1 Hz, 2H), 8.09 (t, J=2.0 Hz, 1H), 7.63 (d, J=11.0 Hz, 1H), 7.39-7.35 (m, 1H), 7.26 (d, J=3.3 Hz, 2H), 6.93 (d, J=8.3 Hz, 1H), 6.83 (d, J=2.0 Hz, 1H), 6.80-6.75 (m, 1H), 6.68 (d, J=6.3 Hz, 1H), 5.26 (s, 2H), 5.20 (s, 2H), 4.32 (s, 4H), 2.30 (s, 3H). LC/MS (Cond. N-1): [M+Na]$^+$533.20, RT=4.334 min.

Example 3000

To a screw capped vial was added 5-((5-((3-(2,3-dihydrobenzo[b][1,4]dioxin-6-yl)-2-methylbenzyl)oxy)-4-fluoro-2-formylphenoxy)methyl)nicotinonitrile (0.045 g, 0.088 mmol), (R)-2-amino-3-hydroxypropanoic acid (0.030 g, 0.282 mmol), sodium triacetoxyhydroborate (0.056 g, 0.264 mmol) and DMF (1 mL). The vial was capped and the reaction mixture was stirred at rt for 16 h. The reaction was diluted with EtOAc and sat. NaCl, the white solid precipitated. The white solid was filtered and washed with EtOAc and water, then dried to yield Example 3000 (0.035 g, 0.055 mmol, 62.9% yield). LC/MS (Cond. N-1): [M+H]$^+$ 600.25, RT=3.594 min $^1$H NMR (400 MHz, DMSO-d$_6$) δ ppm 9.08-8.99 (m, 2H), 8.53 (t, J=2.0 Hz, 1H), 7.42 (d, J=6.5 Hz, 1H), 7.36 (d, J=11.8 Hz, 1H), 7.25 (t, J=7.5 Hz, 1H), 7.21-7.15 (m, 2H), 6.93 (d, J=8.0 Hz, 1H), 6.81-6.73 (m, 2H), 5.38-5.21 (m, 4H), 4.29 (s, 4H), 4.03-3.93 (m, 2H), 3.70 (dd, J=11.3, 4.5 Hz, 1H), 3.61 (dd, J=11.0, 6.3 Hz, 1H), 3.15 (dd, J=6.3, 4.8 Hz, 1H), 2.23 (s, 3H).

Example 3001

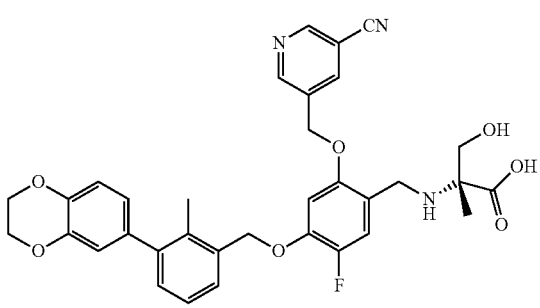

Example 3001 was prepared according to the procedure described for Example 3000. LC/MS (Cond. N-1): [M+H]+ 614.25, RT=3.626 min $^1$H NMR (400 MHz, METHANOL-$d_4$) δ ppm 8.96 (d, J=2.0 Hz, 1H), 8.89 (d, J=2.0 Hz, 1H), 8.42 (s, 1H), 7.39-7.29 (m, 2H), 7.21-7.13 (m, 2H), 7.05 (d, J=7.0 Hz, 1H), 6.88 (d, J=8.3 Hz, 1H), 6.78-6.70 (m, 2H), 5.33 (s, 2H), 5.29 (s, 2H), 4.29 (s, 4H), 4.22 (s, 2H), 3.93 (d, J=12.0 Hz, 1H), 3.72 (d, J=12.0 Hz, 1H), 2.27 (s, 3H), 1.51-1.39 (m, 3H).

Example 3002

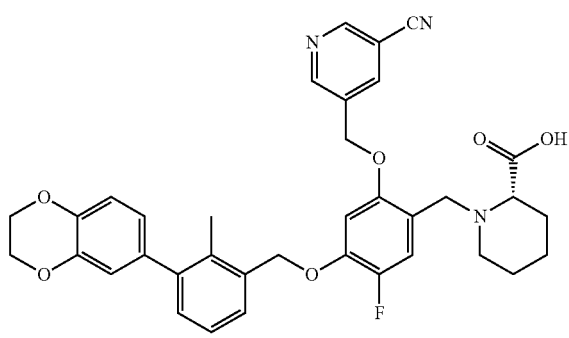 [SMILES: Cc1c(COc2cc(OCc3cncc(C#N)c3)c(CN3CCCC[C@H]3C(=O)O)cc2F)cccc1-c1ccc2c(c1)OCCO2]

Example 3002 was prepared according to the procedure described for Example 3000. The final product was purified via preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minute; Flow: 20 mL/min.). LC/MS (Cond. N-1): [M+H]+ 624.25, RT=3.669 min. $^1$H NMR (500 MHz, DMSO-$d_6$) ppm 9.00 (d, J=9.5 Hz, 2H), 8.45 (s, 1H), 7.42 (d, J=7.3 Hz, 1H), 7.29-7.22 (m, 2H), 7.21-7.16 (m, 1H), 7.14 (d, J=7.3 Hz, 1H), 6.93 (d, J=8.1 Hz, 1H), 6.81-6.73 (m, 2H), 5.33-5.26 (m, 2H), 5.23 (s, 2H), 4.29 (s, 4H), 3.80 (d, J=13.9 Hz, 1H), 3.65 (d, J=13.9 Hz, 1H), 3.19-3.13 (m, 1H), 2.90 (m, 1H), 2.31 (d, J=6.2 Hz, 1H), 2.23 (s, 3H), 1.80 (br. s., 1H), 1.74 (br. s., 1H), 1.50 (br. s., 3H), 1.38 (br. s., 1H).

General Procedure for Reductive Amination of Intermediate-1 with a Variety of Amines and Aminoacids:

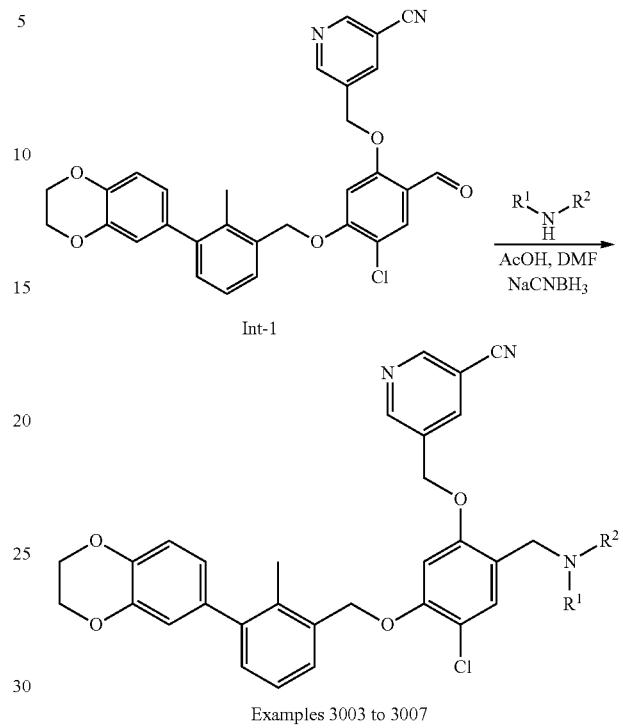

A mixture of Int-1 (1 equiv), appropriate amine or amino acid (3 equiv) and AcOH (5 equiv) in DMF was stirred at RT for 4-16 h. Then sodium cyanoborohydride (3 equiv) was added and the mixture was stirred at RT until reductive amination is complete (typically overnight). Product was purified via preparative HPLC with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 30 minutes, then a 5-minute hold at 100% B; Flow: 20 mL/min. Fractions containing the desired product were combined and dried via centrifugal evaporation.

One of the following LC-MS methods was used to determine the final purity.

LC-MS Conditions 1:
Column: Waters BEH C18, 2.0×50 mm, 1.7-µm particles; Mobile Phase A: 5:95
acetonitrile:water with 10 mM ammonium acetate; Mobile Phase B: 95:5
acetonitrile:water with 10 mM ammonium acetate; Temperature: 50° C.; Gradient: 0% B,
0-100% B over 3 minutes, then a 0.5-minute hold at 100% B; Flow: 1 mL/min;
Detection: UV at 220 nm.

LC-MS Conditions 2:
Column: Waters BEH C18, 2.0×50 mm, 1.7-µm particles; Mobile Phase A: 5:95
methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

| Example | —NR¹R² | LC-MS Method | Retention Time (min) | Obs. Mass ion (M + H)+ |
|---|---|---|---|---|
| 3003 | (threonine-like: O=C(OH)-CH(NH-)-CH(OH)-CH3) | 1 | 1.73 | 642.5 |
| 3004 | (S,S)-4-hydroxyproline-like (HOOC-, OH on ring) | 1 | 1.79 | 612.5 |
| 3005 | (S)-azetidine-2-carboxylic acid | 1 | 1.63 | 630.3 |
| 3006 | 3,4-dihydroxyproline carboxylic acid (1st eluting diastereomer) | 1 | 1.65 | 658.2 |
| 3007 | 3,4-dihydroxyproline carboxylic acid (2nd eluting diastereomer) | 1 | 1.71 | 658.2 |

For examples 3008 to 3030 the following purification methods and LC-MC conditions were utilized.

LCMS Conditions:

Condition ACN-TFA: Column: Waters Aquity UPLC BEHC18, 2.1×50 mm, 1.7-μm particles; Mobile Phase A: 99.95% water with 0.05% trifluoroacetic acid; Mobile Phase B: 99.95% acetonitrile with 0.05% trifluoroacetic acid; Gradient: 2% B, 2-98% B over 1 minutes, then a 0.5-minute hold at 98% B; Flow: 0.8 mL/min; Detection: UV at 220 nm or 254 nm.

Condition ACN-AA: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm or 254 nm.

Condition MeOH-AA: Column: Waters BEH C18, 2.0×50 mm, 1.7-μm particles; Mobile Phase A: 5:95 methanol: water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm or 254 nm.

Purification Conditions:

General purification conditions for final products: Column: XBridge C18, 19×mm, 5-μm particles. Mobile Phase A: 5:95 acetonitrile: water with 10-mM ammonium acetate. Mobile Phase B: 95:5 acetonitrile: water with 10-mM ammonium acetate; Gradient: 0-100% B over 10-20 minutes, then a 0-10-minute hold at 100% B; Flow: 20 mL/min; gradient and hold times may be optionally varied for individual compounds. Fractions containing the desired product were combined and dried via centrifugal evaporation.

Example 3008 ethyl (5-((4-chloro-5-((3-(2,3-dihydrobenzo[b][1,4]dioxin-6-yl)-2-methylbenzyl)oxy)-2-formylphenoxy)methyl)pyridin-3-yl)carbamate

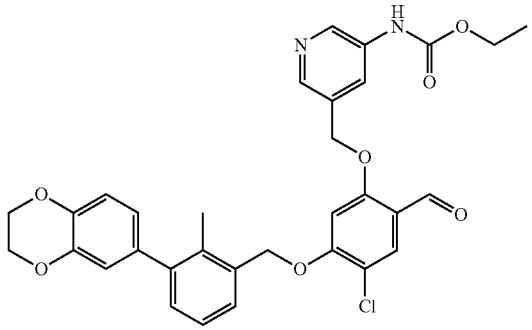 [SMILES: CCOC(=O)Nc1cncc(COc2cc(OCc3cccc(-c4ccc5c(c4)OCCO5)c3C)c(Cl)cc2C=O)c1]

A stirred mixture of 5-chloro-4-((3-(2,3-dihydrobenzo[b][1,4]dioxin-6-yl)-2-methylbenzyl)oxy)-2-hydroxybenzaldehyde (0.071 g, 0.173 mmol), ethyl (5-(chloromethyl)pyridin-3-yl)carbamate hydrochloride (0.056 g, 0.225 mmol), cesium carbonate (0.169 g, 0.519 mmol) and sodium iodide (3 mg, 0.02 mmol) in N,N-dimethylformamide (3 mL) was heated at 75° C. (oil bath) for 90 minutes. The reaction was cooled, diluted with dichloromethane, and washed with water (2×10 mL). The organic layer was dried over sodium sulfate, filtered, and concentrated under reduced pressure, affording the product as a yellow powdery solid after trituration with diethyl ether. LCMS (Condition ACN-TFA, ES+) M+H=589.2, 1.08 minutes, calculated exact mass=588.17. $^1$H NMR (400 MHz, CDCl3) δ: 10.39 (s, 1H), 8.28 (d, J=5.3 Hz, 1H), 8.10 (s, 1H), 7.92 (s, 1H), 7.64 (br. s., 1H), 7.41-7.36 (m, 1H), 7.26-7.23 (m, 2H), 7.08 (d, J=5.0 Hz, 1H), 6.92 (d, J=8.3 Hz, 1H), 6.83 (d, J=2.0 Hz, 1H), 6.78 (dd, J=8.2, 2.1 Hz, 1H), 6.60 (s, 1H), 5.22 (s, 2H), 5.18 (s, 2H), 4.32 (s, 4H), 4.25 (q, J=7.1 Hz, 2H), 2.27 (s, 3H), 1.33 (t, J=7.2 Hz, 3H).

Example 3009

(S)-2-((5-chloro-4-((3-(2,3-dihydrobenzo[b][1,4]dioxin-6-yl)-2-methylbenzyl)oxy)-2-((5-((ethoxycarbonyl)amino)pyridin-3-yl)methoxy)benzyl)amino)-3-hydroxy-2-methylpropanoic acid

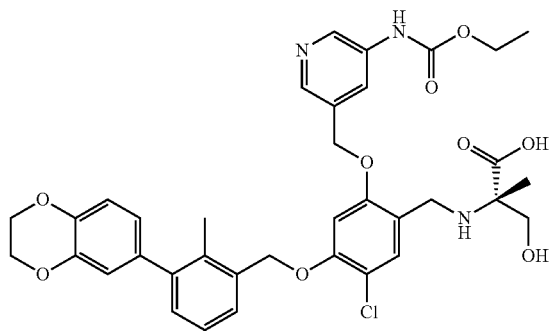 [SMILES: CCOC(=O)Nc1cncc(COc2cc(OCc3cccc(-c4ccc5c(c4)OCCO5)c3C)c(Cl)cc2CN[C@@](C)(CO)C(=O)O)c1]

A solution of ethyl (5-((4-chloro-5-((3-(2,3-dihydrobenzo[b][1,4]dioxin-6-yl)-2-methylbenzyl)oxy)-2-formylphenoxy)methyl)pyridin-3-yl)carbamate (0.042 g, 0.071 mmol) and (S)-2-amino-3-hydroxy-2-methylpropanoic acid (0.027 g, 0.227 mmol) in dry N,N-dimethylformamide (0.75 mL) was treated with glacial acetic acid (10 µl, 0.175 mmol) and stirred for 30 minutes. To the mixture was added sodium triacetoxyborohydride (0.045 g, 0.214 mmol), and the reaction was stirred for 3 hours. Additional portions of the amino acid and sodium triacetoxyborohydride were added periodically until LCMS monitoring indicated no further reaction progression. The reaction was diluted with ethyl acetate and washed with water. The organic layer was dried over sodium sulfate, filtered, and concentrated under reduced pressure. The crude material was purified via general method for preparative LCMS purification. LCMS (Condition ACN-AA, ES+) M+H=692.5, 1.76 minutes, calculated exact mass=691.23. $^1$H NMR (500 MHz, DMSO-$d_6$) δ: 8.24 (d, J=5.1 Hz, 1H), 7.97 (s, 1H), 7.54 (s, 1H), 7.41 (d, J=7.0 Hz, 1H), 7.28-7.12 (m, 3H), 7.09 (s, 1H), 6.92 (d, J=8.1 Hz, 1H), 6.80-6.67 (m, 2H), 5.30 (br. s., 2H), 5.23 (br. s., 2H), 4.27 (s, 4H), 4.11 (q, J=7.1 Hz, 2H), 3.99 (br. s., 2H), 3.89 (s, 1H), 3.69-3.53 (m, 4H), 2.21 (s, 3H), 1.27 (s, 3H), 1.21 (t, J=7.2 Hz, 3H).

Example 3010

N-(4-((4-chloro-5-((3-(2,3-dihydrobenzo[b][1,4]dioxin-6-yl)-2-methylbenzyl)oxy)-2-formylphenoxy)methyl)pyridin-2-yl)acetamide

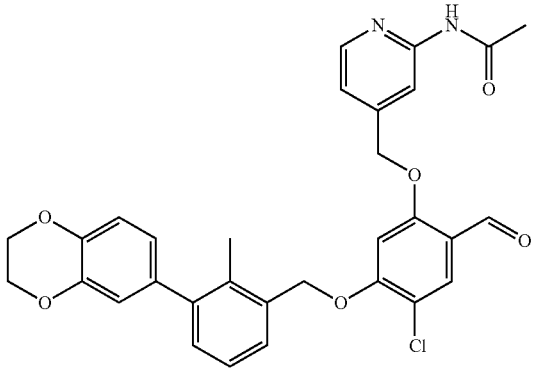 [SMILES: CC(=O)Nc1cc(COc2cc(OCc3cccc(-c4ccc5c(c4)OCCO5)c3C)c(Cl)cc2C=O)ccn1]

Prepared in substantially the same manner as example 3008. LCMS (Condition ACN-TFA, ES+): M+H=559.3, 1.02 minutes, calculated exact mass=558.16. $^1$H NMR (400 MHz, CDCl$_3$) δ: 10.39 (s, 1H), 8.34-8.25 (m, 2H), 7.95 (br. s., 1H), 7.92 (s, 1H), 7.43-7.35 (m, 1H), 7.26-7.23 (m, 2H), 7.15 (d, J=6.3 Hz, 1H), 6.93 (d, J=8.3 Hz, 1H), 6.84 (d, J=2.0 Hz, 1H), 6.81-6.76 (m, 1H), 6.60 (s, 1H), 5.22 (s, 2H), 5.18 (s, 2H), 4.32 (s, 4H), 2.27 (s, 3H), 2.22 (s, 3H).

Example 3011

(S)-2-((2-((2-acetamidopyridin-4-yl)methoxy)-5-chloro-4-((3-(2,3-dihydrobenzo[b][1,4]dioxin-6-yl)-2-methylbenzyl)oxy)benzyl)amino)-3-hydroxy-2-methylpropanoic acid

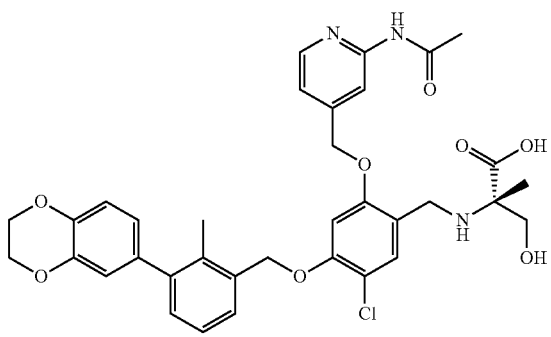 [SMILES: CC(=O)Nc1cc(COc2cc(OCc3cccc(-c4ccc5c(c4)OCCO5)c3C)c(Cl)cc2CN[C@@](C)(CO)C(=O)O)ccn1]

Prepared in substantially the same manner as example 3009. LCMS (Condition ACN-AA, ES+) M+H=662.5, 1.60 minutes, calculated exact mass=661.22. $^1$H NMR (400 MHz, CD$_3$OD) δ: 8.28 (d, J=5.1 Hz, 1H), 8.21 (s, 1H), 7.69-7.55 (m, 1H), 7.54 (s, 1H), 7.37-7.23 (m, 2H), 7.16-7.10 (m, 2H), 6.90 (s, 1H), 6.87 (d, J=8.1 Hz, 1H), 6.73-6.68 (m, 2H), 5.33 (s, 2H), 5.21 (s, 2H), 4.27 (s, 4H), 4.27 (s, 1H), 4.03-3.72 (m, 2H), 2.22 (s, 3H), 2.15 (s, 3H), 1.48 (s, 3H).

Example 3012

(S)-2-((5-chloro-4-((3-(2,3-dihydrobenzo[b][1,4]dioxin-6-yl)-2-methylbenzyl)oxy)-2-((5-(methylsulfonyl)pyridin-3-yl)methoxy)benzyl)amino)-3-hydroxy-2-methylpropanoic acid

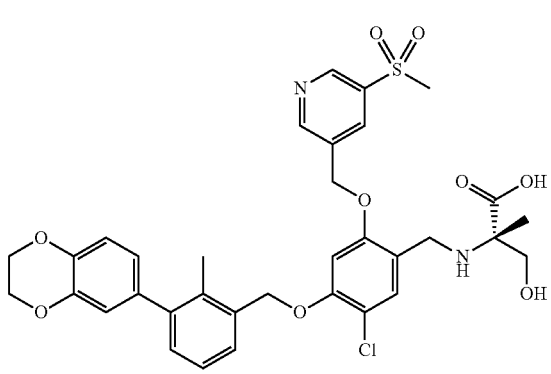 [SMILES: Cc1c(COc2cc(OCc3cncc(S(C)(=O)=O)c3)c(CN[C@@](C)(CO)C(=O)O)cc2Cl)cccc1-c1ccc2c(c1)OCCO2]

Prepared in substantially the same manner as example 3009. LCMS (Condition ACN-AA, ES+) M+H=683.2, 1.63 minutes, calculated exact mass=682.18. ¹H NMR (500 MHz, DMSO-d₆) δ: 9.07 (s, 1H), 9.04 (s, 1H), 8.55 (s, 1H), 7.55 (s, 1H), 7.46 (d, J=7.3 Hz, 1H), 7.29-7.22 (m, 1H), 7.21-7.14 (m, 2H), 6.92 (d, J=8.1 Hz, 1H), 6.79-6.69 (m, 2H), 5.41 (s, 2H), 5.28 (s, 2H), 4.27 (s, 4H), 4.00 (br. s., 2H), 3.63 (d, J=11.7 Hz, 1H), 3.37 (s, 3H), 2.23 (s, 3H), 1.23 (s, 3H); LCMS (ES+) M+H=683.1. Note: methyl signal partially obscured.

Example 3013

(5-chloro-4-{[3-(2,3-dihydro-1,4-benzodioxin-6-yl)-2-methylphenyl]methoxy}-2-[(5-methanesulfonylpyridin-3-yl)methoxy]phenyl)methanol

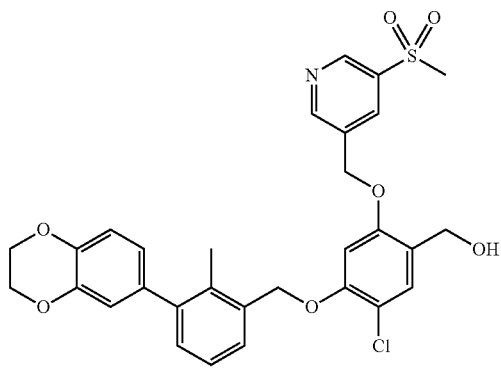 [SMILES: Cc1c(COc2cc(OCc3cncc(S(C)(=O)=O)c3)c(CO)cc2Cl)cccc1-c1ccc2c(c1)OCCO2]

This product was isolated as a by-product from the preparation of example 3012. LCMS (Condition MeOH-AA, ES+) M+H=582.0, 2.87 minutes, calculated exact mass=581.13. ¹H NMR (500 MHz, DMSO-d₆) δ: 9.06 (s, 1H), 9.00 (s, 1H), 8.43 (s, 1H), 7.45 (d, J=7.7 Hz, 1H), 7.36 (s, 1H), 7.28-7.20 (m, 1H), 7.17 (d, J=7.3 Hz, 1H), 7.12 (s, 1H), 6.92 (d, J=8.1 Hz, 1H), 6.81-6.70 (m, 2H), 5.39 (s, 2H), 5.23 (s, 2H), 4.47 (d, J=5.1 Hz, 2H), 4.27 (s, 4H), 3.35 (s, 3H), 2.24 (s, 3H).

Example 3014

(S)-2-((5-chloro-2-((2-chloro-6-methoxypyridin-4-yl)methoxy)-4-((3-(2,3-dihydrobenzo[b][1,4]dioxin-6-yl)-2-methylbenzyl)oxy)benzyl)amino)-3-hydroxy-2-methylpropanoic acid

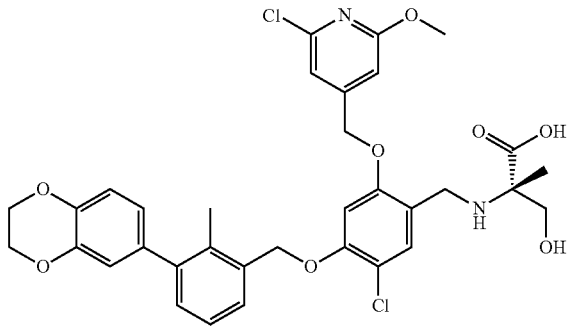 [SMILES: COc1cc(COc2cc(OCc3cccc(-c4ccc5c(c4)OCCO5)c3C)c(Cl)cc2CN[C@@](C)(CO)C(=O)O)cc(Cl)n1]

Prepared in substantially the same manner as example 3009. LCMS (Condition ACN-AA, ES+) M+H=669.6, 1.88 minutes, calculated exact mass=668.17. ¹H NMR (500 MHz, DMSO-d₆) δ: 7.53 (s, 1H), 7.37 (d, J=7.7 Hz, 1H), 7.24 (s, 1H), 7.22-7.11 (m, 2H), 7.00 (s, 1H), 6.95 (s, 1H), 6.92 (d, J=8.1 Hz, 1H), 6.76 (s, 1H), 6.73 (d, J=8.1 Hz, 1H), 5.27 (s, 2H), 5.23 (s, 2H), 4.27 (s, 4H), 3.95 (br. s., 2H), 3.84 (s, 3H), 3.65-3.60 (m, 1H), 3.54 (d, J=11.4 Hz, 1H), 2.22 (s, 3H), 1.26 (s, 3H).

Example 3015

(2S)-2-{[(5-chloro-4-{[3-(2,3-dihydro-1,4-benzodioxin-6-yl)-2-methylphenyl]methoxy}-2-[(2-methoxypyridin-4-yl)methoxy]phenyl)methyl]amino}-3-hydroxy-2-methylpropanoic acid

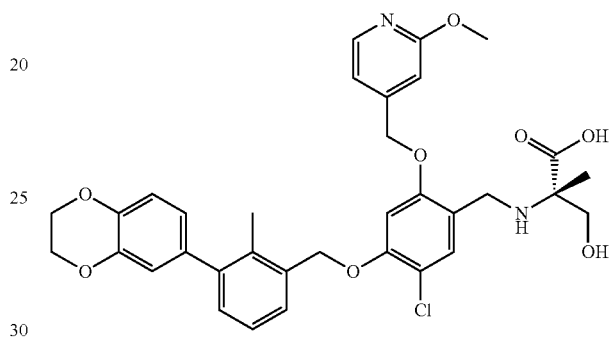

Prepared in substantially the same manner as example 3009. LCMS (Condition MeOH-AA, ES−) M−H=633.2, 2.88 minutes, calculated exact mass=634.21. ¹H NMR (500 MHz, DMSO-d₆) δ 8.15 (d, J=5.5 Hz, 1H), 7.54 (s, 1H), 7.38 (d, J=7.3 Hz, 1H), 7.24-7.18 (m, 1H), 7.18-7.10 (m, 2H), 7.04 (s, 1H), 6.95-6.87 (m, 2H), 6.80-6.68 (m, 2H), 5.26 (s, 2H), 5.23 (s, 2H), 4.27 (s, 4H), 3.97 (s, 2H), 3.84 (s, 3H), 3.64 (d, J=11.0 Hz, 1H), 3.55 (d, J=11.4 Hz, 1H), 2.22 (s, 3H), 1.26 (s, 3H).

Example 3016

(5-chloro-4-{[3-(2,3-dihydro-1,4-benzodioxin-6-yl)-2-methylphenyl]methoxy}-2-[(2-methoxypyridin-4-yl)methoxy]phenyl)methanol

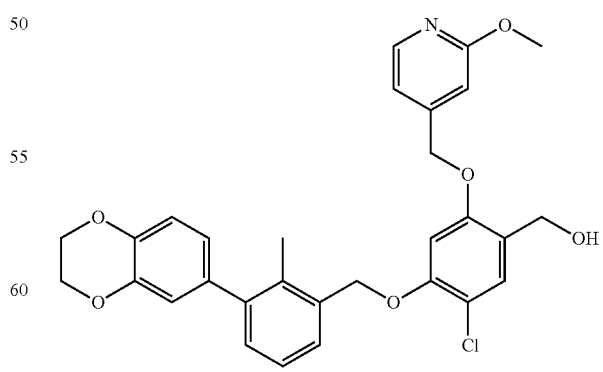

This product was isolated as a by-product from the preparation of example 3015. LCMS (Condition MeOH-AA, ES+) M+H=534.4, 3.18 minutes, calculated exact mass=533.16. $^1$H NMR (500 MHz, DMSO-$d_6$) δ: 8.15 (d, J=5.1 Hz, 1H), 7.38 (d, J=7.3 Hz, 1H), 7.34 (s, 1H), 7.23-7.17 (m, 1H), 7.17-7.11 (m, 1H), 7.03 (d, J=5.1 Hz, 1H), 6.99 (s, 1H), 6.92 (d, J=8.4 Hz, 1H), 6.85 (s, 1H), 6.78-6.68 (m, 2H), 5.22 (s, 2H), 5.19 (s, 2H), 4.49 (d, J=5.5 Hz, 2H), 4.27 (s, 4H), 3.84 (s, 3H), 2.21 (s, 3H).

Example 3017

(S)-1-(5-chloro-4-((3-(2,3-dihydrobenzo[b][1,4]dioxin-6-yl)-2-methylbenzyl)oxy)-2-((2-methoxypyridin-4-yl)methoxy)benzyl)piperidine-2-carboxylic acid

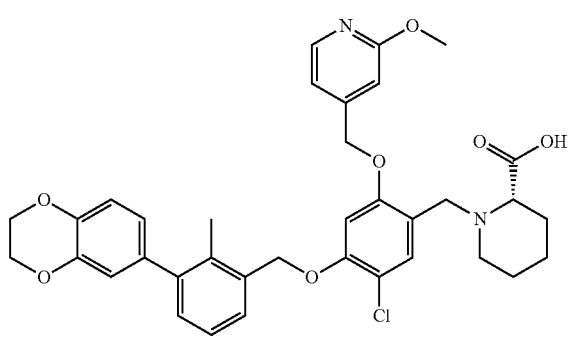 [SMILES: COc1cc(COc2cc(OCc3cccc(-c4ccc5c(c4)OCCO5)c3C)c(Cl)cc2CN2CCCC[C@H]2C(=O)O)ccn1]

A suspension of 5-chloro-4-((3-(2,3-dihydrobenzo[b][1,4]dioxin-6-yl)-2-methylbenzyl)oxy)-2-((2-methoxypyridin-4-yl)methoxy)benzaldehyde (0.037 g, 0.070 mmol) and (S)-piperidine-2-carboxylic acid (0.013 g, 0.104 mmol) in dry N,N-dimethylformamide (0.9 ml) and glacial acetic acid (0.100 ml) was stirred for 20 minutes, treated with borane-2-picoline complex (0.015 g, 0.139 mmol), and then stirred for 16hours. The reaction was diluted with water and ethyl acetate, then quenched by addition of saturated sodium bicarbonate solution. The organic layer was concentrated and the residue was purified via general method for preparative LCMS purification. LCMS (Condition ACN-AA, ESI+) M+H=645.05, 1.88 minutes, calculated exact mass=644.23. $^1$H NMR (500 MHz, DMSO-$d_6$) δ: 8.16 (d, J=5.5 Hz, 1H), 7.45 (s, 1H), 7.41 (d, J=7.7 Hz, 1H), 7.26-7.19 (m, 1H), 7.19-7.13 (m, 1H), 7.05 (d, J=5.1 Hz, 1H), 7.03 (s, 1H), 6.92 (d, J=8.4 Hz, 1H), 6.88 (s, 1H), 6.77 (s, 1H), 6.76-6.71 (m, 1H), 5.23 (s, 2H), 5.20 (s, 2H), 4.27 (s, 4H), 3.89 (s, 1H), 3.84-3.77 (m, 1H), 3.68 (d, J=13.9 Hz, 1H), 3.17 (dd, J=7.7, 4.0 Hz, 1H), 2.96-2.89 (m, 1H), 2.37-2.26 (m, 1H), 2.22 (s, 3H), 1.80 (br. s., 1H), 1.72 (d, J=9.2 Hz, 1H), 1.49 (br. s., 3H), 1.37 (br. s., 1H).

Example 3018

(S)-2-((5-chloro-4-((3-(2,3-dihydrobenzo[b][1,4]dioxin-6-yl)-2-methylbenzyl)oxy)-2-((2-(dimethylcarbamoyl)pyridin-4-yl)methoxy)benzyl)amino)-3-hydroxy-2-methylpropanoic acid

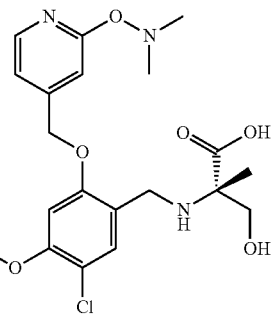

A solution of 4-((4-chloro-5-((3-(2,3-dihydrobenzo[b][1,4]dioxin-6-yl)-2-methylbenzyl)oxy)-2-formylphenoxy)methyl)-N,N-dimethylpicolinamide (0.035 g, 0.061 mmol) and (S)-2-amino-3-hydroxy-2-methylpropanoic acid (0.022 g, 0.183 mmol) in dry N,N-dimethylformamide (1.0 mL) was stirred for 2 hours, then treated with sodium triacetoxyborohydride (0.039 g, 0.183 mmol), and stirred for 40 hours. The reaction was treated with sodium cyanoborohydride (0.023 g, 0.366 mmol), and the reaction was stirred for 18 hours. The reaction was partitioned between ethyl acetate and saturated aqueous sodium bicarbonate, and the organic layer was concentrated under reduced pressure. The residue was suspended in N,N-dimethylformamide, filtered through a cotton plug and the crude material was purified via general preparative LCMS purification conditions. LCMS (Condition ACN-AA, ES+) M+H=676.2, 1.62 minutes, calculated exact mass=675.23. $^1$H NMR (500 MHz, DMSO-$d_6$) δ: 8.57 (d, J=5.1 Hz, 1H), 7.69-7.62 (m, 2H), 7.56 (s, 1H), 7.42 (d, J=7.7 Hz, 1H), 7.39-7.26 (m, 1H), 7.25-7.20 (m, 1H), 7.19-7.13 (m, 1H), 7.09 (s, 1H), 6.92 (d, J=8.1 Hz, 1H), 6.79-6.70 (m, 2H), 5.35 (s, 2H), 5.24 (s, 2H), 4.27 (s, 4H), 4.04 (s, 2H), 3.67 (d, J=11.4 Hz, 1H), 3.57 (d, J=11.4 Hz, 1H), 3.00 (s, 3H), 2.91 (s, 3H), 2.22 (s, 3H), 1.27 (s, 3H).

Example 3019

4-(4-chloro-5-{[3-(2,3-dihydro-1,4-benzodioxin-6-yl)-2-methylphenyl]methoxy}-2-(hydroxymethyl)phenoxymethyl)-N,N-dimethylpyridine-2-carboxamide

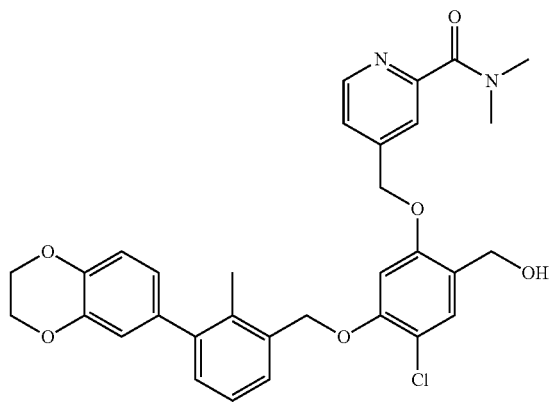 [SMILES: Cc1c(COc2cc(OCc3ccnc(C(=O)N(C)C)c3)c(CO)cc2Cl)cccc1-c1ccc2c(c1)OCCO2]

This product was isolated as a by-product from the preparation of example 3018. LCMS (Condition ACN-AA, ES+) M+H=575.1, 2.00 minutes, calculated exact mass=574.19. $^1$H NMR (500 MHz, DMSO-$d_6$) δ 8.58 (d, J=5.1 Hz, 1H), 7.61 (s, 1H), 7.52 (d, J=4.4 Hz, 1H), 7.41 (d, J=7.7 Hz, 1H), 7.36 (s, 1H), 7.26-7.18 (m, 1H), 7.18-7.12 (m, 1H), 7.03 (s, 1H), 6.92 (d, J=8.1 Hz, 1H), 6.79-6.70 (m, 2H), 5.32 (s, 2H), 5.20 (s, 2H), 4.51 (s, 2H), 4.27 (s, 4H), 3.00 (s, 3H), 2.92 (s, 3H), 2.22 (s, 3H).

Example 3020

5-chloro-4-((3-(2,3-dihydrobenzo[b][1,4]dioxin-6-yl)-2-methylbenzyl)oxy)-2-((3-(methylsulfonyl)benzyl)oxy)benzaldehyde

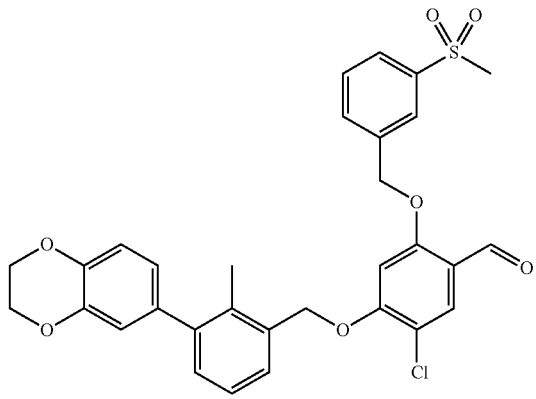 [SMILES: Cc1c(COc2cc(OCc3cccc(S(C)(=O)=O)c3)c(C=O)cc2Cl)cccc1-c1ccc2c(c1)OCCO2]

Prepared in substantially the same manner as example 3008. LCMS (Condition ACN-TFA, ES+) M+Na=601.2, 1.14 minutes, calculated exact mass=578.12. $^1$H NMR (400 MHz, CDCl3) δ: 10.30 (s, 1H), 8.05 (s, 1H), 7.99-7.93 (m, 1H), 7.90 (s, 1H), 7.75 (d, J=7.8 Hz, 1H), 7.67-7.62 (m, 1H), 7.44-7.38 (m, 1H), 7.27-7.23 (m, 2H), 6.92 (d, J=8.3 Hz, 1H), 6.82 (d, J=2.0 Hz, 1H), 6.77 (dd, J=8.3, 2.0 Hz, 1H), 6.68 (s, 1H), 5.24 (s, 2H), 5.22 (s, 2H), 4.31 (s, 4H), 3.09 (s, 3H), 2.29 (s, 3H).

Example 3021

(S)-2-((5-chloro-4-((3-(2,3-dihydrobenzo[b][1,4]dioxin-6-yl)-2-methylbenzyl)oxy)-2-((3-(methylsulfonyl)benzyl)oxy)benzyl)amino)-3-hydroxy-2-methylpropanoic acid

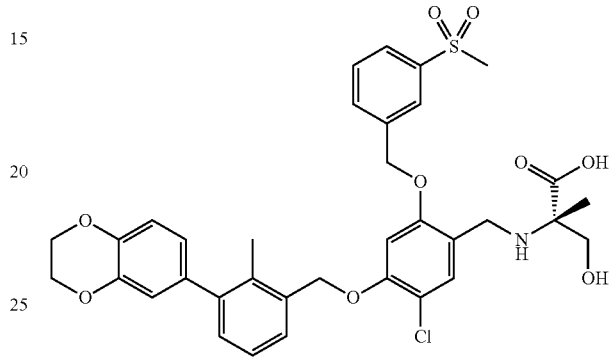

Prepared in substantially the same manner as example 3009. LCMS (Condition MeOH-AA, ES+) M+H=682.7, 2.70 minutes, calculated exact mass=681.18. $^1$H NMR (500 MHz, DMSO-$d_6$) δ: 8.12 (s, 1H), 7.92 (dd, J=15.8, 7.7 Hz, 2H), 7.68 (t, J=7.7 Hz, 1H), 7.54 (s, 1H), 7.45 (d, J=7.3 Hz, 1H), 7.30-7.21 (m, 1H), 7.21-7.09 (m, 2H), 6.92 (d, J=8.4 Hz, 1H), 6.83-6.68 (m, 2H), 5.37 (s, 2H), 5.26 (s, 2H), 4.27 (s, 4H), 3.97 (s, 2H), 3.65-3.58 (m, 1H), 3.52 (d, J=11.4 Hz, 1H), 3.24 (s, 3H), 2.24 (s, 3H), 1.23 (s, 3H).

Example 3022

(S)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-4-oxobutanoic acid

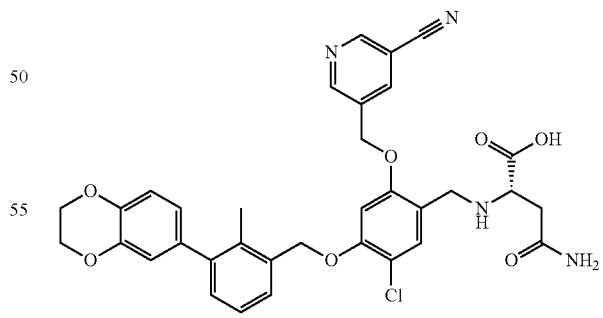

A solution of 5-((4-chloro-5-((3-(2,3-dihydrobenzo[b][1,4]dioxin-6-yl)-2-methylbenzyl)oxy)-2-formylphenoxy)methyl)nicotinonitrile (0.025 g, 0.047 mmol) and L-asparagine (0.021 g, 0.159 mmol) in dry N,N-dimethylformamide (0.70 mL) was treated with acetic acid (0.014 mL, 0.237 mmol) and the mixture was stirred for 30 min. To the mixture was added sodium cyanoborohydride (8.94 mg, 0.142 mmol) and the reaction was stirred for 16 hours. The reaction was filtered (0.45 μm syringe tip filter) and the filtrate was purified via general method for preparative LCMS purification. LCMS (Condition MeOH-AA, ES+) M+H=643.2, 2.67 minutes, calculated exact mass=642.19. ¹H NMR (500 MHz, DMSO-d₆) δ 9.01 (d, J=7.0 Hz, 2H), 8.49 (s, 1H), 7.65 (br. s., 1H), 7.47 (s, 1H), 7.43 (d, J=7.7 Hz, 1H), 7.27-7.20 (m, 1H), 7.17 (d, J=7.3 Hz, 1H), 7.13 (s, 1H), 7.00 (br. s., 1H), 6.92 (d, J=7.7 Hz, 1H), 6.80-6.72 (m, 2H), 5.36 (s, 2H), 5.26 (s, 2H), 4.28 (s, 4H), 4.04-3.92 (m, 2H), 3.38 (d, J=4.4 Hz, 1H), 2.64-2.56 (m, 1H), 2.40 (dd, J=16.3, 8.3 Hz, 1H), 2.23 (s, 3H).

Example 3023

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)succinic acid

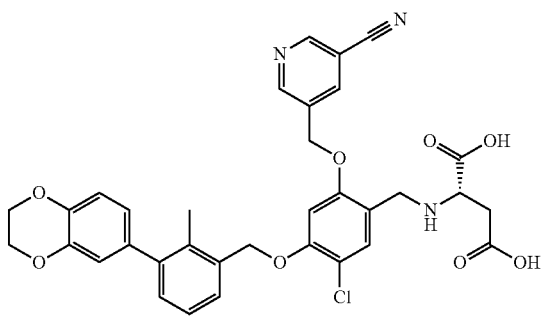 [SMILES: Cc1c(COc2cc(OCc3cncc(C#N)c3)c(CN[C@@H](CC(=O)O)C(=O)O)cc2Cl)cccc1-c1ccc2c(c1)OCCO2]

Prepared in substantially the same manner as example 3022. LCMS (Condition MeOH-AA, ES+) M+H=644.1, 2.58 minutes, calculated exact mass=643.17. ¹H NMR (500 MHz, DMSO-d₆) δ 9.01 (s, 1H), 8.99 (s, 1H), 8.48 (s, 1H), 7.47-7.38 (m, 2H), 7.23 (t, J=7.7 Hz, 1H), 7.16 (d, J=7.7 Hz, 1H), 7.10 (s, 1H), 6.92 (d, J=8.1 Hz, 1H), 6.81-6.70 (m, 2H), 5.34 (s, 2H), 5.24 (s, 2H), 4.27 (s, 4H), 3.94-3.80 (m, 2H), 3.23 (br., 1H), 2.46 (m, 1H), 2.39-2.29 (m, 1H), 2.22 (s, 3H).

Example 3024

(R)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-4-oxobutanoic acid

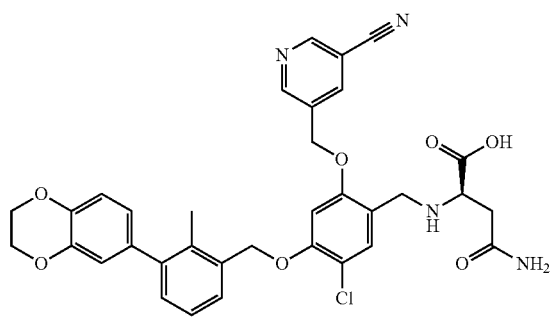 [SMILES: Cc1c(COc2cc(OCc3cncc(C#N)c3)c(CN[C@H](CC(N)=O)C(=O)O)cc2Cl)cccc1-c1ccc2c(c1)OCCO2]

Prepared in substantially the same manner as example 3022. LCMS (Condition ACN-AA, ES+) M+H=643.2, 1.68 minutes, calculated exact mass=642.19. ¹H NMR (500 MHz, DMSO-d₆) δ: 9.01 (d, J=8.1 Hz, 2H), 8.49 (s, 1H), 7.70 (br. s., 1H), 7.47-7.39 (m, 2H), 7.27-7.21 (m, 1H), 7.17 (d, J=7.7 Hz, 1H), 7.12 (s, 1H), 6.96 (br. s., 1H), 6.92 (d, J=8.1 Hz, 1H), 6.80-6.71 (m, 2H), 5.35 (s, 2H), 5.25 (s, 2H), 4.28 (s, 4H), 4.02-3.86 (m, 3H), 3.33 (br. s., 1H), 2.61-2.55 (m, 1H), 2.37 (dd, J=16.0, 8.3 Hz, 1H), 2.23 (s, 3H), 1.90 (s, 1H).

Example 3025

(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)succinic acid

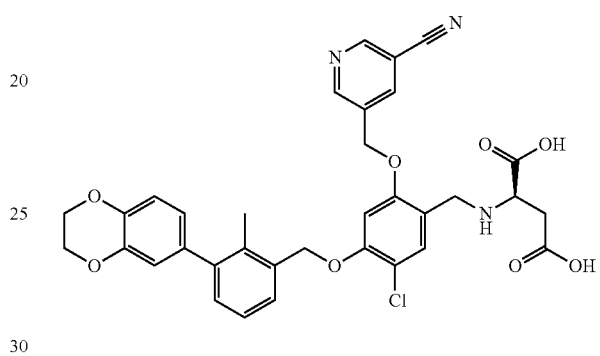

Prepared in substantially the same manner as example 3022. LCMS (Condition ACN-AA, ES+) M+H=644.2, 1.48 minutes, calculated exact mass=643.17. ¹H NMR (500 MHz, DMSO-d₆) δ: 9.00 (d, J=8.1 Hz, 2H), 8.48 (s, 1H), 7.49 (s, 1H), 7.42 (d, J=7.3 Hz, 1H), 7.23 (t, J=7.5 Hz, 1H), 7.17 (d, J=7.3 Hz, 1H), 7.12 (s, 1H), 6.92 (d, J=8.1 Hz, 1H), 6.80-6.71 (m, 2H), 5.35 (s, 2H), 5.26 (s, 2H), 4.27 (s, 4H), 4.07-4.01 (m, 1H), 4.00-3.94 (m, 1H), 2.66 (dd, J=16.1, 8.4 Hz, 1H), 2.23 (s, 3H); some product peaks were solvent obscured.

Example 3026

(S)-1-(5-chloro-4-((3-(2,3-dihydrobenzo[b][1,4]dioxin-6-yl)-2-methylbenzyl)oxy)-2-((2-methoxy-5-(methoxycarbonyl)benzyl)oxy)benzyl)piperidine-2-carboxylic acid

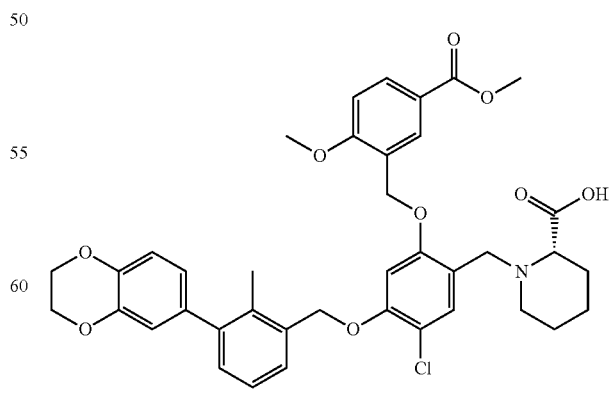

Prepared in substantially the same manner as example 3022. LCMS (Condition MeOH-AA, ES+) M+H=702.9, 3.11 minutes, calculated exact mass=701.24. $^1$H NMR (500 MHz, DMSO-d$_6$) δ: 8.06 (s, 1H), 7.96 (d, J=8.9 Hz, 1H), 7.48 (s, 1H), 7.44 (d, J=7.3 Hz, 1H), 7.27-7.20 (m, 1H), 7.16 (dd, J=7.6, 5.5 Hz, 2H), 7.08 (s, 1H), 6.90 (d, J=8.2 Hz, 1H), 6.80-6.65 (m, 2H), 5.22 (s, 2H), 5.19 (s, 2H), 4.26 (s, 4H), 3.89 (s, 3H), 3.17 (s, 2H), 2.94 (d, J=10.7 Hz, 1H), 2.36 (br. s., 1H), 2.22 (s, 3H), 1.84 (br. s., 1H), 1.67 (d, J=9.8 Hz, 1H), 1.49 (br. s., 3H), 1.32 (br. s., 1H); several signals were solvent obscured.

Example 3027

(S)-1-(2-((5-carboxy-2-methoxybenzyl)oxy)-5-chloro-4-((3-(2,3-dihydrobenzo[b][1,4]dioxin-6-yl)-2-methylbenzyl)oxy)benzyl)piperidine-2-carboxylic acid

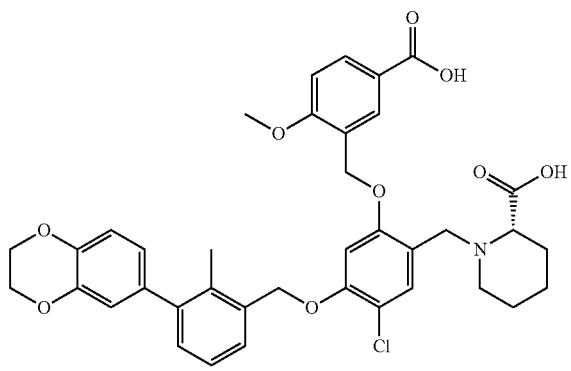 [SMILES: COc1ccc(C(=O)O)cc1COc1cc(OCc2cccc(-c3ccc4c(c3)OCCO4)c2C)c(Cl)cc1CN1CCCC[C@H]1C(=O)O]

A solution of (S)-1-(5-chloro-4-((3-(2,3-dihydrobenzo[b][1,4]dioxin-6-yl)-2-methylbenzyl)oxy)-2-((2-methoxy-5-(methoxycarbonyl)benzyl)oxy)benzyl)piperidine-2-carboxylic acid (0.01442 g, 0.021 mmol) in dry methanol (0.5 mL) was treated with lithium hydroxide monohydrate (8.62 mg, 0.205 mmol), and stirred with heating (65° C. oil bath) for 45 min. The reaction was cooled, then filtered (0.45 μm syringe tip filter) and the filtrate was purified via general method for preparative LCMS purification. LCMS (Condition ACN-AA, ES+) M+H=688.3, 1.54 minutes, calculated exact mass=687.22. $^1$H NMR (500 MHz, DMSO-d$_6$) δ 8.07 (s, 1H), 7.93 (d, J=8.1 Hz, 1H), 7.50-7.39 (m, 2H), 7.30-7.22 (m, 1H), 7.18 (d, J=7.7 Hz, 1H), 7.14 (d, J=8.8 Hz, 1H), 7.10 (s, 1H), 6.92 (d, J=8.1 Hz, 1H), 6.79-6.72 (m, 2H), 5.24 (s, 2H), 5.19 (s, 2H), 4.27 (s, 4H), 3.89 (s, 3H), 3.83 (d, J=13.9 Hz, 1H), 3.68 (d, J=13.6 Hz, 1H), 3.11 (d, J=4.4 Hz, 1H), 2.92 (br. s., 1H), 2.35 (br. s., 1H), 2.24 (s, 3H), 1.81 (br. s., 1H), 1.66 (d, J=10.6 Hz, 1H), 1.49 (br. s., 3H), 1.33 (d, J=5.9 Hz, 1H).

Example 3028

(S)-1-(2-(benzyloxy)-5-chloro-4-((3-(2,3-dihydrobenzo[b][1,4]dioxin-6-yl)-2-methylbenzyl)oxy)benzyl)piperidine-2-carboxylic acid

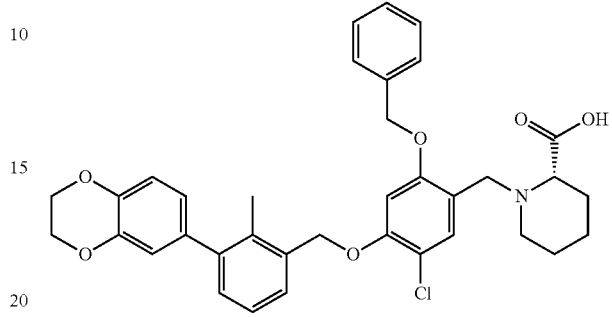

Prepared in substantially the same manner as example 3022. LCMS (Condition ACN-AA, ES+) M+H=614.3, 1.96 minutes, calculated exact mass=613.22. $^1$H NMR (500 MHz, DMSO-d$_6$) δ: 7.49-7.37 (m, 6H), 7.36-7.31 (m, 1H), 7.28-7.21 (m, 1H), 7.18 (d, J=7.3 Hz, 1H), 7.09 (s, 1H), 6.92 (d, J=8.1 Hz, 1H), 6.80-6.72 (m, 2H), 5.22 (s, 2H), 5.21 (s, 2H), 4.28 (s, 4H), 3.77 (d, J=13.9 Hz, 1H), 3.65 (d, J=14.3 Hz, 1H), 3.16 (d, J=8.1 Hz, 1H), 2.89 (br. s., 1H), 2.31 (br. s., 1H), 2.24 (s, 3H), 1.80 (br. s., 1H), 1.70 (d, J=9.2 Hz, 1H), 1.48 (br. s., 3H), 1.36 (br. s., 1H).

Example 3029

(S)-1-(5-chloro-4-((3-(2,3-dihydrobenzo[b][1,4]dioxin-6-yl)-2-methylbenzyl)oxy)-2-((2-methoxybenzyl)oxy)benzyl)piperidine-2-carboxylic acid

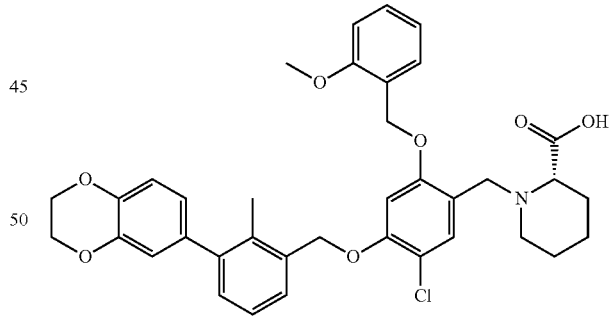

Prepared in substantially the same manner as example 3022. LCMS (Condition MeOH-AA, ES+) M+H=644.2, 3.02 minutes, calculated exact mass=643.23. $^1$H NMR (500 MHz, DMSO-d$_6$) δ: 7.48 (s, 1H), 7.44 (dd, J=10.6, 8.1 Hz, 2H), 7.35 (t, J=7.7 Hz, 1H), 7.28-7.22 (m, 1H), 7.18 (d, J=7.3 Hz, 1H), 7.13 (s, 1H), 7.06 (d, J=8.4 Hz, 1H), 6.96 (t, J=7.3 Hz, 1H), 6.91 (d, J=8.1 Hz, 1H), 6.80-6.70 (m, 2H), 5.25 (br. s., 2H), 5.19 (s, 2H), 4.26 (s, 4H), 4.12-4.06 (m, 1H), 4.03-3.96 (m, 1H), 3.81 (s, 3H), 3.62 (br. s., 1H), 3.12 (d, J=10.6 Hz, 1H), 2.66 (br. s., 1H), 2.23 (s, 3H), 2.00 (d, J=12.8 Hz, 1H), 1.70 (d, J=10.3 Hz, 1H), 1.58 (br. s., 3H), 1.41 (br. s., 1H).

Example 3030

(S)-2-((2-(2-amino-2-oxoethoxy)-5-chloro-4-((3-(2,3-dihydrobenzo[b][1,4]dioxin-6-yl)-2-methylbenzyl)oxy)benzyl)amino)-3-hydroxypropanoic acid

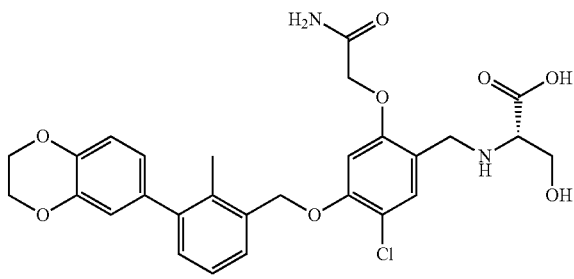 [SMILES: Cc1c(COc2cc(OCC(N)=O)c(CN[C@@H](CO)C(=O)O)cc2Cl)cccc1-c1ccc2c(c1)OCCO2]

Prepared in substantially the same manner as example 3022. LCMS (Condition ACN-AA, ES+) M+H=557.3, 1.49 minutes, calculated exact mass=556.16. $^1$H NMR (400 MHz, CDCl$_3$) δ: 9.18 (s, 1H), 8.72 (s, 1H), 7.43 (t, J=4.5 Hz, 1H), 7.34 (s, 1H), 7.25 (d, J=4.5 Hz, 2H), 6.91 (d, J=8.3 Hz, 1H), 6.83 (d, J=2.0 Hz, 1H), 6.80-6.73 (m, 2H), 5.36-5.25 (m, 1H), 5.23-5.11 (m, 3H), 4.30 (s, 4H), 3.77 (s, 3H), 3.68-3.56 (m, 1H), 3.36 (s, 3H), 2.30 (s, 3H), 1.61 (br. s., 2H).

Preparation of Intermediates ethyl (5-(((tert-butyldimethylsilyl)oxy)methyl)pyridin-3-yl)carbamate

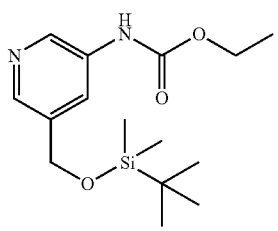 [SMILES: CCOC(=O)Nc1cncc(CO[Si](C)(C)C(C)(C)C)c1]

A cold (0° C. ice bath) solution of 5-(((tert-butyldimethylsilyl)oxy)methyl)pyridin-3-amine (0.100 g, 0.419 mmol) in dry dichloromethane (2.0 mL) was treated with Hunig'sBase (0.110 mL, 0.629 mmol) followed by ethyl chloroformate (0.048 mL, 0.503 mmol). The reaction was stirred for 10 minutes, warmed to room temperature, and stirred for 1 hour. The reaction was treated with sodium hydroxide, 0.2 N in methanol (3.15 mL, 0.629 mmol), and stirred for 3 hours. Additional aqueous 1.0 N sodium hydroxide (1.0 mL) was added, and the reaction was stirred for 16 hours. The reaction was warmed (45° C. water bath), stirred for 2 hours, then concentrated under reduced pressure and diluted with dichloromethane and water. The organic layer was washed with brine, then dried over sodium sulfate, filtered, and concentrated under reduced pressure to afford an off-white solid which was used directly in the following reaction. LCMS (Condition ACN-TFA, ES+) M+H=311.2, 0.94 minutes, calculated exact mass=310.17.

ethyl (5-(hydroxymethyl)pyridin-3-yl)carbamate

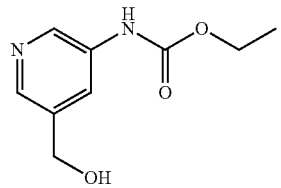

A solution of ethyl (5-(((tert-butyldimethylsilyl)oxy)methyl)pyridin-3-yl)carbamate (0.130 g, 0.419 mmol) in dry THF (5 mL) was treated with solid tetrabutylammonium fluoride (0.329 g, 1.257 mmol) and glacial acetic acid (0.072 mL, 1.257 mmol). The reaction was stirred for 30 minutes, then diluted with ethyl acetate (15 mL) and washed with water (2×10 mL). The organic layer was then dried over sodium sulfate, filtered, and concentrated under reduced pressure, affording the product (0.050 g, 0.255 mmol, 60.8% yield) as an off-white solid. The material was purified by column chromatography, 40 g column, ethyl acetate/Hexanes 10-80%, affording the product (0.050 g, 0.255 mmol, 60.8% yield) as a white powdery solid. LCMS (Condition MeOH-AA, ES+) M+H=197.1, 1.39 minutes, calculated exact mass=196.08. $^1$H NMR (400 MHz, CDCl$_3$) δ: 8.24 (d, J=4.9 Hz, 1H), 7.97 (s, 1H), 7.54 (s, 1H), 7.05 (d, J=5.1 Hz, 1H), 4.77 (d, J=6.1 Hz, 2H), 4.27 (q, J=7.2 Hz, 2H), 1.35 (t, J=7.1 Hz, 3H).

ethyl (5-(chloromethyl)pyridin-3-yl)carbamate hydrochloride

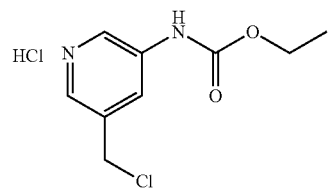

A solution of ethyl (5-(hydroxymethyl)pyridin-3-yl)carbamate (0.050 g, 0.255 mmol) in dry dichloromethane (3 mL) was treated with thionyl chloride (0.112 mL, 1.529 mmol), stirred for 3 hours, then concentrated under reduced pressure to afford the product as a white solid, and which was used immediately in the following experiment. $^1$H NMR (500 MHz, CDCl$_3$) δ: 11.26 (br. s., 1H), 8.63 (br. s., 1H), 8.24 (br. s., 1H), 7.41 (br. s., 1H), 4.69 (s, 2H), 4.34 (q, J=6.9 Hz, 2H), 1.37 (t, J=6.8 Hz, 3H).

N-(4-(hydroxymethyl)pyridin-2-yl)acetamide

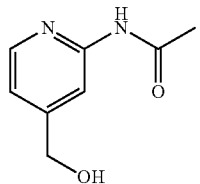

To a cold (0° C. ice bath) solution of 2-acetamidoisonicotinic acid (1.56 g, 8.66 mmol) in anhydrous THF (60 mL), under nitrogen, was added N-methylmorpholine (0.952 mL, 8.66 mmol) and then ethyl chloroformate (0.828 mL, 8.66 mmol). After stirring for 20 minutes sodium borohydride (0.983 g, 26.0 mmol) was added portionwise. The mixture was cooled (−78° C. dry ice acetone bath) and methanol (50 mL) was added over 90 minutes. The temperature was then allowed to rise to room temperature and stirring was continued for 16 hours. The reaction was poured onto a pad of silica gel, and eluted with dichloromethane until turbid flow stopped, then 10% methanol in dichloromethane. The methanol/dichloromethane fraction was concentrated under reduced pressure. The orange oil was dry loaded on celite then purified on a 40 g column over 25 column volumes from 0-10% methanol in dichloromethane to afford the expected product (0.52 g, 3.13 mmol, 36.1% yield) as a white waxy solid. LCMS (Condition MeOH-AA, ESI+) M+H=167.20, 1.34 minutes, calculated exact mass=166.07 $^1$H NMR (400 MHz, CDCl3) δ: 8.24 (d, J=5.1 Hz, 1H), 8.20-8.05 (m, 2H), 7.11 (dt, J=5.2, 0.7 Hz, 1H), 4.76 (s, 2H), 2.22 (s, 3H).

N-(4-(Chloromethyl)pyridin-2-yl)acetamide hydrochloride

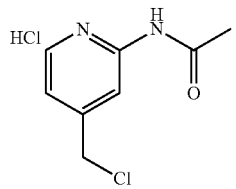

A solution of N-(4-(hydroxymethyl)pyridin-2-yl)acetamide (0.050 g, 0.301 mmol) in dichloromethane (3 mL) was treated with thionyl chloride (0.132 mL, 1.805 mmol), and the reaction was stirred for 3 hours. The reaction was concentrated, then dried under vacuum pump for 30 minutes to afford the product as a white glassy solid, which was used immediately in the following reaction. $^1$H NMR (500 MHz, CDCl$_3$) δ: 12.61 (br. s., 1H), 8.76 (s, 1H), 8.16 (d, J=6.4 Hz, 1H), 7.47 (dd, J=6.4, 1.4 Hz, 1H), 4.69 (s, 2H), 2.43 (s, 3H).

(5-(Methylsulfonyl)pyridin-3-yl)methanol

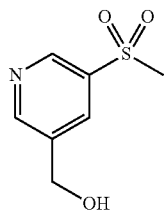

A stirred mixture of (5-bromopyridin-3-yl)methanol (0.386 g, 2.053 mmol), sodium methanesulfinate (0.251 g, 2.464 mmol), copper(I) iodide (0.039 g, 0.205 mmol), L-proline (0.047 g, 0.411 mmol) and sodium hydroxide (0.411 mL, 0.411 mmol) in dimethyl sulfoxide (3 mL) was heated at 100° C. under microwave irradiation for 6 hours. The reaction mixture was diluted with ethyl acetate and washed with water, brine, then dried over sodium sulfate, filtered, and concentrated under reduced pressure. The aqueous layer was diluted with brine and then re-extracted twice with ethyl acetate, and once with dichloromethane. The combined organic layers were dried over sodium sulfate, filtered, and concentrated under reduced pressure. The residue was purified by biotage (RediSep 12 g SiO$_2$, 0% (3 CV), 0-50% (15 CV), 50-100% (10 CV), ethyl acetate in hexanes). Product fractions were pooled and concentrated under reduced pressure, affording the product (0.084 g, 0.449 mmol, 21.86% yield) as a white solid. $^1$H NMR (400 MHz, CDCl3) δ: 9.05 (d, J=2.3 Hz, 1H), 8.86 (d, J=2.0 Hz, 1H), 8.27 (t, J=2.1 Hz, 1H), 4.86 (s, 2H), 3.12 (s, 3H).

3-(Chloromethyl)-5-(methylsulfonyl)pyridine hydrochloride

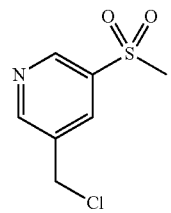

A suspension of (5-(methylsulfonyl)pyridin-3-yl)methanol (0.084 g, 0.449 mmol) in dry chloroform (3.0 mL) was treated with thionyl chloride (0.033 mL, 0.449 mmol), and stirred for 3 hours. The reaction was concentrated under reduced pressure to afford the product as a pale yellow powder, which was used immediately in the following reaction. $^1$H NMR (400 MHz, CDCl$_3$) δ: 9.13 (d, J=2.0 Hz, 1H), 8.91 (d, J=2.0 Hz, 1H) 8.30 (t, J=2.1 Hz, 1H), 4.69 (s, 2H), 3.16 (s, 3H)

5-chloro-4-((3-(2,3-dihydrobenzo[b][1,4]dioxin-6-yl)-2-methylbenzyl)oxy)-2-((5-(methylsulfonyl)pyridin-3-yl)methoxy)benzaldehyde

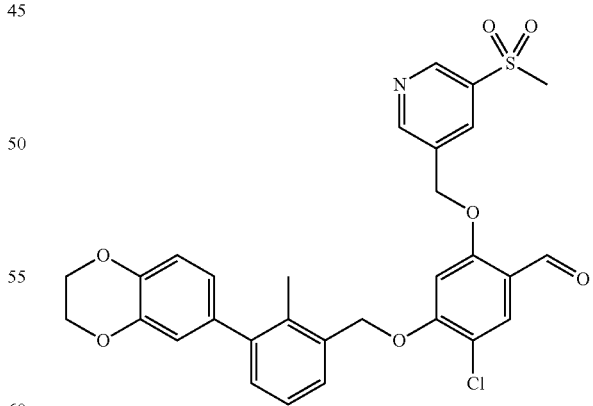

Prepared in substantially the same manner as example 3008. LCMS (Condition ACN-TFA, ES+) M+H=580.1, 1.20 minutes, calculated exact mass=579.11. $^1$H NMR (400 MHz, CDCl3) δ: 10.27 (s, 1H), 9.19 (s, 1H), 8.99 (s, 1H), 8.38 (s, 1H), 7.93 (s, 1H), 7.43 (t, J=4.5 Hz, 1H), 7.28 (br. s., 2H), 6.93 (d, J=8.3 Hz, 1H), 6.84 (d, J=2.0 Hz, 1H), 6.81-6.75 (m, 1H), 6.69 (s, 1H), 5.28 (s, 2H), 5.26 (s, 2H), 4.32 (s, 4H), 3.17 (s, 3H), 2.31 (s, 3H).

2-chloro-4-(chloromethyl)-6-methoxypyridine hydrochloride

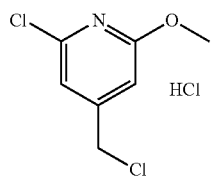

A solution of (2-chloro-6-methoxypyridin-4-yl)methanol (0.050 g, 0.288 mmol) in dichloromethane (5 mL) was treated with thionyl chloride (0.126 mL, 1.728 mmol) and stirred for 3 hours. The reaction was concentrated, then dried under vacuum pump for 30 minutes to afford the product as a clear viscous oil, which was used immediately in the following reaction.

5-chloro-2-((2-chloro-6-methoxypyridin-4-yl)methoxy)-4-((3-(2,3-dihydrobenzo[b][1,4]dioxin-6-yl)-2-methylbenzyl)oxy)benzaldehyde

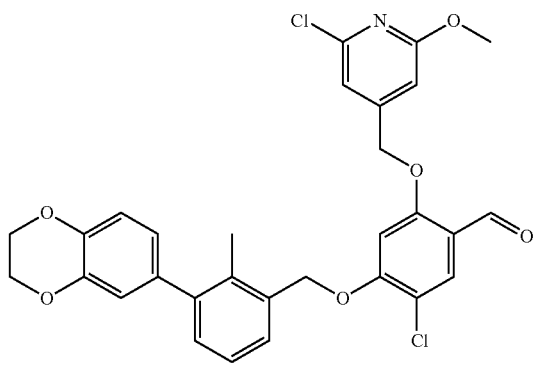 [SMILES: COc1cc(COc2cc(OCc3cccc(-c4ccc5c(c4)OCCO5)c3C)c(Cl)cc2C=O)cc(Cl)n1]

A stirred mixture of 5-chloro-4-((3-(2,3-dihydrobenzo[b][1,4]dioxin-6-yl)-2-methylbenzyl)oxy)-2-hydroxybenzaldehyde (0.091 g, 0.222 mmol), 2-chloro-4-(chloromethyl)-6-methoxypyridine hydrochloride (0.066 g, 0.288 mmol), cesium carbonate (0.217 g, 0.665 mmol) and sodium iodide (3 mg, 0.022 mmol) in N,N-dimethylformamide (3 mL) was heated (75° C. oil bath) for 1.5 hours. The reaction was cooled, diluted with dichloromethane, and washed with water. The organic layer was dried over sodium sulfate, filtered, and concentrated under reduced pressure, affording orange oil that solidified upon standing. The orange solid was triturated with diethyl ether, with decanting of the ether followed by drying under vacuum pump. The residue was purified by biotage (Redi-sep 12 g SiO2, 0% (3 CV), 0-100% (15 CV), 100% (2 CV), ethyl acetate in hexanes). Product fractions were pooled and concentrated under reduced pressure, affording the product (0.036 g, 0.064 mmol, 28.7% yield) as a white solid after trituration with diethyl ether. This material was used as-is in the following experiment. LCMS (Condition ACN-TFA, ES+) M+H=566.2, 1.26 minutes, calculated exact mass=565.11.

(2-methoxypyridin-4-yl)methanol

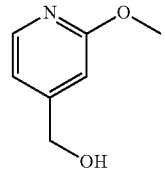

To a cold (0° C. ice bath) solution of 2-methoxyisonicotinic acid (0.285 g, 1.861 mmol) in anhydrous tetrahydrofuran (10 mL), under nitrogen, was added N-methylmorpholine (0.215 mL, 1.954 mmol) and then ethyl chloroformate (0.187 mL, 1.954 mmol). After stirring for 20 minutes sodium borohydride (0.211 g, 5.58 mmol) was added portionwise. The mixture was cooled (−78° C. dry ice acetone bath) and methanol (10 mL) was added over 5 minutes. The temperature was then allowed to rise to room temperature and stirring was continued for 16 hours. The reaction was poured onto a pad of silica gel, and eluted with dichloromethane until turbid flow stopped, then 10% methanol in dichloromethane. The later filtrate was concentrated under reduced pressure, and purified by silica gel column chromatography (24 g SiO2, 0-10% (20CV) methanol in dichloromethane) to afford the product (0.24 g, 1.725 mmol, 93% yield) as an amber oil. LCMS (Condition ACN-TFA, ES+) M+H=140.1, broad elution, calculated exact mass=139.06. $^1$H NMR (400 MHz, CDCl$_3$) δ: 8.13 (d, J=5.4 Hz, 1H), 6.91-6.83 (m, 1H), 6.76 (s, 1H), 4.70 (d, J=5.6 Hz, 2H), 3.94 (s, 3H), 1.91 (br. s., 1H).

4-(chloromethyl)-2-methoxypyridine hydrochloride

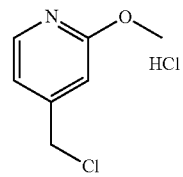

A solution of (2-methoxypyridin-4-yl)methanol (0.100 g, 0.719 mmol) in dry dichloromethane (3 mL) was treated with thionyl chloride (0.315 mL, 4.31 mmol), and stirred under nitrogen at room temperature for 2 hours. The reaction was concentrated under reduced pressure to afford a white solid which was used immediately in the following reaction. $^1$H NMR (400 MHz, CDCl$_3$) δ: 8.38 (d, J=5.8 Hz, 1H), 7.38 (d, J=5.5 Hz, 1H), 7.30 (s, 1H), 4.71 (s, 2H), 4.39 (s, 3H).

275

5-chloro-4-((3-(2,3-dihydrobenzo[b][1,4]dioxin-6-yl)-2-methylbenzyl)oxy)-2-((2-methoxypyridin-4-yl)methoxy)benzaldehyde

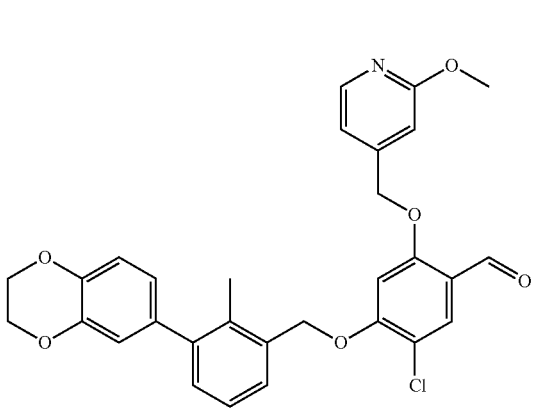 [SMILES: COc1cc(COc2cc(OCc3cccc(-c4ccc5c(c4)OCCO5)c3C)c(Cl)cc2C=O)ccn1]

Prepared in substantially the same manner as example 3008. LCMS (Condition ACN-TFA, ES+) M+H=532.2, 1.27 minutes, calculated exact mass=531.14. $^1$H NMR (400 MHz, CDCl3) δ: 10.38 (s, 1H), 8.20 (d, J=5.3 Hz, 1H), 7.91 (s, 1H), 7.35 (dd, J=6.3, 2.8 Hz, 1H), 7.26-7.20 (m, 2H), 6.95-6.88 (m, 2H), 6.83 (d, J=2.0 Hz, 1H), 6.80-6.75 (m, 2H), 6.55 (s, 1H), 5.16 (s, 2H), 5.15 (s, 2H), 4.32 (s, 4H), 3.96 (s, 3H), 2.26 (s, 3H).

4-(hydroxymethyl)-N,N-dimethylpicolinamide

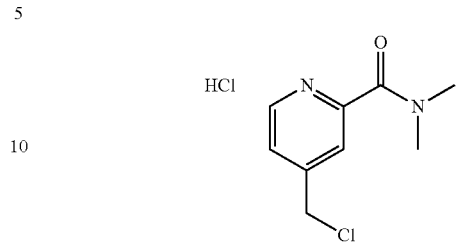

A solution of 4-(hydroxymethyl)picolinic acid (0.100 g, 0.653 mmol) in N,N-dimethylformamide (2.0 mL) was treated with Hunig'sBase (0.228 mL, 1.306 mmol) followed by dimethylamine, 2.0 M in THF (0.392 mL, 0.784 mmol) and HATU (0.323 g, 0.849 mmol). The reaction was stirred for 30 minutes. The product was purified by silica gel column chromatography (24 g SiO$_2$, 0-10% (20 CV), 10-20% (2 CV), 20% (15 CV) methanol in dichloromethane) to afford the product (0.101 g, 0.560 mmol, 86% yield), as a viscous oil. LCMS (Condition MeOH-AA, ES+) M+H=181.1, 0.88 minutes, calculated exact mass=180.09.

276

4-(chloromethyl)-N,N-dimethylpicolinamide hydrochloride

A solution of 4-(hydroxymethyl)-N,N-dimethylpicolinamide (0.100 g, 0.555 mmol) in dry dichloromethane (3.0 mL) was treated with thionyl chloride (0.243 mL, 3.33 mmol). The solution immediately developed a white precipitate upon addition of thionyl chloride. The mixture was stirred for 2 hours, then concentrated under reduced pressure and the residue was used immediately in the following reaction. $^1$H NMR (400 MHz, CDCl$_3$) δ: 8.82 (br. s., 1H), 8.09-7.95 (m, 2H), 4.81 (s, 2H), 3.20 (br. s., 3H), 3.13 (br. s., 3H).

4-((4-chloro-5-((3-(2,3-dihydrobenzo[b][1,4]dioxin-6-yl)-2-methylbenzyl)oxy)-2-formylphenoxy)methyl)-N,N-dimethylpicolinamide

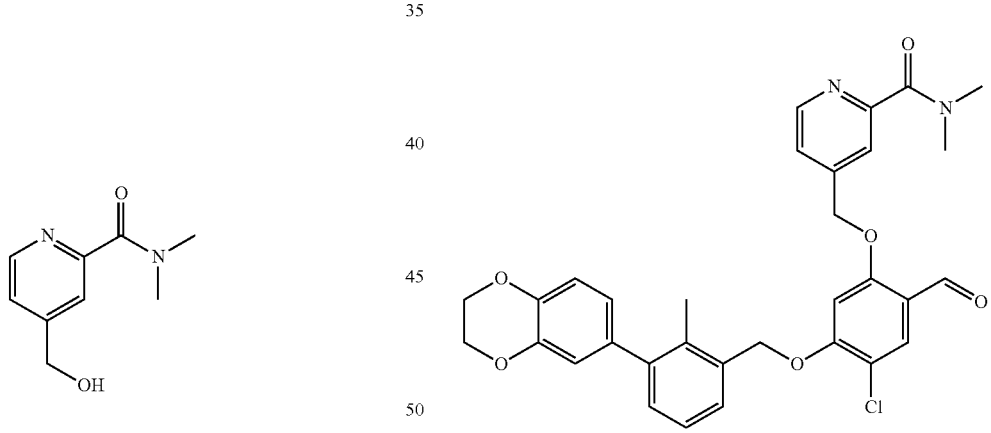

Prepared in substantially the same manner as example 3008, excepting that the residue after work-up was purified by biotage (RediSep 24 g SiO$_2$, 0% (3 CV), 0-20% (15 CV), 20% (3 CV), methanol in dichloromethane). Product fractions were pooled and concentrated under reduced pressure. LCMS (Condition ACN-TFA, ES+) M+H=573.2, 1.10 minutes, calculated exact mass=572.17. $^1$H NMR (400 MHz, CDCl3) δ: 10.37 (s, 1H), 8.64 (d, J=5.0 Hz, 1H), 7.92 (s, 1H), 7.73 (s, 1H), 7.43 (dd, J=5.0, 1.5 Hz, 1H), 7.41-7.37 (m, 1H), 7.27-7.24 (m, 2H), 6.92 (d, J=8.3 Hz, 1H), 6.83 (d, J=2.0 Hz, 1H), 6.78 (dd, J=8.3, 2.3 Hz, 1H), 6.62 (s, 1H), 5.22 (d, J=3.0 Hz, 3H), 4.32 (s, 4H), 3.16 (s, 3H), 3.13 (s, 3H), 2.29 (s, 3H).

1-(chloromethyl)-3-(methylsulfonyl)benzene

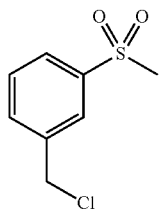

A suspension of (3-(methylsulfonyl)phenyl)methanol (0.106 g, 0.569 mmol) in dry dichloromethane (3.0 mL) was treated with thionyl chloride (0.249 mL, 3.42 mmol) and the mixture was stirred for 2 hours, during which time all solids dissolved. The reaction was concentrated under reduced pressure and the residue was dried twice from dichloromethane. The residue was used immediately in the following experiment. $^1$H NMR (400 MHz, CDCl$_3$) δ: 8.07-7.88 (m, 2H), 7.77-7.54 (m, 2H), 5.22-4.99 (m, 1H), 4.66 (s, 1H), 3.10-3.06 (m, 3H).

methyl 3-(chloromethyl)-4-methoxybenzoate

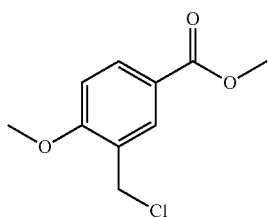

A cold (0° C. ice bath) solution of 3-(chloromethyl)-4-methoxybenzoic acid (0.465 g, 2.318 mmol) in dry dichloromethane (1.5 mL) and methanol (1.5 mL) was treated with TMS-Diazomethane (5.79 mL, 11.59 mmol). The mixture was stirred for 10 minutes, then warmed to room temperature and stirred for 20 minutes. The reaction was concentrated under reduced pressure, dried twice from dichloromethane, then dried under vacuum for 20 minutes to afford the product (0.490 g, 2.283 mmol, 98% yield) as a white powder. LCMS (Condition ACN-TFA, ES+) M+H=215.1, 0.92 minutes, calculated exact mass=214.04. $^1$H NMR (400 MHz, CDCl$_3$) δ: 8.07 (d, J=2.3 Hz, 1H), 8.03 (dd, J=8.5, 2.3 Hz, 1H), 6.93 (d, J=8.5 Hz, 1H), 4.66 (s, 2H), 3.95 (s, 3H), 3.90 (s, 3H).

methyl 3-((4-chloro-5-((3-(2,3-dihydrobenzo[b][1,4]dioxin-6-yl)-2-methylbenzyl)oxy)-2-formylphenoxy)methyl)-4-methoxybenzoate

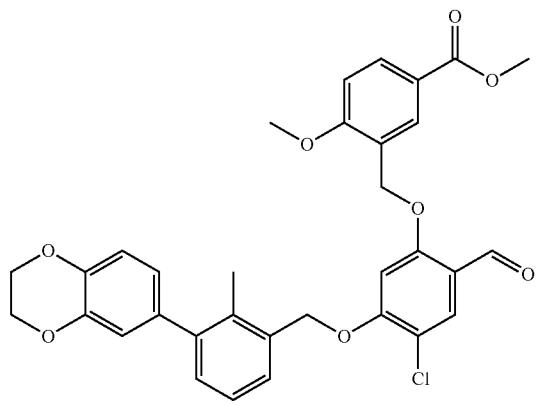 [SMILES: COC(=O)c1ccc(OC)c(COc2cc(OCc3cccc(-c4ccc5c(c4)OCCO5)c3C)c(Cl)cc2C=O)c1]

A solution of 5-chloro-4-((3-(2,3-dihydrobenzo[b][1,4]dioxin-6-yl)-2-methylbenzyl)oxy)-2-hydroxybenzaldehyde (0.100 g, 0.243 mmol) and methyl 3-(chloromethyl)-4-methoxybenzoate (0.107 g, 0.498 mmol) in dry N,N-dimethylformamide (4.0 mL) was treated with cesium carbonate (0.238 g, 0.730 mmol) and sodium iodide (4 mg, 0.03 mmol), and the mixture was heated (75° C. oil bath) for 3.5 hours (timer) then slowly cooled and stirred at room temperature for 16 hours. The reaction was diluted with ethyl acetate (25 mL) and washed with water (2×25 mL), then brine. The organic layer was dried over sodium sulfate, filtered, and concentrated under reduced pressure. The residue was purified by biotage (RediSep 12 g SiO2, 0% (3 CV), 0-100% (15 CV), 100% (2 CV), ethyl acetate in hexanes). Product fractions were pooled and concentrated under reduced pressure, affording the product as a partially purified product, and which was used in the following step without further purification. LCMS (Condition ACN-TFA, ES+) M+Na=613.5, 1.22 minutes, calculated exact mass=588.16. $^1$H NMR (400 MHz, CDCl$_3$) δ: 10.34 (s, 1H), 8.13 (d, J=2.0 Hz, 1H), 8.08 (dd, J=8.8, 2.3 Hz, 1H), 7.89 (s, 1H), 7.43-7.38 (m, 1H), 7.26-7.22 (m, 2H), 6.97 (d, J=8.5 Hz, 1H), 6.92 (d, J=8.3 Hz, 1H), 6.83 (d, J=2.0 Hz, 1H), 6.78 (dd, J=8.2, 2.1 Hz, 1H), 6.72 (s, 1H), 5.22 (s, 2H), 5.20 (s, 2H), 4.31 (s, 4H), 3.93 (s, 3H), 3.90 (s, 3H), 2.29 (s, 3H).

2-(benzyloxy)-5-chloro-4-((3-(2,3-dihydrobenzo[b][1,4]dioxin-6-yl)-2-methylbenzyl)oxy)benzaldehyde

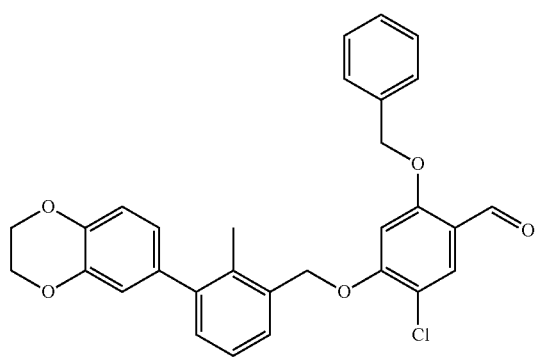 [SMILES: Cc1c(COc2cc(OCc3ccccc3)c(C=O)cc2Cl)cccc1-c1ccc2c(c1)OCCO2]

Prepared in substantially the same manner as example 3008, excepting that the residue after work-up was purified by biotage (RediSep 12 g SiO$_2$, 0% (3 CV), 0-100% (15 CV), 100% (2 CV), ethyl acetate in hexanes). Product fractions were pooled and concentrated under reduced pressure. LCMS (Condition ACN-TFA, ES+) M+H=501.0, 1.23 minutes, calculated exact mass=500.14. $^1$H NMR (400 MHz, CDCl$_3$) δ: 10.36 (s, 1H), 7.89 (s, 1H), 7.43-7.37 (m, 6H), 7.26-7.23 (m, 2H), 6.92 (d, J=8.3 Hz, 1H), 6.83 (d, J=2.0 Hz, 1H), 6.78 (dd, J=8.3, 2.0 Hz, 1H), 6.65 (s, 1H), 5.19 (s, 2H), 5.15 (s, 2H), 4.32 (s, 4H), 2.27 (s, 3H).

5-chloro-4-((3-(2,3-dihydrobenzo[b][1,4]dioxin-6-yl)-2-methylbenzyl)oxy)-2-((2-methoxybenzyl)oxy)benzaldehyde

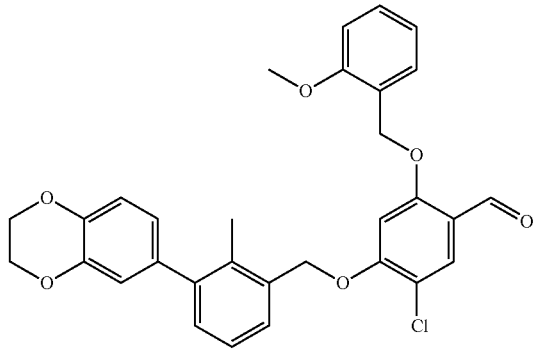 [SMILES: COc1ccccc1COc1cc(OCc2cccc(-c3ccc4c(c3)OCCO4)c2C)c(Cl)cc1C=O]

Prepared in substantially the same manner as example 3008, excepting that the residue after work-up was purified by biotage (RediSep 12 g SiO$_2$, 0% (3 CV), 0-100% (15 CV), 100% (2 CV), ethyl acetate in hexanes). Product fractions were pooled and concentrated under reduced pressure. LCMS (Condition ACN-TFA, ES+) M+H=531.1, 1.25 minutes, calculated exact mass=530.15. $^1$H NMR (400 MHz, CDCl$_3$) δ: 10.36 (s, 1H), 7.88 (s, 1H), 7.44-7.39 (m, 2H), 7.35 (td, J=7.8, 1.6 Hz, 1H), 7.26-7.23 (m, 2H), 7.00 (td, J=7.5, 0.9 Hz, 1H), 6.93 (s, 1H), 6.91 (s, 1H), 6.84 (d, J=2.0 Hz, 1H), 6.78 (dd, J=8.3, 2.0 Hz, 1H), 6.74 (s, 1H), 5.25 (s, 2H), 5.18 (s, 2H), 4.32 (s, 4H), 3.88 (s, 3H), 2.29 (s, 3H).

2-(4-chloro-5-((3-(2,3-dihydrobenzo[b][1,4]dioxin-6-yl)-2-methylbenzyl)oxy)-2-formylphenoxy)acetamide

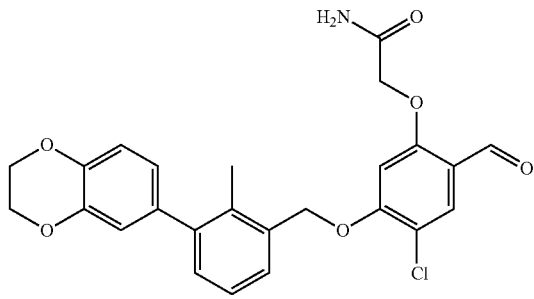 [SMILES: Cc1c(COc2cc(OCC(N)=O)c(C=O)cc2Cl)cccc1-c1ccc2c(c1)OCCO2]

Prepared in substantially the same manner as example 3008. LCMS (Condition ACN-TFA, ES+) M+H=467.9, 1.09 minutes, calculated exact mass=467.11. The residue was used in the following step without additional purification.

BIOLOGICAL ASSAY

The ability of the compounds of formula (I) to bind to PD-L1 was investigated using a PD-1/PD-L1 Homogenous Time-Resolved Fluorescence (HTRF) binding assay.

Homogenous Time-Resolved Fluorescence (HTRF) Binding Assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 µl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD80-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1 (18-239)-TVMV-His] were expressed in HEK293T cells and purified sequentially by ProteinA affinity chromatography and size exclusion chromatography. Human PD-L2-His and CD80-His was obtained through commercial sources.

```
Sequence of recombinant human PD-1-Ig
hPD1(25-167)-3S-IG
                                           (SEQ ID NO: 1)
  1 LDSPDRPWNP PTFSPALLVV TEGDNATFTC SFSNTSESFV
    LNWYRMSPSN

51 QTDKLAAPPE DRSQPGQDCR FRVTQLPNGR DFHMSVVRAR
    RNDSGTYLCG

101 AISLAPKAQI KESLRAELRV TERRAEVPTA HPSPSPRPAG
    QFQGSPGGGG

151 GREPKSSDKT HTSPPSPAPE LLGGSSVFLF PPKPKDTLMI
    SRTPEVTCVV

201 VDVSHEDPEV KFNWYVDGVE VHNAKTKPRE EQYNSTYRVV
    SVLTVLHQDW

251 LNGKEYKCKV SNKALPAFIE KTISKAKGQP REPQYVTLPP
    SRDELTKNQV

301 SLTCLVKGFY PSDIAVEWES NGQPENNYKT TPPVLDSDGS
    FFLYSKLTVD

351 KSRWQQGNVF SCSVHMEALH NHYTQKSLSL SPGK
```

Sequence of recombinant human PD-L1-His
hPDL1(18-239)-TVMV-His
(SEQ ID NO: 2)

```
  1 AFTVTVPKDL YVVSYGSNMT IECKFPVEKQ LDLAALIVYM
    EMEDKNIIQF

51 VHGEEDLKVQ HSSYRQRARL LKDQLSLGNA ALQITDVKLQ
    DAGVYRCMIS

101 YGGADYKRIT VKVNAPYNKI NQRILVVDPV TSEHELTCQA
    EGYPKAEVIW

151 TSSDHQVLSG KTTTTNSKRE EKLFNVTSTL RINTTTNEIF
    YCTFRRLDPE

201 ENHTAELVIP ELPLAHPPNE RTGSSETVRF QGHHHHHH
```

The table below lists the $IC_{50}$ values for representative examples of this disclosure measured in the PD-1/PD-L1 Homogenous Time-Resolved Fluorescence (HTRF) binding assay. Ranges are as follows: A=0.60 nM–10 nM; B=10.01 nM–100 nM; C=100.01 nM–20 μM.

| Example Number | Range or IC50 (nM) |
|---|---|
| 1000 | B |
| 1001 | 2.25 |
| 1002 | A |
| 1003 | A |
| 1004 | B |
| 1005 | A |
| 1006 | A |
| 1007 | A |
| 1008 | A |
| 1009 | A |
| 1010 | A |
| 1011 | A |
| 1012 | B |
| 1013 | A |
| 1014 | A |
| 1015 | A |
| 1016 | 4.55 |
| 1017 | A |
| 1018 | A |
| 1019 | A |
| 1020 | B |
| 1021 | A |
| 1022 | A |
| 1023 | A |
| 1024 | C |
| 1025 | C |
| 1026 | C |
| 1027 | C |
| 1028 | B |
| 1029 | C |
| 1030 | C |
| 1031 | C |
| 1032 | C |
| 1033 | C |
| 1034 | C |
| 1035 | C |
| 1036 | C |
| 1037 | C |
| 1038 | C |
| 1039 | C |
| 1040 | C |
| 1041 | C |
| 1042 | C |
| 1043 | 239.2 |
| 1044 | C |
| 1045 | C |
| 1046 | C |
| 1047 | C |
| 1048 | C |
| 1049 | C |
| 1050 | C |
| 1051 | C |
| 1052 | C |
| 1053 | C |
| 1054 | C |
| 1055 | C |
| 1056 | C |
| 1057 | 985.8 |
| 1058 | C |
| 1059 | C |
| 1060 | C |
| 1061 | C |
| 1062 | C |
| 1063 | C |
| 1064 | C |
| 1065 | C |
| 1066 | C |
| 1067 | C |
| 1068 | C |
| 1069 | C |
| 1070 | C |
| 1071 | C |
| 1072 | C |
| 1073 | C |
| 1074 | C |
| 1075 | C |
| 1076 | B |
| 1077 | C |
| 1078 | C |
| 1079 | C |
| 1080 | C |
| 1081 | C |
| 1082 | 828.4 |
| 1083 | C |
| 1084 | C |
| 1085 | C |
| 1086 | C |
| 1087 | C |
| 1088 | C |
| 1089 | C |
| 1090 | C |
| 1091 | C |
| 1092 | C |
| 1093 | C |
| 1094 | C |
| 1095 | 81.25 |
| 1096 | C |
| 1097 | C |
| 1098 | C |
| 1099 | C |
| 1100 | C |
| 1101 | C |
| 1102 | C |
| 1103 | C |
| 1104 | C |
| 1105 | C |
| 1106 | C |
| 1107 | C |
| 1108 | 624.2 |
| 1109 | C |
| 1110 | C |
| 1111 | B |
| 1112 | C |
| 1113 | C |
| 1114 | B |
| 1115 | C |
| 1116 | C |
| 1117 | B |
| 1118 | C |
| 1119 | 14250 |
| 1120 | B |
| 1121 | A |
| 1122 | A |
| 1123 | A |
| 1124 | A |
| 1125 | A |
| 1126 | A |

| Example Number | Range or IC50 (nM) |
| --- | --- |
| 1127 | A |
| 1128 | A |
| 1129 | A |
| 1130 | B |
| 1131 | A |
| 1132 | B |
| 1133 | A |
| 1134 | A |
| 1135 | A |
| 1136 | A |
| 1137 | A |
| 1138 | B |
| 1139 | A |
| 1140 | A |
| 1141 | A |
| 1142 | A |
| 1143 | A |
| 1144 | A |
| 1145 | B |
| 1146 | A |
| 1147 | A |
| 1148 | A |
| 1149 | A |
| 1150 | B |
| 1151 | A |
| 1152 | A |
| 1153 | A |
| 1154 | A |
| 1155 | A |
| 1156 | A |
| 1157 | A |
| 1158 | A |
| 1159 | B |
| 1160 | B |
| 1161 | B |
| 1162 | C |
| 1163 | A |
| 1164 | A |
| 1165 | A |
| 1166 | 1.4 |
| 1167 | B |
| 1168 | C |
| 1169 | A |
| 1170 | A |
| 1171 | B |
| 1172 | A |
| 1173 | A |
| 1174 | A |
| 1175 | B |
| 1176 | A |
| 1177 | A |
| 1178 | B |
| 1179 | B |
| 1180 | B |
| 1181 | B |
| 1182 | A |
| 1183 | A |
| 1184 | A |
| 1185 | B |
| 1186 | A |
| 1187 | B |
| 1188 | A |
| 1189 | A |
| 1190 | A |
| 1191 | A |
| 1192 | C |
| 1193 | A |
| 1194 | B |
| 1195 | A |
| 1196 | A |
| 1197 | 1.85 |
| 1198 | A |
| 1199 | A |
| 1200 | B |
| 1201 | A |
| 1202 | B |
| 1203 | A |
| 1204 | A |
| 1205 | 2.71 |
| 1206 | A |
| 1207 | B |
| 1208 | A |
| 1209 | — |
| 1210 | 12.74 |
| 1211 | B |
| 1212 | A |
| 1213 | B |
| 1214 | A |
| 1215 | B |
| 1216 | C |
| 1217 | B |
| 1218 | 10.11 |
| 1219 | A |
| 1220 | 6.07 |
| 1221 | A |
| 1222 | B |
| 1223 | A |
| 1224 | B |
| 1225 | A |
| 1226 | B |
| 1227 | C |
| 1228 | B |
| 1229 | A |
| 1230 | A |
| 1231 | C |
| 1232 | C |
| 1233 | C |
| 1234 | C |
| 1235 | C |
| 1236 | C |
| 1237 | C |
| 1238 | C |
| 1239 | 148.9 |
| 1240 | C |
| 1241 | A |
| 1242 | A |
| 1243 | B |
| 1244 | A |
| 1245 | A |
| 1246 | A |
| 1247 | A |
| 1248 | A |
| 1249 | A |
| 1250 | 1.19 |
| 1251 | A |
| 1252 | A |
| 1253 | A |
| 1254 | A |
| 1255 | A |
| 1256 | A |
| 1257 | B |
| 1258 | B |
| 1259 | A |
| 1260 | A |
| 1261 | A |
| 1262 | B |
| 1263 | C |
| 1264 | A |
| 1265 | A |
| 1266 | A |
| 1267 | A |
| 1268 | A |
| 1269 | A |
| 1270 | A |
| 1271 | A |
| 1272 | A |
| 1273 | A |
| 1274 | A |
| 1275 | A |
| 1276 | A |
| 1277 | A |
| 1278 | A |

| Example Number | Range or IC50 (nM) |
|---|---|
| 1279 | A |
| 1280 | A |
| 1281 | A |
| 1282 | A |
| 1283 | A |
| 1284 | A |
| 1285 | A |
| 1286 | A |
| 1287 | A |
| 1288 | 1.88 |
| 1289 | A |
| 1290 | A |
| 1291 | A |
| 1292 | A |
| 1293 | A |
| 1294 | B |
| 1295 | A |
| 1296 | B |
| 1297 | A |
| 1298 | A |
| 1299 | A |
| 1300 | A |
| 1301 | A |
| 1302 | A |
| 1303 | A |
| 1304 | A |
| 1305 | A |
| 1305 | 0.92 |
| 1307 | A |
| 1308 | A |
| 1309 | A |
| 1310 | A |
| 1311 | A |
| 1312 | A |
| 1313 | A |
| 1314 | A |
| 1315 | A |
| 1316 | A |
| 1317 | A |
| 1318 | A |
| 1319 | A |
| 1320 | A |
| 1321 | A |
| 1322 | A |
| 1323 | A |
| 1324 | B |
| 1325 | B |
| 1326 | A |
| 1327 | A |
| 1328 | A |
| 1329 | A |
| 1330 | — |
| 1331 | A |
| 1332 | A |
| 1333 | A |
| 1334 | A |

| Example Number | Range or IC50 (nM) |
|---|---|
| 1335 | C |
| 2000 | C |
| 2001 | A |
| 2002 | 10 nM |
| 2003 | A |
| 2004 | A |
| 2005 | B |
| 2006 | A |
| 2007 | A |
| 2008 | A |
| 2009 | A |
| 2010 | 50 nM |
| 2011 | B |
| 2012 | A |
| 2013 | A |
| 3000 | A |
| 3001 | A |
| 3002 | A |
| 3003 | A |
| 3004 | A |
| 3005 | A |
| 3006 | A |
| 3007 | — |
| 3008 | A |
| 3009 | A |
| 3010 | C |
| 3011 | A |
| 3012 | A |
| 3013 | 80 nM |
| 3014 | A |
| 3015 | A |
| 3016 | C |
| 3017 | B |
| 3018 | A |
| 3019 | C |
| 3020 | C |
| 3021 | A |
| 3022 | A |
| 3023 | A |
| 3024 | 5.54 nM |
| 3025 | A |
| 3026 | C |
| 3027 | C |
| 3028 | C |
| 3029 | 2.35 µM |
| 3030 | A |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, Hepatitis A, B, C, or D and cancer.

What is claimed is:

1. A compound of formula (I):

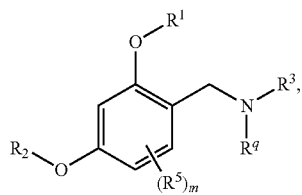

(I)

or a pharmaceutically acceptable salt thereof, wherein:

m is 0, 1, or 2;

$R^1$ is selected from hydrogen, —$(CH_2)_n$X and —$(CH_2)_n$Ar; wherein n is 1, 2, 3, or 4;

X is selected from —$CH_3$, —$CF_3$, CN, —$CO_2R^4$, —$C(O)NH_2$, $OR^4$, and pyrrolidonyl;

$R^4$ is H or $C_1$-$C_3$alkyl;

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, ($C_1$-$C_4$alkyl)carbonyl, ($C_1$-$C_4$alkyl)sulfonyl, amido, aminocarbonyl, aminocarbonyl($C_1$-$C_3$alkyl), —$(CH_2)_qCO_2C_1$-$C_4$alkyl, —$(CH_2)_qOH$, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;

$R^2$ is selected from

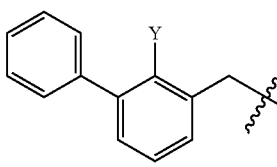

and

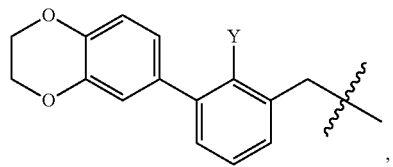

, wherein Y is selected from cyano, chloro, and methyl;
R$^q$ is selected from hydrogen, C$_1$-C$_3$alkyl, and benzyl;
R$^3$ is selected from

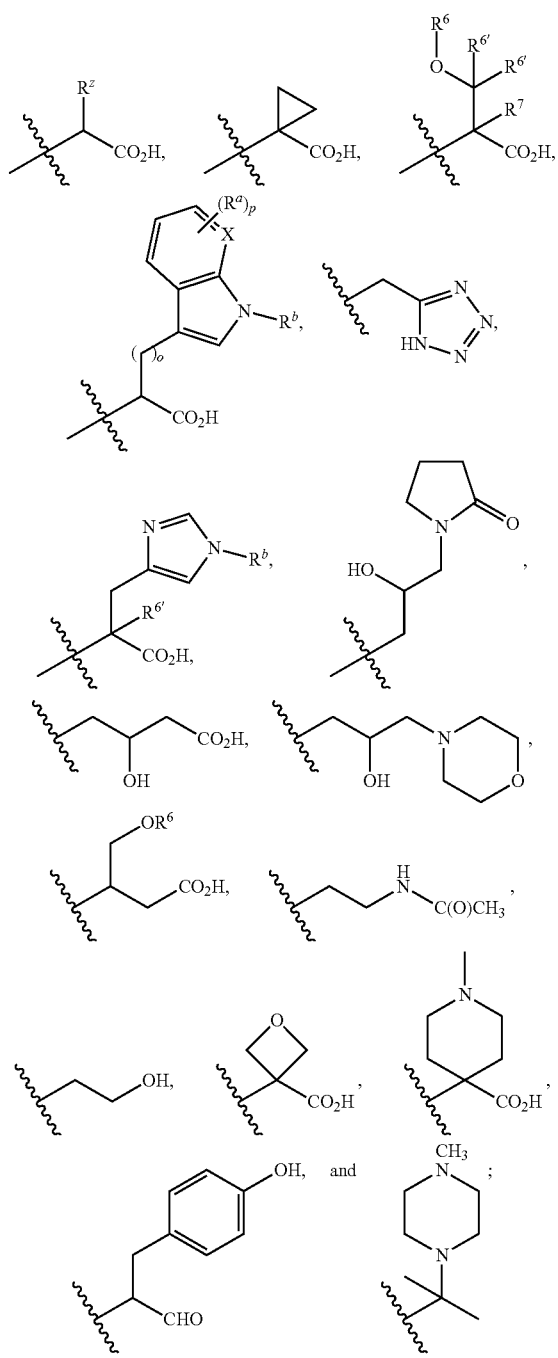

wherein R$^z$ is selected from C$_1$-C$_3$alkyl, C$_1$-C$_3$alkylsulfonylC$_1$-C$_3$alkyl, C$_1$-C$_3$alkylsulfoxylC$_1$-C$_3$alkyl, amidoC$_1$-C$_3$alkyl, aminoC$_1$-C$_4$alkyl, carboxyC$_1$-C$_3$alkyl, cyanoC$_1$-C$_3$alkyl, dimethylamidoC$_1$-C$_3$alkyl, dimethylaminoC$_1$-C$_4$alkyl, haloC$_1$-C$_3$alkyl, hydroxyC$_1$-C$_3$alkyl, C$_1$-C$_3$alkylsulfanylC$_1$-C$_3$alkyl, pyridinylC$_1$-C$_3$alkyl, tetrazolylC$_1$-C$_3$alkyl, imidazolylC$_1$-C$_3$alkyl wherein the imidazole is optionally substituted with methyl or a benzyl group, phenylC$_1$-C$_3$alkyl wherein the phenyl is optionally substituted with cyano, methyl, or hydroxy, thiazolylC$_1$-C$_3$alkyl;

R$^6$ is selected from hydrogen, benzyl, and methyl;
each R$^{6'}$ is independently selected from hydrogen and methyl;
R$^7$ is selected from hydrogen, C$_1$-C$_3$alkyl, and benzyl;
o is 1 or 2;
X is CH or N;
p is 0 or 1;
R$^a$ is hydroxy; and
R$^b$ is selected from hydrogen, benzyl, and methyl; or
R$^3$ and R$^q$, together with the nitrogen atom to which they are attached, form a ring selected from

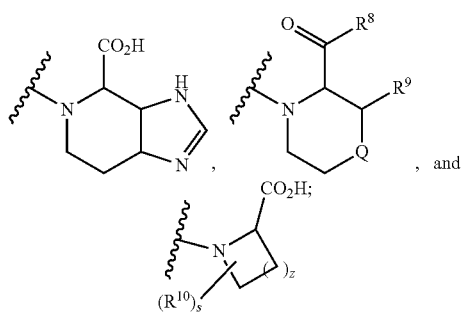

s is 0 or 1;
z is 1, 2, or 3; and
R$^8$ is selected from hydroxy and —NHSO$_2$R$^{11}$;
R$^9$ is selected from hydrogen and —CO$_2$H;
R$^{10}$ is selected from halo and hydroxy;
R$^{11}$ is selected from trifluoromethyl, cyclopropyl, C$_1$-C$_3$alkyl, dimethylamino, and imidazolyl substituted with a methyl group;
Q is selected from CH$_2$, S, O, and NCH$_3$; and
R$^5$ is selected from C$_2$-C$_4$alkenyl, C$_1$-C$_4$alkyl, cyano, methoxy, halo, and trifluoromethyl.

2. A compound of claim 1, or a pharmaceutically acceptable salt thereof, wherein R$^2$ is

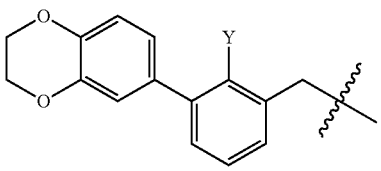

3. A compound of claim 1, or a pharmaceutically acceptable salt thereof, wherein R$^3$ is

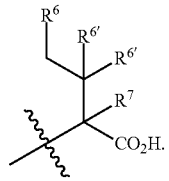

4. A compound of claim 1, or a pharmaceutically acceptable salt thereof, wherein
R² is

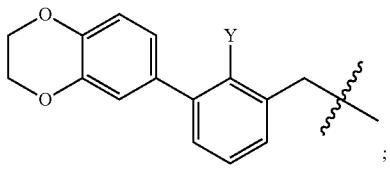

and
R³ is

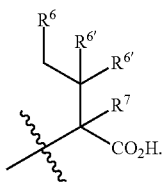

5. A compound selected from
N-(2-(2-(3-cyanobenzyloxy)-4-(3-(2,3-dihydrobenzo[b][1,4]dioxin-6-yl)-2-methylbenzyloxy)-6-methylbenzylamino)ethyl)acetamide;
(R)-2-(2-(3-cyanobenzyloxy)-4-(3-(2,3-dihydrobenzo[b][1,4]dioxin-6-yl)-2-methylbenzyloxy)-6-methylbenzylamino)-3-hydroxy-2-methylpropanoic acid;
(R)-2-(2-(3-cyanobenzyloxy)-4-(3-(2,3-dihydrobenzo[b][1,4]dioxin-6-yl)-2-methylbenzyloxy)-6-methylbenzylamino)-3-hydroxypropanoic acid;
(S)-4-(2-(3-cyanobenzyloxy)-4-(3-(2,3-dihydrobenzo[b][1,4]dioxin-6-yl)-2-methylbenzyloxy)-6-methylbenzylamino)-3-hydroxybutanoic acid;
(S)-1-(2-(3-cyanobenzyloxy)-4-(3-(2,3-dihydrobenzo[b][1,4]dioxin-6-yl)-2-methylbenzyloxy)-6-methylbenzyl)piperidine-2-carboxylic acid;
N-(2-(2-((5-cyanopyridin-3-yl)methoxy)-4-(3-(2,3-dihydrobenzo[b][1,4]dioxin-6-yl)-2-methylbenzyloxy)-6-methylbenzylamino)ethyl)acetamide;
(S)-4-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxybutanoic acid;
(R)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxypropanoic acid;
(R)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxy-2-methylpropanoic acid;
(S)-1-(2-((5-cyanopyridin-3-yl)methoxy)-4-(3-(2,3-dihydrobenzo[b][1,4]dioxin-6-yl)-2-methylbenzyloxy)-6-methylbenzyl)piperidine-2-carboxylic acid;
(S)-2-(2-((5-cyanopyridin-3-yl)methoxy)-4-(3-(2,3-dihydrobenzo[b][1,4]dioxin-6-yl)-2-methylbenzyloxy)-6-methylbenzylamino)-3-hydroxy-2-methylpropanoic acid;
(S)-4-(2-(3-cyanobenzyloxy)-4-((2-methylbiphenyl-3-yl)methoxy)benzylamino)-3-hydroxybutanoic acid;
(2S,3S)-2-((2-((3-cyanobenzyl)oxy)-4-((2-methyl-[1,1'-biphenyl]-3-yl)methoxy)benzyl)amino)-3-hydroxybutanoic acid;
(2R,3R)-2-((2-((3-cyanobenzyl)oxy)-4-((2-methyl-[1,1'-biphenyl]-3-yl)methoxy)benzyl)amino)-3-hydroxybutanoic acid;
2-((2-((3-cyanobenzyl)oxy)-4-((2-methyl-[1,1'-biphenyl]-3-yl)methoxy)benzyl)amino)-3-hydroxy-2-methylpropanoic acid;
(2R,3S)-2-((2-((3-cyanobenzyl)oxy)-4-((2-methyl-[1,1'-biphenyl]-3-yl)methoxy)benzyl)amino)-3-hydroxybutanoic acid;
(R)-2-((2-((3-cyanobenzyl)oxy)-4-((2-methyl-[1,1'-biphenyl]-3-yl)methoxy)benzyl)amino)-3-hydroxypropanoic acid;
2-((2-((3-cyanobenzyl)oxy)-4-((2-methyl-[1,1'-biphenyl]-3-yl)methoxy)benzyl)amino)-3-hydroxypropanoic acid;
(S)-2-((2-((3-cyanobenzyl)oxy)-4-((2-methyl-[1,1'-biphenyl]-3-yl)methoxy)benzyl)amino)-3-hydroxypropanoic acid;
(S)-2-((2-((3-cyanobenzyl)oxy)-4-((2-methyl-[1,1'-biphenyl]-3-yl)methoxy)benzyl)amino)-3-hydroxy-2-methylpropanoic acid;
2-((2-((3-cyanobenzyl)oxy)-4-((2-methyl-[1,1'-biphenyl]-3-yl)methoxy)benzyl)amino)-2-(hydroxymethyl)-3-methylbutanoic acid;
(S)-3-((2-((3-cyanobenzyl)oxy)-4-((2-methyl-[1,1'-biphenyl]-3-yl)methoxy)benzyl)amino)-4-hydroxybutanoic acid;
(R)-3-((2-((3-cyanobenzyl)oxy)-4-((2-methyl-[1,1'-biphenyl]-3-yl)methoxy)benzyl)amino)-4-hydroxybutanoic acid;
(R)-2-((2-((3-cyanobenzyl)oxy)-4-((2-methyl-[1,1'-biphenyl]-3-yl)methoxy)benzyl)amino)-3-hydroxy-2-methylpropanoic acid;
N-(2-((2-(benzyloxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((3-methylbenzyl)oxy)benzyl)amino)ethyl)acetamide;
N-(2-((4-((2-methyl-[1,1'-biphenyl]-3-yl)methoxy)-2-(2,2,2-trifluoroethoxy)benzyl)amino)ethyl)acetamide;
N-(2-((4-((2-methyl-[1,1'-biphenyl]-3-yl)methoxy)-2-propoxybenzyl)amino)ethyl)acetamide;
N-(2-((2-((3-cyanobenzyl)oxy)-4-((2-methyl-[1,1'-biphenyl]-3-yl)methoxy)benzyl)amino)ethyl)acetamide;
N-(2-((2-((4-cyanobenzyl)oxy)-4-((2-methyl-[1,1'-biphenyl]-3-yl)methoxy)benzyl)amino)ethyl)acetamide;
N-(2-((2-(2-hydroxyethoxy)-4-((2-methyl-[1,1'-biphenyl]-3-yl)methoxy)benzyl)amino)ethyl)acetamide;
2-(2-(((2-acetamidoethyl)amino)methyl)-5-((2-methyl-[1,1'-biphenyl]-3-yl)methoxy)phenoxy)acetamide;
methyl 5-(2-(((2-acetamidoethyl)amino)methyl)-5-((2-methyl-[1,1'-biphenyl]-3-yl)methoxy)phenoxy)pentanoate;
N-(2-((4-((2-methyl-[1,1'-biphenyl]-3-yl)methoxy)-2-phenethoxybenzyl)amino)ethyl)acetamide;
methyl 3-((2-(((2-acetamidoethyl)amino)methyl)-5-((2-methyl-[1,1'-biphenyl]-3-yl)methoxy)phenoxy)methyl)benzoate;
N-(2-((2-(3-hydroxypropoxy)-4-((2-methyl-[1,1'-biphenyl]-3-yl)methoxy)benzyl)amino)ethyl)acetamide;
methyl 4-(2-(((2-acetamidoethyl)amino)methyl)-5-((2-methyl-[1,1'-biphenyl]-3-yl)methoxy)phenoxy)butanoate;
N-(2-((2-((3-(hydroxymethyl)benzyl)oxy)-4-((2-methyl-[1,1'-biphenyl]-3-yl)methoxy)benzyl)amino)ethyl)acetamide;

N-(2-((2-((2-(hydroxymethyl)benzyl)oxy)-4-((2-methyl-[1,1'-biphenyl]-3-yl)methoxy)benzyl)amino)ethyl)acetamide;
4-((2-(((2-acetamidoethyl)amino)methyl)-5-((2-methyl-[1,1'-biphenyl]-3-yl)methoxy)phenoxy)methyl)benzamide;
N-(2-((2-((4-acetylbenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((2-(methylsulfonyl)benzyl)oxy)benzyl)amino)ethyl)acetamide;
N-(2-((2-(3-methoxypropoxy)-4-((2-methyl-[1,1'-biphenyl]-3-yl)methoxy)benzyl)amino)ethyl)acetamide;
4-((2-(((2-acetamidoethyl)amino)methyl)-5-((2-methyl-[1,1'-biphenyl]-3-yl)methoxy)phenoxy)methyl)benzoic acid;
N-(2-((2-ethoxy-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((2-methylbenzyl)oxy)benzyl)amino)ethyl)acetamide;
N-(2-((2-((4-(tert-butyl)benzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((4-methylbenzyl)oxy)benzyl)amino)ethyl)acetamide;
N-(2-((2-((2-fluorobenzyl)oxy)-4-((2-methyl-[1,1'-biphenyl]-3-yl)methoxy)benzyl)amino)ethyl)acetamide;
N-(2-((2-((2,6-difluorobenzyl)oxy)-4-((2-methyl-[1,1'-biphenyl]-3-yl)methoxy)benzyl)amino)ethyl)acetamide;
N-(2-((2-((3-fluorobenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((3-(trifluoromethyl)benzyl)oxy)benzyl)amino)ethyl)acetamide;
N-(2-((4-((2-methyl-[1,1'-biphenyl]-3-yl)methoxy)-2-((4-(trifluoromethyl)benzyl)oxy)benzyl)amino)ethyl)acetamide;
N-(2-((2-((2-chlorobenzyl)oxy)-4-((2-methyl-[1,1'-biphenyl]-3-yl)methoxy)benzyl)amino)ethyl)acetamide;
N-(2-((2-((3-chlorobenzyl)oxy)-4-((2-methyl-[1,1'-biphenyl]-3-yl)methoxy)benzyl)amino)ethyl)acetamide;
N-(2-((2-((2-cyanobenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-(naphthalen-2-ylmethoxy)benzyl)amino)ethyl)acetamide;
N-(2-((4-((2-methyl-[1,1'-biphenyl]-3-yl)methoxy)-2-((2-nitrobenzyl)oxy)benzyl)amino)ethyl)acetamide;
N-(2-((4-((2-methyl-[1,1'-biphenyl]-3-yl)methoxy)-2-((4-nitrobenzyl)oxy)benzyl)amino)ethyl)acetamide;
N-(2-((2-((3,4-difluorobenzyl)oxy)-4-((2-methyl-[1,1'-biphenyl]-3-yl)methoxy)benzyl)amino)ethyl)acetamide;
N-(2-((2-((2,5-difluorobenzyl)oxy)-4-((2-methyl-[1,1'-biphenyl]-3-yl)methoxy)benzyl)amino)ethyl)acetamide;
N-(2-((2-((3,5-bis(trifluoromethyl)benzyl)oxy)-4-((2-methyl-[1,1'-biphenyl]-3-yl)methoxy)benzyl)amino)ethyl)acetamide;
N-(2-((2-((3,5-difluorobenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-(naphthalen-1-ylmethoxy)benzyl)amino)ethyl)acetamide;
N-(2-((2-((2,4-difluorobenzyl)oxy)-4-((2-methyl-[1,1'-biphenyl]-3-yl)methoxy)benzyl)amino)ethyl)acetamide;
N-(2-((2-((3,5-dimethylbenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((2-(trifluoromethyl)benzyl)oxy)benzyl)amino)ethyl)acetamide;
methyl 4-((2-(((2-acetamidoethyl)amino)methyl)-5-((2-methyl-[1,1'-biphenyl]-3-yl)methoxy)phenoxy)methyl)benzoate;
N-(2-((2-((4-chlorobenzyl)oxy)-4-((2-methyl-[1,1'-biphenyl]-3-yl)methoxy)benzyl)amino)ethyl)acetamide;
N-(2-((2-((3,4-dichlorobenzyl)oxy)-4-((2-methyl-[1,1'-biphenyl]-3-yl)methoxy)benzyl)amino)ethyl)acetamide;
N-(2-((2-((2-fluoro-3-methylbenzyl)oxy)-4-((2-methyl-[1,1'-biphenyl]-3-yl)methoxy)benzyl)amino)ethyl)acetamide;
N-(2-((2-((2,3-difluorobenzyl)oxy)-4-((2-methyl-[1,1'-biphenyl]-3-yl)methoxy)benzyl)amino)ethyl)acetamide;
N-(2-((2-((3-chloro-2-fluorobenzyl)oxy)-4-((2-methyl-[1,1'-biphenyl]-3-yl)methoxy)benzyl)amino)ethyl)acetamide;
N-(2-((2-((3-benzoylbenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-(quinolin-8-ylmethoxy)benzyl)amino)ethyl)acetamide;
N-(2-((2-((4-fluorobenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((3-nitrobenzyl)oxy)benzyl)amino)ethyl)acetamide;
N-(2-((2-((3-(2-fluorophenoxy)benzyl)oxy)-4-((2-methyl-[1,1'-biphenyl]-3-yl)methoxy)benzyl)amino)ethyl)acetamide;
N-(2-((2-((3-(4-fluorophenoxy)benzyl)oxy)-4-((2-methyl-[1,1'-biphenyl]-3-yl)methoxy)benzyl)amino)ethyl)acetamide;
N-(2-((2-((2-fluoro-3-(trifluoromethyl)benzyl)oxy)-4-((2-methyl-[1,1'-biphenyl]-3-yl)methoxy)benzyl)amino)ethyl)acetamide;
N-(2-((2-((2-fluoro-5-(trifluoromethyl)benzyl)oxy)-4-((2-methyl-[1,1'-biphenyl]-3-yl)methoxy)benzyl)amino)ethyl)acetamide;
N-(2-((2-((3-fluoro-5-(trifluoromethyl)benzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((3-(trifluoromethoxy)benzyl)oxy)benzyl)amino)ethyl)acetamide;
N-(2-((2-((4-chloro-2-(trifluoromethyl)quinolin-6-yl)methoxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((4-(methylsulfonyl)benzyl)oxy)benzyl)amino)ethyl)acetamide;
N-(2-((2-((2-(difluoromethoxy)benzyl)oxy)-4-((2-methyl-[1,1'-biphenyl]-3-yl)methoxy)benzyl)amino)ethyl)acetamide;
N-(2-((2-((3-methoxybenzyl)oxy)-4-((2-methyl-[1,1'-biphenyl]-3-yl)methoxy)benzyl)amino)ethyl)acetamide;
N-(2-((4-((2-methyl-[1,1'-biphenyl]-3-yl)methoxy)-2-((2-(trifluoromethoxy)benzyl)oxy)benzyl)amino)ethyl)acetamide;
N-(2-((2-((4-(difluoromethoxy)benzyl)oxy)-4-((2-methyl-[1,1'-biphenyl]-3-yl)methoxy)benzyl)amino)ethyl)acetamide;
N-(2-((2-((2'-cyano-[1,1'-biphenyl]-4-yl)methoxy)-4-((2-methyl-[1,1'-biphenyl]-3-yl)methoxy)benzyl)amino)ethyl)acetamide;
N-(2-((2-((4-methoxybenzyl)oxy)-4-((2-methyl-[1,1'-biphenyl]-3-yl)methoxy)benzyl)amino)ethyl)acetamide;

N-(2-((2-((3-chloro-5-fluorobenzyl)oxy)-4-((2-methyl-[1,1'-biphenyl]-3-yl)methoxy)benzyl)amino)ethyl)acetamide;

N-(2-((2-((2,6-difluoro-3-methoxybenzyl)oxy)-4-((2-methyl-[1,1'-biphenyl]-3-yl)methoxy)benzyl)amino)ethyl)acetamide;

N-(2-((2-((4-fluoro-3-methoxybenzyl)oxy)-4-((2-methyl-[1,1'-biphenyl]-3-yl)methoxy)benzyl)amino)ethyl)acetamide;

N-(2-((2-((2-fluoro-5-methylbenzyl)oxy)-4-((2-methyl-[1,1'-biphenyl]-3-yl)methoxy)benzyl)amino)ethyl)acetamide;

N-(2-((2-((5-cyano-2-fluorobenzyl)oxy)-4-((2-methyl-[1,1'-biphenyl]-3-yl)methoxy)benzyl)amino)ethyl)acetamide;

N-(2-((2-((3-fluoro-5-methoxybenzyl)oxy)-4-((2-methyl-[1,1'-biphenyl]-3-yl)methoxy)benzyl)amino)ethyl)acetamide;

N-(2-((2-((4-bromo-2-cyanobenzyl)oxy)-4-((2-methyl-[1,1'-biphenyl]-3-yl)methoxy)benzyl)amino)ethyl)acetamide;

N-(2-((2-((1H-indazol-5-yl)methoxy)-4-((2-methyl-[1,1'-biphenyl]-3-yl)methoxy)benzyl)amino)ethyl)acetamide;

N-(2-((4-((2-methyl-[1,1'-biphenyl]-3-yl)methoxy)-2-((1-(tetrahydro-2H-pyran-2-yl)-1H-indazol-5-yl)methoxy)benzyl)amino)ethyl)acetamide;

N-(2-((4-((2-methyl-[1,1'-biphenyl]-3-yl)methoxy)-2-(pyrimidin-4-ylmethoxy)benzyl)amino)ethyl)acetamide;

methyl 2-(3-((2-(((2-acetamidoethyl)amino)methyl)-5-((2-methyl-[1,1'-biphenyl]-3-yl)methoxy)phenoxy)methyl)phenyl)acetate;

N-(2-((2-((1H-indazol-6-yl)methoxy)-4-((2-methyl-[1,1'-biphenyl]-3-yl)methoxy)benzyl)amino)ethyl)acetamide;

methyl 3-((2-(((2-acetamidoethyl)amino)methyl)-5-((2-methyl-[1,1'-biphenyl]-3-yl)methoxy)phenoxy)methyl)-4-fluorobenzoate;

N-(2-((2-((5-methyl-1,2,4-oxadiazol-3-yl)methoxy)-4-((2-methyl-[1,1'-biphenyl]-3-yl)methoxy)benzyl)amino)ethyl)acetamide;

tert-butyl 3-((2-(((2-acetamidoethyl)amino)methyl)-5-((2-methyl-[1,1'-biphenyl]-3-yl)methoxy)phenoxy)methyl)benzoate;

N-(2-((2-((3-fluoro-5-(trifluoromethoxy)benzyl)oxy)-4-((2-methyl-[1,1'-biphenyl]-3-yl)methoxy)benzyl)amino)ethyl)acetamide;

N-(2-((2-((3,5-dimethoxybenzyl)oxy)-4-((2-methyl-[1,1'-biphenyl]-3-yl)methoxy)benzyl)amino)ethyl)acetamide;

N-(2-((2-((4-fluoro-3-methylbenzyl)oxy)-4-((2-methyl-[1,1'-biphenyl]-3-yl)methoxy)benzyl)amino)ethyl)acetamide;

N-(2-((2-((5-chloro-2-fluorobenzyl)oxy)-4-((2-methyl-[1,1'-biphenyl]-3-yl)methoxy)benzyl)amino)ethyl)acetamide;

N-(2-((2-((3-chloro-4-fluorobenzyl)oxy)-4-((2-methyl-[1,1'-biphenyl]-3-yl)methoxy)benzyl)amino)ethyl)acetamide;

N-(2-((4-((2-methyl-[1,1'-biphenyl]-3-yl)methoxy)-2-(pyridin-4-ylmethoxy)benzyl)amino)ethyl)acetamide;

N-(2-((2-((3-(1H-pyrrol-1-yl)benzyl)oxy)-4-((2-methyl-[1,1'-biphenyl]-3-yl)methoxy)benzyl)amino)ethyl)acetamide;

N-(2-((2-((3-fluoro-5-methylbenzyl)oxy)-4-((2-methyl-[1,1'-biphenyl]-3-yl)methoxy)benzyl)amino)ethyl)acetamide;

N-(2-((2-((3-cyano-4-fluorobenzyl)oxy)-4-((2-methyl-[1,1'-biphenyl]-3-yl)methoxy)benzyl)amino)ethyl)acetamide;

N-(2-((4-((2-methyl-[1,1'-biphenyl]-3-yl)methoxy)-2-(5-methylisoxazol-3-yl)methoxy)benzyl)amino)ethyl)acetamide;

N-(2-((2-((3-(difluoromethoxy)benzyl)oxy)-4-((2-methyl-[1,1'-biphenyl]-3-yl)methoxy)benzyl)amino)ethyl)acetamide;

N-(2-((4-((2-methyl-[1,1'-biphenyl]-3-yl)methoxy)-2-(pyridin-3-ylmethoxy)benzyl)amino)ethyl)acetamide;

N-(2-((2-(isoquinolin-1-ylmethoxy)-4-((2-methyl-[1,1'-biphenyl]-3-yl)methoxy)benzyl)amino)ethyl)acetamide;

tert-butyl (3-((2-(((2-acetamidoethyl)amino)methyl)-5-((2-methyl-[1,1'-biphenyl]-3-yl)methoxy)phenoxy)methyl)phenyl)carbamate;

(S)—N-(2-((4-((2-methyl-[1,1'-biphenyl]-3-yl)methoxy)-2-((5-oxopyrrolidin-2-yl)methoxy)benzyl)amino)ethyl)acetamide;

(S)-4-(2-(3-cyanobenzyloxy)-4-(3-(2,3-dihydrobenzo[b][1,4]dioxin-6-yl)-2-methylbenzyloxy)benzylamino)-3-hydroxybutanoic acid;

2-((2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;

(2R,3S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

(2R,3R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

(S)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid;

(R)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

(S)-2-((2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

(R)-3-((2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid;

N-(2-(2-((4-cyanopyridin-2-yl)methoxy)-4-(3-(2,3-dihydrobenzo[b][1,4]dioxin-6-yl)-2-methylbenzyloxy)benzylamino)ethyl)acetamide;

(R)-2-(2-((4-cyanopyridin-2-yl)methoxy)-4-(3-(2,3-dihydrobenzo[b][1,4]dioxin-6-yl)-2-methylbenzyloxy)benzylamino)-3-hydroxy-2-methylpropanoic acid;

(S)-1-(2-((4-cyanopyridin-2-yl)methoxy)-4-(3-(2,3-dihydrobenzo[b][1,4]dioxin-6-yl)-2-methylbenzyloxy)benzyl)piperidine-2-carboxylic acid;

(S)-4-((2-((3-cyanobenzyl)oxy)-6-methoxy-4-((2-methyl-[1,1'-biphenyl]-3-yl)methoxy)benzyl)amino)-3-hydroxybutanoic acid;

(R)-2-((2-((3-cyanobenzyl)oxy)-6-methoxy-4-((2-methyl-[1,1'-biphenyl]-3-yl)methoxy)benzyl)amino)-3-hydroxypropanoic acid;

(2R,3S)-2-((2-((3-cyanobenzyl)oxy)-6-methoxy-4-((2-methyl-[1,1'-biphenyl]-3-yl)methoxy)benzyl)amino)-3-hydroxybutanoic acid;

(2S,3S)-2-((2-((3-cyanobenzyl)oxy)-6-methoxy-4-((2-methyl-[1,1'-biphenyl]-3-yl)methoxy)benzyl)amino)-3-hydroxybutanoic acid;

2-((2-((3-cyanobenzyl)oxy)-6-methoxy-4-((2-methyl-[1,1'-biphenyl]-3-yl)methoxy)benzyl)amino)-3-hydroxy-2-methylpropanoic acid;

(2R,3R)-2-((2-((3-cyanobenzyl)oxy)-6-methoxy-4-((2-methyl-[1,1'-biphenyl]-3-yl)methoxy)benzyl)amino)-3-hydroxybutanoic acid;

(R)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid;

(S)-4-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxybutanoic acid;

(S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxypropanoic acid;

(S)-2-((2-((3-cyanobenzyl)oxy)-4-((3-(2,3-dihydrobenzo[b][1,4]dioxin-6-yl)-2-methylbenzyl)oxy)-6-methoxybenzyl)amino)-3-hydroxy-2-methylpropanoic acid;

(R)-2-((2-(4-cyanobutoxy)-4-((2-methyl-[1,1'-biphenyl]-3-yl)methoxy)benzyl)amino)-3-hydroxypropanoic acid;

(S)-4-((2-(4-cyanobutoxy)-4-((2-methyl-[1,1'-biphenyl]-3-yl)methoxy)benzyl)amino)-3-hydroxybutanoic acid;

(S)-1-(4-(2-chloro-3-(2,3-dihydrobenzo[b][1,4]dioxin-6-yl)benzyloxy)-2-(3-cyanobenzyloxyl)benzyl)piperidine-2-carboxylic acid;

(R)-2-(4-(2-chloro-3-(2,3-dihydrobenzo[b][1,4]dioxin-6-yl)benzyloxy)-2-(3-cyanobenzyloxyl)benzylamino)-3-hydroxypropanoic acid;

(S)-4-(4-(2-chloro-3-(2,3-dihydrobenzo[b][1,4]dioxin-6-yl)benzyloxy)-2-(3-cyanobenzyloxyl)benzylamino)-3-hydroxybutanoic acid;

(R)-2-(4-(2-chloro-3-(2,3-dihydrobenzo[b][1,4]dioxin-6-yl)benzyloxy)-2-(3-cyanobenzyloxyl)benzylamino)-3-hydroxy-2-methylpropanoic acid;

(S)-2-(4-(2-chloro-3-(2,3-dihydrobenzo[b][1,4]dioxin-6-yl)benzyloxy)-2-(3-cyanobenzyloxyl)benzylamino)-3-hydroxy-2-methylpropanoic acid;

N-(2-(4-(2-chloro-3-(2,3-dihydrobenzo[b][1,4]dioxin-6-yl)benzyloxy)-2-(3-cyanobenzyloxyl)benzylamino)ethyl)acetamide;

5-((5-(2-chloro-3-(2,3-dihydrobenzo[b][1,4]dioxin-6-yl)benzyloxy)-2-((2-hydroxyethylamino)methyl)-4-methylphenoxy)methyl)nicotinonitrile;

(S)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid;

(R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid;

(S)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(R)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid;

(R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-hydroxyphenyl)propanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(methylthio)propanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(4-hydroxyphenyl)acetic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3,3,3-trifluoropropanoic acid;

(2R,3R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)propanoic acid;

1-(5-chloro-2-((3-cyanobenzyl)oxy)-4-((3-(2,3-dihydrobenzo[b][1,4]dioxin-6-yl)-2-methylbenzyl)oxy)benzyl)pyrrolidine-2-carboxylic acid;

(2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(5-hydroxy-1H-indol-3-yl)propanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-indol-3-yl)propanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid;

3-((4-chloro-5-((3-(2,3-dihydrobenzo[b][1,4]dioxin-6-yl)-2-methylbenzyl)oxy)-2-(((2-hydroxyethyl)amino)methyl)phenoxy)methyl)benzonitrile;

(S)-2-(benzyl(5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(dimethylamino)propanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-6-(dimethylamino)hexanoic acid;

(2S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfinyl)butanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)succinic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-4-yl)propanoic acid;

1-((5-chloro-2-((3-cyanobenzyl)oxy)-4-((3-(2,3-dihydrobenzo[b][1,4]dioxin-6-yl)-2-methylbenzyl)oxy)benzyl)amino)cyclopropanecarboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-2-yl)propanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxy-3-methylbutanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-cyanopropanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2-hydroxyphenyl)propanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)-3-hydroxypropanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-methoxypropanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-pyrrolo[2,3-b]pyridin-3-yl)propanoic acid;

(S)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(4-hydroxyphenyl)propanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)propanoic acid;

(2S,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

(2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2,3-dicarboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)-2-methylpropanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-indol-3-yl)propanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)butanoic acid;

(R)-3-(benzyloxy)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid;

(2R,3S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

(2S,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;

(2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;

(R)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;

(2R,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylsulfonyl)butanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)butanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-(methylthio)butanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)(methyl)amino)succinic acid;

(2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-4-hydroxybutanoic acid;

(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1-methyl-1H-imidazol-5-yl)propanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(thiazol-4-yl)propanoic acid;

1-(5-chloro-2-((3-cyanobenzyl)oxy)-4-((3-(2,3-dihydrobenzo[b][1,4]dioxin-6-yl)-2-methylbenzyl)oxy)benzyl)azetidine-2-carboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-3-methylbutanoic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(1H-indol-3-yl)acetic acid;

3-((4-chloro-5-((3-(2,3-dihydrobenzo[b][1,4]dioxin-6-yl)-2-methylbenzyl)oxy)-2-(((2-hydroxy-3-morpholinopropyl)amino)methyl)phenoxy)methyl)benzonitrile;

4-(5-chloro-2-((3-cyanobenzyl)oxy)-4-((3-(2,3-dihydrobenzo[b][1,4]dioxin-6-yl)-2-methylbenzyl)oxy)benzyl)morpholine-3-carboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-2-(hydroxymethyl)-3-methylbutanoic acid;

(2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-fluoropyrrolidine-2-carboxylic acid;

2-((5-chloro-2-((3-cyanobenzyl)oxy)-4-((3-(2,3-dihydrobenzo[b][1,4]dioxin-6-yl)-2-methylbenzyl)oxy)benzyl)amino)-4,4,4-trifluorobutanoic acid;

(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(3-cyanophenyl)propanoic acid;

2-benzyl-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;

(2S,3S)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid;

4-((5-chloro-2-((3-cyanobenzyl)oxy)-4-((3-(2,3-dihydrobenzo[b][1,4]dioxin-6-yl)-2-methylbenzyl)oxy)benzyl)amino)-1-methylpiperidine-4-carboxylic acid;
(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(pyridin-2-yl)propanoic acid;
(S)-4-(5-chloro-2-((3-cyanobenzyl)oxy)-4-((3-(2,3-dihydrobenzo[b][1,4]dioxin-6-yl)-2-methylbenzyl)oxy)benzyl)thiomorpholine-3-carboxylic acid;
3-((4-chloro-5-((3-(2,3-dihydrobenzo[b][1,4]dioxin-6-yl)-2-methylbenzyl)oxy)-2-(((2-methyl-1-(4-methylpiperazin-1-yl)propan-2-yl)amino)methyl)phenoxy)methyl)benzonitrile;
1-(5-chloro-2-((3-cyanobenzyl)oxy)-4-((3-(2,3-dihydrobenzo[b][1,4]dioxin-6-yl)-2-methylbenzyl)oxy)benzyl)-4-methylpiperazine-2-carboxylic acid;
3-((4-chloro-5-((3-(2,3-dihydrobenzo[b][1,4]dioxin-6-yl)-2-methylbenzyl)oxy)-2-(((2-hydroxy-3-(2-oxopyrrolidin-1-yl)propyl)amino)methyl)phenoxy)methyl)benzonitrile;
5-(5-chloro-2-((3-cyanobenzyl)oxy)-4-((3-(2,3-dihydrobenzo[b][1,4]dioxin-6-yl)-2-methylbenzyl)oxy)benzyl)-4,5,6,7-tetrahydro-3H-imidazo[4,5-c]pyridine-4-carboxylic acid;
(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(2H-tetrazol-2-yl)propanoic acid;
(R)-3-(1-benzyl-1H-imidazol-4-yl)-2-((5-chloro-2-((3-cyanobenzyl)oxy)-4-((3-(2,3-dihydrobenzo[b][1,4]dioxin-6-yl)-2-methylbenzyl)oxy)benzyl)amino)propanoic acid;
3-((2-((((1H-tetrazol-5-yl)methyl)amino)methyl)-4-chloro-5-((3-(2,3-dihydrobenzo[b][1,4]dioxin-6-yl)-2-methylbenzyl)oxy)phenoxy)methyl)benzonitrile;
(S)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;
(R)-2-((3-chloro-2-((3-cyanobenzyl)oxy)-4-((2-methyl-[1,1'-biphenyl]-3-yl)methoxy)benzyl)amino)-3-hydroxypropanoic acid;
(S)-4-((3-chloro-2-((3-cyanobenzyl)oxy)-4-((2-methyl-[1,1'-biphenyl]-3-yl)methoxy)benzyl)amino)-3-hydroxybutanoic acid;
(S)-1-(3-chloro-2-((3-cyanobenzyl)oxy)-4-((2-methyl-[1,1'-biphenyl]-3-yl)methoxy)benzyl)piperidine-2-carboxylic acid;
N-(2-((3-chloro-2-((3-cyanobenzyl)oxy)-4-((2-methyl-[1,1'-biphenyl]-3-yl)methoxy)benzyl)amino)ethyl)acetamide;
(R)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;
(S)-1-(3-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;
N-(2-((3-chloro-2-((3-cyanobenzyl)oxy)-4-((3-(2,3-dihydrobenzo[b][1,4]dioxin-6-yl)-2-methylbenzyl)oxy)benzyl)amino)ethyl)acetamide;
(S)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(R)-2-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(S)-4-((3-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;
(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxy-2-methylpropanoic acid;
(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid;
3-((5-chloro-2-((3-cyanobenzyl)oxy)-4-((3-(2,3-dihydrobenzo[b][1,4]dioxin-6-yl)-2-methylbenzyl)oxy)benzyl)amino)oxetane-3-carboxylic acid;
(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(S)-4-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;
N-(2-((5-chloro-2-((3-cyanobenzyl)oxy)-4-((3-(2,3-dihydrobenzo[b][1,4]dioxin-6-yl)-2-methylbenzyl)oxy)benzyl)amino)ethyl)acetamide;
(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxy-2-methylpropanoic acid;
(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxypropanoic acid;
(S)-4-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxybutanoic acid;
N-(2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)ethyl)acetamide;
(S)-2-(5-chloro-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;
(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid;
(R)-2-(2-((5-bromopyridin-3-yl)methoxy)-5-chloro-4-(3-(2,3-dihydrobenzo[b][1,4]dioxin-6-yl)-2-methylbenzyloxy)benzylamino)-3-hydroxy-2-methylpropanoic acid;
N-(2-(2-((5-bromopyridin-3-yl)methoxy)-5-chloro-4-(3-(2,3-dihydrobenzo[b][1,4]dioxin-6-yl)-2-methylbenzyloxy)benzylamino)ethyl)acetamide;
(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(methylsulfonyl)piperidine-2-carboxamide;
(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(N,N-dimethylsulfamoyl)piperidine-2-carboxamide;
(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(trifluoromethylsulfonyl)piperidine-2-carboxamide;
(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(cyclopropylsulfonyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(isopropylsulfonyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(1-methyl-1H-imidazol-4-ylsulfonyl)piperidine-2-carboxamide;

(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-N-((4-methylpiperazin-1-yl)sulfonyl)piperidine-2-carboxamide;

(R)-2-(5-chloro-4-(3-(2,3-dihydrobenzo[b][1,4]dioxin-6-yl)-2-methylbenzyloxy)-2-hydroxybenzylamino)-3-hydroxy-2-methylpropanoic acid;

N-(2-((2-((3-cyanobenzyl)oxy)-4-((3-(2,3-dihydrobenzo[b][1,4]dioxin-6-yl)-2-methylbenzyl)oxy)-5-methylbenzyl)amino)ethyl)acetamide;

(S)-4-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxybutanoic acid;

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxypropanoic acid;

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

(S)-1-(2-((3-cyanobenzyl)oxy)-4-((3-(2,3-dihydrobenzo[b][1,4]dioxin-6-yl)-2-methylbenzyl)oxy)-5-methylbenzyl)piperidine-2-carboxylic acid;

(R)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

(S)-4-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxybutanoic acid;

N-(2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)ethyl)acetamide;

(S)-1-(2-((3-cyano-4-fluorobenzyl)oxy)-4-((3-(2,3-dihydrobenzo[b][1,4]dioxin-6-yl)-2-methylbenzyl)oxy)-5-methylbenzyl)piperidine-2-carboxylic acid;

(R)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxypropanoic acid;

(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

N-(2-((4-((3-(2,3-dihydrobenzo[b][1,4]dioxin-6-yl)-2-methylbenzyl)oxy)-5-methyl-2-(pyridin-3-ylmethoxy)benzyl)amino)ethyl)acetamide;

(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxypropanoic acid;

(S)-4-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxybutanoic acid;

(S)-1-(4-((3-(2,3-dihydrobenzo[b][1,4]dioxin-6-yl)-2-methylbenzyl)oxy)-5-methyl-2-(pyridin-3-ylmethoxy)benzyl)piperidine-2-carboxylic acid;

(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid;

(R)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid;

N-(2-(2-((5-cyanopyridin-3-yl)methoxy)-4-(3-(2,3-dihydrobenzo[b][1,4]dioxin-6-yl)-2-methylbenzyloxy)-5-methylbenzylamino)ethyl)acetamide;

(S)-4-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxybutanoic acid;

(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxypropanoic acid;

(S)-1-2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid;

(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid;

(R)-2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid;

(R)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid;

N-(2-(2-(3-cyanobenzyloxy)-4-(3-(2,3-dihydrobenzo[b][1,4]dioxin-6-yl)-2-methylbenzyloxy)-5-ethylbenzylamino)ethyl)acetamide;

(S)-2-(2-(3-cyanobenzyloxy)-4-(3-(2,3-dihydrobenzo[b][1,4]dioxin-6-yl)-2-methylbenzyloxy)-5-ethylbenzylamino)-3-hydroxy-2-methylpropanoic acid;

(R)-2-(2-(3-cyanobenzyloxy)-4-(3-(2,3-dihydrobenzo[b][1,4]dioxin-6-yl)-2-methylbenzyloxy)-5-ethylbenzylamino)-3-hydroxy-2-methylpropanoic acid;

N-(2-(2-(3-cyanobenzyloxy)-4-(3-(2,3-dihydrobenzo[b][1,4]dioxin-6-yl)-2-methylbenzyloxy)-5-vinylbenzylamino)ethyl)acetamide;

(S)-1-(2-(3-cyanobenzyloxy)-4-(3-(2,3-dihydrobenzo[b][1,4]dioxin-6-yl)-2-methylbenzyloxy)-5-vinylbenzyl)piperidine-2-carboxylic acid;

N-(2-(2-(4-cyanobutoxy)-4-(3-(2,3-dihydrobenzo[b][1,4]dioxin-6-yl)-2-methylbenzyloxy)-5-methylbenzylamino)ethyl)acetamide;

(S)-4-(2-(4-cyanobutoxy)-4-(3-(2,3-dihydrobenzo[b][1,4]dioxin-6-yl)-2-methylbenzyloxy)-5-methylbenzylamino)-3-hydroxybutanoic acid;

(S)-1-(2-(4-cyanobutoxy)-4-(3-(2,3-dihydrobenzo[b][1,4]dioxin-6-yl)-2-methylbenzyloxy)-5-methylbenzyl)piperidine-2-carboxylic acid;

(S)-2-(2-(4-cyanobutoxy)-4-(3-(2,3-dihydrobenzo[b][1,4]dioxin-6-yl)-2-methylbenzyloxy)-5-methylbenzylamino)-3-hydroxy-2-methylpropanoic acid;

(S)-1-(5-bromo-2-((5-cyanopyridin-3-yl)methoxy)-4-(2-methylbiphenyl-3-yl)methoxy)benzyl)piperidine-2-carboxylic acid;

N-(2-((5-bromo-2-((3-cyanobenzyl)oxy)-4-((3-(2,3-dihydrobenzo[b][1,4]dioxin-6-yl)-2-methylbenzyl)oxy)benzyl)amino)ethyl)acetamide;

(S)-4-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;

(S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;

(S)-1-(5-bromo-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;

(R)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

(S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

N-(2-(4-(2-cyano-3-(2,3-dihydrobenzo[b][1,4]dioxin-6-yl)benzyloxy)-2-((5-cyanopyridin-3-yl)methoxy)-5-methylbenzylamino)ethyl)acetamide;

5-((5-(2-cyano-3-(2,3-dihydrobenzo[b][1,4]dioxin-6-yl)benzyloxy)-2-((2-hydroxyethylamino)methyl)-4-methylphenoxy)methyl)nicotinonitrile;

(S)-4-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxybutanoic acid;

(S)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(S)-1-(4-(2-cyano-3-(2,3-dihydrobenzo[b][1,4]dioxin-6-yl)benzyloxy)-2-((5-cyanopyridin-3-yl)methoxy)-5-methylbenzyl)piperidine-2-carboxylic acid;

(R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid;

(R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(S)-2-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid;

(S)-1-(5-bromo-4-((2-cyano-3-(2,3-dihydrobenzo[b][1,4]dioxin-6-yl)benzyl)oxy)-2-((3-cyanobenzyl)oxy)benzyl)piperidine-2-carboxylic acid;

(S)-4-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxybutanoic acid;

N-(2-((5-bromo-4-((2-cyano-3-(2,3-dihydrobenzo[b][1,4]dioxin-6-yl)benzyl)oxy)-2-((3-cyanobenzyl)oxy)benzyl)amino)ethyl)acetamide;

(S)-4-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxybutanoic acid;

N-(2-(5-bromo-2-((5-cyanopyridin-3-yl)methoxy)-4-(3-(2,3-dihydrobenzo[b][1,4]dioxin-6-yl)-2-methylbenzyloxy)benzylamino)ethyl)acetamide;

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxypropanoic acid;

(S)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid;

(R)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;

5-((4-bromo-5-(3-(2,3-dihydrobenzo[b][1,4]dioxin-6-yl)-2-methylbenzyloxy)-2-((2-hydroxyethylamino)methyl)phenoxy)methyl)nicotinonitrile;

(R)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid;

(R)-2-((2-((5-cyano-4-methylpyridin-3-yl)methoxy)-4-((2-methyl-[1,1'-biphenyl]-3-yl)methoxy)benzyl)amino)-3-hydroxypropanoic acid;

(R)-2-((2-((3-carbamoylbenzyl)oxy)-4-((3-(2,3-dihydrobenzo[b][1,4]dioxin-6-yl)-2-methylbenzyl)oxy)benzyl)amino)-3-hydroxypropanoic acid;

(R)-2-((2-((3-carbamoylbenzyl)oxy)-4-((3-(2,3-dihydrobenzo[b][1,4]dioxin-6-yl)-2-methylbenzyl)oxy)benzyl)amino)-3-hydroxy-2-methylpropanoic acid;

(R)-2-((2-((5-cyanopyridin-3-yl)methoxy)-4-((2-methyl-[1,1'-biphenyl]-3-yl)methoxy)benzyl)amino)-3-hydroxypropanoic acid;

(S)-4-((2-((5-cyanopyridin-3-yl)methoxy)-4-((2-methyl-[1,1'-biphenyl]-3-yl)methoxy)benzyl)amino)-3-hydroxybutanoic acid;

(S)-1-(2-((5-cyanopyridin-3-yl)methoxy)-4-((2-methyl-[1,1'-biphenyl]-3-yl)methoxy)benzyl)piperidine-2-carboxylic acid;

(S)-4-((2-((3-cyano-4-fluorobenzyl)oxy)-4-((3-(2,3-dihydrobenzo[b][1,4]dioxin-6-yl)-2-methylbenzyl)oxy)benzyl)amino)-3-hydroxybutanoic acid;

(S)-4-((2-((3-cyano-4-fluorobenzyl)oxy)-4-((2-methyl-[1,1'-biphenyl]-3-yl)methoxy)benzyl)amino)-3-hydroxybutanoic acid;

(R)-2-((2-((3-cyano-4-fluorobenzyl)oxy)-4-((2-methyl-[1,1'-biphenyl]-3-yl)methoxy)benzyl)amino)-3-hydroxypropanoic acid;

(R)-2-((2-((3-cyano-4-fluorobenzyl)oxy)-4-((2-methyl-[1,1'-biphenyl]-3-yl)methoxy)benzyl)amino)-3-hydroxy-2-methylpropanoic acid;

(S)-1-(2-((3-cyano-4-fluorobenzyl)oxy)-4-((2-methyl-[1,1'-biphenyl]-3-yl)methoxy)benzyl)piperidine-2-carboxylic acid; and N-(2-((2-methoxy-4-((2-methyl-[1,1'-biphenyl]-3-yl)methoxy)benzyl)amino)ethyl)acetamide;

or a pharmaceutically acceptable salt thereof.

6. A compound selected from

N-(2-((2-((3-cyanobenzyl)oxy)-4-((3-(2,3-dihydrobenzo[b][1,4]dioxin-6-yl)-2-methylbenzyl)oxy)-5-methylbenzyl)amino)ethyl)acetamide;

(S)-4-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxybutanoic acid;

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxypropanoic acid;

(S)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

(S)-1-(2-((3-cyanobenzyl)oxy)-4-((3-(2,3-dihydrobenzo[b][1,4]dioxin-6-yl)-2-methylbenzyl)oxy)-5-methylbenzyl)piperidine-2-carboxylic acid;

(R)-2-((2-((3-cyanobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;

N-(2-((4-((3-(2,3-dihydrobenzo[b][1,4]dioxin-6-yl)-2-methylbenzyl)oxy)-5-methyl-2-(pyridin-3-ylmethoxy)benzyl)amino)ethyl)acetamide;

(S)-4-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxybutanoic acid;

N-(2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)ethyl)acetamide;
(S)-1-(2-((3-cyano-4-fluorobenzyl)oxy)-4-((3-(2,3-dihydrobenzo[b][1,4]dioxin-6-yl)-2-methylbenzyl)oxy)-5-methylbenzyl)piperidine-2-carboxylic acid;
(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxypropanoic acid;
(R)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;
(S)-4-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxybutanoic acid;
(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxypropanoic acid;
(S)-2-((2-((3-cyano-4-fluorobenzyl)oxy)-4-((3-(2,3-dihydrobenzo[b][1,4]dioxin-6-yl)-2-methylbenzyl)oxy)-5-methylbenzyl)amino)-3-hydroxy-2-methylpropanoic acid;
(S)-1-(4-((3-(2,3-dihydrobenzo[b][1,4]dioxin-6-yl)-2-methylbenzyl)oxy)-5-methyl-2-(pyridin-3-ylmethoxy)benzyl)piperidine-2-carboxylic acid;
(S)-2-((4-((3-(2,3-dihydrobenzo[b][1,4]dioxin-6-yl)-2-methylbenzyl)oxy)-5-methyl-2-(pyridin-3-ylmethoxy)benzyl)amino)-3-hydroxy-2-methylpropanoic acid;
N-(2-(2-((5-cyanopyridin-3-yl)methoxy)-4-(3-(2,3-dihydrobenzo[b][1,4]dioxin-6-yl)-2-methylbenzyloxy)-5-methylbenzylamino)ethyl)acetamide;
(S)-4-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxybutanoic acid;
(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxypropanoic acid;
(S)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid;
(S)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid;
(R)-2-(2-((5-cyanopyridin-3-yl)methoxy)-4-(3-(2,3-dihydrobenzo[b][1,4]dioxin-6-yl)-2-methylbenzyloxy)-5-methylbenzylamino)-3-hydroxy-2-methylpropanoic acid;
(R)-1-(2-((5-cyanopyridin-3-yl)methoxy)-4-(3-(2,3-dihydrobenzo[b][1,4]dioxin-6-yl)-2-methylbenzyloxy)-5-methylbenzyl)piperidine-2-carboxylic acid;
N-(2-(2-(4-cyanobutoxy)-4-(3-(2,3-dihydrobenzo[b][1,4]dioxin-6-yl)-2-methylbenzyloxy)-5-methylbenzylamino)ethyl)acetamide;
(S)-1-(2-(4-cyanobutoxy)-4-(3-(2,3-dihydrobenzo[b][1,4]dioxin-6-yl)-2-methylbenzyloxy)-5-methylbenzyl)piperidine-2-carboxylic acid; and
(S)-2-(2-(4-cyanobutoxy)-4-(3-(2,3-dihydrobenzo[b][1,4]dioxin-6-yl)-2-methylbenzyloxy)-5-methylbenzylamino)-3-hydroxy-2-methylpropanoic acid;
or a pharmaceutically acceptable salt thereof.

7. A compound selected from
(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;
(R)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(S)-2-((5-chloro-2-((3-cyanobenzyl)oxy)-4-((3-(2,3-dihydrobenzo[b][1,4]dioxin-6-yl)-2-methylbenzyl)oxy)benzyl)amino)-3-hydroxy-2-methylpropanoic acid;
(S)-1-(5-chloro-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;
(S)-4-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxybutanoic acid;
(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxypropanoic acid;
(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-hydroxy-2-methylpropanoic acid;
(S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)piperidine-2-carboxylic acid;
(S)-2-(5-chloro-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;
(R)-2-(2-((5-bromopyridin-3-yl)methoxy)-5-chloro-4-(3-(2,3-dihydrobenzo[b][1,4]dioxin-6-yl)-2-methylbenzyloxy)benzylamino)-3-hydroxy-2-methylpropanoic acid;
(2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;
2-((5-chloro-2-((3-cyanobenzyl)oxy)-4-((3-(2,3-dihydrobenzo[b][1,4]dioxin-6-yl)-2-methylbenzyl)oxy)benzyl)amino)-3-(1H-imidazol-4-yl)-2-methylpropanoic acid;
(2S,4S)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;
(2S,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid;
(2S,3R)-1-(5-chloro-2-((3-cyanobenzyl)oxy)-4-((3-(2,3-dihydrobenzo[b][1,4]dioxin-6-yl)-2-methylbenzyl)oxy)benzyl)-3-hydroxypyrrolidine-2-carboxylic acid; and
3-((4-chloro-5-((3-(2,3-dihydrobenzo[b][1,4]dioxin-6-yl)-2-methylbenzyl)oxy)-2-(((2-methyl-1-(4-methylpiperazin-1-yl)propan-2-yl)amino)methyl)phenoxy)methyl)benzonitrile;
or a pharmaceutically acceptable salt thereof.

8. A compound selected from
N-(2-((5-bromo-2-((3-cyanobenzyl)oxy)-4-((3-(2,3-dihydrobenzo[b][1,4]dioxin-6-yl)-2-methylbenzyl)oxy)benzyl)amino)ethyl)acetamide;
(S)-4-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxybutanoic acid;
(S)-2-((5-bromo-2-((3-cyanobenzyl)oxy)-4-((3-(2,3-dihydrobenzo[b][1,4]dioxin-6-yl)-2-methylbenzyl)oxy)benzyl)amino)-3-hydroxypropanoic acid;
(S)-1-(5-bromo-2-((3-cyanobenzyl)oxy)-4-((3-(2,3-dihydrobenzo[b][1,4]dioxin-6-yl)-2-methylbenzyl)oxy)benzyl)piperidine-2-carboxylic acid;

(S)-2-((5-bromo-2-((3-cyanobenzyl)oxy)-4-((3-(2,3-di-hydrobenzo[b][1,4]dioxin-6-yl)-2-methylbenzyl)oxy)benzyl)amino)-3-hydroxy-2-methylpropanoic acid;

(R)-2-((5-bromo-2-((3-cyanobenzyl)oxy)-4-((3-(2,3-di-hydrobenzo[b][1,4]dioxin-6-yl)-2-methylbenzyl)oxy)benzyl)amino)-3-hydroxy-2-methylpropanoic acid;

(S)-4-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxybutanoic acid;

N-(2-(5-bromo-2-((5-cyanopyridin-3-yl)methoxy)-4-(3-(2,3-dihydrobenzo[b][1,4]dioxin-6-yl)-2-methylbenzyloxy)benzylamino)ethyl)acetamide;

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxypropanoic acid;

(S)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid;

(R)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;

(S)-2-(5-bromo-2-((5-cyanopyridin-3-yl)methoxy)-4-(3-(2,3-dihydrobenzo[b][1,4]dioxin-6-yl)-2-methylbenzyloxy)benzylamino)-3-hydroxy-2-methylpropanoic acid;

5-((4-bromo-5-(3-(2,3-dihydrobenzo[b][1,4]dioxin-6-yl)-2-methylbenzyloxy)-2-((2-hydroxyethylamino)methyl)phenoxy)methyl)nicotinonitrile; and (R)-1-(5-bromo-2-((5-cyanopyridin-3-yl)methoxy)-4-(3-(2,3-dihydrobenzo[b][1,4]dioxin-6-yl)-2-methylbenzyloxy)benzyl)piperidine-2-carboxylic acid;

or a pharmaceutically acceptable salt thereof.

9. A compound selected from (S)-4-(4-(2-chloro-3-(2,3-dihydrobenzo[b][1,4]dioxin-6-yl)benzyloxy)-2-(3-cyanobenzyloxyl)benzylamino)-3-hydroxybutanoic acid;

(R)-2-(4-(2-chloro-3-(2,3-dihydrobenzo[b][1,4]dioxin-6-yl)benzyloxy)-2-(3-cyanobenzyloxyl)benzylamino)-3-hydroxypropanoic acid;

(R)-2-(4-(2-chloro-3-(2,3-dihydrobenzo[b][1,4]dioxin-6-yl)benzyloxy)-2-(3-cyanobenzyloxyl)benzylamino)-3-hydroxy-2-methylpropanoic acid;

(S)-2-(4-(2-chloro-3-(2,3-dihydrobenzo[b][1,4]dioxin-6-yl)benzyloxy)-2-(3-cyanobenzyloxyl)benzylamino)-3-hydroxy-2-methylpropanoic acid;

N-(2-(4-(2-chloro-3-(2,3-dihydrobenzo[b][1,4]dioxin-6-yl)benzyloxy)-2-(3-cyanobenzyloxyl)benzylamino)ethyl)acetamide;

(S)-1-(4-(2-chloro-3-(2,3-dihydrobenzo[b][1,4]dioxin-6-yl)benzyloxy)-2-(3-cyanobenzyloxyl)benzyl)piperidine-2-carboxylic acid;

5-((5-(2-chloro-3-(2,3-dihydrobenzo[b][1,4]dioxin-6-yl)benzyloxy)-2-((2-hydroxyethylamino)methyl)-4-methylphenoxy)methyl)nicotinonitrile;

(S)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid;

(R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid;

(S)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(R)-1-(4-(2-chloro-3-(2,3-dihydrobenzo[b][1,4]dioxin-6-yl)benzyloxy)-2-((5-cyanopyridin-3-yl)methoxy)-5-methylbenzyl)piperidine-2-carboxylic acid; and (R)-2-(4-(2-chloro-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

or a pharmaceutically acceptable salt thereof.

10. A compound selected from (S)-1-(4-(2-cyano-3-(2,3-dihydrobenzo[b][1,4]dioxin-6-yl)benzyloxy)-2-((5-cyanopyridin-3-yl)methoxy)-5-methylbenzyl)piperidine-2-carboxylic acid;

(S)-2-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid;

(S)-1-(5-bromo-4-((2-cyano-3-(2,3-dihydrobenzo[b][1,4]dioxin-6-yl)benzyl)oxy)-2-((3-cyanobenzyl)oxy)benzyl)piperidine-2-carboxylic acid;

(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxypropanoic acid;

(R)-2-((5-chloro-4-((2-cyano-3-(2,3-dihydrobenzo[b][1,4]dioxin-6-yl)benzyl)oxy)-2-((3-cyanobenzyl)oxy)benzyl)amino)-3-hydroxy-2-methylpropanoic acid;

(S)-4-((5-bromo-4-((2-cyano-3-(2,3-dihydrobenzo[b][1,4]dioxin-6-yl)benzyl)oxy)-2-((3-cyanobenzyl)oxy)benzyl)amino)-3-hydroxybutanoic acid;

N-(2-((5-bromo-4-((2-cyano-3-(2,3-dihydrobenzo[b][1,4]dioxin-6-yl)benzyl)oxy)-2-((3-cyanobenzyl)oxy)benzyl)amino)ethyl)acetamide;

N-(2-(4-(2-cyano-3-(2,3-dihydrobenzo[b][1,4]dioxin-6-yl)benzyloxy)-2-((5-cyanopyridin-3-yl)methoxy)-5-methylbenzylamino)ethyl)acetamide;

5-((5-(2-cyano-3-(2,3-dihydrobenzo[b][1,4]dioxin-6-yl)benzyloxy)-2-((2-hydroxyethylamino)methyl)-4-methylphenoxy)methyl)nicotinonitrile;

(S)-4-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxybutanoic acid;

(S)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

(R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxypropanoic acid; and (R)-2-(4-(2-cyano-3-(2,3-dihydrobenzo[b][1,4]dioxin-6-yl)benzyloxy)-2-((5-cyanopyridin-3-yl)methoxy)-5-methylbenzylamino)-3-hydroxy-2-methylpropanoic acid;

or a pharmaceutically acceptable salt thereof.

11. A compound selected from (S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(methylsulfonyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(N,N-dimethylsulfamoyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(trifluoromethylsulfonyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(cyclopropylsulfonyl)piperidine-2-carboxamide;

(S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(isopropylsulfonyl)piperidine-2-carboxamide; and (S)-1-(5-chloro-2-((5-cyanopyridin-3-yl)methoxy)-4-(3-(2,3-dihydrobenzo[b][1,4]dioxin-6-yl)-2-methylbenzyloxy)benzyl)-N-(1-methyl-1H-imidazol-4-ylsulfonyl)piperidine-2-carboxamide;

or a pharmaceutically acceptable salt thereof.

12. A compound selected from (S)-1-(5-bromo-2-((5-cyanopyridin-3-yl)methoxy)-4-((2-methylbiphenyl-3-yl)methoxy)benzyl)piperidine-2-carboxylic acid;

2-((2-((3-cyanobenzyl)oxy)-6-methoxy-4-((2-methyl-[1,1'-biphenyl]-3-yl)methoxy)benzyl)amino)-3-hydroxy-2-methylpropanoic acid;

(S)-2-((2-((3-cyanobenzyl)oxy)-4-((2-methyl-[1,1'-biphenyl]-3-yl)methoxy)benzyl)amino)-3-hydroxypropanoic acid;

(S)-2-((2-((3-cyanobenzyl)oxy)-4-((2-methyl-[1,1'-biphenyl]-3-yl)methoxy)benzyl)amino)-3-hydroxy-2-methylpropanoic acid;

(S)-4-((2-(4-cyanobutoxy)-4-((2-methyl-[1,1'-biphenyl]-3-yl)methoxy)benzyl)amino)-3-hydroxybutanoic acid;

(R)-2-((2-((3-cyanobenzyl)oxy)-4-((2-methyl-[1,1'-biphenyl]-3-yl)methoxy)benzyl)amino)-3-hydroxy-2-methylpropanoic acid;

(R)-2-((2-((5-cyanopyridin-3-yl)methoxy)-4-((2-methyl-[1,1'-biphenyl]-3-yl)methoxy)benzyl)amino)-3-hydroxypropanoic acid;

(S)-4-((2-((3-cyano-4-fluorobenzyl)oxy)-4-((2-methyl-[1,1'-biphenyl]-3-yl)methoxy)benzyl)amino)-3-hydroxybutanoic acid;

(R)-2-((2-((3-cyano-4-fluorobenzyl)oxy)-4-((2-methyl-[1,1'-biphenyl]-3-yl)methoxy)benzyl)amino)-3-hydroxy-2-methylpropanoic acid; and (R)-2-((2-((3-cyano-4-fluorobenzyl)oxy)-4-((2-methyl-[1,1'-biphenyl]-3-yl)methoxy)benzyl)amino)-3-hydroxypropanoic acid;

or a pharmaceutically acceptable salt thereof.

13. A compound selected from (S)-2-((5-chloro-4-((3-(2,3-dihydrobenzo[b][1,4]dioxin-6-yl)-2-methylbenzyl)oxy)-2-((5-(ethoxycarbonyl)pyridin-3-yl)methoxy)benzyl)amino)-3-hydroxy-2-methylpropanoic acid;

(S)-5-((2-(((2-carboxy-1-hydroxypropan-2-yl)amino)methyl)-4-chloro-5-((3-(2,3-dihydrobenzo[b][1,4]dioxin-6-yl)-2-methylbenzyl)oxy)phenoxy)methyl)nicotinic acid;

(S)-5-((2-(((4-amino-1-carboxybutyl)amino)methyl)-4-chloro-5-((3-(2,3-dihydrobenzo[b][1,4]dioxin-6-yl)-2-methylbenzyl)oxy)phenoxy)methyl)nicotinic acid;

(S)-5-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanoic acid;

(S)-6-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)hexanoic acid;

(S)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)butanoic acid;

(2S,5S)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-5-hydroxypiperidine-2-carboxylic acid;

(2S,4R)-1-(5-chloro-2-((5-cyanopyridin-3-yl)methoxy)-4-((3-(2,3-dihydrobenzo[b][1,4]dioxin-6-yl)-2-methylbenzyl)oxy)benzyl)-4-hydroxypiperidine-2-carboxylic acid;

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-2-yl)propanoic acid;

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-3-yl)propanoic acid;

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-3-(pyridin-4-yl)propanoic acid;

(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)pentanedioic acid;

2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)acetic acid;

ethyl (5-((4-chloro-5-((3-(2,3-dihydrobenzo[b][1,4]dioxin-6-yl)-2-methylbenzyl)oxy)-2-formylphenoxy)methyl)pyridin-3-yl)carbamate;

(S)-2-((5-chloro-4-((3-(2,3-dihydrobenzo[b][1,4]dioxin-6-yl)-2-methylbenzyl)oxy)-2-((5-((ethoxycarbonyl)amino)pyridin-3-yl)methoxy)benzyl)amino)-3-hydroxy-2-methylpropanoic acid;

N-(4-((4-chloro-5-((3-(2,3-dihydrobenzo[b][1,4]dioxin-6-yl)-2-methylbenzyl)oxy)-2-formylphenoxy)methyl)pyridin-2-yl)acetamide;

(S)-2-((2-((2-acetamidopyridin-4-yl)methoxy)-5-chloro-4-((3-(2,3-dihydrobenzo[b][1,4]dioxin-6-yl)-2-methylbenzyl)oxy)benzyl)amino)-3-hydroxy-2-methylpropanoic acid;

(S)-2-((5-chloro-4-((3-(2,3-dihydrobenzo[b][1,4]dioxin-6-yl)-2-methylbenzyl)oxy)-2-((5-(methylsulfonyl)pyridin-3-yl)methoxy)benzyl)amino)-3-hydroxy-2-methylpropanoic acid;

(5-chloro-4-{[3-(2,3-dihydro-1,4-benzodioxin-6-yl)-2-methylphenyl]methoxy}-2-[(5-methanesulfonylpyridin-3-yl)methoxy]phenyl)methanol;

(S)-2-((5-chloro-2-((2-chloro-6-methoxypyridin-4-yl)methoxy)-4-((3-(2,3-dihydrobenzo[b][1,4]dioxin-6-yl)-2-methylbenzyl)oxy)benzyl)amino)-3-hydroxy-2-methylpropanoic acid;

(2S)-2-{[(5-chloro-4-{[3-(2,3-dihydro-1,4-benzodioxin-6-yl)-2-methylphenyl]methoxy}-2-[(2-methoxypyridin-4-yl)methoxy]phenyl)methyl]amino}-3-hydroxy-2-methylpropanoic acid;

(5-chloro-4-{[3-(2,3-dihydro-1,4-benzodioxin-6-yl)-2-methylphenyl]methoxy}-2-[(2-methoxypyridin-4-yl)methoxy]phenyl)methanol;

(S)-1-(5-chloro-4-((3-(2,3-dihydrobenzo[b][1,4]dioxin-6-yl)-2-methylbenzyl)oxy)-2-((2-methoxypyridin-4-yl)methoxy)benzyl)piperidine-2-carboxylic acid;

(S)-2-((5-chloro-4-((3-(2,3-dihydrobenzo[b][1,4]dioxin-6-yl)-2-methylbenzyl)oxy)-2-((2-(dimethylcarbamoyl)pyridin-4-yl)methoxy)benzyl)amino)-3-hydroxy-2-methylpropanoic acid;

4-(4-chloro-5-{[3-(2,3-dihydro-1,4-benzodioxin-6-yl)-2-methylphenyl]methoxy}-2-(hydroxymethyl)phenoxymethyl)-N,N-dimethylpyridine-2-carboxamide;
5-chloro-4-((3-(2,3-dihydrobenzo[b][1,4]dioxin-6-yl)-2-methylbenzyl)oxy)-2-((3-(methylsulfonyl)benzyl)oxy) benzaldehyde;
(S)-2-((5-chloro-4-((3-(2,3-dihydrobenzo[b][1,4]dioxin-6-yl)-2-methylbenzyl)oxy)-2-((3-(methylsulfonyl)benzyl)oxy)benzyl)amino)-3-hydroxy-2-methylpropanoic acid;
(S)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-4-oxobutanoic acid;
(S)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)succinic acid;
(R)-4-amino-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)-4-oxobutanoic acid;
(R)-2-((5-chloro-2-((5-cyanopyridin-3-yl)methoxy)-4-((3-(2,3-dihydrobenzo[b][1,4]dioxin-6-yl)-2-methylbenzyl)oxy)benzyl)amino)succinic acid;
(S)-1-(5-chloro-4-((3-(2,3-dihydrobenzo[b][1,4]dioxin-6-yl)-2-methylbenzyl)oxy)-2-((2-methoxy-5-(methoxycarbonyl)benzyl)oxy)benzyl)piperidine-2-carboxylic acid;
S)-1-(2-((5-carboxy-2-methoxybenzyl)oxy)-5-chloro-4-((3-(2,3-dihydrobenzo[b][1,4]dioxin-6-yl)-2-methylbenzyl)oxy)benzyl)piperidine-2-carboxylic acid;
(S)-1-(2-(benzyloxy)-5-chloro-4-((3-(2,3-dihydrobenzo[b][1,4]dioxin-6-yl)-2-methylbenzyl)oxy)benzyl)piperidine-2-carboxylic acid;
(S)-1-(5-chloro-4-((3-(2,3-dihydrobenzo[b][1,4]dioxin-6-yl)-2-methylbenzyl)oxy)-2-((2-methoxybenzyl)oxy)benzyl)piperidine-2-carboxylic acid; and
(S)-2-((2-(2-amino-2-oxoethoxy)-5-chloro-4-((3-(2,3-dihydrobenzo[b][1,4]dioxin-6-yl)-2-methylbenzyl)oxy)benzyl)amino)-3-hydroxypropanoic acid;
or a pharmaceutically acceptable salt thereof.

14. A compound selected from

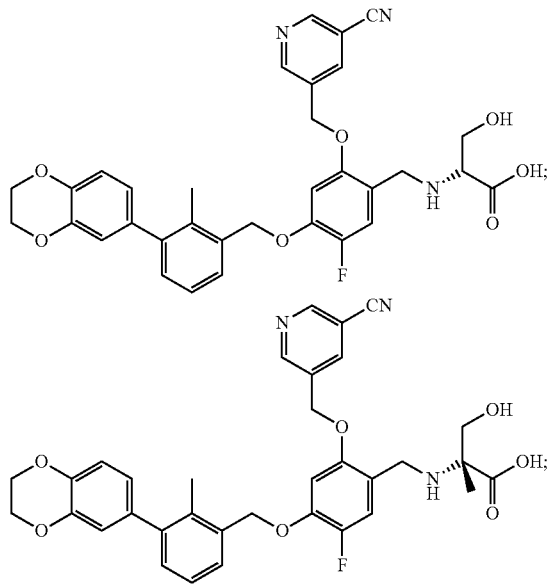

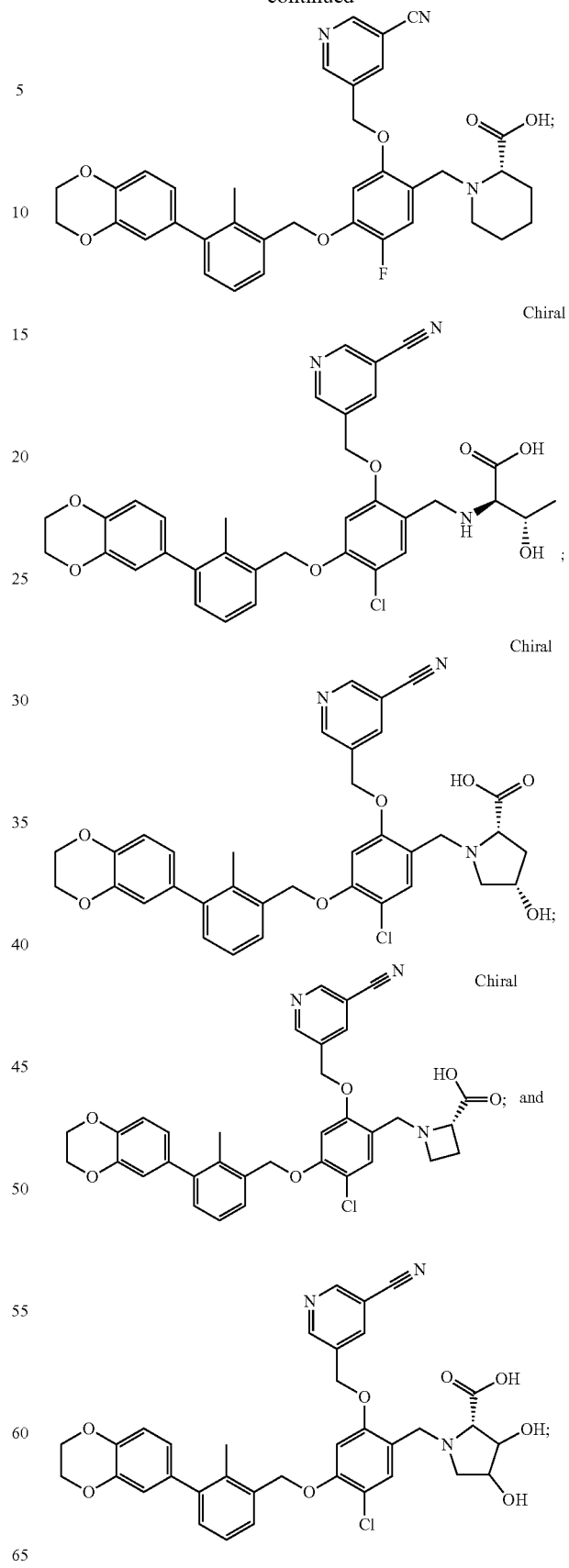

or a pharmaceutically acceptable salt thereof.

15. A pharmaceutical composition comprising a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 9,850,225 B2
APPLICATION NO. : 14/681772
DATED : December 26, 2017
INVENTOR(S) : Chupak et al.

Page 1 of 2

It is certified that error appears in the above-identified patent and that said Letters Patent is hereby corrected as shown below:

In the Claims

In Claim 5, Column 296, Line 28:
Delete "fluorophenoxyl)benzyl)" and insert -- fluorophenoxy)benzyl) --.

In Claim 5, Column 296, Line 31:
Delete "fluorophenoxyl)benzyl)" and insert -- fluorophenoxy)benzyl) --.

In Claim 5, Column 297, Line 27:
Delete "1H -indazol" and insert -- 1H-indazol --.

In Claim 5, Column 299, Line 31:
Delete "cyanobenzyloxyl)benzyl)" and insert -- cyanobenzyloxy)benzyl) --.

In Claim 5, Column 299, Line 34:
Delete "cyanobenzyloxyl)" and insert -- cyanobenzyloxy) --.

In Claim 5, Column 299, Line 37:
Delete "cyanobenzyloxyl)" and insert -- cyanobenzyloxy) --.

In Claim 5, Column 299, Line 40:
Delete "cyanobenzyloxyl)" and insert -- cyanobenzyloxy) --.

In Claim 5, Column 299, Line 43:
Delete "cyanobenzyloxyl)" and insert -- cyanobenzyloxy) --.

In Claim 5, Column 299, Line 46:
Delete "cyanobenzyloxyl)" and insert -- cyanobenzyloxy) --.

Signed and Sealed this
Eleventh Day of December, 2018

Andrei Iancu
*Director of the United States Patent and Trademark Office*

CERTIFICATE OF CORRECTION (continued)
U.S. Pat. No. 9,850,225 B2

In Claim 5, Column 303, Line 12:
Delete "2yl" and insert -- 2-yl --.

In Claim 9, Column 311, Line 38:
Delete "cyanobenzyloxyl)" and insert -- cyanobenzyloxy) --.

In Claim 9, Column 311, Line 41:
Delete "cyanobenzyloxyl)" and insert -- cyanobenzyloxy) --.

In Claim 9, Column 311, Line 44:
Delete "cyanobenzyloxyl)" and insert -- cyanobenzyloxy) --.

In Claim 9, Column 311, Line 47:
Delete "cyanobenzyloxyl)" and insert -- cyanobenzyloxy) --.

In Claim 9, Column 311, Line 50:
Delete "cyanobenzyloxyl)" and insert -- cyanobenzyloxy) --.

In Claim 9, Column 311, Line 53:
Delete "cyanobenzyloxyl)" and insert -- cyanobenzyloxy) --.

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Asn Asp Ser Gly Thr
                85                  90                  95

Tyr Leu Cys Gly Ala Ile Ser Leu Ala Pro Lys Ala Gln Ile Lys Glu
                100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
                180                 185                 190

Thr Pro Glu Val Thr Cys Val Val Asp Val Ser His Glu Asp Pro
    195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
        370                 375                 380

<210> SEQ ID NO 2
<211> LENGTH: 238
<212> TYPE: PRT
<213> ORGANISM: Homo sapiens

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp

-continued

| | | | | 20 | | | | | 25 | | | | | 30 | | |
|---|---|---|---|---|---|---|---|---|---|---|---|---|---|---|---|---|
| Leu | Ala | Ala | Leu | Ile | Val | Tyr | Trp | Glu | Met | Glu | Asp | Lys | Asn | Ile | Ile |
| | | | | 35 | | | | | 40 | | | | | 45 | | |
| Gln | Phe | Val | His | Gly | Glu | Glu | Asp | Leu | Lys | Val | Gln | His | Ser | Ser | Tyr |
| | | | | 50 | | | | | 55 | | | | | 60 | | |
| Arg | Gln | Arg | Ala | Arg | Leu | Leu | Lys | Asp | Gln | Leu | Ser | Leu | Gly | Asn | Ala |
| 65 | | | | | 70 | | | | | 75 | | | | | 80 | |
| Ala | Leu | Gln | Ile | Thr | Asp | Val | Lys | Leu | Gln | Asp | Ala | Gly | Val | Tyr | Arg |
| | | | | 85 | | | | | 90 | | | | | 95 | | |
| Cys | Met | Ile | Ser | Tyr | Gly | Gly | Ala | Asp | Tyr | Lys | Arg | Ile | Thr | Val | Lys |
| | | | | 100 | | | | | 105 | | | | | 110 | | |
| Val | Asn | Ala | Pro | Tyr | Asn | Lys | Ile | Asn | Gln | Arg | Ile | Leu | Val | Val | Asp |
| | | | | 115 | | | | | 120 | | | | | 125 | | |
| Pro | Val | Thr | Ser | Glu | His | Glu | Leu | Thr | Cys | Gln | Ala | Glu | Gly | Tyr | Pro |
| | | | | 130 | | | | | 135 | | | | | 140 | | |
| Lys | Ala | Glu | Val | Ile | Trp | Thr | Ser | Ser | Asp | His | Gln | Val | Leu | Ser | Gly |
| 145 | | | | | 150 | | | | | 155 | | | | | 160 | |
| Lys | Thr | Thr | Thr | Thr | Asn | Ser | Lys | Arg | Glu | Glu | Lys | Leu | Phe | Asn | Val |
| | | | | 165 | | | | | 170 | | | | | 175 | | |
| Thr | Ser | Thr | Leu | Arg | Ile | Asn | Thr | Thr | Thr | Asn | Glu | Ile | Phe | Tyr | Cys |
| | | | | 180 | | | | | 185 | | | | | 190 | | |
| Thr | Phe | Arg | Arg | Leu | Asp | Pro | Glu | Glu | Asn | His | Thr | Ala | Glu | Leu | Val |
| | | | | 195 | | | | | 200 | | | | | 205 | | |
| Ile | Pro | Glu | Leu | Pro | Leu | Ala | His | Pro | Pro | Asn | Glu | Arg | Thr | Gly | Ser |
| | | | | 210 | | | | | 215 | | | | | 220 | | |
| Ser | Glu | Thr | Val | Arg | Phe | Gln | Gly | His | His | His | His | His | His | | |
| 225 | | | | | 230 | | | | | 235 | | | | | | |